(12) United States Patent
Petersen et al.

(10) Patent No.: US 8,377,701 B2
(45) Date of Patent: Feb. 19, 2013

(54) SPECIFIC LIGANDS TO SORTILIN

(75) Inventors: Jens Claus Munck Petersen, Århus C (DK); Poul Nissen, Risskov (DK); Peder Søndergaard Madsen, Risskov (DK); Esben Meldgaard Høgh Quistgaard, Risskov (DK); Morten Keller Grøftehauge, Århus C (DK); Søren Skou Thirup, Risskov (DK); Jacob Flyvholm Cramer, Århus V (DK); Jacob Lauwring Andersen, Århus V (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 12/989,895

(22) PCT Filed: Apr. 27, 2009

(86) PCT No.: PCT/DK2009/050099
§ 371 (c)(1),
(2), (4) Date: Mar. 9, 2011

(87) PCT Pub. No.: WO2009/132656
PCT Pub. Date: Nov. 5, 2009

(65) Prior Publication Data
US 2011/0160439 A1    Jun. 30, 2011

(30) Foreign Application Priority Data
Apr. 27, 2008 (DK) .................. 2008 00592

(51) Int. Cl.
*G01N 31/00* (2006.01)
*C07K 14/00* (2006.01)

(52) U.S. Cl. ............ 436/86; 530/350; 530/418; 702/27
(58) Field of Classification Search .................. None
See application file for complete search history.

(56) References Cited

U.S. PATENT DOCUMENTS

| 2007/0264195 A1 | 11/2007 | Nykjaer et al. |
| 2010/0210523 A1 | 8/2010 | Andersen et al. |

FOREIGN PATENT DOCUMENTS

| WO | 2004056385 A2 | 7/2004 |
| WO | 2007100718 A2 | 9/2007 |
| WO | 2008074329 A2 | 6/2008 |
| WO | 2008086452 A2 | 7/2008 |

OTHER PUBLICATIONS

Database UniprotKB Accession No. P23560, Human BDNF protein sequence, created Nov. 1, 1991.
Database UniprotKB Accession No. P29279, Human CTGF protein sequence, created Dec. 1, 1992.
Dipaola E.D. and Richelson E., 1990, Cardiovascular effects of neurotension and some analogues on rats, Eur. J. Pharmacol., 175:279-283.

(Continued)

*Primary Examiner* — Nashaat Nashed
(74) *Attorney, Agent, or Firm* — Mary Catherine Di Nunzio; Stephen G. Kalinchak; Kitae T. Lim

(57) ABSTRACT

The present invention provides a Sortilin crystal and methods for growing said crystal. The invention furthermore provide methods for design of specific ligands based on the crystal structure of Sortilin. The present invention also relates to the preparation and use of such ligands for the preparation of a medicament for the treatment of disease, damage or disorders of the central and peripheral nervous systems.

12 Claims, 247 Drawing Sheets

OTHER PUBLICATIONS

Fiete D. et al., Jan. 9, 2007, N-Linked Oligosaccharides on the Low Density Lipoprotein Receptor Homolog SorLA/LR11 Are Modified with Terminal GalNac-4-SO4 in Kidney and Brain, J. Biol. Chem, 282(3):1873-1881.

He X.-L. and Garcia K.C., May 7, 2004, Structure of Nerve Growth Factor Complexed with the Shared Neurotrophin Receptor 75, Science, 304:870-875.

Jiang M. et al., 2006, Pitavastatin attenuates the PDGF-induced LR11/uPA receptor-mediated migration of smoothe muscle cells, Biochem. Biophys. Res. Comm., 348:1367-1377.

Knotkova, H. et al., Feb. 2008, Capsaicin (TRPV1 Agonist) Therapy for Pain Relief—Farewell or Revival?, Clin. J. Pain, 24(2):142-154.

Muraki K. et al, Jun. 30, 1987, Neurotensin receptors on the rat liver plasma membranes, Biophys. Res. Comm., 145(3):1071-1079.

Paiardini A. and Caputo V., 2008, Insights into the interaction of sortilin with proneurotrophins: A computational approach, Neuropeptides, 42:205-214.

Riedel, I.B. et al, 2002, SorLA, a member of the LDL receptor family, is expressed in the collecting duct of the murine kidney, Histochem. Cell. Biol., 118:183-191.

Rohe, M. S., Aug. 2008, Role of SORLA in the brain and its relevance for Alzheimer disease (Dissertation of Michael Stephan Rohe, pp. 1-110) Retrieved from the Internet, http://www.diss.fu-berlin.de/diss/servlets/MCRFileNodeServlet/FUDISS_derivate_000000004787/DoktorarbeitMichaelRohe.pdf.

Schmidt V. et al, Nov. 9, 2007, SorLA/LR11 Regulates Processing of Amyloid Precursor Protein via Interaction with Adapters GGA and PACS-1, J. Biol. Chem., 282(45):32956-32964.

Westergaard U.B et al, Nov. 26, 2004, Functional Organization of the Sortilin Vps10p Domain, Ther Journal of Biological Chemistry, 279(48):50221-50229.

Ueberham, U., et al., 2003, Connective Tissue Growth Factor in Alzheimer's Disease, Neuroscience, 116(1):1-6.

Ugolini, G. et al, Feb. 20, 2007, The function neutralizing anti-TrkA antibody MNAC13 reduces inflammatory and neuropathic pain, PNAS, 104(8):2985-2990.

Yamauchi R. et al., 2003, Beta-Lactotensin and Neurotensin rapidly reduce serum cholesterol via NT2 receptor, Peptides, 24:1955-1961.

Yumiko M. et al, 1999, Neuronal localization of a novel mosaic apolipoprotein E. receptor, LR11, in rat and human brain, Brain Res., 833:209-215.

Zhao, Z., et al., Nov. 12, 2003, Role of connective tissue growth factor in Beta-amyloid peptide generation, Abstracts of the Annual Meeting of the Society for Neuroscience, Society for Neuroscience, Washington, DC, US:86.10 (Abstract).

Zhao, Z., et al., Sep. 26, 2005, Connective tissue growth factor (CTGF) expression in the brain is a downstream effector of insulin resistance associated promotion of Alzheimer's disease Beta-amyloid neuropathology, Retrieved from the Internet, FASEB Journal http://www.fasebj.org/content/early/2005/12/01/fj.05-4359fje.full.pdf (pp. 1-25).

Zhu Y. and Hui D. Y., 2006, Hypertriglyceridemia in LR11-deficiency mice, FASEB 20:A84.

Bronfman and Fainzilber, 2004, Multi-tasking by the p75 neurotrophin receptor: sortilin things out?, EMBO Reports, 5(9):867-871.

Hampe et al., 2001, The genes for the human VPS10 domain-containing receptors are large and contain many small exons, Human Genet., 108(6):529-536.

Kitabgi P., 2002, Target neurotensin receptors with agonists and antagonists for therapeutic purposes, Curr. Opin. in Drug Discovery & Development, 5(5):764-776.

Mazella et al., 1998, The 100-kDa Neurotensin Receptor is gp95/Sortilin, A Non-G-Protein-coupled Receptor, Journ. of Biol. Chem., 273(41):26273-26276.

Mazella and Vincent, 2006, Functional roles of the NTS2 and NTS3 receptors, Peptides, 27(10):2469-2475.

Munck-Petersen et al., 1999, Propeptide cleavage conditions sortilin/neurotensin receptor-3 for ligand binding, The EMBO Journal, 18(3):595-604.

Nykjaer et al., 2004, Sortilin is essential for proNGF-induced neuronal cell death, Nature, 427(26):843-848.

Pelaprat D., 2006, Interactions between neurotensin receptors and G proteins, Peptides, 27(10):2476-2487.

Quistgaard et al., 2009, Ligands bind to Sortilin in the tunnel of a ten-bladed B-propeller domain, Nature Structural & Molecular Biology, 16(1):96-98.

Vincent et al., 1999, Neurotensin and neurotensin receptors, TIPS, 20:302-309.

Fig. 5

Refinement Statistics

| Refinement stats | sSort-NTS, |
|---|---|
| Reflections | 53737/2862 |
| R-factor | 0.204 |
| Rfree | 0.229 |
| Mean B-factor (Å$^2$) | |
| sSortilin | 30.4 |
| NTS | 57.1 |
| Glycosylations | 49.2 |
| Solvent | 46.9 |
| Geometry | |
| Rmsd Bond-lengths | 0.021 Å |
| Rmsd Bond angles | 1.832° |
| Phi-Psi distribution | |
| Most favoured | 87.0% |
| Additionally allowed | 12.0% |
| Generously allowed | 0.9% |
| Dissallowed | 0.2% |

Ramachandran plot

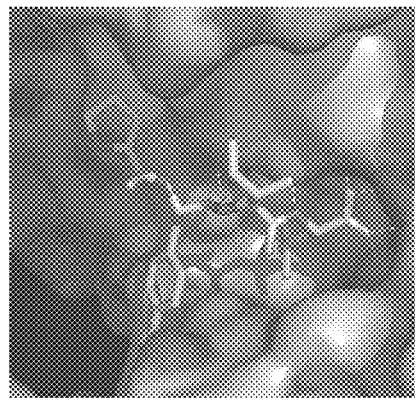
A: 2.0 Å resolution structure with 1.5xNT
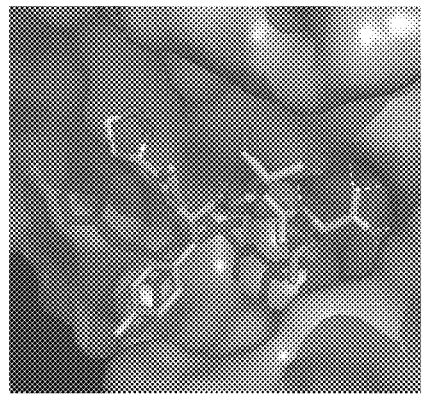
B: 2.64 Å resolution structure with 15xNT
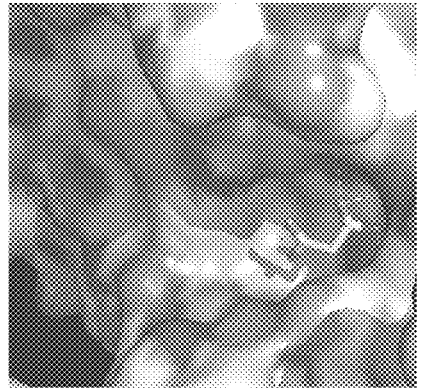
C: 2.8 Å with malonate
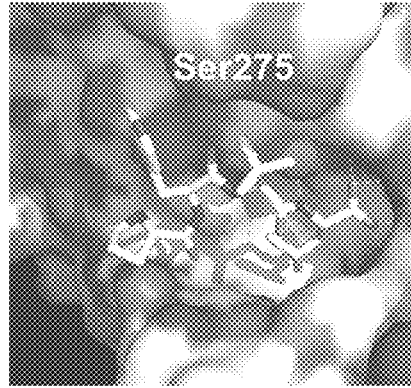
D: 2.6 Å with NT69L (a)
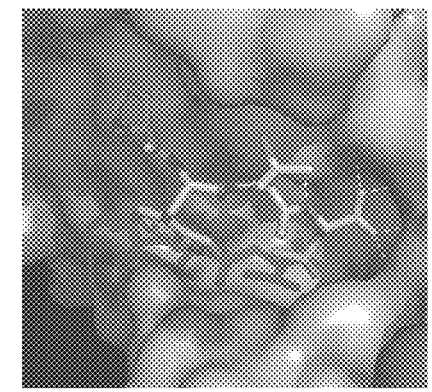
E: 2.6 Å with NT69L (b)
Fig. 13

```
HEADER
COMPND    ----
REMARK    ----                                                    XX-XXX-XX    XXXX
REMARK   3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   3.20
REMARK   3   RESOLUTION RANGE LOW  (ANGSTROMS) :  24.46
REMARK   3   DATA CUTOFF            (SIGMA(F)) :   NONE
REMARK   3   COMPLETENESS FOR RANGE        (%) : 100.00
REMARK   3   NUMBER OF REFLECTIONS             :  22116
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET)  : 0.20457
REMARK   3   R VALUE            (WORKING SET)  : 0.20137
REMARK   3   FREE R VALUE                      : 0.26412
REMARK   3   FREE R VALUE TEST SET SIZE   (%)  :   5.0
REMARK   3   FREE R VALUE TEST SET COUNT       :  1165
REMARK   3
REMARK   3  FIT IN THE HIGHEST RESOLUTION BIN.
REMARK   3   TOTAL NUMBER OF BINS USED           :    20
REMARK   3   BIN RESOLUTION RANGE HIGH           : 3.200
REMARK   3   BIN RESOLUTION RANGE LOW            : 3.282
REMARK   3   REFLECTION IN BIN     (WORKING SET) :  1575
REMARK   3   BIN COMPLETENESS (WORKING+TEST) (%) : 100.00
REMARK   3   BIN R VALUE           (WORKING SET) : 0.300
REMARK   3   BIN FREE R VALUE SET COUNT          :    83
REMARK   3   BIN FREE R VALUE                    : 0.322
REMARK   3
REMARK   3  NUMBER OF NON-HYDROGEN ATOMS USED IN REFINEMENT.
REMARK   3   ALL ATOMS                          :  5349
REMARK   3
REMARK   3  B VALUES.
REMARK   3   FROM WILSON PLOT           (A**2) :  NULL
REMARK   3   MEAN B VALUE     (OVERALL, A**2)  : 50.750
REMARK   3   OVERALL ANISOTROPIC B VALUE.
REMARK   3    B11 (A**2) :  -0.57
REMARK   3    B22 (A**2) :  -0.57
REMARK   3    B33 (A**2) :   1.14
REMARK   3    B12 (A**2) :   0.00
REMARK   3    B13 (A**2) :   0.00
REMARK   3    B23 (A**2) :   0.00
REMARK   3
REMARK   3  ESTIMATED OVERALL COORDINATE ERROR.
REMARK   3   ESU BASED ON R VALUE              (A):   1.787
REMARK   3   ESU BASED ON FREE R VALUE         (A):   0.423
REMARK   3   ESU BASED ON MAXIMUM LIKELIHOOD   (A):   0.366
REMARK   3   ESU FOR B VALUES BASED ON MAXIMUM LIKELIHOOD (A**2): 46.892
REMARK   3
REMARK   3  CORRELATION COEFFICIENTS.
REMARK   3   CORRELATION COEFFICIENT FO-FC      : 0.937
REMARK   3   CORRELATION COEFFICIENT FO-FC FREE : 0.871
REMARK   3
REMARK   3                                                           COUNT       RMS     WEIGHT
REMARK   3  RMS DEVIATIONS FROM IDEAL VALUES            (A).
REMARK   3   BOND LENGTHS REFINED ATOMS                 (A).         5486 ;   0.031 ;   0.022
REMARK   3   BOND ANGLES REFINED ATOMS             (DEGREES).        7441 ;   3.039 ;   1.957
REMARK   3   TORSION ANGLES, PERIOD 1              (DEGREES).         670 ;  13.062 ;   5.000
REMARK   3   TORSION ANGLES, PERIOD 2              (DEGREES).         250 ;  43.178 ;  24.150
REMARK   3   TORSION ANGLES, PERIOD 3              (DEGREES).         890 ;  25.901 ;  15.000
REMARK   3   TORSION ANGLES, PERIOD 4              (DEGREES).          28 ;  21.992 ;  15.000
REMARK   3   CHIRAL-CENTER RESTRAINTS                  (A**3).        824 ;   0.226 ;   0.200
REMARK   3   GENERAL PLANES REFINED ATOMS                 (A).       4135 ;   0.009 ;   0.020
REMARK   3   NON-BONDED CONTACTS REFINED ATOMS            (A).       3221 ;   0.359 ;   0.200
REMARK   3   NON-BONDED TORSION REFINED ATOMS             (A).       3741 ;   0.362 ;   0.200
REMARK   3   H-BOND (X...Y) REFINED ATOMS                 (A).        270 ;   0.302 ;   0.200
REMARK   3   SYMMETRY VDW REFINED ATOMS                   (A).         59 ;   0.322 ;   0.200
REMARK   3   SYMMETRY H-BOND REFINED ATOMS                (A).          2 ;   0.193 ;   0.200
REMARK   3
REMARK   3                                                           COUNT       RMS     WEIGHT
REMARK   3  ISOTROPIC THERMAL FACTOR RESTRAINTS.
REMARK   3   MAIN-CHAIN BOND REFINED ATOMS             (A**2).       3412 ;   1.172 ;   1.500
REMARK   3   MAIN-CHAIN ANGLE REFINED ATOMS            (A**2).       5367 ;   2.124 ;   2.000
REMARK   3   SIDE-CHAIN BOND REFINED ATOMS             (A**2).       2379 ;   2.880 ;   3.000
REMARK   3   SIDE-CHAIN ANGLE REFINED ATOMS            (A**2).       2074 ;   4.615 ;   4.500
REMARK   3
REMARK   3  NCS RESTRAINTS STATISTICS
REMARK   3   NUMBER OF NCS GROUPS : NULL
REMARK   3
REMARK   3  TLS DETAILS
REMARK   3   NUMBER OF TLS GROUPS  :     1
REMARK   3   ATOM RECORD CONTAINS RESIDUAL B FACTORS ONLY
REMARK   3
REMARK   3   TLS GROUP :     1
REMARK   3    NUMBER OF COMPONENTS GROUP :     1
REMARK   3    COMPONENTS        C SSSEQI  TO  C SSSEQI
REMARK   3    RESIDUE RANGE :   A    11        A   672
REMARK   3    ORIGIN FOR THE GROUP (A):  22.0740   41.3390   26.1200
REMARK   3    T TENSOR
REMARK   3      T11:  -0.9170 T22:  -1.0186
REMARK   3      T33:  -0.6032 T12:  -0.1824
REMARK   3      T13:   0.0348 T23:  -0.1947
REMARK   3    L TENSOR
REMARK   3      L11:   3.9426 L22:   2.7211
REMARK   3      L33:  -.8153 L12:   2.1640
REMARK   3      L13:   0.4737 L23:   1.0744
REMARK   3    S TENSOR
REMARK   3      S11:  -0.5533 S12:  -0.2201 S13:  -0.4716
REMARK   3      S21:  -0.1660 S22:   0.7655 S23:  -0.4610
REMARK   3      S31:  -0.2981 S32:   0.0021 S33:  -0.2152
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :  1.20
REMARK   3   ION PROBE RADIUS   :  0.80
REMARK   3   SHRINKAGE RADIUS   :  0.80
REMARK   3
REMARK   3  OTHER REFINEMENT REMARKS:
REMARK   3   HYDROGENS HAVE BEEN ADDED IN THE RIDING POSITIONS
SSBOND   1 CYS A  479    CYS A    9
```

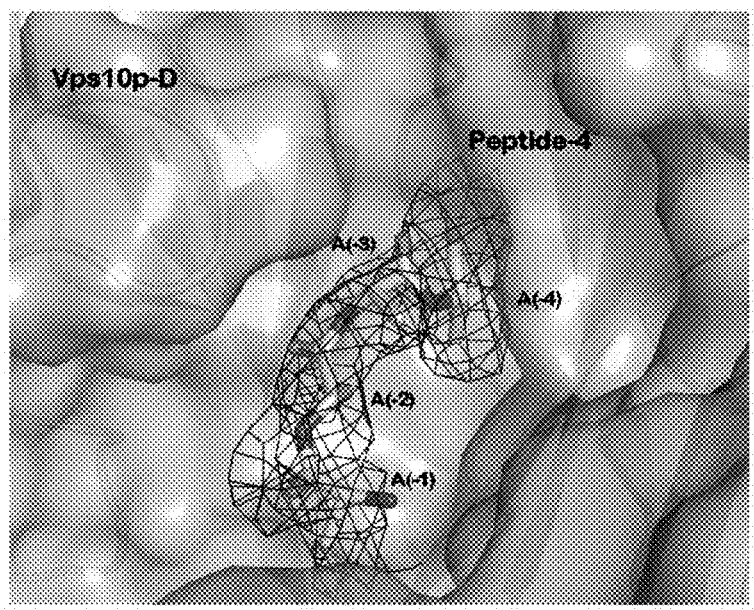
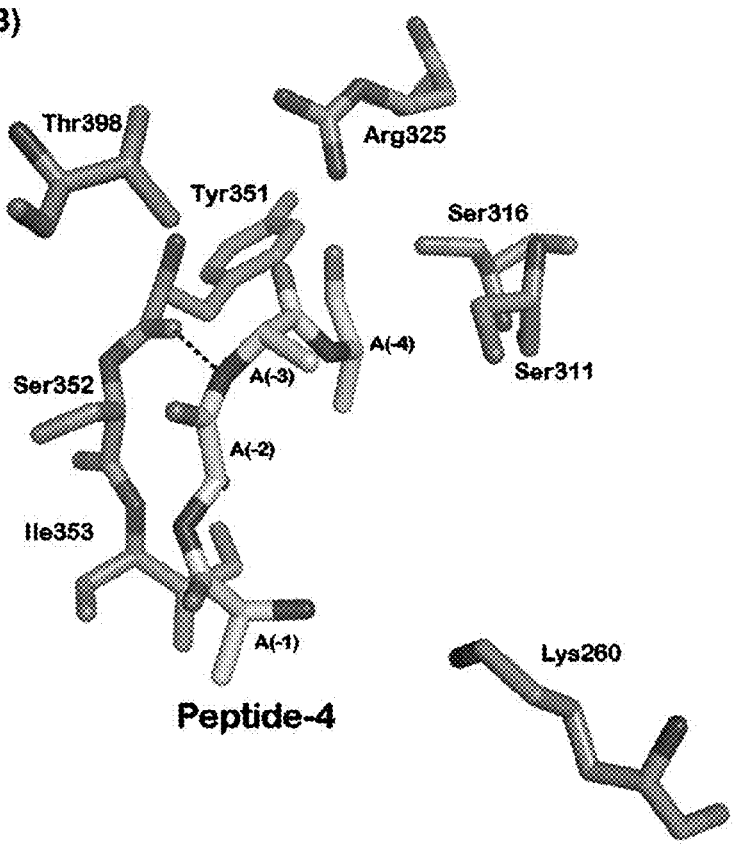
Fig. 25

Competition for binding to immobilized sSortilin between 100 nM GST tagged YIL (GST-YIL) and the specified peptides.
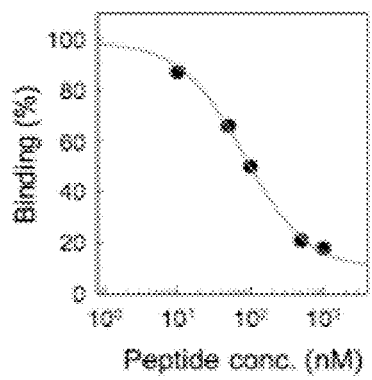
Peptide: NT
EC50: 81nM
Sequence: pELYENKPRRPYIL
Structure:
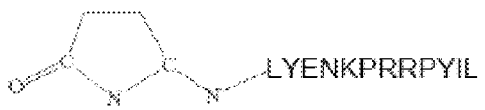
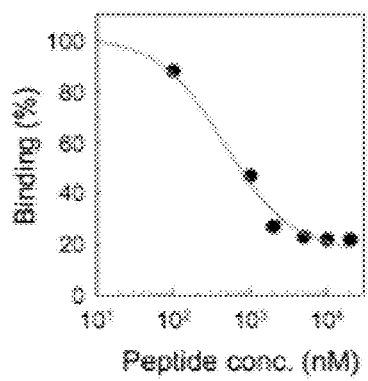
Peptide: NT8-13
EC50: 460nM
Sequence: RRPYIL
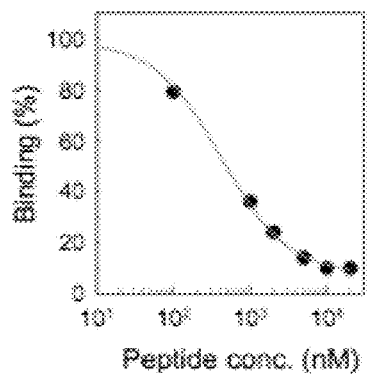
Peptide: RRPYI(chg)
EC50: 420nM
Sequence: RRPYI-cyclo-hexyl-glycine
Structure:
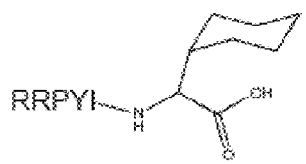
Fig. 26

Competition for binding to immobilized sSortilin between 100 nM GST tagged YIL (GST-YIL) and the specified peptides.
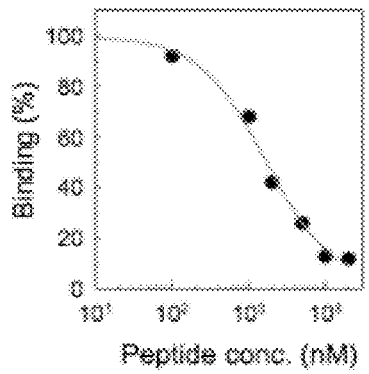
Peptide: iodoYIL
EC50: 1675 nM
Sequence: iodoYIL
Structure:
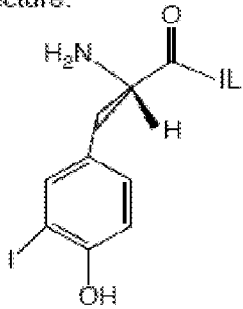
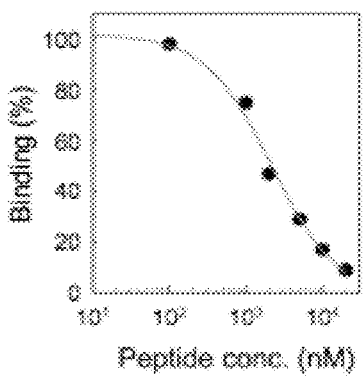
Peptide: QIL
EC50: 1700 nM
Sequence: QIL
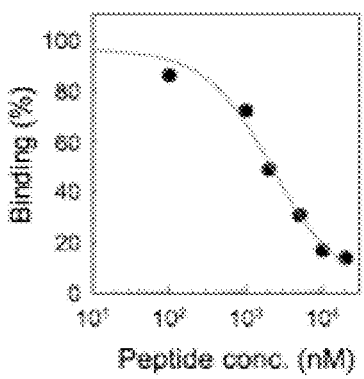
Peptide: YCL
EC50: 2230 nM
Sequence: YCL
Fig. 26, continued Competition for binding to immobilized sSortilin between 100 nM GST tagged YIL (GST-YIL) and the specified peptides.
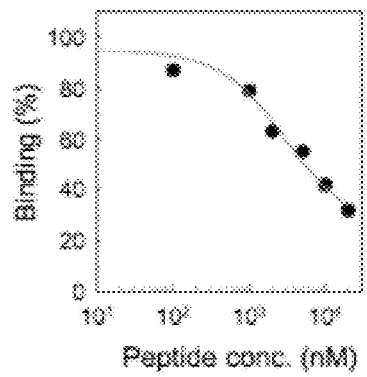
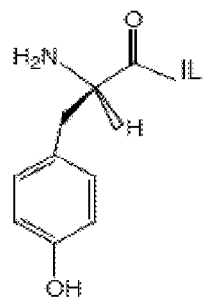
Peptide: dYIL
EC50: 3000 nM
Sequence: dYIL
Structure:
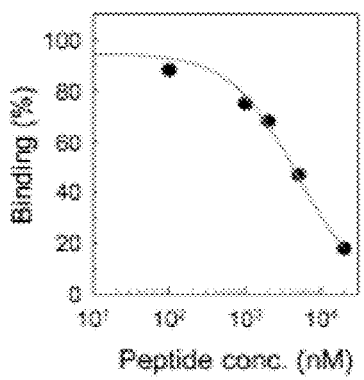
Peptide: YHL
EC50: 4580 nM
Sequence: YHL
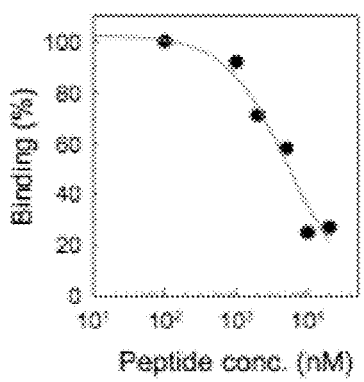
Peptide: NT69L
EC50: 5100 nM
Sequence:
Structure:
Fig. 26, continued

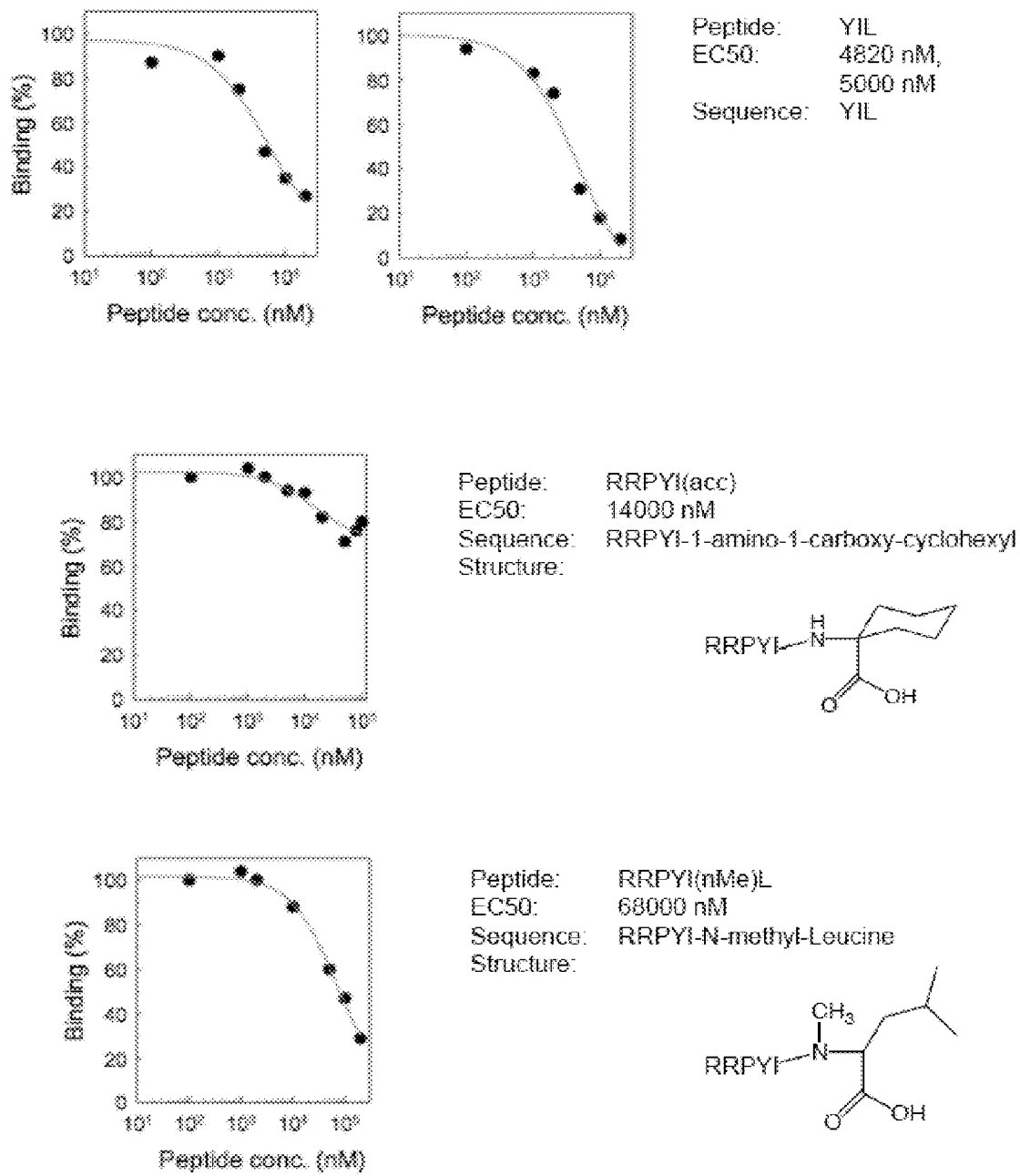
Fig. 26, continued

SEQUENCE LISTING

```
<160> NUMBER OF SEQ ID NOS: 52

<210> SEQ ID NO 1
<211> LENGTH: 831
<212> TYPE: PRT
<213> ORGANISM: Homo sapiens
<220> FEATURE:
<221> NAME/KEY: SIGNAL
<222> LOCATION: (1)..(33)
<223> OTHER INFORMATION: Sortilin Signal Peptide
<220> FEATURE:
<221> NAME/KEY: PROPEP
<222> LOCATION: (34)..(77)
<223> OTHER INFORMATION: Sortilin propeptide
<220> FEATURE:
<221> NAME/KEY: MISC_FEATURE
<222> LOCATION: (78)..(755)
<223> OTHER INFORMATION: Extracellular part of Sortilin (sSortilin)
<220> FEATURE:
<221> NAME/KEY: TRANSMEM
<222> LOCATION: (756)..(778)
<223> OTHER INFORMATION: Membrane spanning part of Sortilin
<220> FEATURE:
<221> NAME/KEY: MISC_FEATURE
<222> LOCATION: (779)..(831)
<223> OTHER INFORMATION: Intracellular (cytoplasmic) domain of Sortilin

<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
                100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
        130                 135                 140
```

```
Tyr Arg Ser Glu Asp Tyr Gly Lys Asn Phe Lys Asp Ile Thr Asp Leu
145                 150                 155                 160
Ile Asn Asn Thr Phe Ile Arg Thr Glu Phe Gly Met Ala Ile Gly Pro
            165                 170                 175
Glu Asn Ser Gly Lys Val Val Leu Thr Ala Glu Val Ser Gly Gly Ser
        180                 185                 190
Arg Gly Gly Arg Ile Phe Arg Ser Ser Asp Phe Ala Lys Asn Phe Val
    195                 200                 205
Gln Thr Asp Leu Pro Phe His Pro Leu Thr Gln Met Met Tyr Ser Pro
210                 215                 220
Gln Asn Ser Asp Tyr Leu Leu Ala Leu Ser Thr Glu Asn Gly Leu Trp
225                 230                 235                 240
Val Ser Lys Asn Phe Gly Gly Lys Trp Glu Glu Ile His Lys Ala Val
                245                 250                 255
Cys Leu Ala Lys Trp Gly Ser Asp Asn Thr Ile Phe Phe Thr Thr Tyr
            260                 265                 270
Ala Asn Gly Ser Cys Lys Ala Asp Leu Gly Ala Leu Glu Leu Trp Arg
        275                 280                 285
Thr Ser Asp Leu Gly Lys Ser Phe Lys Thr Ile Gly Val Lys Ile Tyr
    290                 295                 300
Ser Phe Gly Leu Gly Gly Arg Phe Leu Phe Ala Ser Val Met Ala Asp
305                 310                 315                 320
Lys Asp Thr Thr Arg Arg Ile His Val Ser Thr Asp Gln Gly Asp Thr
                325                 330                 335
Trp Ser Met Ala Gln Leu Pro Ser Val Gly Gln Glu Gln Phe Tyr Ser
            340                 345                 350
Ile Leu Ala Ala Asn Asp Asp Met Val Phe Met His Val Asp Glu Pro
        355                 360                 365
Gly Asp Thr Gly Phe Gly Thr Ile Phe Thr Ser Asp Asp Arg Gly Ile
    370                 375                 380
Val Tyr Ser Lys Ser Leu Asp Arg His Leu Tyr Thr Thr Thr Gly Gly
385                 390                 395                 400
Glu Thr Asp Phe Thr Asn Val Thr Ser Leu Arg Gly Val Tyr Ile Thr
                405                 410                 415
Ser Val Leu Ser Glu Asp Asn Ser Ile Gln Thr Met Ile Thr Phe Asp
            420                 425                 430
Gln Gly Gly Arg Trp Thr His Leu Arg Lys Pro Glu Asn Ser Glu Cys
        435                 440                 445
Asp Ala Thr Ala Lys Asn Lys Asn Glu Cys Ser Leu His Ile His Ala
    450                 455                 460
Ser Tyr Ser Ile Ser Gln Lys Leu Asn Val Pro Met Ala Pro Leu Ser
465                 470                 475                 480
Glu Pro Asn Ala Val Gly Ile Val Ile Ala His Gly Ser Val Gly Asp
                485                 490                 495
Ala Ile Ser Val Met Val Pro Asp Val Tyr Ile Ser Asp Asp Gly Gly
            500                 505                 510
Tyr Ser Trp Thr Lys Met Leu Glu Gly Pro His Tyr Tyr Thr Ile Leu
        515                 520                 525
Asp Ser Gly Gly Ile Ile Val Ala Ile Glu His Ser Ser Arg Pro Ile
    530                 535                 540
Asn Val Ile Lys Phe Ser Thr Asp Glu Gly Gln Cys Trp Gln Thr Tyr
545                 550                 555                 560
Thr Phe Thr Arg Asp Pro Ile Tyr Phe Thr Gly Leu Ala Ser Glu Pro
```

```
                     565                 570                 575
Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
            595                 600                 605

Glu Arg Asn Cys Glu Glu Lys Asp Tyr Thr Ile Trp Leu Ala His Ser
            610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
                660                 665                 670

Phe Leu Cys Asp Phe Gly Tyr Tyr Arg Pro Glu Asn Asp Ser Lys Cys
            675                 680                 685

Val Glu Gln Pro Glu Leu Lys Gly His Asp Leu Glu Phe Cys Leu Tyr
            690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
                740                 745                 750

Lys Ser Asn Ser Val Pro Ile Ile Leu Ala Ile Val Gly Leu Met Leu
            755                 760                 765

Val Thr Val Val Ala Gly Val Leu Ile Val Lys Lys Tyr Val Cys Gly
            770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
                820                 825                 830

<210> SEQ ID NO 2
<211> LENGTH: 2214
<212> TYPE: PRT
<213> ORGANISM: Homo sapiens
<220> FEATURE:
<221> NAME/KEY: SIGNAL
<222> LOCATION: (1)..(28)
<223> OTHER INFORMATION: Signal peptide of SorLA
<220> FEATURE:
<221> NAME/KEY: PROPEP
<222> LOCATION: (29)..(81)
<223> OTHER INFORMATION: Propeptide of SorLA

<400> SEQUENCE: 2

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80
```

-continued

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Leu Gly Phe Asp Arg
    210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
        435                 440                 445

Thr Trp Glu Phe Leu Gln Ala Pro Ala Phe Thr Gly Tyr Gly Glu Lys
    450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys

```
                500             505             510
Asn Leu Ala Ser Lys Thr Asn Val Tyr Ile Ser Ser Ser Ala Gly Ala
            515                 520             525

Arg Trp Arg Glu Ala Leu Pro Gly Pro His Tyr Tyr Thr Trp Gly Asp
            530             535                 540

His Gly Gly Ile Ile Thr Ala Ile Ala Gln Gly Met Glu Thr Asn Glu
545                         550                 555             560

Leu Lys Tyr Ser Thr Asn Glu Gly Glu Thr Trp Lys Thr Phe Ile Phe
                    565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
            595                 600                 605

Ser Trp Leu Ile Leu Gln Val Asn Ala Thr Asp Ala Leu Gly Val Pro
            610                 615                 620

Cys Thr Glu Asn Asp Tyr Lys Leu Trp Ser Pro Ser Asp Glu Arg Gly
625                         630                 635                 640

Asn Glu Cys Leu Leu Gly His Lys Thr Val Phe Lys Arg Arg Thr Pro
                    645                 650                 655

His Ala Thr Cys Phe Asn Gly Glu Asp Phe Asp Arg Pro Val Val Val
                660                 665                 670

Ser Asn Cys Ser Cys Thr Arg Glu Asp Tyr Glu Cys Asp Phe Gly Phe
            675                 680                 685

Lys Met Ser Glu Asp Leu Ser Leu Glu Val Cys Val Pro Asp Pro Glu
            690                 695                 700

Phe Ser Gly Lys Ser Tyr Ser Pro Val Pro Cys Pro Val Gly Ser
705                 710                 715                 720

Thr Tyr Arg Arg Thr Arg Gly Tyr Arg Lys Ile Ser Gly Asp Thr Cys
                    725                 730                 735

Ser Gly Gly Asp Val Glu Ala Arg Leu Glu Gly Glu Leu Val Pro Cys
                740                 745                 750

Pro Leu Ala Glu Glu Asn Glu Phe Ile Leu Tyr Ala Val Arg Lys Ser
            755                 760                 765

Ile Tyr Arg Tyr Asp Leu Ala Ser Gly Ala Thr Glu Gln Leu Pro Leu
            770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                    805                 810                 815

Leu Asn Gly Ser Thr Gly Gln Glu Val Ile Ile Asn Ser Gly Leu Glu
                820                 825                 830

Thr Val Glu Ala Leu Ala Phe Glu Pro Leu Ser Gln Leu Leu Tyr Trp
            835                 840                 845

Val Asp Ala Gly Phe Lys Lys Ile Glu Val Ala Asn Pro Asp Gly Asp
            850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                    885                 890                 895

Asp Leu Lys Pro Gly Ile Tyr Arg Ser Asn Met Asp Gly Ser Ala Ala
            900                 905                 910

Tyr His Leu Val Ser Glu Asp Val Lys Trp Pro Asn Gly Ile Ser Val
            915                 920                 925
```

-continued

Asp Asp Gln Trp Ile Tyr Trp Thr Asp Ala Tyr Leu Glu Cys Ile Glu
930              935              940

Arg Ile Thr Phe Ser Gly Gln Gln Arg Ser Val Ile Leu Asp Asn Leu
945              950              955              960

Pro His Pro Tyr Ala Ile Ala Val Phe Lys Asn Glu Ile Tyr Trp Asp
            965              970              975

Asp Trp Ser Gln Leu Ser Ile Phe Arg Ala Ser Lys Tyr Ser Gly Ser
            980              985              990

Gln Met Glu Ile Leu Ala Asn Gln Leu Thr Gly Leu Met Asp Met Lys
        995              1000             1005

Ile Phe Tyr Lys Gly Lys Asn Thr Gly Ser Asn Ala Cys Val Pro
    1010             1015             1020

Arg Pro Cys Ser Leu Leu Cys Leu Pro Lys Ala Asn Asn Ser Arg
    1025             1030             1035

Ser Cys Arg Cys Pro Glu Asp Val Ser Ser Val Leu Pro Ser
    1040             1045             1050

Gly Asp Leu Met Cys Asp Cys Pro Gln Gly Tyr Gln Leu Lys Asn
    1055             1060             1065

Asn Thr Cys Val Lys Glu Glu Asn Thr Cys Leu Arg Asn Gln Tyr
    1070             1075             1080

Arg Cys Ser Asn Gly Asn Cys Ile Asn Ser Ile Trp Trp Cys Asp
    1085             1090             1095

Phe Asp Asn Asp Cys Gly Asp Met Ser Asp Glu Arg Asn Cys Pro
    1100             1105             1110

Thr Thr Ile Cys Asp Leu Asp Thr Gln Phe Arg Cys Gln Glu Ser
    1115             1120             1125

Gly Thr Cys Ile Pro Leu Ser Tyr Lys Cys Asp Leu Glu Asp Asp
    1130             1135             1140

Cys Gly Asp Asn Ser Asp Glu Ser His Cys Glu Met His Gln Cys
    1145             1150             1155

Arg Ser Asp Glu Tyr Asn Cys Ser Ser Gly Met Cys Ile Arg Ser
    1160             1165             1170

Ser Trp Val Cys Asp Gly Asp Asn Asp Cys Arg Asp Trp Ser Asp
    1175             1180             1185

Glu Ala Asn Cys Thr Ala Ile Tyr His Thr Cys Glu Ala Ser Asn
    1190             1195             1200

Phe Gln Cys Arg Asn Gly His Cys Ile Pro Gln Arg Trp Ala Cys
    1205             1210             1215

Asp Gly Asp Thr Asp Cys Gln Asp Gly Ser Asp Glu Asp Pro Val
    1220             1225             1230

Asn Cys Glu Lys Lys Cys Asn Gly Phe Arg Cys Pro Asn Gly Thr
    1235             1240             1245

Cys Ile Pro Ser Ser Lys His Cys Asp Gly Leu Arg Asp Cys Ser
    1250             1255             1260

Asp Gly Ser Asp Glu Gln His Cys Glu Pro Leu Cys Thr His Phe
    1265             1270             1275

Met Asp Phe Val Cys Lys Asn Arg Gln Gln Cys Leu Phe His Ser
    1280             1285             1290

Met Val Cys Asp Gly Ile Ile Gln Cys Arg Asp Gly Ser Asp Glu
    1295             1300             1305

Asp Ala Ala Phe Ala Gly Cys Ser Gln Asp Pro Glu Phe His Lys
    1310             1315             1320

Val Cys Asp Glu Phe Gly Phe Gln Cys Gln Asn Gly Val Cys Ile
    1325             1330             1335

```
Ser Leu Ile Trp Lys Cys Asp Gly Met Asp Asp Cys Gly Asp Tyr
    1340            1345                1350
Ser Asp Glu Ala Asn Cys Glu Asn Pro Thr Glu Ala Pro Asn Cys
    1355            1360                1365
Ser Arg Tyr Phe Gln Phe Arg Cys Glu Asn Gly His Cys Ile Pro
    1370            1375                1380
Asn Arg Trp Lys Cys Asp Arg Glu Asn Asp Cys Gly Asp Trp Ser
    1385            1390                1395
Asp Glu Lys Asp Cys Gly Asp Ser His Ile Leu Pro Phe Ser Thr
    1400            1405                1410
Pro Gly Pro Ser Thr Cys Leu Pro Asn Tyr Tyr Arg Cys Ser Ser
    1415            1420                1425
Gly Thr Cys Val Met Asp Thr Trp Val Cys Asp Gly Tyr Arg Asp
    1430            1435                1440
Cys Ala Asp Gly Ser Asp Glu Glu Ala Cys Pro Leu Leu Ala Asn
    1445            1450                1455
Val Thr Ala Ala Ser Thr Pro Thr Gln Leu Gly Arg Cys Asp Arg
    1460            1465                1470
Phe Glu Phe Glu Cys His Gln Pro Lys Thr Cys Ile Pro Asn Trp
    1475            1480                1485
Lys Arg Cys Asp Gly His Gln Asp Cys Gln Asp Gly Arg Asp Glu
    1490            1495                1500
Ala Asn Cys Pro Thr His Ser Thr Leu Thr Cys Met Ser Arg Glu
    1505            1510                1515
Phe Gln Cys Glu Asp Gly Glu Ala Cys Ile Val Leu Ser Glu Arg
    1520            1525                1530
Cys Asp Gly Phe Leu Asp Cys Ser Asp Glu Ser Asp Glu Lys Ala
    1535            1540                1545
Cys Ser Asp Glu Leu Thr Val Tyr Lys Val Gln Asn Leu Gln Trp
    1550            1555                1560
Thr Ala Asp Phe Ser Gly Asp Val Thr Leu Thr Trp Met Arg Pro
    1565            1570                1575
Lys Lys Met Pro Ser Ala Ser Cys Val Tyr Asn Val Tyr Tyr Arg
    1580            1585                1590
Val Val Gly Glu Ser Ile Trp Lys Thr Leu Glu Thr His Ser Asn
    1595            1600                1605
Lys Thr Asn Thr Val Leu Lys Val Leu Lys Pro Asp Thr Thr Tyr
    1610            1615                1620
Gln Val Lys Val Gln Val Gln Cys Leu Ser Lys Ala His Asn Thr
    1625            1630                1635
Asn Asp Phe Val Thr Leu Arg Thr Pro Glu Gly Leu Pro Asp Ala
    1640            1645                1650
Pro Arg Asn Leu Gln Leu Ser Leu Pro Arg Glu Ala Glu Gly Val
    1655            1660                1665
Ile Val Gly His Trp Ala Pro Pro Ile His Thr His Gly Leu Ile
    1670            1675                1680
Arg Glu Tyr Ile Val Glu Tyr Ser Arg Ser Gly Ser Lys Met Trp
    1685            1690                1695
Ala Ser Gln Arg Ala Ala Ser Asn Phe Thr Glu Ile Lys Asn Leu
    1700            1705                1710
Leu Val Asn Thr Leu Tyr Thr Val Arg Val Ala Ala Val Thr Ser
    1715            1720                1725
Arg Gly Ile Gly Asn Trp Ser Asp Ser Lys Ser Ile Thr Thr Ile
```

```
                     1730                1735                1740

Lys  Gly  Lys  Val  Ile  Pro  Pro  Asp  Ile  His  Ile  Asp  Ser  Tyr
     1745                1750                1755

Gly  Glu  Asn  Tyr  Leu  Ser  Phe  Thr  Leu  Thr  Met  Glu  Ser  Asp  Ile
     1760                1765                1770

Lys  Val  Asn  Gly  Tyr  Val  Val  Asn  Leu  Phe  Trp  Ala  Phe  Asp  Thr
     1775                1780                1785

His  Lys  Gln  Glu  Arg  Arg  Thr  Leu  Asn  Phe  Arg  Gly  Ser  Ile  Leu
     1790                1795                1800

Ser  His  Lys  Val  Gly  Asn  Leu  Thr  Ala  His  Thr  Ser  Tyr  Glu  Ile
     1805                1810                1815

Ser  Ala  Trp  Ala  Lys  Thr  Asp  Leu  Gly  Asp  Ser  Pro  Leu  Ala  Phe
     1820                1825                1830

Glu  His  Val  Met  Thr  Arg  Gly  Val  Arg  Pro  Ala  Pro  Ser  Leu
     1835                1840                1845

Lys  Ala  Lys  Ala  Ile  Asn  Gln  Thr  Ala  Val  Glu  Cys  Thr  Trp  Thr
     1850                1855                1860

Gly  Pro  Arg  Asn  Val  Val  Tyr  Gly  Ile  Phe  Tyr  Ala  Thr  Ser  Phe
     1865                1870                1875

Leu  Asp  Leu  Tyr  Arg  Asn  Pro  Lys  Ser  Leu  Thr  Thr  Ser  Leu  His
     1880                1885                1890

Asn  Lys  Thr  Val  Ile  Val  Ser  Lys  Asp  Glu  Gln  Tyr  Leu  Phe  Leu
     1895                1900                1905

Val  Arg  Val  Val  Val  Pro  Tyr  Gln  Gly  Pro  Ser  Ser  Asp  Tyr  Val
     1910                1915                1920

Val  Val  Lys  Met  Ile  Pro  Asp  Ser  Arg  Leu  Pro  Pro  Arg  His  Leu
     1925                1930                1935

His  Val  Val  His  Thr  Gly  Lys  Thr  Ser  Val  Val  Ile  Lys  Trp  Glu
     1940                1945                1950

Ser  Pro  Tyr  Asp  Ser  Pro  Asp  Gln  Asp  Leu  Leu  Tyr  Ala  Ile  Ala
     1955                1960                1965

Val  Lys  Asp  Leu  Ile  Arg  Lys  Thr  Asp  Arg  Ser  Tyr  Lys  Val  Lys
     1970                1975                1980

Ser  Arg  Asn  Ser  Thr  Val  Glu  Tyr  Thr  Leu  Asn  Lys  Leu  Glu  Pro
     1985                1990                1995

Gly  Gly  Lys  Tyr  His  Ile  Ile  Val  Gln  Leu  Gly  Asn  Met  Ser  Lys
     2000                2005                2010

Asp  Ser  Ser  Ile  Lys  Ile  Thr  Thr  Val  Ser  Leu  Ser  Ala  Pro  Asp
     2015                2020                2025

Ala  Leu  Lys  Ile  Ile  Thr  Glu  Asn  Asp  His  Val  Leu  Leu  Phe  Trp
     2030                2035                2040

Lys  Ser  Leu  Ala  Leu  Lys  Glu  Lys  His  Phe  Asn  Glu  Ser  Arg  Gly
     2045                2050                2055

Tyr  Glu  Ile  His  Met  Phe  Asp  Ser  Ala  Met  Asn  Ile  Thr  Ala  Tyr
     2060                2065                2070

Leu  Gly  Asn  Thr  Thr  Asp  Asn  Phe  Phe  Lys  Ile  Ser  Asn  Leu  Lys
     2075                2080                2085

Met  Gly  His  Asn  Tyr  Thr  Phe  Thr  Val  Gln  Ala  Arg  Cys  Leu  Phe
     2090                2095                2100

Gly  Asn  Gln  Ile  Cys  Gly  Glu  Pro  Ala  Ile  Leu  Leu  Tyr  Asp  Glu
     2105                2110                2115

Leu  Gly  Ser  Gly  Ala  Asp  Ala  Ser  Ala  Thr  Gln  Ala  Ala  Arg  Ser
     2120                2125                2130
```

-continued

```
Thr Asp Val Ala Ala Val Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210

<210> SEQ ID NO 3
<211> LENGTH: 1168
<212> TYPE: PRT
<213> ORGANISM: Homo sapiens

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Pro His Pro Ser Ser Ala Pro Arg
            35                  40                  45

Ser Ala Ser Thr Pro Arg Gly Phe Ser His Gln Gly Arg Pro Gly Arg
    50                  55                          60

Ala Pro Ala Thr Pro Leu Pro Leu Val Val Arg Pro Leu Phe Ser Val
65                  70                      75                  80

Ala Pro Gly Asp Arg Ala Leu Ser Leu Glu Arg Ala Arg Gly Thr Gly
                85                  90                  95

Ala Ser Met Ala Val Ala Ala Arg Ser Gly Arg Arg Arg Ser Gly
                100                 105                 110

Ala Asp Gln Glu Lys Ala Glu Arg Gly Glu Gly Ala Ser Arg Ser Pro
                115                 120                 125

Arg Gly Val Leu Arg Asp Gly Gly Gln Gln Glu Pro Gly Thr Arg Glu
    130                 135                     140

Arg Asp Pro Asp Lys Ala Thr Arg Phe Arg Met Glu Glu Leu Arg Leu
145                 150                 155                 160

Thr Ser Thr Thr Phe Ala Leu Thr Gly Asp Ser Ala His Asn Gln Ala
                165                 170                 175

Met Val His Trp Ser Gly His Asn Ser Ser Val Ile Leu Ile Leu Thr
                180                 185                 190

Lys Leu Tyr Asp Tyr Asn Leu Gly Ser Ile Thr Glu Ser Ser Leu Trp
    195                 200                     205

Arg Ser Thr Asp Tyr Gly Thr Thr Tyr Glu Lys Leu Asn Asp Lys Val
    210                 215                     220

Gly Leu Lys Thr Ile Leu Gly Tyr Leu Tyr Val Cys Pro Thr Asn Lys
225                 230                 235                 240

Arg Lys Ile Met Leu Leu Thr Asp Pro Glu Ile Glu Ser Ser Leu Leu
                245                 250                 255

Ile Ser Ser Asp Glu Gly Ala Thr Tyr Gln Lys Tyr Arg Leu Asn Phe
                260                 265                 270

Tyr Ile Gln Ser Leu Leu Phe His Pro Lys Gln Glu Asp Trp Ile Leu
    275                 280                     285
```

```
Ala Tyr Ser Gln Asp Gln Lys Leu Tyr Ser Ser Ala Glu Phe Gly Arg
    290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
            340                 345                 350
Cys Thr Glu Ala Asn Arg Asn Gln Pro Phe Pro Gly Tyr Ile Asp Pro
        355                 360                 365
Asp Ser Leu Ile Val Gln Asp His Tyr Val Phe Val Gln Leu Thr Ser
    370                 375                 380
Gly Gly Arg Pro His Tyr Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
            420                 425                 430
Asn Asp Thr Tyr Asn Leu Tyr Ile Ser Asp Thr Arg Gly Val Tyr Phe
        435                 440                 445
Thr Leu Ala Leu Glu Asn Val Gln Ser Ser Arg Gly Pro Glu Gly Asn
    450                 455                 460
Ile Met Ile Asp Leu Tyr Glu Val Ala Gly Ile Lys Gly Met Phe Leu
465                 470                 475                 480
Ala Asn Lys Lys Ile Asp Tyr Gln Val Lys Thr Phe Ile Thr Tyr Asn
                485                 490                 495
Lys Gly Arg Asp Trp Arg Leu Leu Gln Ala Pro Asp Thr Asp Leu Arg
            500                 505                 510
Gly Asp Pro Val His Cys Leu Leu Pro Tyr Cys Ser Leu His Leu His
        515                 520                 525
Leu Lys Val Ser Glu Asn Pro Tyr Thr Ser Gly Ile Ile Ala Ser Lys
    530                 535                 540
Asp Thr Ala Pro Ser Ile Ile Val Ala Ser Gly Asn Ile Gly Ser Glu
545                 550                 555                 560
Leu Ser Asp Thr Asp Ile Ser Met Phe Val Ser Ser Asp Ala Gly Asn
                565                 570                 575
Thr Trp Arg Gln Ile Phe Glu Glu His Ser Val Leu Tyr Leu Asp
            580                 585                 590
Gln Gly Gly Val Leu Val Ala Met Lys His Thr Ser Leu Pro Ile Arg
        595                 600                 605
His Leu Trp Leu Ser Phe Asp Glu Gly Arg Ser Trp Ser Lys Tyr Ser
    610                 615                 620
Phe Thr Ser Ile Pro Leu Phe Val Asp Gly Val Leu Gly Glu Pro Gly
625                 630                 635                 640
Glu Glu Thr Leu Ile Met Thr Val Phe Gly His Phe Ser His Arg Ser
                645                 650                 655
Glu Trp Gln Leu Val Lys Val Asp Tyr Lys Ser Ile Phe Asp Arg Arg
            660                 665                 670
Cys Ala Glu Glu Asp Tyr Arg Pro Trp Gln Leu His Ser Gln Gly Glu
        675                 680                 685
Ala Cys Ile Met Gly Ala Lys Arg Ile Tyr Lys Arg Lys Ser Glu
    690                 695                 700
Arg Lys Cys Met Gln Gly Lys Tyr Ala Gly Ala Met Glu Ser Glu Pro
705                 710                 715                 720
```

```
Cys Val Cys Thr Glu Ala Asp Phe Asp Cys Asp Tyr Gly Tyr Glu Arg
                725                 730                 735

His Ser Asn Gly Gln Cys Leu Pro Ala Phe Trp Phe Asn Pro Ser Ser
            740                 745                 750

Leu Ser Lys Asp Cys Ser Leu Gly Gln Ser Tyr Leu Asn Ser Thr Gly
            755                 760                 765

Tyr Arg Lys Val Val Ser Asn Asn Cys Thr Asp Gly Val Arg Glu Gln
        770                 775                 780

Tyr Thr Ala Lys Pro Gln Lys Cys Pro Gly Lys Ala Pro Arg Gly Leu
785                 790                 795                 800

Arg Ile Val Thr Ala Asp Gly Lys Leu Thr Ala Glu Gln Gly His Asn
                805                 810                 815

Val Thr Leu Met Val Gln Leu Glu Glu Gly Asp Val Gln Arg Thr Leu
                820                 825                 830

Ile Gln Val Asp Phe Gly Asp Gly Ile Ala Val Ser Tyr Val Asn Leu
                835                 840                 845

Ser Ser Met Glu Asp Gly Ile Lys His Val Tyr Gln Asn Val Gly Ile
        850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
                900                 905                 910

Leu Trp Pro Ser Gln Val Gly Thr Leu Thr Tyr Val Trp Trp Tyr Gly
            915                 920                 925

Asn Asn Thr Glu Pro Leu Ile Thr Leu Glu Gly Ser Ile Ser Phe Arg
        930                 935                 940

Phe Thr Ser Glu Gly Met Asn Thr Ile Thr Val Gln Val Ser Ala Gly
945                 950                 955                 960

Asn Ala Ile Leu Gln Asp Thr Lys Thr Ile Ala Val Tyr Glu Glu Phe
                965                 970                 975

Arg Ser Leu Arg Leu Ser Phe Ser Pro Asn Leu Asp Asp Tyr Asn Pro
            980                 985                 990

Asp Ile Pro Glu Trp Arg Arg Asp Ile Gly Arg Val Ile Lys Lys Ser
            995                1000                1005

Leu Val Glu Ala Thr Gly Val Pro Gly Gln His Ile Leu Val Ala
        1010                1015                1020

Val Leu Pro Gly Leu Pro Thr Thr Ala Glu Leu Phe Val Leu Pro
     1025                1030                1035

Tyr Gln Asp Pro Ala Gly Glu Asn Lys Arg Ser Thr Asp Asp Leu
     1040                1045                1050

Glu Gln Ile Ser Glu Leu Leu Ile His Thr Leu Asn Gln Asn Ser
     1055                1060                1065

Val His Phe Glu Leu Lys Pro Gly Val Arg Val Leu Val His Ala
     1070                1075                1080

Ala His Leu Thr Ala Ala Pro Leu Val Asp Leu Thr Pro Thr His
     1085                1090                1095

Ser Gly Ser Ala Met Leu Met Leu Leu Ser Val Val Phe Val Gly
     1100                1105                1110

Leu Ala Val Phe Val Ile Tyr Lys Phe Lys Arg Arg Val Ala Leu
     1115                1120                1125

Pro Ser Pro Pro Ser Pro Ser Thr Gln Pro Gly Asp Ser Ser Leu
```

-continued

```
                1130                1135                1140

Arg Leu Gln Arg Ala Arg His Ala Thr Pro Pro Ser Thr Pro Lys
    1145                1150                1155

Arg Gly Ser Ala Gly Ala Gln Tyr Ala Ile
    1160                1165

<210> SEQ ID NO 4
<211> LENGTH: 907
<212> TYPE: PRT
<213> ORGANISM: Homo sapiens

<400> SEQUENCE: 4

Leu Ile Phe His Pro Lys Glu Glu Asp Lys Val Leu Ala Tyr Thr Lys
1               5                  10                  15

Glu Ser Lys Leu Tyr Val Ser Ser Asp Leu Gly Lys Lys Trp Thr Leu
            20                  25                  30

Leu Gln Glu Arg Val Thr Lys Asp His Val Phe Trp Ser Val Ser Gly
        35                  40                  45

Val Asp Ala Asp Pro Asp Leu Val His Val Glu Ala Gln Asp Leu Gly
    50                  55                  60

Gly Asp Phe Arg Tyr Val Thr Cys Ala Ile His Asn Cys Ser Glu Lys
65                  70                  75                  80

Met Leu Thr Ala Pro Phe Ala Gly Pro Ile Asp His Gly Ser Leu Thr
                85                  90                  95

Val Gln Asp Asp Tyr Ile Phe Phe Lys Ala Thr Ser Ala Asn Gln Thr
            100                 105                 110

Lys Tyr Tyr Val Ser Tyr Arg Arg Asn Glu Phe Val Leu Met Lys Leu
        115                 120                 125

Pro Lys Tyr Ala Leu Pro Lys Asp Leu Gln Ile Ile Ser Thr Asp Glu
    130                 135                 140

Ser Gln Val Phe Val Ala Val Gln Glu Trp Tyr Gln Met Asp Thr Tyr
145                 150                 155                 160

Asn Leu Tyr Gln Ser Asp Pro Arg Gly Val Arg Tyr Ala Leu Val Leu
                165                 170                 175

Gln Asp Val Arg Ser Ser Arg Gln Ala Glu Glu Ser Val Leu Ile Asp
            180                 185                 190

Ile Leu Glu Val Arg Gly Val Lys Gly Val Phe Leu Ala Asn Gln Lys
        195                 200                 205

Ile Asp Gly Lys Val Met Thr Leu Ile Thr Tyr Asn Lys Gly Arg Asp
    210                 215                 220

Trp Asp Tyr Leu Arg Pro Pro Ser Met Asp Met Asn Gly Lys Pro Thr
225                 230                 235                 240

Asn Cys Lys Pro Pro Asp Cys His Leu His Leu His Leu Arg Trp Ala
                245                 250                 255

Asp Asn Pro Tyr Val Ser Gly Thr Val His Thr Lys Asp Thr Ala Pro
            260                 265                 270

Gly Leu Ile Met Gly Ala Gly Asn Leu Gly Ser Gln Leu Val Glu Tyr
        275                 280                 285

Lys Glu Glu Met Tyr Ile Thr Ser Asp Cys Gly His Thr Trp Arg Gln
    290                 295                 300

Val Phe Glu Glu His His Ile Leu Tyr Leu Asp His Gly Gly Val
305                 310                 315                 320

Ile Val Ala Ile Lys Asp Thr Ser Ile Pro Leu Lys Ile Leu Lys Phe
                325                 330                 335

Ser Val Asp Glu Gly Leu Thr Trp Ser Thr His Asn Phe Thr Ser Thr
```

```
                340             345             350
Ser Val Phe Val Asp Gly Leu Leu Ser Glu Pro Gly Asp Glu Thr Leu
            355                 360             365

Val Met Thr Val Phe Gly His Ile Ser Phe Arg Ser Asp Trp Glu Leu
        370             375             380

Val Lys Val Asp Phe Arg Pro Ser Phe Ser Arg Gln Cys Gly Glu Glu
385             390             395             400

Asp Tyr Ser Ser Trp Glu Leu Ser Asn Leu Gln Gly Asp Arg Cys Ile
            405             410             415

Met Gly Gln Gln Arg Ser Phe Arg Lys Arg Lys Ser Thr Ser Trp Cys
        420             425             430

Ile Lys Gly Arg Ser Phe Thr Ser Ala Leu Thr Ser Arg Val Cys Glu
        435             440             445

Cys Arg Asp Ser Asp Phe Leu Cys Asp Tyr Gly Phe Glu Arg Ser Pro
        450             455             460

Ser Ser Glu Ser Ser Thr Asn Lys Cys Ser Ala Asn Phe Trp Phe Asn
465             470             475             480

Pro Leu Ser Pro Pro Asp Asp Cys Ala Leu Gly Gln Thr Tyr Thr Ser
            485             490             495

Ser Leu Gly Tyr Arg Lys Val Val Ser Asn Val Cys Glu Gly Gly Val
            500             505             510

Asp Met Gln Gln Ser Gln Val Gln Leu Gln Cys Pro Leu Thr Pro Pro
        515             520             525

Arg Gly Leu Gln Val Ser Ile Gln Gly Glu Ala Val Ala Val Arg Pro
        530             535             540

Gly Glu Asp Val Leu Phe Val Val Arg Gln Glu Gln Gly Asp Val Leu
545             550             555             560

Thr Thr Lys Tyr Gln Val Asp Leu Gly Asp Gly Phe Lys Ala Met Tyr
            565             570             575

Val Asn Leu Thr Leu Thr Gly Glu Pro Ile Arg His Arg Tyr Glu Ser
        580             585             590

Pro Gly Ile Tyr Arg Val Ser Val Arg Ala Glu Asn Thr Ala Gly His
        595             600             605

Asp Glu Ala Val Leu Phe Val Gln Val Asn Ser Pro Leu Gln Ala Leu
610             615             620

Tyr Leu Glu Val Val Pro Val Ile Gly Leu Asn Gln Glu Val Asn Leu
625             630             635             640

Thr Ala Val Leu Leu Pro Leu Asn Pro Asn Leu Thr Val Phe Tyr Trp
            645             650             655

Trp Ile Gly His Ser Leu Gln Pro Leu Leu Ser Leu Asp Asn Ser Val
        660             665             670

Thr Thr Arg Phe Ser Asp Thr Gly Asp Val Arg Val Thr Val Gln Ala
        675             680             685

Ala Cys Gly Asn Ser Val Leu Gly Asp Ser Arg Val Leu Arg Val Leu
        690             695             700

Asp Gln Phe Gln Val Met Pro Leu Gln Phe Ser Lys Glu Leu Asp Ala
705             710             715             720

Tyr Asn Pro Asn Thr Pro Glu Trp Arg Glu Asp Val Gly Leu Val Val
            725             730             735

Thr Arg Leu Leu Ser Lys Glu Thr Ser Val Pro Gln Glu Leu Leu Val
            740             745             750

Thr Val Val Lys Pro Gly Leu Pro Thr Leu Ala Asp Leu Tyr Val Leu
            755             760             765
```

-continued

Leu Pro Pro Arg Pro Thr Arg Lys Arg Ser Leu Ser Ser Asp Lys
    770                 775                 780

Arg Leu Ala Ala Ile Gln Gln Val Leu Asn Ala Gln Lys Ile Ser Phe
785                 790                 795                 800

Leu Leu Arg Gly Gly Val Arg Val Leu Val Ala Leu Arg Asp Thr Gly
                805                 810                 815

Thr Gly Ala Glu Gln Leu Gly Gly Gly Gly Tyr Trp Ala Val Val
            820                 825                 830

Val Leu Phe Val Ile Gly Leu Phe Ala Ala Gly Ala Phe Ile Leu Tyr
                835                 840                 845

Lys Phe Lys Arg Lys Arg Pro Gly Arg Thr Val Tyr Ala Gln Met His
    850                 855                 860

Asn Glu Lys Glu Gln Glu Met Thr Ser Pro Val Ser His Ser Glu Asp
865                 870                 875                 880

Val Gln Gly Ala Val Gln Gly Asn His Ser Gly Val Val Leu Ser Ile
                885                 890                 895

Asn Ser Arg Glu Met His Ser Tyr Leu Val Ser
                900                 905

<210> SEQ ID NO 5
<211> LENGTH: 1222
<212> TYPE: PRT
<213> ORGANISM: Homo sapiens

<400> SEQUENCE: 5

Met Glu Ala Ala Arg Thr Glu Arg Pro Ala Gly Arg Pro Gly Ala Pro
1               5                   10                  15

Leu Val Arg Thr Gly Leu Leu Leu Leu Ser Thr Trp Val Leu Ala Gly
                20                  25                  30

Ala Glu Ile Thr Trp Asp Ala Thr Gly Gly Pro Gly Arg Pro Ala Ala
            35                  40                  45

Pro Ala Ser Arg Pro Pro Ala Leu Ser Pro Leu Ser Pro Arg Ala Val
    50                  55                  60

Ala Ser Gln Trp Pro Glu Glu Leu Ala Ser Ala Arg Arg Ala Ala Val
65                  70                  75                  80

Leu Gly Arg Arg Ala Gly Pro Glu Leu Leu Pro Gln Gln Gly Gly Gly
                85                  90                  95

Arg Gly Gly Glu Met Gln Val Glu Ala Gly Thr Ser Pro Ala Gly
            100                 105                 110

Glu Arg Arg Gly Arg Gly Ile Pro Ala Pro Ala Lys Leu Gly Gly Ala
    115                 120                 125

Arg Arg Ser Arg Arg Ala Gln Pro Pro Ile Thr Gln Glu Arg Gly Asp
130                 135                 140

Ala Trp Ala Thr Ala Pro Ala Asp Gly Ser Arg Gly Ser Arg Pro Leu
145                 150                 155                 160

Ala Lys Gly Ser Arg Glu Glu Val Lys Ala Pro Arg Ala Gly Gly Ser
                165                 170                 175

Ala Ala Glu Asp Leu Arg Leu Pro Ser Thr Ser Phe Ala Leu Thr Gly
            180                 185                 190

Asp Ser Ala His Asn Gln Ala Met Val His Trp Ser Gly His Asn Ser
    195                 200                 205

Ser Val Ile Leu Ile Leu Thr Lys Leu Tyr Asp Phe Asn Leu Gly Ser
210                 215                 220

Val Thr Glu Ser Ser Leu Trp Arg Ser Thr Asp Tyr Gly Thr Thr Tyr
225                 230                 235                 240

```
Glu Lys Leu Asn Asp Lys Val Gly Leu Lys Thr Val Leu Ser Tyr Leu
                245                 250                 255

Tyr Val Asn Pro Thr Asn Lys Arg Lys Ile Met Leu Leu Ser Asp Pro
            260                 265                 270

Glu Met Glu Ser Ser Ile Leu Ile Ser Ser Asp Glu Gly Ala Thr Tyr
        275                 280                 285

Gln Lys Tyr Arg Leu Thr Phe Tyr Ile Gln Ser Leu Leu Phe His Pro
    290                 295                 300

Lys Gln Glu Asp Trp Val Leu Ala Tyr Ser Leu Asp Gln Lys Leu Tyr
305                 310                 315                 320

Ser Ser Met Asp Phe Gly Arg Arg Trp Gln Leu Met His Glu Arg Ile
                325                 330                 335

Thr Pro Asn Arg Phe Tyr Trp Ser Val Ala Gly Leu Asp Lys Glu Ala
            340                 345                 350

Asp Leu Val His Met Glu Val Arg Thr Thr Asp Gly Tyr Ala His Tyr
        355                 360                 365

Leu Thr Cys Arg Ile Gln Glu Cys Ala Glu Thr Thr Arg Ser Gly Pro
    370                 375                 380

Phe Ala Arg Ser Ile Asp Ile Ser Ser Leu Val Val Gln Asp Glu Tyr
385                 390                 395                 400

Ile Phe Ile Gln Val Thr Thr Ser Gly Arg Ala Ser Tyr Tyr Val Ser
                405                 410                 415

Tyr Arg Arg Glu Ala Phe Ala Gln Ile Lys Leu Pro Lys Tyr Ser Leu
            420                 425                 430

Pro Lys Asp Met His Ile Ile Ser Thr Asp Glu Asn Gln Val Phe Ala
        435                 440                 445

Ala Val Gln Glu Trp Asn Gln Asn Asp Thr Tyr Asn Leu Tyr Ile Ser
    450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Ile Glu Leu Tyr Glu Val Ala
                485                 490                 495

Gly Ile Lys Gly Ile Phe Leu Ala Asn Lys Lys Val Asp Gln Val
            500                 505                 510

Lys Thr Tyr Ile Thr Tyr Asn Lys Gly Arg Asp Trp Arg Leu Leu Gln
    515                 520                 525

Ala Pro Asp Val Asp Leu Arg Gly Ser Pro Val His Cys Leu Leu Pro
        530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
                565                 570                 575

Thr Gly Asn Ile Gly Pro Glu Leu Ser Tyr Thr Asp Ile Gly Val Phe
            580                 585                 590

Ile Ser Ser Asp Gly Gly Asn Thr Trp Arg Gln Ile Phe Asp Glu Glu
        595                 600                 605

Tyr Asn Val Trp Phe Leu Asp Trp Gly Gly Ala Leu Val Ala Met Lys
    610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
                645                 650                 655

Gly Ala Leu Val Glu Ala Gly Met Glu Thr His Ile Met Thr Val Phe
            660                 665                 670
```

```
Gly His Phe Ser Leu Arg Ser Glu Trp Gln Leu Val Lys Val Asp Tyr
            675                 680                 685

Lys Ser Ile Phe Ser Arg His Cys Thr Lys Glu Asp Tyr Gln Thr Trp
690                 695                 700

His Leu Leu Asn Gln Gly Glu Pro Cys Val Met Gly Glu Arg Lys Ile
705                 710                 715                 720

Phe Lys Lys Arg Lys Pro Gly Ala Gln Cys Ala Leu Gly Arg Asp His
                725                 730                 735

Ser Gly Ser Val Val Ser Glu Pro Cys Val Cys Ala Asn Trp Asp Phe
                740                 745                 750

Glu Cys Asp Tyr Gly Tyr Glu Arg His Gly Glu Ser Gln Cys Val Pro
            755                 760                 765

Ala Phe Trp Tyr Asn Pro Ala Ser Pro Ser Lys Asp Cys Ser Leu Gly
770                 775                 780

Gln Ser Tyr Leu Asn Ser Thr Gly Tyr Arg Arg Ile Val Ser Asn Asn
785                 790                 795                 800

Cys Thr Asp Gly Leu Arg Glu Lys Tyr Thr Ala Lys Ala Gln Met Cys
                805                 810                 815

Pro Gly Lys Ala Pro Arg Gly Leu His Val Val Thr Thr Asp Gly Arg
                820                 825                 830

Leu Val Ala Glu Gln Gly His Asn Ala Thr Phe Ile Ile Leu Met Glu
            835                 840                 845

Glu Gly Asp Leu Gln Arg Thr Asn Ile Gln Leu Asp Phe Gly Asp Gly
850                 855                 860

Ile Ala Val Ser Tyr Ala Asn Phe Ser Pro Ile Glu Asp Gly Ile Lys
865                 870                 875                 880

His Val Tyr Lys Ser Ala Gly Ile Phe Gln Val Thr Ala Tyr Ala Glu
                885                 890                 895

Asn Asn Leu Gly Ser Asp Thr Ala Val Leu Phe Leu His Val Val Cys
                900                 905                 910

Pro Val Glu His Val His Leu Arg Val Pro Phe Val Ala Ile Arg Asn
            915                 920                 925

Lys Glu Val Asn Ile Ser Ala Val Val Trp Pro Ser Gln Leu Gly Thr
930                 935                 940

Leu Thr Tyr Phe Trp Trp Phe Gly Asn Ser Thr Lys Pro Leu Ile Thr
945                 950                 955                 960

Leu Asp Ser Ser Ile Ser Phe Thr Phe Leu Ala Glu Gly Thr Asp Thr
                965                 970                 975

Ile Thr Val Gln Val Ala Ala Gly Asn Ala Leu Ile Gln Asp Thr Lys
                980                 985                 990

Glu Ile Ala Val His Glu Tyr Phe Gln Ser Gln Leu Leu Ser Phe Ser
            995                 1000                1005

Pro Asn Leu Asp Tyr His Asn Pro Asp Ile Pro Glu Trp Arg Lys
    1010                1015                1020

Asp Ile Gly Asn Val Ile Lys Arg Ala Leu Val Lys Val Thr Ser
    1025                1030                1035

Val Pro Glu Asp Gln Ile Leu Ile Ala Val Phe Pro Gly Leu Pro
    1040                1045                1050

Thr Ser Ala Glu Leu Phe Ile Leu Pro Pro Lys Asn Leu Thr Glu
    1055                1060                1065

Arg Arg Lys Gly Asn Glu Gly Asp Leu Glu Gln Ile Val Glu Thr
    1070                1075                1080

Leu Phe Asn Ala Leu Asn Gln Asn Leu Val Gln Phe Glu Leu Lys
```

-continued

```
              1085                1090                1095

Pro Gly Val Gln Val Ile Val Tyr Val Thr Gln Leu Thr Leu Ala
        1100                1105                1110

Pro Leu Val Asp Ser Ser Ala Gly His Ser Ser Ser Ala Met Leu
        1115                1120                1125

Met Leu Leu Ser Val Val Phe Val Gly Leu Ala Val Phe Leu Ile
        1130                1135                1140

Tyr Lys Phe Lys Arg Lys Ile Pro Trp Ile Asn Ile Tyr Ala Gln
        1145                1150                1155

Val Gln His Asp Lys Glu Gln Glu Met Ile Gly Ser Val Ser Gln
        1160                1165                1170

Ser Glu Asn Ala Pro Lys Ile Thr Leu Ser Asp Phe Thr Glu Pro
        1175                1180                1185

Glu Glu Leu Leu Asp Lys Glu Leu Asp Thr Arg Val Ile Gly Gly
        1190                1195                1200

Ile Ala Thr Ile Ala Asn Ser Glu Ser Thr Lys Glu Ile Pro Asn
        1205                1210                1215

Cys Thr Ser Val
        1220

<210> SEQ ID NO 6
<211> LENGTH: 241
<212> TYPE: PRT
<213> ORGANISM: Homo sapiens
<220> FEATURE:
<221> NAME/KEY: SIGNAL
<222> LOCATION: (1)..(18)
<223> OTHER INFORMATION: Signal peptide of NGF
<220> FEATURE:
<221> NAME/KEY: PROPEP
<222> LOCATION: (19)..(121)
<223> OTHER INFORMATION: Propeptide of NGF (NGFpro)
<220> FEATURE:
<221> NAME/KEY: MISC_FEATURE
<222> LOCATION: (19)..(241)
<223> OTHER INFORMATION: proNGF
<220> FEATURE:
<221> NAME/KEY: MISC_FEATURE
<222> LOCATION: (122)..(241)
<223> OTHER INFORMATION: Mature NGF

<400> SEQUENCE: 6

Met Ser Met Leu Phe Tyr Thr Leu Ile Thr Ala Phe Leu Ile Gly Ile
1               5                  10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140
```

```
Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
            195                 200                 205

Lys Ala Leu Thr Met Asp Gly Lys Gln Ala Ala Trp Arg Phe Ile Arg
        210                 215                 220

Ile Asp Thr Ala Cys Val Cys Val Leu Ser Arg Lys Ala Val Arg Arg
225                 230                 235                 240

Ala

<210> SEQ ID NO 7
<211> LENGTH: 246
<212> TYPE: PRT
<213> ORGANISM: Homo sapiens
<220> FEATURE:
<221> NAME/KEY: SIGNAL
<222> LOCATION: (1)..(18)
<223> OTHER INFORMATION: Signal peptide of BDNF
<220> FEATURE:
<221> NAME/KEY: PROPEP
<222> LOCATION: (19)..(127)
<223> OTHER INFORMATION: Propeptide of BDNF (BDNFpro)
<220> FEATURE:
<221> NAME/KEY: MISC_FEATURE
<222> LOCATION: (19)..(246)
<223> OTHER INFORMATION: proBDNF
<220> FEATURE:
<221> NAME/KEY: MISC_FEATURE
<222> LOCATION: (128)..(246)
<223> OTHER INFORMATION: Mature peptide of BDNF

<400> SEQUENCE: 7

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Gly Leu Thr Ser Leu Ala Asp Thr Phe Glu His
50                  55                  60

Val Ile Glu Glu Leu Leu Asp Glu Asp Gln Lys Val Arg Pro Asn Glu
65                  70                  75                  80

Glu Asn Asn Lys Asp Ala Asp Leu Tyr Thr Ser Arg Val Met Leu Ser
                85                  90                  95

Ser Gln Val Pro Leu Glu Pro Pro Leu Leu Phe Leu Leu Glu Glu Tyr
            100                 105                 110

Lys Asn Tyr Leu Asp Ala Ala Asn Met Ser Met Arg Val Arg Arg His
        115                 120                 125

Ser Asp Pro Ala Arg Arg Gly Glu Leu Ser Val Cys Asp Ser Ile Ser
130                 135                 140

Glu Trp Val Thr Ala Ala Asp Lys Lys Thr Ala Val Asp Met Ser Gly
145                 150                 155                 160

Gly Thr Val Thr Val Leu Glu Lys Val Pro Val Ser Lys Gly Gln Leu
                165                 170                 175

Lys Gln Tyr Phe Tyr Glu Thr Lys Cys Asn Pro Met Gly Tyr Thr Lys
            180                 185                 190
```

```
Glu Gly Cys Arg Gly Ile Asp Lys Arg His Trp Asn Ser Gln Cys Arg
            195                 200                 205
Thr Thr Gln Ser Tyr Val Arg Ala Leu Thr Met Asp Ser Lys Lys Arg
            210                 215                 220
Ile Gly Trp Arg Phe Ile Arg Ile Asp Thr Ser Cys Val Cys Thr Leu
225                 230                 235                 240
Thr Ile Lys Arg Gly Arg
            245

<210> SEQ ID NO 8
<211> LENGTH: 257
<212> TYPE: PRT
<213> ORGANISM: Homo sapiens
<220> FEATURE:
<221> NAME/KEY: SIGNAL
<222> LOCATION: (1)..(16)
<223> OTHER INFORMATION: Signal peptide of NT3
<220> FEATURE:
<221> NAME/KEY: PROPEP
<222> LOCATION: (17)..(140)
<223> OTHER INFORMATION: Propeptide of NT3 (NT3pro)
<220> FEATURE:
<221> NAME/KEY: MISC_FEATURE
<222> LOCATION: (17)..(257)
<223> OTHER INFORMATION: proNT3
<220> FEATURE:
<221> NAME/KEY: MISC_FEATURE
<222> LOCATION: (141)..(257)
<223> OTHER INFORMATION: Mature peptide of NT3

<400> SEQUENCE: 8

Met Ser Ile Leu Phe Tyr Val Ile Phe Leu Ala Tyr Leu Arg Gly Ile
1               5                   10                  15
Gln Gly Asn Asn Met Asp Gln Arg Ser Leu Pro Glu Asp Ser Leu Asn
            20                  25                  30
Ser Leu Ile Ile Lys Leu Ile Gln Ala Asp Ile Leu Lys Asn Lys Leu
        35                  40                  45
Ser Lys Gln Met Val Asp Val Lys Glu Asn Tyr Gln Ser Thr Leu Pro
    50                  55                  60
Lys Ala Glu Ala Pro Arg Glu Pro Glu Arg Gly Gly Pro Ala Lys Ser
65                  70                  75                  80
Ala Phe Gln Pro Val Ile Ala Met Asp Thr Glu Leu Leu Arg Gln Gln
                85                  90                  95
Arg Arg Tyr Asn Ser Pro Arg Val Leu Leu Ser Asp Ser Thr Pro Leu
            100                 105                 110
Glu Pro Pro Pro Leu Tyr Leu Met Glu Asp Tyr Val Gly Ser Pro Val
        115                 120                 125
Val Ala Asn Arg Thr Ser Arg Arg Lys Arg Tyr Ala Glu His Lys Ser
    130                 135                 140
His Arg Gly Glu Tyr Ser Val Cys Asp Ser Glu Ser Leu Trp Val Thr
145                 150                 155                 160
Asp Lys Ser Ser Ala Ile Asp Ile Arg Gly His Gln Val Thr Val Leu
                165                 170                 175
Gly Glu Ile Lys Thr Gly Asn Ser Pro Val Lys Gln Tyr Phe Tyr Glu
            180                 185                 190
Thr Arg Cys Lys Glu Ala Arg Pro Val Lys Asn Gly Cys Arg Gly Ile
        195                 200                 205
Asp Asp Lys His Trp Asn Ser Gln Cys Lys Thr Ser Gln Thr Tyr Val
    210                 215                 220
Arg Ala Leu Thr Ser Glu Asn Asn Lys Leu Val Gly Trp Arg Trp Ile
225                 230                 235                 240
```

```
Arg Ile Asp Thr Ser Cys Val Cys Ala Leu Ser Arg Lys Ile Gly Arg
                245                 250                 255

Thr

<210> SEQ ID NO 9
<211> LENGTH: 210
<212> TYPE: PRT
<213> ORGANISM: Homo sapiens
<220> FEATURE:
<221> NAME/KEY: SIGNAL
<222> LOCATION: (1)..(24)
<223> OTHER INFORMATION: Signal peptide of NT4/5
<220> FEATURE:
<221> NAME/KEY: PROPEP
<222> LOCATION: (25)..(80)
<223> OTHER INFORMATION: Propeptide of NT4/5
<220> FEATURE:
<221> NAME/KEY: MISC_FEATURE
<222> LOCATION: (25)..(210)
<223> OTHER INFORMATION: proNT4/5
<220> FEATURE:
<221> NAME/KEY: MISC_FEATURE
<222> LOCATION: (81)..(210)
<223> OTHER INFORMATION: Mature peptide of NT4/5

<400> SEQUENCE: 9

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Ser Thr Leu Pro
            20                  25                  30

Pro Phe Leu Ala Pro Glu Trp Asp Leu Ser Pro Arg Val Val Leu
            35                  40                  45

Ser Arg Gly Ala Pro Ala Gly Pro Pro Leu Leu Phe Leu Leu Glu Ala
50                  55                  60

Gly Ala Phe Arg Glu Ser Ala Gly Ala Pro Ala Asn Arg Ser Arg Arg
65                  70                  75                  80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110

Leu Arg Gly Arg Glu Val Glu Val Leu Gly Glu Val Pro Ala Ala Gly
            115                 120                 125

Gly Ser Pro Leu Arg Gln Tyr Phe Phe Glu Thr Arg Cys Lys Ala Asp
130                 135                 140

Asn Ala Glu Glu Gly Gly Pro Gly Ala Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
            180                 185                 190

Ile Arg Ile Asp Thr Ala Cys Val Cys Thr Leu Leu Ser Arg Thr Gly
            195                 200                 205

Arg Ala
    210

<210> SEQ ID NO 10
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
```

```
<223> OTHER INFORMATION: Neurotensin

<400> SEQUENCE: 10

Gln Leu Tyr Glu Asn Lys Pro Arg Arg Pro Tyr Ile Leu
1               5                   10

<210> SEQ ID NO 11
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Four C-terminal amino acids of Neurotensin

<400> SEQUENCE: 11

Pro Tyr Ile Leu
1

<210> SEQ ID NO 12
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa = N-methyl-Arg
<220> FEATURE:
<221> NAME/KEY: MISC_FEATURE
<222> LOCATION: (1)..(6)
<223> OTHER INFORMATION: NT69L
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 12

Xaa Lys Pro Xaa Xaa Leu
1               5

<210> SEQ ID NO 13
<211> LENGTH: 357
<212> TYPE: PRT
<213> ORGANISM: Homo sapiens
<220> FEATURE:
<221> NAME/KEY: MISC_FEATURE
<222> LOCATION: (1)..(357)
<223> OTHER INFORMATION: RAP

<400> SEQUENCE: 13

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95
```

```
Lys Leu Asp Gly Leu Asp Glu Asp Gly Glu Lys Glu Ala Arg Leu Ile
            100                 105                 110
Arg Asn Leu Asn Val Ile Leu Ala Lys Tyr Gly Leu Asp Gly Lys Lys
            115                 120                 125
Asp Ala Arg Gln Val Thr Ser Asn Ser Leu Ser Gly Thr Gln Glu Asp
        130                 135                 140
Gly Leu Asp Asp Pro Arg Leu Glu Lys Leu Trp His Lys Ala Lys Thr
145                 150                 155                 160
Ser Gly Lys Phe Ser Gly Glu Leu Asp Lys Leu Trp Arg Glu Phe
                165                 170                 175
Leu His His Lys Glu Lys Val His Glu Tyr Asn Val Leu Leu Glu Thr
                180                 185                 190
Leu Ser Arg Thr Glu Glu Ile His Glu Asn Val Ile Ser Pro Ser Asp
            195                 200                 205
Leu Ser Asp Ile Lys Gly Ser Val Leu His Ser Arg His Thr Glu Leu
        210                 215                 220
Lys Glu Lys Leu Arg Ser Ile Asn Gln Gly Leu Asp Arg Leu Arg Arg
225                 230                 235                 240
Val Ser His Gln Gly Tyr Ser Thr Glu Ala Glu Phe Glu Glu Pro Arg
                245                 250                 255
Val Ile Asp Leu Trp Asp Leu Ala Gln Ser Ala Asn Leu Thr Asp Lys
            260                 265                 270
Glu Leu Glu Ala Phe Arg Glu Leu Lys His Phe Glu Ala Lys Ile
        275                 280                 285
Glu Lys His Asn His Tyr Gln Lys Gln Leu Glu Ile Ala His Glu Lys
        290                 295                 300
Leu Arg His Ala Glu Ser Val Gly Asp Gly Glu Arg Val Ser Arg Ser
305                 310                 315                 320
Arg Glu Lys His Ala Leu Leu Glu Gly Arg Thr Lys Glu Leu Gly Tyr
                325                 330                 335
Thr Val Lys Lys His Leu Gln Asp Leu Ser Gly Arg Ile Ser Arg Ala
            340                 345                 350
Arg His Asn Glu Leu
        355

<210> SEQ ID NO 14
<211> LENGTH: 674
<212> TYPE: PRT
<213> ORGANISM: Bos taurus
<220> FEATURE:
<221> NAME/KEY: MISC_FEATURE
<223> OTHER INFORMATION: Bos taurus sortilin

<400> SEQUENCE: 14

Ser Ala Pro Gly Glu Asp Glu Asp Cys Gly Gly Val Gln Asp Phe Val
1               5                   10                  15
Ser Arg Leu Ala Asn Asn Thr His Gln His Val Phe Asp Asp Leu Ser
            20                  25                  30
Gly Ser Val Ser Leu Ser Trp Val Gly Asp Ser Thr Gly Ile Ile Leu
        35                  40                  45
Val Leu Thr Thr Phe His Val Pro Leu Val Ile Met Thr Phe Gly Gln
    50                  55                  60
Ser Lys Leu Tyr Arg Ser Glu Asp Tyr Gly Lys Asn Phe Lys Asp Ile
65              70                  75                  80
Thr Asn Leu Ile Asn Asn Thr Phe Ile Arg Thr Glu Phe Gly Met Ala
                85                  90                  95
```

Ile Gly Pro Glu Asn Ser Gly Lys Val Ile Leu Thr Ala Glu Val Ser
            100                 105                 110

Gly Gly Ser His Gly Gly Arg Ile Phe Arg Ser Ser Asp Phe Ala Lys
        115                 120                 125

Asn Phe Val Gln Thr Asn Leu Pro Phe His Pro Leu Thr Gln Met Met
130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Ala Val Cys Leu Ala Lys Trp Gly Ser Glu Asn Ile Ile Phe Phe
            180                 185                 190

Thr Thr Tyr Val Asn Gly Ser Cys Lys Ala Asp Leu Gly Ala Leu Glu
        195                 200                 205

Leu Arg Arg Thr Ser Asp Leu Gly Lys Ser Phe Lys Thr Ile Gly Val
210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Ser Val Gly Gln Glu Gln
            260                 265                 270

Phe Tyr Ser Ile Leu Ala Ala Asn Asp Asp Met Val Phe Met His Val
        275                 280                 285

Asp Glu Pro Gly Asp Thr Gly Phe Gly Thr Ile Phe Thr Ser Asp Asp
290                 295                 300

Arg Gly Ile Val Tyr Ser Lys Ser Leu Asp Arg His Leu Tyr Thr Thr
305                 310                 315                 320

Thr Gly Gly Glu Thr Asp Phe Thr Asn Val Thr Ser Leu Arg Gly Val
                325                 330                 335

Tyr Met Thr Ser Val Leu Ser Glu Asp Asn Ser Ile Gln Thr Met Ile
            340                 345                 350

Thr Phe Asp Gln Gly Gly Arg Trp Lys His Leu Arg Lys Pro Glu Asn
        355                 360                 365

Ser Glu Cys Asp Ala Thr Ala Lys Asn Lys Asn Glu Cys Ser Leu His
370                 375                 380

Ile His Ala Ser Tyr Ser Ile Ser Gln Lys Leu Asn Val Pro Met Ala
385                 390                 395                 400

Pro Leu Ser Glu Pro Asn Ala Val Gly Ile Val Ile Ala His Gly Ser
                405                 410                 415

Val Gly Asp Ala Ile Ser Val Met Val Pro Asp Val Tyr Ile Ser Asp
            420                 425                 430

Asp Gly Gly Tyr Ser Trp Met Lys Met Leu Glu Gly Pro His Tyr Tyr
        435                 440                 445

Thr Ile Leu Asp Ser Gly Gly Ile Ile Val Ala Ile Glu His Ser Ser
450                 455                 460

His Pro Ile Asn Val Ile Lys Phe Ser Thr Asp Glu Gly Gln Cys Trp
465                 470                 475                 480

Gln Thr Tyr Thr Phe Thr Lys Glu Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Ala Arg Gln Trp Val Ser Tyr Thr Ile Asp Phe Lys

```
                    515                 520                 525
Asp Ile Leu Glu Arg Asn Cys Glu Glu Lys Asp Tyr Thr Ile Trp Leu
530                 535                 540

Ala His Ser Thr Asp Pro Gly Asp Tyr Gly Asp Gly Cys Ile Leu Gly
545                 550                 555                 560

Tyr Lys Glu Gln Tyr Leu Arg Leu Arg Lys Ser Ser Val Cys Gln Asn
                565                 570                 575

Gly Arg Asn Tyr Val Val Thr Lys Gln Pro Ser Val Cys Pro Cys Ser
                580                 585                 590

Leu Glu Asp Phe Leu Cys Asp Phe Gly Tyr Phe Arg Pro Glu Asn Asp
                595                 600                 605

Ser Lys Cys Val Glu Gln Pro Glu Leu Lys Gly His Asp Leu Glu Phe
                610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
                660                 665                 670

Gln Asn

<210> SEQ ID NO 15
<211> LENGTH: 679
<212> TYPE: PRT
<213> ORGANISM: Canis familiaris
<220> FEATURE:
<221> NAME/KEY: MISC_FEATURE
<223> OTHER INFORMATION: Canis familiaris sortilin

<400> SEQUENCE: 15

Ser Ala Leu Gln Asp Asp Gln Asp Cys Gly Arg Val Arg Asp Val Val
1               5                   10                  15

Ala Lys Leu Ala Asn Asn Thr His Gln His Val Phe Asp Asp Leu Ser
                20                  25                  30

Val Ser Val Ser Leu Ser Trp Val Gly Asp Gly Thr Gly Ile Ile Leu
                35                  40                  45

Val Leu Thr Thr Phe His Val Pro Leu Val Ile Met Thr Phe Gly Gln
50                  55                  60

Ser Lys Leu Tyr Arg Ser Glu Asp Tyr Gly Lys Asn Phe Lys Asp Ile
65              70                  75                  80

Thr Asn Leu Ile Asn Asn Thr Phe Ile Arg Thr Glu Phe Gly Met Ala
                85                  90                  95

Ile Gly Pro Glu Asn Ser Gly Lys Val Ile Leu Thr Ala Glu Val Ser
                100                 105                 110

Gly Gly Ser His Gly Gly Arg Ile Phe Arg Ser Ser Asp Phe Ala Lys
                115                 120                 125

Asn Phe Val Gln Ser Asn Leu Pro Phe His Pro Leu Thr Gln Met Met
                130                 135                 140

Tyr Ser Pro Gln Asn Ser Asp Tyr Leu Leu Ala Leu Ser Thr Glu Asn
145                 150                 155                 160

Gly Leu Trp Val Ser Lys Asp Phe Gly Gly Lys Trp Glu Glu Ile His
                165                 170                 175

Lys Ala Val Cys Leu Ala Lys Trp Gly Ser Glu Asn Thr Ile Phe Phe
                180                 185                 190

Thr Thr Tyr Ala Asn Gly Ser Cys Lys Ala Asp Leu Gly Ala Leu Glu
                195                 200                 205
```

```
Leu Trp Arg Thr Ser Asp Leu Gly Lys Ser Phe Lys Thr Ile Gly Val
    210                 215                 220
Lys Ile Tyr Ser Phe Gly Leu Gly Gly Arg Phe Leu Phe Ala Ser Val
225                 230                 235                 240
Met Ala Asp Lys Asp Thr Thr Arg Arg Ile His Val Ser Thr Asp Gln
                245                 250                 255
Gly Asp Thr Trp Ser Met Ala Gln Leu Pro Ser Val Gly Gln Glu Gln
            260                 265                 270
Phe Tyr Ser Ile Leu Ala Ala Asn Asp Asp Met Val Phe Met His Val
        275                 280                 285
Asp Glu Pro Gly Asp Thr Gly Tyr Gly Thr Ile Phe Thr Ser Asp Asp
    290                 295                 300
Arg Gly Ile Val Tyr Ser Lys Ser Leu Asp Arg His Leu Tyr Thr Thr
305                 310                 315                 320
Thr Gly Gly Glu Thr Asp Phe Thr Asn Val Thr Ser Leu Arg Gly Val
                325                 330                 335
Tyr Ile Thr Ser Val Leu Ser Glu Asp Asn Ser Ile Gln Thr Met Ile
            340                 345                 350
Thr Phe Asp Gln Gly Gly Arg Trp Lys His Leu Arg Lys Pro Glu Asn
        355                 360                 365
Ser Glu Cys Asp Ala Thr Ala Lys Asn Lys Asn Glu Cys Ser Leu His
    370                 375                 380
Ile His Ala Ser Tyr Ser Ile Ser Gln Lys Leu Asn Val Pro Met Ala
385                 390                 395                 400
Pro Leu Ser Glu Pro Lys Ala Val Gly Ile Val Ile Ala His Gly Ser
                405                 410                 415
Val Gly Asp Ala Ile Ser Val Met Ile Pro Asp Val Tyr Ile Ser Asp
            420                 425                 430
Asp Gly Gly Tyr Ser Trp Ala Lys Met Leu Glu Gly Pro His Tyr Tyr
        435                 440                 445
Thr Ile Leu Asp Ser Gly Gly Ile Ile Val Ala Ile Glu His Ser Ser
    450                 455                 460
His Pro Ile Asn Val Ile Lys Phe Ser Thr Asp Glu Gly Gln Cys Trp
465                 470                 475                 480
Gln Thr Tyr Met Phe Thr Arg Glu Pro Ile Tyr Phe Thr Gly Leu Ala
                485                 490                 495
Ser Glu Pro Gly Ala Arg Ser Met Asn Ile Ser Ile Trp Gly Phe Thr
            500                 505                 510
Glu Ser Phe Leu Thr Arg Gln Trp Val Ser Tyr Thr Ile Asp Phe Lys
        515                 520                 525
Asp Val Leu Glu Arg Asn Cys Glu Glu Lys Asp Tyr Thr Ile Trp Leu
    530                 535                 540
Ala His Ser Ala Asp Pro Gly Asp Tyr Gly Asp Gly Cys Ile Leu Gly
545                 550                 555                 560
Tyr Lys Glu Gln Tyr Leu Arg Leu Arg Lys Ser Ser Val Cys Gln Asn
                565                 570                 575
Gly Arg Asp Tyr Val Val Thr Lys Gln Pro Ser Val Cys Pro Cys Ser
            580                 585                 590
Leu Glu Asp Phe Leu Cys Asp Phe Gly Tyr Phe Arg Pro Glu Asn Asp
        595                 600                 605
Ser Lys Cys Val Glu Gln Pro Glu Leu Lys Gly His Asp Leu Glu Phe
    610                 615                 620
Cys Leu Tyr Gly Arg Glu Glu His Leu Thr Thr Asn Gly Tyr Arg Lys
```

```
                    625                 630                 635                 640
Ile Pro Gly Asp Arg Cys Gln Gly Gly Val Asn Pro Val Arg Glu Val
                    645                 650                 655

Lys Asp Leu Lys Lys Lys Cys Thr Ser Asn Phe Leu Ser Pro Glu Lys
                    660                 665                 670

Gln Asn Ser Lys Ser Asn Ser
                    675

<210> SEQ ID NO 16
<211> LENGTH: 679
<212> TYPE: PRT
<213> ORGANISM: Rattus norvegicus
<220> FEATURE:
<221> NAME/KEY: misc_feature
<223> OTHER INFORMATION: Rattus norvegicus sortilin

<400> SEQUENCE: 16

Gly Ala Pro Ala Glu Asp Gln Asp Cys Gly Arg Leu Pro Asp Phe Ile
1               5                   10                  15

Ala Lys Leu Thr Asn Asn Thr His Gln His Val Phe Asp Asp Leu Ser
                20                  25                  30

Gly Ser Val Ser Leu Ser Trp Val Gly Asp Ser Thr Gly Val Ile Leu
            35                  40                  45

Val Leu Thr Thr Phe Gln Val Pro Leu Val Ile Val Ser Phe Gly Gln
    50                  55                  60

Ser Lys Leu Tyr Arg Ser Glu Asp Tyr Gly Lys Asn Phe Lys Asp Ile
65                  70                  75                  80

Thr Asn Leu Ile Asn Asn Thr Phe Ile Arg Thr Glu Phe Gly Met Ala
                85                  90                  95

Ile Gly Pro Glu Asn Ser Gly Lys Val Ile Leu Thr Ala Glu Val Ser
            100                 105                 110

Gly Gly Ser Arg Gly Gly Arg Val Phe Arg Ser Ser Asp Phe Ala Lys
        115                 120                 125

Asn Phe Val Gln Thr Asp Leu Pro Phe His Pro Leu Thr Gln Met Met
130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Glu Lys Trp Glu Glu Ile His
                165                 170                 175

Lys Ala Val Cys Leu Ala Lys Trp Gly Pro Asn Asn Ile Ile Phe Phe
            180                 185                 190

Thr Thr His Val Asn Gly Ser Cys Lys Ala Asp Leu Gly Ala Leu Glu
        195                 200                 205

Leu Trp Arg Thr Ser Asp Leu Gly Lys Thr Phe Lys Thr Ile Gly Val
    210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Ser Val Gly Gln Glu Gln
            260                 265                 270

Phe Tyr Ser Ile Leu Ala Ala Asn Asp Asp Met Val Phe Met His Val
        275                 280                 285

Asp Glu Pro Gly Asp Thr Gly Phe Gly Thr Ile Phe Thr Ser Asp Asp
    290                 295                 300

Arg Gly Ile Val Tyr Ser Lys Ser Leu Asp Arg His Leu Tyr Thr Thr
```

```
            305                 310                 315                 320

Thr Gly Gly Glu Thr Asp Phe Thr Asn Val Thr Ser Leu Arg Gly Val
                    325                 330                 335

Tyr Ile Thr Ser Thr Leu Ser Glu Asp Asn Ser Ile Gln Ser Met Ile
                    340                 345                 350

Thr Phe Asp Gln Gly Gly Arg Trp Glu His Leu Gln Lys Pro Glu Asn
                    355                 360                 365

Ser Lys Cys Asp Ala Thr Ala Lys Asn Lys Asn Glu Cys Ser Leu His
                370                 375                 380

Ile His Ala Ser Tyr Ser Ile Ser Gln Lys Leu Asn Val Pro Met Ala
    385                 390                 395                 400

Pro Leu Ser Glu Pro Asn Ala Val Gly Ile Val Ile Ala His Gly Ser
                    405                 410                 415

Val Gly Asp Ala Ile Ser Val Met Val Pro Asp Val Tyr Ile Ser Asp
                    420                 425                 430

Asp Gly Gly Tyr Ser Trp Ala Lys Met Leu Glu Gly Pro His Tyr Tyr
                    435                 440                 445

Thr Ile Leu Asp Ser Gly Gly Ile Ile Val Ala Ile Glu His Ser Asn
                450                 455                 460

Arg Pro Ile Asn Val Ile Lys Phe Ser Thr Asp Gly Gln Cys Trp
    465                 470                 475                 480

Gln Ser Tyr Val Phe Ser Gln Glu Pro Val Tyr Phe Thr Gly Leu Ala
                    485                 490                 495

Ser Glu Pro Gly Ala Arg Ser Met Asn Ile Ser Ile Trp Gly Phe Thr
                    500                 505                 510

Glu Ser Phe Leu Thr Arg Gln Trp Val Ser Tyr Thr Ile Asp Phe Lys
                    515                 520                 525

Asp Ile Leu Glu Arg Asn Cys Glu Glu Asn Asp Tyr Thr Thr Trp Leu
                530                 535                 540

Ala His Ser Thr Asp Pro Gly Asp Tyr Lys Asp Gly Cys Ile Leu Gly
    545                 550                 555                 560

Tyr Lys Glu Gln Phe Leu Arg Leu Arg Lys Ser Ser Val Cys Gln Asn
                    565                 570                 575

Gly Arg Asp Tyr Val Val Ala Lys Gln Pro Ser Ile Cys Pro Cys Ser
                    580                 585                 590

Leu Glu Asp Phe Leu Cys Asp Phe Gly Tyr Phe Arg Pro Glu Asn Ala
                    595                 600                 605

Ser Glu Cys Val Glu Gln Pro Glu Leu Lys Gly His Glu Leu Glu Phe
                610                 615                 620

Cys Leu Tyr Gly Lys Glu Glu His Leu Thr Thr Asn Gly Tyr Arg Lys
    625                 630                 635                 640

Ile Pro Gly Asp Arg Cys Gln Gly Gly Met Asn Pro Ala Arg Glu Val
                    645                 650                 655

Lys Asp Leu Lys Lys Lys Cys Thr Ser Asn Phe Leu Asn Pro Lys Lys
                    660                 665                 670

Gln Asn Ser Lys Ser Ser Ser
                675

<210> SEQ ID NO 17
<211> LENGTH: 679
<212> TYPE: PRT
<213> ORGANISM: Mus musculus
<220> FEATURE:
<221> NAME/KEY: MISC_FEATURE
<223> OTHER INFORMATION: Mus musculus sortilin
```

<400> SEQUENCE: 17

```
Gly Ala Pro Ala Glu Asp Gln Asp Cys Gly Arg Leu Pro Asp Phe Ile
1               5                   10                  15
Ala Lys Leu Thr Asn Asn Thr His Gln His Val Phe Asp Asp Leu Ser
                20                  25                  30
Gly Ser Val Ser Leu Ser Trp Val Gly Asp Ser Thr Gly Val Ile Leu
            35                  40                  45
Val Leu Thr Thr Phe Gln Val Pro Leu Val Ile Val Ser Phe Gly Gln
        50                  55                  60
Ser Lys Leu Tyr Arg Ser Glu Asp Tyr Gly Lys Asn Phe Lys Asp Ile
65                  70                  75                  80
Thr Asn Leu Ile Asn Asn Thr Phe Ile Arg Thr Glu Phe Gly Met Ala
                85                  90                  95
Ile Gly Pro Glu Asn Ser Gly Lys Val Ile Leu Thr Ala Glu Val Ser
            100                 105                 110
Gly Gly Ser Arg Gly Arg Val Phe Arg Ser Ser Asp Phe Ala Lys
        115                 120                 125
Asn Phe Val Gln Thr Asp Leu Pro Phe His Pro Leu Thr Gln Met Met
    130                 135                 140
Tyr Ser Pro Gln Asn Ser Asp Tyr Leu Leu Ala Leu Ser Thr Glu Asn
145                 150                 155                 160
Gly Leu Trp Val Ser Lys Asn Phe Gly Glu Lys Trp Glu Glu Ile His
                165                 170                 175
Lys Ala Val Cys Leu Ala Lys Trp Gly Pro Asn Asn Ile Ile Phe Phe
            180                 185                 190
Thr Thr His Val Asn Gly Ser Cys Lys Ala Asp Leu Gly Ala Leu Glu
        195                 200                 205
Leu Trp Arg Thr Ser Asp Leu Gly Lys Thr Phe Lys Thr Ile Gly Val
    210                 215                 220
Lys Ile Tyr Ser Phe Gly Leu Gly Gly Arg Phe Leu Phe Ala Ser Val
225                 230                 235                 240
Met Ala Asp Lys Asp Thr Thr Arg Arg Ile His Val Ser Thr Asp Gln
                245                 250                 255
Gly Asp Thr Trp Ser Met Ala Gln Leu Pro Ser Val Gly Gln Glu Gln
            260                 265                 270
Phe Tyr Ser Ile Leu Ala Ala Asn Glu Asp Met Val Phe Met His Val
        275                 280                 285
Asp Glu Pro Gly Asp Thr Gly Phe Gly Thr Ile Phe Thr Ser Asp Asp
    290                 295                 300
Arg Gly Ile Val Tyr Ser Lys Ser Leu Asp Arg His Leu Tyr Thr Thr
305                 310                 315                 320
Thr Gly Gly Glu Thr Asp Phe Thr Asn Val Thr Ser Leu Arg Gly Val
                325                 330                 335
Tyr Ile Thr Ser Thr Leu Ser Glu Asp Asn Ser Ile Gln Ser Met Ile
            340                 345                 350
Thr Phe Asp Gln Gly Gly Arg Trp Glu His Leu Arg Lys Pro Glu Asn
        355                 360                 365
Ser Lys Cys Asp Ala Thr Ala Lys Asn Lys Asn Glu Cys Ser Leu His
    370                 375                 380
Ile His Ala Ser Tyr Ser Ile Ser Gln Lys Leu Asn Val Pro Met Ala
385                 390                 395                 400
Pro Leu Ser Glu Pro Asn Ala Val Gly Ile Val Ile Ala His Gly Ser
                405                 410                 415
```

Val Gly Asp Ala Ile Ser Val Met Val Pro Asp Val Tyr Ile Ser Asp
                420                 425                 430

Asp Gly Gly Tyr Ser Trp Ala Lys Met Leu Glu Gly Pro His Tyr Tyr
            435                 440                 445

Thr Ile Leu Asp Ser Gly Gly Ile Ile Val Ala Ile Glu His Ser Asn
450                 455                 460

Arg Pro Ile Asn Val Ile Lys Phe Ser Thr Asp Glu Gly Gln Cys Trp
465                 470                 475                 480

Gln Ser Tyr Val Phe Thr Gln Glu Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Ile Thr Arg Gln Trp Val Ser Tyr Thr Val Asp Phe Lys
        515                 520                 525

Asp Ile Leu Glu Arg Asn Cys Glu Glu Asp Tyr Thr Thr Trp Leu
530                 535                 540

Ala His Ser Thr Asp Pro Gly Asp Tyr Lys Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Ala Lys Gln Pro Ser Val Cys Pro Cys Ser
            580                 585                 590

Leu Glu Asp Phe Leu Cys Asp Phe Gly Tyr Phe Arg Pro Glu Asn Ala
        595                 600                 605

Ser Glu Cys Val Glu Gln Pro Glu Leu Lys Gly His Glu Leu Glu Phe
610                 615                 620

Cys Leu Tyr Gly Lys Glu Glu His Leu Thr Thr Asn Gly Tyr Arg Lys
625                 630                 635                 640

Ile Pro Gly Asp Lys Cys Gln Gly Gly Met Asn Pro Ala Arg Glu Val
                645                 650                 655

Lys Asp Leu Lys Lys Lys Cys Thr Ser Asn Phe Leu Asn Pro Thr Lys
            660                 665                 670

Gln Asn Ser Lys Ser Asn Ser
        675

<210> SEQ ID NO 18
<211> LENGTH: 662
<212> TYPE: PRT
<213> ORGANISM: Ornithorhynchus anatinus
<220> FEATURE:
<221> NAME/KEY: MISC_FEATURE
<223> OTHER INFORMATION: Ornithorhynchus anatinus sortilin

<400> SEQUENCE: 18

Asn Cys Ala Arg Leu Ala Gln Ser His Val Phe Asp Asp Leu Ser Gly
1               5                   10                  15

Ser Val Ser Leu Ser Trp Val Gly Asp Ser Thr Gly Val Ile Leu Val
            20                  25                  30

Leu Thr Thr Phe His Ile Pro Leu Val Ile Met Thr Phe Gly Gln Ser
        35                  40                  45

Lys Leu Tyr Arg Ser Glu Asp Tyr Gly Lys Asn Phe Lys Asp Ile Thr
    50                  55                  60

Asn Leu Ile Asn Asn Thr Phe Ile Arg Thr Glu Phe Gly Met Ala Ile
65                  70                  75                  80

Gly Pro Glu Asn Ser Gly Lys Val Ile Leu Thr Gly Asp Val Ser Gly
                85                  90                  95

-continued

```
Gly Ser Arg Gly Gly Arg Ile Phe Arg Ser Ser Asp Phe Ala Lys Asn
            100                 105                 110

Phe Val Gln Thr Asp Leu Pro Phe His Pro Leu Thr Gln Met Ile Tyr
            115                 120                 125

Asn Pro Gln Asn Ala Asn Tyr Leu Leu Ala Leu Ser Ser Glu Asn Gly
130                 135                 140

Leu Trp Val Ser Lys Asp Phe Gly Lys Trp Glu Glu Ile His Lys
145                 150                 155                 160

Ala Val Cys Leu Ala Lys Trp Gly Ser Glu Ser Thr Ile Phe Phe Thr
                165                 170                 175

Thr Tyr Val Asn Gly Ser Cys Lys Ala Asp Leu Gly Val Leu Glu Leu
            180                 185                 190

Arg Arg Thr Phe Asp Leu Gly Lys Ser Phe Lys Thr Ile Gly Ala Lys
        195                 200                 205

Ile Tyr Ser Phe Gly Leu Gly Gly Arg Phe Leu Phe Ala Ser Val Met
        210                 215                 220

Thr Glu Lys Gly Thr Thr Arg Arg Ile His Val Ser Leu Asp Gln Gly
225                 230                 235                 240

Glu Thr Trp Ser Met Ala Gln Leu Pro Ser Val Gly Gln Glu Gln Phe
                245                 250                 255

Tyr Ser Ile Leu Ala Ala Asn Asp Asp Met Val Phe Met His Val Asp
            260                 265                 270

Glu Pro Gly Asp Thr Gly Tyr Gly Thr Ile Tyr Thr Ser Asp Asp Arg
        275                 280                 285

Gly Ile Val Tyr Ser Lys Ser Leu Asp Arg His Leu Tyr Thr Thr Thr
        290                 295                 300

Gly Gly Asp Thr Asp Phe Thr Asn Val Thr Ser Leu Arg Gly Val Tyr
305                 310                 315                 320

Met Thr Ser Val Leu Ser Glu Asp Asn Ser Ile Gln Ser Val Ile Thr
                325                 330                 335

Phe Asp Gln Gly Gly Lys Trp Arg Leu Leu Arg Lys Pro Glu Asn Ser
            340                 345                 350

Lys Cys Asp Ser Thr Ala Lys Asn Lys Glu Glu Cys Ser Leu His Ile
        355                 360                 365

His Ala Ser Tyr Ser Ile Ser Gln Lys Leu Asn Val Pro Met Val Pro
        370                 375                 380

Leu Ser Glu Pro Asn Ala Val Gly Ile Val Ile Ala His Gly Glu Glu
385                 390                 395                 400

Glu Asp Cys Ser Ala Leu Leu Ser Val Ser Leu Gln Leu Leu Ser Pro
                405                 410                 415

Ser Arg Thr Gln Trp Arg Pro Leu Ser Ala Pro His Phe Ala Ser
            420                 425                 430

Leu Leu Phe Leu Gly Gln Ser Phe Leu Pro Leu Phe His Pro Thr Gln
        435                 440                 445

Ser Ser His Val Leu Arg Phe Ser Thr Asp Glu Gly Gln Cys Trp Asn
450                 455                 460

Leu Tyr Thr Phe Ser Lys Glu Pro Ile Tyr Phe Thr Gly Leu Ala Ser
465                 470                 475                 480

Glu Pro Gly Ala Arg Ser Met Asn Val Ser Ile Trp Gly Phe Arg Lys
                485                 490                 495

Ser Phe Pro Ser Gln Lys Trp Val Ser Tyr Thr Ile Asp Phe Lys Glu
            500                 505                 510

Leu Leu Ser Arg Asn Cys Glu Glu Lys Asp Tyr Thr Ile Trp Leu Ala
        515                 520                 525
```

His Ser Thr Asp Pro Gly Ala Gln Asn Asp Gly Cys Ile Leu Gly Tyr
    530                 535                 540

Lys Glu Gln Tyr Arg Arg Leu Arg Lys Ser Ser Val Cys Gln Asn Gly
545                 550                 555                 560

Arg Asp Tyr Arg Leu Thr Gly Gln Pro Ala Val Cys Thr Cys Thr Leu
                565                 570                 575

Glu Asp Phe Leu Cys Asp Phe Gly Tyr Phe Arg Pro Glu Asn Glu Ser
                580                 585                 590

Lys Cys Val Glu Gln Pro Glu Leu Lys Gly His Asp Leu Glu Phe Cys
                595                 600                 605

Leu Tyr Gly Arg Glu Glu His Leu Thr Thr Asn Gly Tyr Arg Lys Ile
610                 615                 620

Pro Gly Asp Lys Cys Gln Gly Gly Met Ser Pro Asp Arg Glu Glu Lys
625                 630                 635                 640

Asp Leu Lys Arg Lys Cys Arg Ser Asn Phe Leu Ser Pro Asp Lys Gln
                645                 650                 655

Lys Ala Ser Ser Asn Pro
                660

<210> SEQ ID NO 19
<211> LENGTH: 710
<212> TYPE: PRT
<213> ORGANISM: Tetraodon nigroviridis
<220> FEATURE:
<221> NAME/KEY: MISC_FEATURE
<223> OTHER INFORMATION: Tetraodon nigroviridis sortilin

<400> SEQUENCE: 19

Arg Ser Thr Glu Gln Gly Glu Ser Cys Ser Gly Leu Leu Gly Ala Asp
1               5                   10                  15

Ala Lys Leu Ala Gly Asn Thr His Gln His Ile Phe Asn Asp Leu Ser
                20                  25                  30

Gly Ser Val Ser Leu Ala Trp Val Gly Asp Gly Thr Gly Val Ile Leu
                35                  40                  45

Ala Leu Thr Thr Phe Gln Val Pro Ile Phe Met Ile Thr Ile Gly Gln
            50                  55                  60

Ser Lys Leu Tyr Arg Ser Glu Asp Tyr Gly Lys Ser Phe Glu Asp Val
65              70                  75                  80

Thr Asn Leu Ile Asn Asn Thr Phe Ile Arg Ser Asp Phe Gly Ile Ala
                85                  90                  95

Ile Gly Pro Glu Asn Ser Gly Lys Val Gly His Met Leu Gly Arg Trp
            100                 105                 110

Ser Gln Met Ser Arg Arg Cys Asn Ala Asn Pro Ser Ser His Pro Ile
            115                 120                 125

Leu Phe Leu Asp Phe Gln Val Ile Leu Thr Ala Asp Val Ser Gly Ser
    130                 135                 140

His Gly Ser Arg Ile Phe Val Ser Ser Asp Phe Gly Lys Ser Phe Thr
145                 150                 155                 160

His Gln Glu Leu Pro Phe Val Pro Leu Met Gln Ile Thr Tyr Asn Pro
                165                 170                 175

Glu Asn Ser Asn Val Leu Leu Ala Leu Ser Asn Lys Asn Glu Leu Trp
                180                 185                 190

Leu Ser Glu Asp Phe Gly Thr Asn Trp Lys Lys Leu Tyr Asp Thr Val
            195                 200                 205

Cys Leu Ala Lys Trp Gly Arg Lys Gly Thr Ile Phe Phe Thr Ala Asn
210                 215                 220

```
His Asn Gly Ser Cys Ser Asp Arg Gly Met Leu Glu Leu Glu Arg Thr
225                 230                 235                 240

Thr Asp Tyr Gly Lys Ser Phe Lys Thr Val Ala Ser Lys Ile Tyr Ser
            245                 250                 255

Phe Gly Leu Gly Gly Lys Phe Leu Phe Ala Ser Val Met Thr Gly Lys
                260                 265                 270

Gly Thr Leu Arg Ala Ile His Val Ser Val Asp Asp Gly Asp Thr Trp
            275                 280                 285

Asn Met Ala Gln Leu Pro Pro Val Gly His Glu Gln Phe Tyr Ser Ile
    290                 295                 300

Leu Ala Ala Asn Asp Glu Met Val Phe Met His Val Asp Glu Pro Gly
305                 310                 315                 320

Asp Ser Gly Phe Gly Thr Ile Tyr Val Ser Asp Arg Gly Thr Val
                325                 330                 335

Tyr Ser Lys Ser Leu Glu Arg His Leu Tyr Thr Thr Thr Gly Gly Glu
            340                 345                 350

Thr Asp Phe Ile Asn Val Thr Ser Leu Arg Gly Val Phe Thr Thr Ser
        355                 360                 365

Ile Leu Ala Glu Asp Lys Ser Val Gln Ser Val Ile Ser Phe Asp Gln
370                 375                 380

Gly Gly Glu Trp Val Pro Leu Arg Lys Pro Ala Asp Ser Lys Cys Asp
385                 390                 395                 400

Ala Thr Ala Arg Asp Pro Glu Lys Cys Ser Leu His Ile His Ala Ala
                405                 410                 415

Tyr Ser Ile Ala Thr Gly Leu Asn Val Pro Met Leu Pro Leu Ser Glu
                420                 425                 430

Pro Asn Ala Val Gly Leu Val Leu Ala His Gly Ser Val Gly Asp Ala
            435                 440                 445

Ile Ser Val Met Arg Pro Asp Val Tyr Val Ser Asp Asp Gly Gly Tyr
450                 455                 460

Thr Trp Ile Lys Ala Leu Glu Gly Pro His His Tyr Ala Ile Leu Asp
465                 470                 475                 480

Ser Gly Gly Leu Leu Val Ala Val Glu Gln Asn Ala His Gln Gly Val
                485                 490                 495

Asn Gln Ile Lys Phe Ser Thr Asp Glu Gly Gln Cys Trp Gly Val Tyr
            500                 505                 510

Asn Phe Thr Lys Asp Pro Ile Phe Phe Thr Gly Leu Ala Ser Glu Pro
        515                 520                 525

Gly Ala Arg Ser Met Asn Val Ser Leu Trp Gly Tyr Arg Ser Ser Leu
            530                 535                 540

Phe His Gln Tyr Trp Ile Ser Phe Thr Ile Asp Phe Arg Asp Leu Ile
545                 550                 555                 560

Thr Arg Asn Cys Thr Asp Lys Asp Tyr Val Gln Trp Leu Ala His Ser
                565                 570                 575

Asp Asp Ile Ser Asp Pro Asn Asp Gly Cys Met Leu Gly Tyr Lys Glu
            580                 585                 590

Lys Phe Leu Arg Leu Lys Lys Asp Ser Val Cys Leu Asn Gly Arg Asp
        595                 600                 605

Tyr Glu Val Asn Thr Gln Pro Thr Pro Cys Leu Cys Thr Leu Asp Asp
    610                 615                 620

Phe Leu Cys Asp Phe Gly Tyr Tyr Arg Lys Glu Asn Ser Ser Glu Cys
625                 630                 635                 640

Val Glu Gln Pro Asp Leu Lys Gly Lys Val Leu Glu Phe Cys Leu His
```

```
                    645                 650                 655
Gly Thr Glu Glu Leu Leu Thr Asn Gly Tyr Arg Lys Ile Pro Gly
            660                 665                 670

Asp Lys Cys Glu Gly Gln Ile Pro Glu Arg Lys Glu Ile Asn Leu
            675                 680                 685

Arg Arg Arg Cys Val Ser Asp Leu Leu Gly Pro Glu Phe Leu Val Lys
            690                 695                 700

Lys Ser Ser Ser Lys Thr
705                 710

<210> SEQ ID NO 20
<211> LENGTH: 679
<212> TYPE: PRT
<213> ORGANISM: Danio rerio
<220> FEATURE:
<221> NAME/KEY: MISC_FEATURE
<223> OTHER INFORMATION: Danio rerio sortilin

<400> SEQUENCE: 20

Ser Glu Glu Ser Ala Gln Asn Gln Cys Glu Ser Leu His Gly Tyr Gln
1               5                   10                  15

Ser Thr Leu Gln Asn Asp Thr His Thr His Asn Phe Asn Asp Leu Ser
                20                  25                  30

Gly Ser Val Ser Leu Ala Trp Val Gly Asp Gly Thr Gly Val Leu Leu
            35                  40                  45

Val Leu Thr Thr Phe Gln Val Pro Leu Phe Ile Met Arg Phe Gly Gln
    50                  55                  60

Ser Lys Leu Tyr Arg Ser Glu Asp Tyr Gly Lys Thr Phe Gln Asp Ile
65              70                  75                  80

Thr Asp Leu Ile Asn Asn Thr Phe Ile Gln Thr Glu Phe Gly Ile Ala
                85                  90                  95

Ile Gly Pro Asp Asn Ser Gly Lys Val Ile Leu Thr Gly Asp Leu Ala
            100                 105                 110

Glu Gly Lys Val Thr Lys Ile Phe Arg Ser Val Asp Phe Gly Lys Ser
        115                 120                 125

Phe Val Thr Ser Glu Leu Pro Phe His Pro Leu Met Gln Ile Thr Tyr
    130                 135                 140

Asn Pro Lys Asp Ser Asn Ile Leu Met Val Tyr Ser Ile Asn Tyr Asp
145                 150                 155                 160

Leu Trp Leu Ser Lys Asp Phe Gly Ala Asn Trp Lys Lys Ile His Glu
                165                 170                 175

Ser Val Cys Leu Val Lys Trp Gly Ile Asp Asp Thr Ile Phe Leu Thr
            180                 185                 190

Thr Asn Pro Asn Gly Ser Cys Ser Asp Arg Gly Thr Leu Glu Leu Arg
        195                 200                 205

Lys Ser Leu Asp Tyr Gly Lys Thr Phe Lys Thr Ile Gly Asn Arg Ile
    210                 215                 220

Tyr Ser Phe Gly Leu Gly Gly Arg Phe Val Phe Ala Ser Ile Met Thr
225                 230                 235                 240

Asp Ser Gly Ser Thr Arg Met Ile His Val Ser Val Asp Gln Gly Glu
                245                 250                 255

Thr Trp Asp Met Ala Gln Leu Pro Thr Val Gly His Glu Gln Phe Tyr
            260                 265                 270

Ser Ile Leu Ala Ala Asn Asn Asp Met Val Phe Met His Val Asp Glu
        275                 280                 285

Pro Gly Asp Ser Gly Ile Gly Thr Ile Tyr Ile Ser Asp Asp Arg Gly
```

```
                290                 295                 300
Ile Val Phe Ser Lys Ser Leu Glu Arg His Leu Tyr Thr Thr Thr Gly
305                 310                 315                 320

Gly Asp Thr Asp Phe Thr Asn Ile Thr Ser Leu Arg Gly Val Tyr Ile
                325                 330                 335

Thr Ser Val Leu Ala Glu Asp Gly Ser Val Gln Thr Val Ile Thr Phe
                340                 345                 350

Asn Gln Gly Gly Glu Trp Arg Pro Leu Met Lys Pro Trp Asn Gly Val
            355                 360                 365

Cys Asp Ser Thr Ala Lys His Pro Ser Glu Cys Ser Leu His Ile His
370                 375                 380

Ala Ser Tyr Ser Ile Ser Met Lys Leu Asn Val Pro Met Gln Pro Leu
385                 390                 395                 400

Ser Glu Thr Asn Ala Val Gly Leu Val Leu Ala His Gly Ser Val Gly
                405                 410                 415

Gly Ala Val Ser Val Leu Ser Pro Asp Val Tyr Val Ser Asp Asp Gly
            420                 425                 430

Gly Tyr Thr Trp Phe Gln Ala Leu Lys Gly Pro His His Tyr Ala Ile
            435                 440                 445

Leu Asp Ser Gly Gly Leu Leu Val Ala Val Glu His Asn Pro Thr His
450                 455                 460

Pro Ile Ser Gln Ile Lys Phe Ser Thr Asp Glu Gly Gln Cys Trp His
465                 470                 475                 480

Ala His Asn Phe Thr Asp Asp Pro Ile Tyr Phe Thr Gly Leu Ala Ser
                485                 490                 495

Glu Pro Gly Ala Arg Ser Met Asn Val Ser Leu Trp Gly Tyr Arg Asp
            500                 505                 510

Thr Ile Leu Asn Gln Tyr Trp Val Ser Val Thr Val Asp Phe Arg Gln
            515                 520                 525

Leu Leu Ser Arg Asp Cys Gln Glu Asn Asp Tyr Ile Gln Trp Leu Ala
530                 535                 540

His Ser Ser Asp Ile Asn Ser Pro Thr Asp Gly Cys Val Leu Gly Tyr
545                 550                 555                 560

Lys Glu Arg Phe Leu Arg Leu Arg Arg Asp Ser Val Cys Trp Asn Gly
                565                 570                 575

Arg Asp Tyr Lys Val Thr Lys Glu Pro Thr Thr Cys Pro Cys Thr Leu
            580                 585                 590

Thr Asp Phe His Asp Phe Gly Phe Tyr His Glu Glu Asn Ser Ser Val
            595                 600                 605

Cys Val Glu Gln Pro Asp Leu Ile Gly His Ser Leu Glu Phe Cys Leu
610                 615                 620

His Gly Arg Lys Glu Gln Leu Gln Thr Ser Gly Tyr Arg Lys Ile Pro
625                 630                 635                 640

Gly Asp His Cys Glu Gly Ile Thr Pro Glu Arg Lys Glu Ile Asp
                645                 650                 655

Leu Ser Lys Lys Cys Val Ser Asn Leu Leu Arg Thr Glu Gln Leu Thr
                660                 665                 670

Lys Glu His Ser Phe Asn Ser
            675

<210> SEQ ID NO 21
<211> LENGTH: 44
<212> TYPE: PRT
<213> ORGANISM: Homo sapiens
<220> FEATURE:
```

```
<221> NAME/KEY: MISC_FEATURE
<222> LOCATION: (1)..(44)
<223> OTHER INFORMATION: Residues 34-76 of SEQ ID NO:1 (Sortilin)

<400> SEQUENCE: 21

Gln Asp Arg Leu Asp Ala Pro Pro Pro Ala Ala Pro Leu Pro Arg
1               5                   10                  15

Trp Ser Gly Pro Ile Gly Ser Val Ser Trp Gly Leu Arg Ala Ala
                20                  25                  30

Ala Gly Gly Ala Phe Pro Arg Gly Gly Arg Trp Arg
            35                  40

<210> SEQ ID NO 22
<211> LENGTH: 6
<212> TYPE: PRT
<213> ORGANISM: Artificial Sequence
<220> FEATURE:
<223> OTHER INFORMATION: Synthetic His 6 Tag

<400> SEQUENCE: 22

His His His His His His
1               5

<210> SEQ ID NO 23
<211> LENGTH: 103
<212> TYPE: PRT
<213> ORGANISM: Homo sapiens
<220> FEATURE:
<221> NAME/KEY: MISC_FEATURE
<222> LOCATION: (1)..(103)
<223> OTHER INFORMATION: NGFpro/1-103

<400> SEQUENCE: 23

Glu Pro His Ser Glu Ser Asn Val Pro Ala Gly His Thr Ile Pro Gln
1               5                   10                  15

Ala His Trp Thr Lys Leu Gln His Ser Leu Asp Thr Ala Leu Arg Arg
                20                  25                  30

Ala Arg Ser Ala Pro Ala Ala Ala Ile Ala Ala Arg Val Ala Gly Gln
            35                  40                  45

Thr Arg Asn Ile Thr Val Asp Pro Arg Leu Phe Lys Lys Arg Arg Leu
        50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg
            100

<210> SEQ ID NO 24
<211> LENGTH: 20
<212> TYPE: PRT
<213> ORGANISM: Artificial Sequence
<220> FEATURE:
<223> OTHER INFORMATION: Synthetic icosapeptide of the NGF propeptide

<400> SEQUENCE: 24

Glu Pro His Ser Glu Ser Asn Val Pro Ala Gly His Thr Ile Pro Gln
1               5                   10                  15

Ala His Trp Thr
                20

<210> SEQ ID NO 25
<211> LENGTH: 20
```

```
<212> TYPE: PRT
<213> ORGANISM: Artificial Sequence
<220> FEATURE:
<223> OTHER INFORMATION: Synthetic icosapeptide of the NGF propeptide

<400> SEQUENCE: 25

His Trp Thr Lys Leu Gln His Ser Leu Asp Thr Ala Leu Arg Arg Ala
1               5                   10                  15

Arg Ser Ala Pro
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic icosapeptide of the NGF propeptide

<400> SEQUENCE: 26

Ser Ala Pro Ala Ala Ala Ile Ala Ala Arg Val Ala Gly Gln Thr Arg
1               5                   10                  15

Asn Ile Thr Val
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic icosapeptide of the NGF propeptide

<400> SEQUENCE: 27

Ile Thr Val Asp Pro Arg Leu Phe Lys Lys Arg Arg Leu Arg Ser Pro
1               5                   10                  15

Arg Val Leu Phe
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic icosapeptide of the NGF propeptide

<400> SEQUENCE: 28

Val Leu Phe Ser Thr Gln Pro Pro Arg Glu Ala Ala Asp Thr Gln Asp
1               5                   10                  15

Leu Asp Phe Glu
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic icosapeptide of the NGF propeptide

<400> SEQUENCE: 29

Asp Leu Asp Phe Glu Val Gly Gly Ala Ala Pro Phe Asn Arg Thr His
1               5                   10                  15

Arg Ser Lys Arg
            20

<210> SEQ ID NO 30
<211> LENGTH: 13
```

```
<212> TYPE: PRT
<213> ORGANISM: Artificial Sequence
<220> FEATURE:
<223> OTHER INFORMATION: Synthetic Peptide

<400> SEQUENCE: 30

Glu Leu Tyr Glu Asn Lys Pro Arg Arg Pro Tyr Ile Leu
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 31

Arg Arg Pro Tyr Ile Leu
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 32

Arg Arg Pro Tyr Ile
1               5

<210> SEQ ID NO 33
<211> LENGTH: 678
<212> TYPE: PRT
<213> ORGANISM: Homo sapiens
<220> FEATURE:
<221> NAME/KEY: misc_feature
<223> OTHER INFORMATION: sSortilin (amino acid residues 78-755 of SEQ ID
      NO:1)

<400> SEQUENCE: 33

Ser Ala Pro Gly Glu Asp Glu Glu Cys Gly Arg Val Arg Asp Phe Val
1               5                   10                  15

Ala Lys Leu Ala Asn Asn Thr His Gln His Val Phe Asp Asp Leu Arg
            20                  25                  30

Gly Ser Val Ser Leu Ser Trp Val Gly Asp Ser Thr Gly Val Ile Leu
        35                  40                  45

Val Leu Thr Thr Phe His Val Pro Leu Val Ile Met Thr Phe Gly Gln
    50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95

Ile Gly Pro Glu Asn Ser Gly Lys Val Val Leu Thr Ala Glu Val Ser
            100                 105                 110

Gly Gly Ser Arg Gly Gly Arg Ile Phe Arg Ser Ser Asp Phe Ala Lys
        115                 120                 125

Asn Phe Val Gln Thr Asp Leu Pro Phe His Pro Leu Thr Gln Met Met
    130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175
```

```
Lys Ala Val Cys Leu Ala Lys Trp Gly Ser Asp Asn Thr Ile Phe Phe
                180                 185                 190
Thr Thr Tyr Ala Asn Gly Ser Cys Lys Ala Asp Leu Gly Ala Leu Glu
            195                 200                 205
Leu Trp Arg Thr Ser Asp Leu Gly Lys Ser Phe Lys Thr Ile Gly Val
    210                 215                 220
Lys Ile Tyr Ser Phe Gly Leu Gly Gly Arg Phe Leu Phe Ala Ser Val
225                 230                 235                 240
Met Ala Asp Lys Asp Thr Thr Arg Arg Ile His Val Ser Thr Asp Gln
                245                 250                 255
Gly Asp Thr Trp Ser Met Ala Gln Leu Pro Ser Val Gly Gln Glu Gln
            260                 265                 270
Phe Tyr Ser Ile Leu Ala Ala Asn Asp Asp Met Val Phe Met His Val
        275                 280                 285
Asp Glu Pro Gly Asp Thr Gly Phe Gly Thr Ile Phe Thr Ser Asp Asp
    290                 295                 300
Arg Gly Ile Val Tyr Ser Lys Ser Leu Asp Arg His Leu Tyr Thr Thr
305                 310                 315                 320
Thr Gly Gly Glu Thr Asp Phe Thr Asn Val Thr Ser Leu Arg Gly Val
                325                 330                 335
Tyr Ile Thr Ser Val Leu Ser Glu Asp Asn Ser Ile Gln Thr Met Ile
            340                 345                 350
Thr Phe Asp Gln Gly Gly Arg Trp Thr His Leu Arg Lys Pro Glu Asn
        355                 360                 365
Ser Glu Cys Asp Ala Thr Ala Lys Asn Lys Asn Glu Cys Ser Leu His
    370                 375                 380
Ile His Ala Ser Tyr Ser Ile Ser Gln Lys Leu Asn Val Pro Met Ala
385                 390                 395                 400
Pro Leu Ser Glu Pro Asn Ala Val Gly Ile Val Ile Ala His Gly Ser
                405                 410                 415
Val Gly Asp Ala Ile Ser Val Met Val Pro Asp Val Tyr Ile Ser Asp
            420                 425                 430
Asp Gly Gly Tyr Ser Trp Thr Lys Met Leu Glu Gly Pro His Tyr Tyr
        435                 440                 445
Thr Ile Leu Asp Ser Gly Gly Ile Ile Val Ala Ile Glu His Ser Ser
    450                 455                 460
Arg Pro Ile Asn Val Ile Lys Phe Ser Thr Asp Glu Gly Gln Cys Trp
465                 470                 475                 480
Gln Thr Tyr Thr Phe Thr Arg Asp Pro Ile Tyr Phe Thr Gly Leu Ala
                485                 490                 495
Ser Glu Pro Gly Ala Arg Ser Met Asn Ile Ser Ile Trp Gly Phe Thr
            500                 505                 510
Glu Ser Phe Leu Thr Ser Gln Trp Val Ser Tyr Thr Ile Asp Phe Lys
        515                 520                 525
Asp Ile Leu Glu Arg Asn Cys Glu Glu Lys Asp Tyr Thr Ile Trp Leu
    530                 535                 540
Ala His Ser Thr Asp Pro Glu Asp Tyr Glu Asp Gly Cys Ile Leu Gly
545                 550                 555                 560
Tyr Lys Glu Gln Phe Leu Arg Leu Arg Lys Ser Val Cys Gln Asn
                565                 570                 575
Gly Arg Asp Tyr Val Val Thr Lys Gln Pro Ser Ile Cys Leu Cys Ser
            580                 585                 590
Leu Glu Asp Phe Leu Cys Asp Phe Gly Tyr Tyr Arg Pro Glu Asn Asp
```

-continued

```
                595                 600                 605
Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Cys Thr Ser Asn Phe Leu Ser Pro Glu Lys
                660                 665                 670

Gln Asn Ser Lys Ser Asn
        675

<210> SEQ ID NO 34
<211> LENGTH: 663
<212> TYPE: PRT
<213> ORGANISM: Homo sapiens
<220> FEATURE:
<221> NAME/KEY: MISC_FEATURE
<223> OTHER INFORMATION: sSortilin fragment (amino acid residues 86-748
      of SEQ ID NO:1)

<400> SEQUENCE: 34

Cys Gly Arg Val Arg Asp Phe Val Ala Lys Leu Ala Asn Asn Thr His
1               5                   10                  15

Gln His Val Phe Asp Asp Leu Arg Gly Ser Val Ser Leu Ser Trp Val
                20                  25                  30

Gly Asp Ser Thr Gly Val Ile Leu Val Leu Thr Thr Phe His Val Pro
            35                  40                  45

Leu Val Ile Met Thr Phe Gly Gln Ser Lys Leu Tyr Arg Ser Glu Asp
50                  55                  60

Tyr Gly Lys Asn Phe Lys Asp Ile Thr Asp Leu Ile Asn Asn Thr Phe
65                  70                  75                  80

Ile Arg Thr Glu Phe Gly Met Ala Ile Gly Pro Glu Asn Ser Gly Lys
                85                  90                  95

Val Val Leu Thr Ala Glu Val Ser Gly Gly Ser Arg Gly Gly Arg Ile
            100                 105                 110

Phe Arg Ser Ser Asp Phe Ala Lys Asn Phe Val Gln Thr Asp Leu Pro
        115                 120                 125

Phe His Pro Leu Thr Gln Met Met Tyr Ser Pro Gln Asn Ser Asp Tyr
    130                 135                 140

Leu Leu Ala Leu Ser Thr Glu Asn Gly Leu Trp Val Ser Lys Asn Phe
145                 150                 155                 160

Gly Gly Lys Trp Glu Glu Ile His Lys Ala Val Cys Leu Ala Lys Trp
                165                 170                 175

Gly Ser Asp Asn Thr Ile Phe Phe Thr Thr Tyr Ala Asn Gly Ser Cys
            180                 185                 190

Lys Ala Asp Leu Gly Ala Leu Glu Leu Trp Arg Thr Ser Asp Leu Gly
        195                 200                 205

Lys Ser Phe Lys Thr Ile Gly Val Lys Ile Tyr Ser Phe Gly Leu Gly
    210                 215                 220

Gly Arg Phe Leu Phe Ala Ser Val Met Ala Asp Lys Asp Thr Thr Arg
225                 230                 235                 240

Arg Ile His Val Ser Thr Asp Gln Gly Asp Thr Trp Ser Met Ala Gln
                245                 250                 255

Leu Pro Ser Val Gly Gln Glu Gln Phe Tyr Ser Ile Leu Ala Ala Asn
            260                 265                 270
```

-continued

```
Asp Asp Met Val Phe Met His Val Asp Glu Pro Gly Asp Thr Gly Phe
        275                 280                 285

Gly Thr Ile Phe Thr Ser Asp Arg Gly Ile Val Tyr Ser Lys Ser
    290                 295                 300

Leu Asp Arg His Leu Tyr Thr Thr Thr Gly Gly Glu Thr Asp Phe Thr
305                 310                 315                 320

Asn Val Thr Ser Leu Arg Gly Val Tyr Ile Thr Ser Val Leu Ser Glu
                325                 330                 335

Asp Asn Ser Ile Gln Thr Met Ile Thr Phe Asp Gln Gly Gly Arg Trp
            340                 345                 350

Thr His Leu Arg Lys Pro Glu Asn Ser Glu Cys Asp Ala Thr Ala Lys
        355                 360                 365

Asn Lys Asn Glu Cys Ser Leu His Ile His Ala Ser Tyr Ser Ile Ser
    370                 375                 380

Gln Lys Leu Asn Val Pro Met Ala Pro Leu Ser Glu Pro Asn Ala Val
385                 390                 395                 400

Gly Ile Val Ile Ala His Gly Ser Val Gly Asp Ala Ile Ser Val Met
                405                 410                 415

Val Pro Asp Val Tyr Ile Ser Asp Asp Gly Gly Tyr Ser Trp Thr Lys
            420                 425                 430

Met Leu Glu Gly Pro His Tyr Tyr Thr Ile Leu Asp Ser Gly Gly Ile
        435                 440                 445

Ile Val Ala Ile Glu His Ser Ser Arg Pro Ile Asn Val Ile Lys Phe
    450                 455                 460

Ser Thr Asp Glu Gly Gln Cys Trp Gln Thr Tyr Thr Phe Thr Arg Asp
465                 470                 475                 480

Pro Ile Tyr Phe Thr Gly Leu Ala Ser Glu Pro Gly Ala Arg Ser Met
                485                 490                 495

Asn Ile Ser Ile Trp Gly Phe Thr Glu Ser Phe Leu Thr Ser Gln Trp
            500                 505                 510

Val Ser Tyr Thr Ile Asp Phe Lys Asp Ile Leu Glu Arg Asn Cys Glu
        515                 520                 525

Glu Lys Asp Tyr Thr Ile Trp Leu Ala His Ser Thr Asp Pro Glu Asp
    530                 535                 540

Tyr Glu Asp Gly Cys Ile Leu Gly Tyr Lys Glu Gln Phe Leu Arg Leu
545                 550                 555                 560

Arg Lys Ser Ser Val Cys Gln Asn Gly Arg Asp Tyr Val Val Thr Lys
                565                 570                 575

Gln Pro Ser Ile Cys Leu Cys Ser Leu Glu Asp Phe Leu Cys Asp Phe
            580                 585                 590

Gly Tyr Tyr Arg Pro Glu Asn Asp Ser Lys Cys Val Glu Gln Pro Glu
        595                 600                 605

Leu Lys Gly His Asp Leu Glu Phe Cys Leu Tyr Gly Arg Glu Glu His
    610                 615                 620

Leu Thr Thr Asn Gly Tyr Arg Lys Ile Pro Gly Asp Lys Cys Gln Gly
625                 630                 635                 640

Gly Val Asn Pro Val Arg Glu Val Lys Asp Leu Lys Lys Lys Cys Thr
                645                 650                 655

Ser Asn Phe Leu Ser Pro Glu
            660

<210> SEQ ID NO 35
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 35

Ala Ala Ala Ala
1

<210> SEQ ID NO 36
<211> LENGTH: 663
<212> TYPE: PRT
<213> ORGANISM: Homo sapiens
<220> FEATURE:
<221> NAME/KEY: MISC_FEATURE
<223> OTHER INFORMATION: sSortilin fragment (amino acid residues 87-749
      of SEQ ID NO:1)

<400> SEQUENCE: 36

Gly Arg Val Arg Asp Phe Val Ala Lys Leu Ala Asn Asn Thr His Gln
1               5                   10                  15

His Val Phe Asp Asp Leu Arg Gly Ser Val Ser Leu Ser Trp Val Gly
                20                  25                  30

Asp Ser Thr Gly Val Ile Leu Val Leu Thr Thr Phe His Val Pro Leu
            35                  40                  45

Val Ile Met Thr Phe Gly Gln Ser Lys Leu Tyr Arg Ser Glu Asp Tyr
        50                  55                  60

Gly Lys Asn Phe Lys Asp Ile Thr Asp Leu Ile Asn Asn Thr Phe Ile
65                  70                  75                  80

Arg Thr Glu Phe Gly Met Ala Ile Gly Pro Glu Asn Ser Gly Lys Val
                85                  90                  95

Val Leu Thr Ala Glu Val Ser Gly Gly Ser Arg Gly Gly Arg Ile Phe
            100                 105                 110

Arg Ser Ser Asp Phe Ala Lys Asn Phe Val Gln Thr Asp Leu Pro Phe
        115                 120                 125

His Pro Leu Thr Gln Met Met Tyr Ser Pro Gln Asn Ser Asp Tyr Leu
    130                 135                 140

Leu Ala Leu Ser Thr Glu Asn Gly Leu Trp Val Ser Lys Asn Phe Gly
145                 150                 155                 160

Gly Lys Trp Glu Glu Ile His Lys Ala Val Cys Leu Ala Lys Trp Gly
                165                 170                 175

Ser Asp Asn Thr Ile Phe Phe Thr Thr Tyr Ala Asn Gly Ser Cys Lys
            180                 185                 190

Ala Asp Leu Gly Ala Leu Glu Leu Trp Arg Thr Ser Asp Leu Gly Lys
        195                 200                 205

Ser Phe Lys Thr Ile Gly Val Lys Ile Tyr Ser Phe Gly Leu Gly Gly
    210                 215                 220

Arg Phe Leu Phe Ala Ser Val Met Ala Asp Lys Asp Thr Thr Arg Arg
225                 230                 235                 240

Ile His Val Ser Thr Asp Gln Gly Asp Thr Trp Ser Met Ala Gln Leu
                245                 250                 255

Pro Ser Val Gly Gln Glu Gln Phe Tyr Ser Ile Leu Ala Ala Asn Asp
            260                 265                 270

Asp Met Val Phe Met His Val Asp Glu Pro Gly Asp Thr Gly Phe Gly
        275                 280                 285

Thr Ile Phe Thr Ser Asp Asp Arg Gly Ile Val Tyr Ser Lys Ser Leu
    290                 295                 300

Asp Arg His Leu Tyr Thr Thr Thr Gly Gly Glu Thr Asp Phe Thr Asn
305                 310                 315                 320
```

```
Val Thr Ser Leu Arg Gly Val Tyr Ile Thr Ser Val Leu Ser Glu Asp
            325                 330                 335

Asn Ser Ile Gln Thr Met Ile Thr Phe Asp Gln Gly Gly Arg Trp Thr
        340                 345                 350

His Leu Arg Lys Pro Glu Asn Ser Glu Cys Asp Ala Thr Ala Lys Asn
    355                 360                 365

Lys Asn Glu Cys Ser Leu His Ile His Ala Ser Tyr Ser Ile Ser Gln
370                 375                 380

Lys Leu Asn Val Pro Met Ala Pro Leu Ser Glu Pro Asn Ala Val Gly
385                 390                 395                 400

Ile Val Ile Ala His Gly Ser Val Gly Asp Ala Ile Ser Val Met Val
            405                 410                 415

Pro Asp Val Tyr Ile Ser Asp Asp Gly Gly Tyr Ser Trp Thr Lys Met
        420                 425                 430

Leu Glu Gly Pro His Tyr Tyr Thr Ile Leu Asp Ser Gly Gly Ile Ile
    435                 440                 445

Val Ala Ile Glu His Ser Ser Arg Pro Ile Asn Val Ile Lys Phe Ser
450                 455                 460

Thr Asp Glu Gly Gln Cys Trp Gln Thr Tyr Thr Phe Thr Arg Asp Pro
465                 470                 475                 480

Ile Tyr Phe Thr Gly Leu Ala Ser Glu Pro Gly Ala Arg Ser Met Asn
            485                 490                 495

Ile Ser Ile Trp Gly Phe Thr Glu Ser Phe Leu Thr Ser Gln Trp Val
        500                 505                 510

Ser Tyr Thr Ile Asp Phe Lys Asp Ile Leu Glu Arg Asn Cys Glu Glu
    515                 520                 525

Lys Asp Tyr Thr Ile Trp Leu Ala His Ser Thr Asp Pro Glu Asp Tyr
530                 535                 540

Glu Asp Gly Cys Ile Leu Gly Tyr Lys Glu Gln Phe Leu Arg Leu Arg
545                 550                 555                 560

Lys Ser Ser Val Cys Gln Asn Gly Arg Asp Tyr Val Val Thr Lys Gln
            565                 570                 575

Pro Ser Ile Cys Leu Cys Ser Leu Glu Asp Phe Leu Cys Asp Phe Gly
        580                 585                 590

Tyr Tyr Arg Pro Glu Asn Asp Ser Lys Cys Val Glu Gln Pro Glu Leu
    595                 600                 605

Lys Gly His Asp Leu Glu Phe Cys Leu Tyr Gly Arg Glu Glu His Leu
610                 615                 620

Thr Thr Asn Gly Tyr Arg Lys Ile Pro Gly Asp Lys Cys Gln Gly Gly
625                 630                 635                 640

Val Asn Pro Val Arg Glu Val Lys Asp Leu Lys Lys Lys Cys Thr Ser
            645                 650                 655

Asn Phe Leu Ser Pro Glu Lys
            660
```

<210> SEQ ID NO 37
<211> LENGTH: 661
<212> TYPE: PRT
<213> ORGANISM: Homo sapiens
<220> FEATURE:
<221> NAME/KEY: MISC_FEATURE
<223> OTHER INFORMATION: sSortilin fragment (amino acid residues 86-747 of SEQ ID NO:1)

<400> SEQUENCE: 37

```
Gly Arg Val Arg Asp Phe Val Ala Lys Leu Ala Asn Asn Thr His Gln
1               5                   10                  15
```

His Val Phe Asp Asp Leu Arg Gly Ser Val Ser Leu Ser Trp Val Gly
            20                  25                  30

Asp Ser Thr Gly Val Ile Leu Val Leu Thr Thr Phe His Val Pro Leu
        35                  40                  45

Val Ile Met Thr Phe Gly Gln Ser Lys Leu Tyr Arg Ser Glu Asp Tyr
    50                  55                  60

Gly Lys Asn Phe Lys Asp Ile Thr Asp Leu Ile Asn Asn Thr Phe Ile
65                  70                  75                  80

Arg Thr Glu Phe Gly Met Ala Ile Gly Pro Glu Asn Ser Gly Lys Val
                85                  90                  95

Val Leu Thr Ala Glu Val Ser Gly Ser Arg Gly Gly Arg Ile Phe
            100                 105                 110

Arg Ser Ser Asp Phe Ala Lys Asn Phe Val Gln Thr Asp Leu Pro Phe
        115                 120                 125

His Pro Leu Thr Gln Met Met Tyr Ser Pro Gln Asn Ser Asp Tyr Leu
    130                 135                 140

Leu Ala Leu Ser Thr Glu Asn Gly Leu Trp Val Ser Lys Asn Phe Gly
145                 150                 155                 160

Gly Lys Trp Glu Glu Ile His Lys Ala Val Cys Leu Ala Lys Trp Gly
                165                 170                 175

Ser Asp Asn Thr Ile Phe Phe Thr Thr Tyr Ala Asn Gly Ser Cys Lys
            180                 185                 190

Ala Asp Leu Gly Ala Leu Glu Leu Trp Arg Thr Ser Asp Leu Gly Lys
        195                 200                 205

Ser Phe Lys Thr Ile Gly Val Lys Ile Tyr Ser Phe Gly Leu Gly Gly
    210                 215                 220

Arg Phe Leu Phe Ala Ser Val Met Ala Asp Lys Asp Thr Thr Arg Arg
225                 230                 235                 240

Ile His Val Ser Thr Asp Gln Gly Asp Thr Trp Ser Met Ala Gln Leu
                245                 250                 255

Pro Ser Val Gly Gln Glu Gln Phe Tyr Ser Ile Leu Ala Ala Asn Asp
            260                 265                 270

Asp Met Val Phe Met His Val Asp Glu Pro Gly Asp Thr Gly Phe Gly
        275                 280                 285

Thr Ile Phe Thr Ser Asp Asp Arg Gly Ile Val Tyr Ser Lys Ser Leu
    290                 295                 300

Asp Arg His Leu Tyr Thr Thr Thr Gly Gly Glu Thr Asp Phe Thr Asn
305                 310                 315                 320

Val Thr Ser Leu Arg Gly Val Tyr Ile Thr Ser Val Leu Ser Glu Asp
                325                 330                 335

Asn Ser Ile Gln Thr Met Ile Thr Phe Asp Gln Gly Gly Arg Trp Thr
            340                 345                 350

His Leu Arg Lys Pro Glu Asn Ser Glu Cys Asp Ala Thr Ala Lys Asn
        355                 360                 365

Lys Asn Glu Cys Ser Leu His Ile His Ala Ser Tyr Ser Ile Ser Gln
    370                 375                 380

Lys Leu Asn Val Pro Met Ala Pro Leu Ser Glu Pro Asn Ala Val Gly
385                 390                 395                 400

Ile Val Ile Ala His Gly Ser Val Gly Asp Ala Ile Ser Val Met Val
                405                 410                 415

Pro Asp Val Tyr Ile Ser Asp Asp Gly Gly Tyr Ser Trp Thr Lys Met
            420                 425                 430

Leu Glu Gly Pro His Tyr Tyr Thr Ile Leu Asp Ser Gly Gly Ile Ile

```
                    435                 440                 445
Val Ala Ile Glu His Ser Ser Arg Pro Ile Asn Val Ile Lys Phe Ser
        450                 455                 460

Thr Asp Glu Gly Gln Cys Trp Gln Thr Tyr Thr Phe Thr Arg Asp Pro
465                 470                 475                 480

Ile Tyr Phe Thr Gly Leu Ala Ser Glu Pro Gly Ala Arg Ser Met Asn
                485                 490                 495

Ile Ser Ile Trp Gly Phe Thr Glu Ser Phe Leu Thr Ser Gln Trp Val
                500                 505                 510

Ser Tyr Thr Ile Asp Phe Lys Asp Ile Leu Glu Arg Asn Cys Glu Glu
                515                 520                 525

Lys Asp Tyr Thr Ile Trp Leu Ala His Ser Thr Asp Pro Glu Asp Tyr
        530                 535                 540

Glu Asp Gly Cys Ile Leu Gly Tyr Lys Glu Gln Phe Leu Arg Leu Arg
545                 550                 555                 560

Lys Ser Ser Val Cys Gln Asn Gly Arg Asp Tyr Val Val Thr Lys Gln
                565                 570                 575

Pro Ser Ile Cys Leu Cys Ser Leu Glu Asp Phe Leu Cys Asp Phe Gly
                580                 585                 590

Tyr Tyr Arg Pro Glu Asn Asp Ser Lys Cys Val Glu Gln Pro Glu Leu
                595                 600                 605

Lys Gly His Asp Leu Glu Phe Cys Leu Tyr Gly Arg Glu Glu His Leu
        610                 615                 620

Thr Thr Asn Gly Tyr Arg Lys Ile Pro Gly Asp Lys Cys Gln Gly Gly
625                 630                 635                 640

Val Asn Pro Val Arg Glu Val Lys Asp Leu Lys Lys Cys Thr Ser
                645                 650                 655

Asn Phe Leu Ser Pro
            660

<210> SEQ ID NO 38
<211> LENGTH: 5
<212> TYPE: PRT
<213> ORGANISM: Homo sapiens
<220> FEATURE:
<221> NAME/KEY: MISC_FEATURE
<223> OTHER INFORMATION: Neurotensin Fragment

<400> SEQUENCE: 38

Glu Asn Lys Pro Arg
1               5

<210> SEQ ID NO 39
<211> LENGTH: 667
<212> TYPE: PRT
<213> ORGANISM: Homo sapiens
<220> FEATURE:
<221> NAME/KEY: MISC_FEATURE
<223> OTHER INFORMATION: sSortilin fragment (amino acid residues 83-749
      of SEQ ID NO:1)

<400> SEQUENCE: 39

Asp Glu Glu Cys Gly Arg Val Arg Asp Phe Val Ala Lys Leu Ala Asn
1               5                   10                  15

Asn Thr His Gln His Val Phe Asp Leu Arg Gly Ser Val Ser Leu
                20                  25                  30

Ser Trp Val Gly Asp Ser Thr Gly Val Ile Leu Val Leu Thr Thr Phe
            35                  40                  45

His Val Pro Leu Val Ile Met Thr Phe Gly Gln Ser Lys Leu Tyr Arg
```

```
            50                  55                  60
Ser Glu Asp Tyr Gly Lys Asn Phe Lys Asp Ile Thr Asp Leu Ile Asn
 65                  70                  75                  80

Asn Thr Phe Ile Arg Thr Glu Phe Gly Met Ala Ile Gly Pro Glu Asn
                     85                  90                  95

Ser Gly Lys Val Val Leu Thr Ala Glu Val Ser Gly Gly Ser Arg Gly
                100                 105                 110

Gly Arg Ile Phe Arg Ser Ser Asp Phe Ala Lys Asn Phe Val Gln Thr
                115                 120                 125

Asp Leu Pro Phe His Pro Leu Thr Gln Met Met Tyr Ser Pro Gln Asn
            130                 135                 140

Ser Asp Tyr Leu Leu Ala Leu Ser Thr Glu Asn Gly Leu Trp Val Ser
145                 150                 155                 160

Lys Asn Phe Gly Gly Lys Trp Glu Glu Ile His Lys Ala Val Cys Leu
                165                 170                 175

Ala Lys Trp Gly Ser Asp Asn Thr Ile Phe Phe Thr Thr Tyr Ala Asn
                180                 185                 190

Gly Ser Cys Lys Ala Asp Leu Gly Ala Leu Glu Leu Trp Arg Thr Ser
            195                 200                 205

Asp Leu Gly Lys Ser Phe Lys Thr Ile Gly Val Lys Ile Tyr Ser Phe
            210                 215                 220

Gly Leu Gly Gly Arg Phe Leu Phe Ala Ser Val Met Ala Asp Lys Asp
225                 230                 235                 240

Thr Thr Arg Arg Ile His Val Ser Thr Asp Gln Gly Asp Thr Trp Ser
                245                 250                 255

Met Ala Gln Leu Pro Ser Val Gly Gln Glu Gln Phe Tyr Ser Ile Leu
            260                 265                 270

Ala Ala Asn Asp Asp Met Val Phe Met His Val Asp Glu Pro Gly Asp
            275                 280                 285

Thr Gly Phe Gly Thr Ile Phe Thr Ser Asp Asp Arg Gly Ile Val Tyr
            290                 295                 300

Ser Lys Ser Leu Asp Arg His Leu Tyr Thr Thr Thr Gly Gly Glu Thr
305                 310                 315                 320

Asp Phe Thr Asn Val Thr Ser Leu Arg Gly Val Tyr Ile Thr Ser Val
                325                 330                 335

Leu Ser Glu Asp Asn Ser Ile Gln Thr Met Ile Thr Phe Asp Gln Gly
            340                 345                 350

Gly Arg Trp Thr His Leu Arg Lys Pro Glu Asn Ser Glu Cys Asp Ala
            355                 360                 365

Thr Ala Lys Asn Lys Asn Glu Cys Ser Leu His Ile His Ala Ser Tyr
370                 375                 380

Ser Ile Ser Gln Lys Leu Asn Val Pro Met Ala Pro Leu Ser Glu Pro
385                 390                 395                 400

Asn Ala Val Gly Ile Val Ile Ala His Gly Ser Val Gly Asp Ala Ile
                405                 410                 415

Ser Val Met Val Pro Asp Val Tyr Ile Ser Asp Asp Gly Gly Tyr Ser
                420                 425                 430

Trp Thr Lys Met Leu Glu Gly Pro His Tyr Tyr Thr Ile Leu Asp Ser
            435                 440                 445

Gly Gly Ile Ile Val Ala Ile Glu His Ser Ser Arg Pro Ile Asn Val
            450                 455                 460

Ile Lys Phe Ser Thr Asp Glu Gly Gln Cys Trp Gln Thr Tyr Thr Phe
465                 470                 475                 480
```

```
Thr Arg Asp Pro Ile Tyr Phe Thr Gly Leu Ala Ser Glu Pro Gly Ala
            485                 490                 495

Arg Ser Met Asn Ile Ser Ile Trp Gly Phe Thr Glu Ser Phe Leu Thr
            500                 505                 510

Ser Gln Trp Val Ser Tyr Thr Ile Asp Phe Lys Asp Ile Leu Glu Arg
        515                 520                 525

Asn Cys Glu Glu Lys Asp Tyr Thr Ile Trp Leu Ala His Ser Thr Asp
        530                 535                 540

Pro Glu Asp Tyr Glu Asp Gly Cys Ile Leu Gly Tyr Lys Glu Gln Phe
545                 550                 555                 560

Leu Arg Leu Arg Lys Ser Ser Val Cys Gln Asn Gly Arg Asp Tyr Val
            565                 570                 575

Val Thr Lys Gln Pro Ser Ile Cys Leu Cys Ser Leu Glu Asp Phe Leu
            580                 585                 590

Cys Asp Phe Gly Tyr Tyr Arg Pro Glu Asn Asp Ser Lys Cys Val Glu
            595                 600                 605

Gln Pro Glu Leu Lys Gly His Asp Leu Glu Phe Cys Leu Tyr Gly Arg
        610                 615                 620

Glu Glu His Leu Thr Thr Asn Gly Tyr Arg Lys Ile Pro Gly Asp Lys
625                 630                 635                 640

Cys Gln Gly Gly Val Asn Pro Val Arg Glu Val Lys Asp Leu Lys Lys
            645                 650                 655

Lys Cys Thr Ser Asn Phe Leu Ser Pro Glu Lys
            660                 665

<210> SEQ ID NO 40
<211> LENGTH: 103
<212> TYPE: PRT
<213> ORGANISM: Homo sapiens
<220> FEATURE:
<221> NAME/KEY: MISC_FEATURE
<223> OTHER INFORMATION: NGF pro domain (amino acid residues 19 to 121
      of SEQ ID NO 6)

<400> SEQUENCE: 40

Glu Pro His Ser Glu Ser Asn Val Pro Ala Gly His Thr Ile Pro Gln
1               5                   10                  15

Val His Trp Thr Lys Leu Gln His Ser Leu Asp Thr Ala Leu Arg Arg
            20                  25                  30

Ala Arg Ser Ala Pro Ala Ala Ala Ile Ala Ala Arg Val Ala Gly Gln
        35                  40                  45

Thr Arg Asn Ile Thr Val Asp Pro Arg Leu Phe Lys Lys Arg Arg Leu
    50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg
            100

<210> SEQ ID NO 41
<211> LENGTH: 124
<212> TYPE: PRT
<213> ORGANISM: Homo sapiens
<220> FEATURE:
<221> NAME/KEY: MISC_FEATURE
<223> OTHER INFORMATION: NT propeptide (amino acid residues 17-140 of
      SEQ ID NO:8)

<400> SEQUENCE: 41
```

```
Gln Gly Asn Asn Met Asp Gln Arg Ser Leu Pro Glu Asp Ser Leu Asn
1               5                   10                  15

Ser Leu Ile Ile Lys Leu Ile Gln Ala Asp Ile Leu Lys Asn Lys Leu
            20                  25                  30

Ser Lys Gln Met Val Asp Val Lys Glu Asn Tyr Gln Thr Leu Pro
        35                  40                  45

Lys Ala Glu Ala Pro Arg Glu Pro Glu Arg Gly Gly Pro Ala Lys Ser
    50                  55                  60

Ala Phe Gln Pro Val Ile Ala Met Asp Thr Glu Leu Leu Arg Gln Gln
65                  70                  75                  80

Arg Arg Tyr Asn Ser Pro Arg Val Leu Leu Ser Asp Ser Thr Pro Leu
                85                  90                  95

Glu Pro Pro Pro Leu Tyr Leu Met Glu Asp Tyr Val Gly Ser Pro Val
            100                 105                 110

Val Ala Asn Arg Thr Ser Arg Arg Lys Arg Tyr Ala
            115                 120

<210> SEQ ID NO 42
<211> LENGTH: 103
<212> TYPE: PRT
<213> ORGANISM: Homo sapiens
<220> FEATURE:
<221> NAME/KEY: MISC_FEATURE
<223> OTHER INFORMATION: NGF pro-domain (amino acid residues 19-121 of
      SEQ ID NO 6)

<400> SEQUENCE: 42

Glu Pro His Ser Glu Ser Asn Val Pro Ala Gly His Thr Ile Pro Gln
1               5                   10                  15

Val His Trp Thr Lys Leu Gln His Ser Leu Asp Thr Ala Leu Arg Arg
            20                  25                  30

Ala Arg Ser Ala Pro Ala Ala Ala Ile Ala Ala Arg Val Ala Gly Gln
            35                  40                  45

Thr Arg Asn Ile Thr Val Asp Pro Arg Leu Phe Lys Lys Arg Arg Leu
    50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg
            100

<210> SEQ ID NO 43
<211> LENGTH: 228
<212> TYPE: PRT
<213> ORGANISM: Homo sapiens
<220> FEATURE:
<221> NAME/KEY: MISC_FEATURE
<223> OTHER INFORMATION: pro BDNF (amino acid residues 19-246 of SEQ ID
      NO 7)

<400> SEQUENCE: 43

Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Gly Leu Thr Ser Leu Ala Asp Thr Phe Glu His Val Ile
            35                  40                  45

Glu Glu Leu Leu Asp Glu Asp Gln Lys Val Arg Pro Asn Glu Glu Asn
```

```
                50                  55                  60
Asn Lys Asp Ala Asp Leu Tyr Thr Ser Arg Val Met Leu Ser Ser Gln
 65                  70                  75                  80

Val Pro Leu Glu Pro Pro Leu Leu Phe Leu Leu Glu Glu Tyr Lys Asn
                 85                  90                  95

Tyr Leu Asp Ala Ala Asn Met Ser Met Arg Val Arg Arg His Ser Asp
                100                 105                 110

Pro Ala Arg Arg Gly Glu Leu Ser Val Cys Asp Ser Ile Ser Glu Trp
            115                 120                 125

Val Thr Ala Ala Asp Lys Lys Thr Ala Val Asp Met Ser Gly Gly Thr
        130                 135                 140

Val Thr Val Leu Glu Lys Val Pro Val Ser Lys Gly Gln Leu Lys Gln
145                 150                 155                 160

Tyr Phe Tyr Glu Thr Lys Cys Asn Pro Met Gly Tyr Thr Lys Glu Gly
                165                 170                 175

Cys Arg Gly Ile Asp Lys Arg His Trp Asn Ser Gln Cys Arg Thr Thr
            180                 185                 190

Gln Ser Tyr Val Arg Ala Leu Thr Met Asp Ser Lys Lys Arg Ile Gly
        195                 200                 205

Trp Arg Phe Ile Arg Ile Asp Thr Ser Cys Val Cys Thr Leu Thr Ile
210                 215                 220

Lys Arg Gly Arg
225

<210> SEQ ID NO 44
<211> LENGTH: 109
<212> TYPE: PRT
<213> ORGANISM: Homo sapiens
<220> FEATURE:
<221> NAME/KEY: misc_feature
<223> OTHER INFORMATION: BDNF pro domain (amino acid residues 19-127 of
      SEQ ID NO:7)

<400> SEQUENCE: 44

Ala Pro Met Lys Glu Ala Asn Ile Arg Gly Gln Gly Gly Leu Ala Tyr
 1               5                  10                  15

Pro Gly Val Arg Thr His Gly Thr Leu Glu Ser Val Asn Gly Pro Lys
                20                  25                  30

Ala Gly Ser Gly Leu Thr Ser Leu Ala Asp Thr Phe Glu His Val Ile
            35                  40                  45

Glu Glu Leu Leu Asp Glu Asp Gln Lys Val Arg Pro Asn Glu Glu Asn
        50                  55                  60

Asn Lys Asp Ala Asp Leu Tyr Thr Ser Arg Val Met Leu Ser Ser Gln
 65                  70                  75                  80

Val Pro Leu Glu Pro Pro Leu Leu Phe Leu Leu Glu Glu Tyr Lys Asn
                 85                  90                  95

Tyr Leu Asp Ala Ala Asn Met Ser Met Arg Val Arg Arg
                100                 105

<210> SEQ ID NO 45
<211> LENGTH: 241
<212> TYPE: PRT
<213> ORGANISM: Homo sapiens
<220> FEATURE:
<221> NAME/KEY: MISC_FEATURE
<223> OTHER INFORMATION: Pro NT3 (amino acid residues 17-257 of SEQ ID
      NO:8)

<400> SEQUENCE: 45
```

Gln Gly Asn Asn Met Asp Gln Arg Ser Leu Pro Glu Asp Ser Leu Asn
1               5                   10                  15

Ser Leu Ile Ile Lys Leu Ile Gln Ala Asp Ile Leu Lys Asn Lys Leu
            20                  25                  30

Ser Lys Gln Met Val Asp Val Lys Glu Asn Tyr Gln Ser Thr Leu Pro
            35                  40                  45

Lys Ala Glu Ala Pro Arg Glu Pro Glu Arg Gly Gly Pro Ala Lys Ser
        50                  55                  60

Ala Phe Gln Pro Val Ile Ala Met Asp Thr Glu Leu Leu Arg Gln Gln
65                  70                  75                  80

Arg Arg Tyr Asn Ser Pro Arg Val Leu Leu Ser Asp Ser Thr Pro Leu
                85                  90                  95

Glu Pro Pro Pro Leu Tyr Leu Met Glu Asp Tyr Val Gly Ser Pro Val
                100                 105                 110

Val Ala Asn Arg Thr Ser Arg Arg Lys Arg Tyr Ala Glu His Lys Ser
            115                 120                 125

His Arg Gly Glu Tyr Ser Val Cys Asp Ser Glu Ser Leu Trp Val Thr
        130                 135                 140

Asp Lys Ser Ser Ala Ile Asp Ile Arg Gly His Gln Val Thr Val Leu
145                 150                 155                 160

Gly Glu Ile Lys Thr Gly Asn Ser Pro Val Lys Gln Tyr Phe Tyr Glu
                165                 170                 175

Thr Arg Cys Lys Glu Ala Arg Pro Val Lys Asn Gly Cys Arg Gly Ile
                180                 185                 190

Asp Asp Lys His Trp Asn Ser Gln Cys Lys Thr Ser Gln Thr Tyr Val
            195                 200                 205

Arg Ala Leu Thr Ser Glu Asn Asn Lys Leu Val Gly Trp Arg Trp Ile
        210                 215                 220

Arg Ile Asp Thr Ser Cys Val Cys Ala Leu Ser Arg Lys Ile Gly Arg
225                 230                 235                 240

Thr

<210> SEQ ID NO 46
<211> LENGTH: 124
<212> TYPE: PRT
<213> ORGANISM: Homo sapiens
<220> FEATURE:
<221> NAME/KEY: MISC_FEATURE
<223> OTHER INFORMATION: NT3 pro domain (amino acid residues 17-140 of
      SEQ ID NO:8)

<400> SEQUENCE: 46

Gln Gly Asn Asn Met Asp Gln Arg Ser Leu Pro Glu Asp Ser Leu Asn
1               5                   10                  15

Ser Leu Ile Ile Lys Leu Ile Gln Ala Asp Ile Leu Lys Asn Lys Leu
            20                  25                  30

Ser Lys Gln Met Val Asp Val Lys Glu Asn Tyr Gln Ser Thr Leu Pro
            35                  40                  45

Lys Ala Glu Ala Pro Arg Glu Pro Glu Arg Gly Gly Pro Ala Lys Ser
        50                  55                  60

Ala Phe Gln Pro Val Ile Ala Met Asp Thr Glu Leu Leu Arg Gln Gln
65                  70                  75                  80

Arg Arg Tyr Asn Ser Pro Arg Val Leu Leu Ser Asp Ser Thr Pro Leu
                85                  90                  95

Glu Pro Pro Pro Leu Tyr Leu Met Glu Asp Tyr Val Gly Ser Pro Val
                100                 105                 110

Val Ala Asn Arg Thr Ser Arg Arg Lys Arg Tyr Ala
        115                 120

<210> SEQ ID NO 47
<211> LENGTH: 186
<212> TYPE: PRT
<213> ORGANISM: Homo sapiens
<220> FEATURE:
<221> NAME/KEY: MISC_FEATURE
<223> OTHER INFORMATION: proNT 4/5 (amino acid residues 25-210 of SEQ ID
      NO 9)

<400> SEQUENCE: 47

Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
        35                  40                  45

Ala Pro Ala Asn Arg Ser Arg Arg Gly Val Ser Glu Thr Ala Pro Ala
    50                  55                  60

Ser Arg Arg Gly Glu Leu Ala Val Cys Asp Ala Val Ser Gly Trp Val
65                  70                  75                  80

Thr Asp Arg Arg Thr Ala Val Asp Leu Arg Gly Arg Glu Val Glu Val
                85                  90                  95

Leu Gly Glu Val Pro Ala Ala Gly Gly Ser Pro Leu Arg Gln Tyr Phe
            100                 105                 110

Phe Glu Thr Arg Cys Lys Ala Asp Asn Ala Glu Glu Gly Gly Pro Gly
        115                 120                 125

Ala Gly Gly Gly Gly Cys Arg Gly Val Asp Arg Arg His Trp Val Ser
    130                 135                 140

Glu Cys Lys Ala Lys Gln Ser Tyr Val Arg Ala Leu Thr Ala Asp Ala
145                 150                 155                 160

Gln Gly Arg Val Gly Trp Arg Trp Ile Arg Ile Asp Thr Ala Cys Val
                165                 170                 175

Cys Thr Leu Leu Ser Arg Thr Gly Arg Ala
            180                 185

<210> SEQ ID NO 48
<211> LENGTH: 56
<212> TYPE: PRT
<213> ORGANISM: Homo sapiens
<220> FEATURE:
<221> NAME/KEY: MISC_FEATURE
<223> OTHER INFORMATION: NT4/5 pro domain (amino acid residues 25-80 of
      SEQ ID NO 9)

<400> SEQUENCE: 48

Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
        35                  40                  45

Ala Pro Ala Asn Arg Ser Arg Arg
    50                  55

<210> SEQ ID NO 49
<211> LENGTH: 44
<212> TYPE: PRT
<213> ORGANISM: Homo sapiens

```
<220> FEATURE:
<221> NAME/KEY: MISC_FEATURE
<223> OTHER INFORMATION: Sortilin propeptide (amino acid residues 34-77
      of SEQ ID NO:1)

<400> SEQUENCE: 49

Gln Asp Arg Leu Asp Ala Pro Pro Pro Ala Ala Pro Leu Pro Arg
1               5                   10                  15

Trp Ser Gly Pro Ile Gly Val Ser Trp Gly Leu Arg Ala Ala Ala
            20                  25                  30

Gly Gly Ala Phe Pro Arg Gly Gly Arg Trp Arg Arg
        35                  40

<210> SEQ ID NO 50
<211> LENGTH: 25
<212> TYPE: PRT
<213> ORGANISM: Homo sapiens
<220> FEATURE:
<221> NAME/KEY: misc_feature
<223> OTHER INFORMATION: Sortilin propeptide fragment (amino acid
      residues 37-61 of SEQ ID NO:1)

<400> SEQUENCE: 50

Leu Asp Ala Pro Pro Pro Ala Ala Pro Leu Pro Arg Trp Ser Gly
1               5                   10                  15

Pro Ile Gly Val Ser Trp Gly Leu Arg
            20                  25

<210> SEQ ID NO 51
<211> LENGTH: 20
<212> TYPE: PRT
<213> ORGANISM: Homo sapiens
<220> FEATURE:
<221> NAME/KEY: MISC_FEATURE
<223> OTHER INFORMATION: Peptide-4

<400> SEQUENCE: 51

Ile Thr Val Asp Pro Arg Leu Phe Lys Lys Arg Arg Leu Arg Ser Pro
1               5                   10                  15

Arg Val Leu Phe
            20

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Ala Ala Ala Ala Ala Ala Ala Ala Ala Ala
1               5                   10
```

US 8,377,701 B2

SPECIFIC LIGANDS TO SORTILIN

CROSS-REFERENCE TO RELATED APPLICATIONS

The present application is a §371 U.S. National Stage Application of International Application No. PCT/DK2009/050099, filed Apr. 27, 2009, which claims the benefit of priority under 35 U.S.C. §119(a)-(d) of Danish Patent Application No. PA200800592, filed Apr. 27, 2008. Each of these applications is hereby incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

All patent and non-patent references cited in the application, or in the present application, are hereby incorporated by reference in their entirety.

FIELD OF INVENTION

The present invention relates to the three dimensional structure of a Vps10p-domain receptor described by the atomic coordinates obtained by X-ray crystallography of the human receptor Sortilin. The invention further relates to methods of growing crystals of Sortilin. Based on the three dimensional structure, detailed information regarding specific functionalities of Sortilin is obtained. The invention further relates to methods for screening, identification and/or design of specific ligands of Vps10p-domain receptors based on the crystal structure of Sortilin. The present invention furthermore relates to preparation and use of said ligands for inhibiting the formation of a ternary complex between Sortilin, p75$^{NTR}$ and proneurotrophins such as pro-NGF and proBDNF. The invention further relates to identification of ligands capable of acting as agonists of Sortilin. The present invention also relates to the preparation and use of such ligands for treating disease damage or disorders of the central and peripheral nervous systems.

BACKGROUND OF INVENTION

Sortilin (SEQ ID NO:1) sometimes also referred to as Neurotensin receptor 3 (NTR3), Glycoprotein 95 (Gp95) or 100 kDa NT receptor of Swiss Prot ID No. Q99523 is the archetypical member of a mammalian family of neuronal receptors (1-3) defined by the unique Vps10p-domain (Vps10p-D) that among other ligands binds neurotrophic factors and neuropeptides (4-8). This domain constitutes the entire luminal part of Sortilin (sSortilin) and is activated for ligand binding by enzymatic propeptide cleavage (4, 5). Sortilin is a multifunctional type-1 receptor capable of endocytosis as well as intracellular sorting (9-11), and as shown recently, it also engages in signaling by triggering proneurotrophin-induction of p75$^{NTR}$-mediated neuronal apoptosis (6, 7, 12, 13). Sortilin is synthesized as a proprotein, which is converted to mature Sortilin by enzymatic cleavage and removal of a short N-terminal propeptide. Only the mature receptor binds ligands and interestingly, all its known ligands, e.g. Neurotensin (NT; SEQ ID NO:10), lipoprotein lipase, the proforms of nerve growth factor-β (proNGF) and brain derived neurotrophic factor (proBDNF), receptor associated protein (RAP), and its own propeptide, compete for binding (5-7, 10), indicating that the diverse ligands target a shared or partially shared binding site. NT is a tridecapeptide, which binds to Sortilin, SorLA (another Vps10p-D receptor) and the two G-protein coupled receptors NTR1 and NTR2 (4, 14-16). The physiological role of NT in relation to Sortilin has not been fully elucidated (17), still NT is an important tool, as it inhibits all other ligands from binding to the Sortilin Vps10p-D.

SUMMARY OF THE INVENTION

In a main aspect, the present invention relates to a crystal comprising
  a) a polypeptide of SEQ ID NO. 1;
  b) a sequence variant of said polypeptide wherein the variant has at least 60% sequence identity to said SEQ ID NO. 1;
  c) a fragment comprising at least 200 contiguous amino acids of any of a) through b), wherein the fragment exhibits sortilin activity,
  d) any of a) through c) in complex with at least one ligand.

In a further aspect, the present invention furthermore relates to a method of growing a crystal comprising the steps of:
  a. obtaining a composition comprising 4.5 to 5.5 mg/mL of a polypeptide of Sortilin (SEQ ID NO. 1) or a fragment or variant thereof, in a buffer containing 50 mM Tris-HCl pH 7.9 and 150 mM NaCl,
  b. mixing said composition with Neurotensin (SEQ ID NO:10) at a molar ratio of:
    i. 1:1.5 to 1:15 (sSortilin (SEQ ID NO: 33): NT (SEQ ID NO:10) or,
    ii. 1:4 (sSortilin (SEQ ID NO: 33): NT propeptide (residues 17-140 of SEQ ID NO:8; SEQ ID NO:41),
  c. subjecting equal volumes of said composition and a crystallization solution respectively, said crystallization solution containing
    iii. 18-21% w/v PEG 6000, and
    iv. 0-15% Glycerol, and
    v. Tris-HEPES pH 7.2-7.8 (40-93 mM Tris and 100 mM HEPES) or 100 mM Tris-HCl pH 7.9, 3-6% glycerol and
    vi. 300-900 mM NaCl or 150-400 mM $C_3H_2Na_2O_4$ wherein said $C_3H_2Na_2O_4$ is adjusted to pH 6-7.5 by malonic acid, or 300-500 mM LiSO$_4$ or 500-700 mM KCl and,
  d. obtaining crystals comprising Sortilin (SEQ ID NO. 1) or a fragment or variant thereof.

In another aspect the present invention relates to a computer-readable data storage medium comprising a data storage material encoded with at least a portion of the structure coordinates of Sortilin as set forth in any of FIGS. 17 to 20.

In yet another aspect the present invention relates to use of atomic coordinates of sSortilin (SEQ ID NO:33) as presented in any of FIGS. 17 to 20 or atomic coordinates selected from a three-dimensional structure that deviates from the three-dimensional structure as presented in any of FIGS. 17 to 20 by a root mean square deviation over protein backbone atoms of not more than 3 Å in a method for identifying a ligand capable of binding to one or more of:
  a. binding site 1, or
  b. binding site 2, or
  c. binding site 3,
    or a fragment or variant of a through c.

In a further aspect the present invention relates to a method of identifying a ligand capable of binding to binding site 1 and/or binding site 2 and/or binding site 3 of SEQ ID NO. 1 (Sortilin), or a fragment or variant thereof said method comprising the steps of:
  a) generating the spatial structure of the binding site on a computer screen using atomic coordinates as presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å,
  b) generating potential ligands with their spatial structure on the computer screen, and
  c) selecting ligands that can bind to at least 1 amino acid residue of the set of binding interaction sites without steric interference.

In another aspect the present invention relates to a computer-assisted method for identifying a ligand of sortilin capable of binding to binding site 1 and/or binding site 2 and/or binding site 3 of Sortilin (SEQ ID NO. 1), or a fragment or variant thereof, using a programmed computer comprising a processor, a data storage system, a data input device and a data output device, comprising the following steps:
  a) inputting into the programmed computer through said input device data comprising: atomic coordinates of a subset of the atoms of said sortilin, thereby generating a criteria data set; wherein said atomic coordinates are selected from the three-dimensional structure presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å,
  b) comparing, using said processor, the criteria data set to a computer data base of low-molecular weight organic chemical structures and peptide fragments stored in the data storage system; and
  c) selecting from said data base, using computer methods, a chemical structure having a portion that is structurally complementary to the criteria data set and being free of steric interference with the receptor sortilin.

In yet another aspect the present invention relates to a method for identifying a ligand, said method comprising the steps of:
  a) selecting a potential ligand using atomic coordinates in conjunction with computer modelling, wherein said atomic coordinates are the atomic coordinates presented in any of FIGS. 17 to 20 or wherein the atomic coordinates are selected from a three-dimensional structure that deviates from the three-dimensional structure presented in any of FIGS. 17 to 20 by a root mean square deviation over protein backbone atoms of not more than 3 Å, by docking potential ligands into a set of binding interaction sites in binding site 1 and/or binding site 2 and/or binding site 3 of Sortilin (SEQ ID NO:1), or a fragment or variant thereof, said binding interaction generated by computer modelling and selecting a potential ligand capable of binding to at least one amino acid in said set of binding interaction sites of sortilin,
  b) providing said potential ligand and said receptor sortilin
  c) contacting the potential ligand with said receptor sortilin and
  d) detecting binding of said receptor sortilin by the potential ligand.

In a further aspect the present invention relates to a method of identifying a potential ligand of binding site 1 and/or binding site 2 and/or binding site 3 of sortilin, or a fragment or variant thereof said method comprising the steps of
  a) introducing into a computer, information derived from atomic coordinates defining a conformation of binding site 1 and/or binding site 2 and/or binding site 3 of Sortilin (SEQ ID NO:1), or a fragment or variant thereof, based on three-dimensional structure determination, whereby a computer program utilizes or displays on the computer screen the structure of said conformation; wherein said atomic coordinates are selected from the three-dimensional structure as presented in any of FIGS. 17 to 20 or atomic coordinates selected from a three-dimensional structure that deviates from any one of the tree-dimensional structure represented by any of FIGS. 17 to 20 by a root mean square deviation over protein backbone atoms of not more than 3 Å;
  b) generating a three-dimensional representation of binding site 1, binding site 2 or binding site 3 of sortilin by said computer program on a computer screen;
  c) superimposing a model of a potential ligand on the representation of said binding site 1, binding site 2 and binding site 3,
  d) assessing the possibility of bonding and the absence of steric interference of the potential ligand with binding site 1 (the high affinity neurotensin binding site), binding site 2 (the low affinity neurotensin binding site), binding site 3 (the pro-neurotrophin binding site) of Sortilin or a fragment or a variant thereof;
  e) incorporating said potential ligand compound in a binding assay of said receptor sortilin and
  f) determining whether said potential ligand inhibits binding of a competing ligand selected from the group consisting of amino acid residues 19 to 241 of proNGF (SEQ ID NO:6), amino acid residues 19 to 121 of SEQ ID NO 6 (NGF pro domain; SEQ ID NO:42), amino acid residues 19 to 246 of SEQ ID NO 7 (proBDNF; SEQ ID NO:43), amino acid residues 19 to 127 of SEQ ID NO 7 (BDNF pro domain; SEQ ID NO:44), amino acid residues 17 to 257 of SEQ ID NO 8 (proNT3; SEQ ID NO:45), amino acid residues 17 to 140 of SEQ ID NO 8 (NT3 pro domain; SEQ ID NO:46), amino acid residues 25 to 210 of SEQ ID NO 9 (proNT4/5; SEQ ID NO:47), amino acid residues 25 to 80 of SEQ ID NO 9 (NT4/5 pro domain; SEQ ID NO:48), SEQ ID NO. 10 (Neurotensin), SEQ ID NO. 11 (PYIL), amino acid residues 11 to 13 of SEQ ID NO. 10 (YIL) and SEQ ID NO. 12 (NT69L).

In another aspect the present invention relate to a method for building an atomic model of a Vps10p-domain receptor protein molecule comprising the steps of:
  a. identifying a Vps10p-domain receptor, or a fragment or variant thereof, having at least 20% sequence identity to SEQ ID NO. 1, and
  b. utilizing the atomic coordinates as presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å,
    to obtain an atomic model of the identified Vps10p-domain receptor by homology modelling.

In an important aspect the present invention relates to ligand compounds identified by the methods defined herein above.

In a further aspect the present invention relates to a ligand identified by the method described herein above, said ligand capable of binding to at least one interaction point of said binding site 1, said interaction points comprising $X_1, X_2, X_3, X_4, R_1, R_2, J_1, J_2$ and $J_3$ of FIG. 14 wherein $X_1$ comprises the amino acid residues R325, S316 and Y351 of SEQ ID NO:1, and wherein $X_2$ comprises the backbone carbonyl of Y351 of SEQ ID NO:1 and wherein $X_3$ comprises the backbone of I353 of SEQ ID NO:1 and wherein $X_4$ comprises the amino group of K260 of SEQ ID NO:1 and wherein $R_1$ comprises amino acid residues I327, F314, Y351, I353 and M363 of SEQ ID NO:1 and wherein $R_2$ comprises F350 of SEQ ID NO:1 and at least one amino acid from the loop comprising amino acid residues T397 to E401 of SEQ ID NO:1 and wherein $J_1$ comprises S305 of SEQ ID NO:1 and wherein $J_2$ comprises the backbone amide of F306 of SEQ ID NO:1 and wherein $J_3$ comprises the backbone carbonyl of F306 of SEQ ID NO:1.

In another aspect the present invention relates to a medicament comprising an inhibitor of Sortilin identified as described herein above.

In a further aspect the present invention relates to a the use of at least one ligand identified by the method described herein above, for the manufacture of a medicament, wherein said medicament is for the treatment of a disease, disorder, or damage of the nervous system in an individual.

In an important aspect, the present invention relates to a Vps10p-domain receptor ligand identified by the method defined herein, said ligand having the general structure of formula (I):

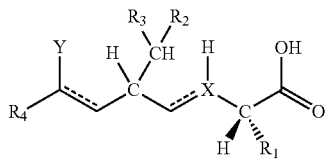

(I)

wherein X is an atom acting as hydrogen donor said atom selected from the group consisting of N, O, S, P and wherein Y is an electronegative atom acting as hydrogen bond acceptor selected from the group consisting of O, N, S, F, Cl, Br, I, and wherein $R_1$ is C3-6 alkyl, C4-6 cyclyl, a heterocyclic or a heteroaromatic structure having one ring, 4 to 6 ring members in each and 1 to 3 heteroatoms, or a heteroalkyl comprising 1 to 3 heteroatoms selected from the group consisting of N, O, $S(O)_{0-2}$, and wherein $R_2$ is a hydrogen, a C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, $S(O)_{0-2}$, and wherein $R_3$ is hydrogen, SH, imidazole, C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, S, and wherein $R_4$ is selected from the functional groups C1-100 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), thiocyanate, disulfide, a linker L2 or L3, and an amino acid sequence being at least 50% identical to SEQ ID NO: 10 or a fragment thereof.

In a further important aspect, the present invention relates to a Vps10p-domain receptor ligand identified by the method defined herein, said ligand having the general structure of formula (II):

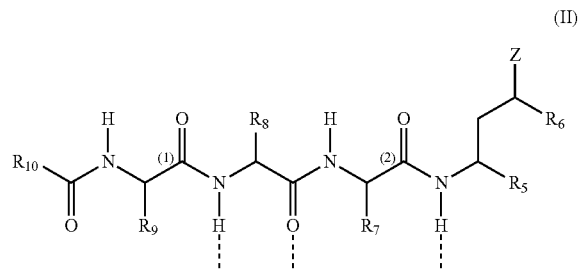

(II)

wherein Z is a hydrogen bond donor or acceptor selected from the group consisting of carbonyl, hydroxyl, amino, imino, amide, sulfhydryl, chloro, fluoro, and wherein $R_5$ is selected from the group consisting of H, $CH_3$, and a linker L2, and wherein $R_6$ is selected from the group consisting of H, —$CH_3$, —$CH_2CH_3$ and —$OCH_3$, and wherein $R_7$ is selected from the group consisting of side chains of glutamate, glutamine, lysine, arginine, histidine, tyrosine, methionine, cysteine, aliphatic C4-6 groups, and wherein $R_8$ is selected from the group consisting of side chains of tyrosine, histidine, serine, threonine, aspartate, asparagine, cysteine, phenylalanine, iodo-tyrosine and —$CH_2$—$NH_2$, and wherein $R_9$ is selected from the group consisting of side chain of lysine, arginine, glutamine, C3-8 aliphatic and heteroaliphatic groups, carbocyclic and heterocyclic groups comprising 5 or 6 membered rings, and wherein $R_{10}$ is selected from the group consisting of a pyroglutamate, poly-carbohydrates and a polypeptide of length greater than equal to 10, and wherein $R_{11}$ and $R_{12}$ individually are selected from the group consisting of H, C1-12 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), and wherein the covalent bonds (1) and (2) individually are selected from the group consisting of single bonds and double bonds.

In a very important aspect, the present invention relates to a Vps10p-domain receptor ligand identified by the method defined herein, said ligand having the general structure of formula (III):

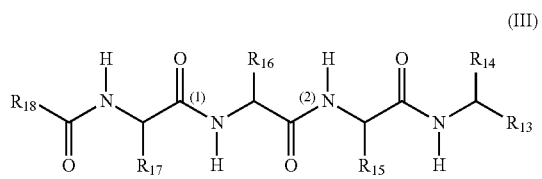

(III)

wherein $R_{13}$ is selected from the group consisting of H, C1-12 alkyl, alkenyl, alkynyl and a linker L3, and wherein $R_{14}$, $R_{15}$, $R_{17}$, $R_{19}$, $R_{20}$ individually are selected from the group consisting of H, C1-12 alkyl, alkenyl and alkynyl, and wherein $R_{16}$ is selected from the group consisting of sidechains of phenylalanine, leucine, isoleucine, valine, methionine, histidine, cysteine, lysine and aliphatic C3-7, and wherein $R_{18}$ is selected from the group consisting of H, —$CH_3$ and —$CH_2OH$, and wherein the covalent bonds (1) and (2) individually are selected from the group consisting of single bonds and double bonds.

In a further aspect, the present invention relates to a Vps10p-domain receptor ligand identified by the method defined herein, said ligand, wherein said ligand is RRPYI (chg) depicted in FIG. 26.

In a further aspect, the present invention relates to a Vps10p-domain receptor ligand identified by the method defined herein, said ligand, wherein said ligand is QIL depicted in FIG. 26.

In a further aspect, the present invention relates to a Vps10p-domain receptor ligand identified by the method defined herein, said ligand, wherein said ligand is YCL depicted in FIG. 26.

In a further aspect, the present invention relates to a Vps10p-domain receptor ligand identified by the method defined herein, said ligand, wherein said ligand is dYIL depicted in FIG. 26.

In a further aspect, the present invention relates to a Vps10p-domain receptor ligand identified by the method defined herein, said ligand, wherein said ligand is YHL depicted in FIG. 26.

In a further aspect, the present invention relates to a Vps10p-domain receptor ligand identified by the method defined herein, said ligand, wherein said ligand is RRPYI (acc) depicted in FIG. 26.

In a further aspect, the present invention relates to a Vps10p-domain receptor ligand identified by the method defined herein, said ligand, wherein said ligand is RRPYI (nMe)L depicted in FIG. 26.

In a further aspect, the present invention relates to a Vps10p-domain receptor ligand identified by the method defined herein, said ligand, wherein said ligand is YIL depicted in FIG. 26.

In another aspect the present invention relates to a method of treatment of a pathological condition in a subject comprising administering to an individual in need thereof a therapeutically effective amount of the medicament described herein above.

In a further aspect the present invention relates to a method of preventing apoptosis in a mammalian neuronal cell, said method comprising exposing said neuronal cell to the ligand molecule as defined herein above.

In a further aspect the present invention relates to a method of enhancing survival of a mammalian neuronal cell, said method comprising exposing said neuronal cell to the ligand molecule as defined herein above.

In a further aspect the present invention relates to a method of expanding a composition of mammalian cells, comprising administering to said composition the ligand molecule as defined herein above.

In a further aspect the present invention relates to a method of differentiating a composition of mammalian cells, comprising administering to said composition the ligand molecule as defined herein above.

In a further aspect the present invention relates to an antibody capable of binding to binding site 1 of SEQ ID NO. 1.

In a further aspect the present invention relates to an antibody capable of binding to binding site 2 of SEQ ID NO. 1.

In a further aspect the present invention relates to an antibody capable of binding to binding site 3 of SEQ ID NO. 1.

In a further aspect the present invention relates to an immunoconjugate comprising an antibody as described herein above and a conjugate selected from the group consisting of: a cytotoxic agent such as a chemotherapeutic agent, a toxin, or a radioactive isotope; a member of a specific binding pair, such as avidin or streptavidin or an antigen; an enzyme capable of producing a detectable product.

DETAILED DESCRIPTION ON THE INVENTION

Definitions

Adjuvant: Any substance whose admixture with an administered immunogenic determinant/antigen increases or otherwise modifies the immune response to said determinant.

Affinity: The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Ligand binding is often characterized in terms of the concentration of ligand at which half of the receptor binding sites are occupied, known as the dissociation constant ($k_d$).

Alcohol: A class of organic compounds containing one or more hydroxyl groups (OH). In this context a saturated or unsaturated, branched or unbranched hydrocarbon group sitting as a substituent on a larger molecule.

Alicyclic group: the term "alicyclic group" means a cyclic hydrocarbon group having properties resembling those of aliphatic groups.

Aliphatic group: in the context of the present invention, the term "aliphatic group" means a saturated or unsaturated linear or branched hydrocarbon group. This term is used to encompass alkyl, alkenyl, and alkynyl groups, for example.

Alkyl group: the term "alkyl group" means a saturated linear or branched hydrocarbon group including, for example, methyl, ethyl, isopropyl, t-butyl, heptyl, dodecyl, octadecyl, amyl, 2-ethylhexyl, and the like.

Alkenyl group: the term "alkenyl group" means an unsaturated, linear or branched hydrocarbon group with one or more carbon-carbon double bonds, such as a vinyl group.

Alkynyl group: the term "alkynyl group" means an unsaturated, linear or branched hydrocarbon group with one or more carbon-carbon triple bonds.

Amphiphil: substance containing both polar, water-soluble and nonpolar, water-insoluble groups.

Agonist: An agonist is a compound capable of increasing the activity of an effector such as a receptor. Specifically, a Sortilin agonist is a compound capable of binding to one or more of binding sites 1, 2 and 3 thereby inducing the same physiological response as a given endogenous agonist ligand compound.

Antagonist: An antagonist is a compound capable of decreasing the activity of an effector such as a receptor. Specifically, a Sortilin antagonist is a compound capable of binding to one or more of binding sites 1, 2 and 3 thereby inhibiting binding of another ligand thus inhibiting a physiological response.

Apoptosis: Apoptosis is a process of suicide by a cell in a multi-cellular organism. It is one of the main types of programmed cell death (PCD), and involves an orchestrated series of biochemical events leading to a characteristic cell morphology and death.

Apoptosis inhibitor: Any compound capable of decreasing the process of apoptosis.

Aromatic group: the term "aromatic group" or "aryl group" means a mono- or poly-cyclic aromatic hydrocarbon group.

Binding: The term "binding" or "associated with" refers to a condition of proximity between chemical entities or compounds, or portions thereof. The association may be non-covalent-wherein the juxtaposition is energetically favoured by hydrogen bonding or van der Waals or electrostatic interactions-or it may be covalent.

Binding site: The term "binding site" or "binding pocket", as used herein, refers to a region of a molecule or molecular complex that, as a result of its shape, favourably associates with another molecule, molecular complex, chemical entity or compound. As used herein, the pocket comprises at least a deep cavity and, optionally a shallow cavity.

Binding site 1: A high affinity binding site of neurotensin or synonymously binding site 1 is a binding site of sortilin (SEQ ID NO. 1) having high affinity for neurotensin or a fragment or variant of neurotensin, and having affinity for the sortilin propeptide or a fragment thereof (Amino acid residues 34-77 of SEQ ID NO. 1) said binding site comprising amino acid residues R325, S316, Y351, I353, K260, I327, F314, F350 to M363, S305, F306, T398 to G400, I303-G309, Q349-A356, Y395 and T402 of SEQ ID NO. 1. More preferably, binding site 1 comprises amino acids R325, S316, Y351, I353, K260, I327, F314, F350 to M363, S305, F306 and T398 to G400 of SEQ ID NO. 1. Most preferably binding site 1 of sortilin comprises amino acids R325, S316, Y351, I353, K260, I327, F314 and F350 to M363 of SEQ ID NO. 1. Binding site 1 is a promiscuous binding site.

Binding site 2: A binding site of sortilin having low affinity for neurotensin or a fragment or variant of neurotensin, said binding site comprising amino acid residues L572, L114, V112, R109 to S111, S115 to G118, T570, G571, W586, W597, T168-I174, L572, A573 and S584 to F588 of SEQ ID NO. 1. More preferably the sortilin low affinity binding site of neurotensin comprises amino acids L572, L114, V112, R109 to S111, S115 to G118, T570, G571, W586 and W597 of SEQ ID NO. 1. Most preferably the sortilin low affinity binding site of neurotensin comprises amino acids L572, L114 and V112 of SEQ ID NO:1. Binding site 2 is promiscuous and may bind the propeptide of Sortilin (amino acid residues 34-77 of SEQ ID NO. 1).

Binding site 3: A promiscuous binding site of sortilin comprising amino acid residues D403, S420, D422, N423, S424, I425, E426, T451, Y466, E470, I498, S499 and V500 of SEQ ID NO. 1, more preferably comprising amino acid residues D403, N423, S424, I425, T451, Y466, I498 and V500 of SEQ ID NO. 1, most preferably comprising amino acid residues T451, Y466, I498 and V500 of SEQ ID NO. 1.

Bioreactive agent: The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Cerebral ischemia: Global cerebral ischemia is an ischemic condition where the brain does not receive enough blood flow to maintain normal neurological function.

Cationic group: A chemical group capable of functioning as a proton donor when a compound comprising the chemical group is dissolved in a solvent, preferably when dissolved in water.

Complex: As used herein the term "complex" refers to the combination of a molecule or a protein, conservative analogues or truncations thereof associated with a chemical entity.

Coordinate: The term "coordinate" as use herein, refers to the information of the three dimensional organization of the atoms contributing to a protein structure. The final map containing the atomic coordinates of the constituents of the crystal may be stored on a data carrier; typically the data is stored in PDB format or in mmCIF format, both of which are known to the person skilled in the art. However, crystal coordinates may as well be stored in simple tables or text formats. The PDB format is organized according to the instructions and guidelines given by the Research Col-laboratory for Structural Biology.

Crystal: The term "crystal" refers to an ordered state of matter. Proteins, by their nature are difficult to purify to homogeneity. Even highly purified proteins may be chronically heterogeneous due to modifications, the binding of ligands or a host of other effects. In addition, proteins are crystallized from generally complex solutions that may include not only the target molecule but also buffers, salts, precipitating agents, water and any number of small binding proteins. It is important to note that protein crystals are composed not only of protein, but also of a large percentage of solvents molecules, in particular water. These may vary from 30 to even 90%. Protein crystals may accumulate greater quantities and a diverse range of impurities which cannot be listed here or anticipated in detail. Frequently, heterogeneous masses serve as nucleation centers and the crystals simply grow around them. The skilled person knows that some crystals diffract better than others. Crystals vary in size from a barely observable 20 micron to 1 or more millimeters. Crystals useful for X-ray analysis are typically single, 0.05 mm or larger, and free of cracks and defects.

Cyclic group: the term "cyclic group" means a closed ring hydrocarbon group that is classified as an alicyclic group, aromatic group, or heterocyclic group.

Cycloalkenyl: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino.

Cycloalkyl: means a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Dipole-dipole interaction: The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Electrostatic interaction: The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent.

Form a ring: means that the atoms mentioned are connected through a bond when the ring structure is formed.

Fragments: The polypeptide fragments according to the present invention, including any functional equivalents thereof, may in one embodiment comprise less than 500 amino acid residues, such as less than 450 amino acid residues, for example less than 400 amino acid residues, such as less than 350 amino acid residues, for example less than 300 amino acid residues, for example less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues. Fragments of neurotensin include but is not limited to the C-terminal amino acids of neurotensin PYIL (SEQ ID NO:11) and YIL (residues 11-13 of SEQ ID NO:10).

Group: (Moiety/substitution) as is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety".

Heterocyclic group: the term "heterocyclic group" means a closed ring hydrocarbon in which one or more of the atoms in the ring is an element other than carbon (e.g., nitrogen, oxygen, sulphur, etc.). Heterocyclyl means a monovalent saturated cyclic radical, consisting of one to two rings, of three to eight atoms per ring, incorporating one or two ring heteroatoms (chosen from N, O or $S(O)_{0-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, aryl-aminocarbonyl, alkylcarbonylamino, or arylcarbonylamino.

Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Homology: The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1 to 13, respectively, are to be considered as falling within the scope of the present invention when they are preferably at least about 60 percent homologous, for example at least 65 percent homologous, for example at least 70 percent homologous, for example at least 75 percent homologous, for example at least 80 percent homologous, for example at least 85 percent homologous, for example at least 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined proneurotrophin activity modulator, or a fragment thereof, it may also be desirable to introduce non-conservative substitutions in any one or more positions of such a proneurotrophin activity modulator.

A non-conservative substitution leading to the formation of a functionally equivalent fragment of proneurotrophin activity modulator would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other pro-neurotrophin activity modulator fragments and/or proneurotrophin activity modulator molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of proneurotrophin activity modulator according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-neurotrophin activity modulator antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of proneurotrophin activity modulator can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the ligand of binding site 1, 2 or 3 is an oligopeptide synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of proneurotrophin activity modulator according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of sortilin inhibitors according to the invention are also provided and fall under the scope of the invention. Proneurotrophin activity modulator functional equivalents and variants can be produced as homodimers or heterodimers with other amino acid sequences or with native sortilin inhibitor sequences. Heterodimers include dimers containing immunoreactive sortilin inhibiting fragments as well as sortilin inhibiting fragments that need not have or exert any biological activity.

Sortilin inhibiting peptide fragments may be synthesised both in vitro and in vivo. Method for in vitro synthesis are well known, and methods being suitable or suitably adaptable to the synthesis in vivo of sortilin inhibitors are also described in the prior art. When synthesized in vivo, a host cell is transformed with vectors containing DNA encoding a sortilin peptide inhibitor or a fragment thereof. A vector is defined as a replicable nucleic acid construct. Vectors are used to mediate expression of proneurotrophin activity modulator. An expression vector is a replicable DNA construct in which a nucleic acid sequence encoding the predetermined sortilin inhibiting fragment, or any functional equivalent thereof that can be expressed in vivo, is operably linked to suitable control sequences capable of effecting the expression of the fragment or equivalent in a suitable host. Such control sequences are well known in the art. Both prokaryotic and eukaryotic cells may be used for synthesising ligands.

Cultures of cells derived from multicellular organisms however represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and W138, BHK, COS-7, 293 and MDCK cell lines. Preferred host cells are eukaryotic cells known to synthesize endogenous sortilin inhibitors. Cultures of such host cells may be isolated and used as a source of the fragment, or used in therapeutic methods of treatment, including therapeutic methods aimed at promoting or inhibiting a growth state, or diagnostic methods carried out on the human or animal body.

Hydrophobic bond: The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: The term "hydrophobic interaction" as used herein refers to any interaction occurring between essentially non-polar (hydrophobic) components located within attraction range of one another in a polar environment (e.g. water). As used herein, attraction range is on the scale of from 0.1 up to 2 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution.

Inhibiting: The term inhibiting as used herein refers to the prevention of binding between two or more components.

Ligands identified by the present invention are capable of inhibiting binding between a Vps10p-domain receptor and a pro-neurotrophin.

Inhibiting binding: The term inhibiting binding between a proneurotrophin and sortilin as used herein refer to a method of providing a ligand identified by the present invention said ligand being capable of preventing the binding of a pro-neurotrophin to binding site 3 of sortilin thus preventing formation of a ternary complex between sortilin, proNGF and p75$^{NTR}$ or any fragment or variant thereof. The term inhibiting binding may also refer to inhibiting binding of neurotensin and/or Sortilin propeptide to binding site 1 or 2 of the Vps10p-domain receptor Sortilin.

In vitro/in vivo: the terms are used in their normal meaning.

In silico: a method of performing an in vitro or in vivo operation by computer simulation.

Ischemia: Restriction in blood supply with resultant dysfunction or damage of tissue.

Ischemic tissue damage: Tissue damage due to ischemia.

Ligand: a substance or compound that is able to bind to and form a complex with a biomolecule to serve a biological purpose. In a narrower sense, it is a signal triggering molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors may alter the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters. Radioligands are radioisotope labeled compounds and used in vivo as tracers in PET studies and for in vitro binding studies.

Moieties of a particular compound cover group(s) or part(s) of said particular compound.

Pharmaceutical agent: The terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent," "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" encompass both the inactive drug and the active metabolite.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: "Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to i) a polynucleotide comprising a predetermined coding sequence, or ii) a polynucleotide encoding a predetermined amino acid sequence, or iii) a polynucleotide encoding a fragment of a polypeptide encoded by polynucleotides (i) or (ii), wherein said fragment has at least one predetermined activity as specified herein; and iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and v) a polynucleotide comprising a nucleotide sequence which is degenerate to the nucleotide sequence of polynucleotides (iii) or (iv);

or the complementary strand of such a polynucleotide.

Purified antibody: The term a "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Root mean square deviation: The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

Sequence identity: Sequence identity is determined in one embodiment by utilising fragments of proneurotrophin activity modulator peptides comprising at least 25 contiguous amino acids and having an amino acid sequence which is at least 80%, such as 85%, for example 90%, for example 91%, such as 92%, e.g. 93%, for example 94%, such as 95%, for example 96%, such as 97%, for example 98%, such as 99% identical to the amino acid sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9 and SEQ ID NO:10 respectively, or a fragment of any of said SEQ ID NOs. wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of SEQ ID NO:1, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO:1 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with one of the proneurotrophin activity modulator polypeptide sequences of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

Substituted lower alkyl means a lower alkyl having one to three substituents selected from the group consisting of hydroxyl, alkoxy, amino, amido, carboxyl, acyl, halogen, cyano, nitro and thiol.

Treatment: The term "treatment" as used herein refers to a method involving therapy including surgery of a clinical condition in an individual including a human or animal body. The therapy may be ameliorating, curative or prophylactic, i.e. reducing the risk of acquiring a disease.

Variants: The term "variants" as used herein refers to amino acid sequence variants said variants preferably having at least 60% identity, for example at least 63% identity, such as at least 66% identity, for example at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences. Examples of variants and fragments of neurotensin are listed in FIG. 26 and include but are not limited to RRPYI(chg) (SEQ ID NO:32), iodoYIL, QIL, YCL, dYIL, YHL, RRPYI(acc) (SEQ ID NO:32), RRPYI(nMe)L (SEQ ID NO:31), YIL. In one embodiment of the invention, the ligand is not NT69L (SEQ ID NO:12), NT8-13 (SEQ ID NO:31) or native Neurotensin (SEQ ID NO:10).

Up-regulation of expression: a process leading to increased expression of genes, preferably of endogenous genes.

Sortilin Crystal

To clarify the structural organization and ligand binding of the Vps10p-domain and of human Sortilin in particular, the present inventors have determined the crystal structures of sSortilin in complex with NT and with residues 4-29 of its own propeptide (at resolutions of 2.0 and 3.2 Å respectively). Data on the sSortilin:NT complex was obtained from crystals grown with a slight (molar ratio 1:1.5) as well as with a large (molar ratio 1:15) excess of NT. (See Example 5) The inventors have furthermore determined the structure of sSortilin in complex with the pro-domain of Nerve Growth Factor (NGF).

Accordingly, in one embodiment the present invention relates to a crystal comprising
  a) a polypeptide of SEQ ID NO. 1; and/or
  b) a sequence variant of said polypeptide wherein the variant has at least 60% sequence identity to said SEQ ID NO. 1; and/or
  c) a fragment comprising at least 200 contiguous amino acids of any of a) through b), wherein the fragment exhibits sortilin activity, and
  d) optionally any of a) through c) in complex with at least one ligand.

In one embodiment the crystal of the present comprises a sequence variant of SEQ ID NO. 1 wherein the variant has at least 50% sequence identity to SEQ ID NO. 1.

In a further embodiment the crystal of the present comprises a sequence variant of SEQ ID NO. 1 wherein the variant has at least 60% sequence identity to SEQ ID NO. 1.

In one embodiment the crystal of the present comprises a sequence variant of SEQ ID NO. 1 wherein the variant has at least 63% sequence identity to SEQ ID NO. 1.

In one embodiment the crystal of the present comprises a sequence variant of SEQ ID NO. 1 wherein the variant has at least 65% sequence identity to SEQ ID NO. 1.

In one embodiment the crystal of the present comprises a sequence variant of SEQ ID NO. 1 wherein the variant has at least 70% sequence identity to SEQ ID NO. 1.

In one embodiment the crystal of the present comprises a sequence variant of SEQ ID NO. 1 wherein the variant has at least 75% sequence identity to SEQ ID NO. 1.

In one embodiment the crystal of the present comprises a sequence variant of SEQ ID NO. 1 wherein the variant has at least 80% sequence identity to SEQ ID NO. 1.

In one embodiment the crystal of the present comprises a sequence variant of SEQ ID NO. 1 wherein the variant has at least 85% sequence identity to SEQ ID NO. 1.

In one embodiment the crystal of the present comprises a sequence variant of SEQ ID NO. 1 wherein the variant has at least 90% sequence identity to SEQ ID NO. 1.

In one embodiment the crystal of the present comprises a sequence variant of SEQ ID NO. 1 wherein the variant has at least 91% sequence identity to SEQ ID NO. 1.

In one embodiment the crystal of the present comprises a sequence variant of SEQ ID NO. 1 wherein the variant has at least 92% sequence identity to SEQ ID NO. 1.

In one embodiment the crystal of the present comprises a sequence variant of SEQ ID NO. 1 wherein the variant has at least 93% sequence identity to SEQ ID NO. 1.

In one embodiment the crystal of the present comprises a sequence variant of SEQ ID NO. 1 wherein the variant has at least 94% sequence identity to SEQ ID NO. 1.

In one embodiment the crystal of the present comprises a sequence variant of SEQ ID NO. 1 wherein the variant has at least 95% sequence identity to SEQ ID NO. 1.

In one embodiment the crystal of the present comprises a sequence variant of SEQ ID NO. 1 wherein the variant has at least 96% sequence identity to SEQ ID NO. 1.

In one embodiment the crystal of the present comprises a sequence variant of SEQ ID NO. 1 wherein the variant has at least 97% sequence identity to SEQ ID NO. 1.

In one embodiment the crystal of the present comprises a sequence variant of SEQ ID NO. 1 wherein the variant has at least 98% sequence identity to SEQ ID NO. 1.

In one embodiment the crystal of the present comprises a sequence variant of SEQ ID NO. 1 wherein the variant has at least 99% sequence identity to SEQ ID NO. 1.

In one embodiment the crystal of the present comprises a fragment comprising at least 50 contiguous amino acids of any of SEQ ID NO. 1.

In a further embodiment the crystal of the present comprises a fragment comprising at least 100 contiguous amino acids of any of SEQ ID NO. 1.

In a further embodiment the crystal of the present comprises a fragment comprising at least 200 contiguous amino acids of any of SEQ ID NO. 1.

In a further embodiment the crystal of the present comprises a fragment comprising at least 300 contiguous amino acids of any of SEQ ID NO. 1.

In a further embodiment the crystal of the present comprises a fragment comprising at least 400 contiguous amino acids of any of SEQ ID NO. 1.

In a further embodiment the crystal of the present comprises a fragment comprising at least 500 contiguous amino acids of any of SEQ ID NO. 1.

In a further embodiment the crystal of the present comprises a fragment comprising at least 600 contiguous amino acids of any of SEQ ID NO. 1.

In a further embodiment the crystal of the present comprises a fragment comprising at least 700 contiguous amino acids of any of SEQ ID NO. 1.

In a preferred embodiment of the present invention the at least one ligand is bound to binding site 1 (high affinity neurotensin binding site and sortilin propeptide binding site) comprising amino acid residues R325, S316, Y351, I353, K260, I327, F314, F350 to M363, S305, F306 and T398 to G400 of SEQ ID NO. 1.

In a more preferred embodiment of the present invention the at least one ligand is bound to binding site 1 (high affinity neurotensin binding site and sortilin propeptide binding site) comprising amino acid residues R325, S316, Y351, I353, K260, I327, F314 and F350 to M363 of SEQ ID NO. 1.

In a highly preferred embodiment of the present invention the at least one ligand is bound to binding site 1 (high affinity neurotensin binding site and sortilin propeptide binding site) comprising amino acid residues R325, S316, Y351, I353, K260, I327, F314 and F350 to M363 of SEQ ID NO. 1.

In another embodiment of the present invention the at least one ligand is bound to binding site 2 (low affinity neurotensin binding site and sortilin propeptide binding site) comprising amino acid residues L572, L114, V112, R109 to S111, S115 to G118, T570, G571, W586, W597, T168-I174, L572, A573 and S584 to F588 of SEQ ID NO. 1.

In yet another embodiment of the present invention the at least one ligand is bound to binding site 2 (low affinity neurotensin binding site and sortilin propeptide binding site) comprising amino acid residues L572, L114, V112, R109 to S111, S115 to G118, T570, G571, W586 and W597 of SEQ ID NO. 1.

In a preferred embodiment the at least one ligand of the present invention is bound to binding site 2 (low affinity neurotensin binding site and sortilin propeptide binding site) comprising amino acid residues L572, L114 and V112 of SEQ ID NO. 1.

In another preferred embodiment of the present invention the at least one ligand is bound to binding site 3 (neurotrophin-propeptide binding site) comprising amino acid residues D403, S420, D422, N423, S424, I425, E426, T451, Y466, E470, I498, S499 and V500 of SEQ ID NO. 1. As binding site 3 bind the pro-domain of neurotrophins, said binding site 3 may also bind the entire pro-neurotrophin. Accordingly binding site 3 may be referred to as pro-neurotrophin binding site or neurotrophin prodomain binding site or a synonymous expression of identical biochemical meaning.

In a more preferred embodiment the at least one ligand of the present invention is bound to binding site 3 (neurotrophin-propeptide binding site) comprising amino acid residues D403, N423, S424, I425, T451, Y466, I498 and V500 of SEQ ID NO. 1

In a highly preferred embodiment of the present invention the at least one ligand is bound to binding site 3 (neurotrophin-propeptide binding site) comprising amino acid residues T451, Y466, I498 and V500 of SEQ ID NO. 1.

In another embodiment of the present invention binding site 3 (the pro-neurotrophin binding site) is a proNGF binding site.

In another embodiment of the present invention binding site 3 (the pro-neurotrophin binding site) is a proBDNF binding site.

In another embodiment of the present invention binding site 3 (the pro-neurotrophin binding site) is a proNT3 binding site.

In another embodiment of the present invention binding site 3 (the pro-neurotrophin binding site) is a proNT4/5 binding site.

The crystal according to claim 1 wherein the polypeptide comprises amino acid residue no. 78 to 755 of SEQ ID NO. 1.

In another embodiment the crystal defined herein above is of a monoclinic space group.

In one embodiment the crystal of the monoclinic space group belong to space group C2.

In another embodiment the crystal defined herein above is of an orthorhombic space group.

In one embodiment the crystal of the orthorhombic space group is $P2_12_12_1$.

In another embodiment the crystal defined herein above is of a triclinic space group.

In one embodiment the crystal of the triclinic space group belong to space group P1.

In another embodiment of the present invention the crystal as defined herein above comprises a polypeptide variant comprising amino acid residues 78 to 755 (sSortilin) of SEQ ID NO. 1, or a fragment or variant thereof.

In one embodiment of the present invention the crystal as defined herein above comprises a sortilin polypeptide wherein one or more or all methionine(s) have been replaced by Se-methionine (seleno-methionine).

In another embodiment of the present invention the crystal as defined herein above comprises a polypeptide ligand selected from the group consisting of amino acid residues 19 to 241 of SEQ ID NO 6 (proNGF), amino acid residues 19 to 121 of SEQ ID NO 6 (NGF pro domain), amino acid residues 19 to 246 of SEQ ID NO 7 (proBDNF), amino acid residues 19 to 127 of SEQ ID NO 7 (BDNF pro domain), amino acid residues 17 to 257 of SEQ ID NO 8 (proNT3), amino acid residues 17 to 140 of SEQ ID NO 8 (NT3 pro domain), amino acid residues 25 to 210 of SEQ ID NO 9 (proNT4/5), amino acid residues 25 to 80 of SEQ ID NO 9 (NT4/5 pro domain), SEQ ID NO. 10 (Neurotensin), SEQ ID NO. 11 (PYIL), amino acid residues 11 to 13 of SEQ ID NO. 10 (YIL) or a fragment or variant thereof.

Method of Growing a Sortilin Crystal

In a further aspect, the present invention furthermore relates to a method of growing a sortilin crystal comprising the steps of:
a. obtaining a composition comprising 4.5 to 5.5 mg/mL of a polypeptide of Sortilin (SEQ ID NO:1) or a fragment or variant thereof, in a buffer containing 50 mM Tris-HCl pH 7.9 and 150 mM NaCl,
b. mixing said composition with Neurotensin (NT; SEQ ID NO:10) at a molar ratio of:
vii. 1:1.5 to 1:15 (sSortilin (SEQ ID NO:33):NT (SEQ ID NO:10) or,
viii. 1:4 (sSortilin (SEQ ID NO:33):propeptide (SEQ ID NO:49),
c. subjecting equal volumes of said composition and a crystallization solution respectively, said crystallization solution containing
ix. 18-21% w/v PEG 6000, and
x. 0-15% Glycerol, and xi. Tris-HEPES pH 7.2-7.8 (40-93 mM Tris and 100 mM HEPES) or 100 mM Tris-HCl pH 7.9, 3-6% glycerol and xii. 300-900 mM NaCl or 150-400 mM $C_3H_2Na_2O_4$ wherein said $C_3H_2Na_2O_4$ is adjusted to pH 6-7.5 by malonic acid, or 300-500 mM $LiSO_4$ or 500-700 mM KCl and, d. obtaining crystals comprising SEQ ID NO. 1 or a fragment or variant thereof.

In a further embodiment of the present invention the cysteine residues of SEQ ID NO. 1 are replaced by selenomethionine.

In another embodiment of the present invention the method of obtaining crystals as defined herein above further comprises the steps of:

a. isolating an initial precipitate and
b. growing these by vapour diffusion from hanging drops.

In yet another embodiment of the present invention the crystal as defined herein above further comprises a ligand bound to Sortilin for determination of the three dimensional structure of Sortilin or a fragment or variant thereof in complex with said ligand.

Sortilin Structure

The inventors have found that residues 78-609 of Sortilin (SEQ ID NO. 1) constitute the first example of a 10-bladed β-propeller. Long extensions are found both between the four-stranded up-and-down blades and between individual β-strands of the blades (FIG. 1A). The smaller 10 cysteine containing C-terminal part (10 CC), residues 610-758, presents itself as two similar structural domains with an overall shape and architecture reminiscent of the cysteine-rich domains found in $p75^{NTR}$ (18) (FIG. 1B). The interface between the two 10 CC domains and the propeller domain comprises extensive hydrophobic and electrostatic interactions and covers approximately 180° of one face of the propeller.

Overall the propeller domain is oval-shaped and forms a wide slightly conical tunnel narrowing towards the side of the 10 CC-interacting face. In the equatorial plane the cross section of the tunnel is approximately 25 by 40 Å (FIG. 1C+D). Access to the tunnel from the narrow 10 CC-interacting side is furthermore partially blocked by an Asn406-linked glycosylation located on the inner rim at the end of strand one of blade 7 (FIG. 1C+D). Two more glycosylations are found at Asn162 and Asn582, both on the outer rim and both on the 10 CC interacting side of the propeller.

Notably, two protruding hydrophobic loops connecting strand two and three of blades 1 and 10 emerge from the opposite face (FIG. 1B), suggesting that this face, and the loops in particular, might mediate contact with the cell membrane or serve in interactions with other proteins.

In both structures of sSortilin in complex with NT, the inventors have found that the four C-terminal residues (Pro10-Tyr11-Ile12-Leu13) of NT (residues 10-13 of SEQ ID NO:10) form a short β-strand to strand one of blade 6 (referred to herein as the high affinity NT binding site). The hydroxyl group of Tyr11 forms a hydrogen bond to Lys260 of Sortilin (SEQ ID NO:1), and the C-terminal leucine fits into a hydrophobic pocket formed by Phe314, Ile327 and Ile353 of SEQ ID NO:1. However, the major contribution to binding is clearly the C-terminal carboxylate of NT, which forms a salt bridge with the guanidinium group of Arg325 of SEQ ID NO:1 and hydrogen bonds to the side chain of Ser316 and the main chain amide of Tyr351 of SEQ ID NO:1 (FIG. 2B).

In the structure determined with a large excess of NT two additional binding sites are found. Binding site 2 (FIG. 2A) is found at the inner rim of the propeller. Here the N-terminal half of Neurotensin (residues 2-6 of SEQ ID NO:10) is modelled as a short β-strand interacting with the first strand of blade 1. No specific side chain interactions with the receptor are observed in this site (FIG. 2B). The distance from Cα of Lys6 to Cα of Pro10 is 17.7 Å and no electron density is present in the intervening region. Hence, the inventors conclude that at high concentration of NT two molecules are bound inside the propeller.

The results presented above indicate that Sortilin has a high affinity binding site for the C-terminus of NT, and a secondary low affinity subsite engaging the N-terminal part of the peptide. Accordingly, the inventors examined the ability of NT-derived fragments to inhibit Sortilins binding of its own propeptide (Sort-pro). It has previously been shown (5) that the binding of Sort-pro is completely abolished in the presence of 5 fold excess of NT and the C-terminal peptide Arg9-Pro-Tyr-Ile-Leu13 (residues 9-13 of SEQ ID NO:10) is equally effective (FIG. 3A). In contrast, the present inventors have found that both the N-terminal peptide NT(1-8) (residues 1-8 of SEQ ID NO:10) and Arg8-Arg-Pro-Tyr-Ile-Leu13-NH2 (residues 8-13 of SEQ ID NO:10) i.e. with the terminal carboxylate replaced by amide, fails to inhibit (FIG. 3A+B), whereas the C-terminal tripeptide Tyr11-Ile-Leu13 of SEQ ID NO:10 proves sufficient for full inhibition of Sort-pro binding (FIG. 3B). Tyr11-Ile-Leu13 of SEQ ID NO:10 also hampers binding of the prodomain of NGF (FIG. 3C) and RAP (FIG. 3D) although not as efficiently as full length NT. The latter indicates that proNGF and RAP could be subjects to sterical hindrance and have different or more extended binding sites than Tyr11-Ile-Leu13 of SEQ ID NO:10.

Neurotensin and Sort-pro (residues 34-77 of SEQ ID NO:1) have no sequence similarity. Yet, the structure of sSortilin in complex with a fragment of Sort-pro (residues 4-29; corresponding to residues 37-62 of SEQ ID NO:1) shows both binding sites inside the propeller to be occupied (FIGS. 2C-E). The density for the peptide is strong but not sufficiently defined to allow modelling of the peptide. However, an overlay with the sSortilin:NT structure clearly shows that the Sort-pro density overlaps with that of the C- and N-terminal parts of NT (FIG. 2C+D) and fills the cavity in between (FIG. 2E). Since the propeptide does not contain a Tyr-Ile-Leu motif and its binding does not depend on a free C-terminus (8), it could be speculated that an intrinsic acidic residue in Sort-pro or other ligands, e.g. proNGF, may assume a role in binding similar to that of the C-terminal Leu-carboxylate of NT.

To investigate this, the inventors generated sSortilin-mutant constructs in which either Ser316 or Arg325 of Sortilin (SEQ ID NO:1) were exchanged for Glu and Ala respectively. The S316E mutant was subsequently expressed and purified, whereas the R325A mutant proved unstable and disintegrated during the purification procedure. Interestingly both mutants were seriously delayed in secretion (FIG. 4A), an effect also observed for Sortilin expressed without the propeptide (8). The S316E displayed no binding of Sort-pro but did bind the NGF-prodomain and BDNF with affinities similar to that of wtSortilin. As expected the presence of NT had no effect on binding of the NGF-prodomain to the S316E mutant. These results strongly support the finding that Sort-pro and NT bind to the same structural site (binding site 1 and 2), and that other ligands, e.g. pro-domains of neurotrophins such as but not limited to NGF-prodomain and the full pro-NGF, bind at a closely situated but independent separate site (binding site 3).

Accordingly, in an embodiment of the present invention, ligands are designed to specifically bind to one or more of the three binding sites of sortilin. Accordingly said ligands are capable of inhibiting binding of endogenous ligands to the same site. Said endogenous ligands are selected from the group consisting of neurotensin, propeptide of sortilin, p75$^{NTR}$ and pro-neurotrophins, said pro-neurotrophins selected from the group consisting of pro-NGF, proBDNF, pro-NT3 and proNT4/5.

The pairwise sequence identity between Sortilin from eight species is within 60-95%. Sequence alignment (FIG. 5) maps large patches of conserved residues to the inner surface of the propeller cavity and smaller scattered patches to the outer rim and to the 10 CC domain (FIG. 1E). The pattern of conservation in the cavity would agree with the presence of additional or supplementary binding sites and suggests that such alternative sites might implicate other propeller blades in formation of β-strand interactions. The existence of alternative sites is evidently an important point as several ligands target Sortilin. It is well known that the full length ligands all compete for binding, but the efficiency of competition varies and not all are effectively antagonized by the Tyr-Ile-Leu tripeptide. Accordingly, it is likely that all ligands must bind inside the propeller cavity in overlapping sites. Thus, small peptides like Tyr-Ile-Leu, may inhibit by occupying highly specific shared sites, whereas larger ligands may provide additional inhibition by blocking access to the confined space of the cavity.

In summary, the inventors have determined the first known structure of a member of the Vps10p-D protein family and of an NT-binding receptor. The results disclose that in fact the Vps10p-D consists of two distinct but structurally interdependent domains, i.e. the first example of a 10 bladed β-propeller and the 10 CC composed of two similar structural domains. The propeller tunnel comprises the ligand binding region of Sortilin, and we have mapped the specific sites for its interaction with NT and its own propeptide. In addition we have demonstrated that an essential part of the recognition site for the proneurotrophins also are located within this area. The finding that the tripeptide Tyr-Ile-Leu targets Sortilin with high affinity, provides the first NT-derived ligand with a potential to discriminate between Sortilin, SorLA and the G-protein coupled NTRs and it opens for design of specific inhibitors that may reduce apoptosis mediated by the Sortilin: p75$^{NTR}$:proNGF complex. Finally, our structure and binding analysis may prove useful in future modeling of structures and interactions of other Vps10p-D receptors, and in the study of their putative roles in diseases like diabetes and Alzheimers disease (19-21).

In another aspect the present invention relates to a computer-readable data storage medium comprising a data storage material encoded with at least a portion of the structure coordinates of Sortilin as set forth in any of FIGS. 17 to 20.

In a further aspect the present invention relates to the use of the atomic coordinates of sSortilin (SEQ ID NO:33) as presented in any of FIGS. 17 to 20 or atomic coordinates selected from a three-dimensional structure that deviates from the three-dimensional structure as presented in any of FIGS. 17 to 20 by a root mean square deviation over protein backbone atoms of not more than 3 Å in a method for identifying a ligand capable of binding to one or more of:
 a. binding site 1, or
 b. binding site 2, or
 c. binding site 3,
 or a fragment or variant of a through c.

In yet another aspect the present invention relate to use of the crystal as described herein above for determination of the three dimensional structure of Sortilin or a fragment or variant thereof.

In yet another aspect the present invention relates to use of atomic coordinates of sSortilin (SEQ ID NO:33) as presented in any of FIGS. 17 to 20 or atomic coordinates selected from a three-dimensional structure that deviates from the three-dimensional structure as presented in any of FIGS. 17 to 20 by a root mean square deviation over protein backbone atoms of not more than 3 Å in a method for identifying a ligand capable of binding to one or more of:
 a. binding site 1, or
 b. binding site 2, or
 c. binding site 3,
 or a fragment or variant of a through c.

Methods of Ligand Identification and Design

The present invention provide methods for identification and design of ligands capable of binding specifically to any of the three binding sites (1, 2 and 3) of Sortilin as defined herein above.

In a preferred embodiment identified and designed ligands are potential inhibitors of sortilin thereby preventing binding of Sortilin to the pro-domain of neurotrophins, especially the pro-domains of proNGF and proBDNF.

A potential inhibitor may then be designed de novo in conjunction with computer modelling. Models of chemical structures or molecule fragments may be generated on a computer screen using information derived from known low-molecular weight organic chemical structures stored in a computer data base or are built using the general knowledge of an organic chemist regarding bonding types, conformations etc. Suitable computer programs may aid in this process in order to build chemical structures of realistic geometries. Chemical structures or molecule fragments may be selected and/or used to construct a potential inhibitor such that favourable interactions to said subset or criteria data set become possible. The more favourable interactions become possible, the stronger the potential inhibitor will bind to sortilin. Preferably, favourable interactions to at least one amino acid residues should become possible. Such favourable interactions may occur with any atom of the amino acid residue e.g. atoms of the peptide back-bone or/and atoms of the side chains.

Favourable interactions are any non-covalent attractive forces which may exist between chemical structures such as hydrophobic or van-der-Waals interactions and polar interactions such as hydrogen bonding, salt-bridges etc. Unfavourable interactions such as hydrophobic-hydrophilic interactions should be avoided but may be accepted if they are weaker than the sum of the attractive forces. Steric interference such as clashes or overlaps of portions of the inhibitor being selected or constructed with protein moieties will prevent binding unless resolvable by conformational changes. The binding strength of a potential inhibitor thus created may be assessed by comparing favourable and unfavourable interactions on the computer screen or by using computational methods implemented in commercial computer programs.

Conformational freedom of the potential inhibitor and amino acid side chains of the sortilin should be taken into account. Accessible conformations of a potential inhibitor may be determined using known rules of molecular geometry, notably torsion angles, or computationally using computer programs having implemented procedures of molecular mechanics and/or dynamics or quantum mechanics or combinations thereof.

A potential inhibitor is at least partially complementary to at least a portion of the binding site 1, binding site 2 or binding site 3 of Sortilin in terms of shape and in terms of hydrophilic or hydrophobic properties.

Databases of chemical structures (e.g. cambridge structural database or from Chemical Abstracts Service; for a review see: Rusinko (1993) Chem. Des. Auto. News 8, 44-47) may be used to varying extents. In a totally automatic embodiment, all structures in a data base may be compared to the active site or to the binding pockets of the sortilin for complementarity and lack of steric interference computationally using the processor of the computer and a suitable computer program. In this case, computer modelling which comprises manual user interaction at a computer screen may not be necessary. Alternatively, molecular fragments may be selected from a data base and assembled or constructed on a computer screen e.g. manually. Also, the ratio of automation to manual interaction by a person skilled in the art in the process of selecting may vary a lot. As computer programs for drug design and docking of molecules to each other become better, the need for manual interaction decreases.

Programs usable for computer modelling include Quanta (Molecular Simulations, Inc.) and Sibyl (Tripos Associates). Other useful programs are Autodock (Scripps Research Institute, La Jolla, described in Goodsell and Olsen (1990) Proteins: Structure, Function and Genetics, 8, 195-201), Dock (University of California, San Francisco, described in: Kuntz et al. (1982) J. Mol. Biol. 161, 269-288.

In a further aspect the present invention relates to a method of identifying a ligand capable of binding to binding site 1 and/or binding site 2 and/or binding site 3 of SEQ ID NO. 1 (Sortilin), or a fragment or variant thereof said method comprising the steps of:
  a. generating the spatial structure of the binding site on a computer screen using atomic coordinates of sSortilin (SEQ ID NO:33) as presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å,
  b. generating potential ligands with their spatial structure on the computer screen, and
  c. selecting ligands that can bind to at least 1 amino acid residue of the set of binding interaction sites without steric interference.

In another aspect the present invention relates to a computer-assisted method for identifying a ligand of sortilin capable of binding to binding site 1 and/or binding site 2 and/or binding site 3 of SEQ ID NO. 1 (Sortilin), or a fragment or variant thereof, using a programmed computer comprising a processor, a data storage system, a data input device and a data output device, comprising the following steps:
  a. inputting into the programmed computer through said input device data comprising: atomic coordinates of a subset of the atoms of said sortilin, thereby generating a criteria data set; wherein said atomic coordinates are selected from the three-dimensional structure of sSortilin (SEQ ID NO:33) presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å,
  b. comparing, using said processor, the criteria data set to a computer data base of low-molecular weight organic chemical structures and peptide fragments stored in the data storage system; and
  c. selecting from said data base, using computer methods, a chemical structure having a portion that is structurally complementary to the criteria data set and being free of steric interference with the receptor sortilin.

In yet another aspect the present invention relates to a method for identifying a ligand, said method comprising the steps of:
  a. selecting a potential ligand using atomic coordinates in conjunction with computer modelling, wherein said atomic coordinates are the atomic coordinates of sSortilin (SEQ ID NO:33) presented in any of FIGS. 17 to 20 or wherein the atomic coordinates are selected from a three-dimensional structure that deviates from the three-dimensional structure presented in any of FIGS. 17 to 20 by a root mean square deviation over protein backbone atoms of not more than 3 Å, by docking potential ligands into a set of binding interaction sites in binding site 1 and/or binding site 2 and/or binding site 3 of SEQ ID NO. 1 (Sortilin), or a fragment or variant thereof, said binding interaction generated by computer modelling and selecting a potential ligand capable of binding to at least one amino acid in said set of binding interaction sites of sortilin,
  b. providing said potential ligand and said receptor sortilin
  c. contacting the potential ligand with said receptor sortilin and
  d. detecting binding of said receptor sortilin by the potential ligand.

In one embodiment of the present invention the docking of potential ligand molecules is performed by employing a three-dimensional structure defined by atomic coordinates of the three dimensional structure of sSortilin (SEQ ID NO:33) presented in any of FIGS. 17 to 20 and such that said potential ligand is capable of binding to at least three amino acids in the binding site 1 and/or binding site 2 and/or binding site 3 of SEQ ID NO. 1 (Sortilin), or a fragment or variant thereof.

In a further aspect the present invention relates to a method of identifying a potential ligand of binding site 1, binding site 2 or binding site 3 of sortilin, or a fragment or variant thereof said method comprising the steps of
  a. introducing into a computer, information derived from atomic coordinates defining a conformation of binding site 1 and/or binding site 2 and/or binding site 3 of SEQ ID NO. 1 (Sortilin), or a fragment or variant thereof, based on three-dimensional structure determination, whereby a computer program utilizes or displays on the computer screen the structure of said conformation; wherein said atomic coordinates are selected from the three-dimensional structure of sSortilin (SEQ ID NO:33) as presented in any of FIGS. 17 to 20 or atomic coordinates selected from a three-dimensional structure that deviates from any one of the tree-dimensional structure represented by any of FIGS. 17 to 20 by a root mean square deviation over protein backbone atoms of not more than 3 Å;
  b. generating a three-dimensional representation of binding site 1, binding site 2 or binding site 3 of sortilin by said computer program on a computer screen;
  c. superimposing a model of a potential ligand on the representation of said binding site 1, binding site 2 or binding site 3 of Sortilin or a fragment or variant thereof,
  d. assessing the possibility of bonding and the absence of steric interference of the potential ligand with the high affinity neurotensin binding site, the low affinity neurotensin binding site, the sortilin propeptide binding site or the pro-neurotrophin binding site of sortilin;
  e. incorporating said potential ligand compound in a binding assay of said receptor sortilin and f. determining whether said potential ligand inhibit binding of a competing ligand selected from the group consisting of, but not limited to, amino acid residues 19 to 241 of proNGF (SEQ ID NO:6), amino acid residues 19 to 121 of SEQ ID NO 6 (NGF pro domain; SEQ ID NO:42), amino acid residues 19 to 246 of SEQ ID NO 7 (proBDNF; SEQ ID NO:43), amino acid residues 19 to 127 of SEQ ID NO 7 (BDNF pro domain; SEQ ID NO:44), amino acid residues 17 to 257 of SEQ ID NO 8 (proNT3; SEQ ID NO:45), amino acid residues 17 to 140 of SEQ ID NO 8 (NT3 pro domain; SEQ ID NO:46), amino acid residues 25 to 210 of SEQ ID NO 9 (proNT4/5; SEQ ID NO:47), amino acid residues 25 to 80 of SEQ ID NO 9 (NT4/5 pro domain; SEQ ID NO:48), SEQ ID NO. 10 (Neurotensin), SEQ ID NO. 11 (PYIL), amino acid residues 11 to 13 of SEQ ID NO. 10 (YIL) and SEQ ID NO. 12 (NT69L).

In a further embodiment of the present invention the information derived from the atomic coordinates of at least one of the following amino acid residues of binding site 1: R325, S316, Y351, I353, K260, I327, F314, F350 to M363, S305, F306, T398 to G400, I303-G309, Q349-A356, Y395 and T402 of SEQ ID NO. 1 are used.

In a further embodiment of the present invention the information derived from the atomic coordinates of at least one of the following amino acid residues of binding site 2: L572, L114, V112, R109 to S111, S115 to G118, T570, G571, W586, W597, T168-I174, L572, A573 and S584 to F588 of SEQ ID NO. 1 are used for ligand prediction and/or design.

In a further embodiment of the present invention information derived from the atomic coordinates of at least one of the following amino acid residues of binding site 3: D403, S420, D422, N423, S424, I425, E426, T451, Y466, E470, I498, S499 and V500 of SEQ ID NO. 1 are used.

In a further embodiment of the present invention the data criteria set or binding interaction set comprise at least 3 amino acid residues selected from the identified groups.

In a further embodiment of the present invention the atomic coordinates are determined to a resolution of at least 5 Å.

In a further embodiment of the present invention the atomic coordinates are determined to a resolution of at least 4 Å.

In a further embodiment of the present invention the atomic coordinates are determined to a resolution of at least 3 Å.

In a further embodiment of the present invention the atomic coordinates are determined to a resolution of at least 2 Å.

In a further embodiment of the present invention the atomic coordinates are determined to a resolution of at least 1.5 Å.

In a further embodiment of the present invention the potential ligand molecule interacts with at least amino acids in the high affinity Neurotensin binding site of SEQ ID NO. 1.

Properties of Vps10p-Domain Receptor Ligands

Ligands identified by the method defined herein above bind specifically to the binding sites identified through the crystal structure of Sortilin. Due to the homology of the Vps10p-domain in between the five members of the Vps10p-domain family, ligands identified as binding to binding sites 1-3 of Sortilin is likely to interact also with the Vps10p-domain of the other Vps10-p domain receptors.

In one embodiment of the present invention the potential ligand molecule interacts with at least amino acids in the low affinity Neurotensin binding site of SEQ ID NO. 1.

In a further embodiment of the present invention the potential ligand molecule interacts with at least amino acids in the Sortilin propeptide binding site of SEQ ID NO. 1.

In a further embodiment of the present invention the potential ligand molecule interacts with at least amino acids in the pro-neurotrophin binding site of SEQ ID NO. 1.

In a further embodiment of the present invention the potential ligand is selected from the group consisting of non-hydrolyzable peptides and peptide analogues, organic compounds and inorganic compounds.

In a further embodiment of the present invention a library of small organic molecules are screened.

In a further embodiment of the present invention a library of potential peptide ligands are screened.

In a further aspect the present invention relates to a ligand identified by the method described herein above, said ligand capable of binding to at least one interaction point of said binding site 1, said interaction points comprising $X_1, X_2, X_3, X_4, R_1, R_2, J_1, J_2$ and $J_3$ of FIG. 14 wherein $X_1$ comprises the amino acid residues R325, S316 and Y351 of SEQ ID NO:1, and wherein $X_2$ comprises the backbone carbonyl of Y351 of SEQ ID NO:1 and wherein $X_3$ comprises the backbone of I353 of SEQ ID NO:1 and wherein $X_4$ comprises the amino group of K260 of SEQ ID NO:1 and wherein $R_1$ comprises amino acid residues I327, F314, Y351, I353 and M363 of SEQ ID NO:1 and wherein $R_2$ comprises F350 of SEQ ID NO:1 and at least one amino acid from the loop comprising amino acid residues T397 to E401 of SEQ ID NO:1 and wherein $J_1$ comprises S305 of SEQ ID NO:1 and wherein $J_2$ comprises the backbone amide of F306 of SEQ ID NO:1 and wherein $J_3$ comprises the backbone carbonyl of F306 of SEQ ID NO:1.

In a further embodiment of the present invention interaction point $X_1$ comprises a negative charge and/or hydrogen acceptor properties said negative charge and/or hydrogen acceptor properties selected from the group consisting of carboxylate, sulfonic acid, di-fluoro said difluoro lacking a negative charge to compensate the positive charge of the Arginine, di-chloro said di-chloro lacking a negative charge to compensate the positive charge of the Arginine.

In a further embodiment of the present invention the ligand as defined herein above comprises at interaction point $X_2$ a hydrogen bond donor selected from the group consisting of hydroxyl, amino and amido.

In a further embodiment of the present invention the ligand as defined herein above comprises at interaction point $X_3$ comprises a hydrogen bond acceptor selected from the group consisting of carbonyl, chloro and fluoro.

In a further embodiment of the present invention the ligand as defined herein above comprises at interaction point $R_1$ a bulky hydrophobic group selected from the group consisting of cyclohexyl-alanine, leucine, isoleucine methionine and phenylalanine.

In a further embodiment of the present invention the ligand as defined herein above comprises at interaction point $R_2$ a hydrophobic amino acid residue selected from the group consisting of isoleucine, leucine, cysteine, or a partially hydrophobic group selected from the group consisting of histidine, glutamine, lysine, arginine and glutamate.

In an important aspect, the present invention relates to a Vps10p-domain receptor ligand identified by the method defined herein, said ligand having the general structure of formula (I):

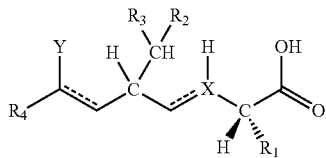

(I)

wherein X is an atom acting as hydrogen donor said atom selected from the group consisting of N, O, S, P and wherein Y is an electronegative atom acting as hydrogen bond acceptor selected from the group consisting of O, N, S, F, Cl, Br, I, and wherein $R_1$ is C3-6 alkyl, C4-6 cyclyl, a heterocyclic or a heteroaromatic structure having one ring, 4 to 6 ring members in each and 1 to 3 heteroatoms, or a heteroalkyl comprising 1 to 3 heteroatoms selected from the group consisting of N, O, $S(O)_{0-2}$, and wherein $R_2$ is a hydrogen, a C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, $S(O)_{0-2}$, and wherein $R_3$ is hydrogen, SH, imidazole, C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, S, and wherein $R_4$ is selected from the functional groups C1-100 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), thiocyanate, disulfide, a linker L2 or L3, and an amino acid sequence being at least 50% identical to SEQ ID NO: 10 or a fragment thereof.

In a further important aspect, the present invention relates to a Vps10p-domain receptor ligand identified by the method defined herein, said ligand having the general structure of formula (II):

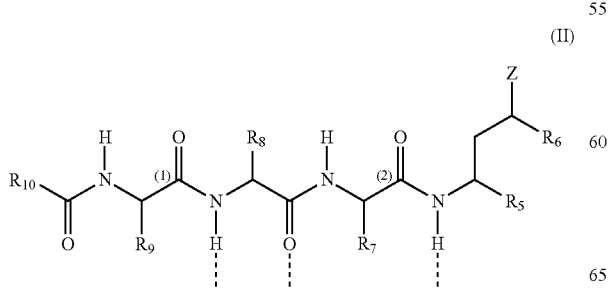

(II)

wherein Z is a hydrogen bond donor or acceptor selected from the group consisting of carbonyl, hydroxyl, amino, imino, amide, sulfhydryl, chloro, fluoro, and wherein $R_5$ is selected from the group consisting of H, $CH_3$, and a linker L2, and wherein $R_6$ is selected from the group consisting of H, $-CH_3$, $-CH_2CH_3$ and $-OCH_3$, and wherein $R_7$ is selected from the group consisting of side chains of glutamate, glutamine, lysine, arginine, histidine, tyrosine, methionine, cysteine, aliphatic C4-6 groups, and wherein $R_8$ is selected from the group consisting of side chains of tyrosine, histidine, serine, threonine, aspartate, asparagine, cysteine, phenylalanine, iodo-tyrosine and $-CH_2-NH_2$, and wherein $R_9$ is selected from the group consisting of side chain of lysine, arginine, glutamine, C3-8 aliphatic and heteroaliphatic groups, carbocyclic and heterocyclic groups comprising 5 or 6 membered rings, and wherein $R_{10}$ is selected from the group consisting of a pyroglutamate, poly-carbohydrates and a polypeptide of length greater than equal to 10, and wherein $R_{11}$ and $R_{12}$ individually are selected from the group consisting of H, C1-12 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), and wherein the covalent bonds (1) and (2) individually are selected from the group consisting of single bonds and double bonds.

In a very important aspect, the present invention relates to a Vps10p-domain receptor ligand identified by the method defined herein, said ligand having the general structure of formula (III):

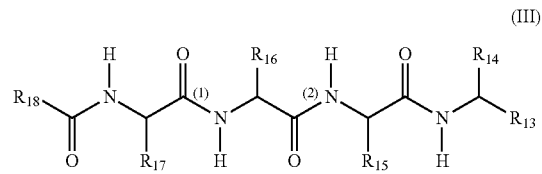

(III)

wherein $R_{13}$ is selected from the group consisting of H, C1-12 alkyl, alkenyl, alkynyl and a linker L3, and wherein $R_{14}$, $R_{15}$, $R_{17}$, $R_{19}$, $R_{20}$ individually are selected from the group consisting of H, C1-12 alkyl, alkenyl and alkynyl, and wherein $R_{16}$ is selected from the group consisting of sidechains of phenylalanine, leucine, isoleucine, valine, methionine, histidine, cysteine, lysine and aliphatic C3-7, and wherein $R_{18}$ is selected from the group consisting of H, $-CH_3$ and $-CH_2OH$, and wherein the covalent bonds (1) and (2) individually are selected from the group consisting of single bonds and double bonds.

In one embodiment of the present invention the ligand of formula (I) is linked by the linker L2 to the ligand of formula (II), thereby forming the general formula (IV):

[Formula (I)]–[Linker L2]–[Formula (II)]     (IV)

wherein said formula (IV) is capable of simultaneously blocking binding sites 1 and 2 of Sortilin, and wherein the linker L2 mentioned herein above is selected from the group consisting of a peptide backbone of 5 to 6 residues, C15-20 alkyl, C15-20 alkenyl and C15-20 alkynyl.

In one embodiment of the present invention the ligand of formula (I) is linked by the linker L3 to the ligand of formula (III), thereby forming the general formula (V):

[Formula (I)]–[Linker L3]–[Formula (III)]     (V)

wherein said formula (V) is capable of simultaneously blocking binding sites 1 and 3 of Sortilin, and wherein the linker L3 is selected from the group consisting of a peptide backbone of 12 to 20 residues, C30-60 alkyl, C30-60 alkenyl, C30-60 alkynyl.

In a further embodiment, the ligand identified by the method of the present invention is selected from the group consisting of RRPYI(chg) (SEQ ID NO:32), iodoYIL, QIL, YCL, dYIL, YHL, RRPYI(acc) (SEQ ID NO:32), RRPYI(nMe)L (SEQ ID NO:31), YIL depicted in FIG. 26.

In a further aspect, the present invention relates to a Vps10p-domain receptor ligand identified by the method defined herein, said ligand, wherein said ligand is RRPYI(chg) (SEQ ID NO:32) depicted in FIG. 26.

In a further aspect, the present invention relates to a Vps10p-domain receptor ligand identified by the method defined herein, said ligand, wherein said ligand is iodoYIL depicted in FIG. 26.

In a further aspect, the present invention relates to a Vps10p-domain receptor ligand identified by the method defined herein, said ligand, wherein said ligand is QIL depicted in FIG. 26.

In a further aspect, the present invention relates to a Vps10p-domain receptor ligand identified by the method defined herein, said ligand, wherein said ligand is YCL depicted in FIG. 26.

In a further aspect, the present invention relates to a Vps10p-domain receptor ligand identified by the method defined herein, said ligand, wherein said ligand is dYIL depicted in FIG. 26.

In a further aspect, the present invention relates to a Vps10p-domain receptor ligand identified by the method defined herein, said ligand, wherein said ligand is YHL depicted in FIG. 26.

In a further aspect, the present invention relates to a Vps10p-domain receptor ligand identified by the method defined herein, said ligand, wherein said ligand is RRPYI(acc) (SEQ ID NO:32) depicted in FIG. 26.

In a further aspect, the present invention relates to a Vps10p-domain receptor ligand identified by the method defined herein, said ligand, wherein said ligand is RRPYI(nMe)L (SEQ ID NO:31) depicted in FIG. 26.

In a further aspect, the present invention relates to a Vps10p-domain receptor ligand identified by the method defined herein, said ligand, wherein said ligand is YIL depicted in FIG. 26.

In one embodiment, the ligand is not selected from the group consisting of native Neurotensin (SEQ ID NO:10), NT8-13 (SEQ ID NO:31) or NT69L (SEQ ID NO:12).

In a further embodiment of the present invention the ligand as identified by the method described herein above is capable of inhibiting binding to binding site 1 and/or binding site 2 and/or binding site 3 of the Vps10p-domain receptor Sortilin, or a fragment or variant thereof.

In another aspect the present invention relate to a method for building an atomic model of a Vps10p-domain receptor protein molecule comprising the steps of:
 a. identifying a Vps10p-domain receptor, or a fragment or variant thereof, having at least 20% sequence identity to SEQ ID NO. 1, and
 b. utilizing the atomic coordinates as presented in any of FIGS. 17 to 20 or atomic coordinates selected from a three-dimensional structure that deviates from the three-dimensional structure presented in any of FIGS. 17 to 20 by a root mean square deviation over protein backbone atoms of not more than 3 Å, to obtain an atomic model of the identified Vps10p-domain receptor by homology modelling.

In a further embodiment of the present invention the Vps10p-domain receptor to be built according to the method defined herein above is selected from the group consisting of SEQ ID NO. 2 (SorLA), SEQ ID NO. 3 (SorCS1), SEQ ID NO. 4 (SorCS2) and SEQ ID NO. 5 (SorCS3) or a fragment or variant thereof.

In a further aspect the present invention relate to a method of identifying a potential ligand of a Vps10p-domain receptor, or a fragment or variant thereof said method comprising the steps of:
 a) introducing into a computer, information derived from atomic coordinates defining a conformation of a binding site having at least 20% sequence identity to 1 and/or binding site 2 and/or binding site 3 of SEQ ID NO. 1 (Sortilin), or a fragment or variant thereof, based on three-dimensional structure determination, whereby a computer program utilizes or displays on the computer screen the structure of said conformation; wherein said atomic coordinates are selected from the three-dimensional structure as presented in any of FIGS. 17 to 20 or atomic coordinates selected from a three-dimensional structure that deviates from any one of the tree-dimensional structure represented by any of FIGS. 17 to 20 by a root mean square deviation over protein backbone atoms of not more than 3 Å
 b) generating a three-dimensional representation of a binding site having at least 20% sequence identity to binding site 1, binding site 2 or binding site 3 of Sortilin, or a fragment or variant thereof, by said computer program on a computer screen;
 c) superimposing a model of a potential ligand on the representation of said binding site having at least 20% sequence identity to site 1, binding site 2 or binding site 3 of Sortilin,
 d) assessing the possibility of bonding and the absence of steric interference of the potential ligand with the binding site having at least 20% sequence identity to binding site 1, binding site 2 or binding site 3 of Sortilin or a fragment or variant thereof;
 e) incorporating said potential ligand compound in a binding assay of said Vps10p-domain receptor and
 f) determining whether said potential ligand is capable of binding to said binding site having at least 20% sequence identity to binding site 1 and/or binding site 2 and/or binding site 3 of SEQ ID NO. 1 by performing a biochemical or biophysical competitive binding assay wherein the competing ligand is selected from the group consisting of amino acid residues 19 to 241 of proNGF (SEQ ID NO:6), amino acid residues 19 to 121 of SEQ ID NO 6 (NGF pro domain; SEQ ID NO:42), amino acid residues 19 to 246 of SEQ ID NO 7 (proBDNF; SEQ ID NO:43), amino acid residues 19 to 127 of SEQ ID NO 7 (BDNF pro domain; SEQ ID NO:44), amino acid residues 17 to 257 of SEQ ID NO 8 (proNT3; SEQ ID NO:45), amino acid residues 17 to 140 of SEQ ID NO 8 (NT3 pro domain; SEQ ID NO:46), amino acid residues 25 to 210 of SEQ ID NO 9 (proNT4/5; SEQ ID NO:47), amino acid residues 25 to 80 of SEQ ID NO 9 (NT4/5 pro domain; SEQ ID NO:48), SEQ ID NO. 10 (Neurotensin), SEQ ID NO. 11 (PYIL), amino acid residues 11 to 13 of SEQ ID NO. 10 (YIL) and SEQ ID NO. 12 (NT69L Indications In one aspect the present invention relates to a medicament comprising an inhibitor of Sortilin and/or of Sortilin:proNGF:p75$^{NTR}$ induced apoptosis.

In one embodiment of the present invention the at least one ligand as identified by the methods described herein above is used for the manufacture of a medicament, wherein said medicament is for the treatment, and prevention or treatment and prevention of and/or protection against a disease, disorder, or damage of the nervous system in an individual.

In a further embodiment of the present invention the above mentioned individual is a human being.

In a further embodiment of the present invention the above mentioned medicament is for the treatment of a disease, disorder, or damage involving injury to the brain, brain stem, the spinal cord, and/or peripheral nerves.

In an embodiment of the present invention the injury defined herein above is due to stroke, traumatic brain injury, spinal cord injury, diffuse axonal injury, and epilepsy.

In an embodiment of the present invention the nervous system disorder involves degeneration of neurons and their processes in the brain, brain stem, the spinal cord, and/or the peripheral nerves.

In a further embodiment of the present invention the degeneration of neurons is due to Parkinson's Disease, Alzheimer's Disease, senile dementia, Huntington's Disease, amyotrophic lateral sclerosis, and neuronal injury associated with multiple sclerosis.

In one embodiment of the present invention the neurodegenerative disease as described herein above is Parkinson' Disease.

In one embodiment of the present invention the neurodegenerative disease as described herein above is Huntington's Disease.

In one embodiment of the present invention the neurodegenerative disease as described herein above is amyotrophic lateral sclerosis.

In one embodiment of the present invention the nervous system disorder as described herein above is a disease, disorder, or damage involving dysfunction and/or loss of neurons in the brain, brain stem, the spinal cord, and/or peripheral nerves.

In a further embodiment of the present invention the above mentioned disease, disorder, or damage involving dysfunction and/or loss of neurons in the brain, brain stem, the spinal cord, and/or peripheral nerves is selected from the group consisting of conditions caused by metabolic diseases, nutritional deficiency, toxic injury, malignancy, and/or genetic or idiopathic conditions including but not limited to diabetes, renal dysfunction, alcoholism, chemotherapy, chemical agents, drug abuse, vitamin deficiency, and infection.

In one embodiment of the present invention the nervous system disorder is a disease, disorder, or damage involving degeneration or sclerosis of glia, wherein said glia is selected from the group consisting of oligodendrocytes, astrocytes and Schwann cells in the brain, brain stem, the spinal cord, and the peripheral nerves.

In one embodiment of the present invention said disease, disorder, or damage involving degeneration or sclerosis of glia is selected from the group consisting of multiple sclerosis, optic neuritis, cerebral sclerosis, post-infectious encephalomyelitis, and epilepsy.

In one embodiment of the present invention the disease or disorder is multiple sclerosis, sensory ataxus, neurodegenerative spinocerebellar disorders, hereditary ataxis, cerebellar atrophies, and alcoholism.

In one embodiment of the present invention the nervous system disorder, disease, or damage involves the retina, photoreceptors, and associated nerves.

In one embodiment of the present invention the nervous system disorder, disease, or damage involving the retina, photoreceptors, and associated nerves is selected from the group consisting of retinitis pigmentosa, macular degeneration, glaucoma, and diabetic retinopathy.

In one embodiment of the present invention the nervous system disorder, disease, or damage involves the sensory epithelium and associated ganglia of the vestibuloacoustic complex.

In one embodiment of the present invention said nervous system disorder, disease, or damage involving the sensory epithelium and associated ganglia of the vestibuloacoustic complex is selected from the group consisting of noise-induced hearing loss, deafness, tinnitus, otitis, labyrintitis, hereditary and cochleovestibular atrophies, and Menieres Disease.

In one embodiment of the present invention the medicament as defined herein above optionally comprises a pharmaceutically acceptable carrier.

In one embodiment of the present invention the medicament as described herein above comprises a second active ingredient selected from the group consisting of a ligand capable of binding to the high affinity Neurotensin binding site (binding site 1), a ligand capable of binding to the low affinity Neurotensin binding site (binding site 2), a ligand capable of binding to the Sortilin propeptide binding sites (binding sites 1 and 2) and a ligand capable of binding to the pro-neurotrophin binding site (binding site 3) of SEQ ID NO. 1.

Administration Forms

The main routes of drug delivery, in the treatment method are intravenous, oral, and topical. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compounds of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. Powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl- β-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In one embodiment of the present invention the pH of the medicament composition as described herein above is between pH 5 and pH 9.

In one embodiment of the present invention the medicament as described herein above is formulated for administration by injection, suppository, oral administration, sublingual tablet or spray, cutaneous administration, or inhalation.

In one embodiment of the present invention said medicament is formulated for administration by injection wherein the injection is intravenous, intramuscular, intraspinal, intraperitoneal, subcutaneous, a bolus or a continuous administration.

In one embodiment the medicament according to the present invention is administered at intervals of 30 minutes to 24 hours.

In one embodiment the medicament according to the present invention is administered at intervals of 1 to 6 hours.

In one embodiment according to the present invention duration of administration of the medicament as defined herein above is from 6 to 72 hours.

In one embodiment according to the present invention, the dosage of the medicament defined herein above is between 10 µg to 10 mg per kg body mass.

Method of Treatment

In a further aspect the present invention relates to a the use of at least one ligand identified by the method described herein above, for the manufacture of a medicament, wherein said medicament is for the treatment of a disease, disorder, or damage of the nervous system in an individual.

In another aspect the present invention relates to a method of treatment of a pathological condition in a subject comprising administering to an individual in need thereof a therapeutically effective amount of the medicament described herein above.

In one embodiment of the present invention said medicament is for the treatment of a disease, disorder, or damage associated with the nervous system.

In another embodiment of the present invention said medicament is for the treatment of a disease, disorder, or damage involving injury to the brain, brain stem, the spinal cord, and/or peripheral nerves, including but not limited to conditions such as stroke, traumatic brain injury, spinal cord injury, diffuse axonal injury, and epilepsy.

In another embodiment of the present invention said medicament is for the treatment of a disease, disorder, or damage involving injury to the brain, brain stem, the spinal cord, and/or peripheral nerves.

In a further embodiment of the present invention the nervous system disorder described herein above involves degeneration of neurons and their processes in the brain, brain stem, the spinal cord, and/or the peripheral nerves.

In a further embodiment of the present invention said degeneration of neurons is due to Parkinson's Disease, Alzheimer's Disease, senile dementia, Huntington's Disease, amyotrophic lateral sclerosis, and neuronal injury associated with multiple sclerosis.

In one embodiment of the present invention said neurodegenerative disease is Parkinson's Disease.

In a further embodiment of the present invention said neurodegenerative disease is Huntington's Disease.

In a further embodiment of the present invention said neurodegenerative disease is amyotrophic lateral sclerosis.

In a further embodiment of the present invention the nervous system disorder disclosed herein above is a disease, disorder, or damage involving dysfunction and/or loss of neurons in the brain, brain stem, the spinal cord, and/or peripheral nerves.

In a further embodiment of the present invention said disease, disorder, or damage involving dysfunction and/or loss of neurons in the brain, brain stem, the spinal cord, and/or peripheral nerves is selected from the group consisting of conditions caused by metabolic diseases, nutritional deficiency, toxic injury, malignancy, and/or genetic or idiopathic conditions including but not limited to diabetes, renal dysfunction, alcoholism, chemotherapy, chemical agents, drug abuse, vitamin deficiency, and infection.

In a further embodiment of the present invention said nervous system disorder is a disease, disorder, or damage involving degeneration or sclerosis of glia, wherein said glia is selected from the group consisting of oligodendrocytes, astrocytes and Schwann cells in the brain, brain stem, the spinal cord, and the peripheral nerves.

In a further embodiment of the present invention said disease, disorder, or damage involving degeneration or sclerosis of glia is selected from the group consisting of multiple sclerosis, optic neuritis, cerebral sclerosis, post-infectious encephalomyelitis, and epilepsy.

In a further embodiment of the present invention said disease or disorder is multiple sclerosis, sensory ataxus, neurodegenerative spinocerebellar disorders, hereditary ataxis, cerebellar atrophies, and alcoholism.

In a further embodiment of the present invention said nervous system disorder, disease, or damage involves the retina, photoreceptors, and associated nerves wherein said nervous system disorder, disease, or damage involving the retina, photoreceptors, and associated nerves is selected from the group consisting of retinitis pigmentosa, macular degeneration, glaucoma, and diabetic retinopathy.

In a further embodiment of the present invention said nervous system disorder, disease, or damage involves the sensory epithelium and associated ganglia of the vestibuloacoustic complex.

In a further embodiment of the present invention said nervous system disorder, disease, or damage involving the sensory epithelium and associated ganglia of the vestibuloacoustic complex is selected from the group consisting of noise-induced hearing loss, deafness, tinnitus, otitis, labyrintitis, hereditary and cochleovestibular atrophies, and Menieres Disease.

In one embodiment of the present invention the subject as described herein above is a human being.

Apoptosis

Apoptosis can occur when a cell is damaged beyond repair, infected with a virus, or undergoing stress conditions such as starvation. The "decision" for apoptosis can come from the cell itself, from the surrounding tissue, or from a cell that is part of the immune system. In these cases apoptosis functions to remove the damaged cell thus preventing it from sapping further nutrients from the organism, or to prevent the spread of viral infection.

Sortilin is a multifunctional type-1 receptor capable of endocytosis as well as intracellular sorting (9-11), and as shown recently, it also engages in signalling by triggering proneurotrophin-induction of $p75^{NTR}$-mediated neuronal apoptosis (6, 7, 12, 13).

The present invention provide methods for designing ligands binding specifically to binding site 1, binding site 2 and binding site 3 respectively, of Sortilin.

It is within the scope of the present invention to design and provide ligand molecules capable of binding to Sortilin binding site 1 and/or binding site 2 and/or binding site 3 as defined herein above, thereby preventing formation of a ternary complex between Sortilin, proNGF and p75$^{NTR}$ thereby inhibiting apoptosis.

Accordingly in one embodiment, the ligands designed according to the present invention are capable of inhibiting apoptosis.

In a further aspect the present invention relates to a method of preventing apoptosis in a mammalian neuronal cell, said method comprising exposing said neuronal cell to the ligand molecule as defined herein above.

In a further aspect the present invention relates to a method of enhancing survival of a mammalian neuronal cell, said method comprising exposing said neuronal cell to the ligand molecule as defined herein above.

In a further aspect the present invention relates to a method of expanding a composition of mammalian cells, comprising administering to said composition the ligand molecule as defined herein above.

In a further aspect the present invention relates to a method of differentiating a composition of mammalian cells, comprising administering to said composition the ligand molecule as defined herein above.

Antibodies

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Conceptually, antibodies directed against a target receptor may inhibit ligand binding in two ways: competitive or allosteric. Competitive inhibition involves the direct binding of the antibody to or near the ligand binding site on the receptor, thereby displacing the ligand from its receptor or sterically inhibiting the approach of the ligand to the ligand binding site. Allosteric inhibition involves the binding of the antibody to a site on the receptor polypeptide that is distinct from the ligand binding epitope. However, binding to this site will induce a conformational change in the overall structure of the receptor that makes it more difficult or even impossible for the ligand to bind to its cognate recognition site.

Accordingly, in one important aspect of the present invention an antibody has been raised, said antibody capable of binding specifically to binding site 1 of SEQ ID NO. 1.

In a further embodiment the antibody raised is capable of binding specifically to the epitope of the endogenous or exogenous ligand capable of binding to binding site 1 of SEQ ID NO. 1, thus sterically hindering binding of said ligand to said binding site 1 of SEQ ID NO. 1.

In another aspect of the present invention an antibody has been raised, said antibody capable of binding specifically to binding site 2 of SEQ ID NO. 1.

In a further embodiment the antibody raised is capable of binding specifically to the epitope of the endogenous or exogenous ligand capable of binding to binding site 2 of SEQ ID NO. 1, thus sterically hindering binding of said ligand to said binding site 2 of SEQ ID NO. 1.

In a further highly preferred embodiment of the present invention an antibody has been raised, said antibody capable of binding specifically to binding site 3 of SEQ ID NO. 1.

In a further embodiment the antibody raised is capable of binding specifically to the epitope of the endogenous or exogenous ligand capable of binding to binding site 3 of SEQ ID NO. 1, thus sterically hindering binding of said ligand to said binding site 3 of SEQ ID NO. 1.

In a further embodiment of the present invention the antibody as defined herein above bind to at least one amino acid residue of or around binding site 1 including but not limited to R325, S316, Y351, I353, K260, I327, F314, F350 to M363, S305, F306, T398 to G400, I303-G309, Q349-A356, Y395 and T402 of SEQ ID NO. 1.

In a further embodiment of the present invention the antibody as defined herein above bind to at least one amino acid residue of or around binding site 1 including but not limited to R325, S316, Y351, I353, K260, I327, F314, F350 to M363, S305, F306 and T398 to G400 of SEQ ID NO. 1.

In a further embodiment of the present invention the antibody as defined herein above bind to at least one amino acid residue of or around binding site 1 including but not limited to R325, S316, Y351, I353, K260, I327, F314 and F350 to M363 of SEQ ID NO. 1.

In a further embodiment of the present invention the antibody as defined herein above bind to at least one amino acid residue of or around binding site 2 including but not limited to L572, L114, V112, R109 to S111, S115 to G118, T570, G571, W586, W597, T168-I174, L572, A573 and S584 to F588 of SEQ ID NO. 1.

In a further embodiment of the present invention the antibody as defined herein above bind to at least one amino acid residue of or around binding site 2 including but not limited to L572, L114, V112, R109 to S111, S115 to G118, T570, G571, W586 and W597 of SEQ ID NO. 1.

In a further embodiment of the present invention the antibody as defined herein above bind to at least one amino acid residue of or around binding site 2 including but not limited to L572, L114 and V112 of SEQ ID NO. 1.

In a further embodiment of the present invention the antibody as defined herein above bind to at least one amino acid residue of or around binding site 3 including but not limited to D403, S420, D422, N423, S424, I425, E426, T451, Y466, E470, I498, S499 and V500 of SEQ ID NO. 1.

In a further embodiment of the present invention the antibody as defined herein above bind to at least one amino acid residue of or around binding site 3 including but not limited to D403, N423, S424, I425, T451, Y466, I498 and V500 of SEQ ID NO. 1.

In a further embodiment of the present invention the antibody as defined herein above bind to at least one amino acid residue of or around binding site 3 including but not limited to T451, Y466, I498 and V500 of SEQ ID NO. 1.

In a further embodiment of the present invention the antibody as described herein above is selected from the group consisting of: polyclonal antibodies, monoclonal antibodies, humanised antibodies, single chain antibodies, recombinant antibodies.

In a further aspect the present invention relates to an immunoconjugate comprising an antibody as described herein above and a conjugate selected from the group consisting of: a cytotoxic agent such as a chemotherapeutic agent, a toxin, or a radioactive isotope; a member of a specific binding pair, such as avidin or streptavidin or an antigen; an enzyme capable of producing a detectable product.

B) View of sSortilin(a) following a 90° rotation around a horizontal axis. The propeller is shown as a surface representation in grey. The hydrophobic loops extending from blades 1 and 10 are in dark grey. The 10 CC domains is shown as a cartoon representation.

C) Surface representation of the sSortilin:NT complex shown in (a). The surface of the propeller is light grey, the 10 CC domains, N and C-terminal parts of NT are dark grey, the hydrophobic loops are black. The dimensions of the tunnel along the dashed lines in the equatorial plane are shown. The grey line indicates the position of the cross-section shown in d.

D) Cross-section of the propeller with NT shown as sticks. The same colour scheme is used as in (c). This view is rotated 180° around a vertical axis with respect to the view used in (b).
The dashed line shows the largest dimension in the equatorial plane.

Figure 5:
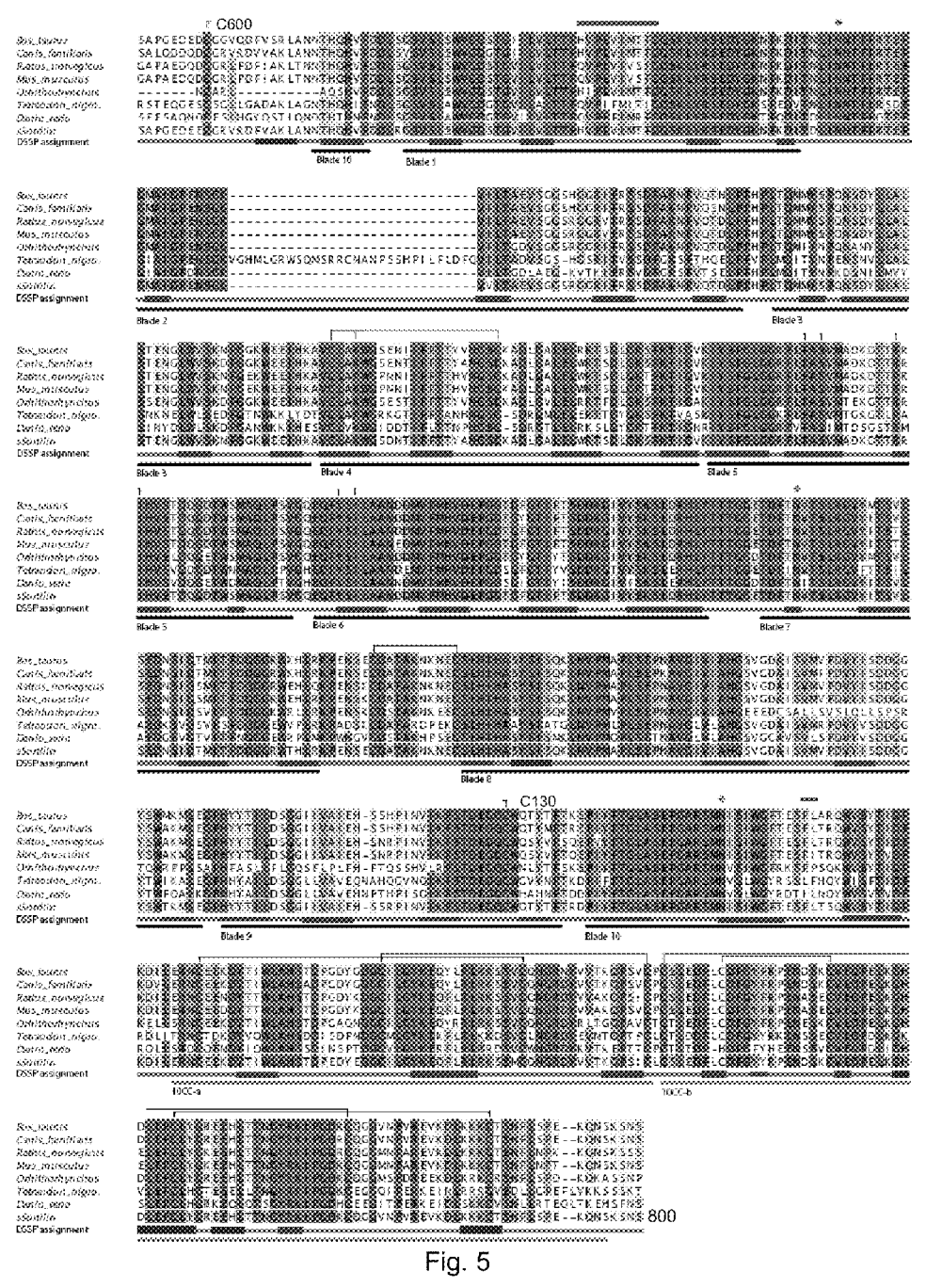

E) The surface representation of sSortilin coloured by sequence conservation (FIG. 5). Invariant positions are coloured dark grey. All three peptide fragments found in the 2.6 Å Sortilin:NT structure with 15 fold excess of NT as well as glycosylations are shown as sticks. Left: Top view of sSortilin, i.e. same orientation as in C Right: Bottom view of sSortilin i.e. 180° rotation of the top view around a vertical axis.

Figure 2:
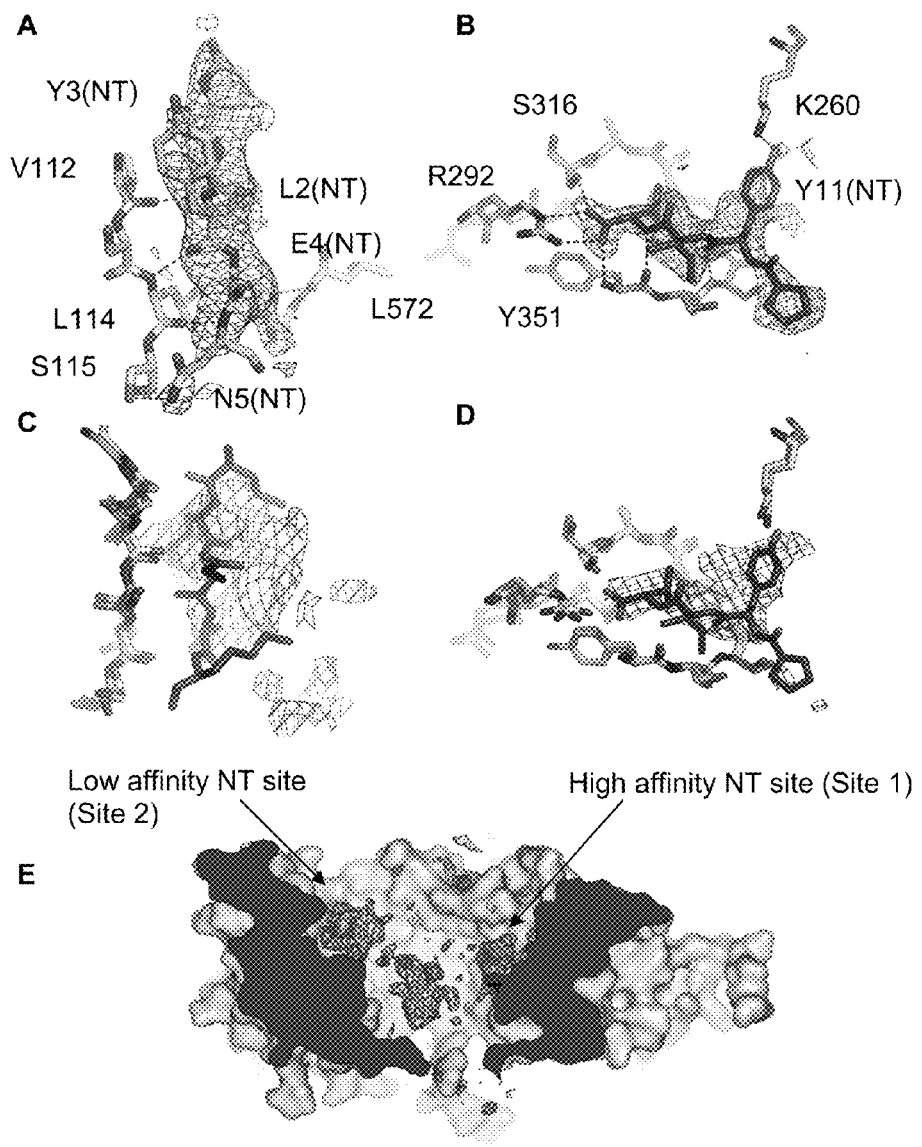

FIG. 2: Details of ligand binding

A) Binding of the N-terminal part of NT to sSortilin as seen in the 2.6 Å structure. Atom types are indicated by shades of grey: Carbon (sSortilin)—light grey, Nitrogen—darker grey, Oxygen—darker grey, and Carbon (NT)—darkest grey. Neurotensin residues are overlaid with the 1σ level of the final 2.6 Å 2Fo-Fc electron density map shown as a wire mesh. The dashed lines indicate the positions of hydrogen bonds.

B) Binding of the C-terminal part of NT to sortilin as seen in the 2.0 Å structure. Residues Pro10-Tyr-Ile-Leu13 (residues 10-13 of SEQ ID NO:10) and the residues of sSortilin forming the binding pocket are shown as sticks. Colour coding as in (a).

The electron density map contoured at 1σ is the final 3Fo-2Fc map of the 2.0 Å structure.

C) Electron density of the propeptide at propeller binding site 2. The same set of atoms of sSortilin as in panel (a) is superimposed on strand 1 of blade 1 of the sSortilin:propeptide. Color coding as in panel (a). The 1σ surface of the final 3.2 Å 3Fc-2Fo electron density is shown indicating the position of the bound propeptide.

D) Electron density of the propeptide at propeller the high affinity NT binding site. The same set of atoms of sSortilin as in panel (b) is superimposed on strand 1 of blade 6 of the sSortilin:propeptide. The 1σ surface of the final 3.2 Å 3Fc-2Fo electron density is shown indicating the position of the bound propeptide.

Figure 1:
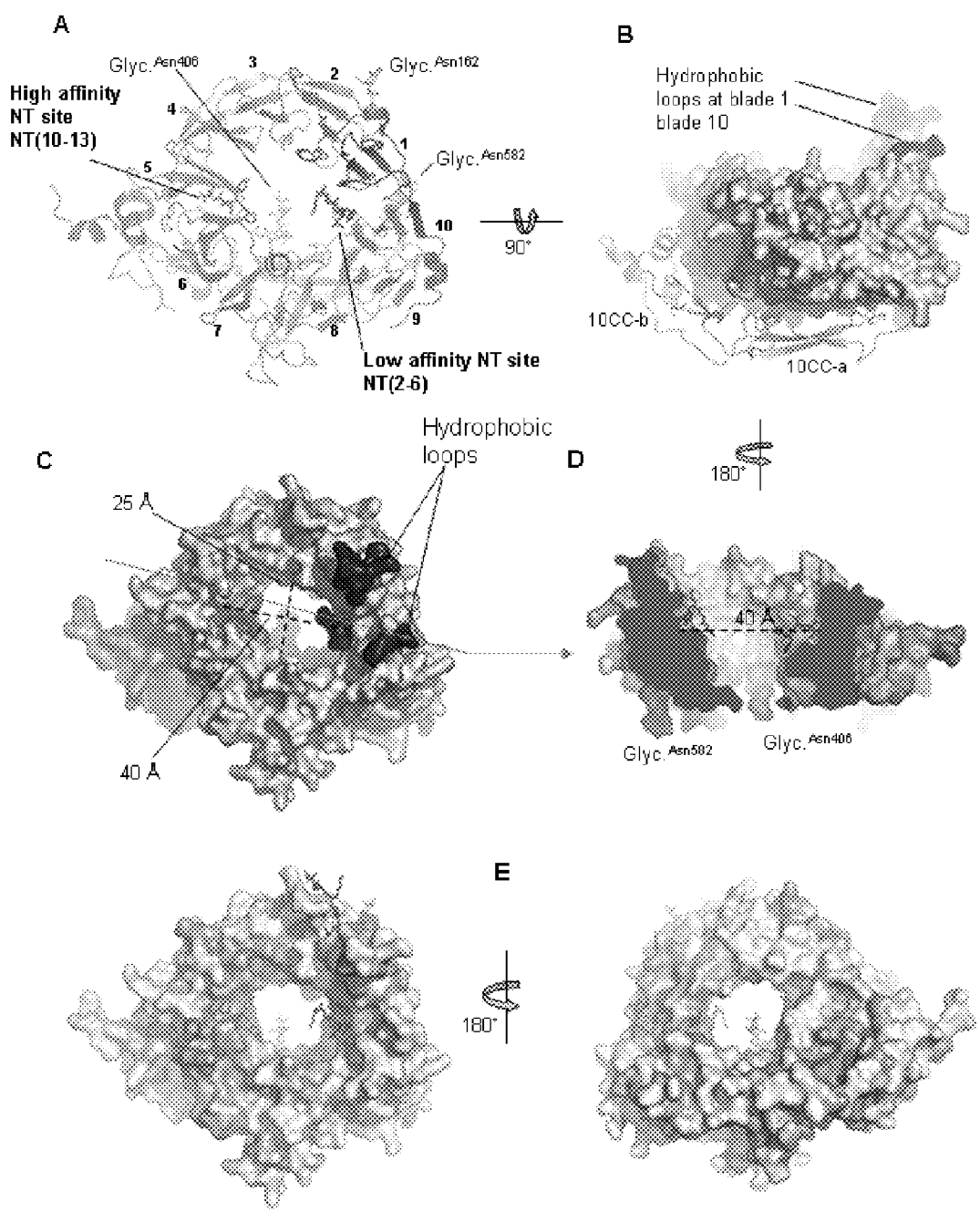
FIG. 1: Overview of Sortilin structure
A) Cartoon illustration of sSortilin:NT at 2.6 Å resolution as viewed down the propeller axis from the open side of the tunnel. Individual propeller blades are numbered along the outer rim. NT (Pro10-Tyr-Ile-Leu13); residues 10-13 of SEQ ID NO:10) in the high affinity NT binding site (binding site 1) at blade 6 and NT (Leu2-Tyr-Glu-Asn-Lys6; residues 2-6 of SEQ ID NO:10) in binding site 2 at blade 1 is shown as sticks. The oligosaccharide moieties of the glycosylation at Asn206, Asn450, and Asn626 of sSortilin (SEQ ID NO. 33) are also shown as sticks. The oligosaccharide moieties of the glycosylation at Asn206, Asn450, and Asn626 are also shown as sticks.

E) Propeptide binding across the tunnel. Cross section of the sSortilin:propeptide structure as in FIG. 1*d*. The 1σ surface of the final 3.2 Å 3Fc-2Fo electron density is shown.

Figure 3:
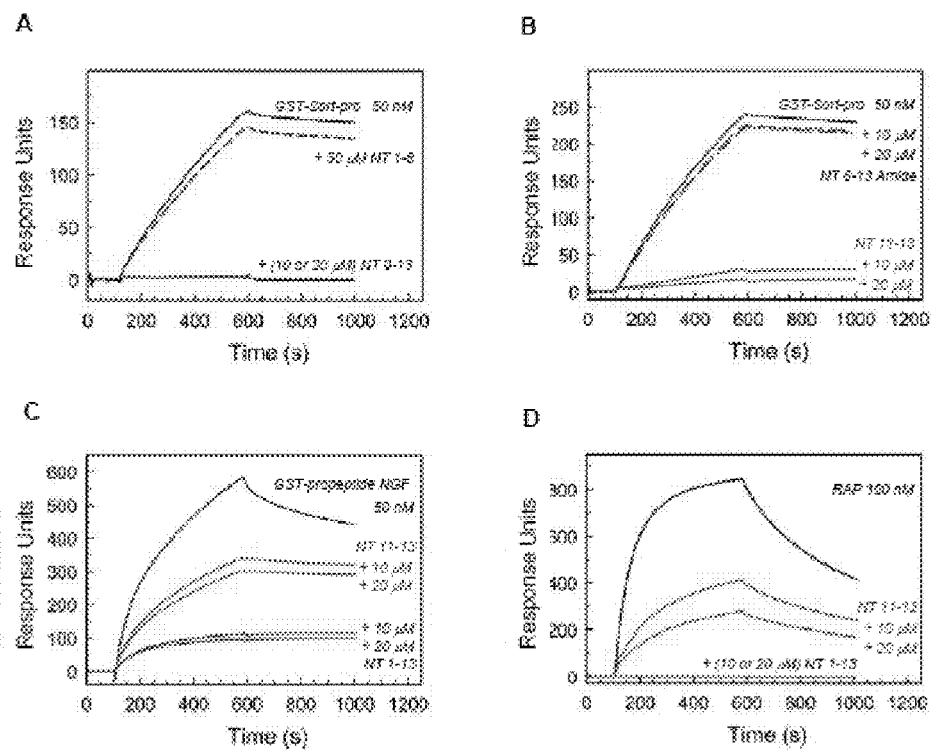

FIG. 3: Effects of NT and derived peptides on sSortilin binding

Surface plasmon resonance analysis of ligand binding to immobilized sSortilin in the absence or presence of Neurotensin derived peptides. The numbering indicates which amino acids of NT (1-13) that are contained in the individual peptides. Binding in the presence of the C-terminal tripeptide 11-YIL-13 (NT 11-13) is indicated. A-B) Binding of the GSTtagged Sortilin propeptide (GST-Sort-pro); C) Binding of the GST-tagged propeptide of NGF; D) Binding of RAP.

Figure 4:
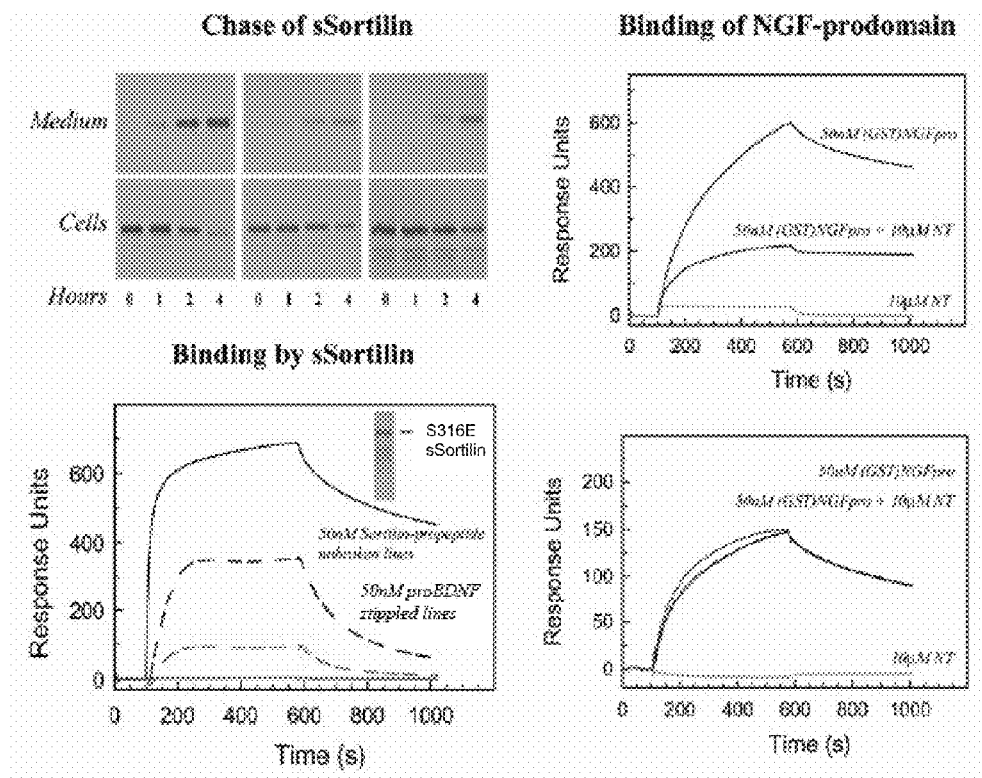

FIG. 4: Secretion and ligand binding of sSortilin and sSortilin mutant receptors A) A pulse chase of $^{35}$S-biolabelled sSortilin in CHO cells. Receptors, wt or mutant receptors with the indicated amino acid substitutions, were immunoprecipitated from cell lysates or medium at the indicated times.

B) Binding of BDNF and the Sortilin-propeptide to wt sSortilin and to the purified S283E mutant. The receptors were immobilized at similar concentrations (0.06 pM/mm$^2$) and binding was analyzed by SPR. A silver stain of the purified mutant receptor is shown as an inset. C) Binding of the NGF-prodomain to wt sSortilin (upper panel) and to the S316E mutant (lower panel) in the absence or presence of a surplus of Neurotensin.

FIG. 5: Sequence alignment of Sortilin sequences. The numbering corresponds to pre-pro-Sortilin numbering (according to SEQ ID NO. 1. Sequences were identified by a BLAST search in the non-redundant protein database at NCBI:

*Bos_taurus*: ref|XP 588956.3| (SEQ ID NO:14);
*Canis_familiaris*: ref|XP 537041.2| (SEQ ID NO:15);
*Rattus_norvegicus*: ref|XP_001076150.1| (SEQ ID NO:16);
*Mus_musculus*: ref|NP 064356.2| (SEQ ID NO:17);
*Ornithorhynchus_anatinus*: ref|XP 001505243.1| (SEQ ID NO:18);
*Tetraodon_nigroviridis*: emb|CAG07500.1| (SEQ ID NO:19);
*Danio_rerio*: ref|NP 998395.1| (SEQ ID NO:20);

and subsequently aligned to the sSortilin construct using ClustalW. Only the region corresponding to the sSortilin construct is shown with the C-terminal His-tag omitted. The alignment view was created using Jalview (34) and coloured shades of grey according to conservation at each position. Below the sequences thick bars indicate the position of secondary structure as assigned by DSSP (34). Below this line bars labelled Blade 1 through 10 indicate the position of the individual blades of the propeller or indicate the extent of the two domains of 10 CC. The disulphide linkages are indicated above the sequences by thin lines either connecting the two cysteines or labelled with the residue number of the disulphide partner. The blue bars show the position of the two hydrophobic loops. Asterisks identifies glycosylated asparagine residues.

Capital N identifies residues involved in binding of the C-terminal part of Neurotensin whereas lowercase n identifies residues involved in binding of the N-terminal part of Neurotensin.

Figure 6:
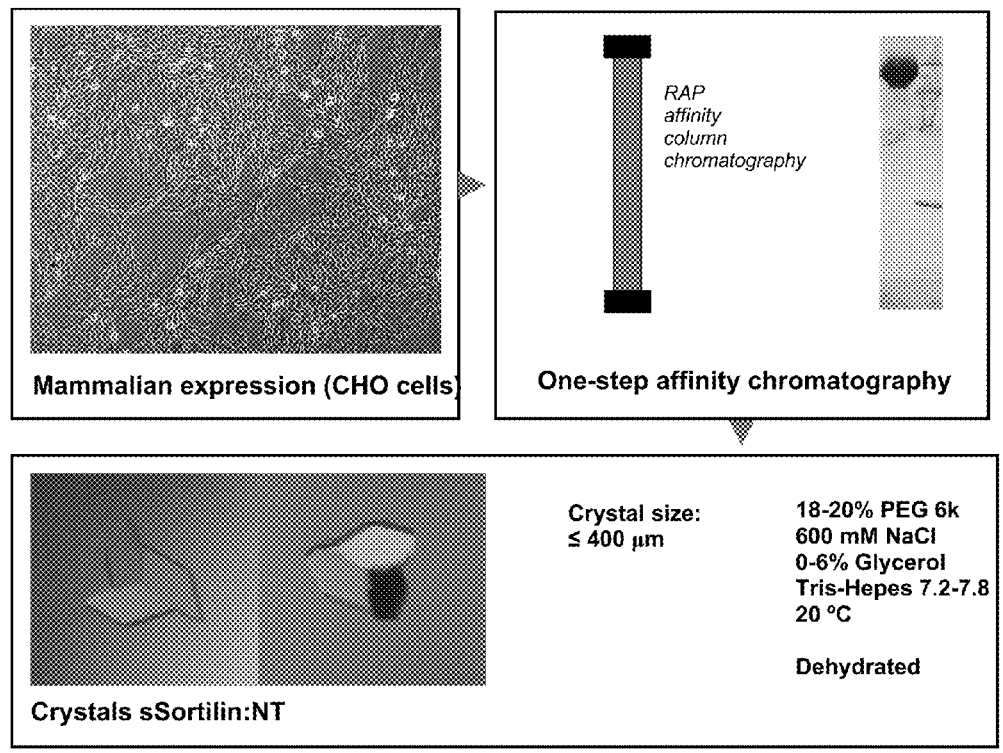
Figure 7:
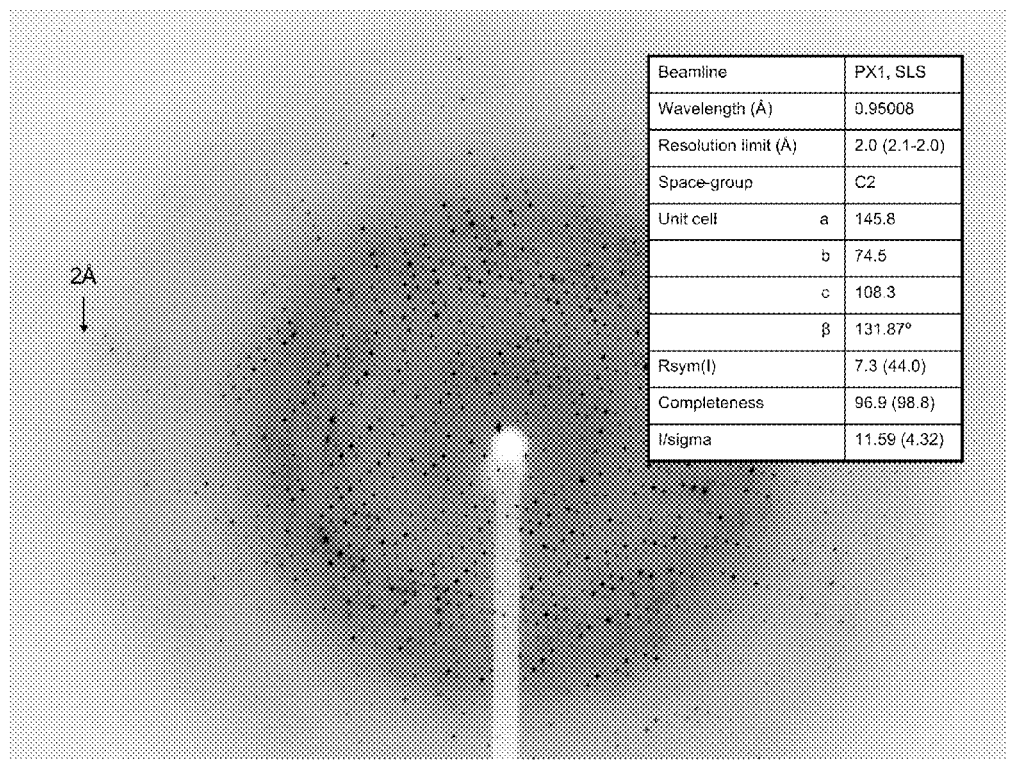
Figure 8:
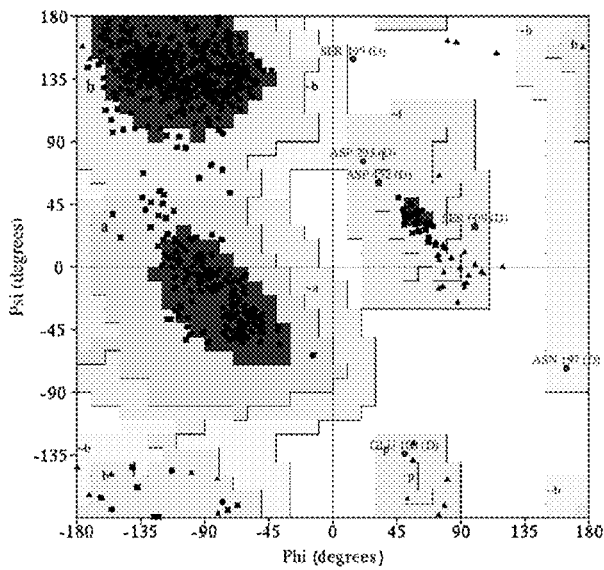
Figure 9:
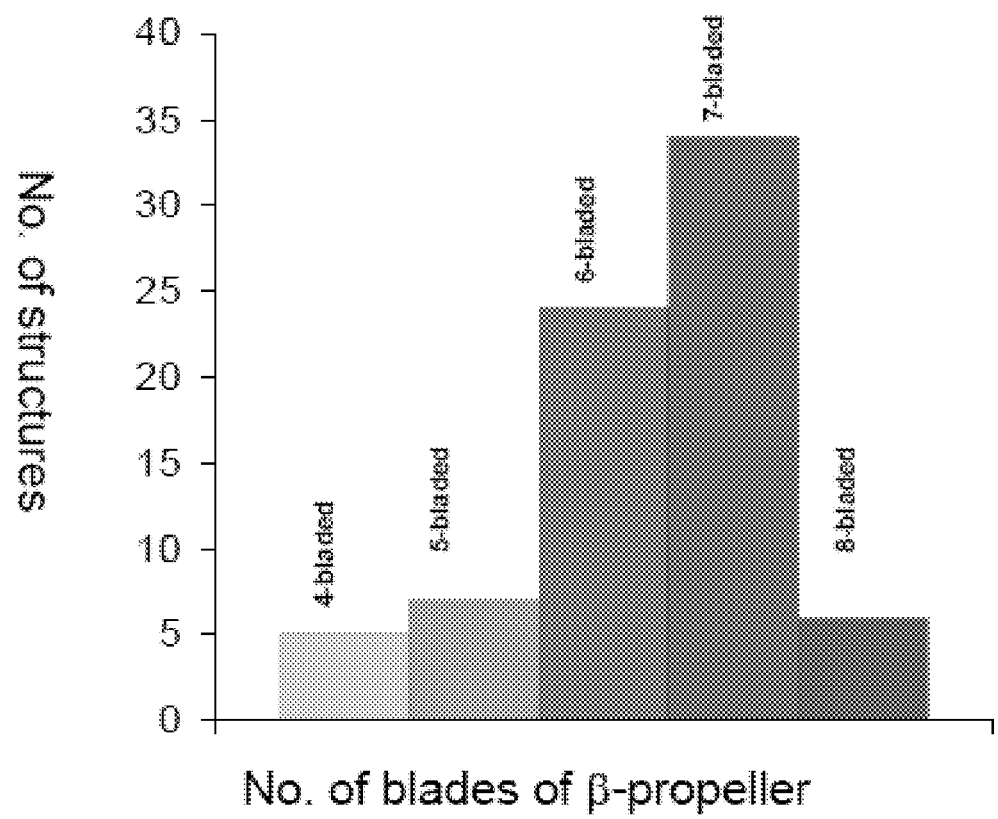
Figure 10:
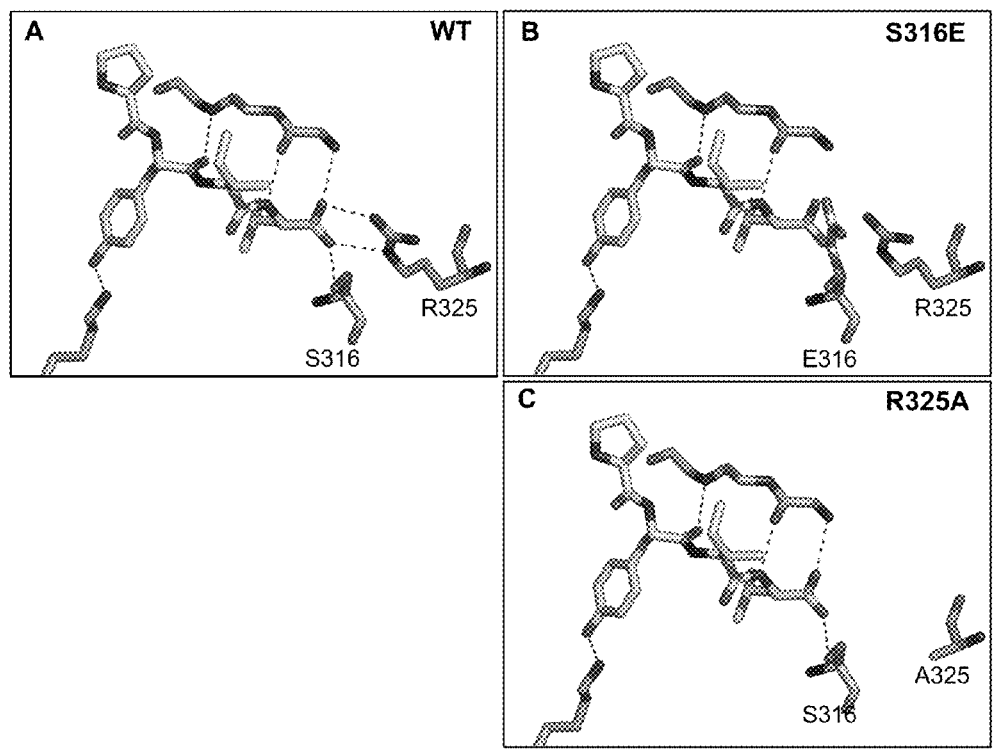
Figure 11:
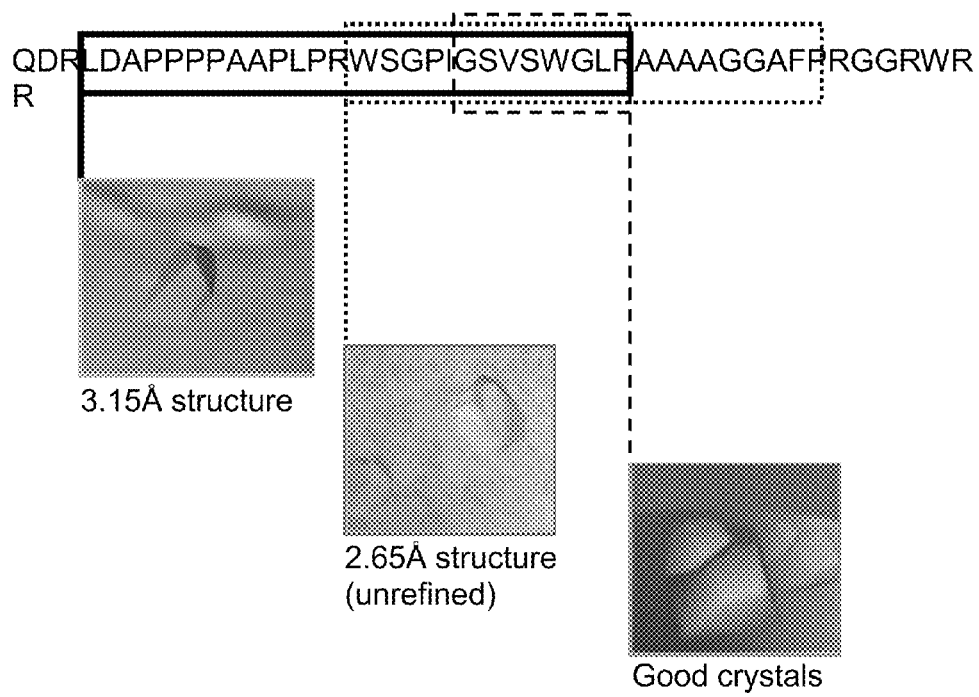
Figure 12:
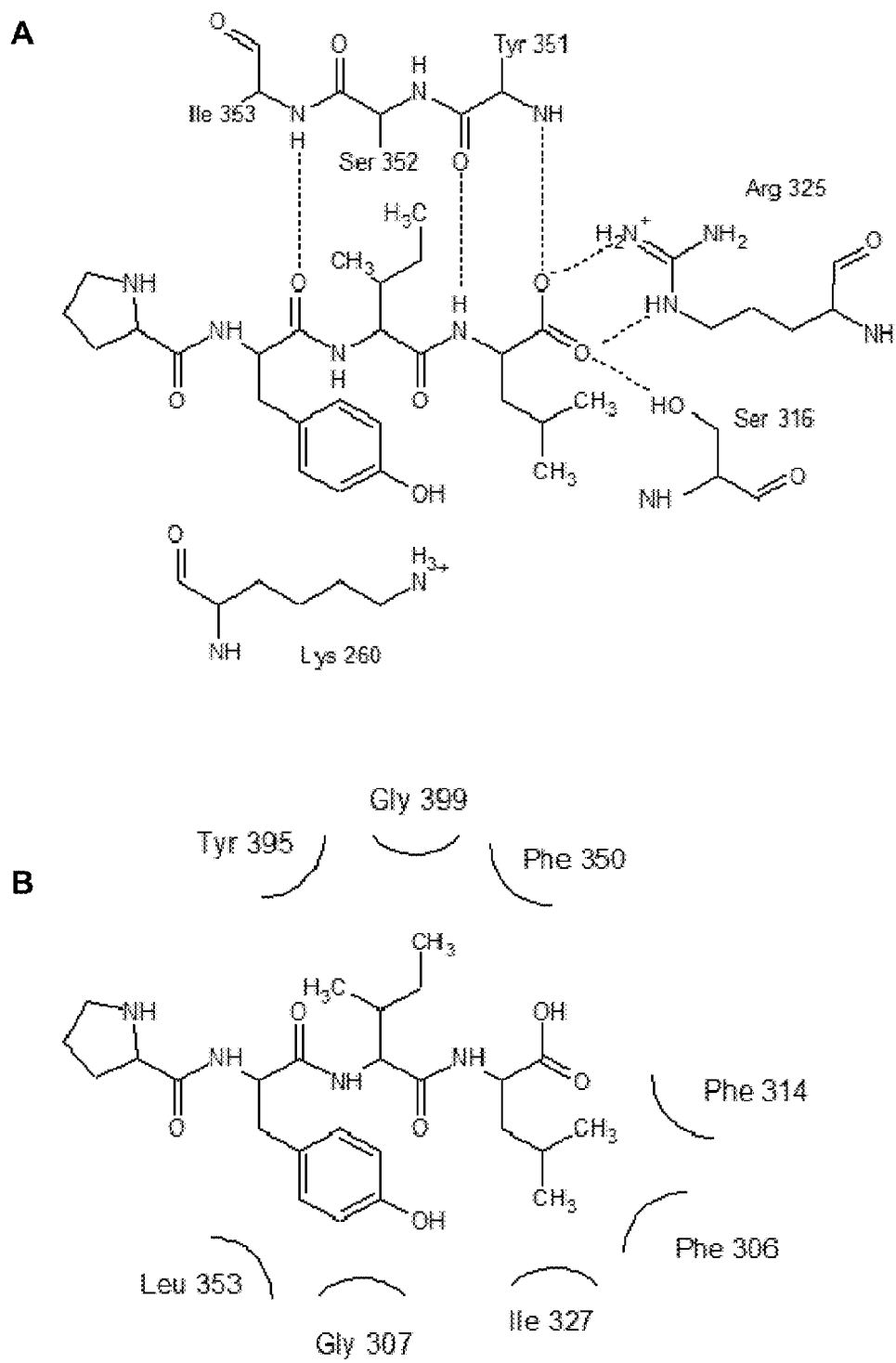

FIG. 6: Overview of expression and crystallization
FIG. 7: X-ray diffraction pattern to 2 Å resolution
FIG. 8: Refinement statistics and Ramachandran plot
FIG. 9: Statistics of β-propeller structures demonstrating that the 10-bladed Sortilin β-propeller is unique, new and unexpected.
FIG. 10: Overview of binding of PYIL (SEQ ID NO:11) ligand to Sortilin mutant structures S316E and R325A of sSortilin (SEQ ID NO.33) as compared to wild type (WT).
FIG. 11: Optimisation of Sortilin crystals comprising a fragment (SEQ ID NO:21) of the Sortilin propeptide FIG. 12: The figure represents the hydrogen bonding arrangement from the C-terminal of neurotensin, shown as Pro-Tyr-Ile-Leu (SEQ ID NO:11), and sortilin as seen in the 2.0 Å structure of luminal sortilin complexed with neurotensin. Only the hydrogen bonds of the neurotensin leucine are invariable while that of isoleucine-353 and lysine-260 of sSortilin (SEQ ID NO. 33) to the neurotensin tyrosine are variable. sSortilin (SEQ ID NO:33) has the sequence of amino acid residues 78 to 755 of SEQ ID NO. 1. Residue numbers in the Figure refer to the positions of residues in SEQ ID NO:1

To illustrate the hydrophobic interactions between sortilin and neurotensin, residues of sortilin with carbon atoms within 4.2 Å of neurotensin carbon atoms have been listed next to their interaction partners.

FIG. 13: Mapping of specific interactions of binding site 1 with C-terminal of neurotensin (NT) bound.

Figure 14:
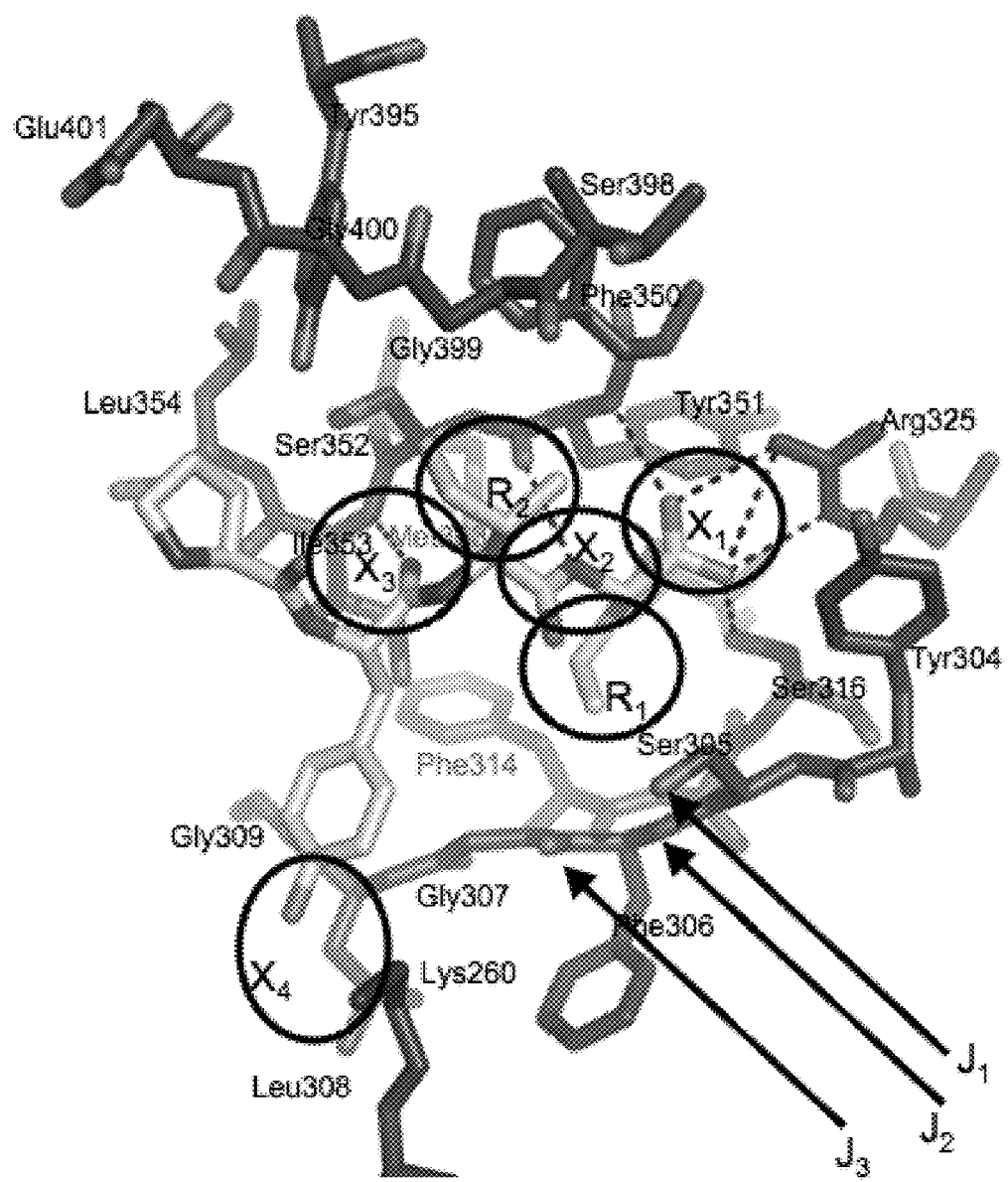

FIG. 14: Mapping of specific interactions of binding site 1 of sSortilin (SEQ ID NO:33) with artificial peptide NT69L (SEQ ID NO. 12) bound. sSortilin (SEQ ID NO:33) has the sequence of amino acid residues 78 to 755 of SEQ ID NO. 1. Residue numbers in the Figure refer to the positions of residues in SEQ ID NO:1.

Figure 15:
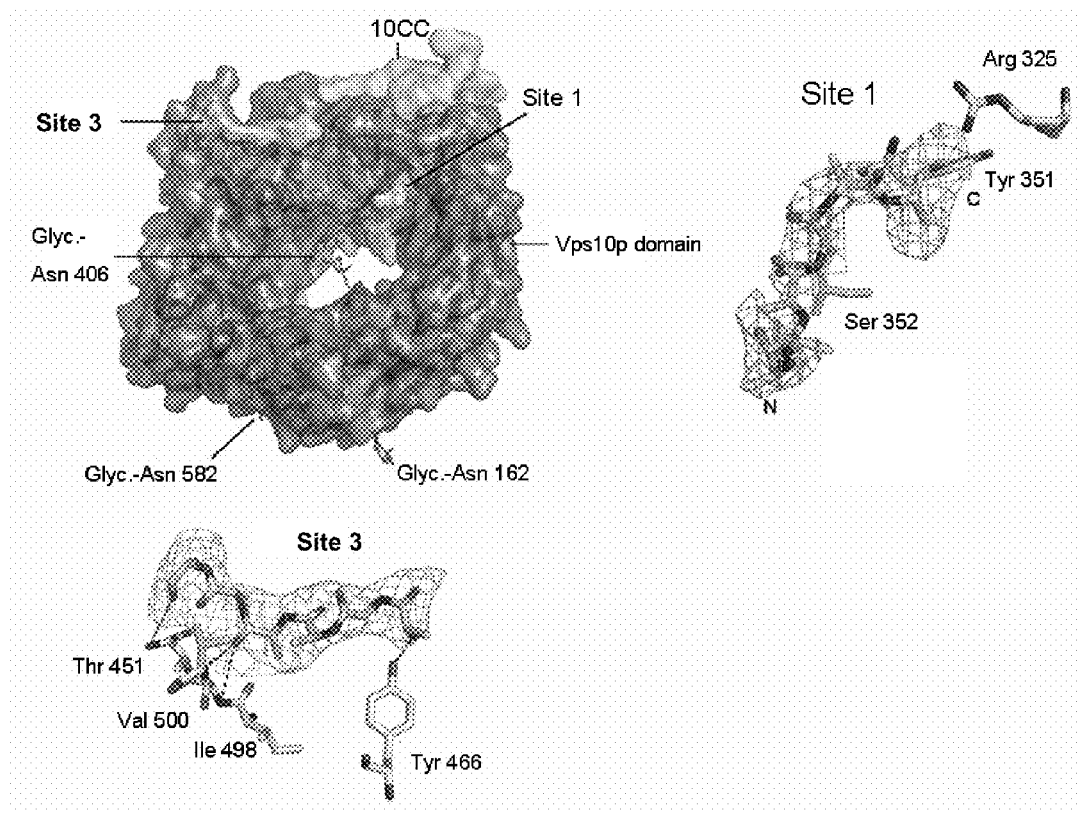

FIG. 15: Overview of the density at the two binding sites of Sortilin. The novel binding site for the pro-domain of Nerve Growth Factor is Site 3.

Figure 16:
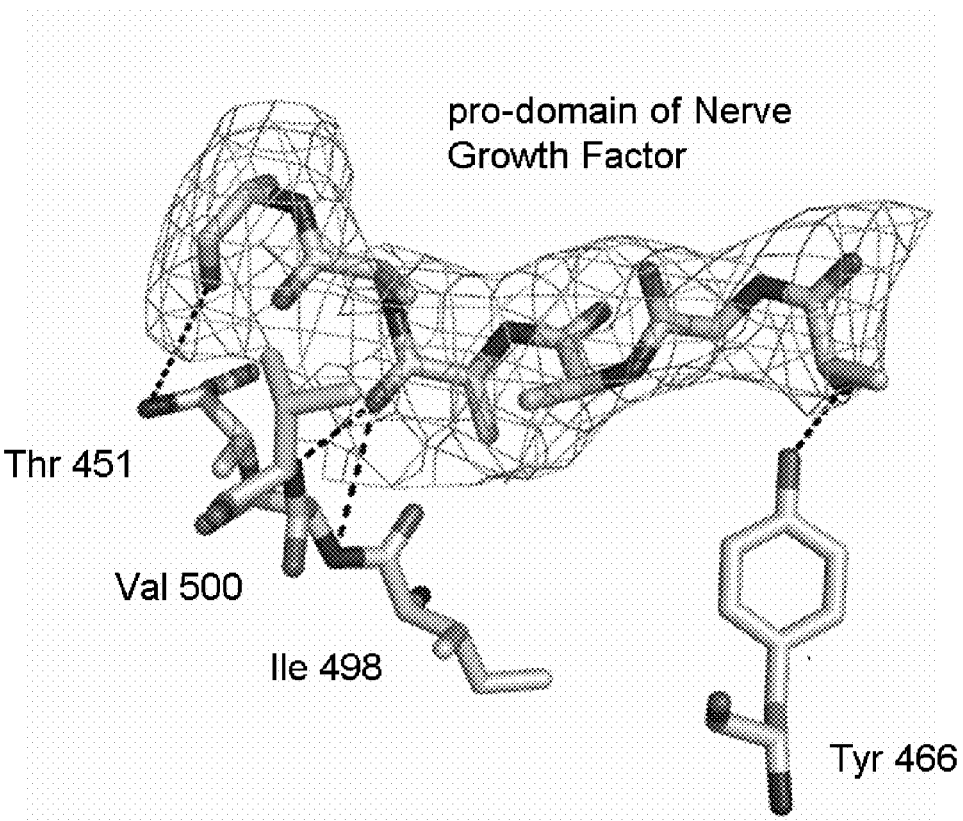

FIG. 16: Fo-Fc density at site 3 shown at 2.6. Residues of sortilin involved in binding shown as sticks and labelled with amino acid type and residue number. The peptide backbone of the prodomain of Nerve Growth factor is shown overlaid with the electron density.

Figure 17:
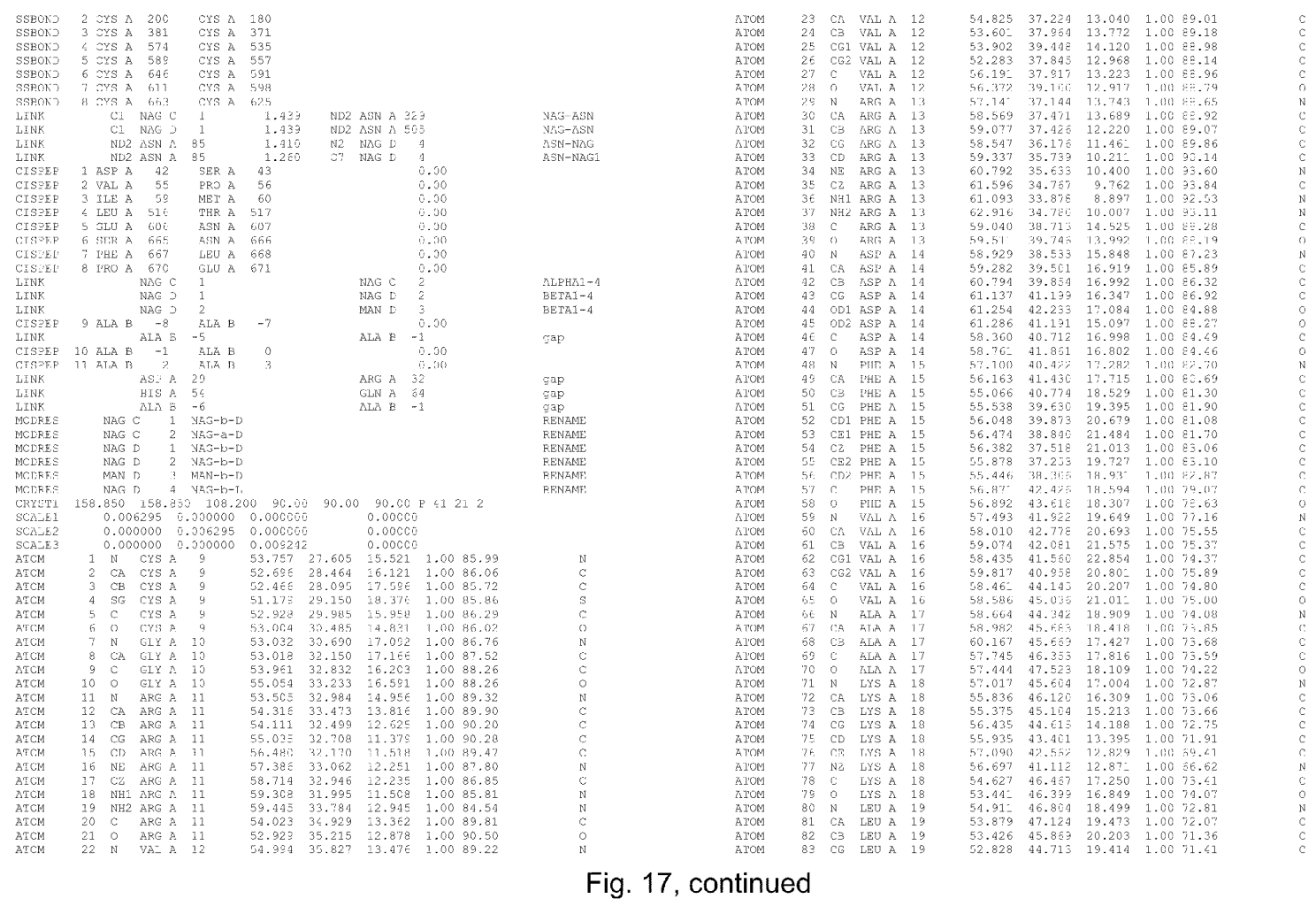
Figure 17:
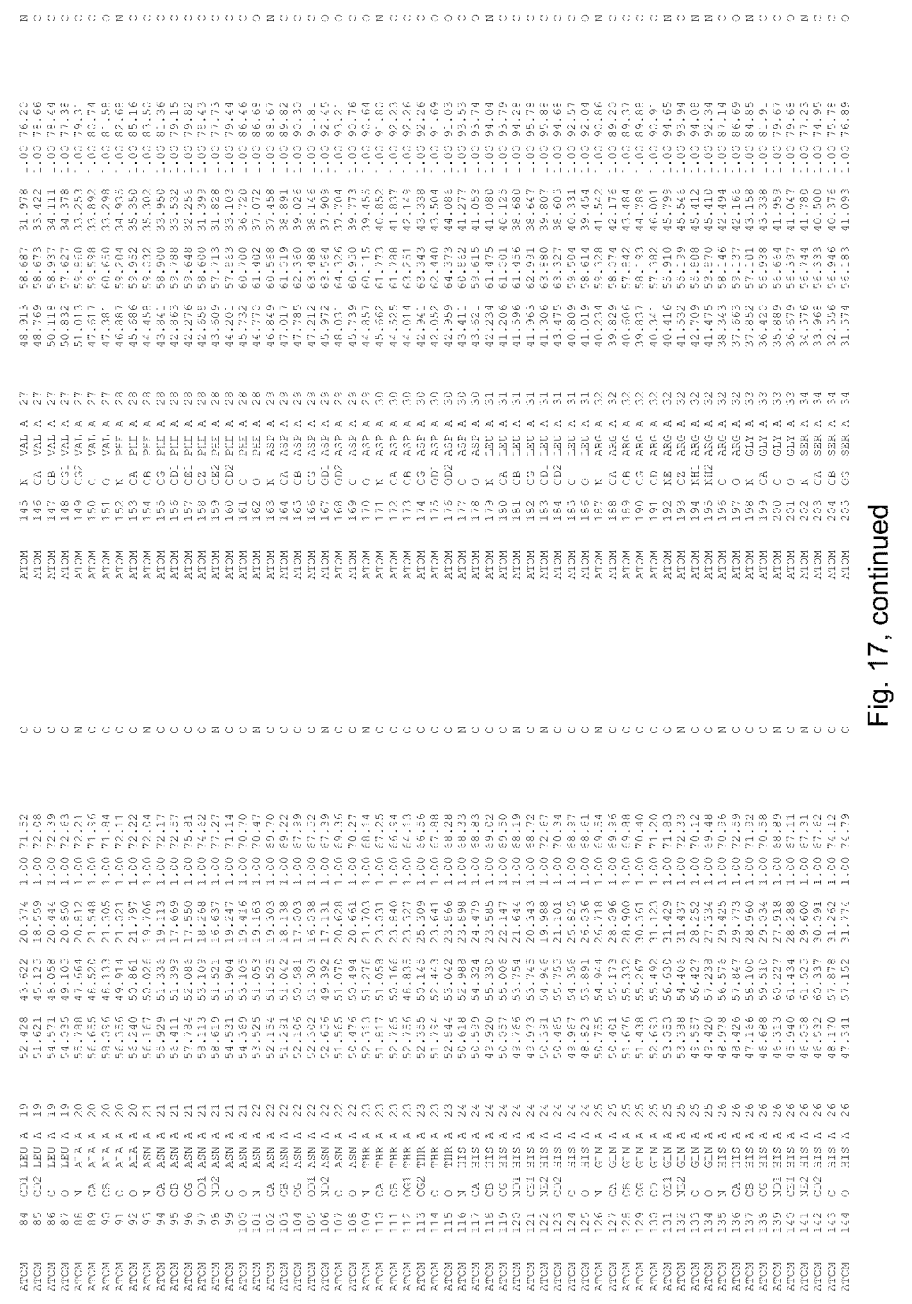
Figure 17:
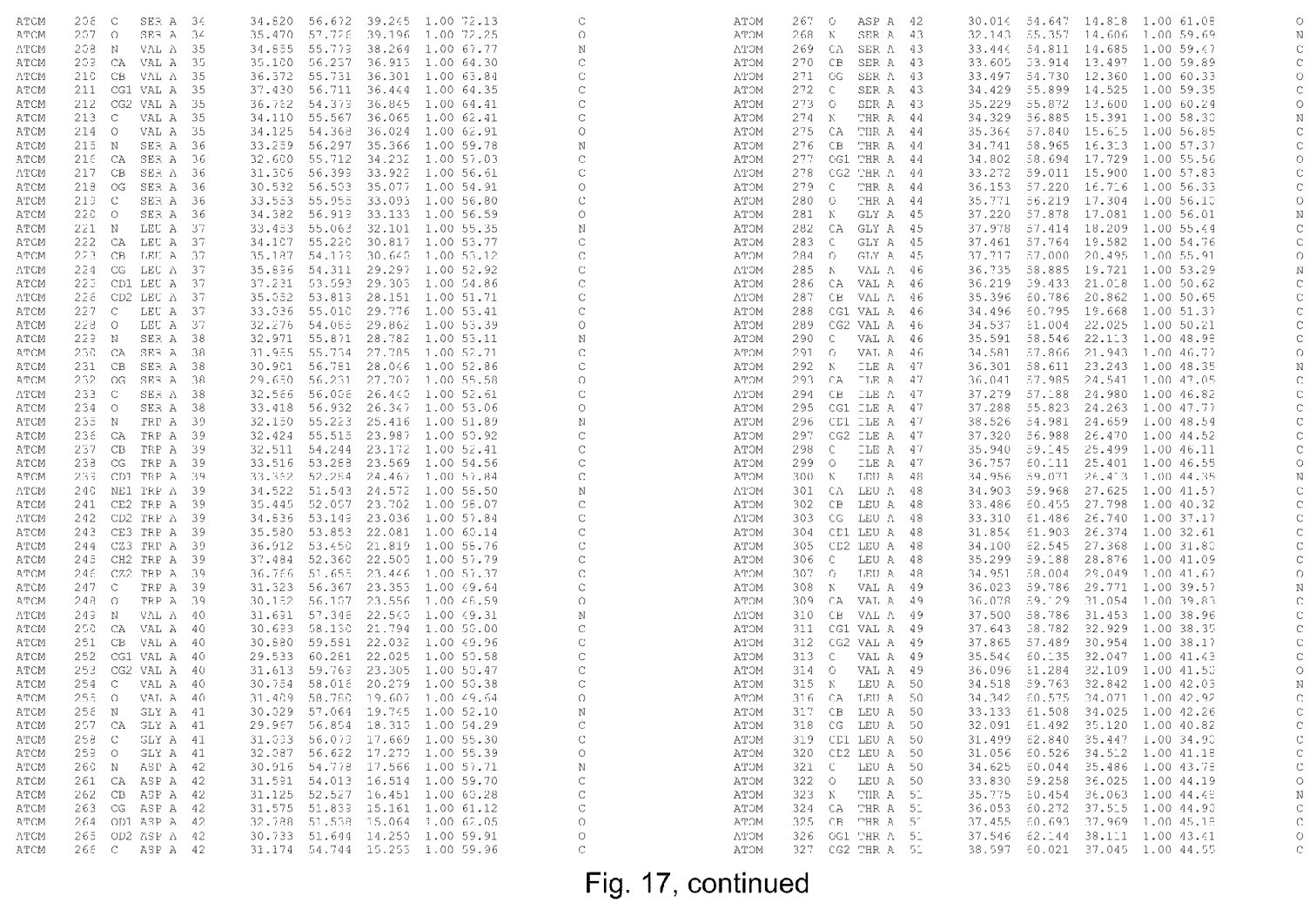
Figure 17:
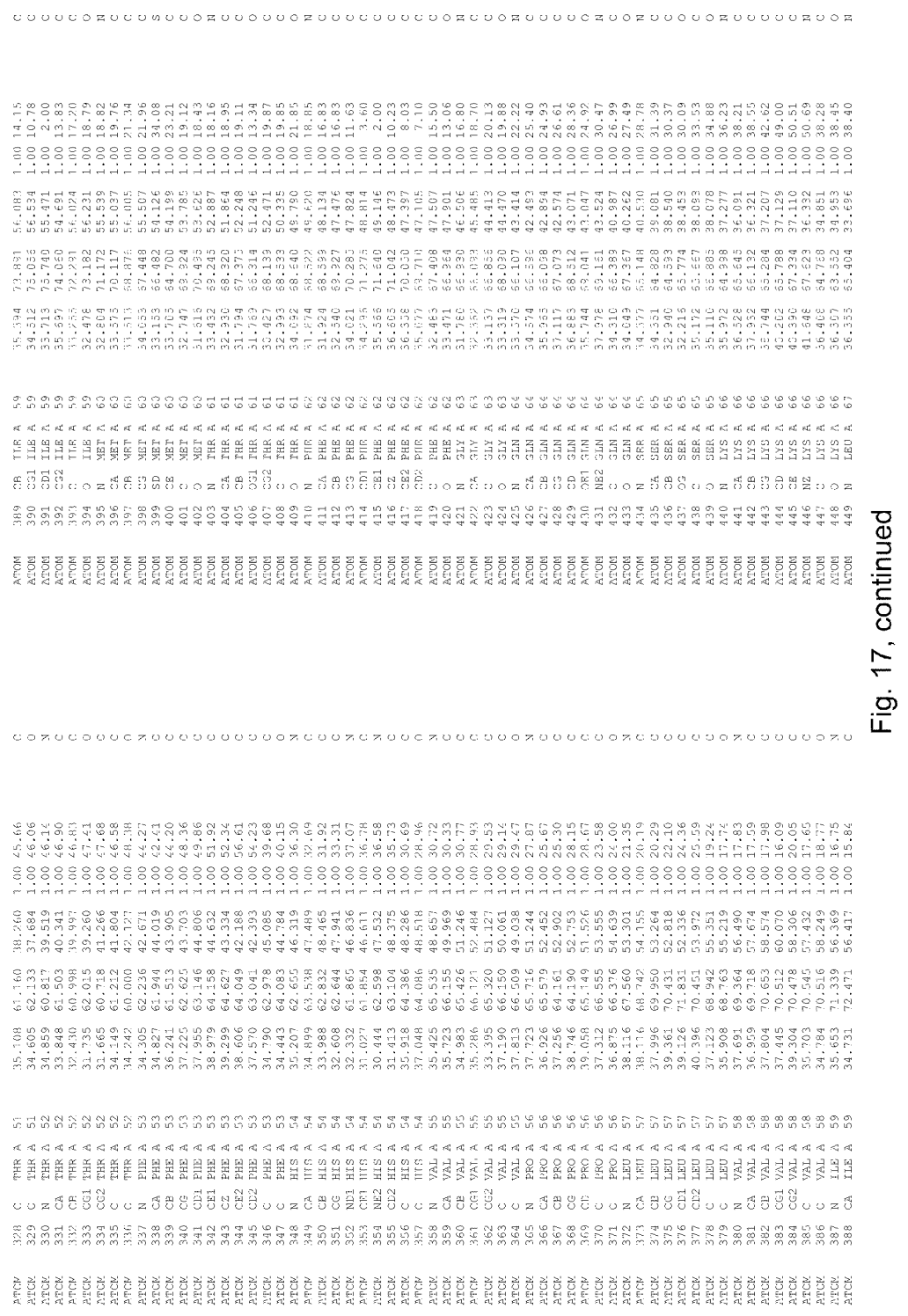
Figure 17:
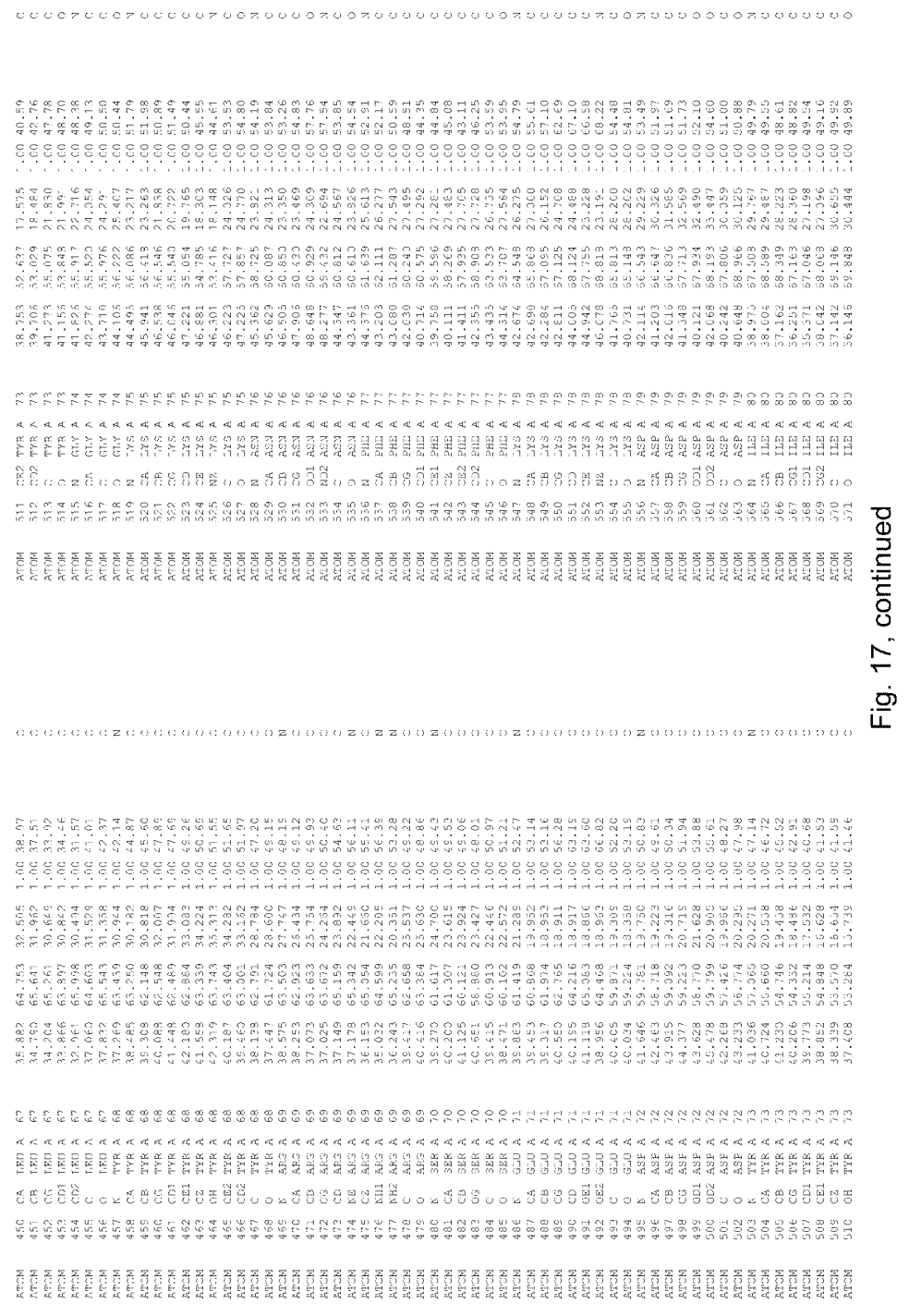
Figure 17:
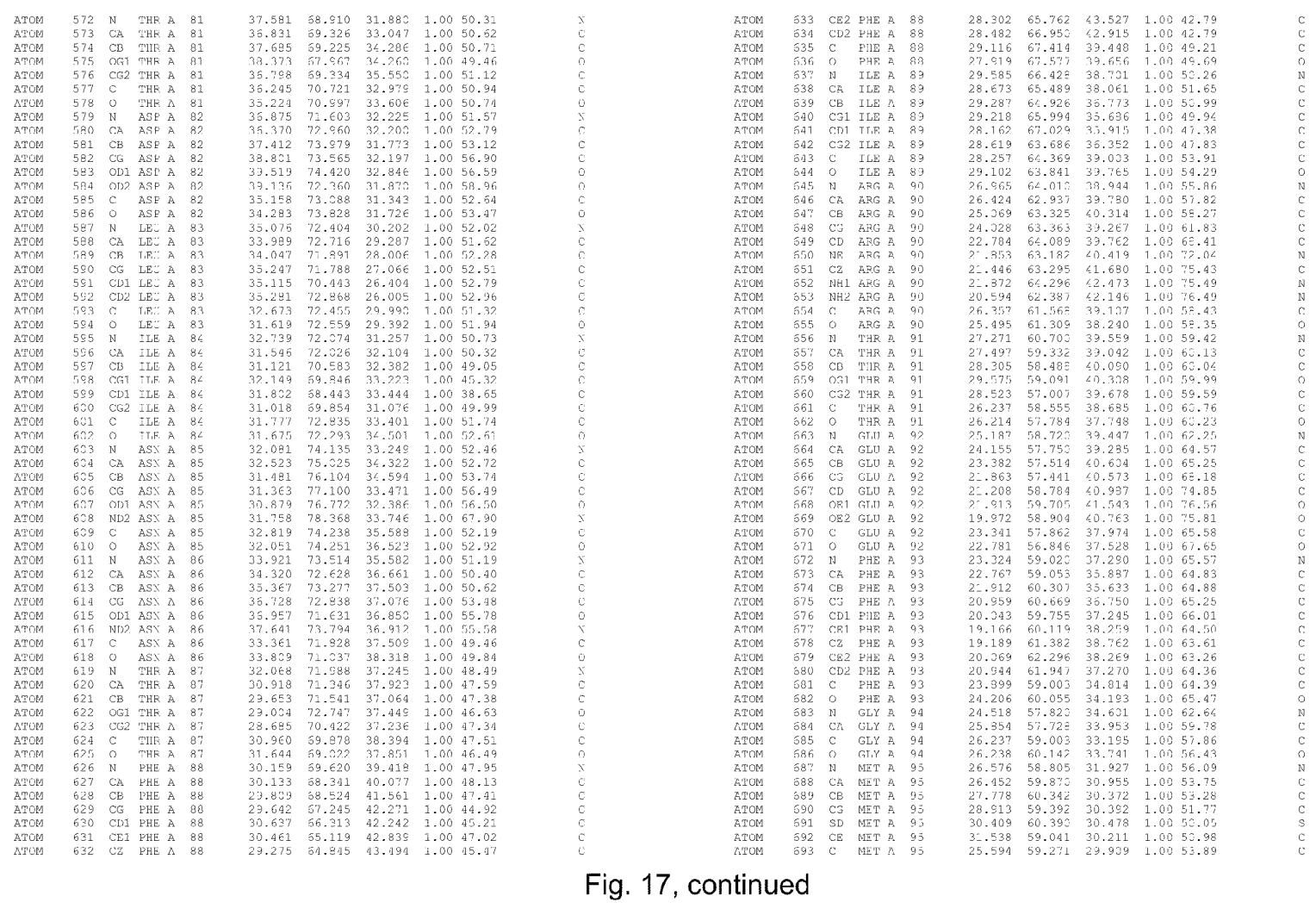
Figure 17:
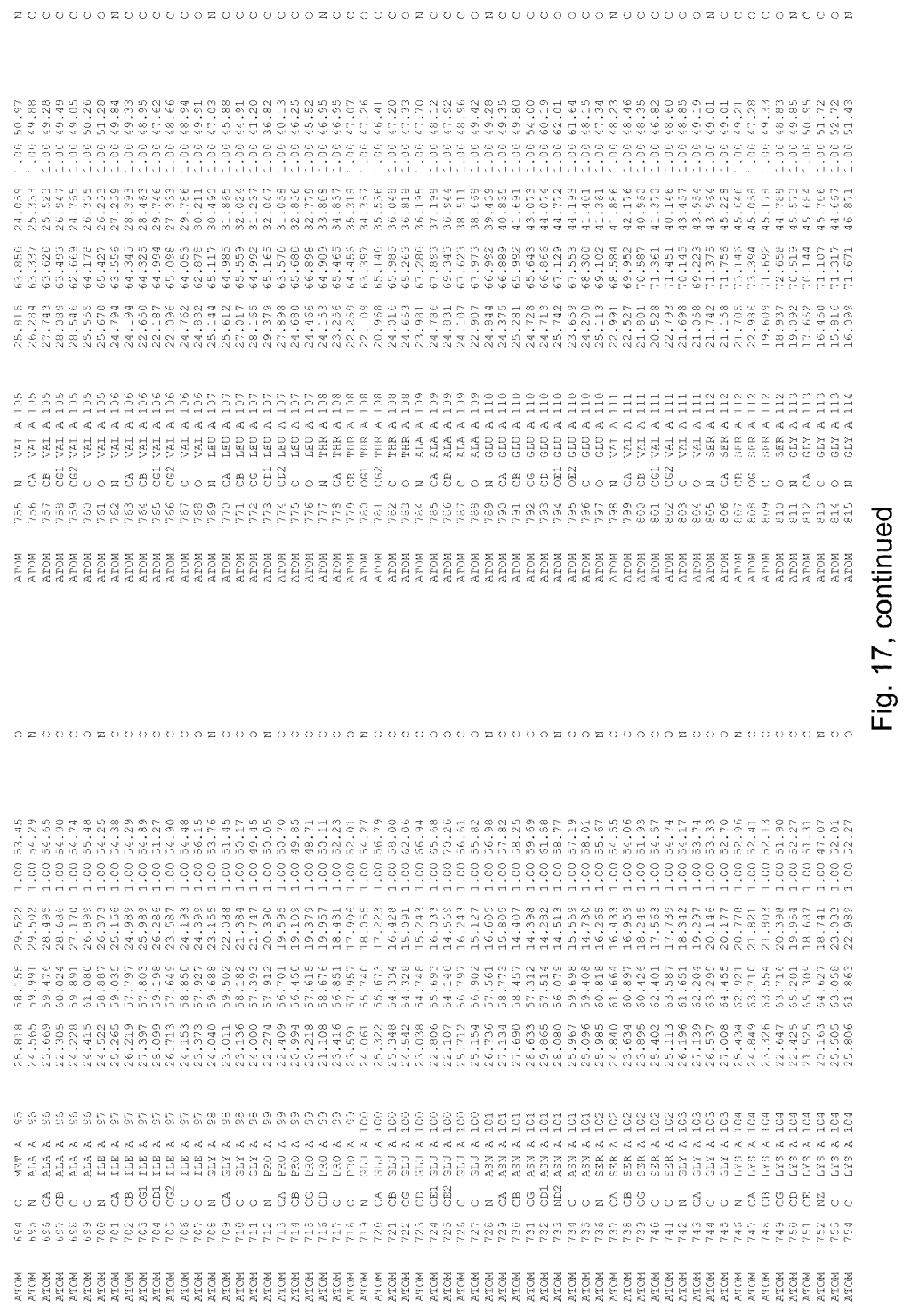
Figure 17:
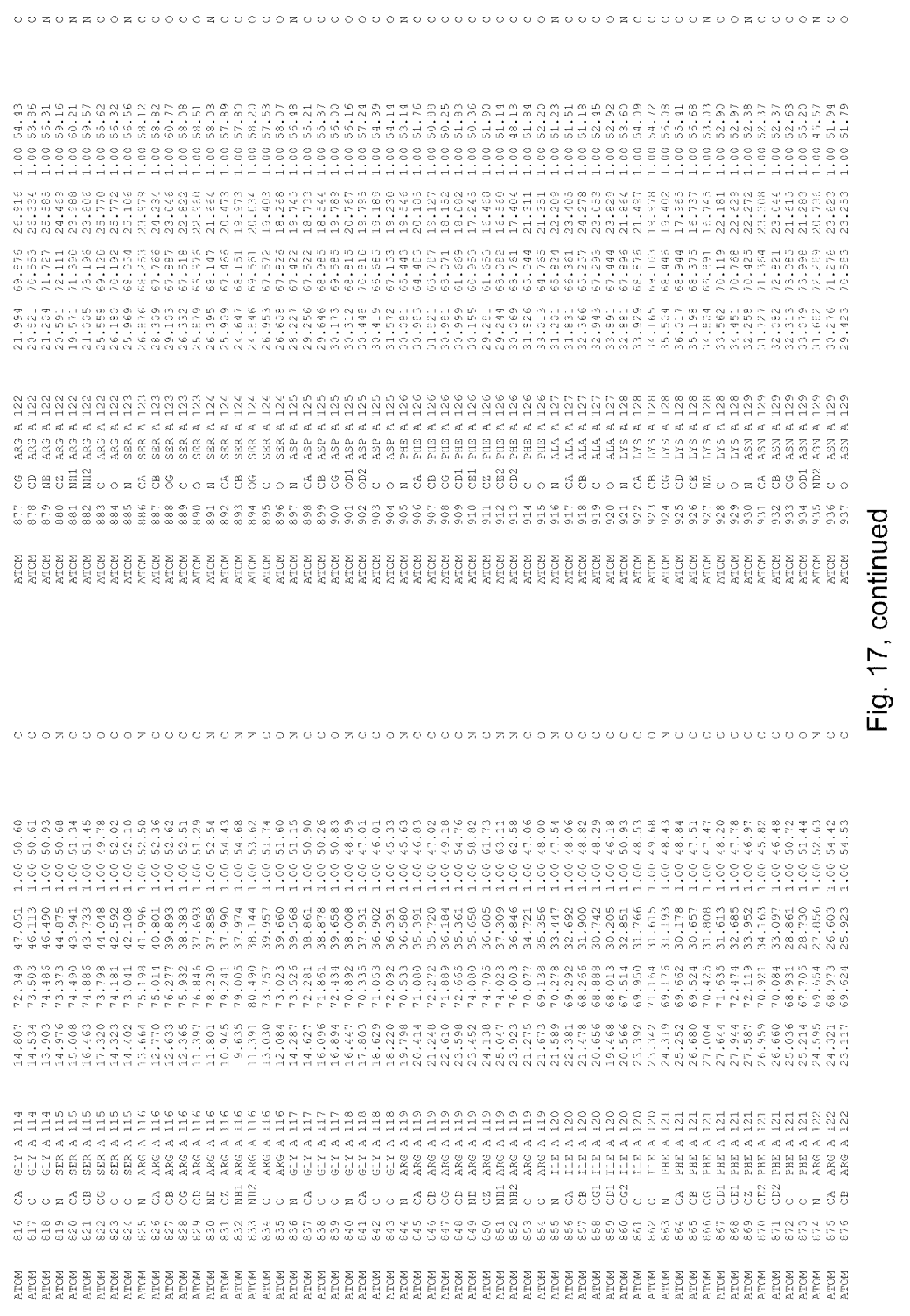
Figure 17:
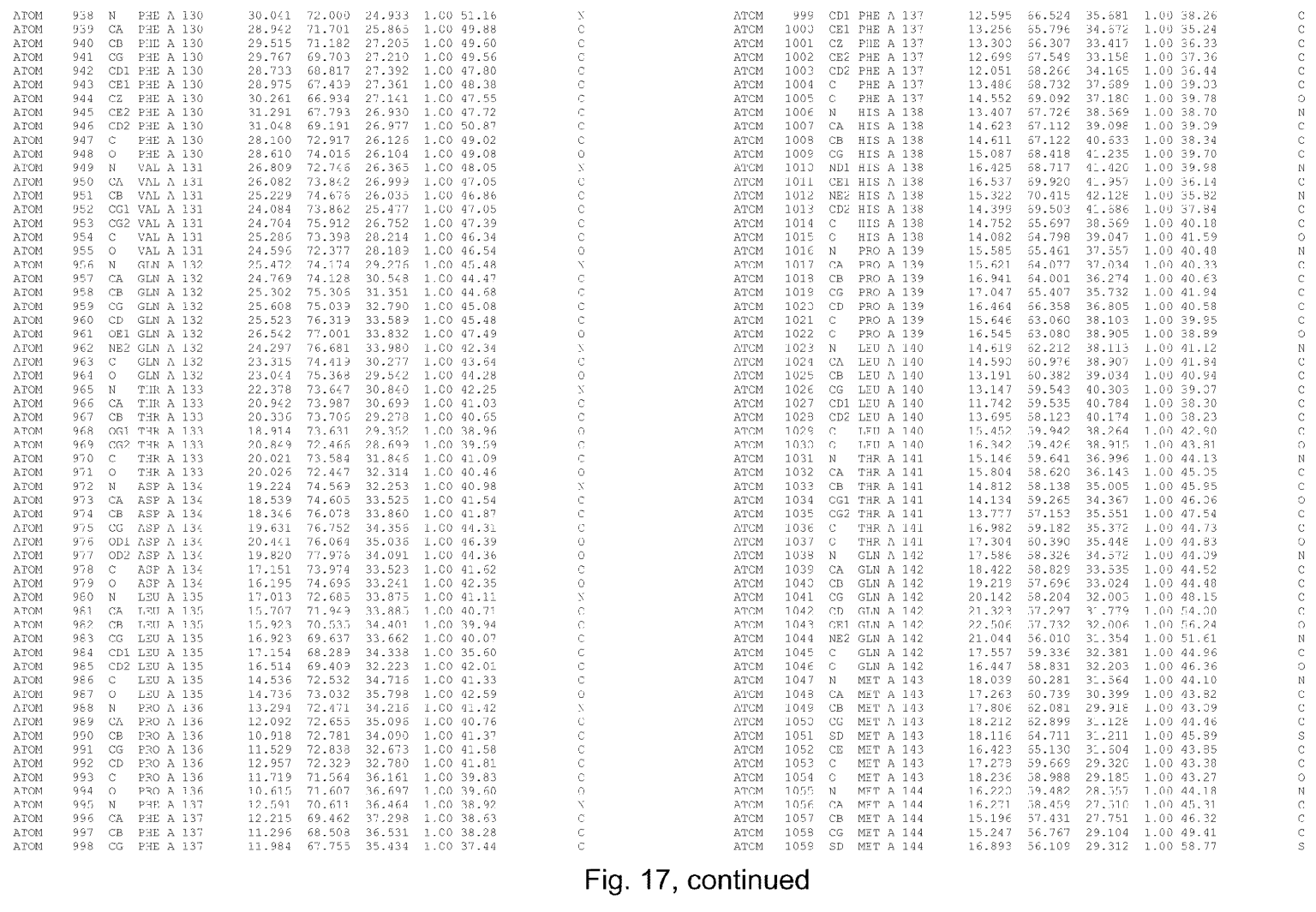
Figure 17:
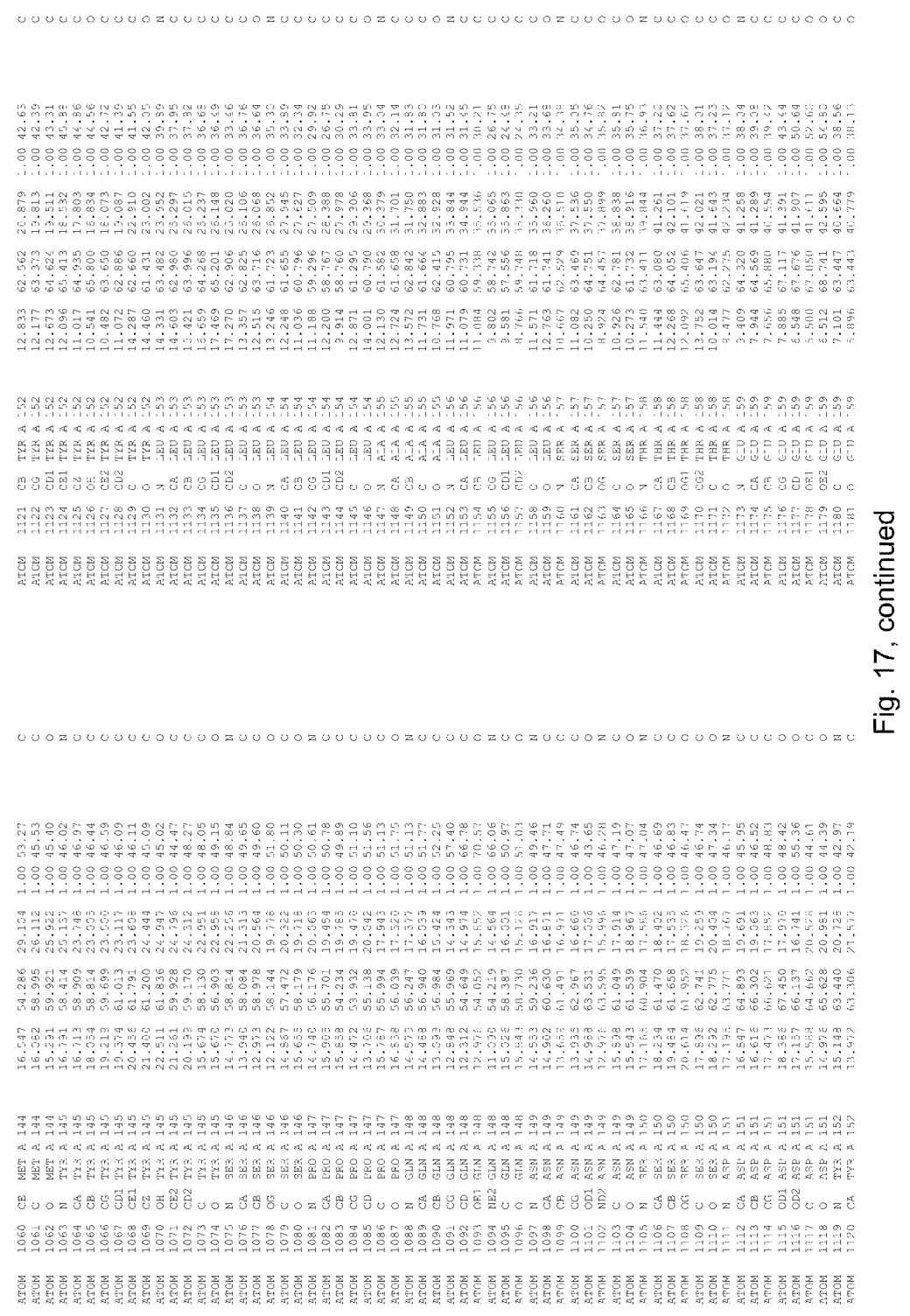
Figure 17:
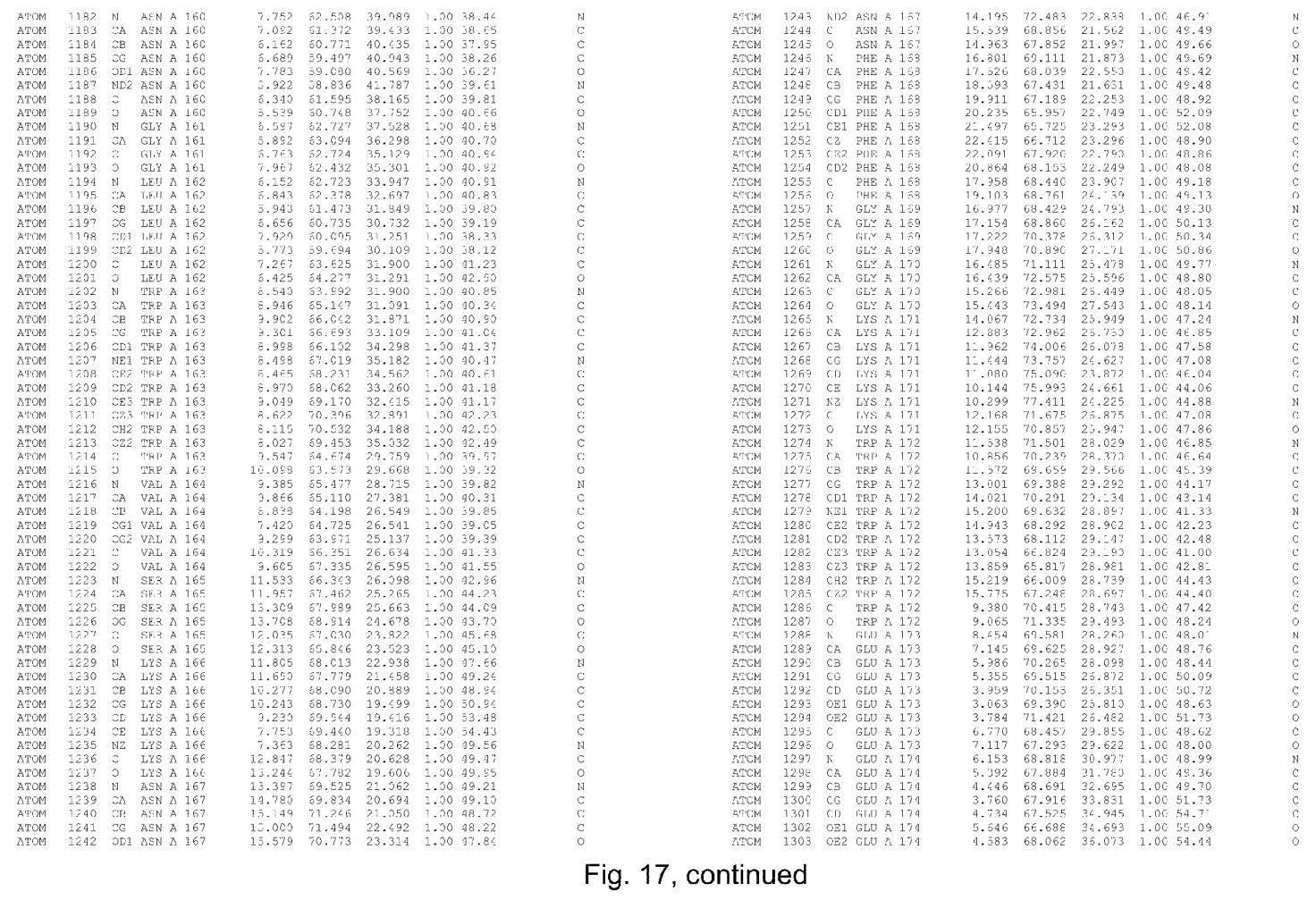
Figure 17:
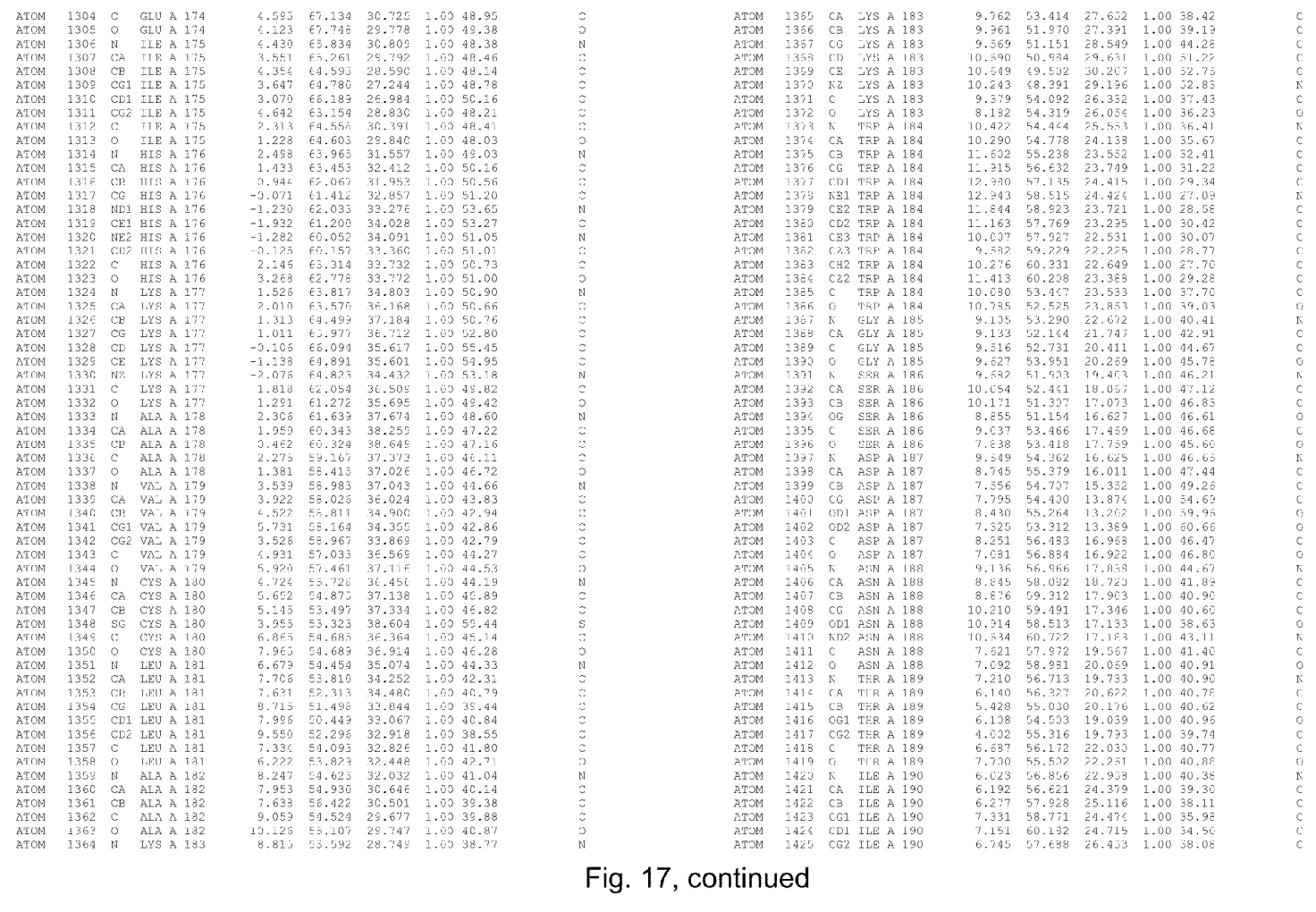
Figure 17:
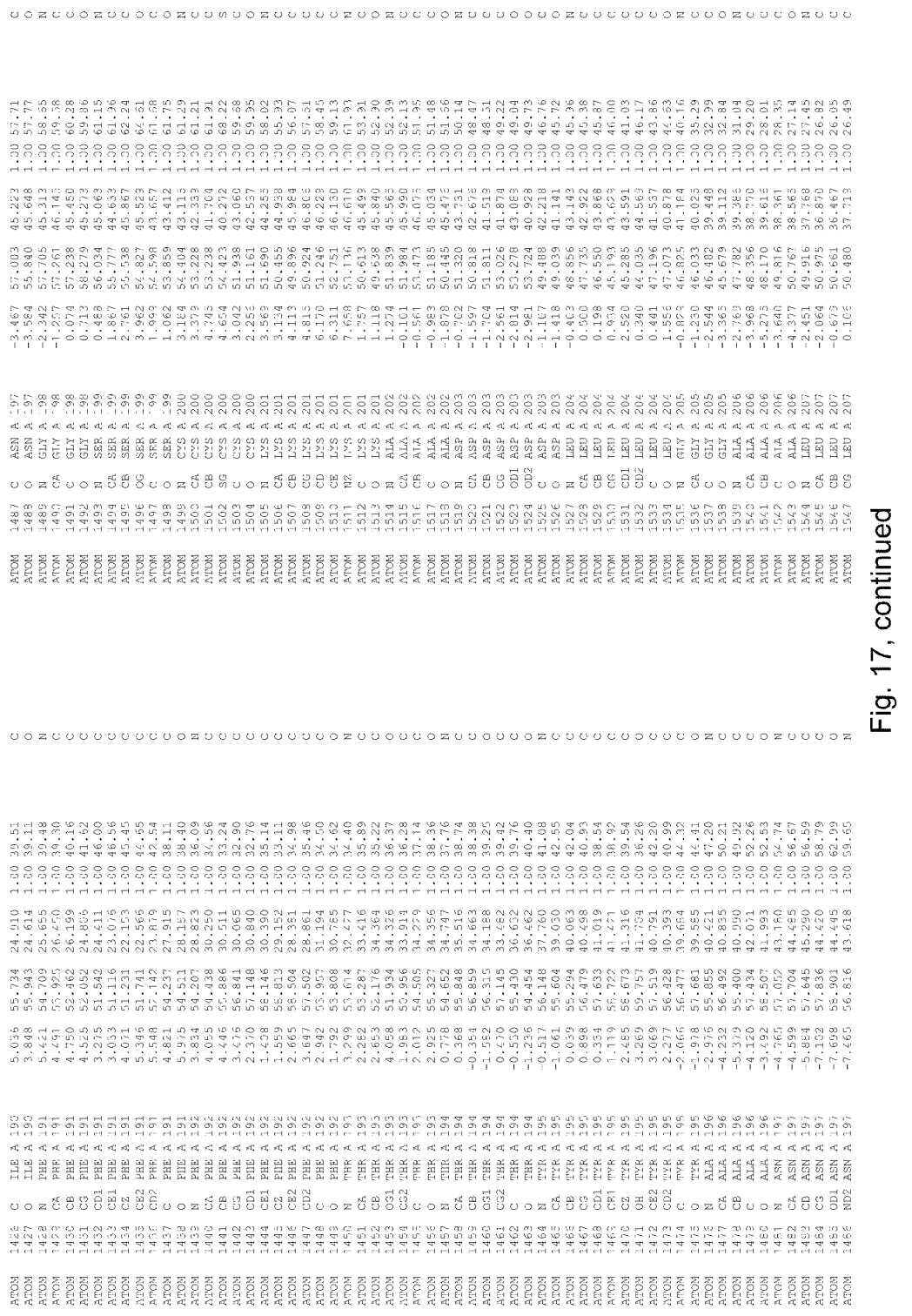
Figure 17:
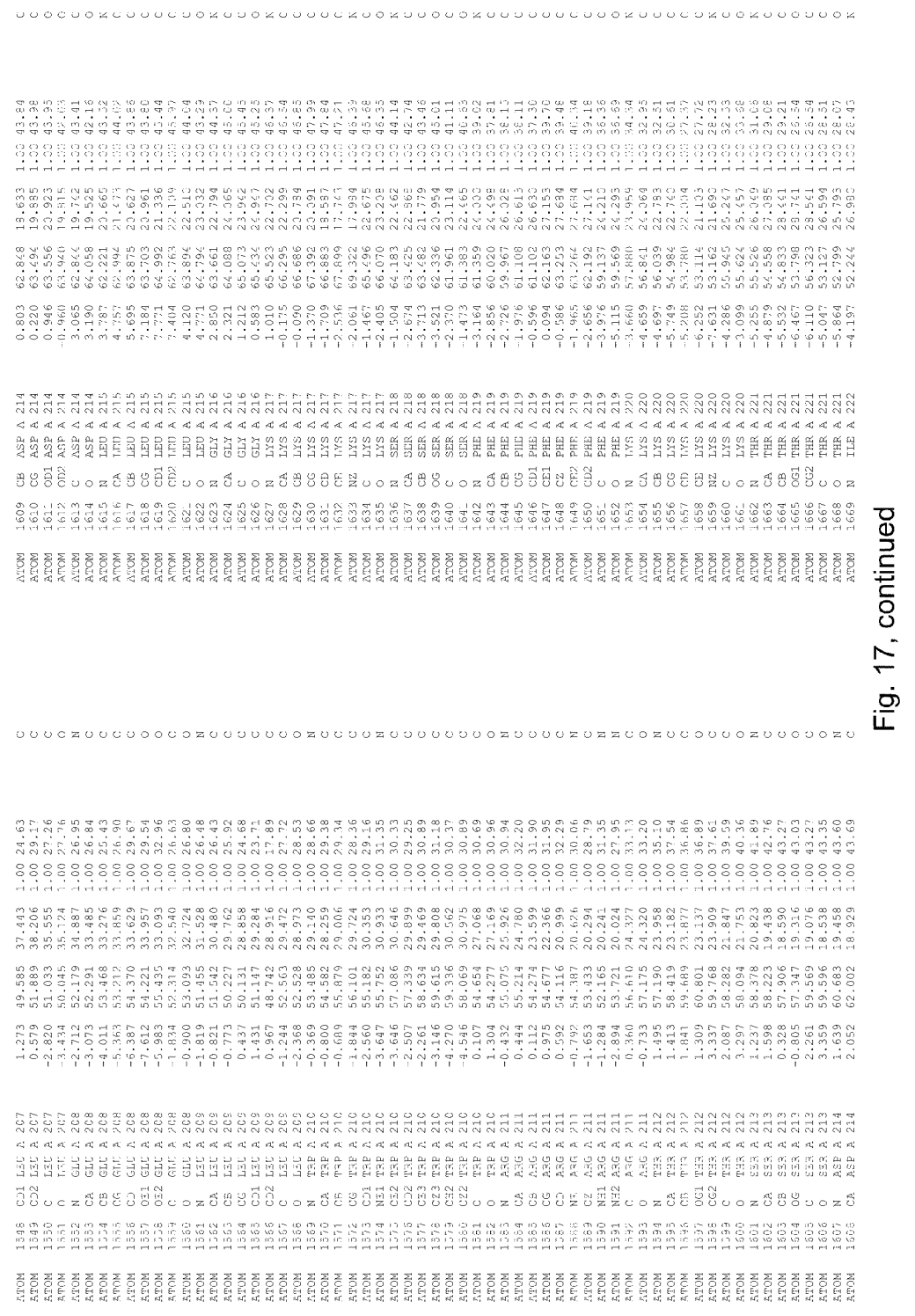
Figure 17:
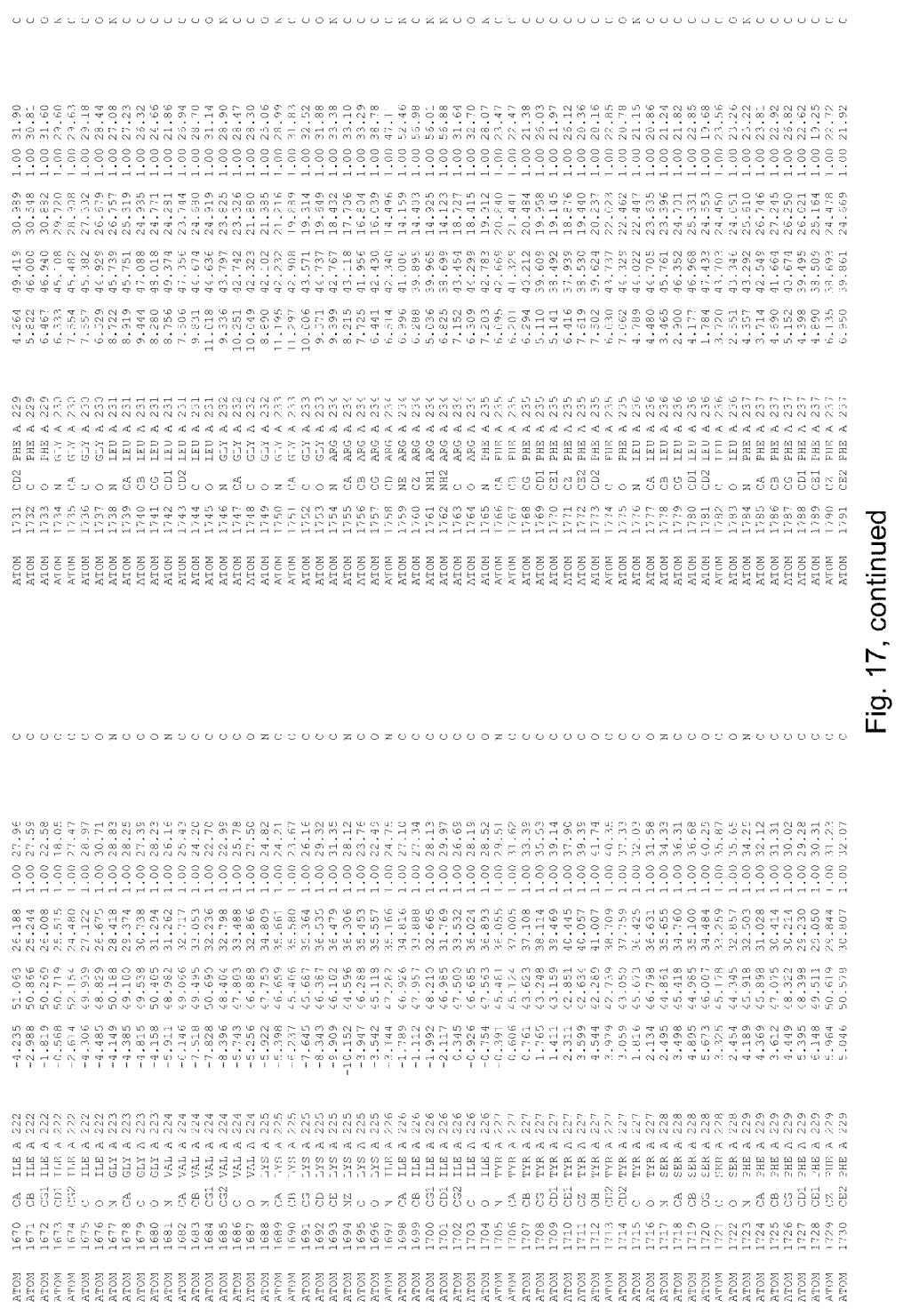
Figure 17:
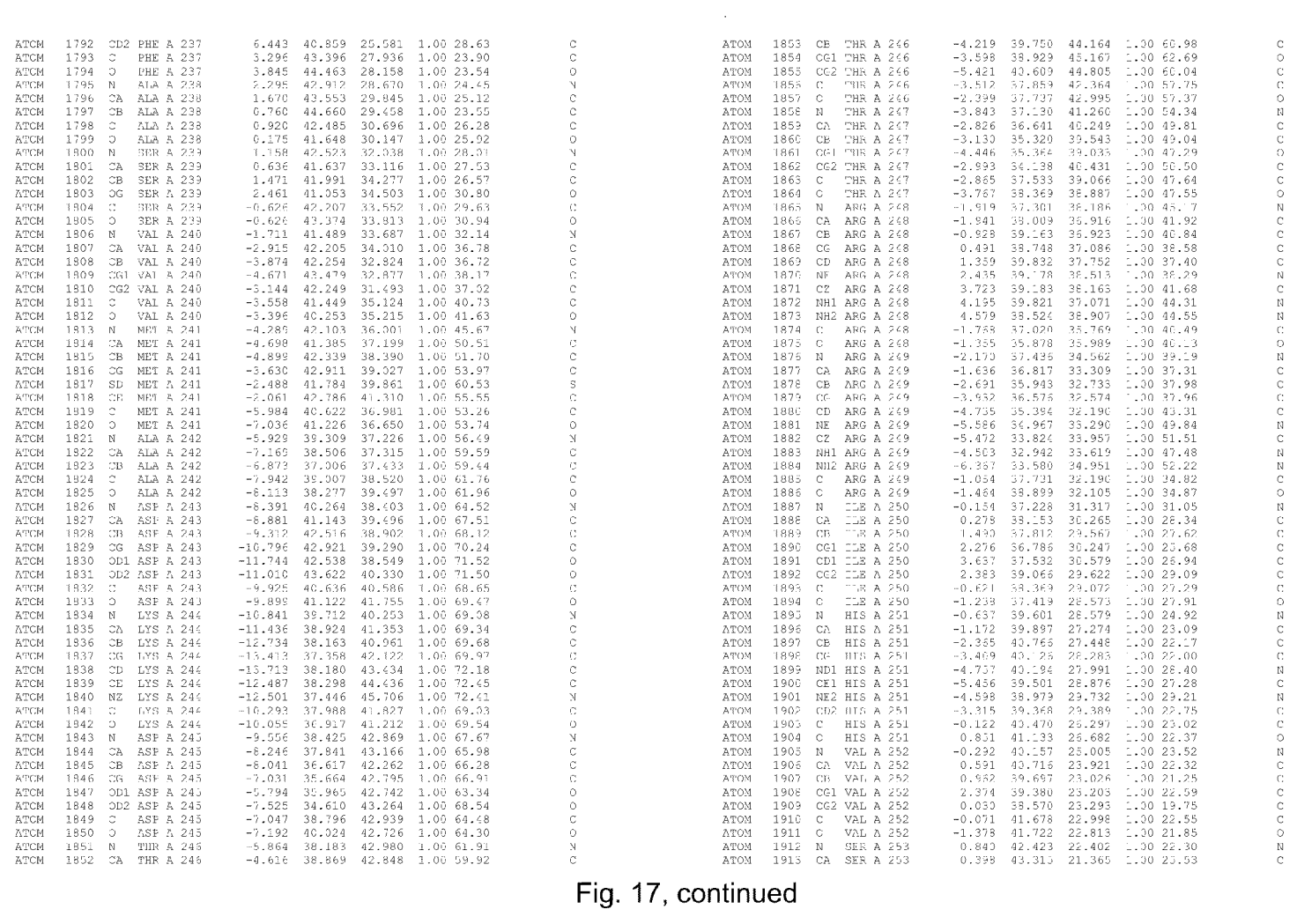
Figure 17:
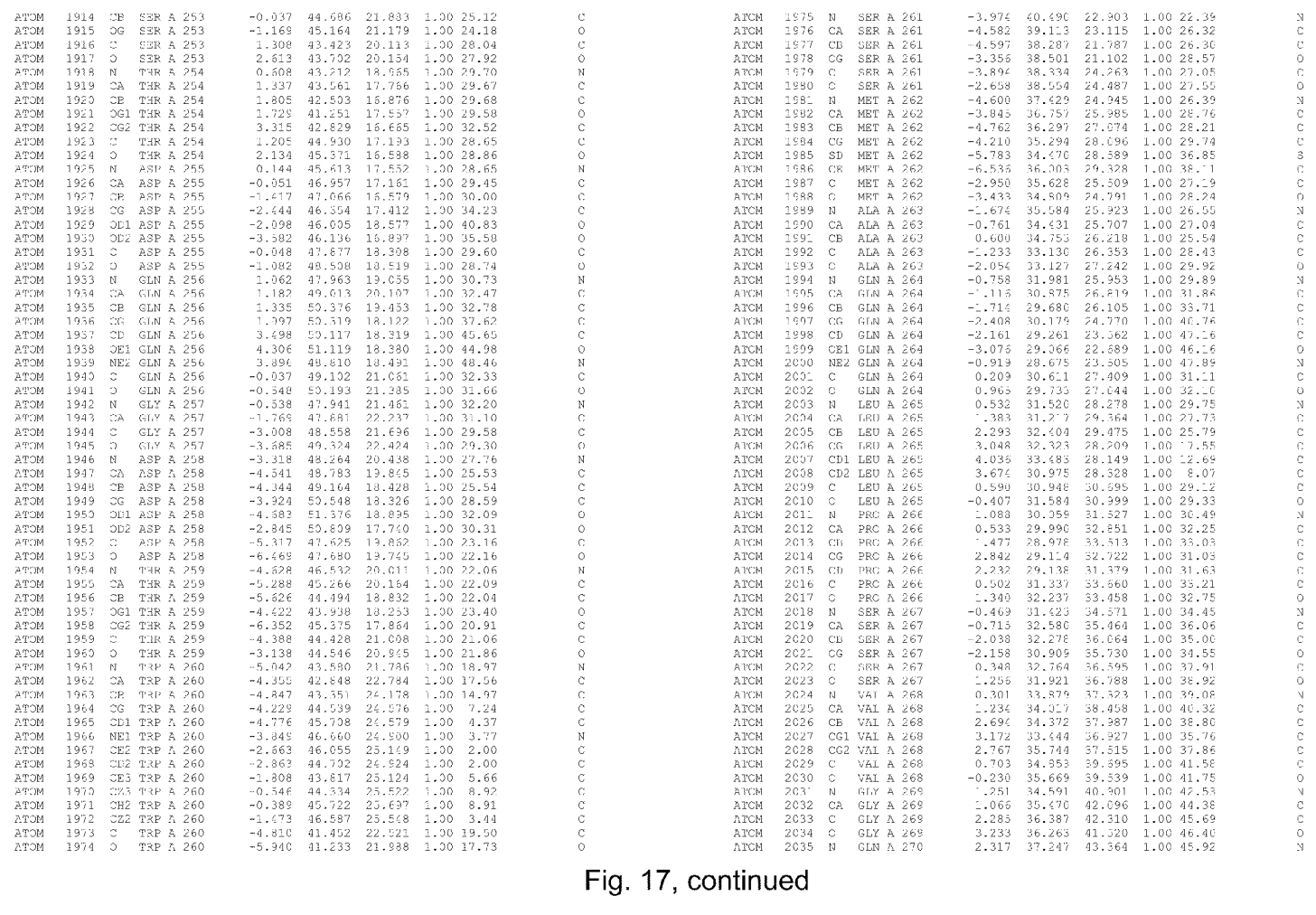
Figure 17:
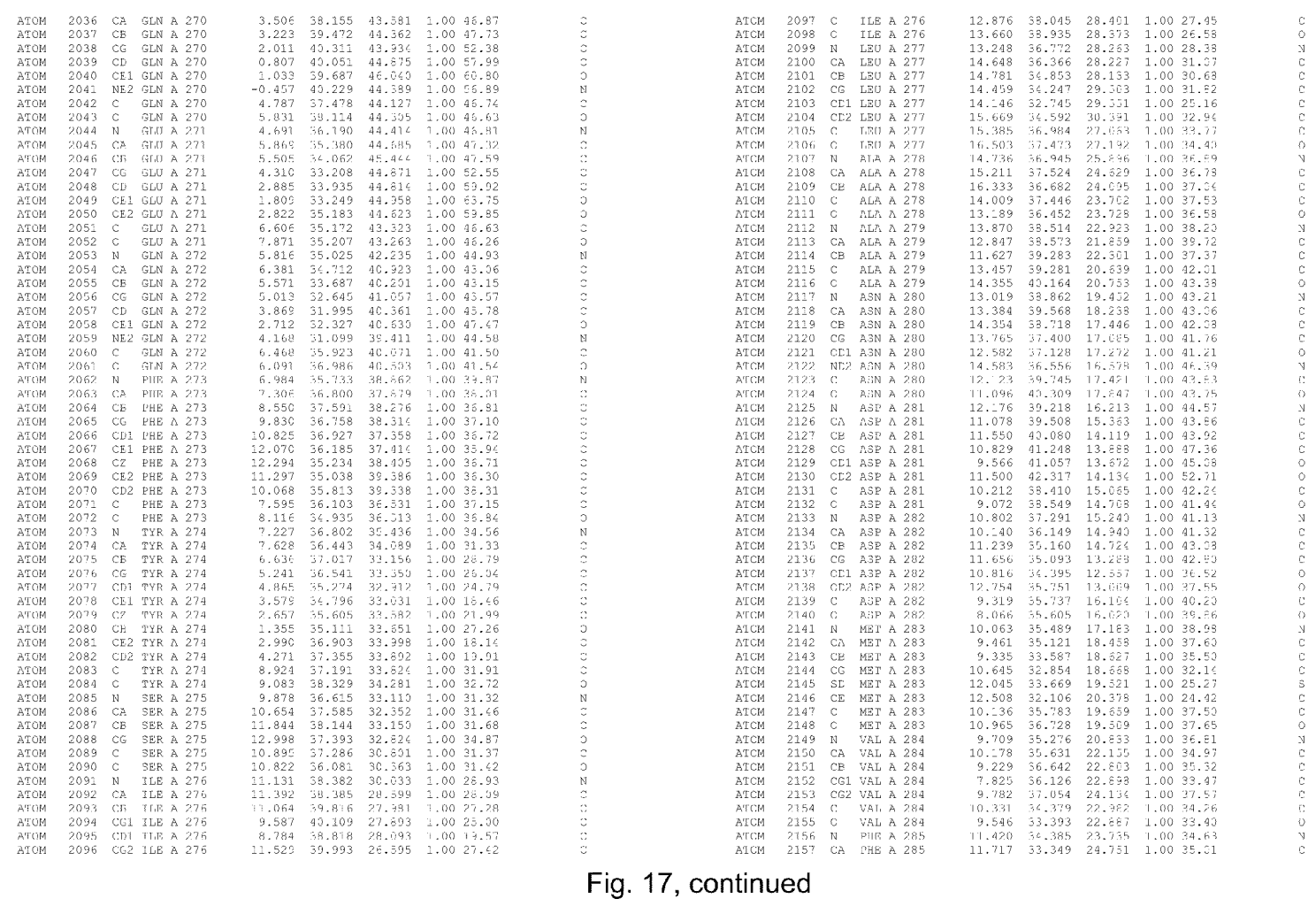
Figure 17:
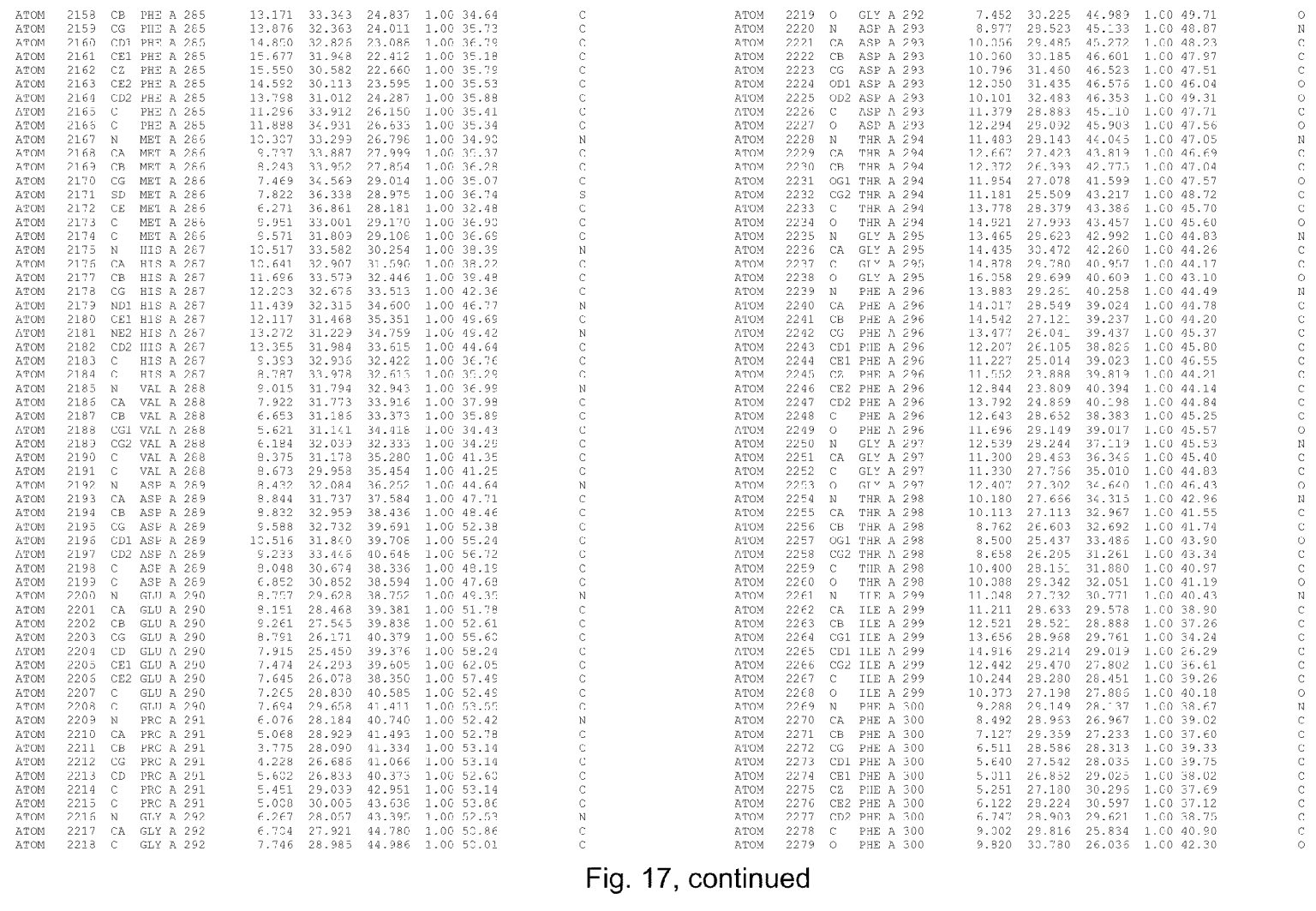
Figure 17:
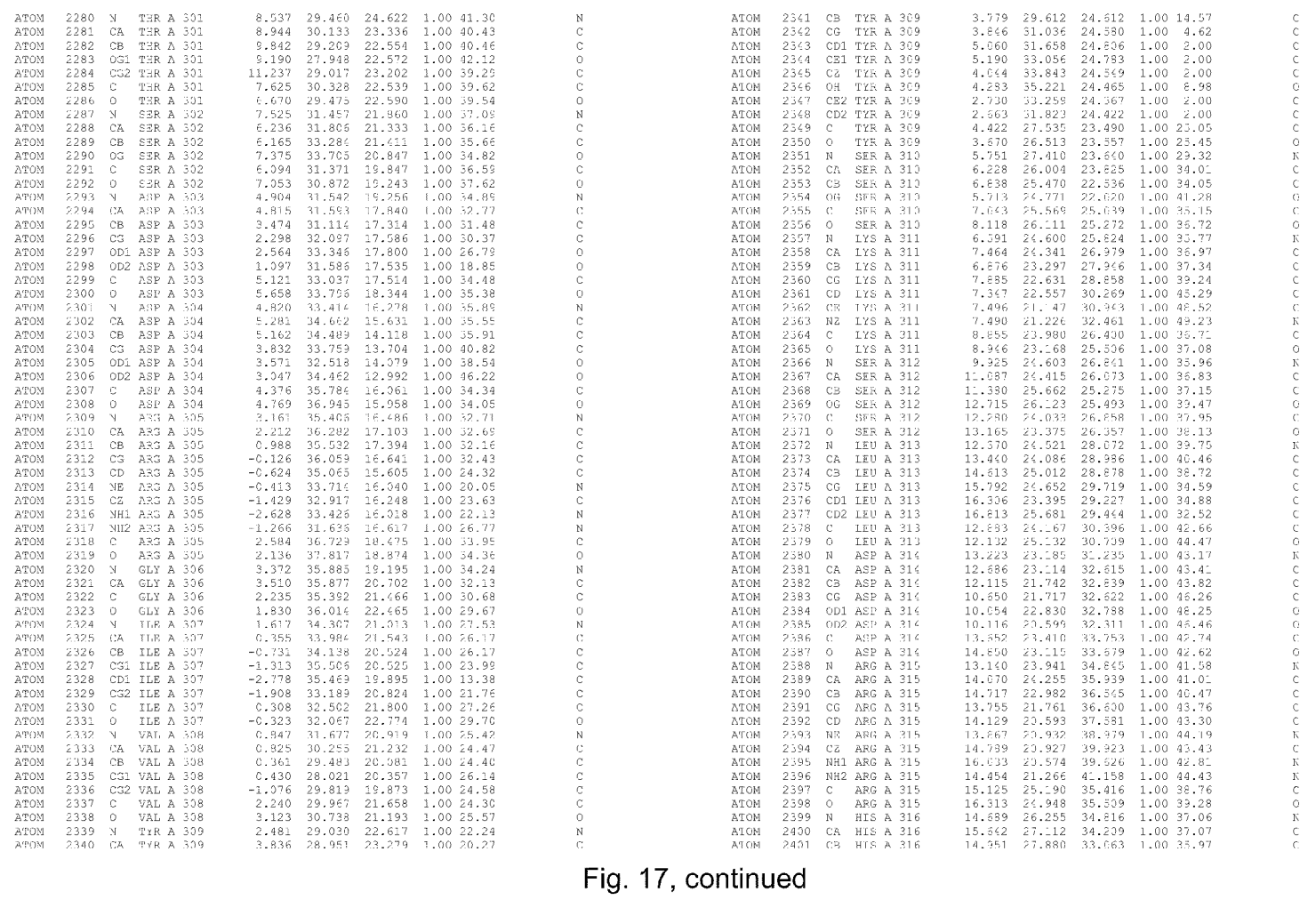
Figure 17:
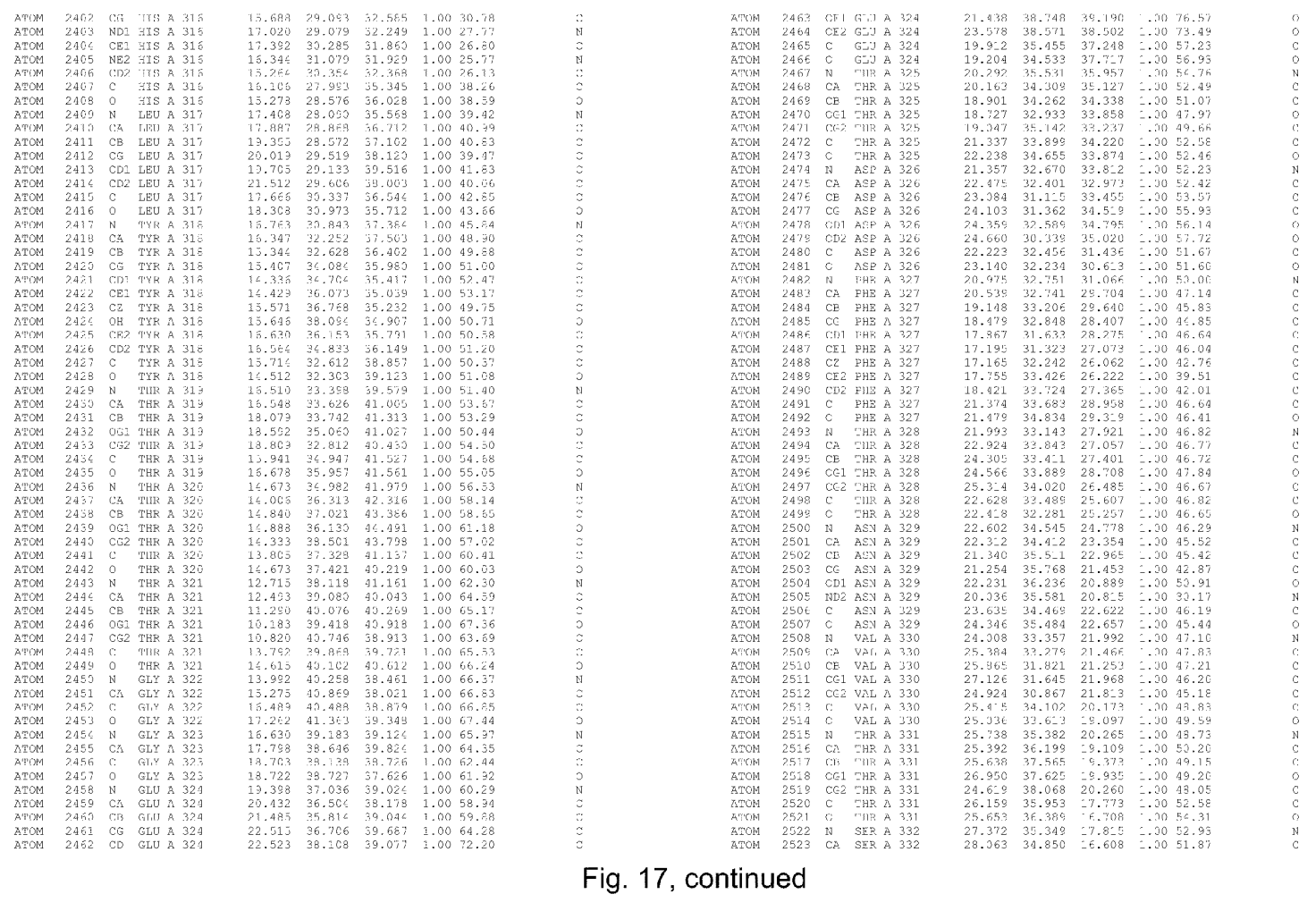
Figure 17:
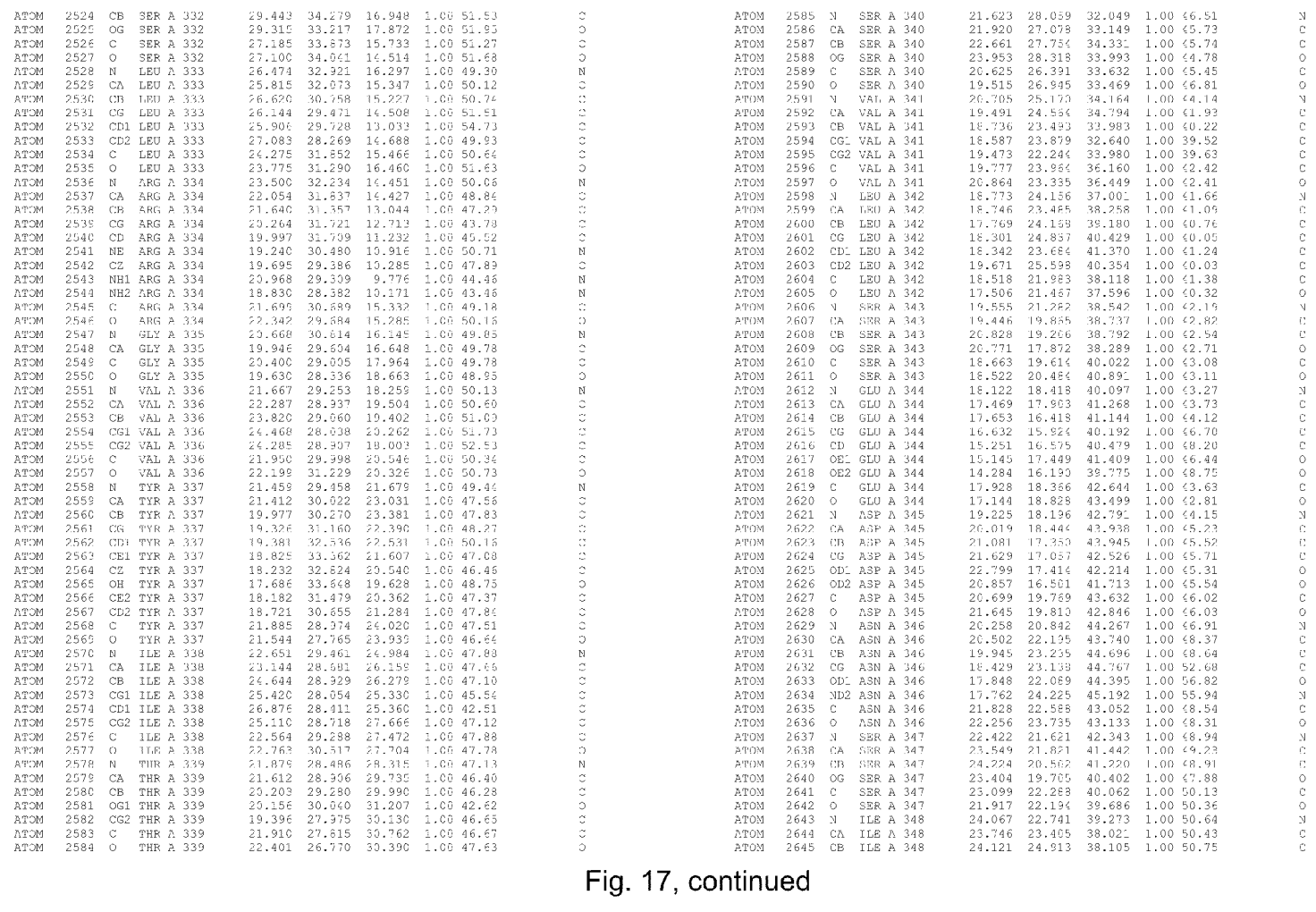
Figure 17:
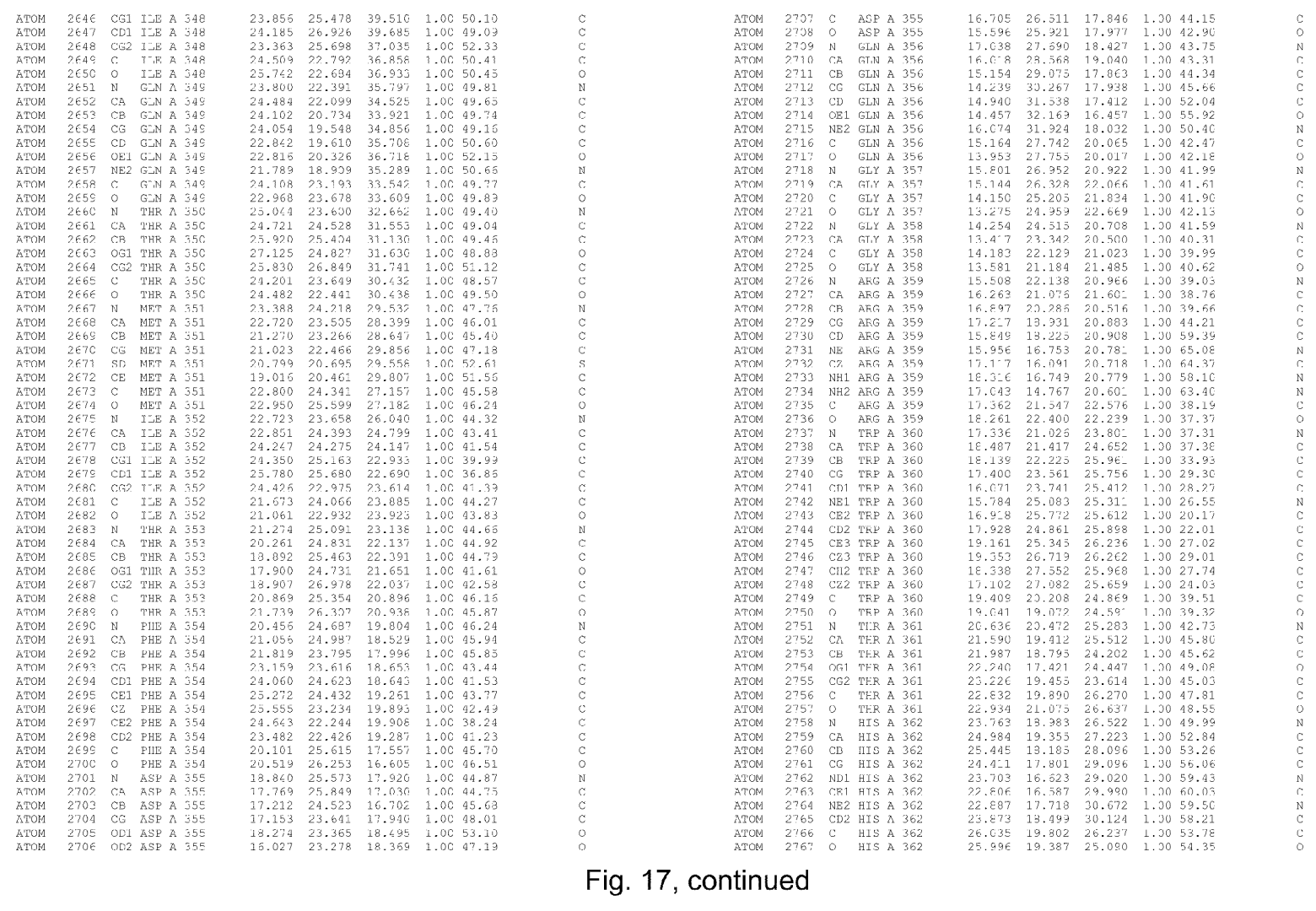
Figure 17:
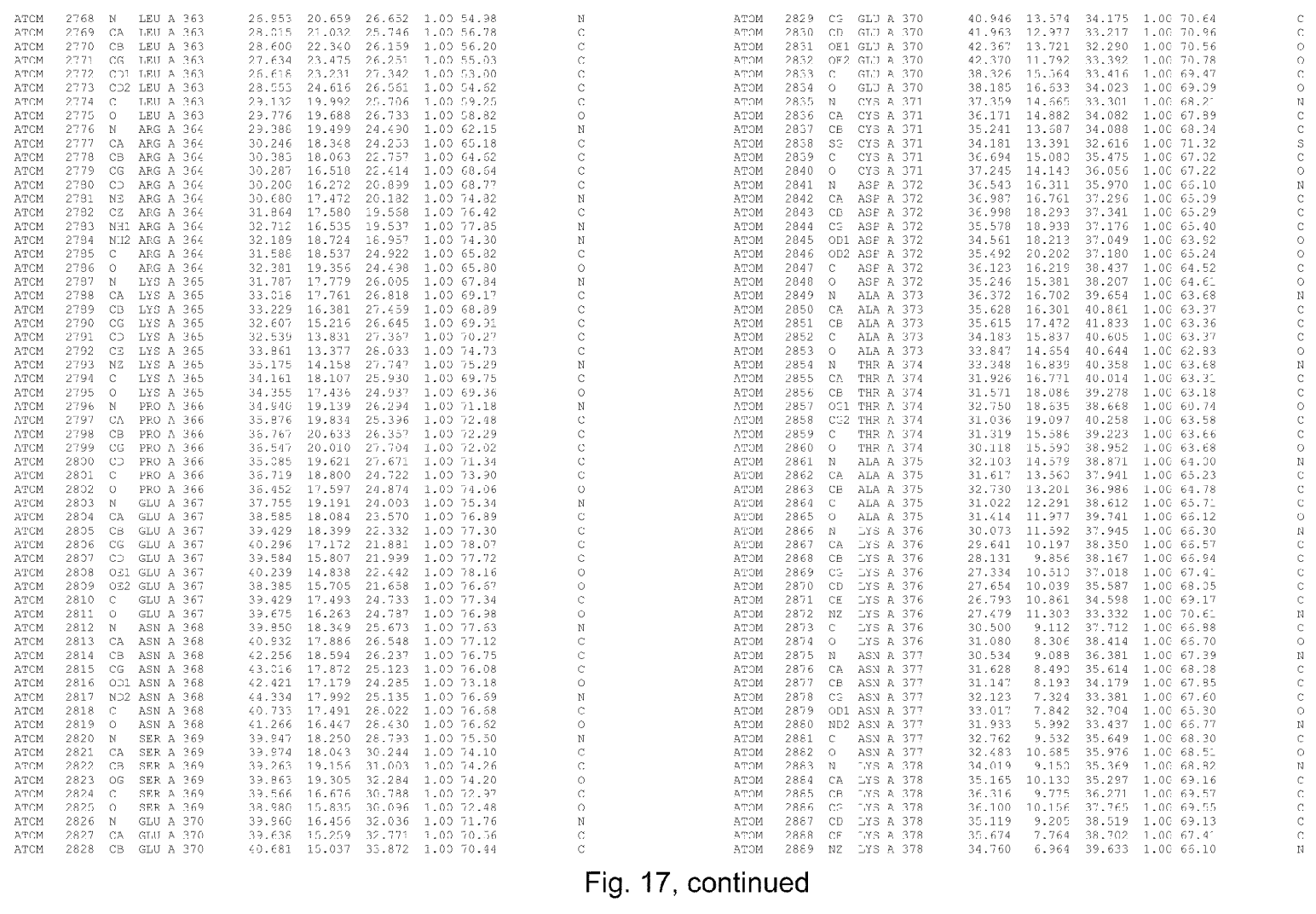
Figure 17:
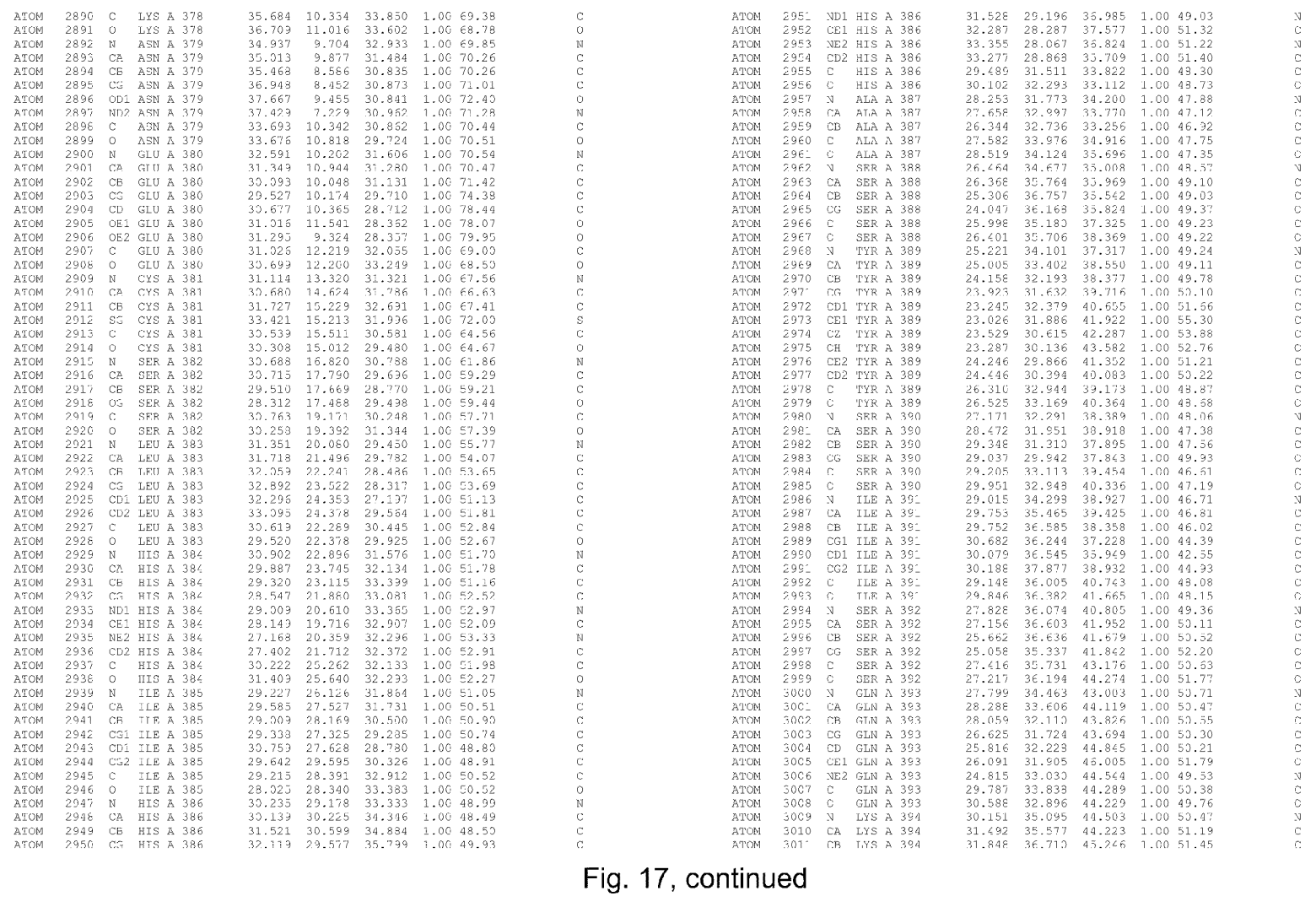
Figure 17:
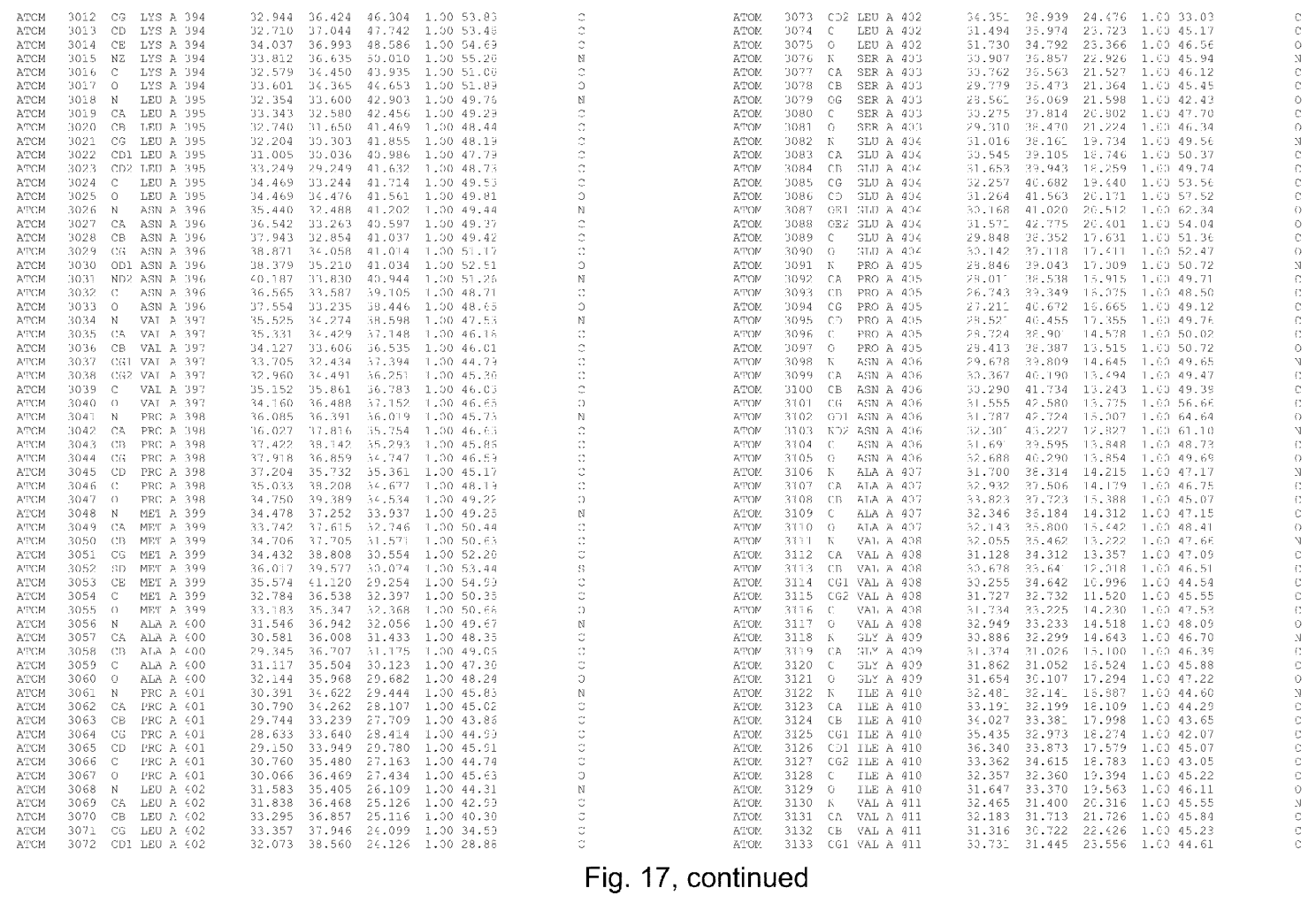
Figure 17:
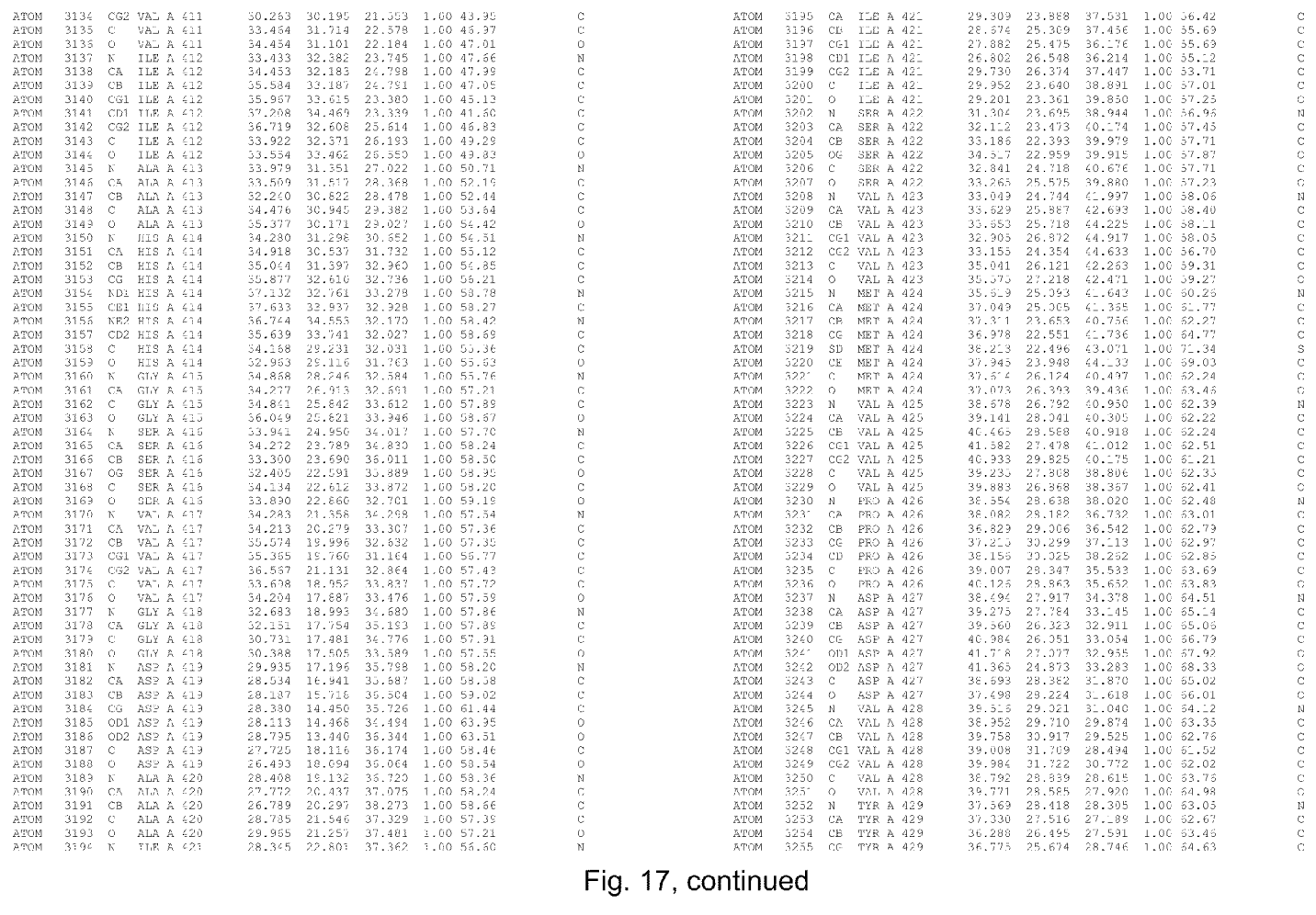
Figure 17:
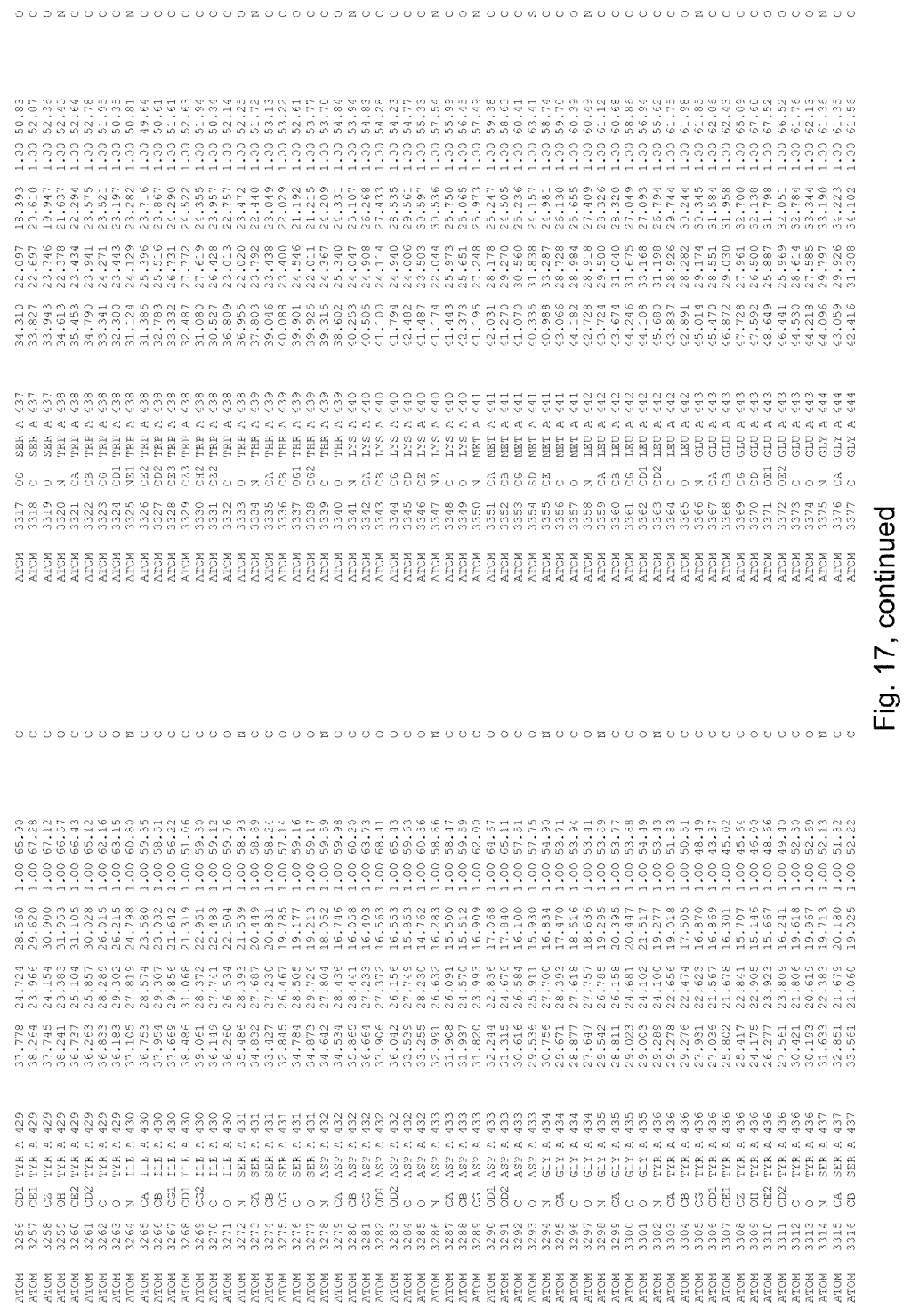
Figure 17:
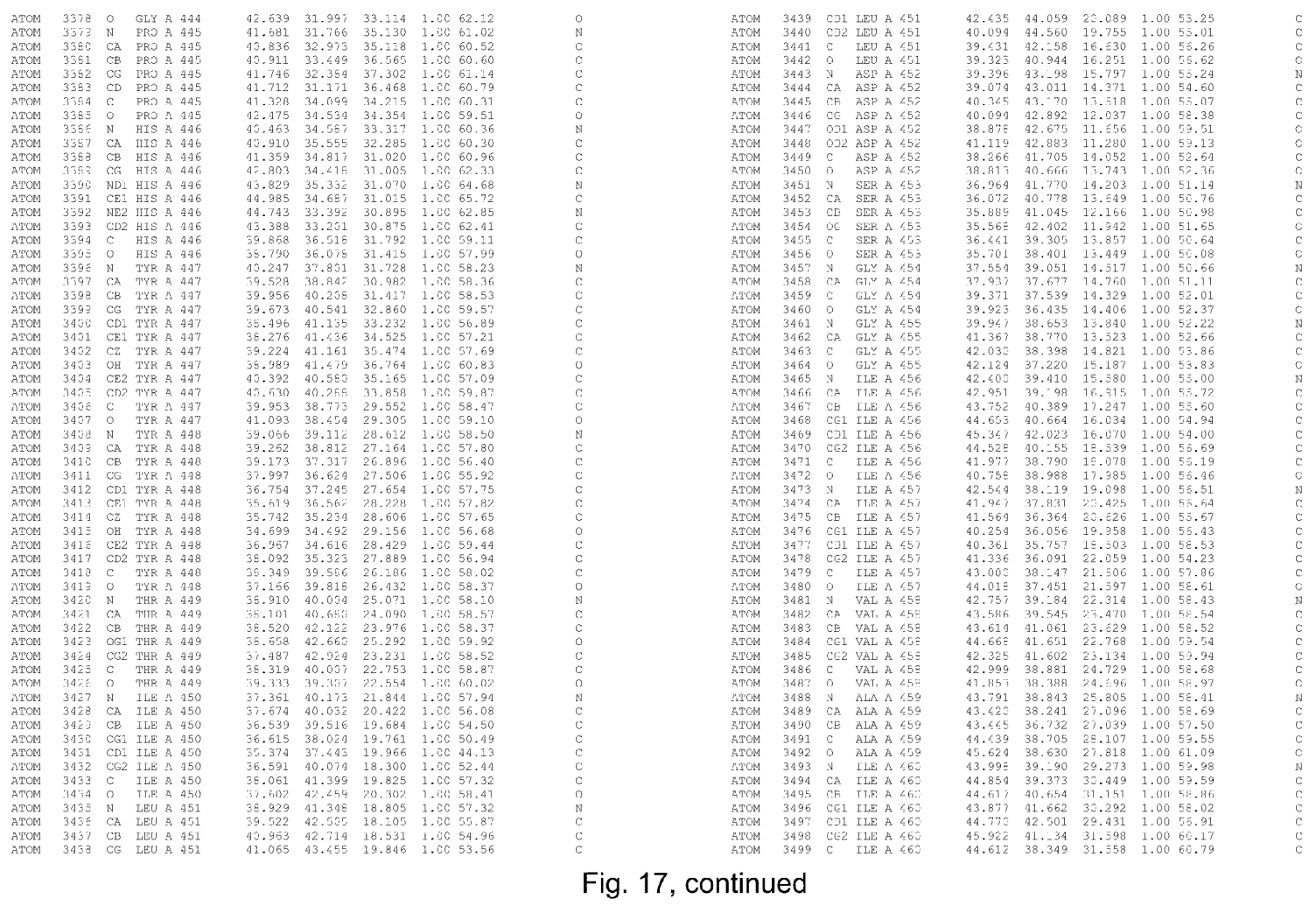
Figure 17:
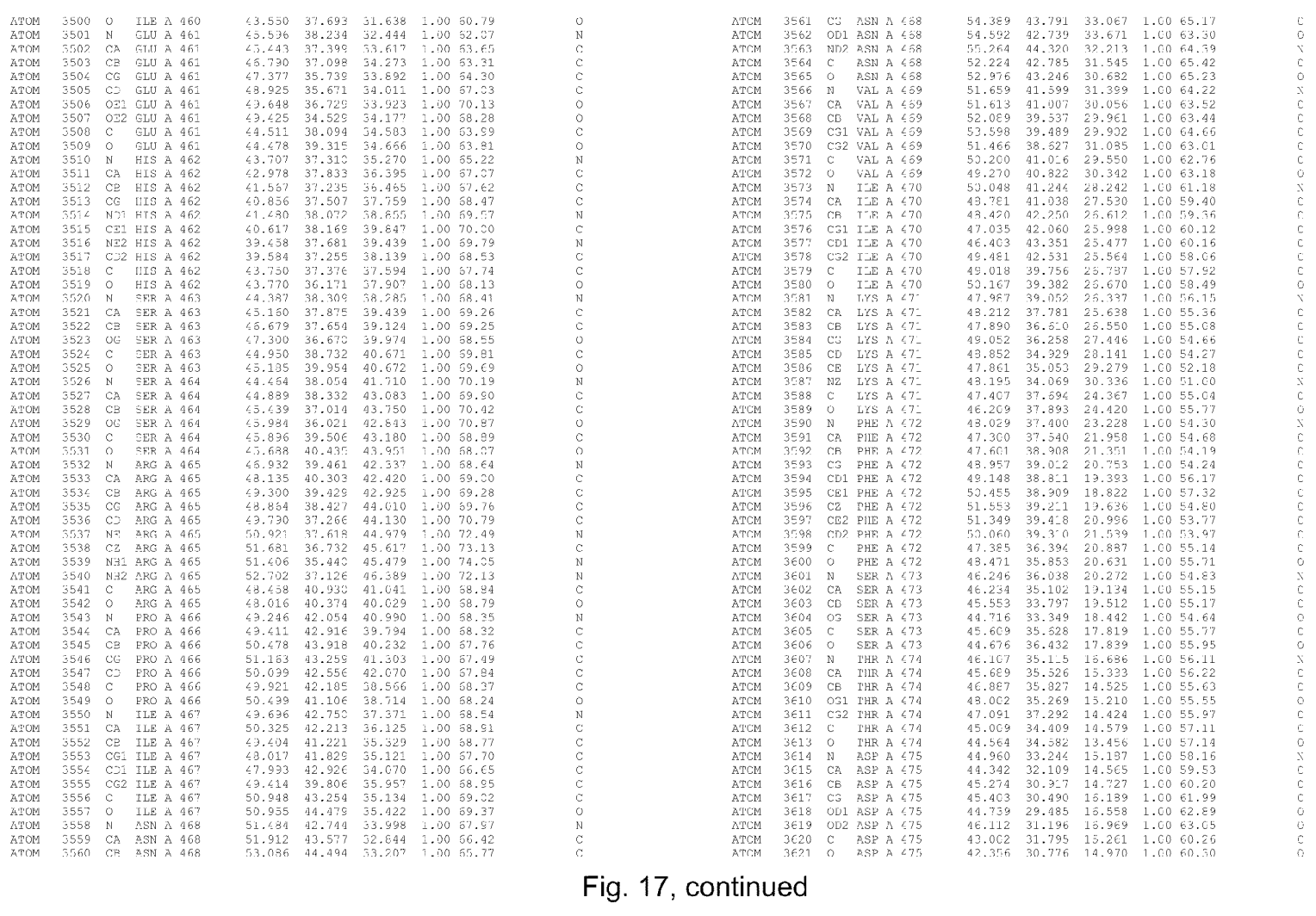
Figure 17:
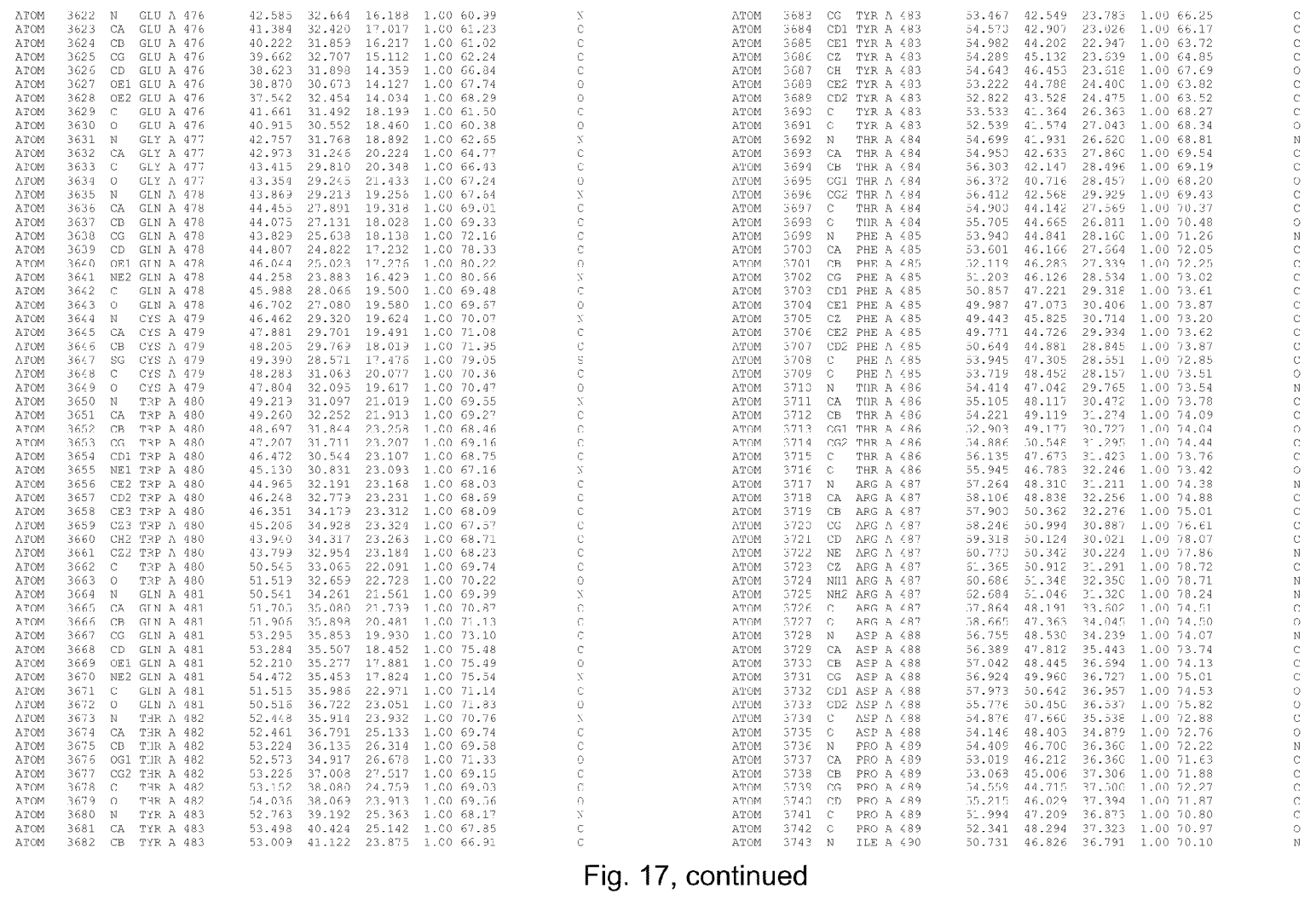
Figure 17:
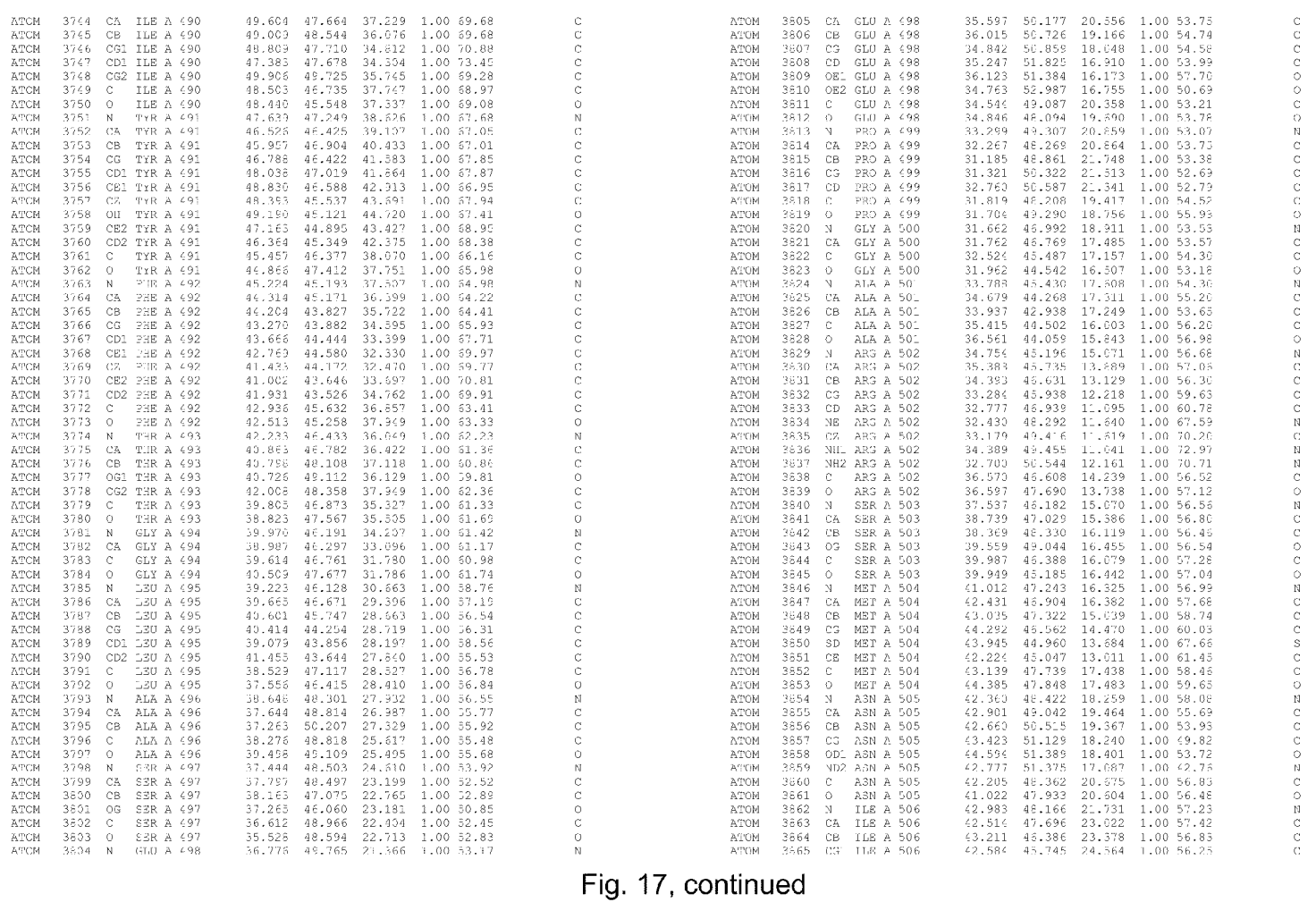
Figure 17:
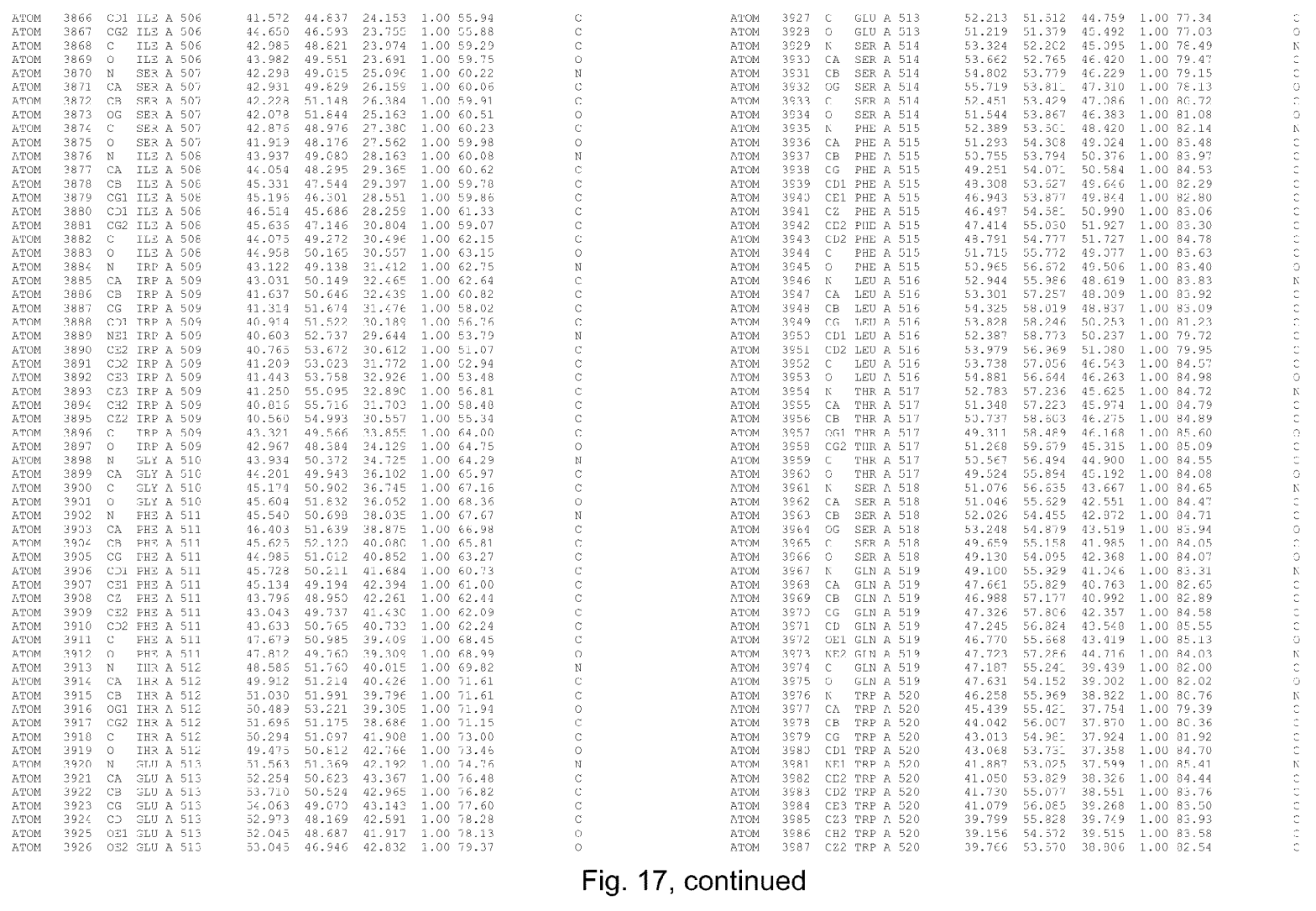
Figure 17:
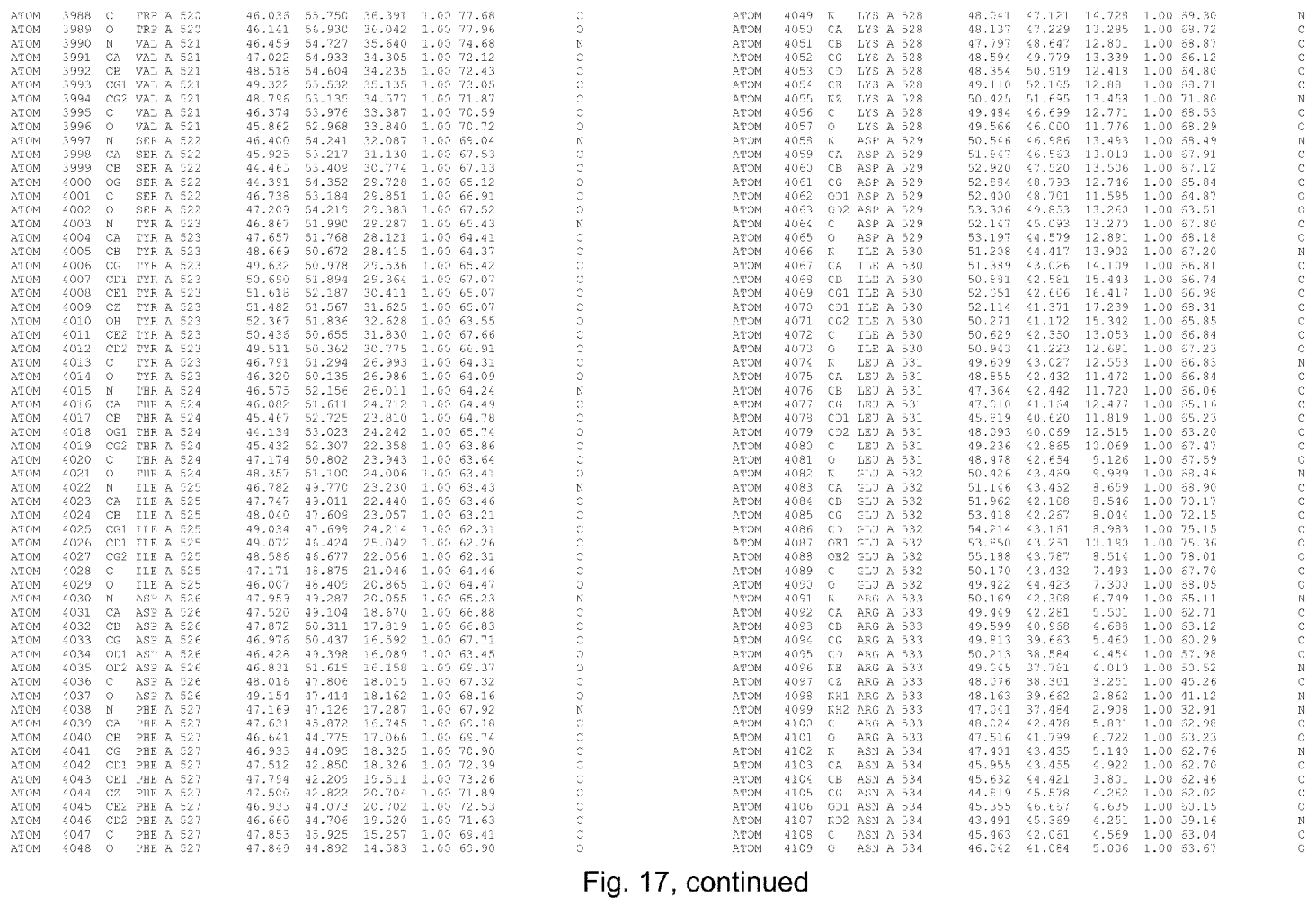
Figure 17:
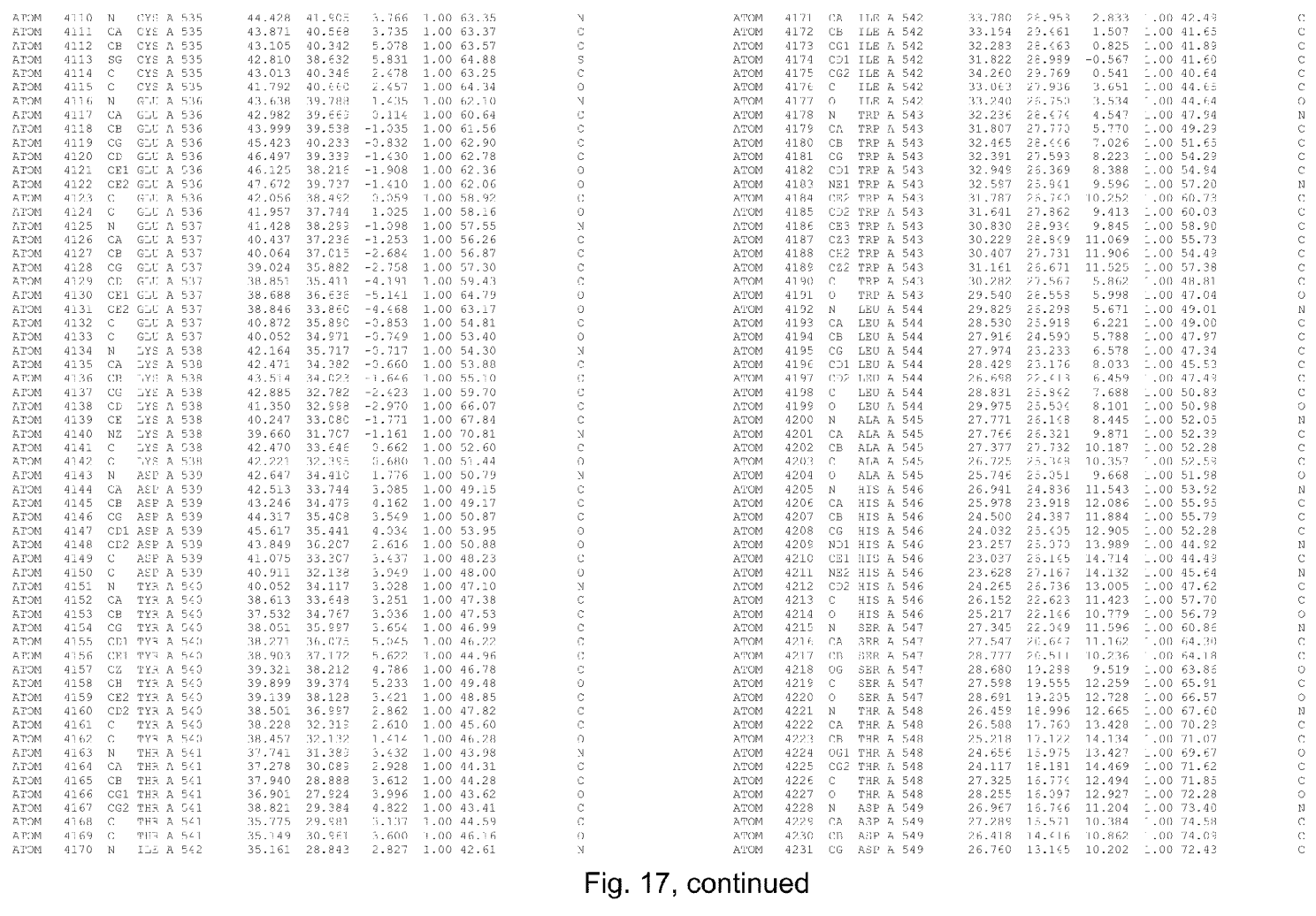
Figure 17:
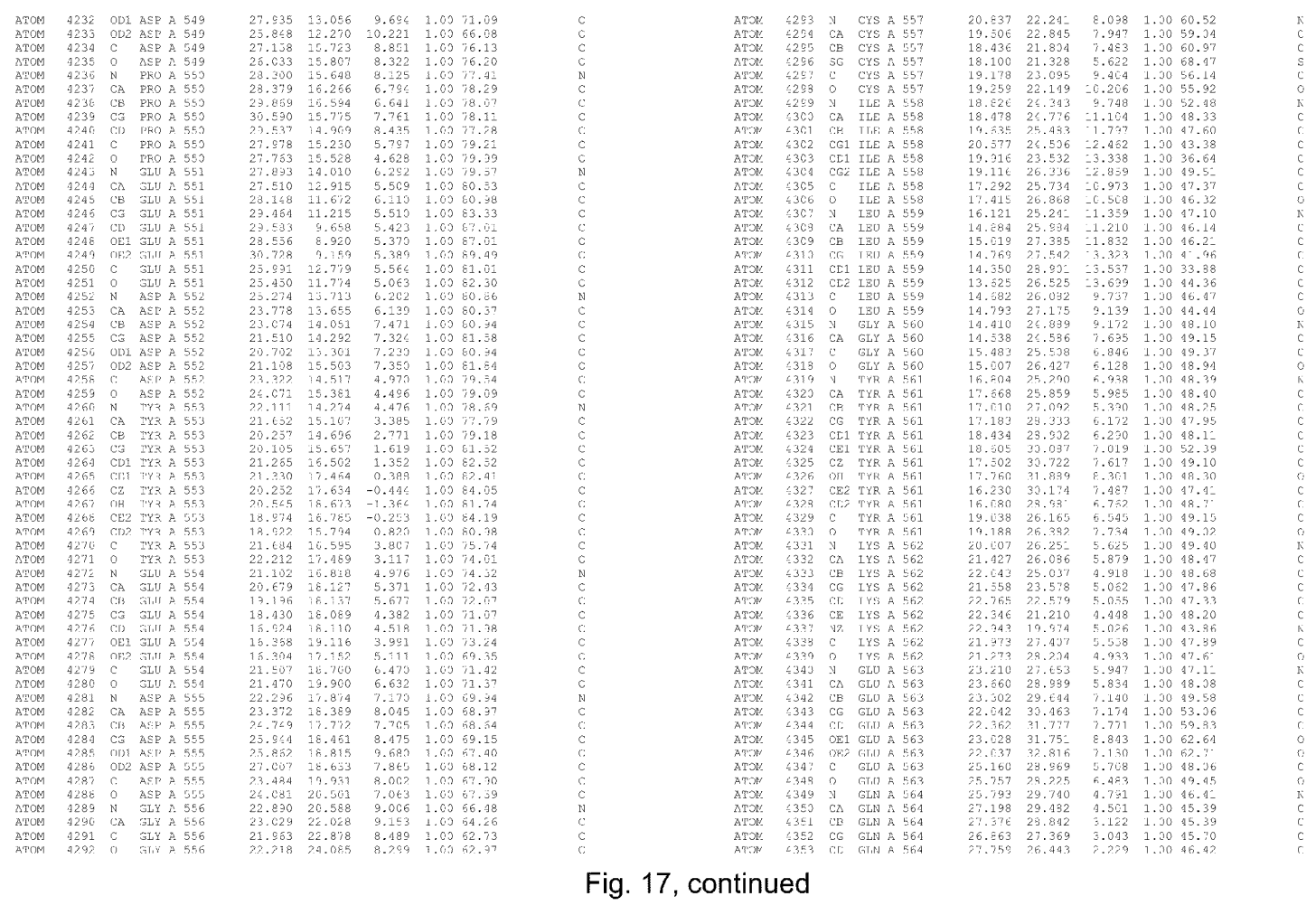
Figure 17:
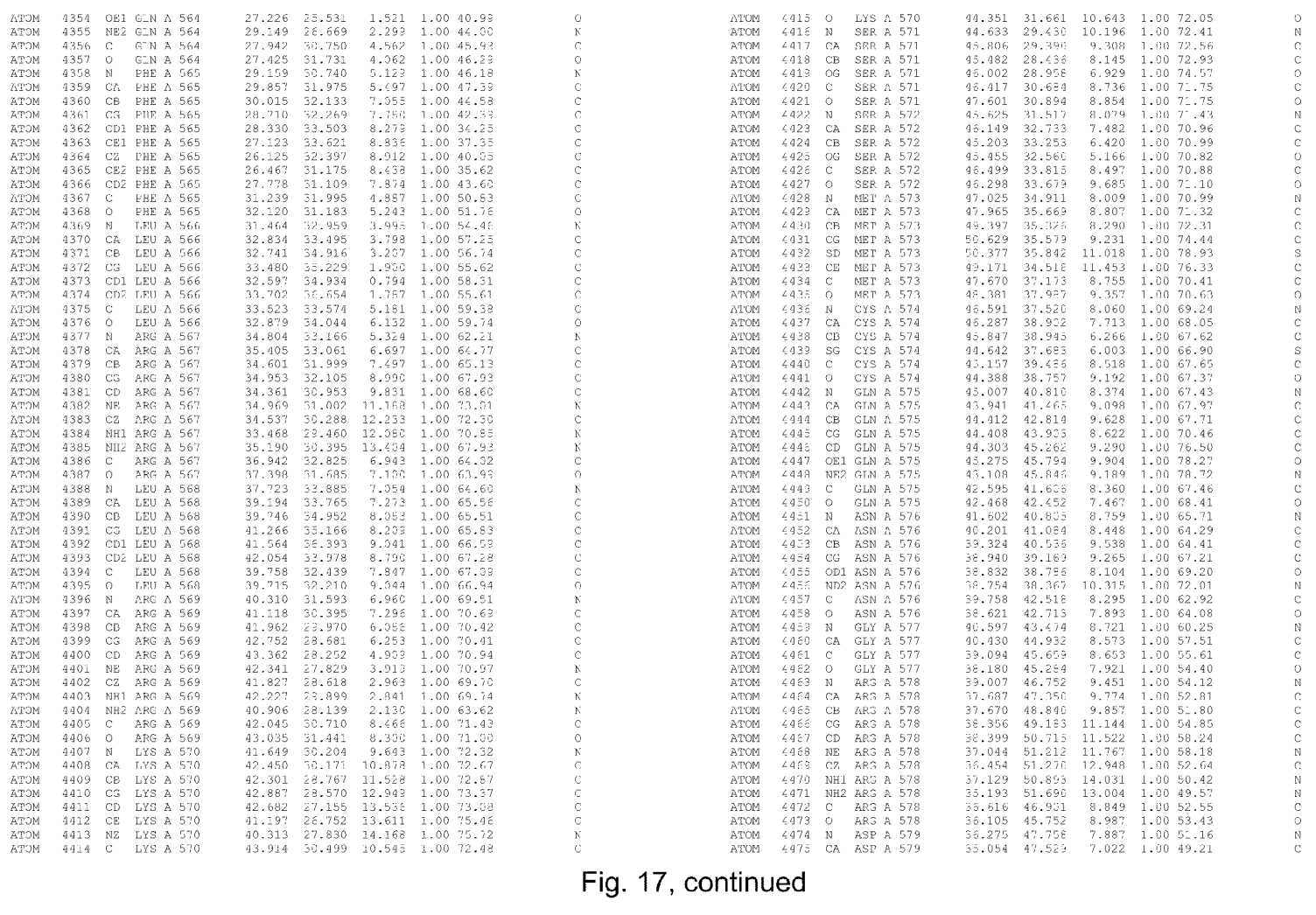
Figure 17:
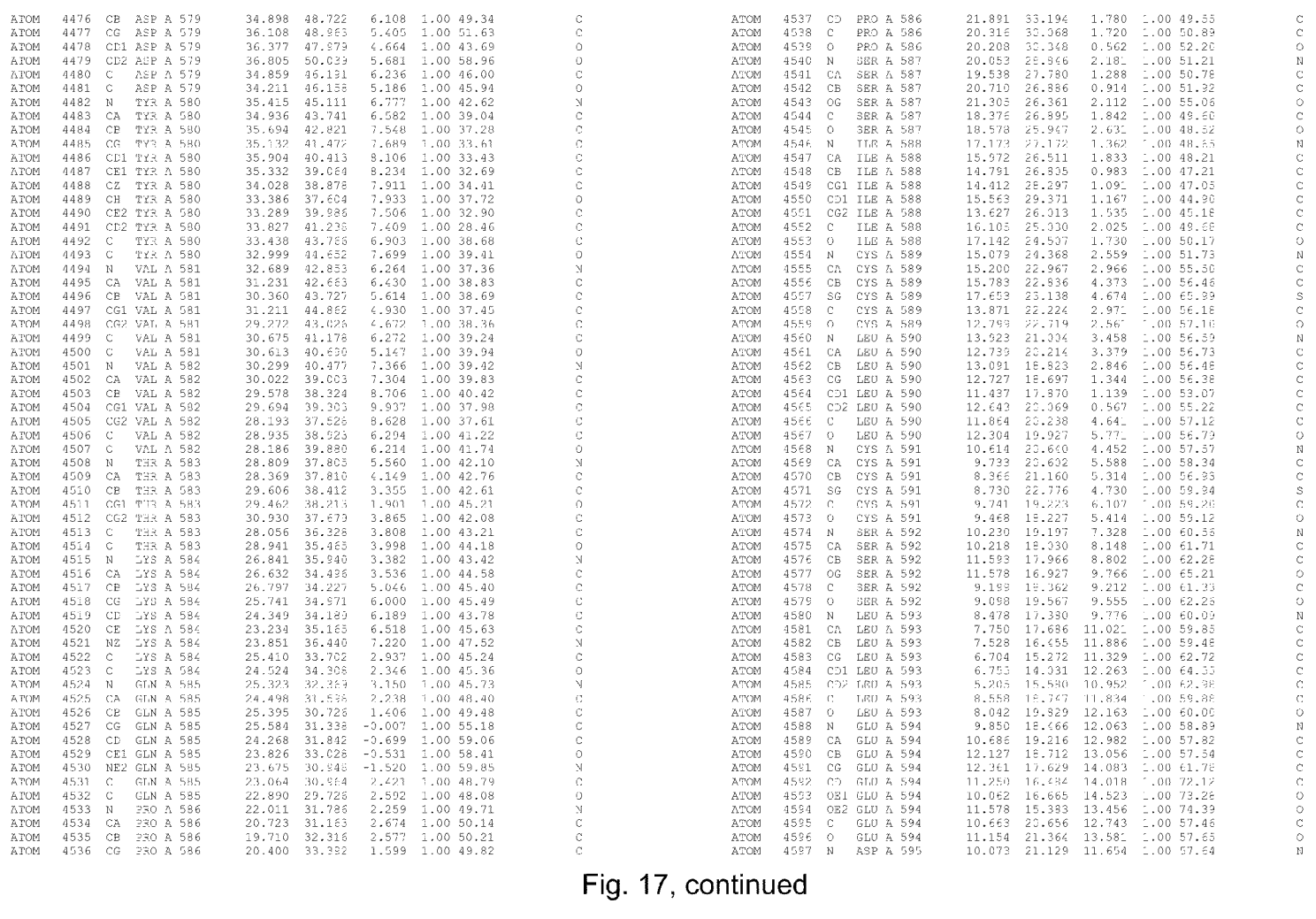
Figure 17:
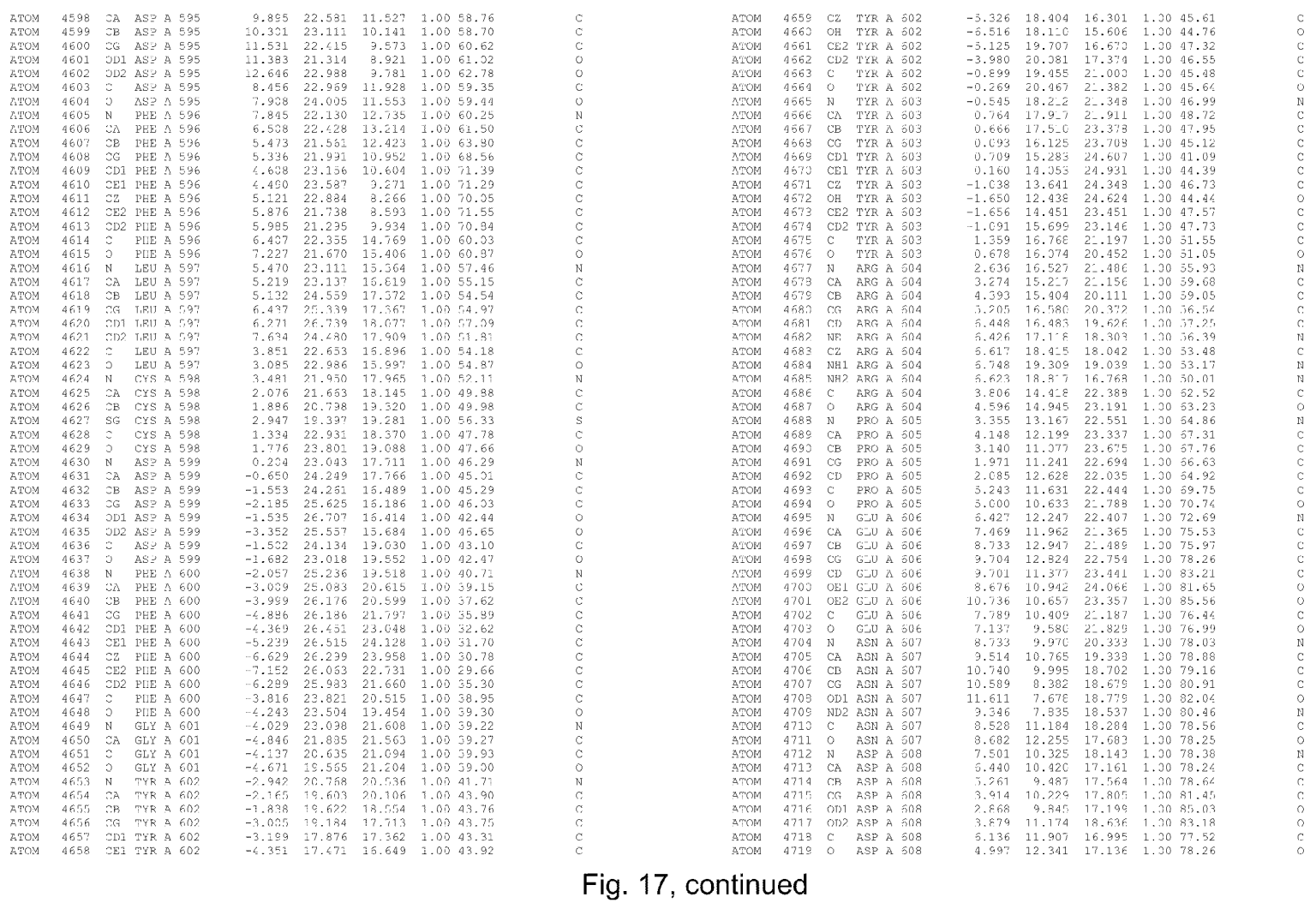
Figure 17:
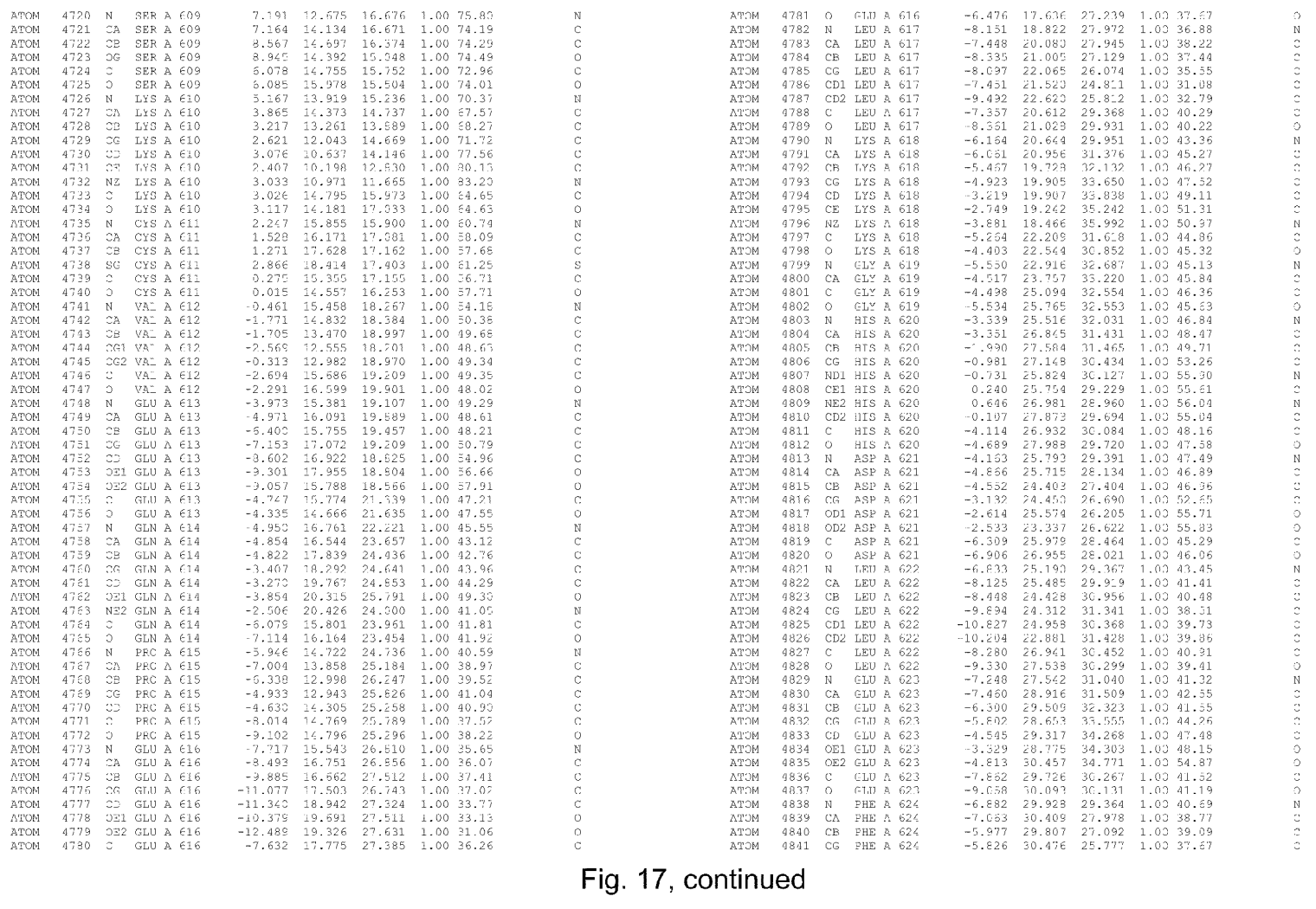
Figure 17:
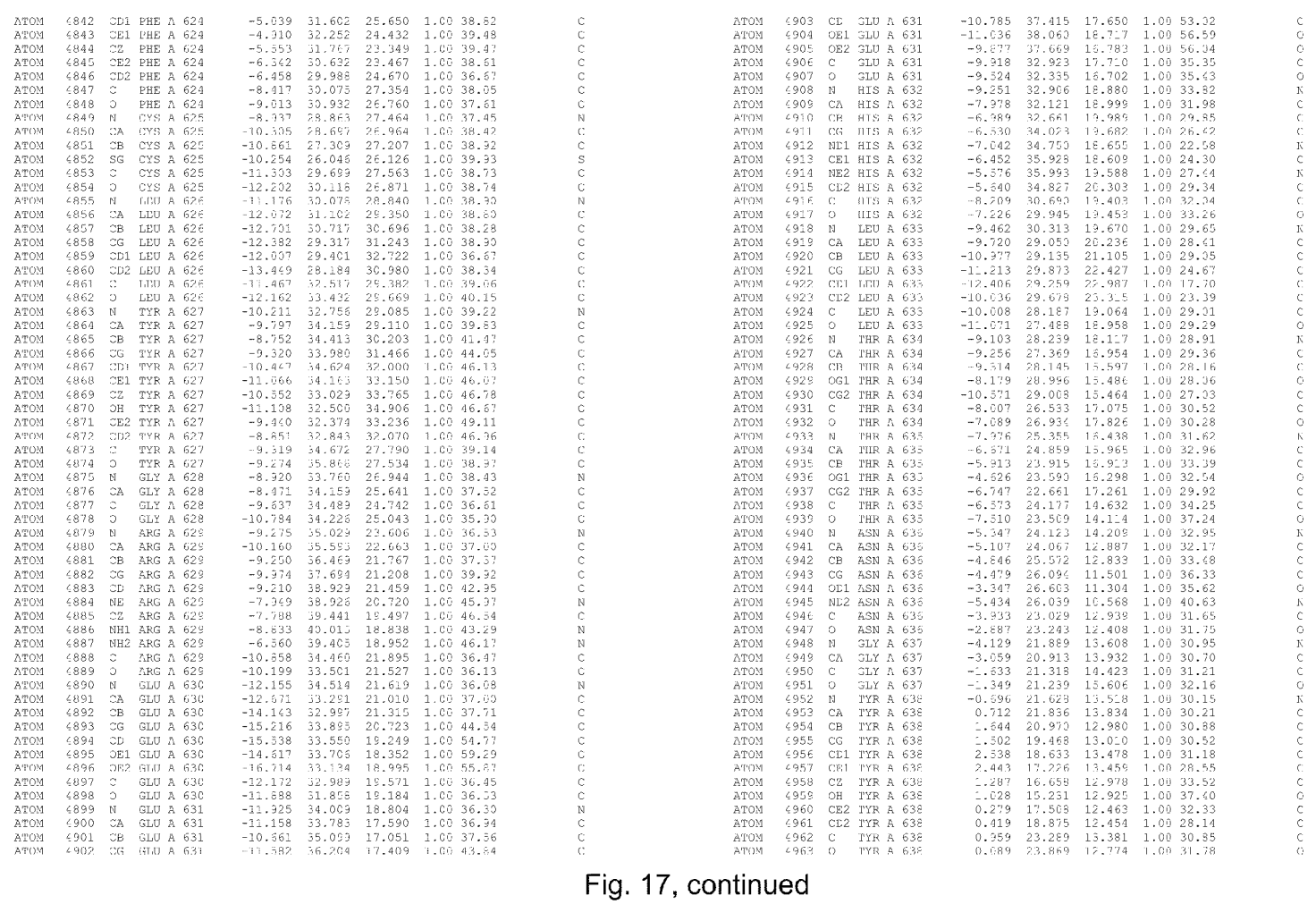
Figure 17:
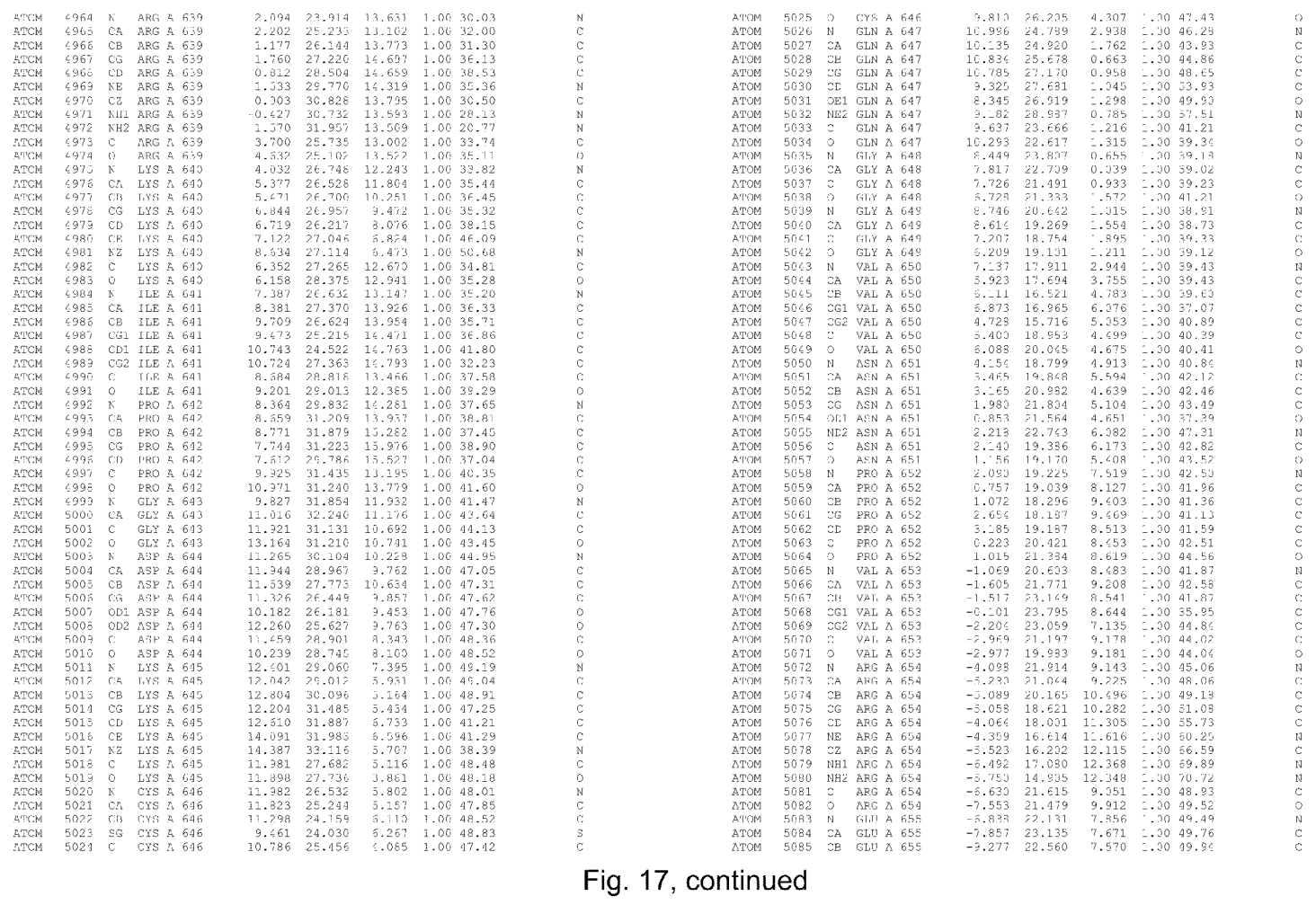
Figure 17:
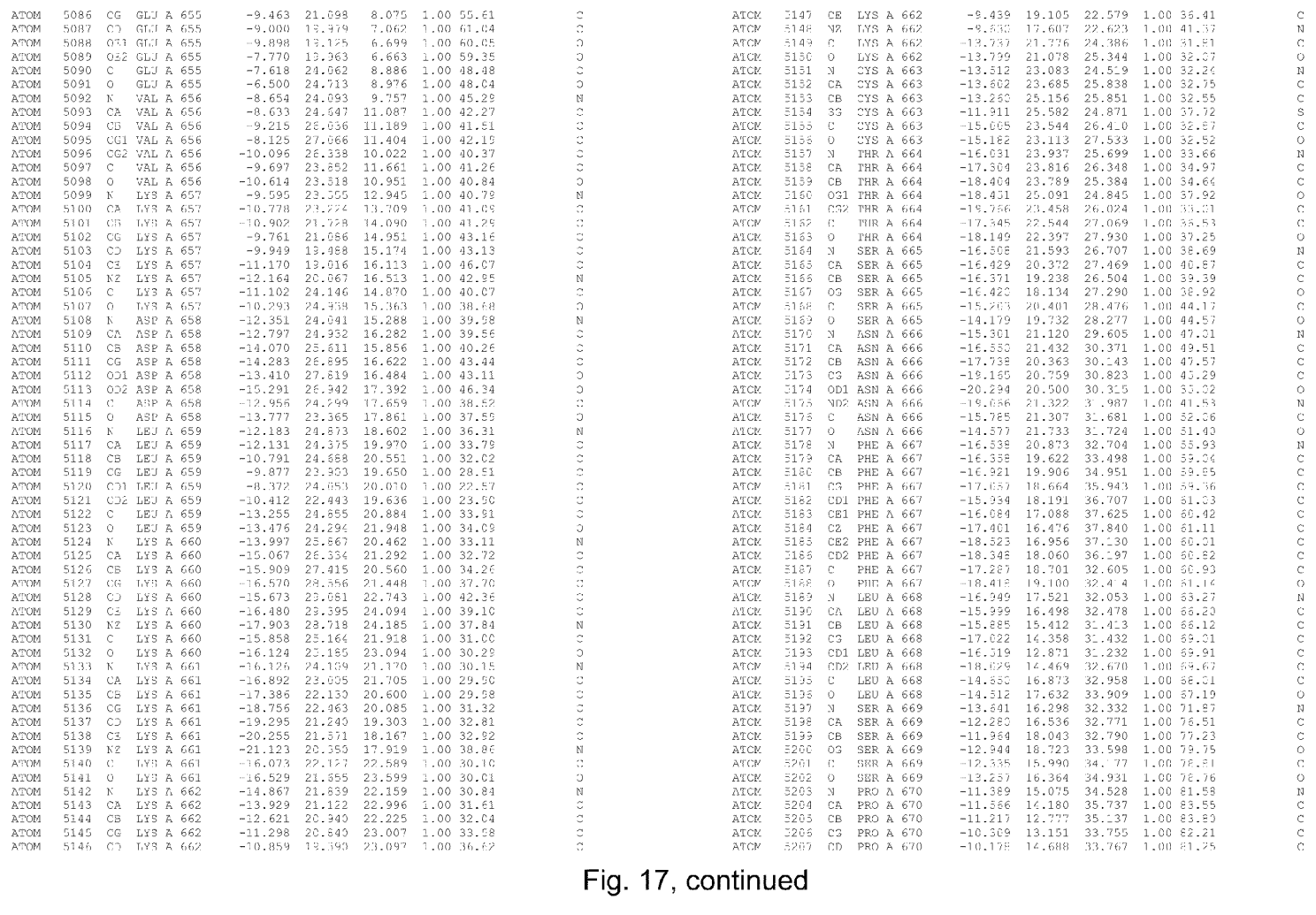
Figure 17:
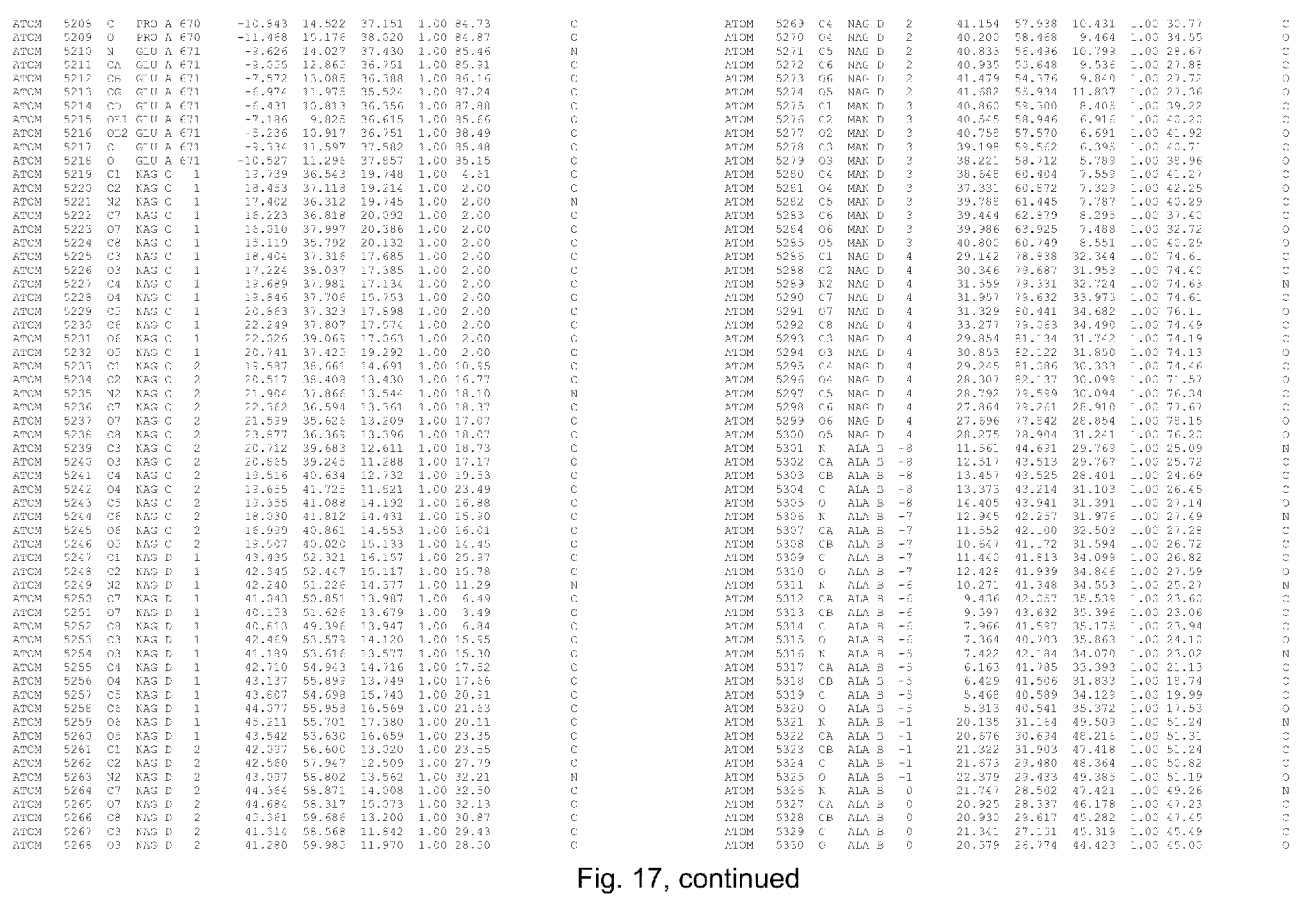
Figure 17:
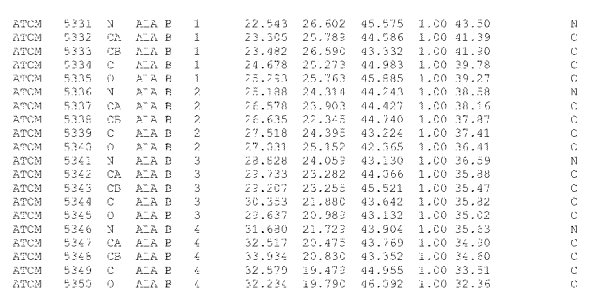

FIG. 17: Atomic coordinates of sSortilin when in complex with a fragment of the NGFprodomain. sSortilin (SEQ ID NO:33) has the sequence of amino acid residues 78 to 755 of SEQ ID NO. 1; the NGF pro domain (SEQ ID NO:40) has the sequence of amino acid residues 19 to 121 of SEQ ID NO 6. The numbering of the first built Sortilin amino acid residues of this pdb file is C9 which corresponds to C86 of SEQ ID NO: 1 which is numbered in accordance with the Expasy database entry Q99523 as of the filing date of the present application. Thus, the sSortilin coordinates provided are those of SEQ ID NO:34 (which corresponds to amino acid residues Cys86 to Glu748 of SEQ ID NO. 1) (atom 1 corresponds to an atom of the first residue (Cys) of SEQ ID NO:34 (Cys86 of SEQ ID NO:1); atom 5218 corresponds to an atom of the last residue (Glu) of SEQ ID NO:34 (Glu748 of SEQ ID NO:1). The coordinates of the NGF prodomain are not shown. The coordinates of an AAAA tetrapeptide (SEQ ID NO:35) are shown commencing with atom 5301. NAG (N-acetyl-d-glucosamine).

Figure 18:
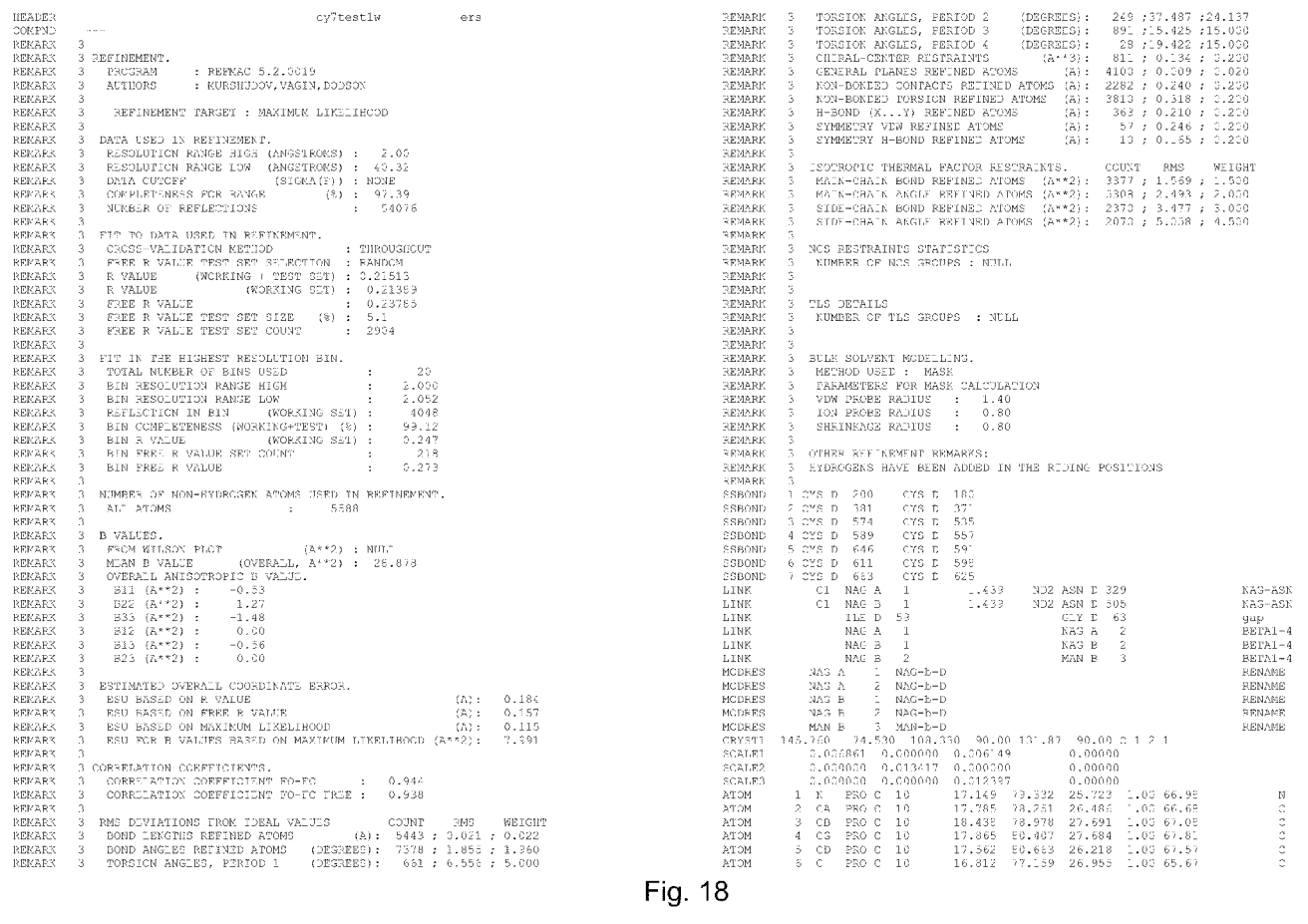
Figure 18:
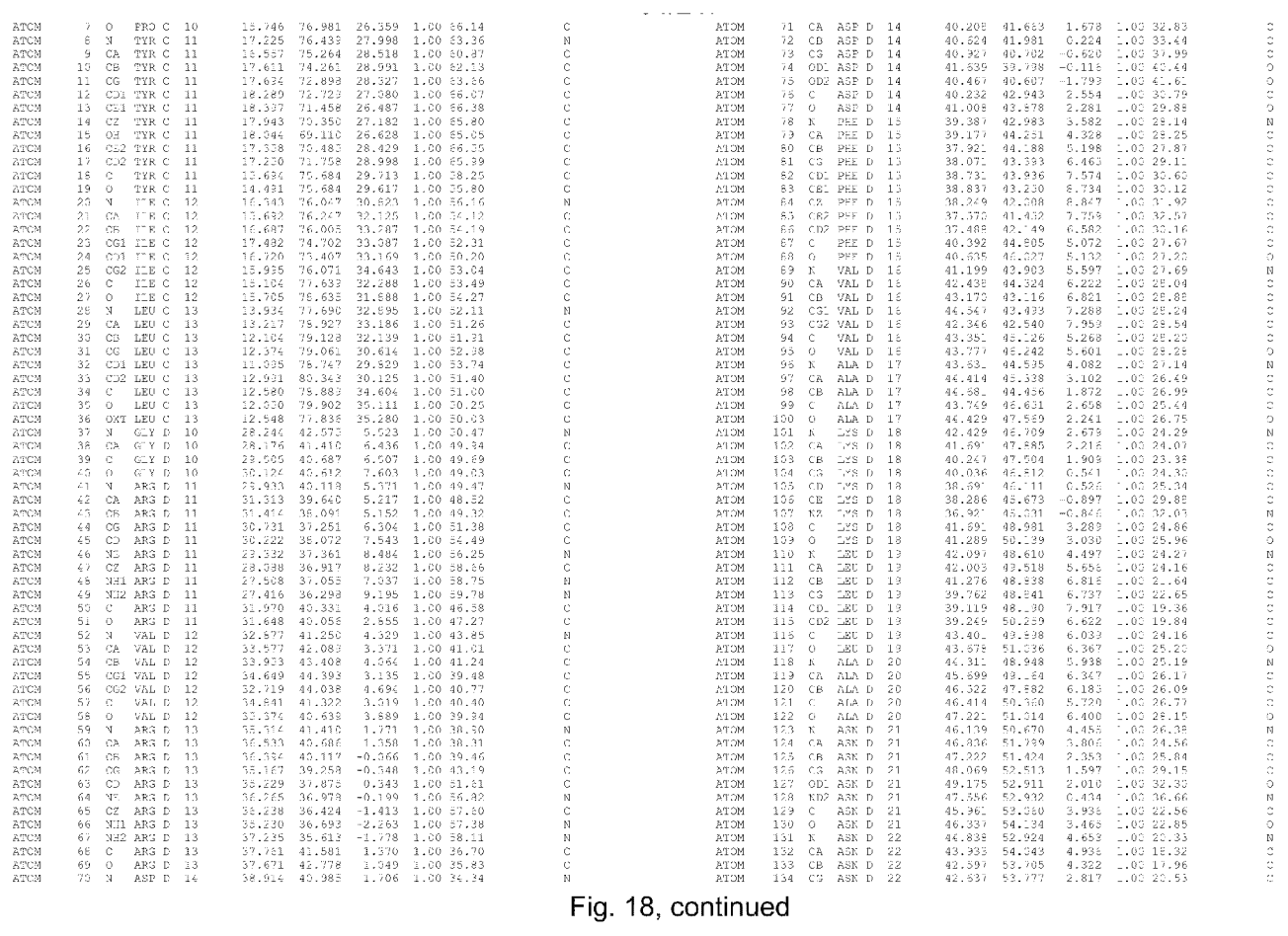
Figure 18:
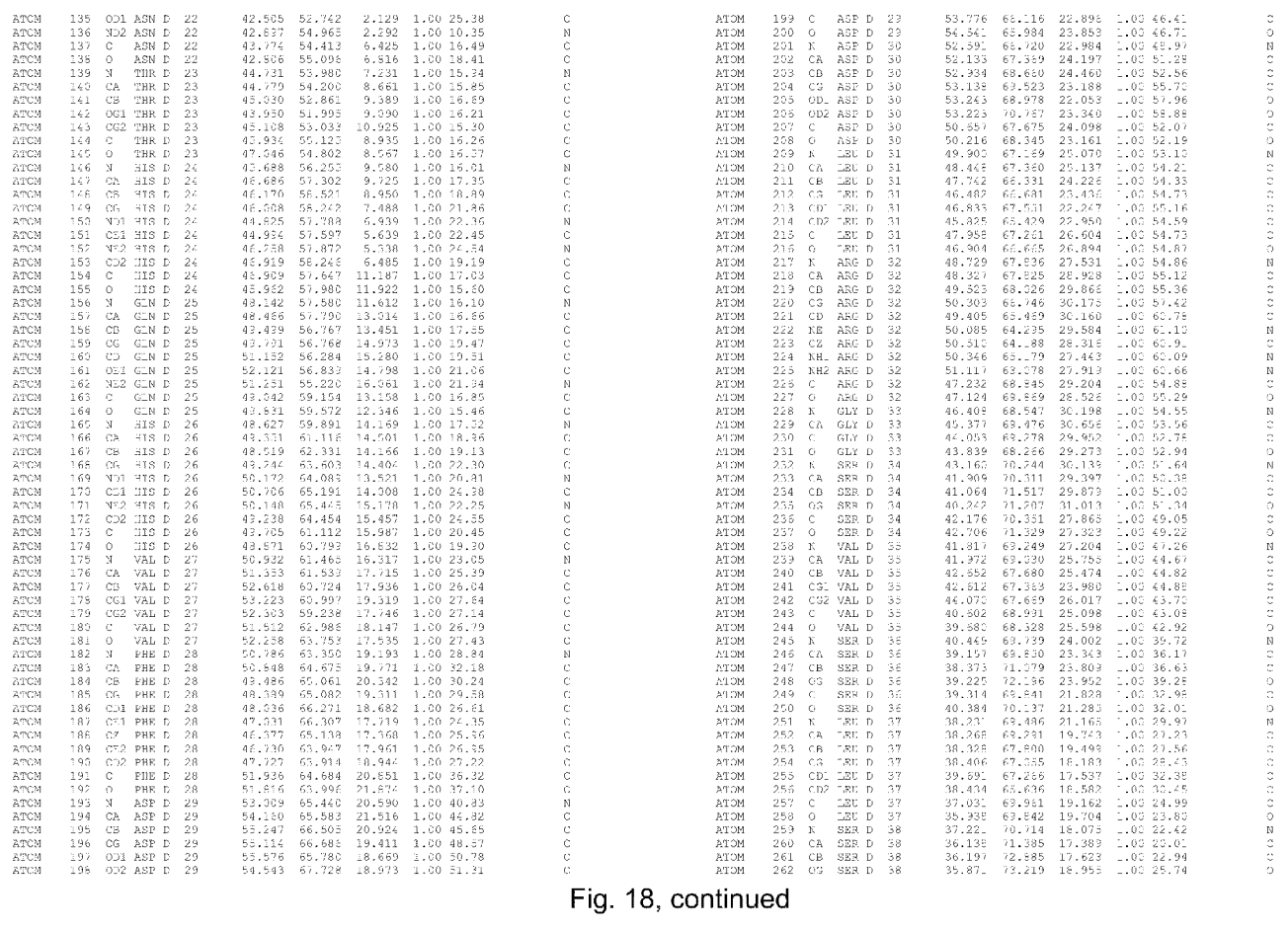
Figure 18:
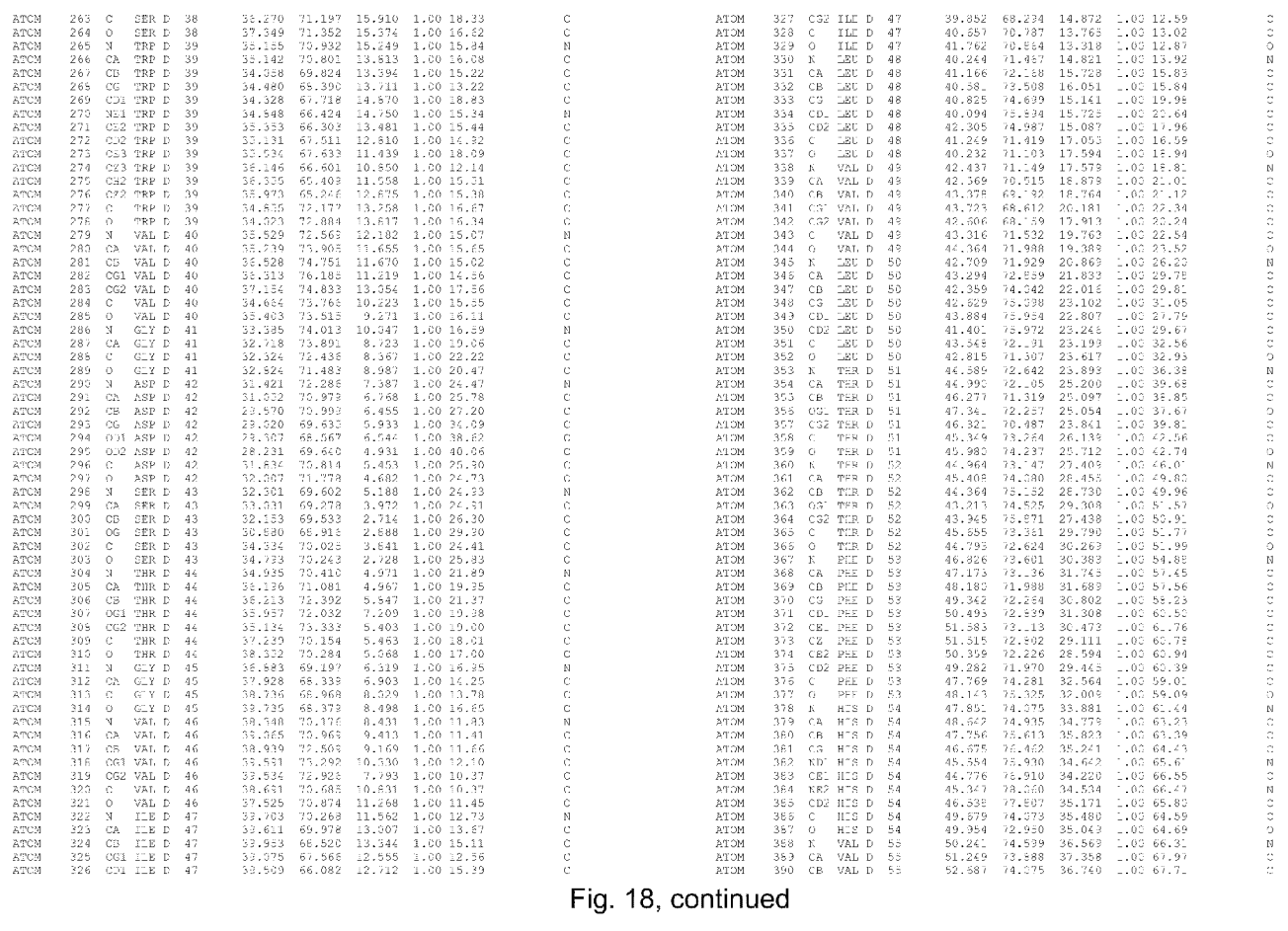
Figure 18:
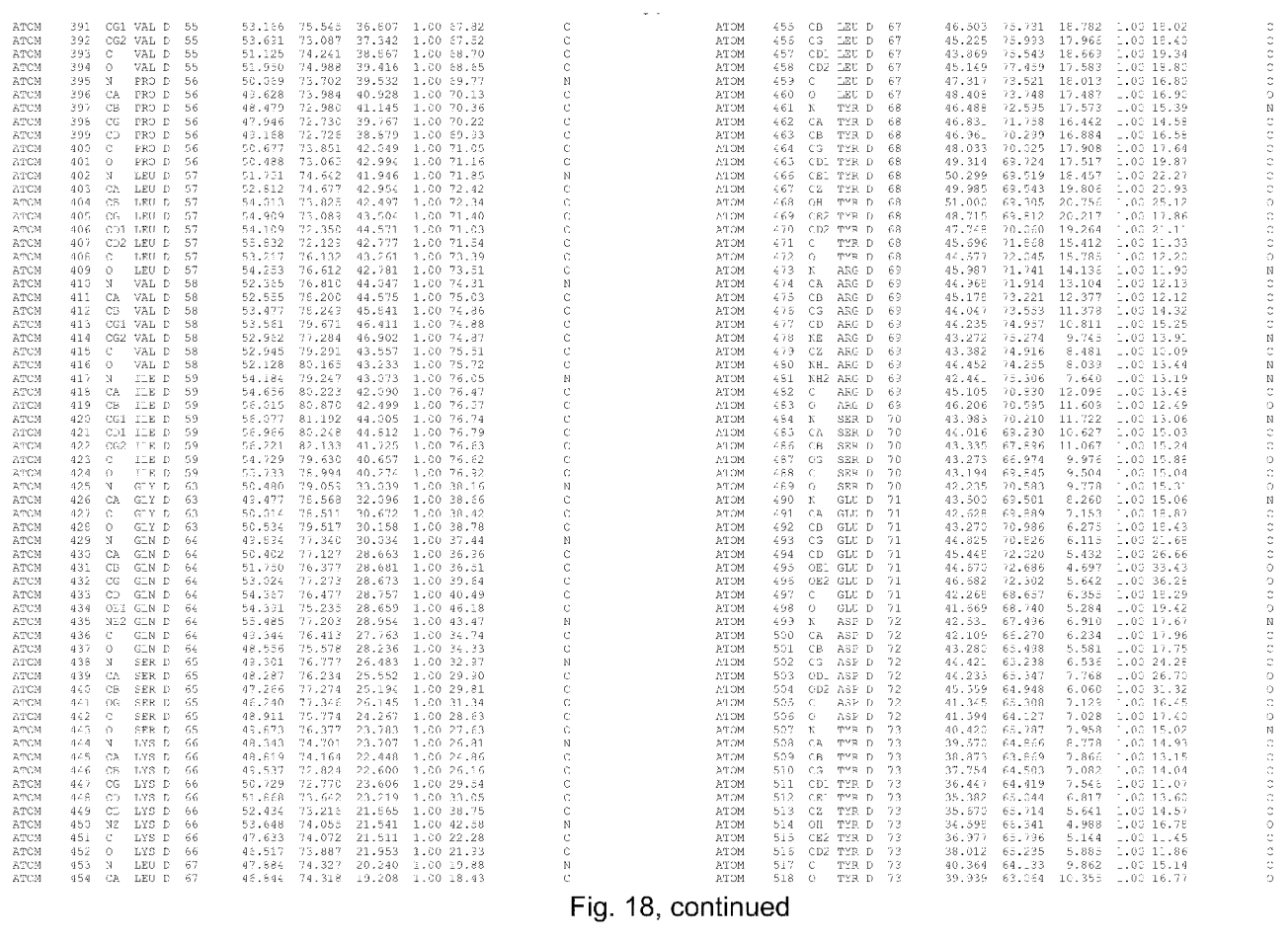
Figure 18:
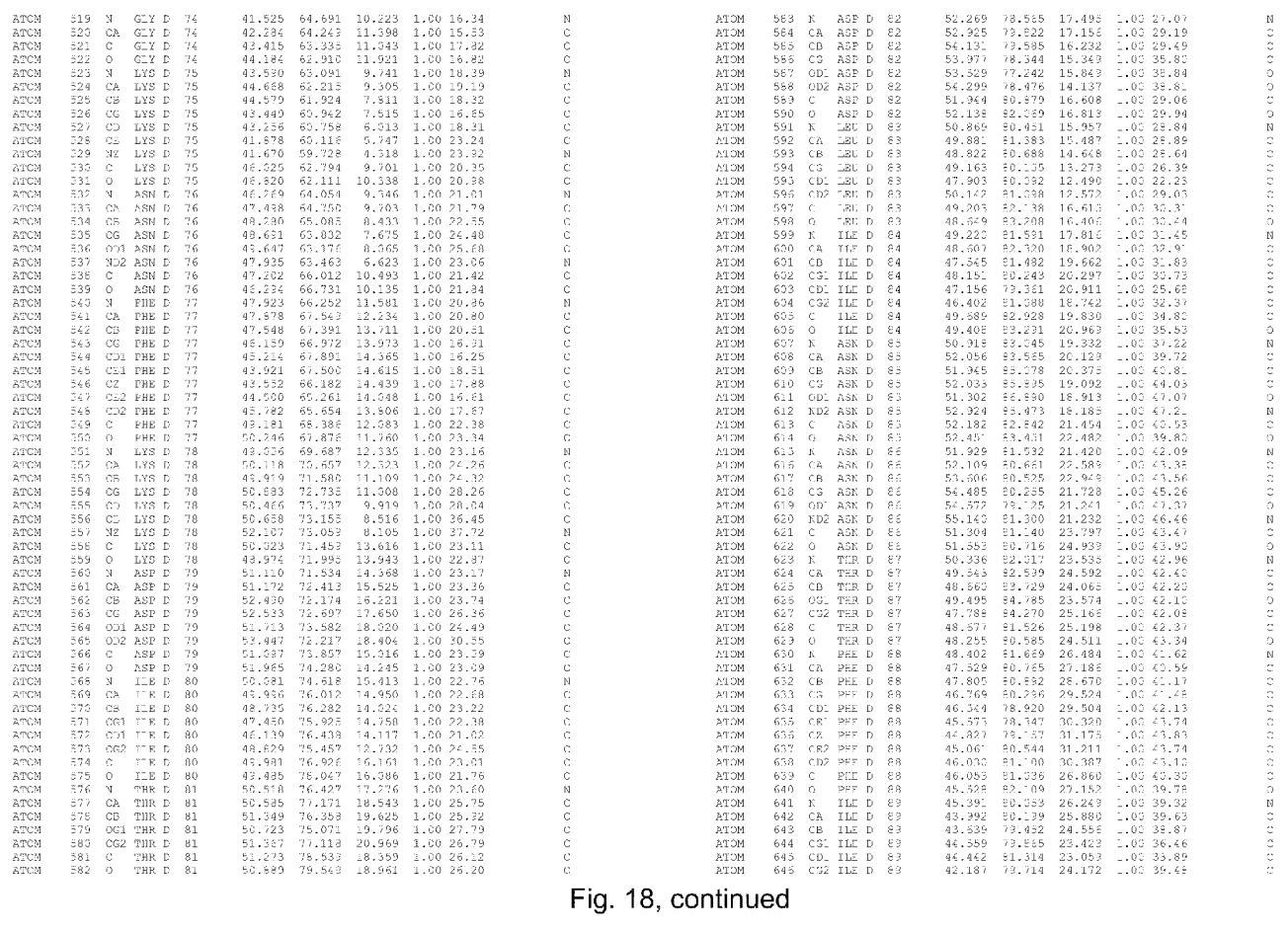
Figure 18:
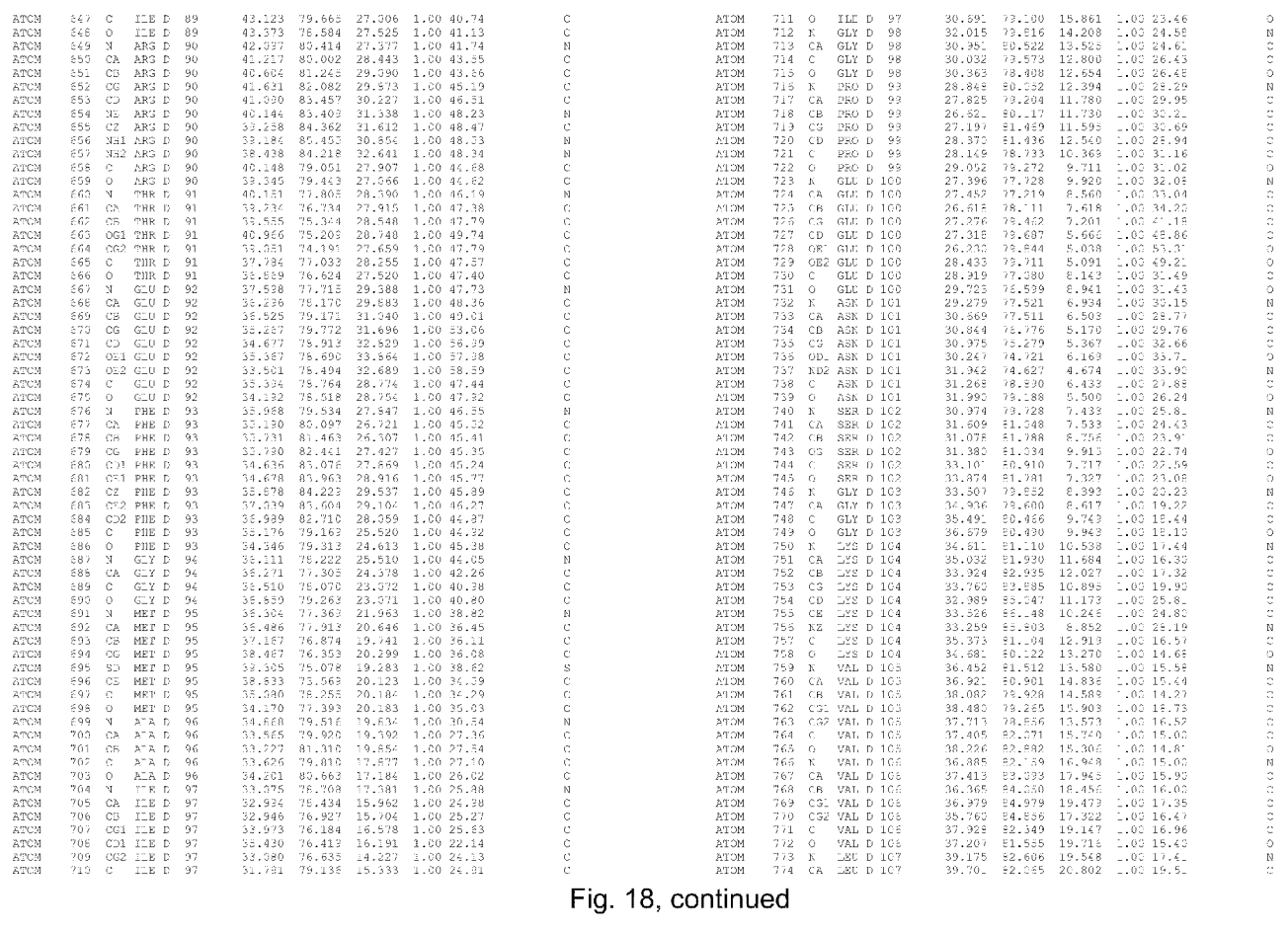
Figure 18:
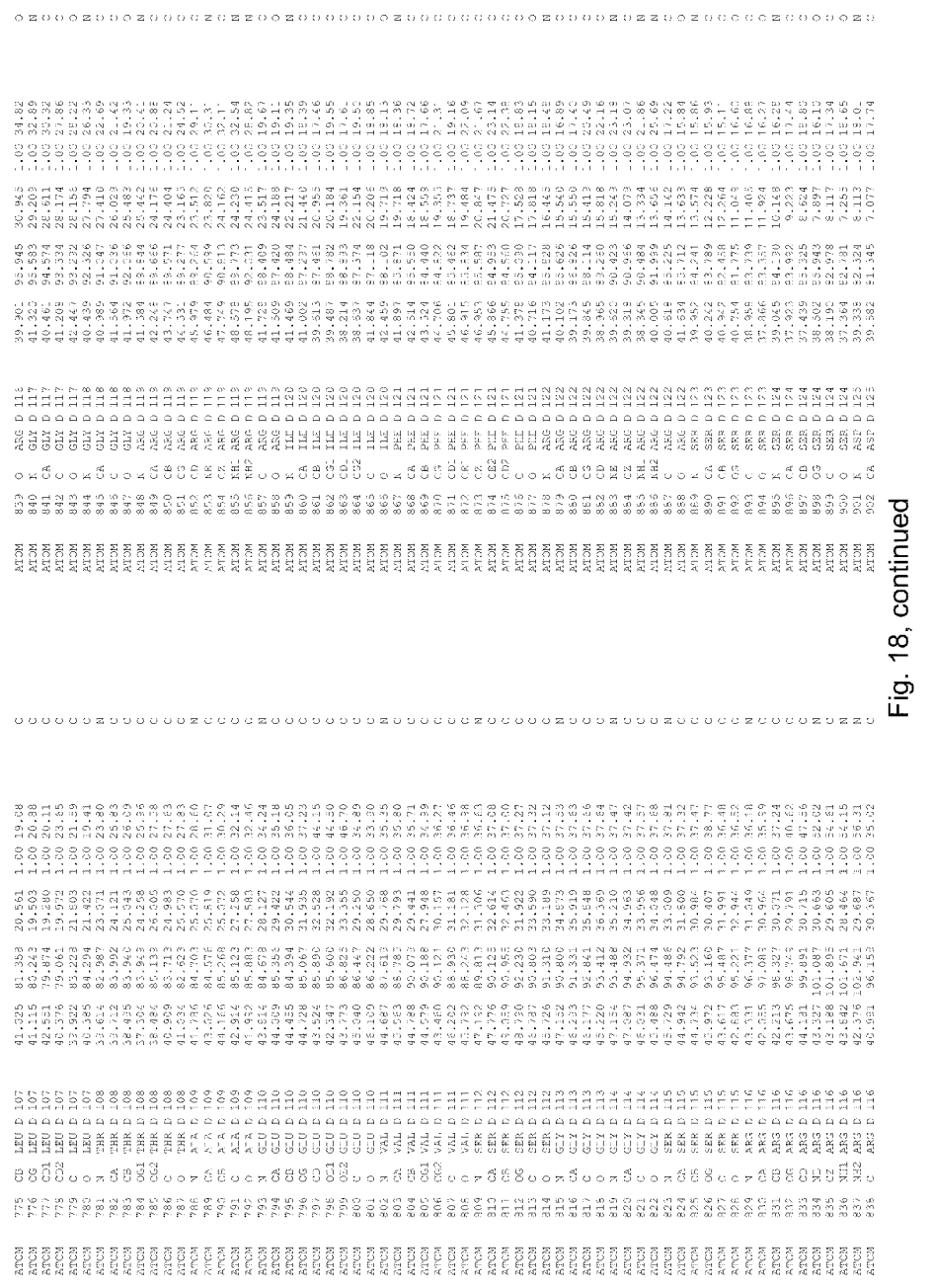
Figure 18:
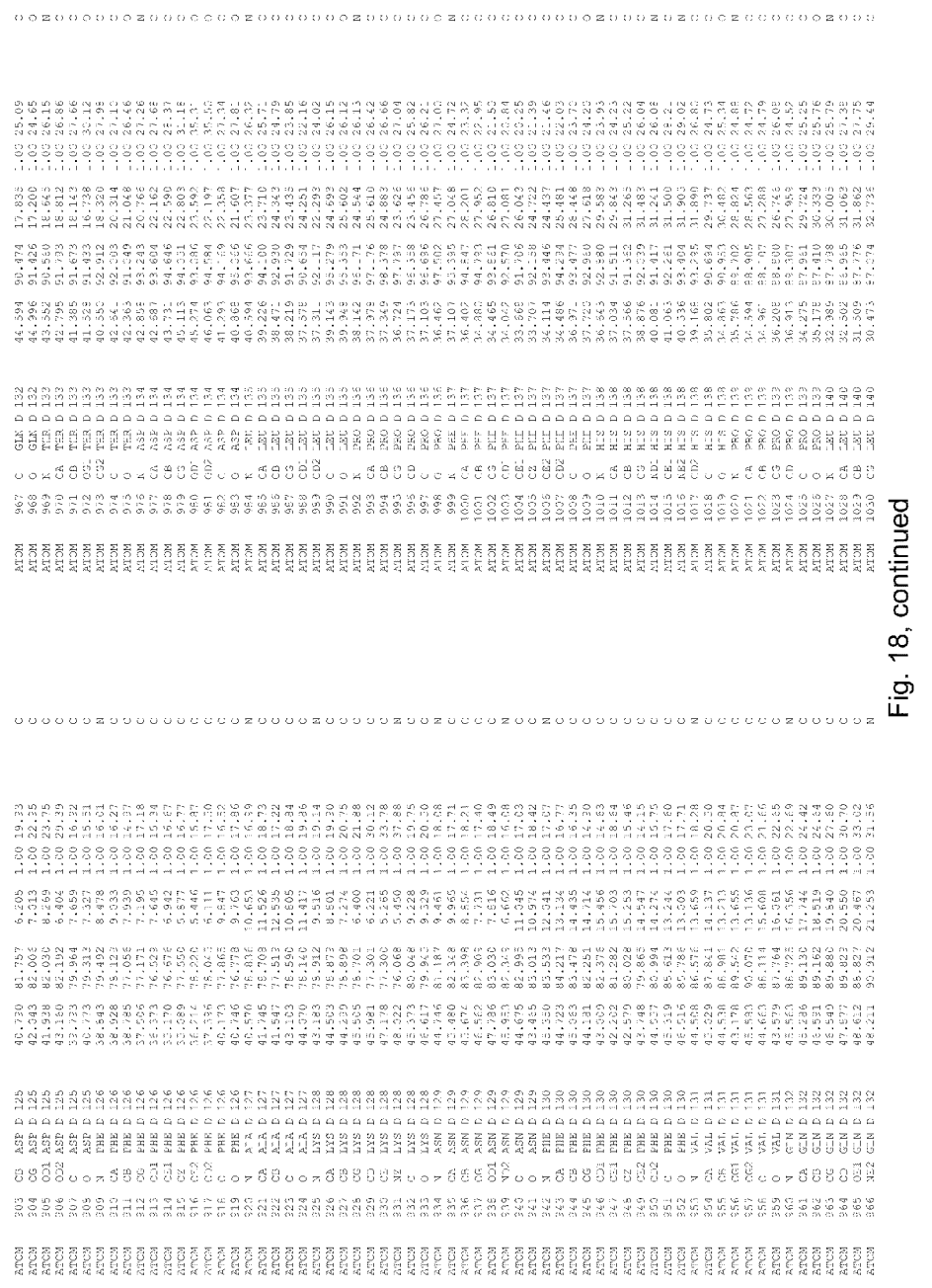
Figure 18:
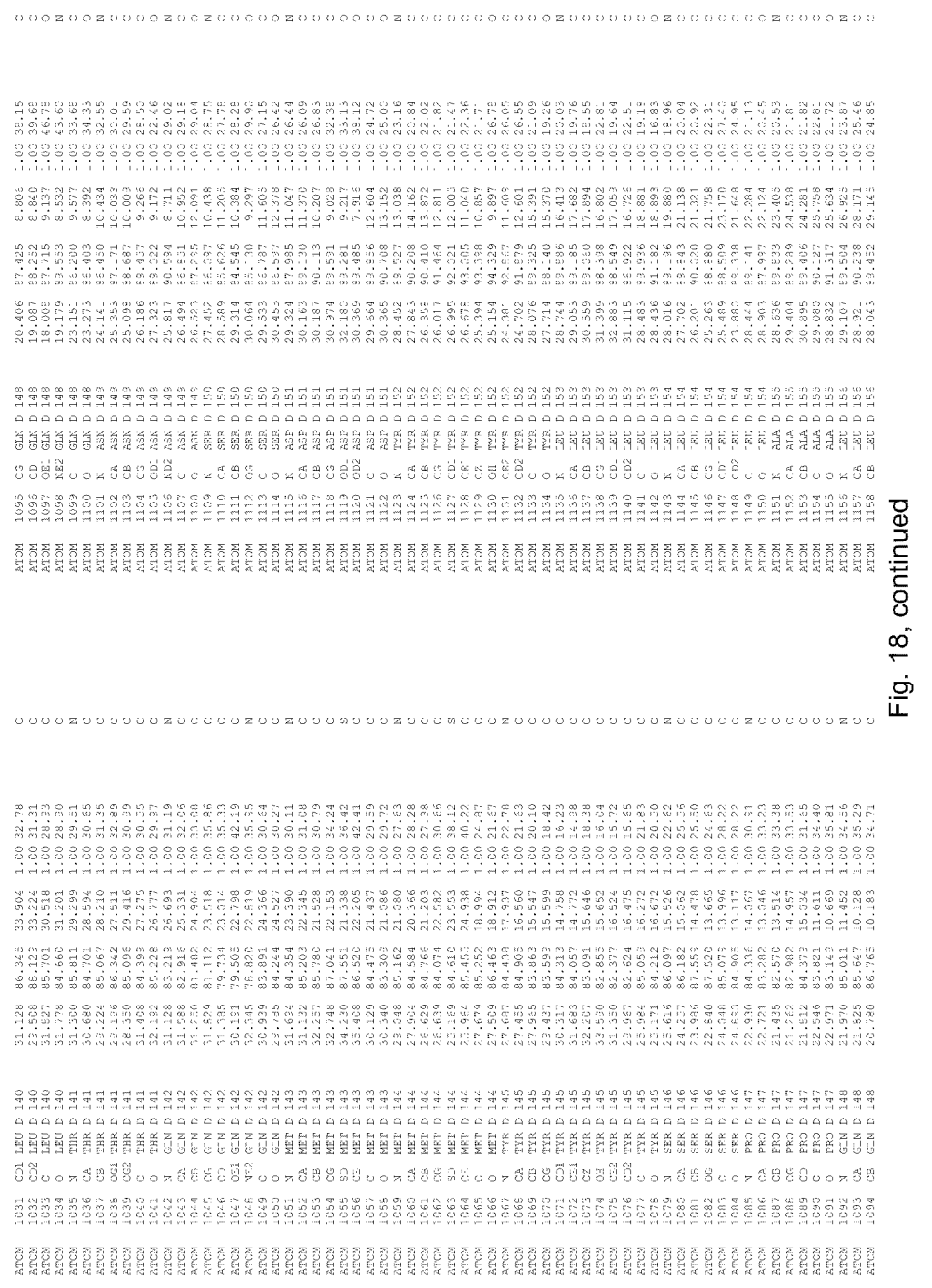
Figure 18:
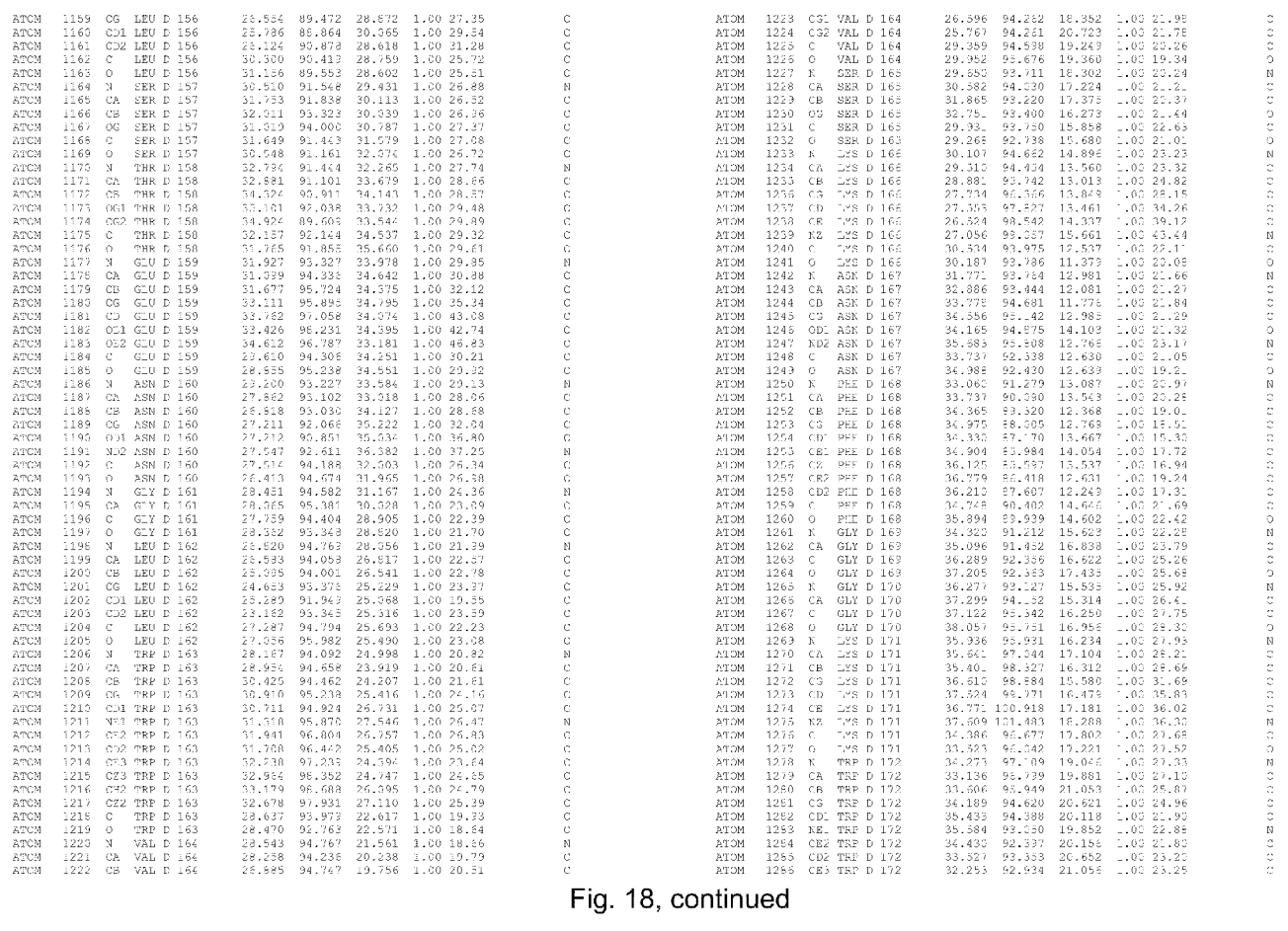
Figure 18:
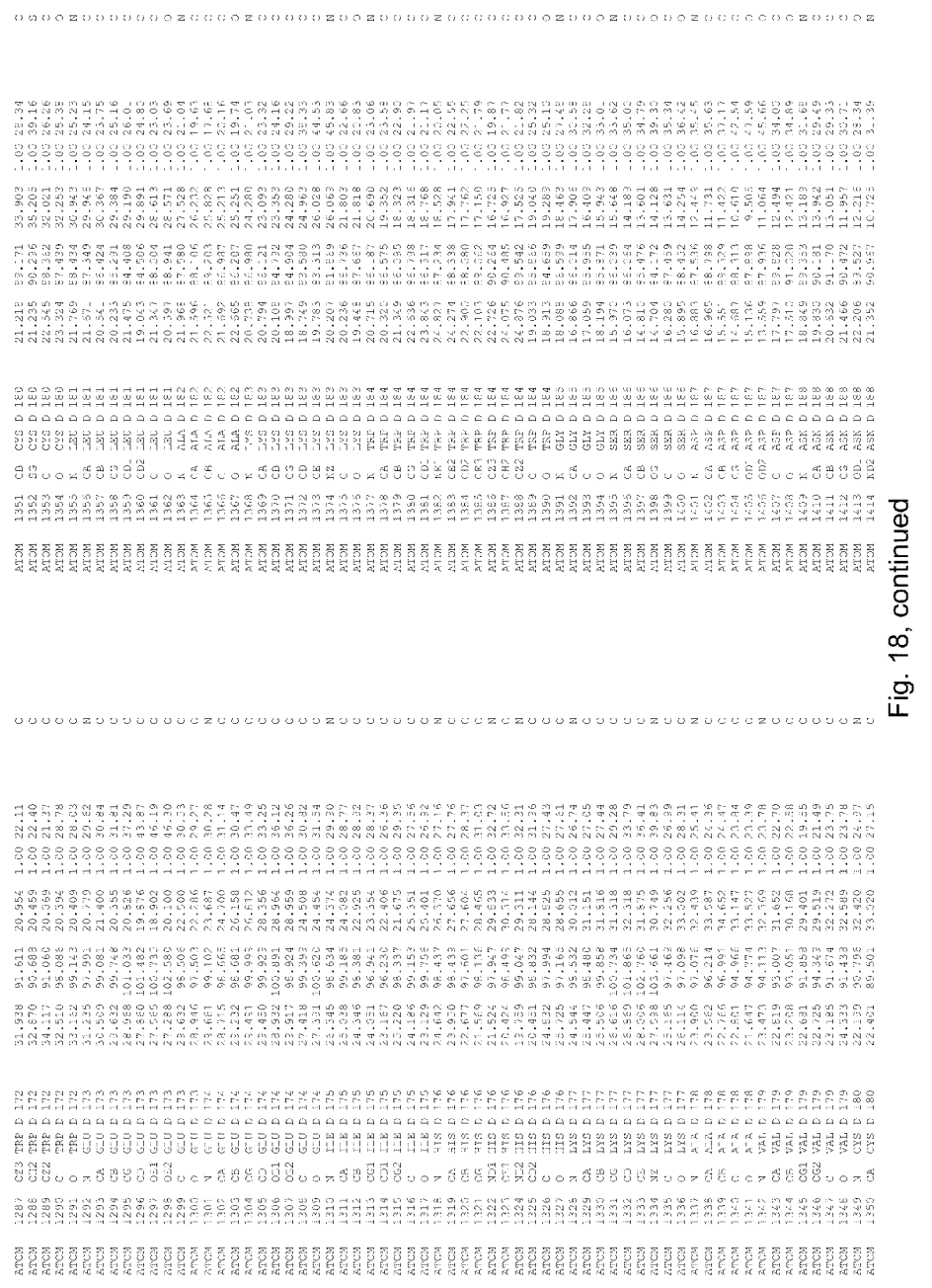
Figure 18:
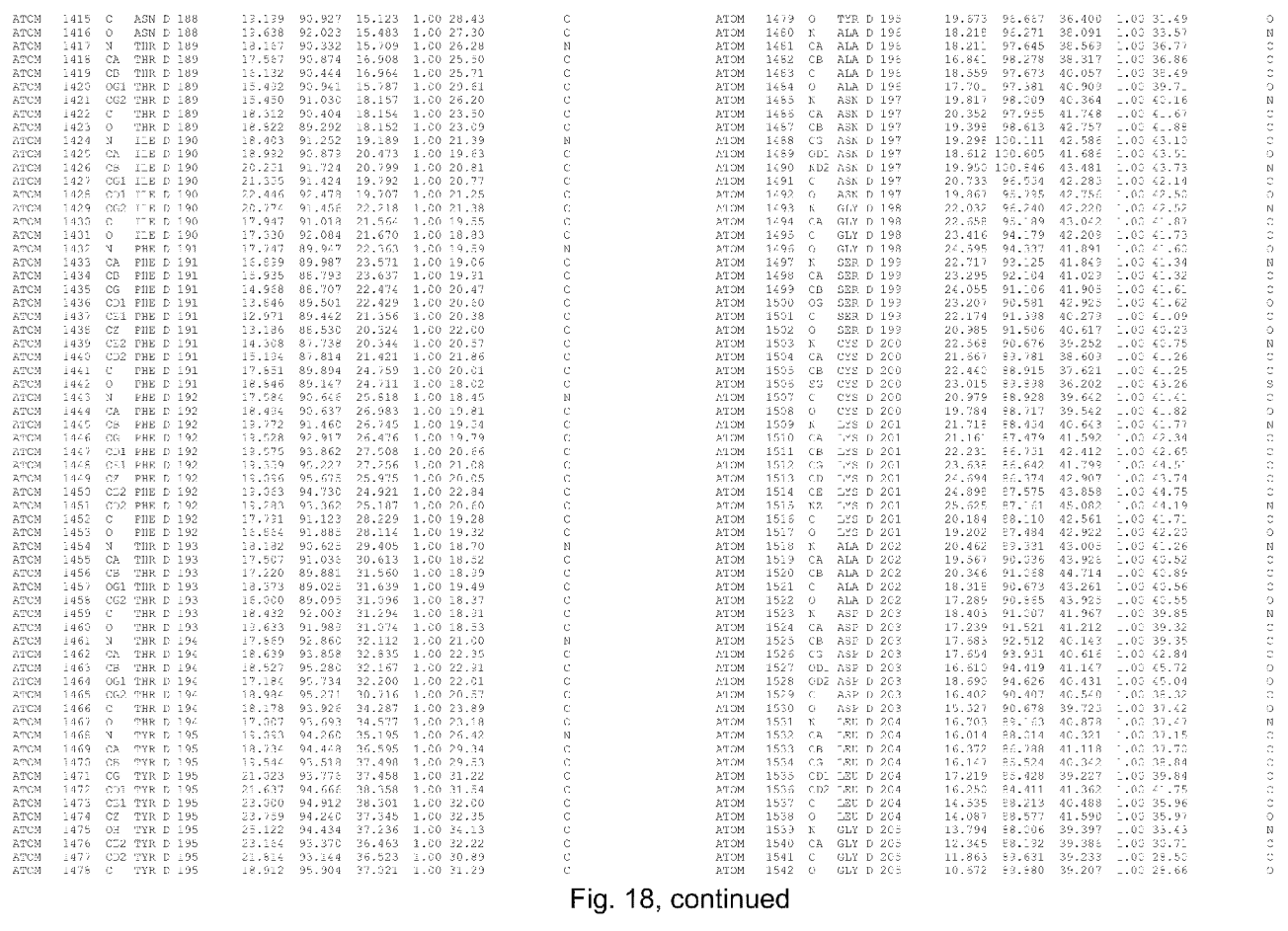
Figure 18:
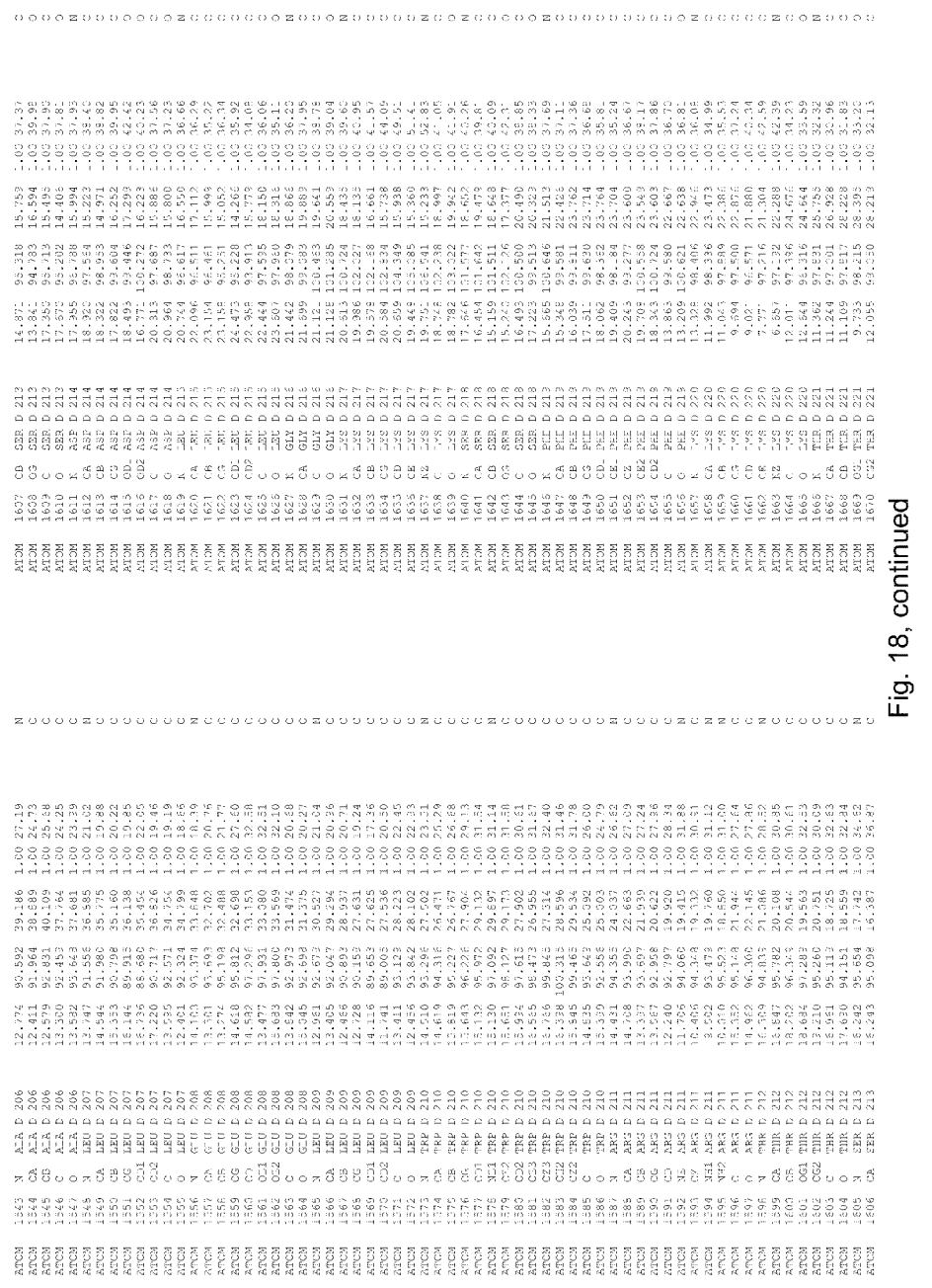
Figure 18:
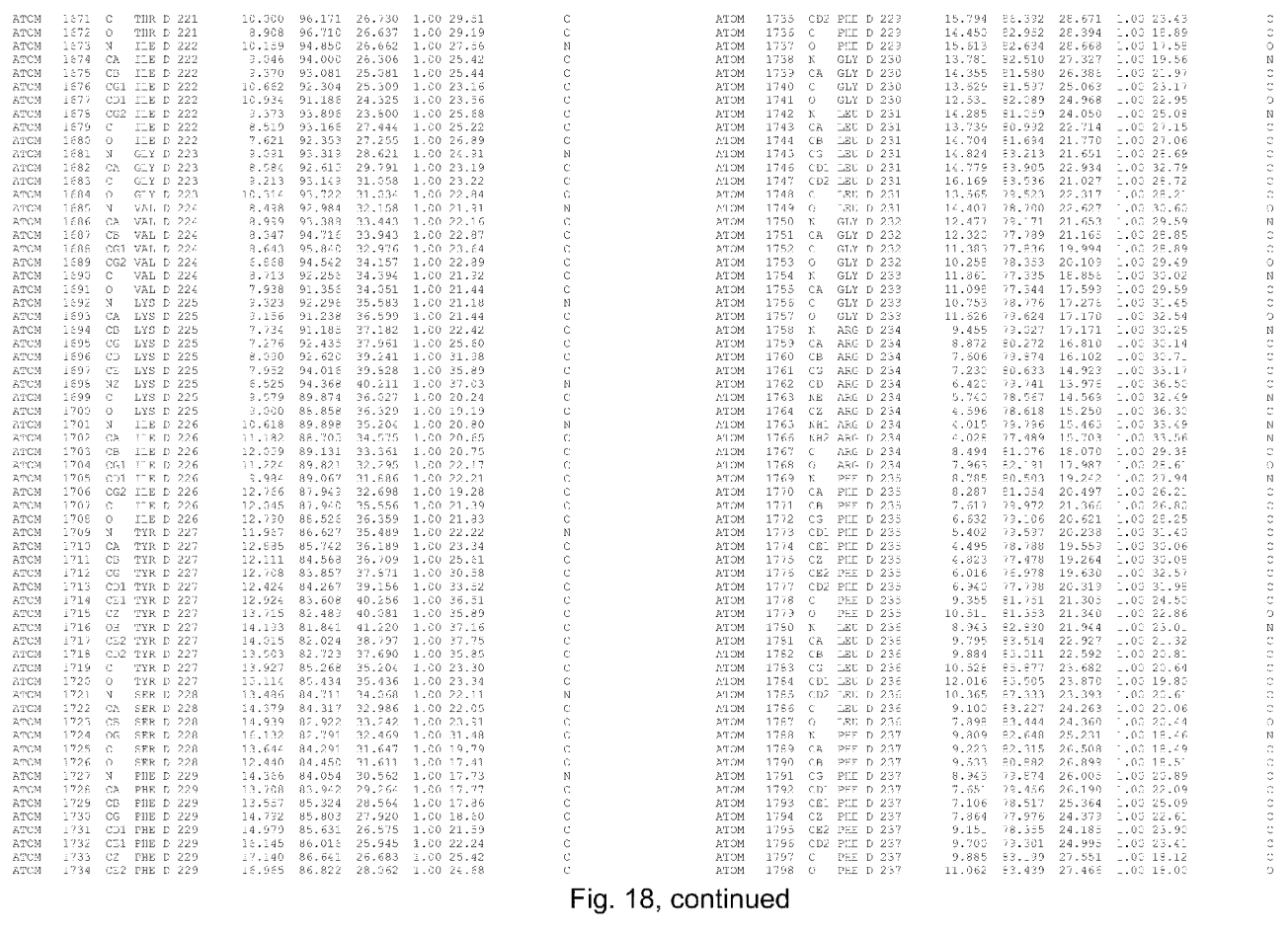
Figure 18:
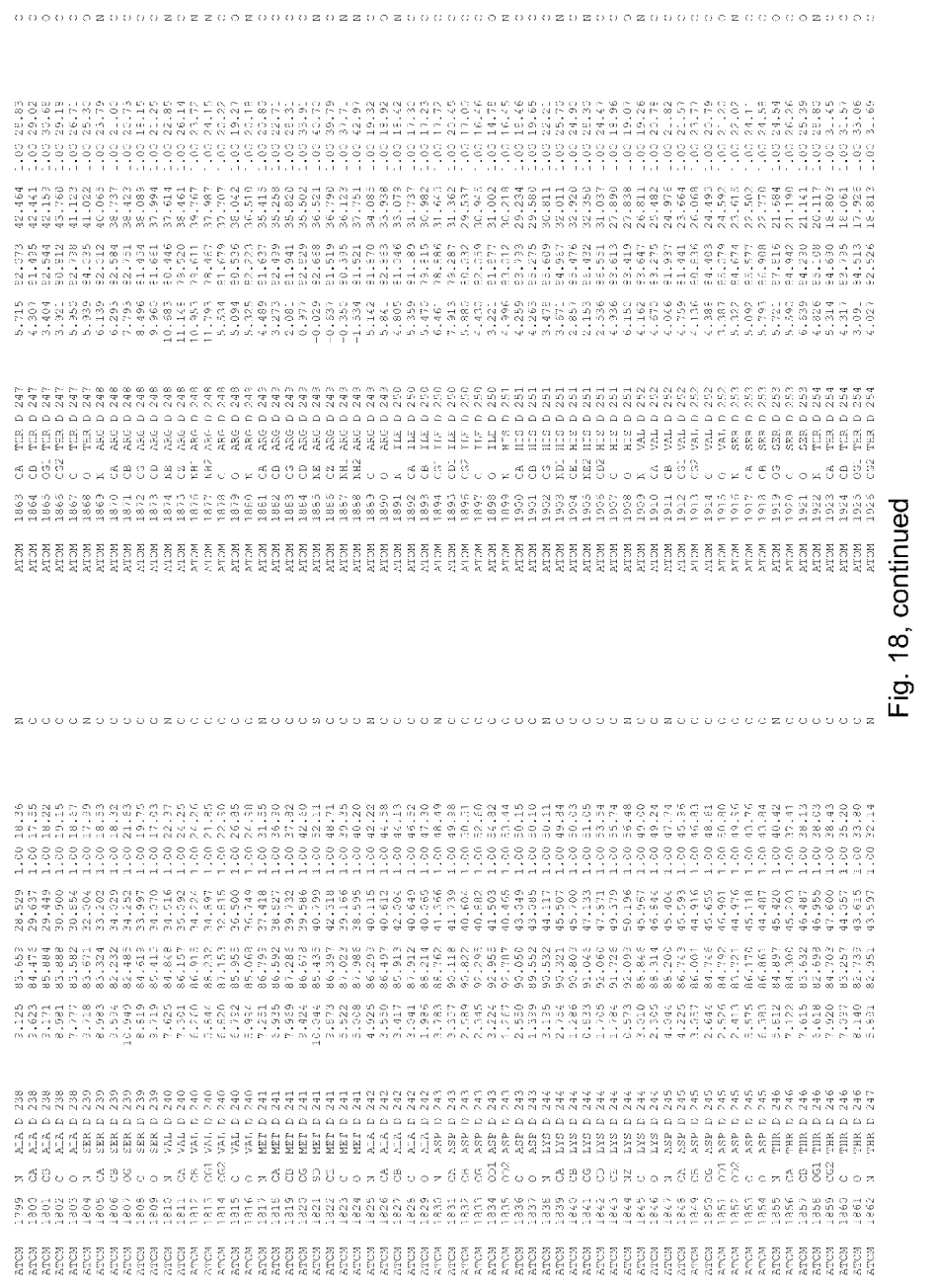
Figure 18:
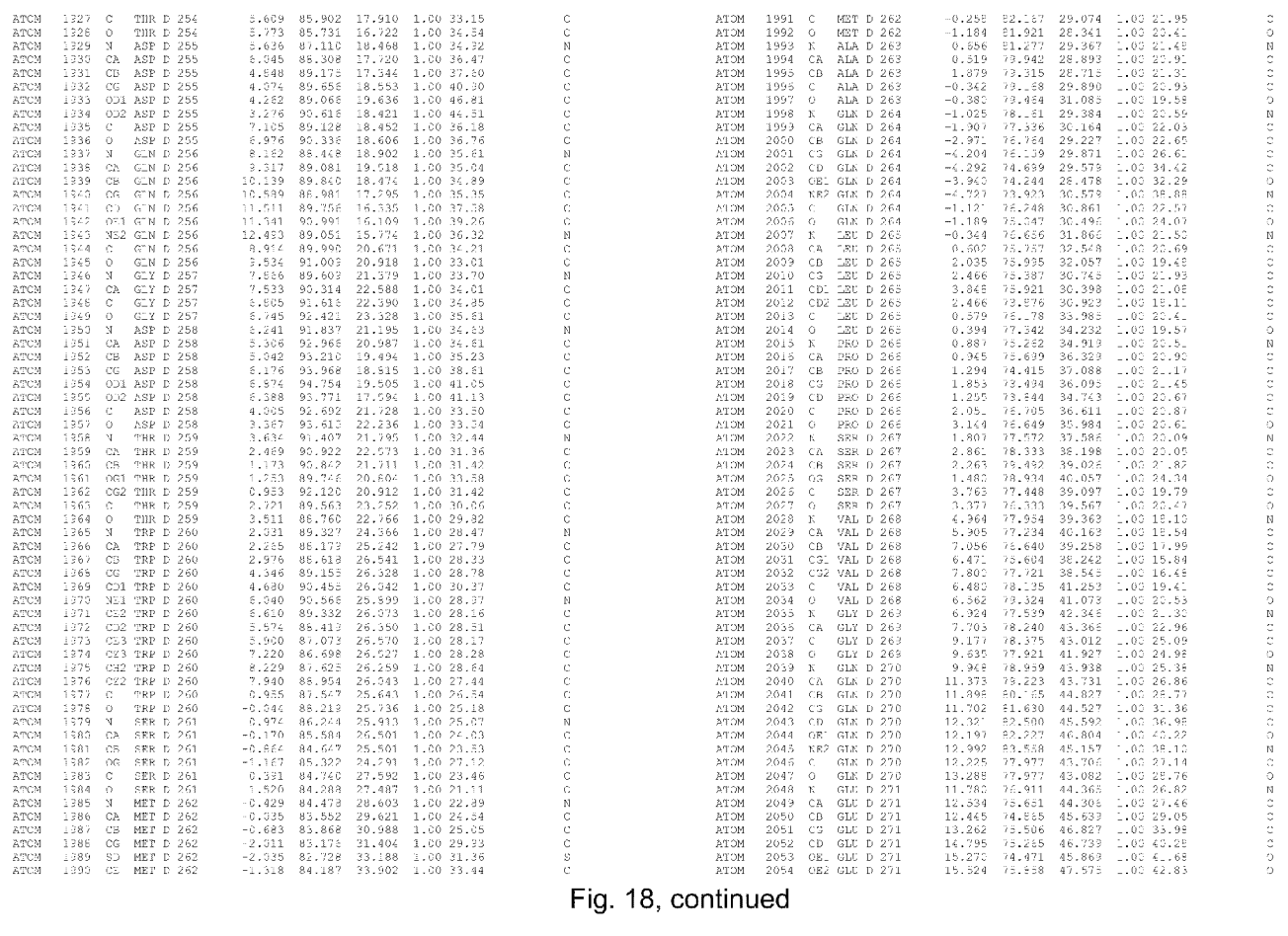
Figure 18:
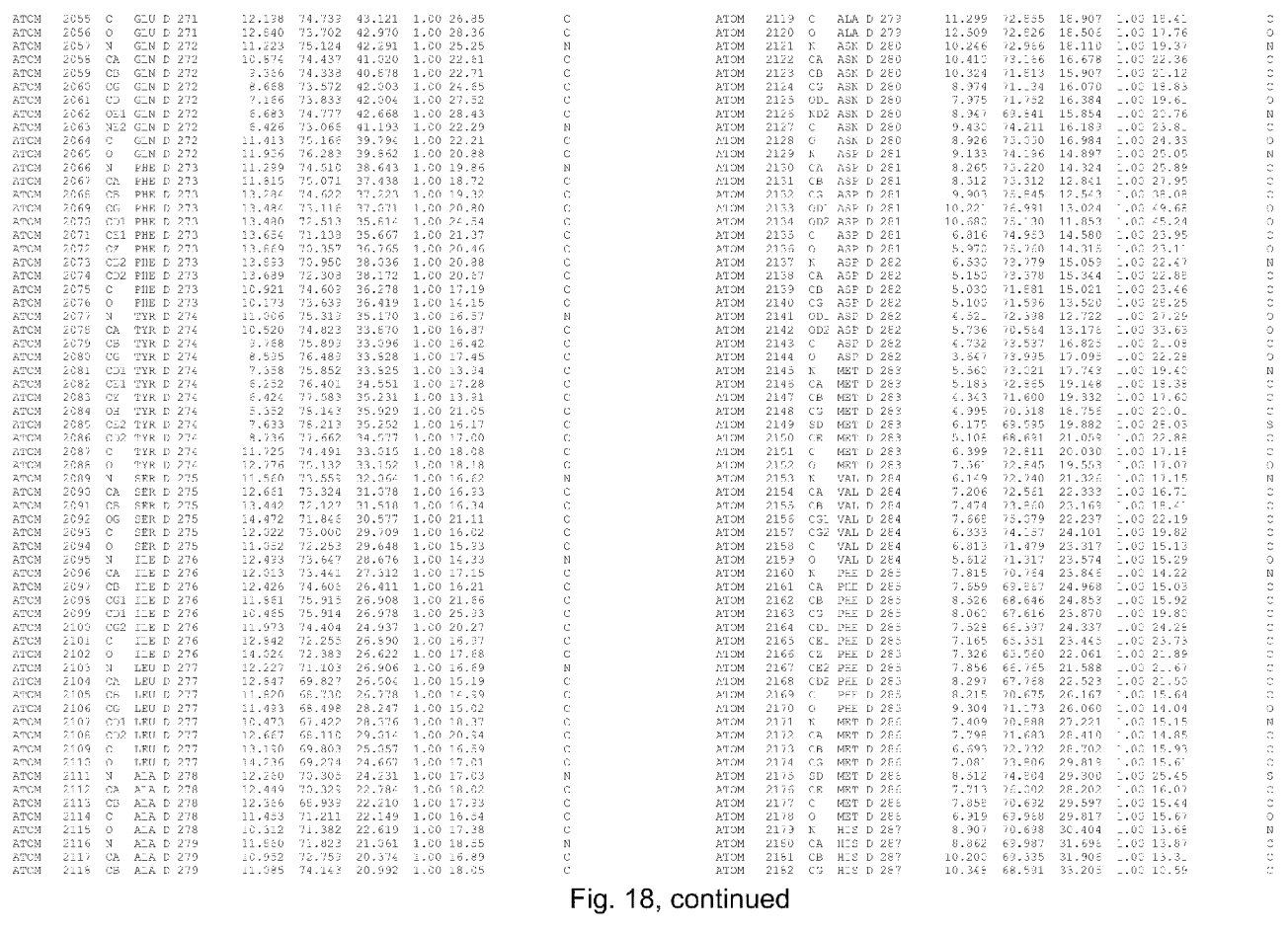
Figure 18:
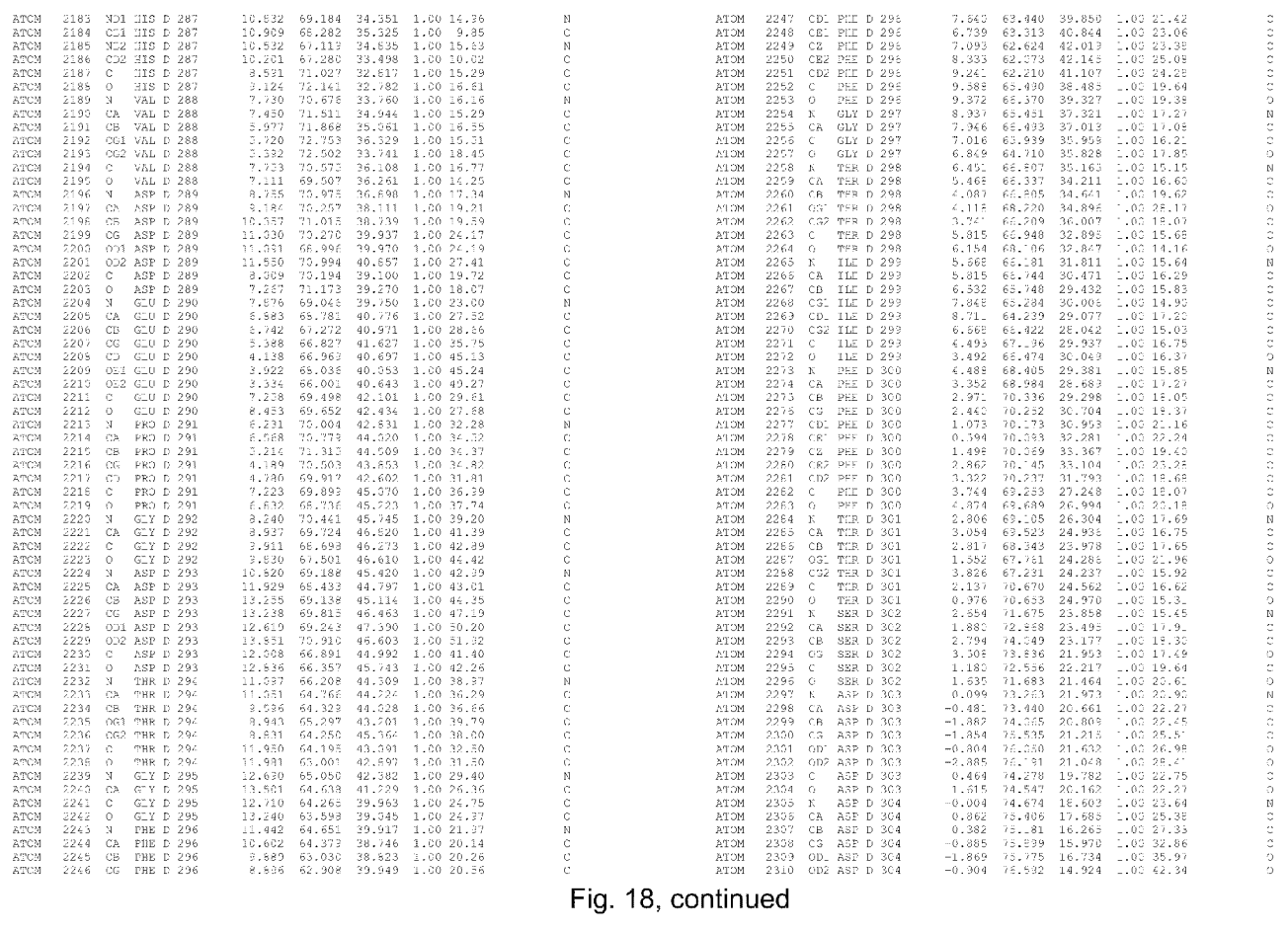
Figure 18:
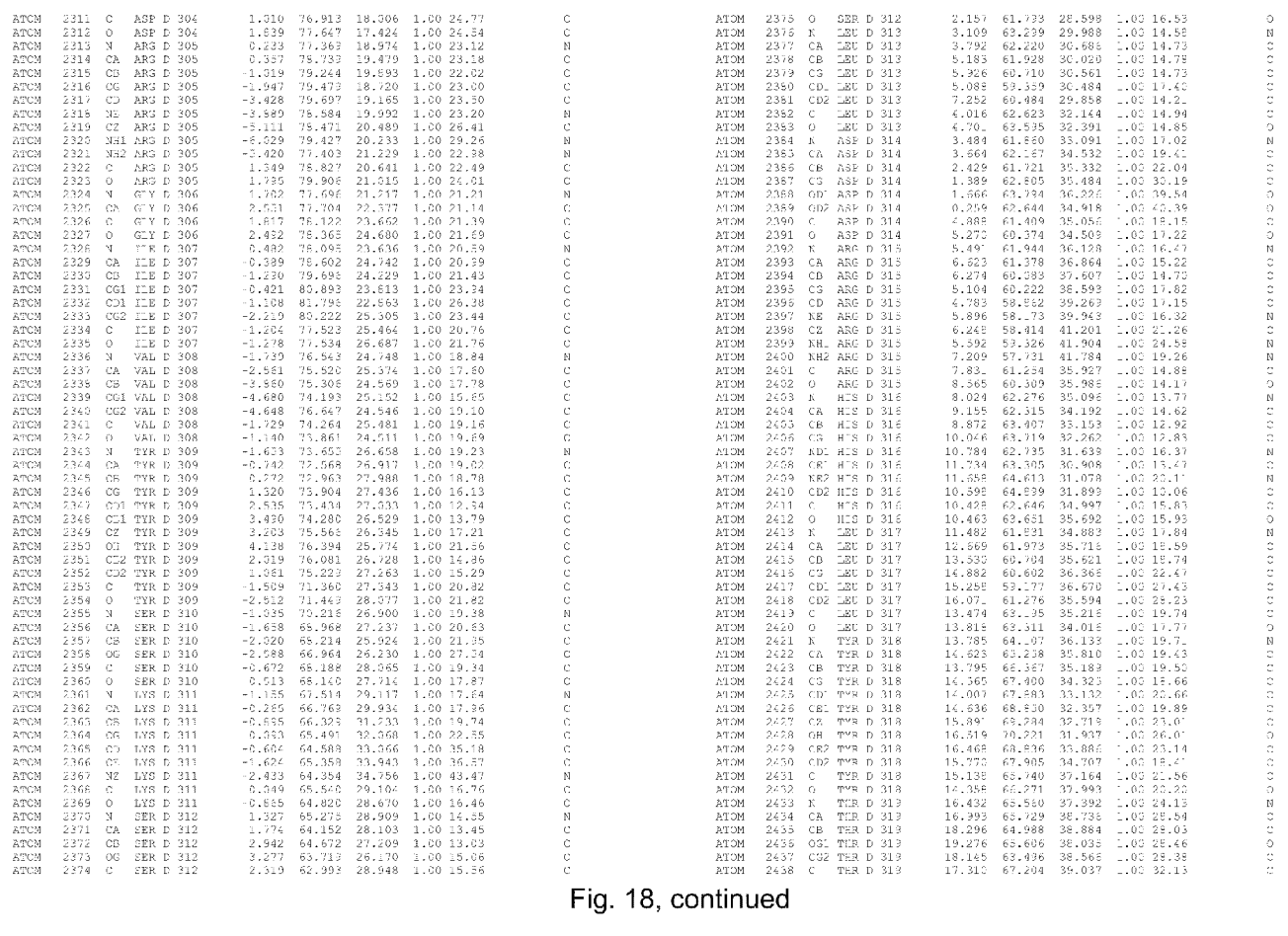
Figure 18:
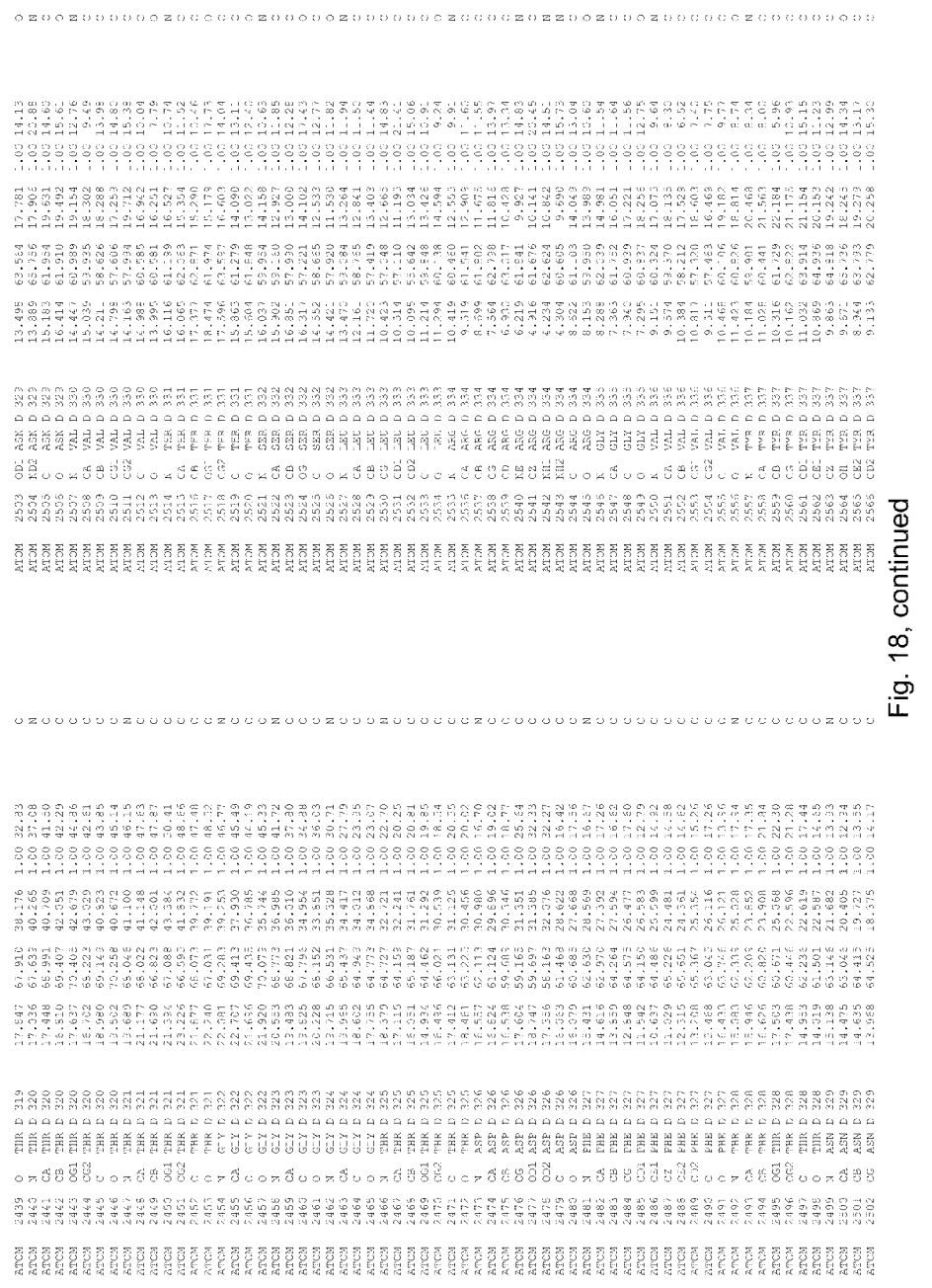
Figure 18:
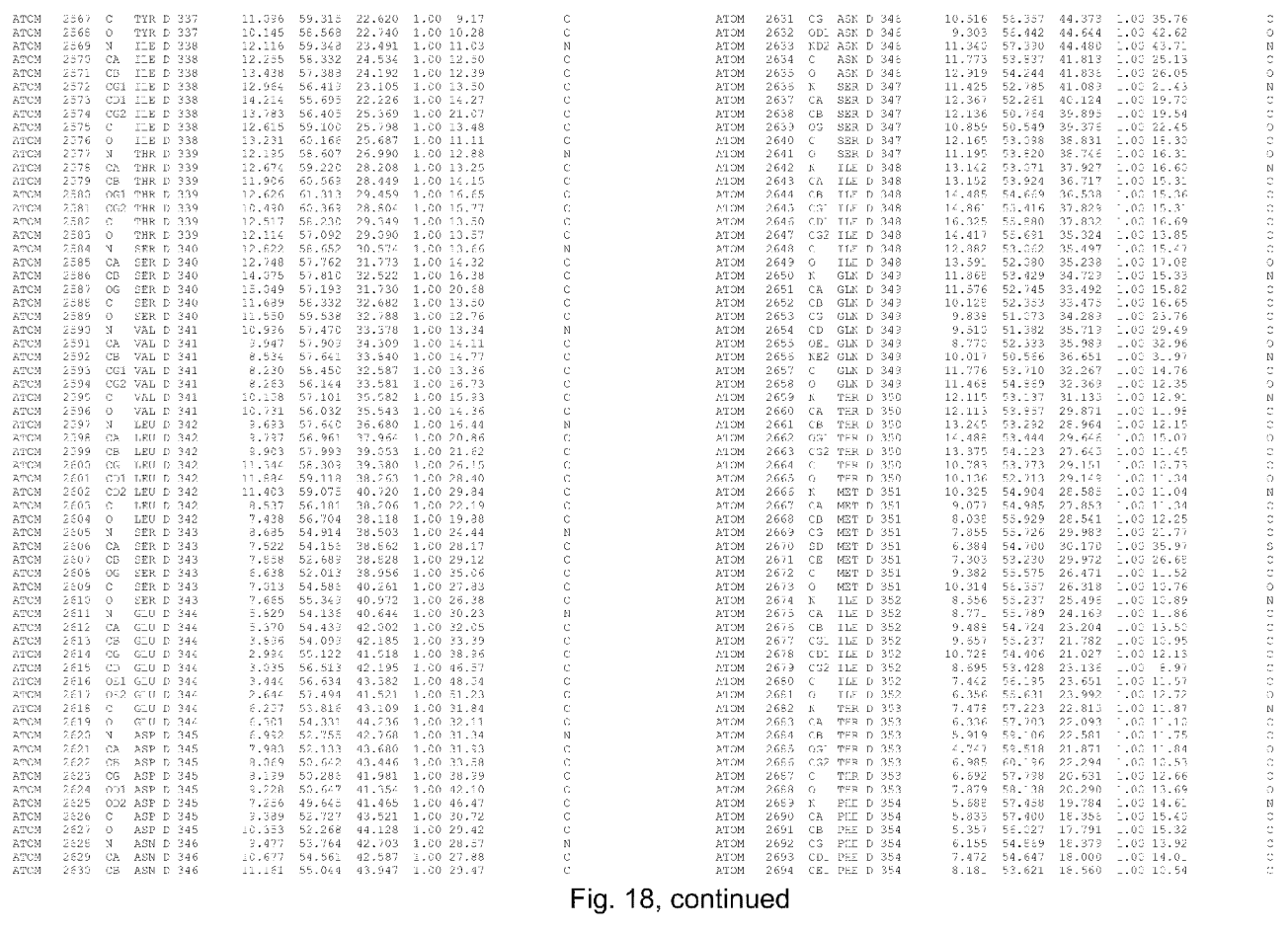
Figure 18:
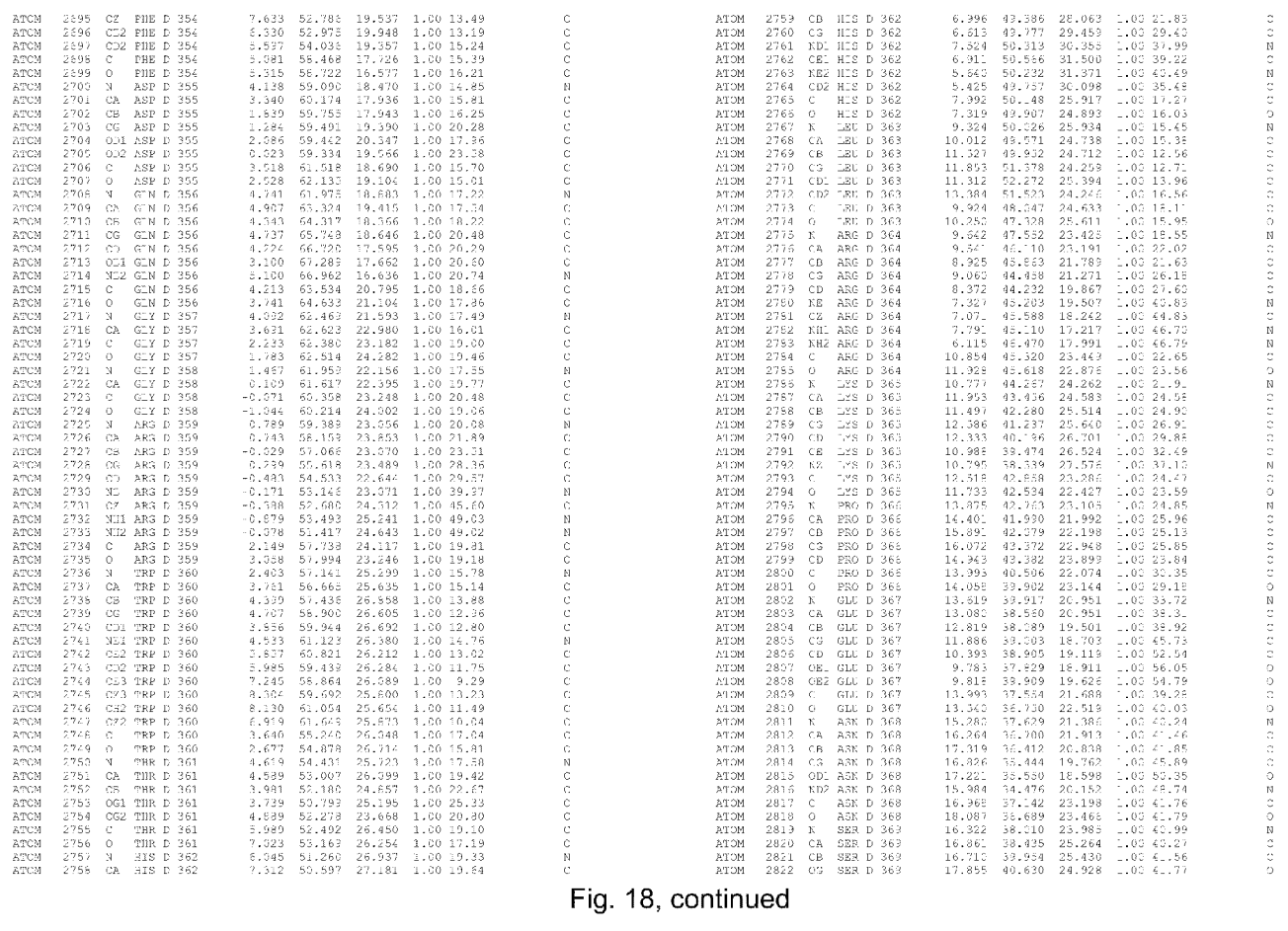
Figure 18:
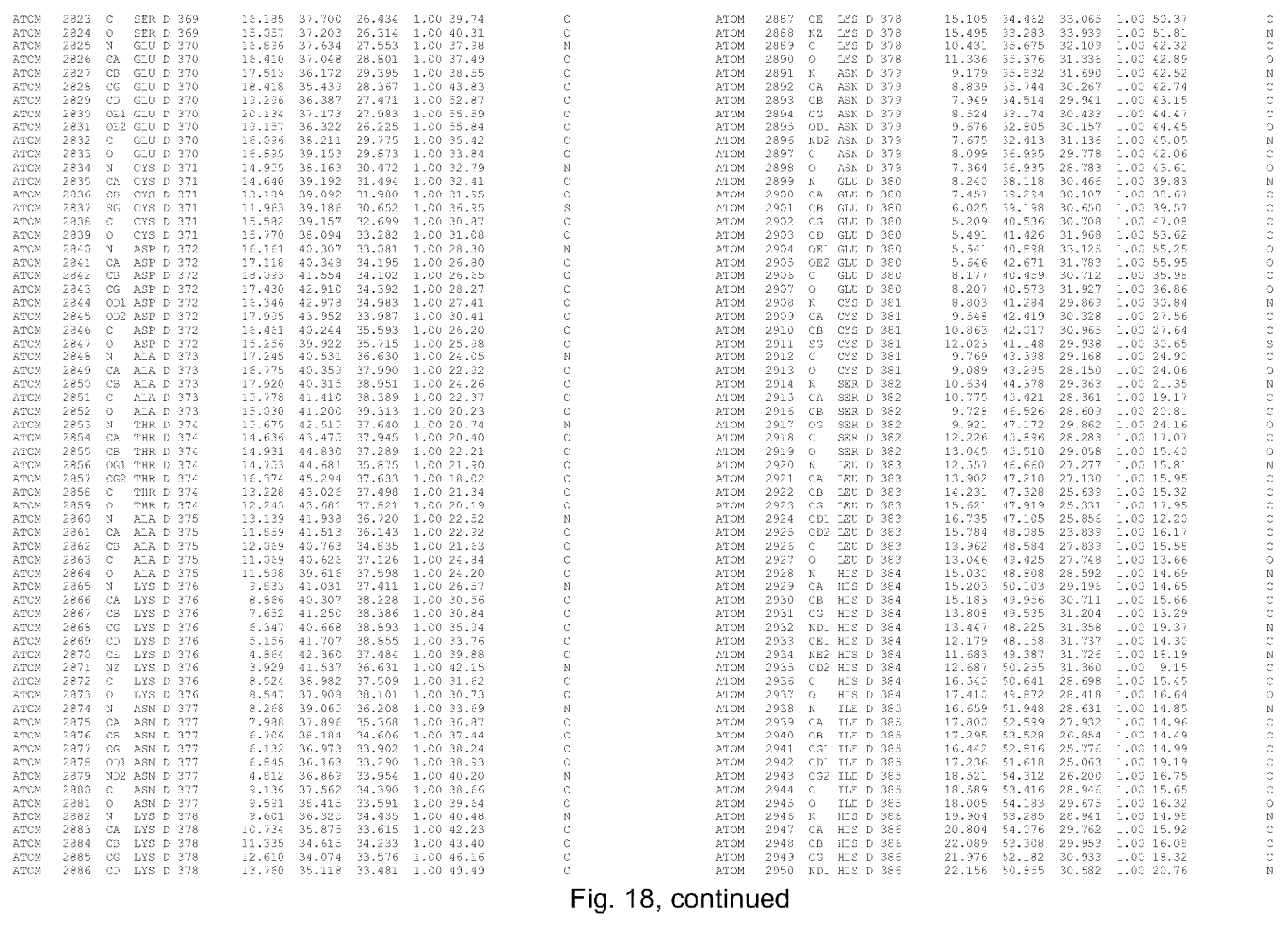
Figure 18:
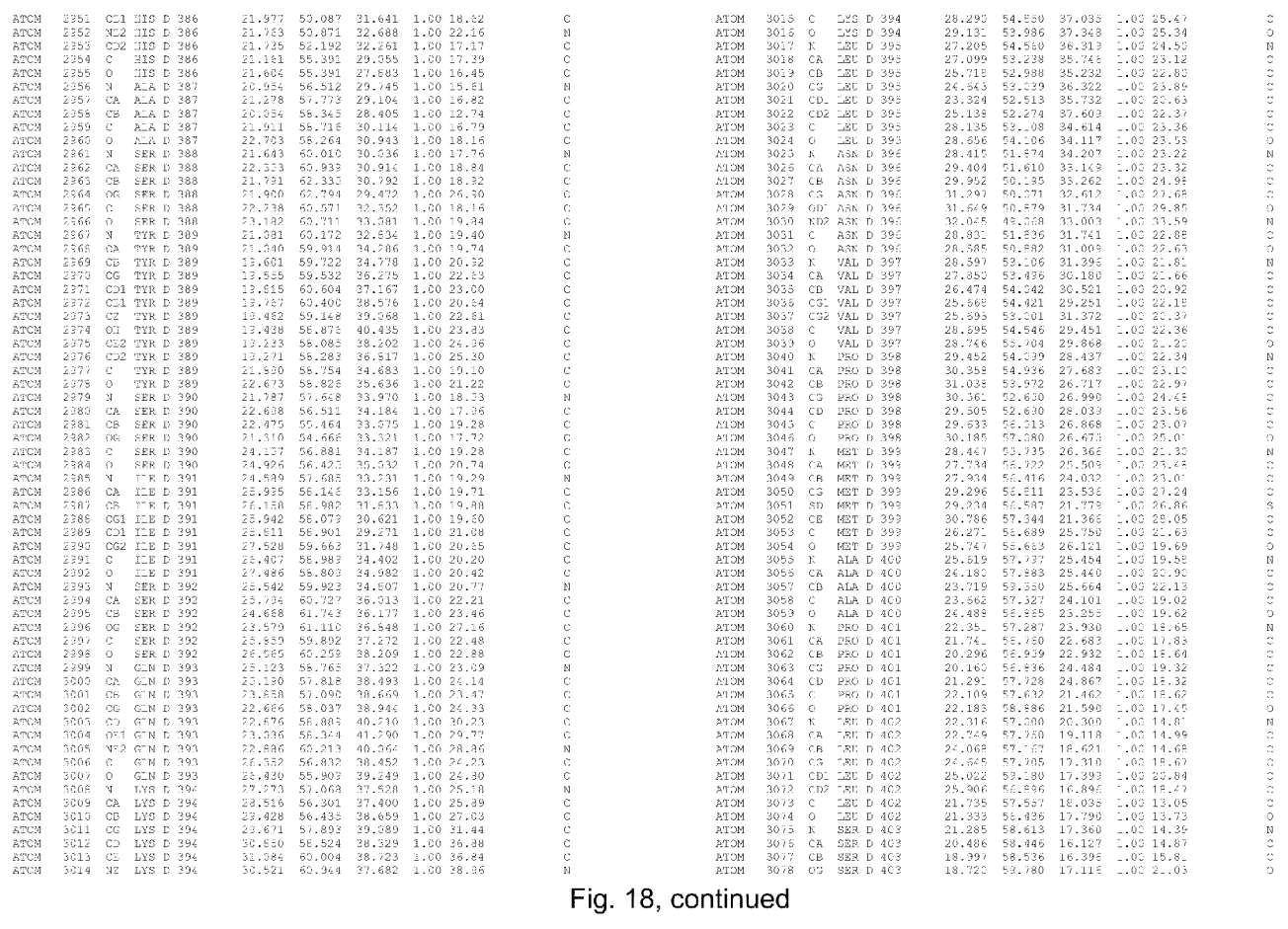
Figure 18:
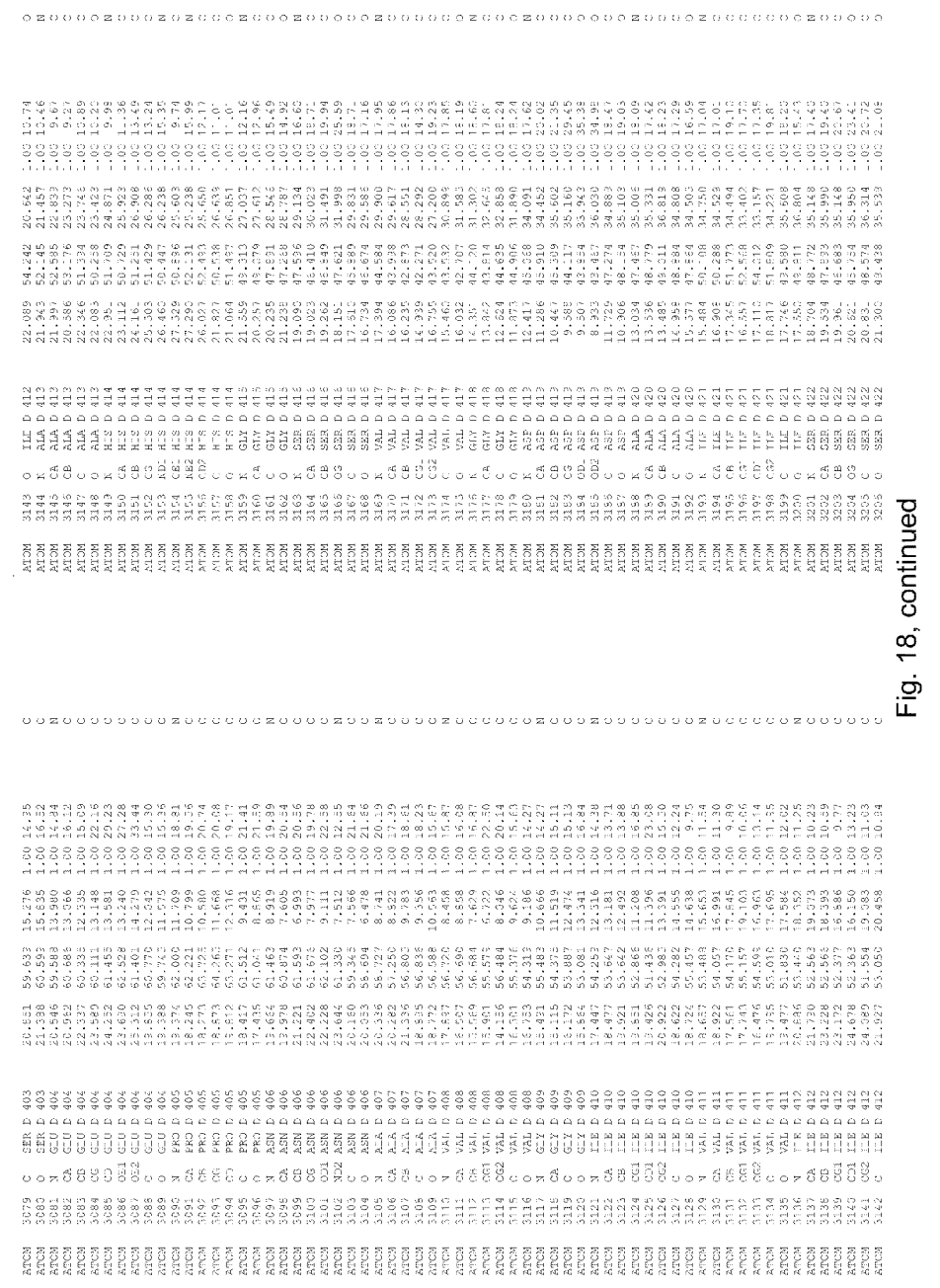
Figure 18:
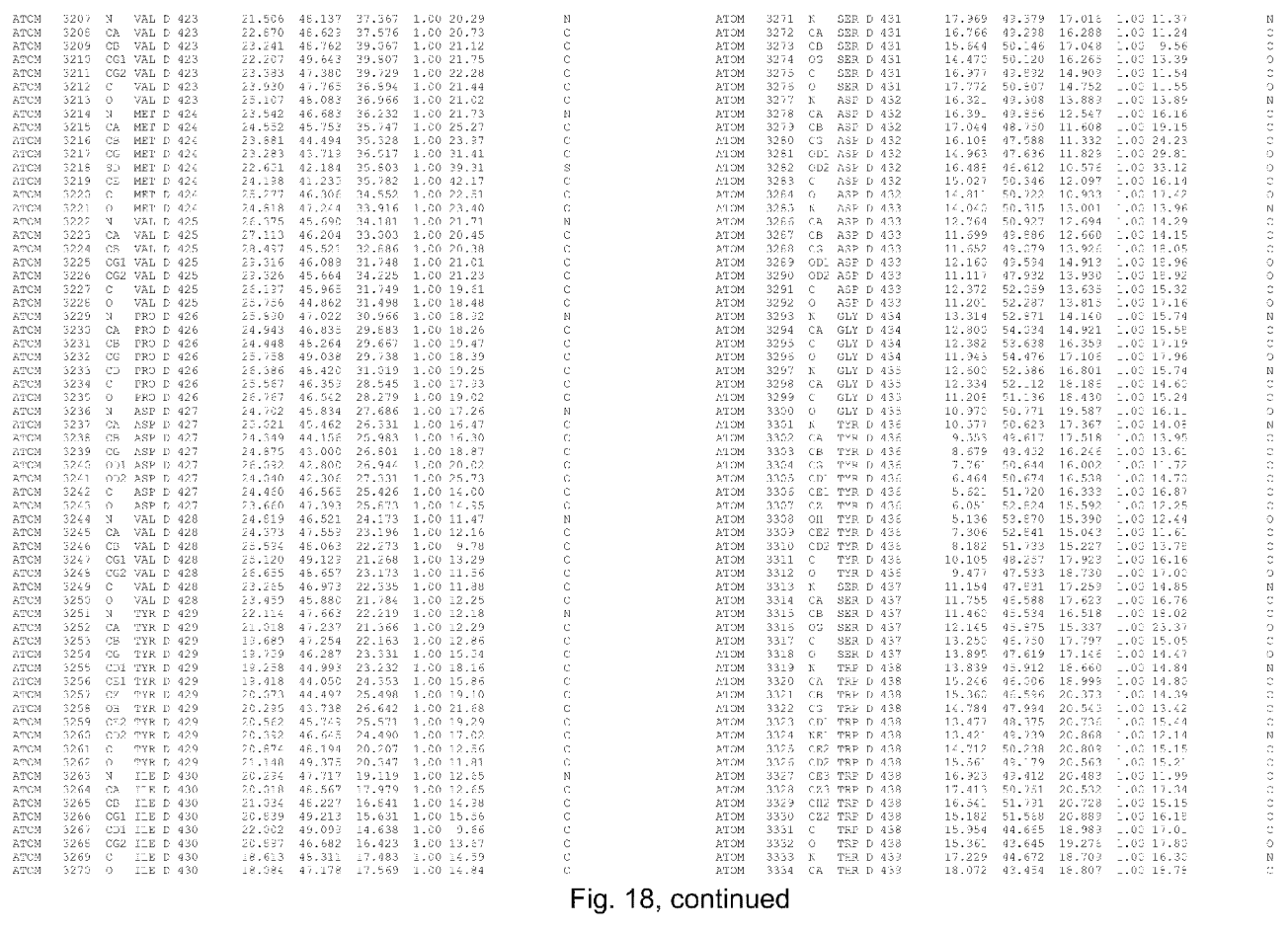
Figure 18:
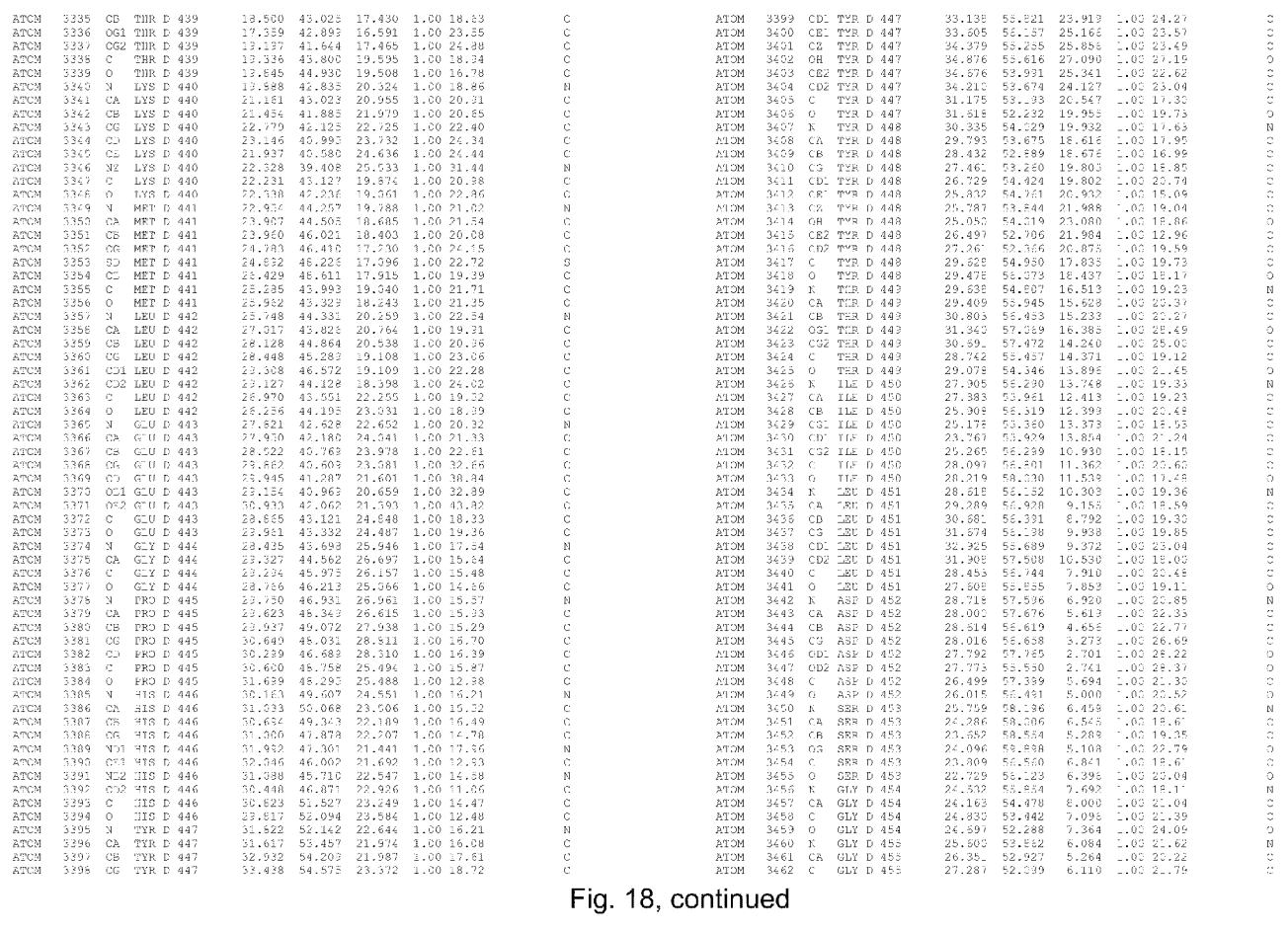
Figure 18:
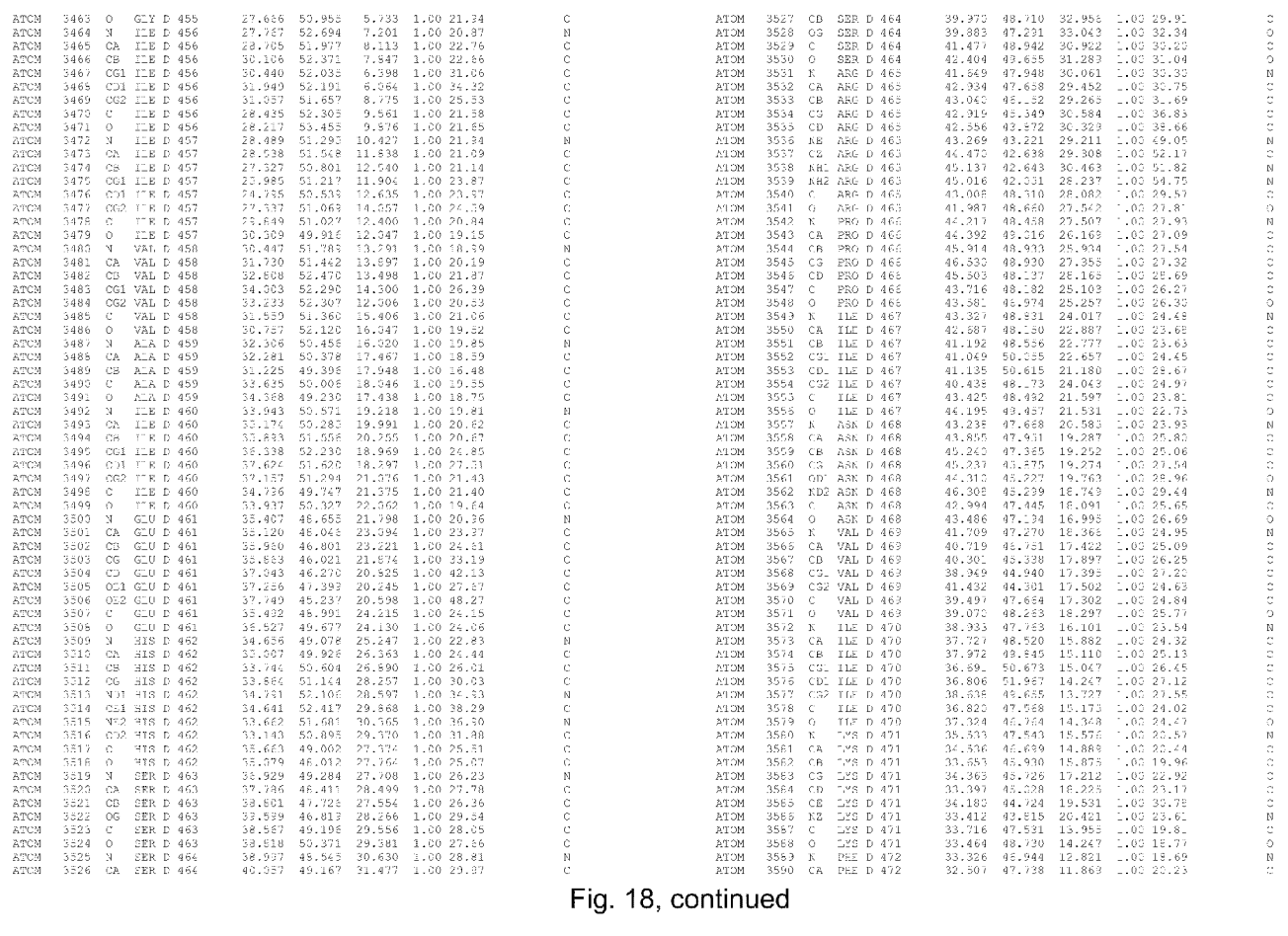
Figure 18:
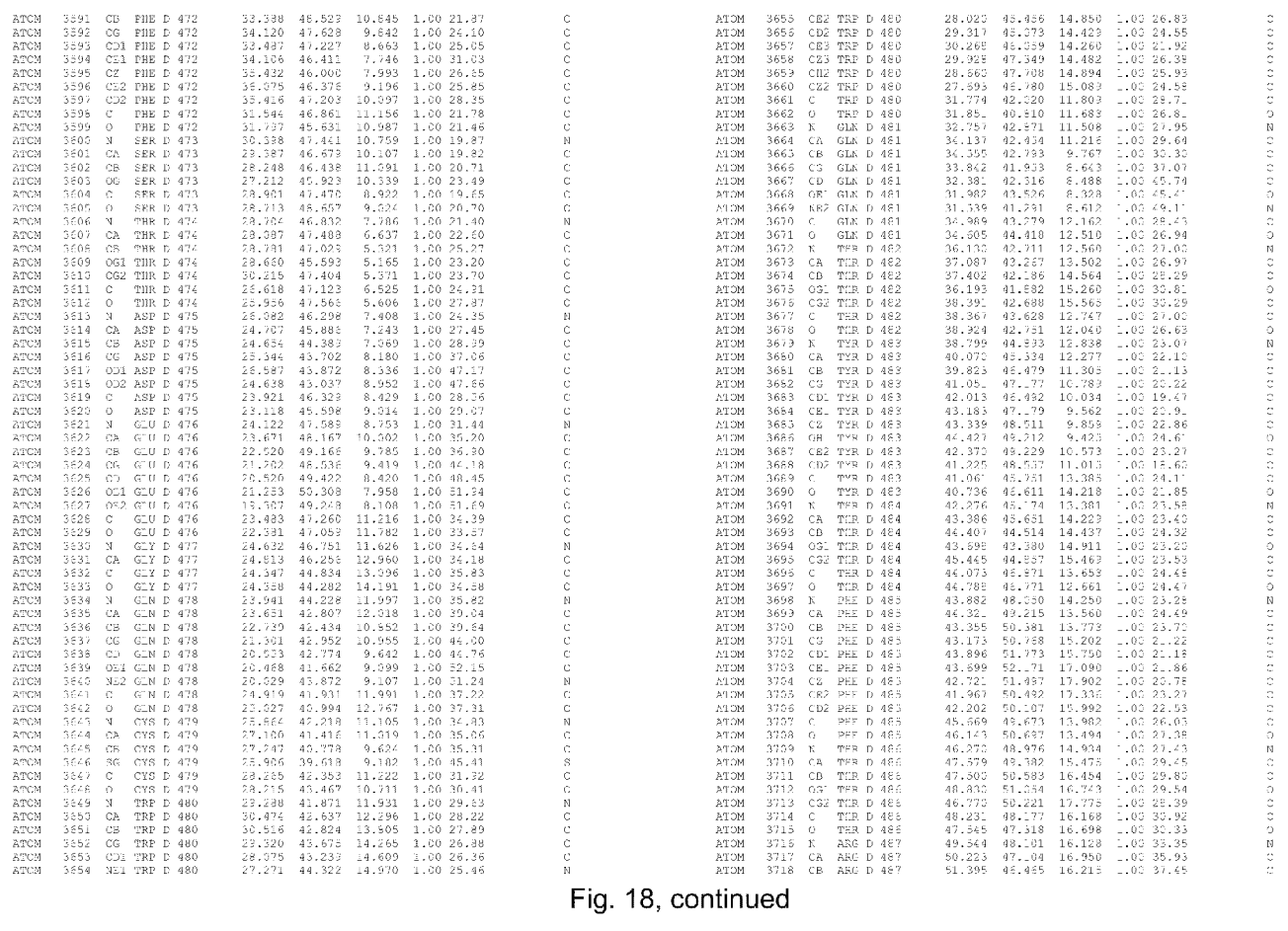
Figure 18:
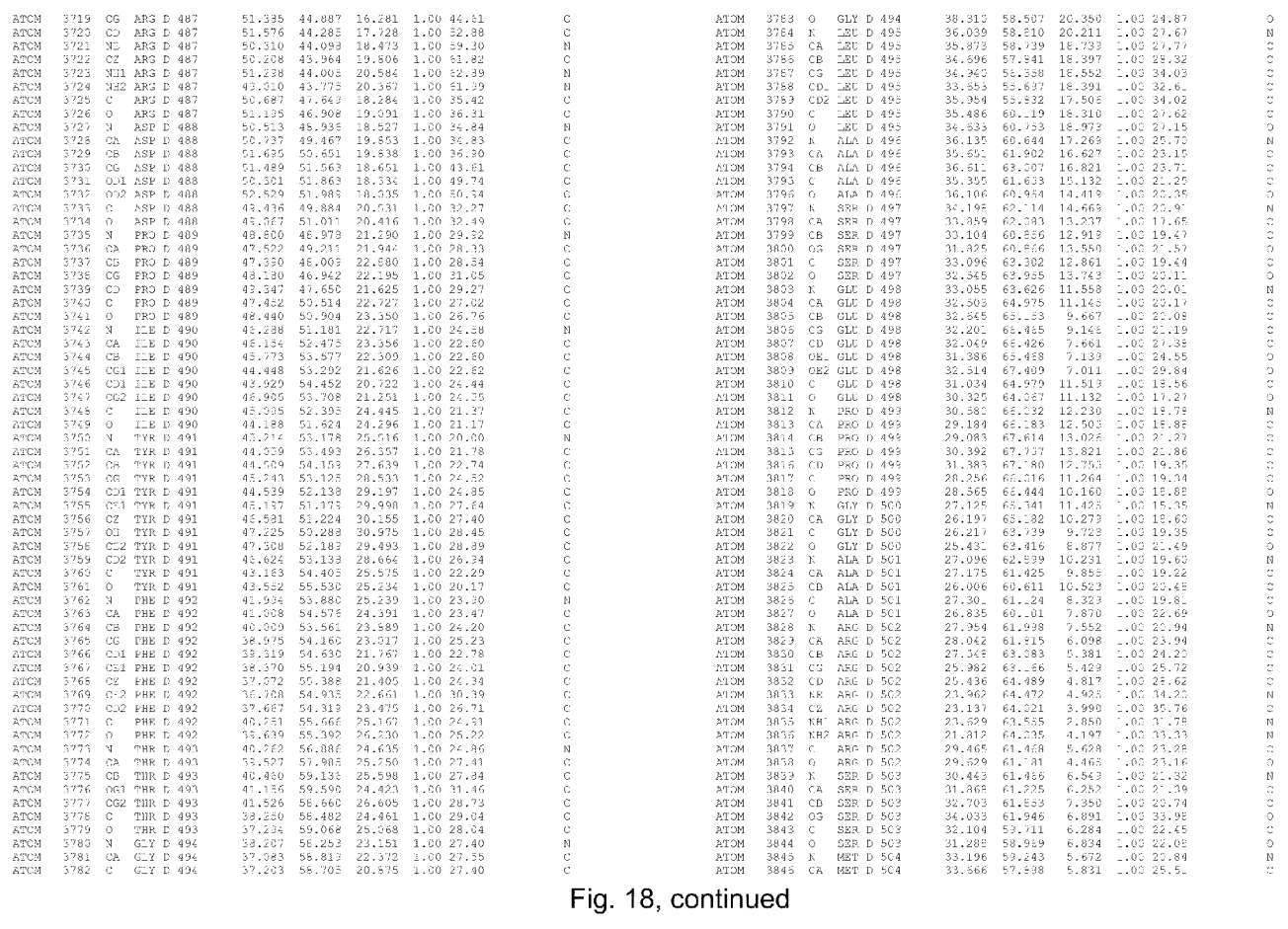
Figure 18:
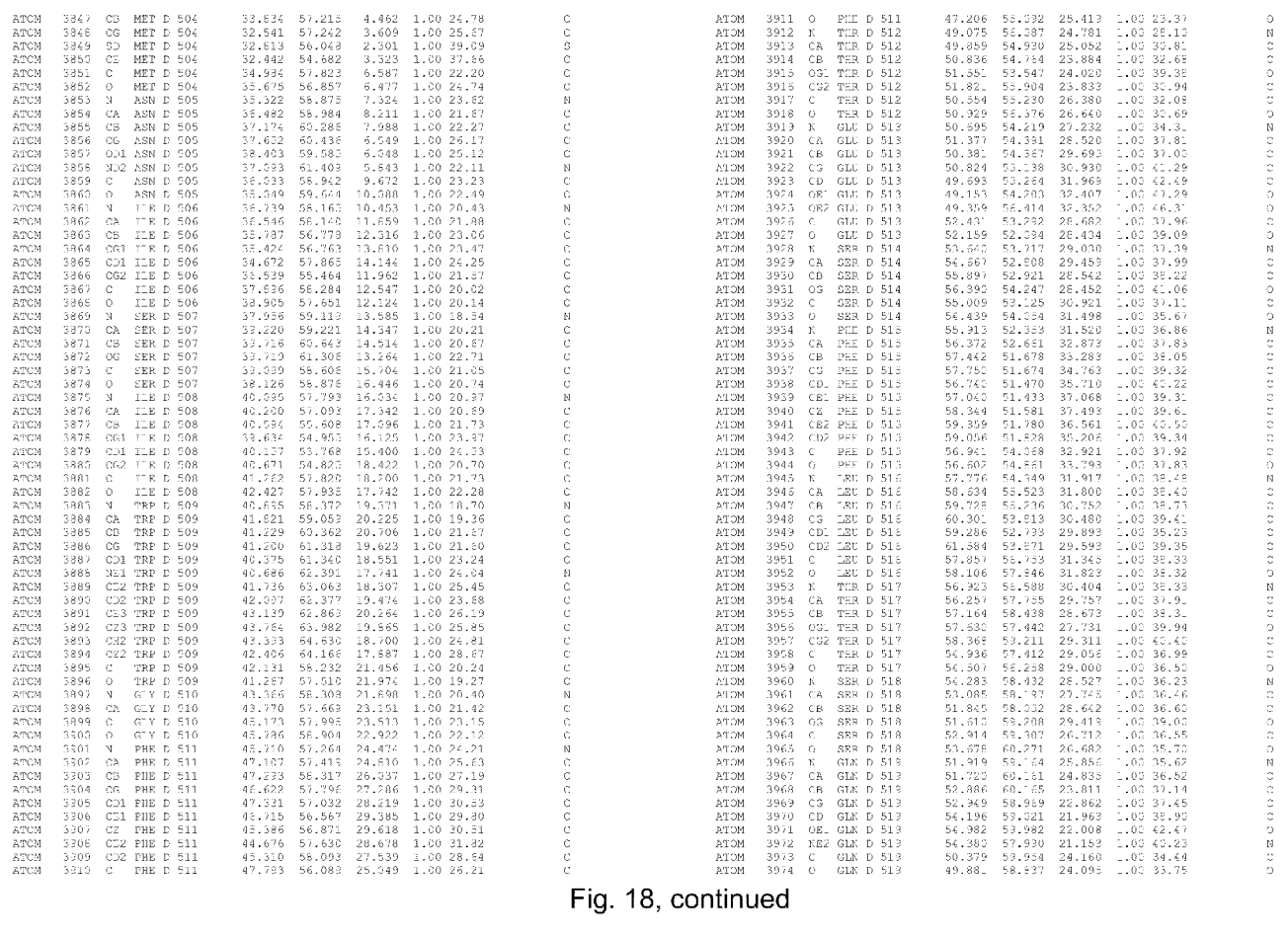
Figure 18:
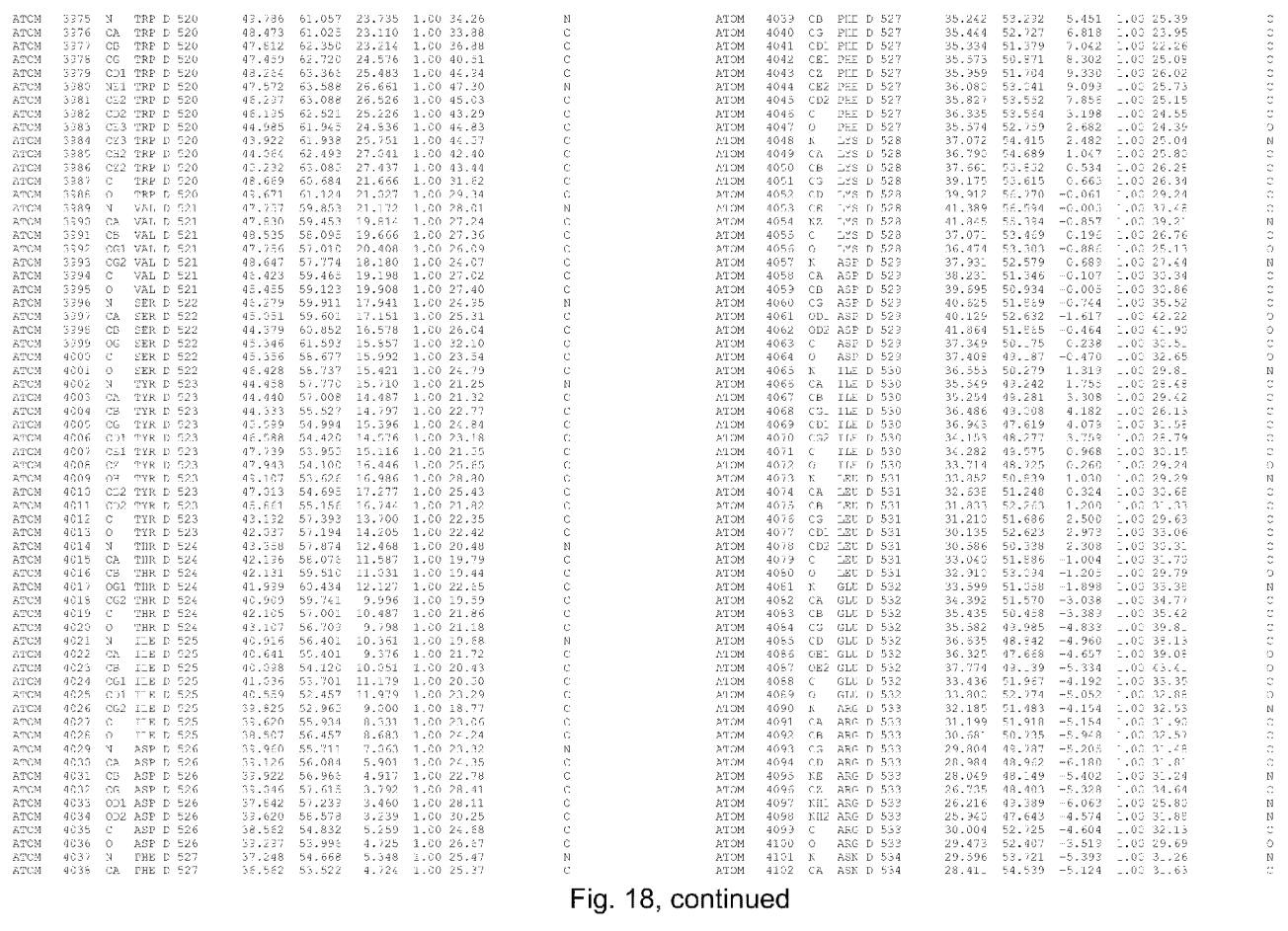
Figure 18:
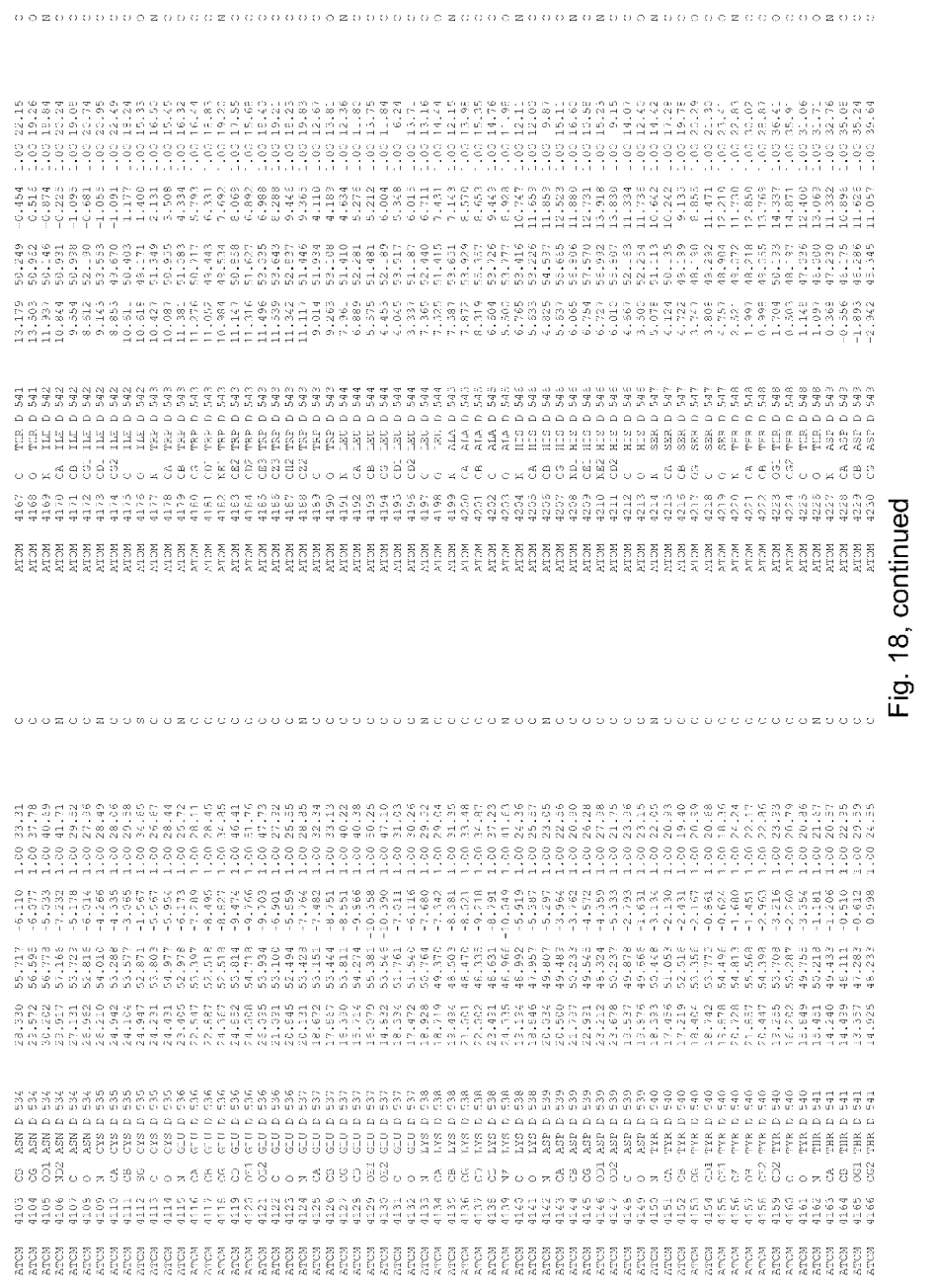
Figure 18:
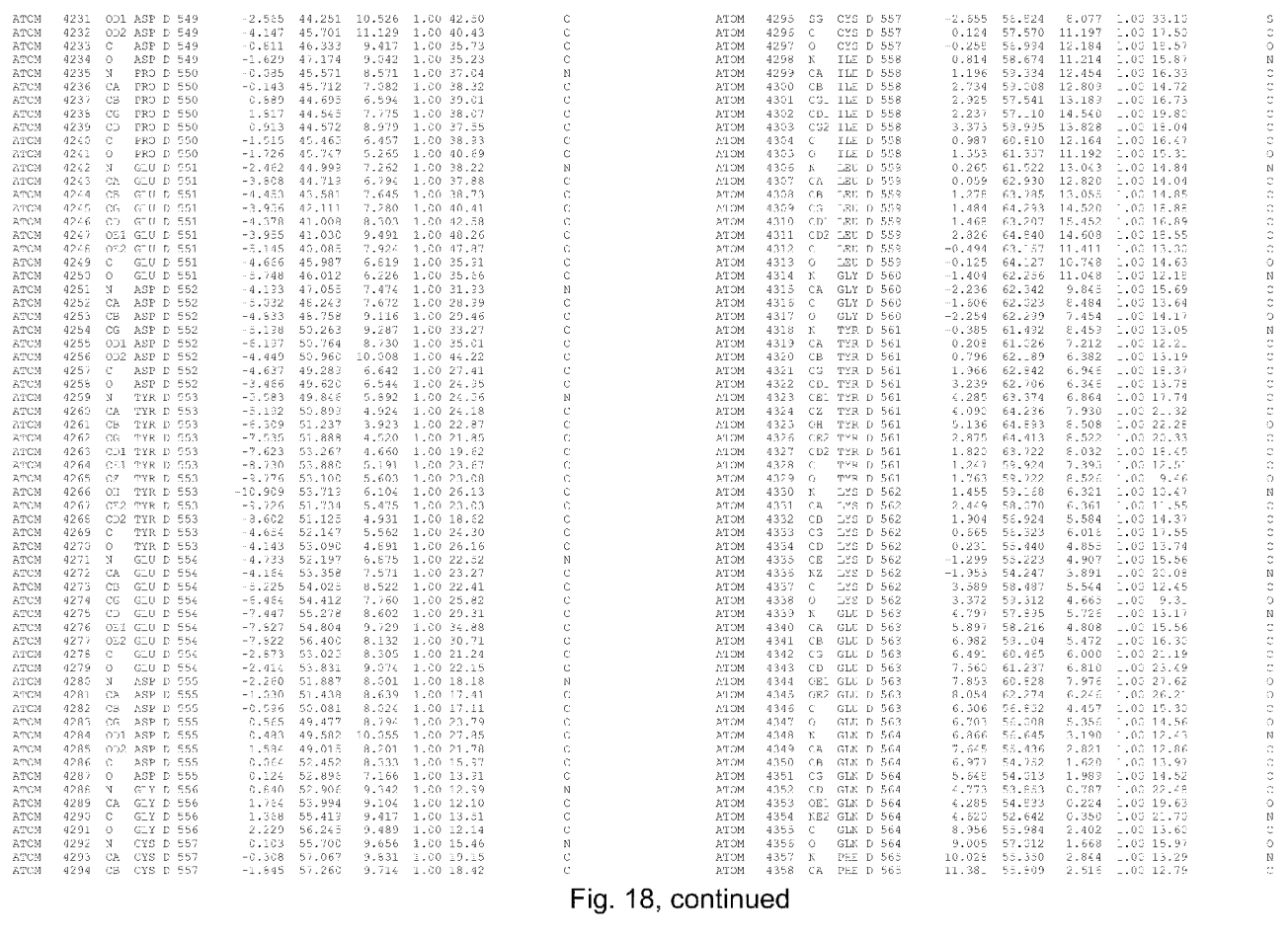
Figure 18:
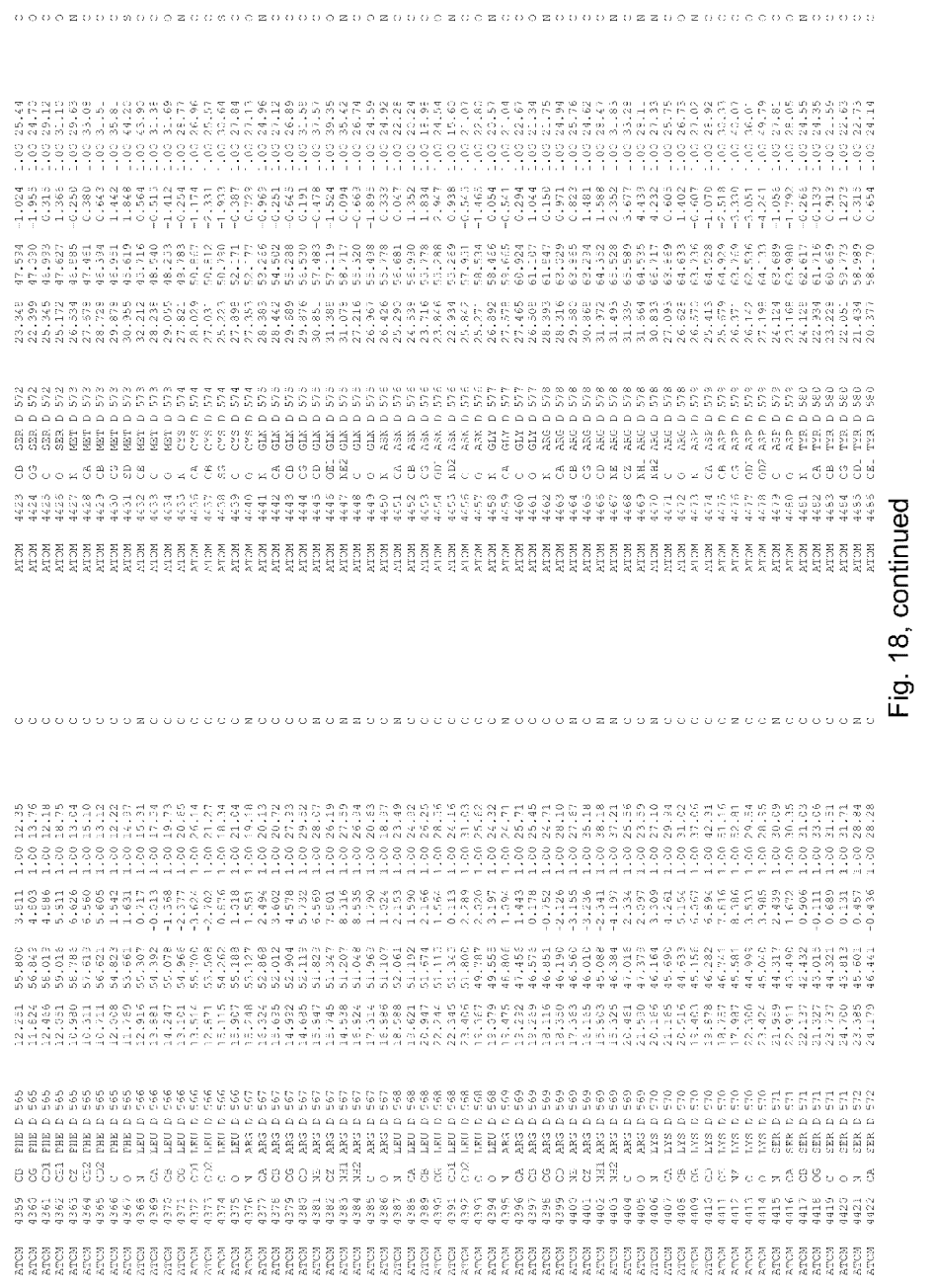
Figure 18:
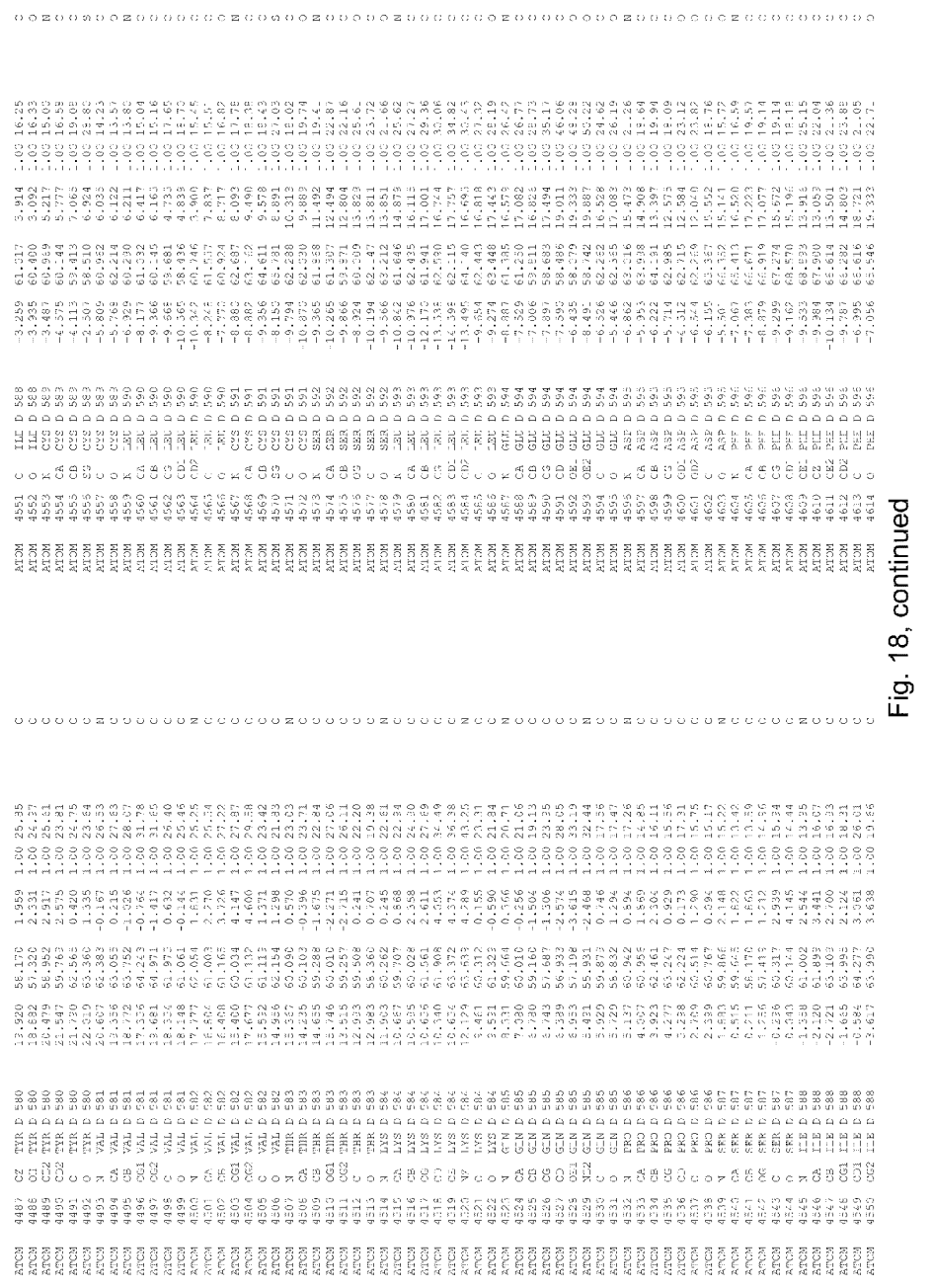
Figure 18:
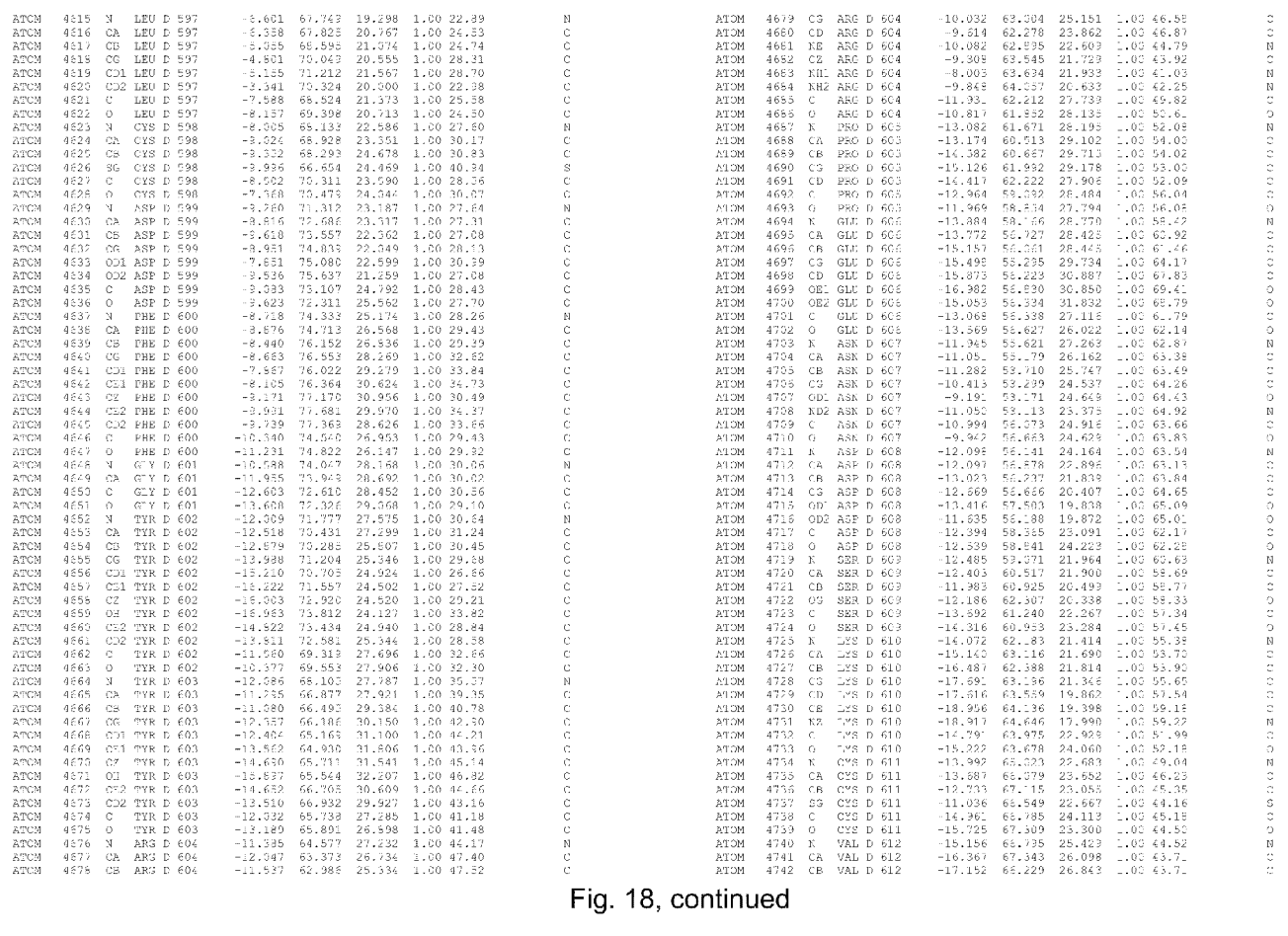
Figure 18:
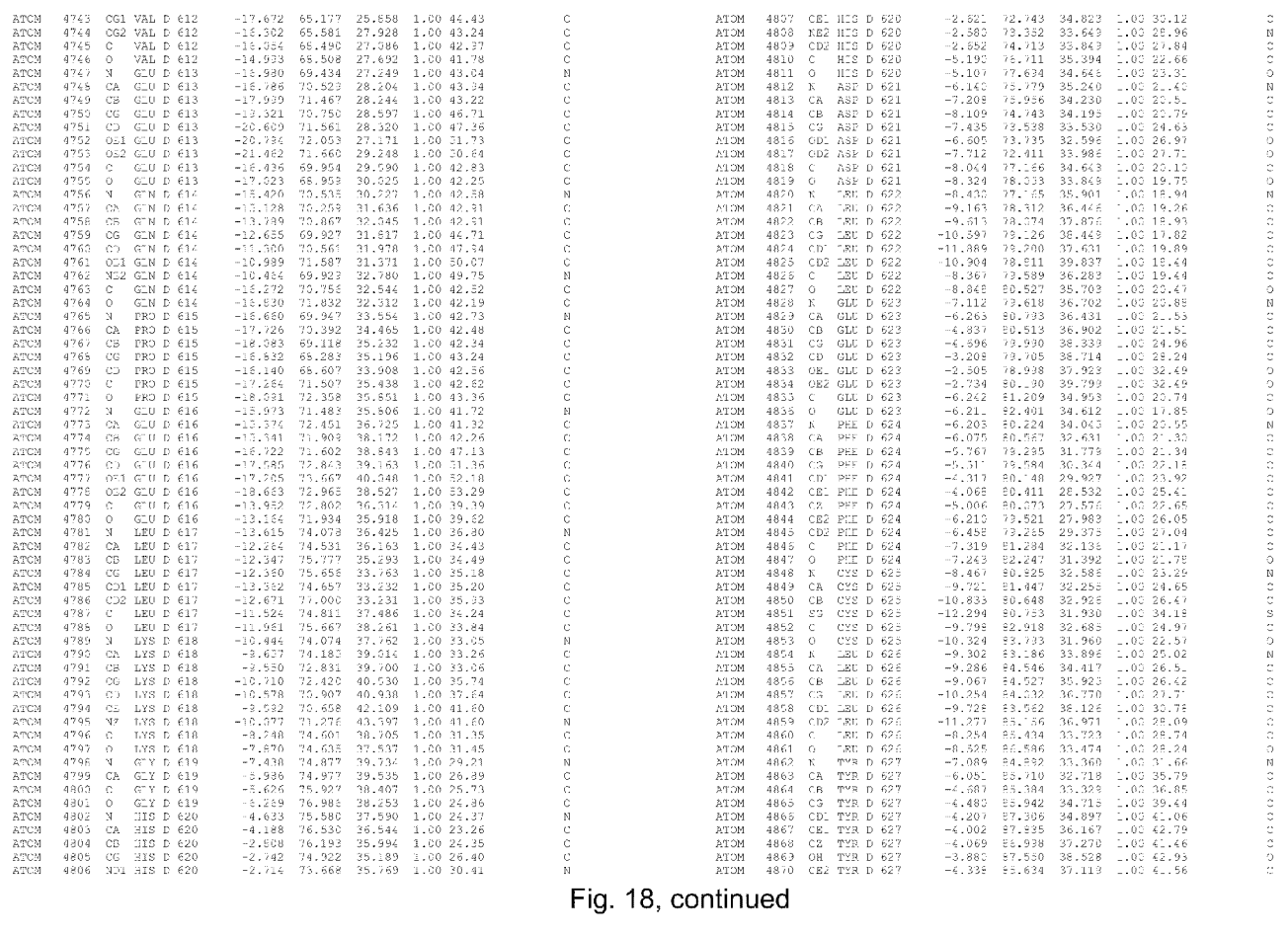
Figure 18:
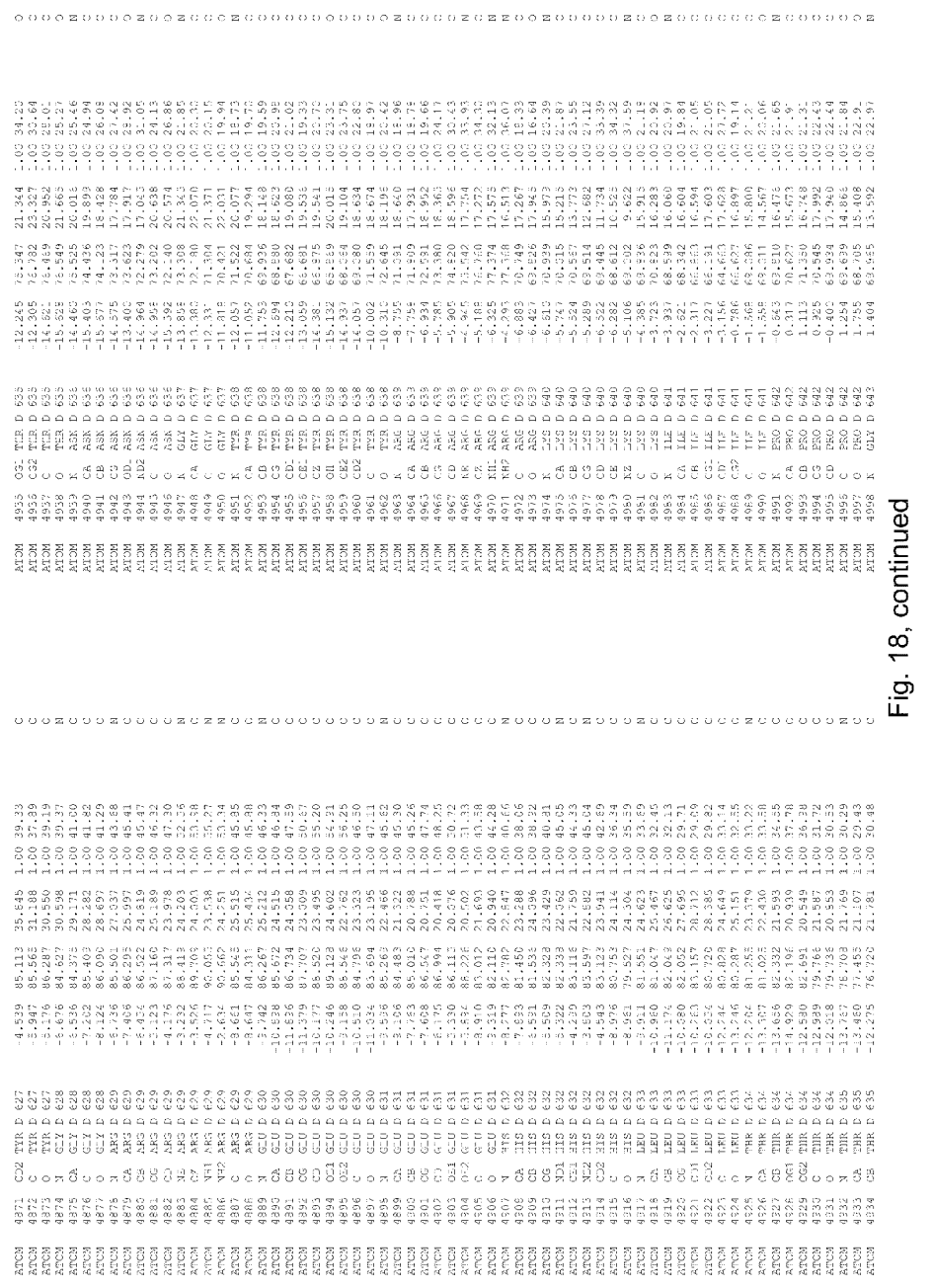
Figure 18:
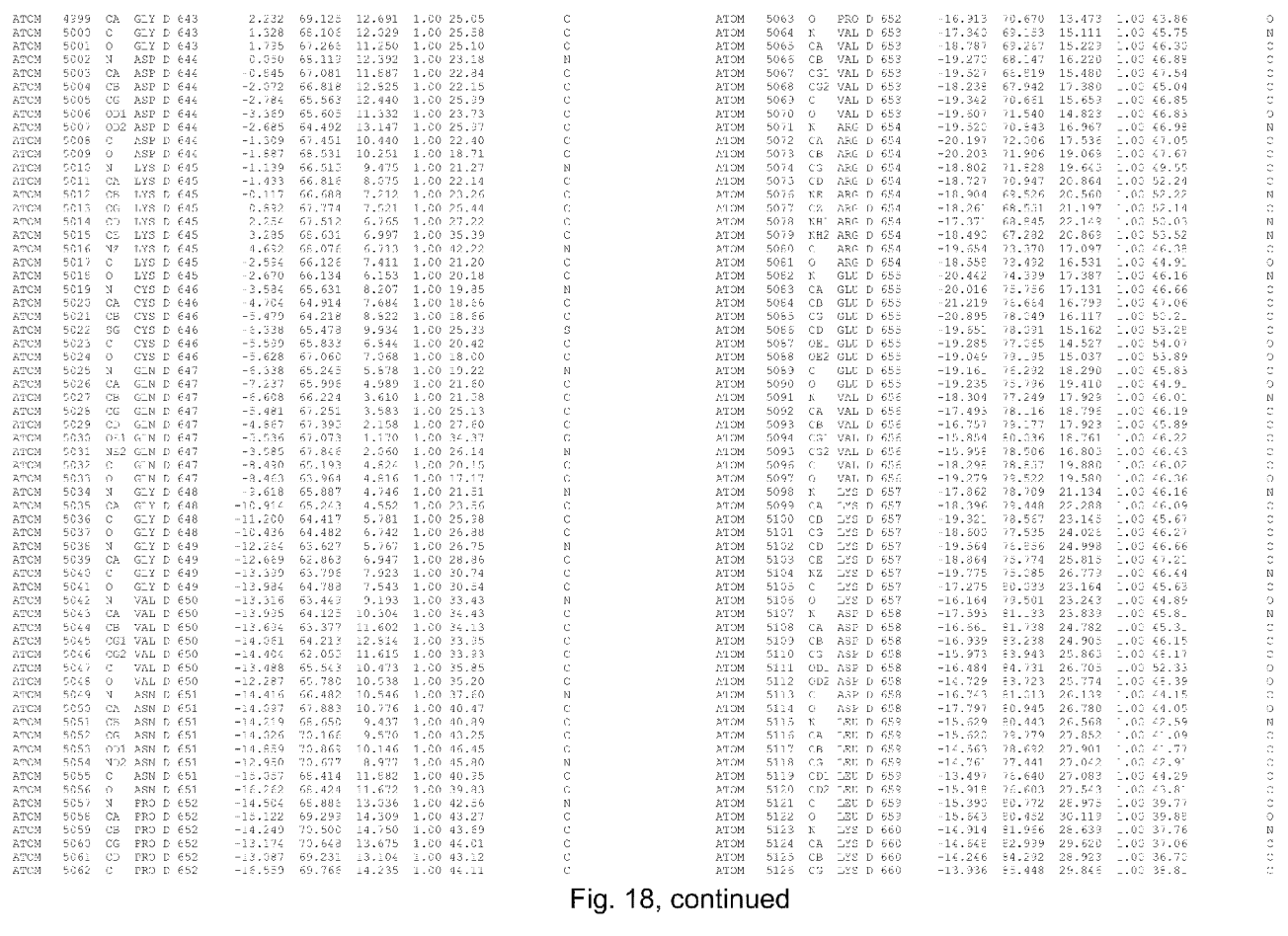
Figure 18:
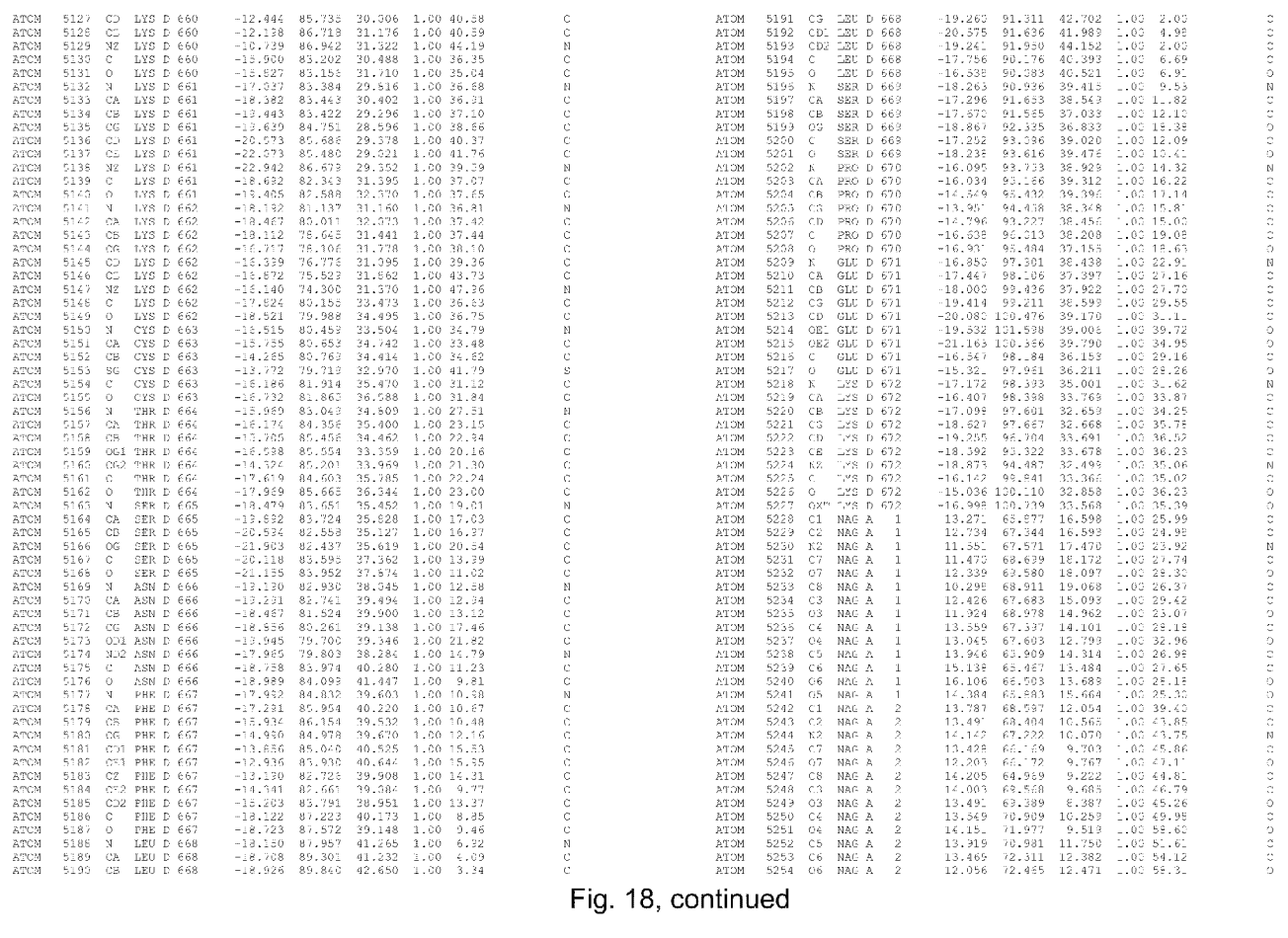
Figure 18:
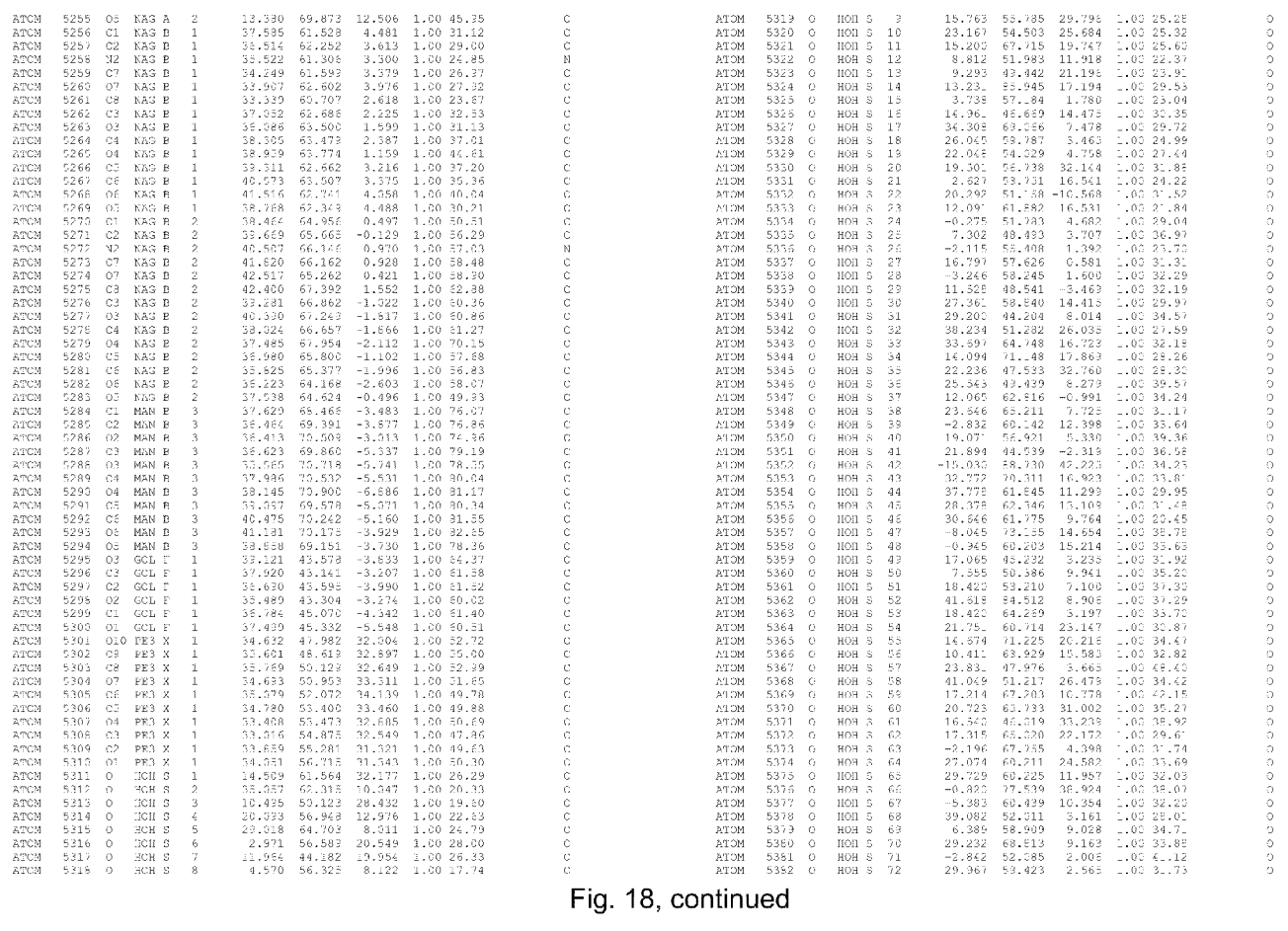
Figure 18:
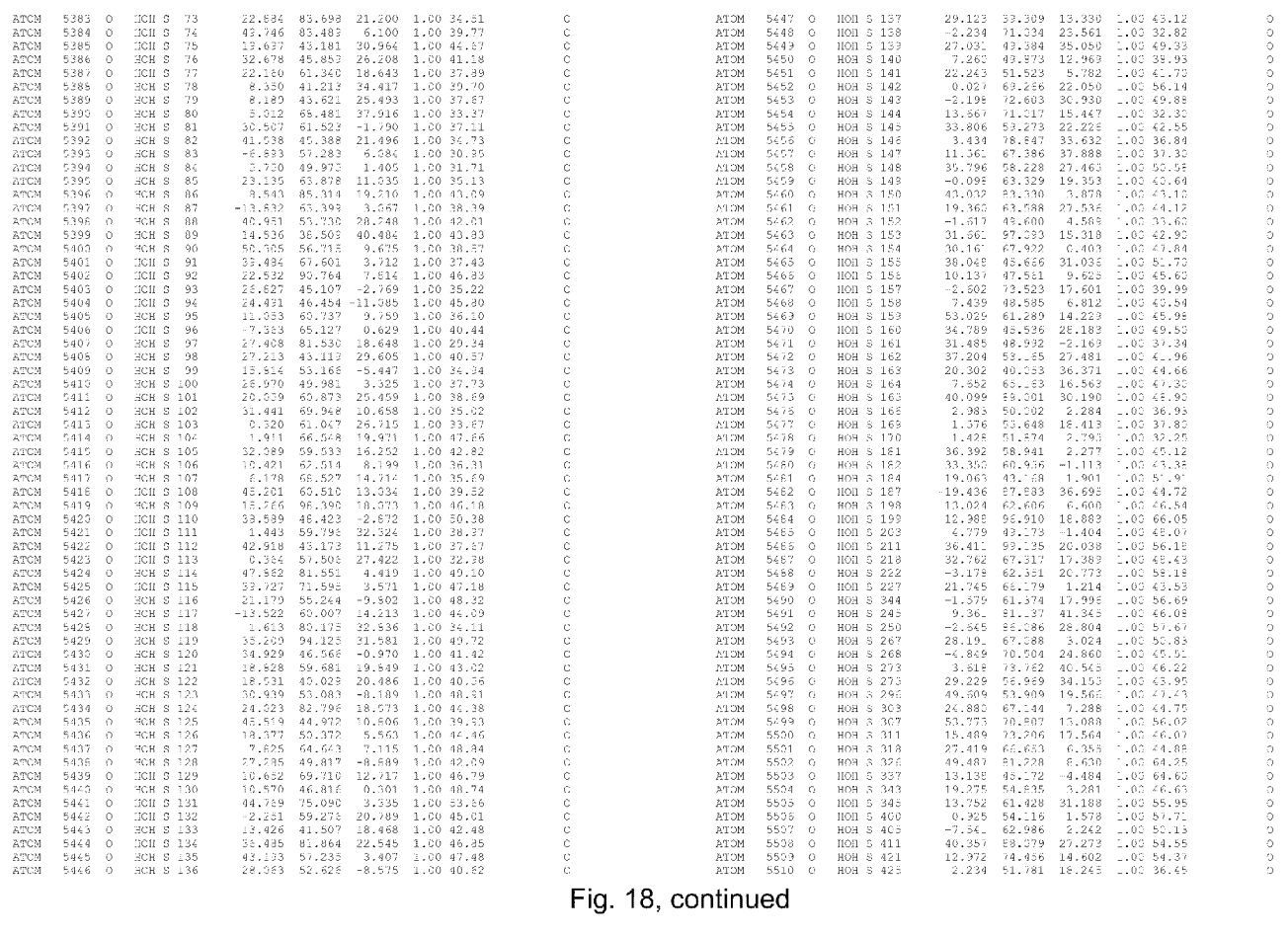
Figure 18:
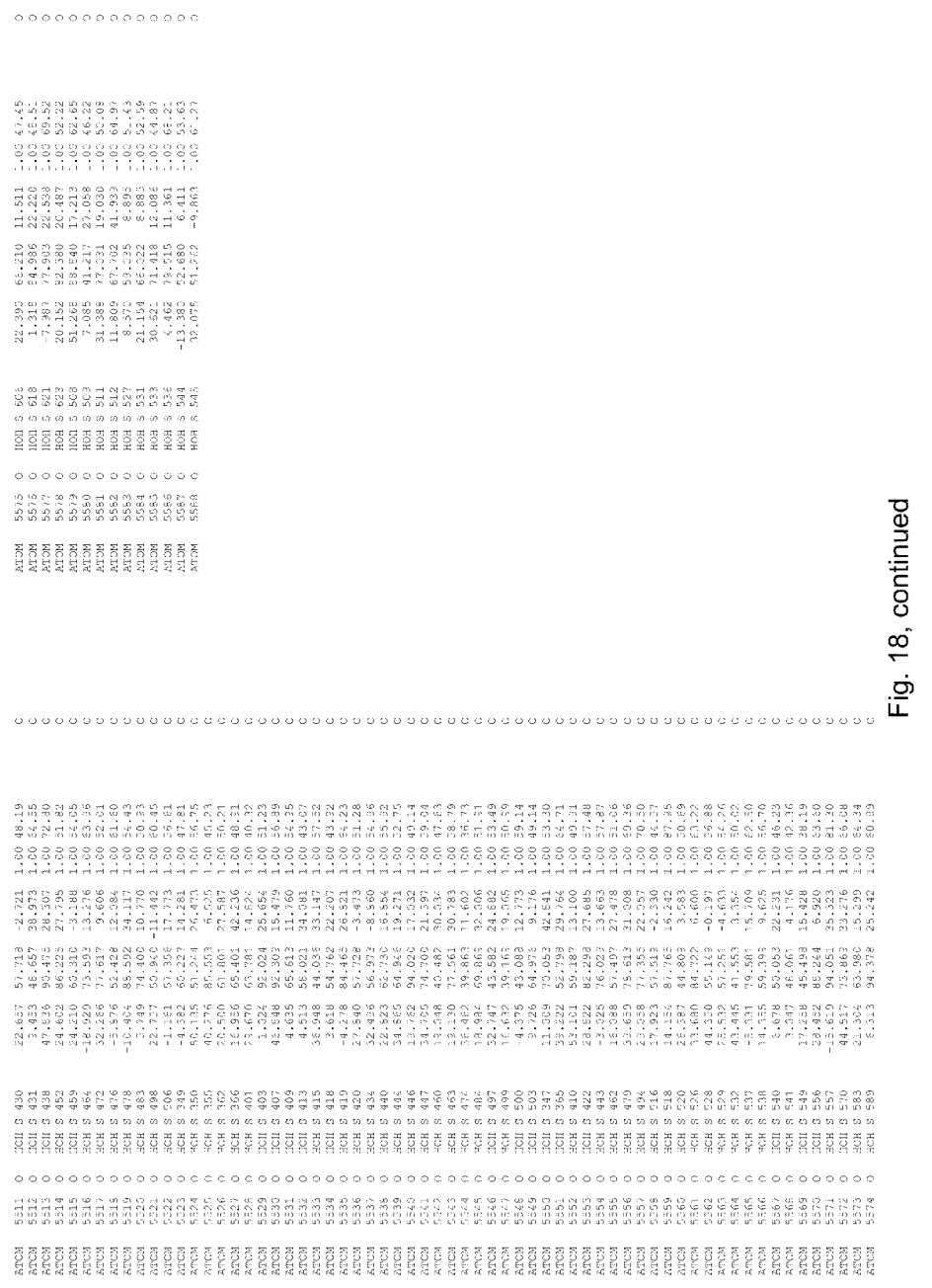

FIG. 18: Atomic coordinates at high resolution (2 A) of sSortilin in complex with Neurotensin provided in a molar ration of 1:1.5 resulting in occupation of binding site 1. sSortilin (SEQ ID NO:33) has the sequence of amino acid residues 78 to 755 of SEQ ID NO. 1. Neurotensin has the sequence of SEQ ID NO:10. The numbering of the first built Sortilin amino acid residues of this pdb file is G10 which corresponds to G87 of SEQ ID NO:1 which is numbered in accordance with the Expasy database entry Q99523 as of the filing date of the present application. Thus, the sSortilin coordinates provided are those of SEQ ID NO:36 (which corresponds to amino acid residues Gly87 to Lys749 of SEQ ID NO. 1) (atom 1 corresponds to the N-terminal Pro of SEQ ID NO:11; atom 37 is an atom of the first residue (Gly) of SEQ ID NO:36 (Gly87 of SEQ ID NO:1); atom 5227 corresponds to an atom of the last residue (Lys) of SEQ ID NO:36 (Lys749 of SEQ ID NO:1). NAG (N-acetyl-d-glucosamine); MAN (manose); PE3 (polyethylene glycol).

FIG. 18: Atomic coordinates at high resolution (2 Å) of sSortilin in complex with Neurotensin provided in a molar ration of 1:1.5 resulting in occupation of binding site 1. The numbering of the first built Sortilin amino acid residues of this pdb file is G10 which corresponds to G87 of SEQ ID NO:1 which is numbered in accordance with the Expasy database entry Q99523 as of the filing date of the present application.

Figure 19:
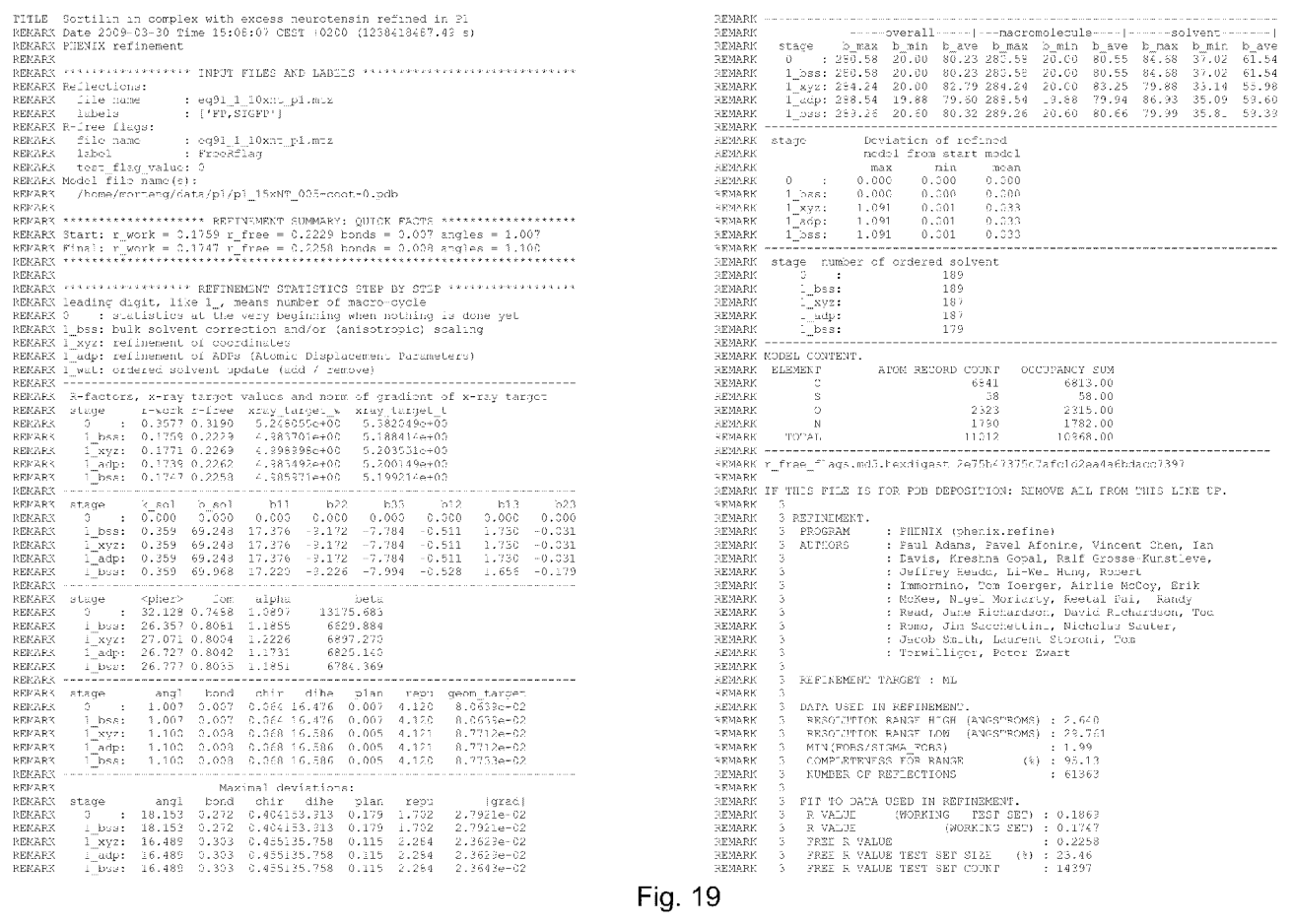
Figure 19:
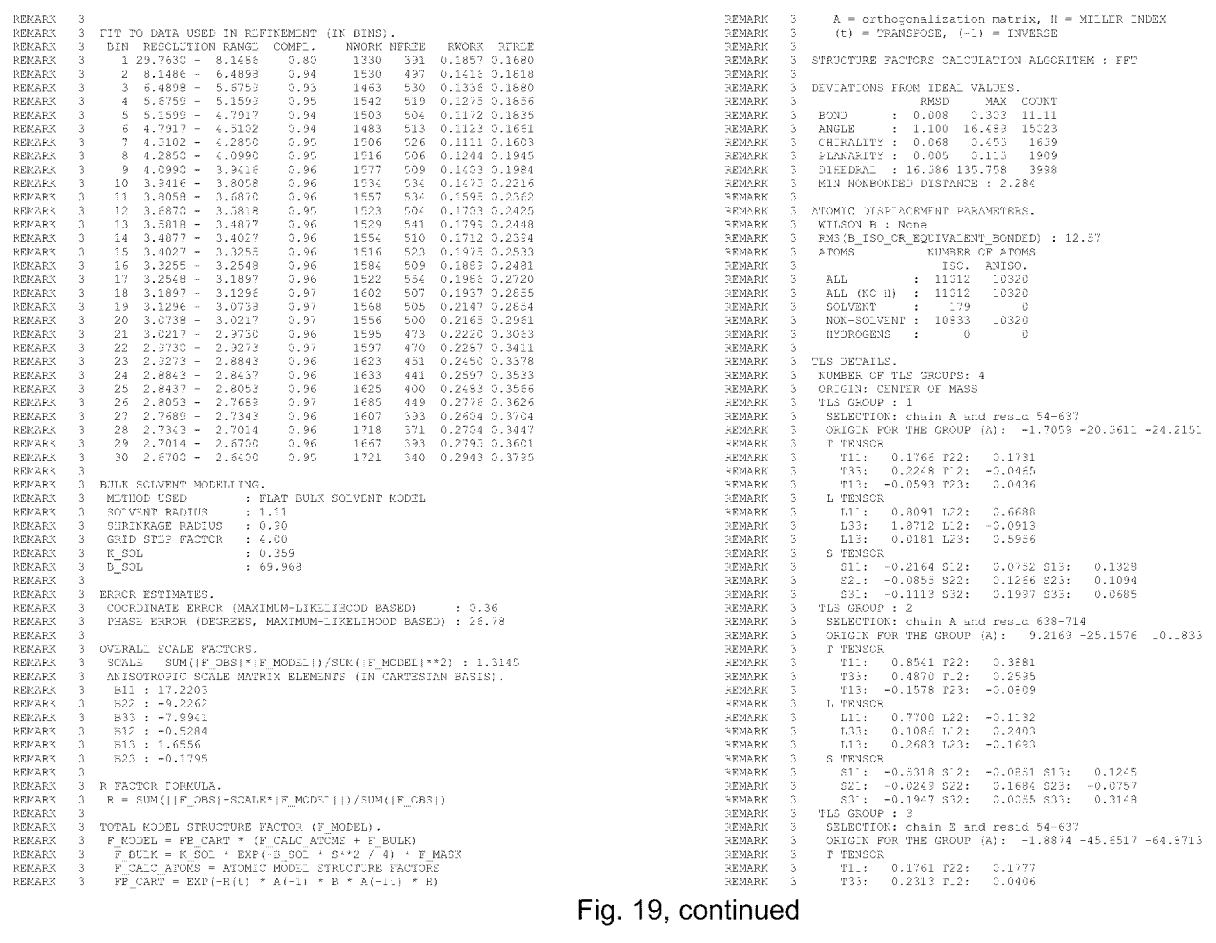
Figure 19:
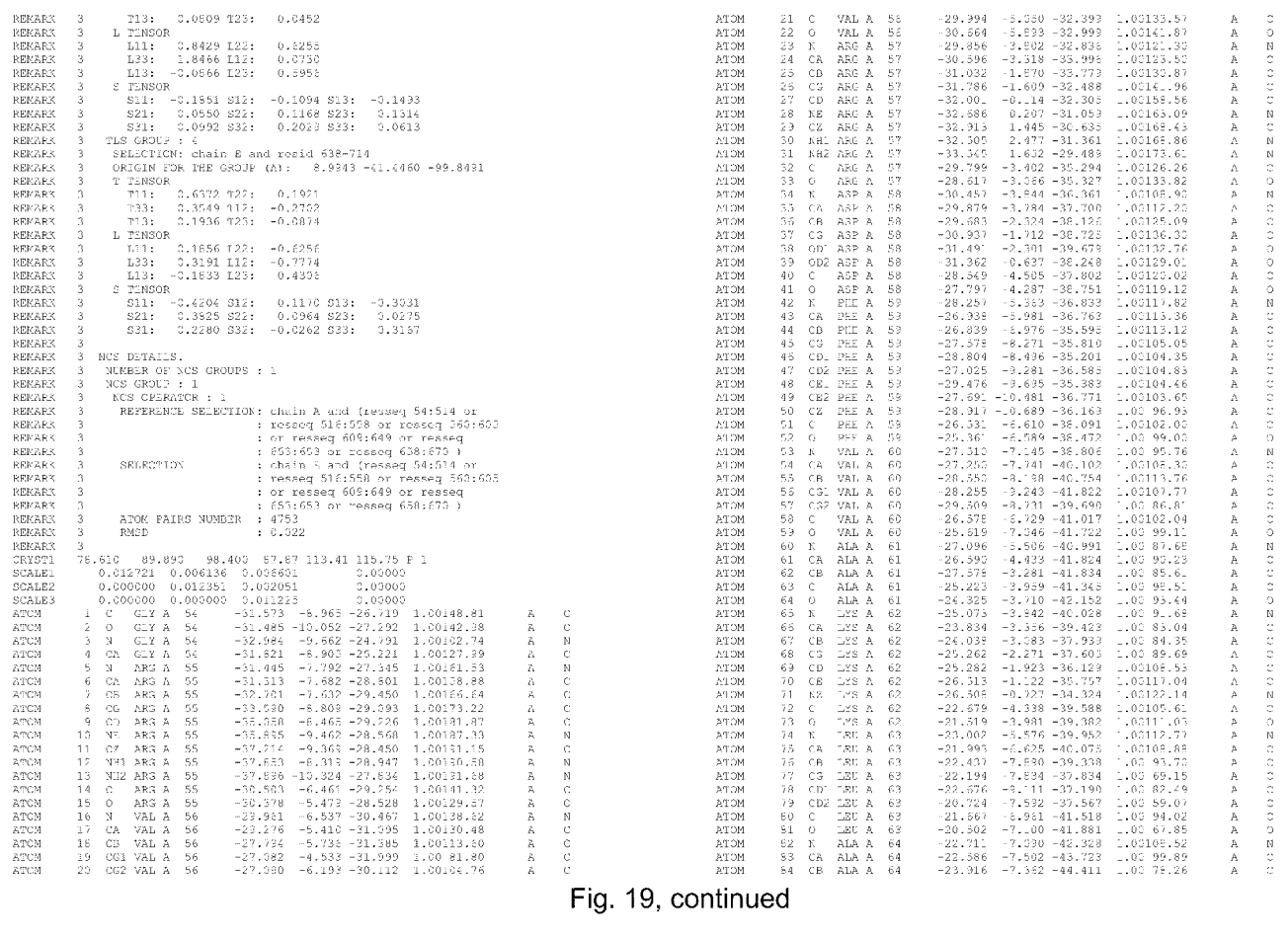
Figure 19:
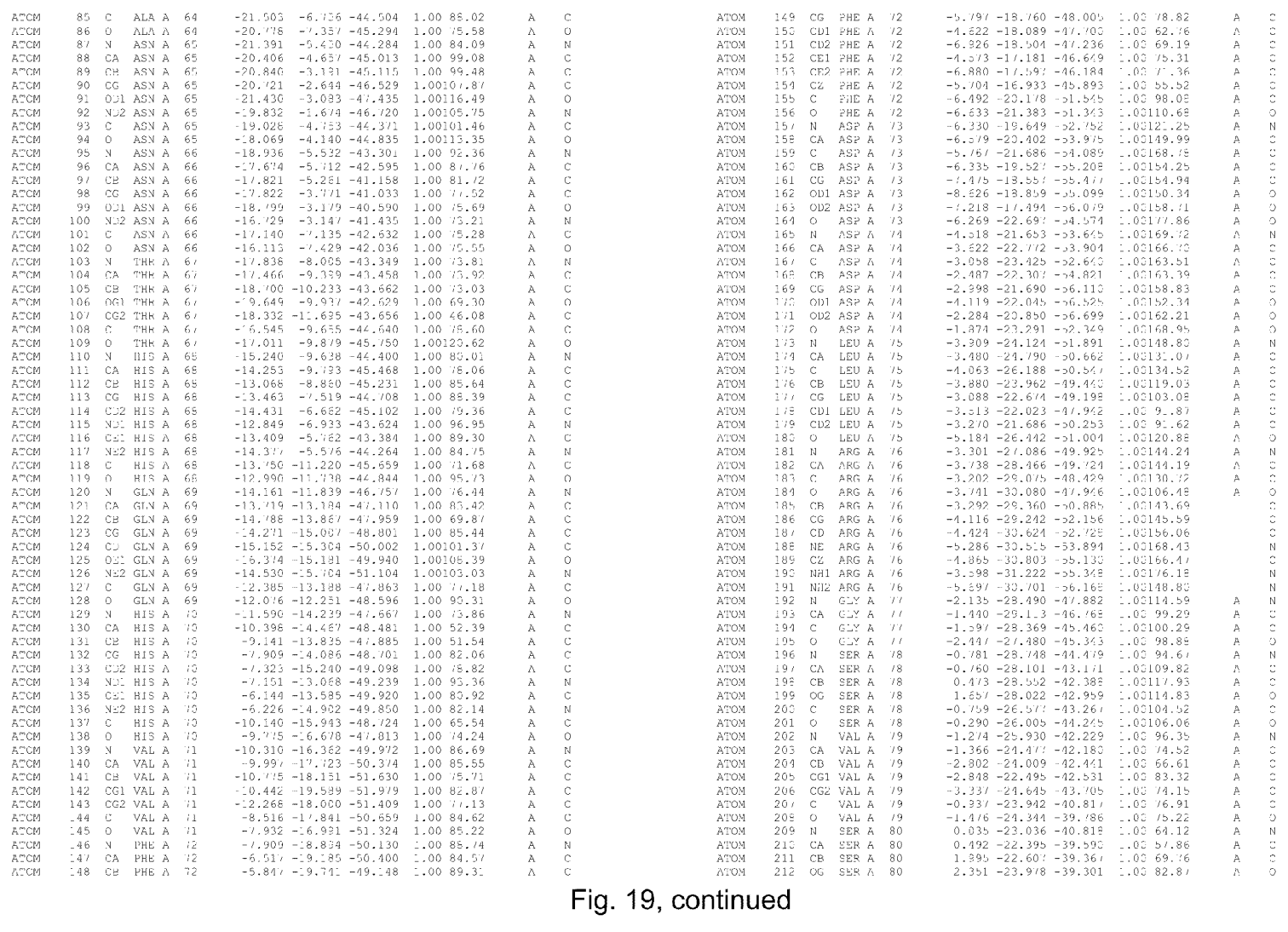
Figure 19:
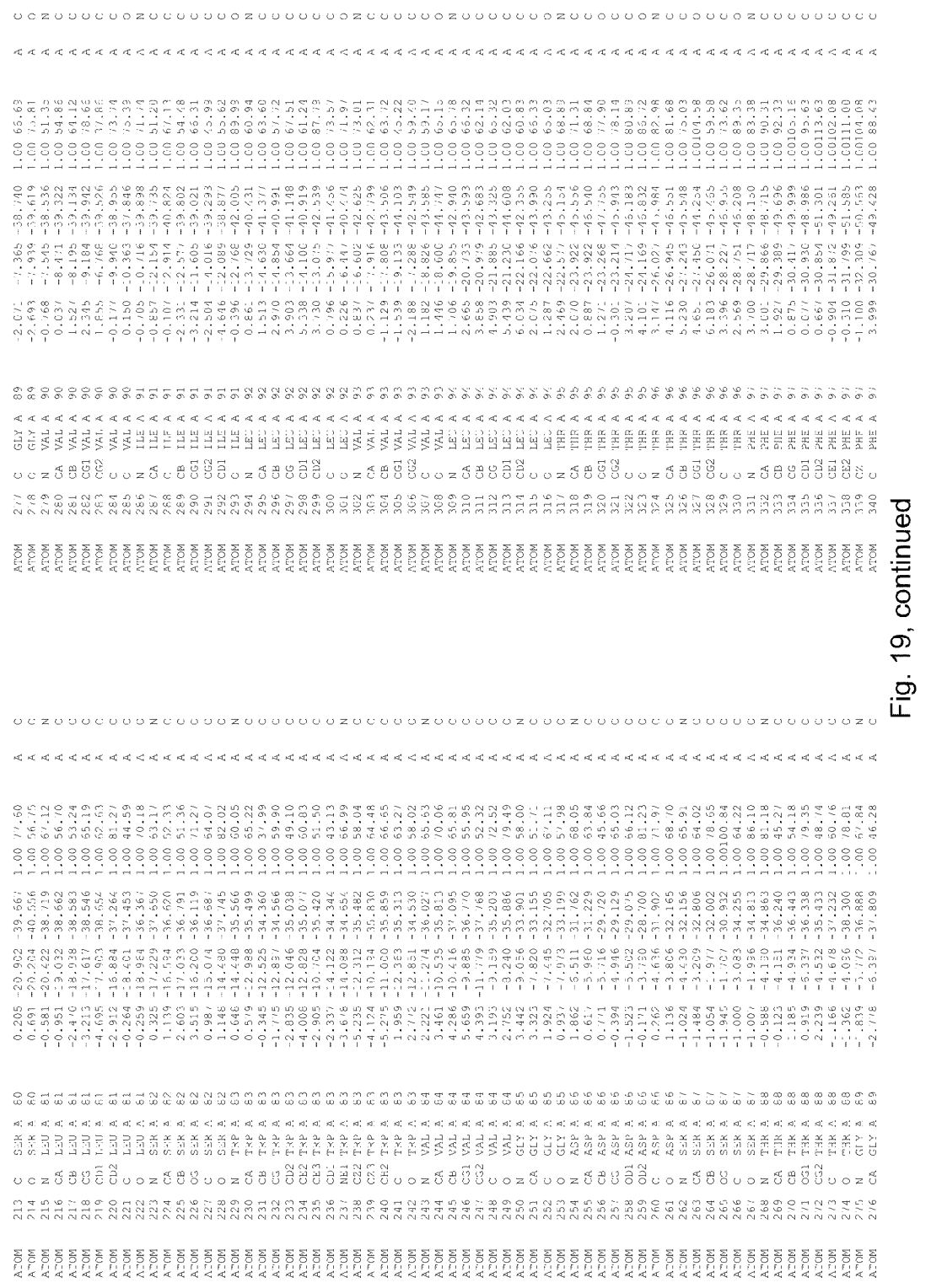
Figure 19:
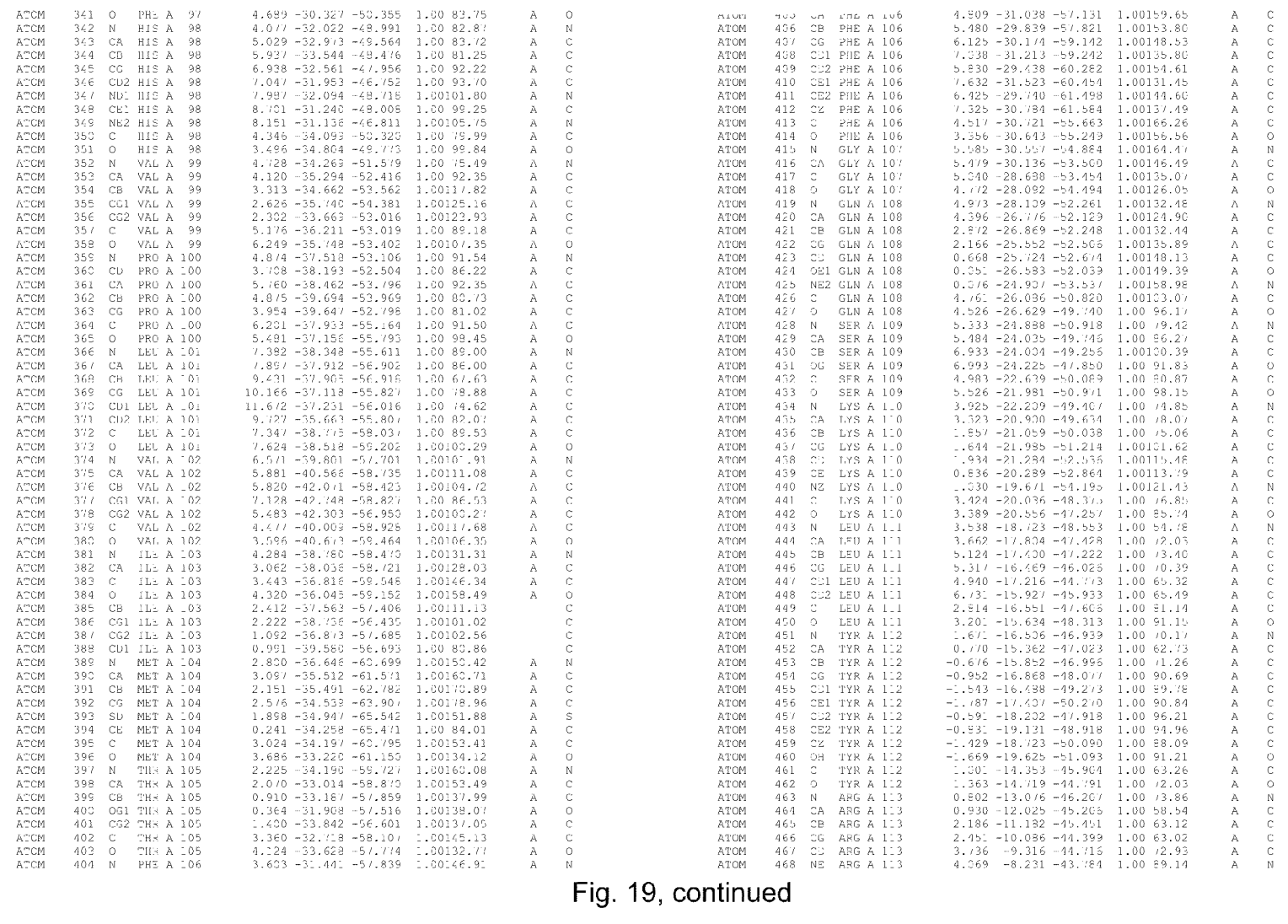
Figure 19:
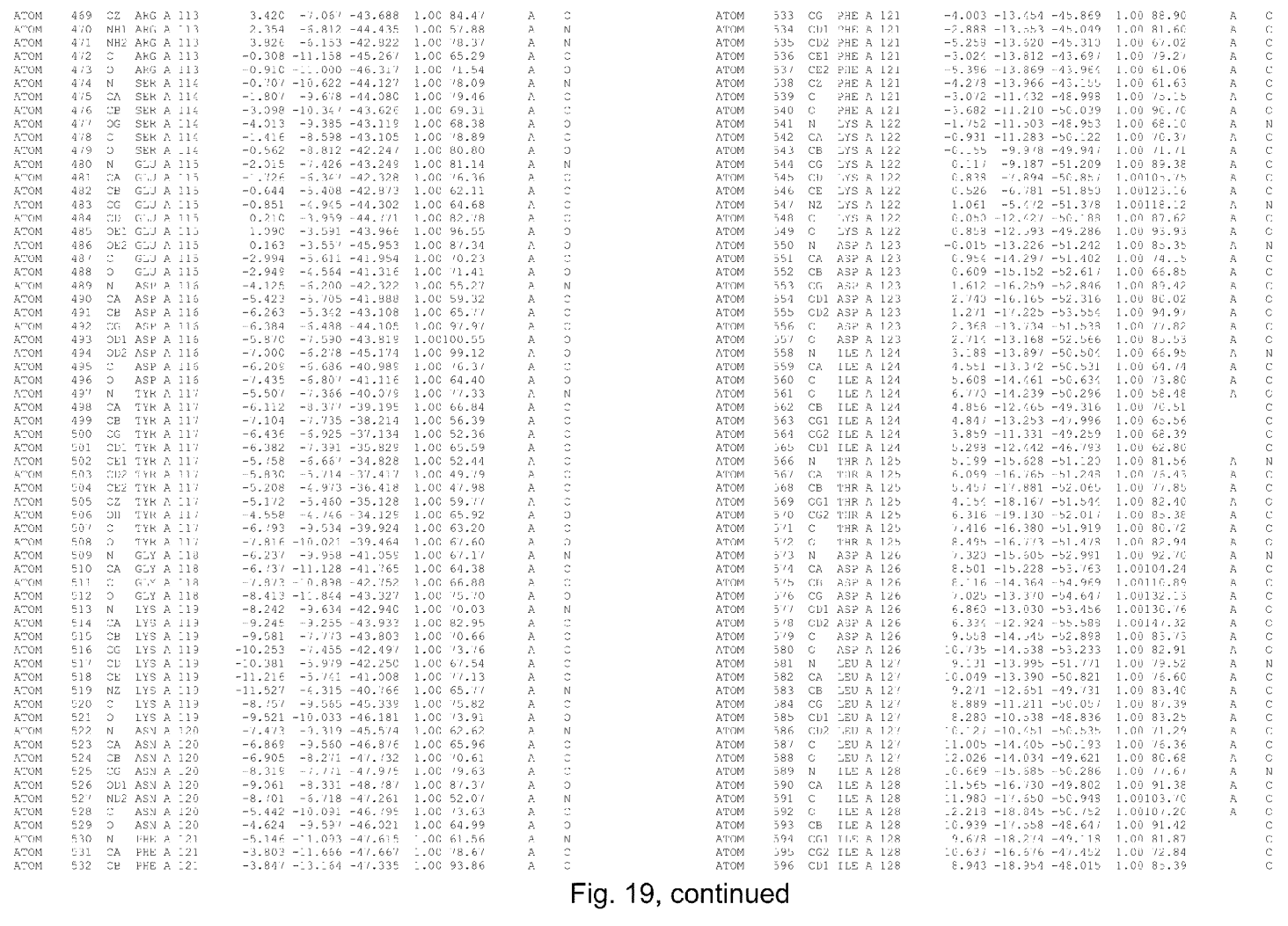
Figure 19:
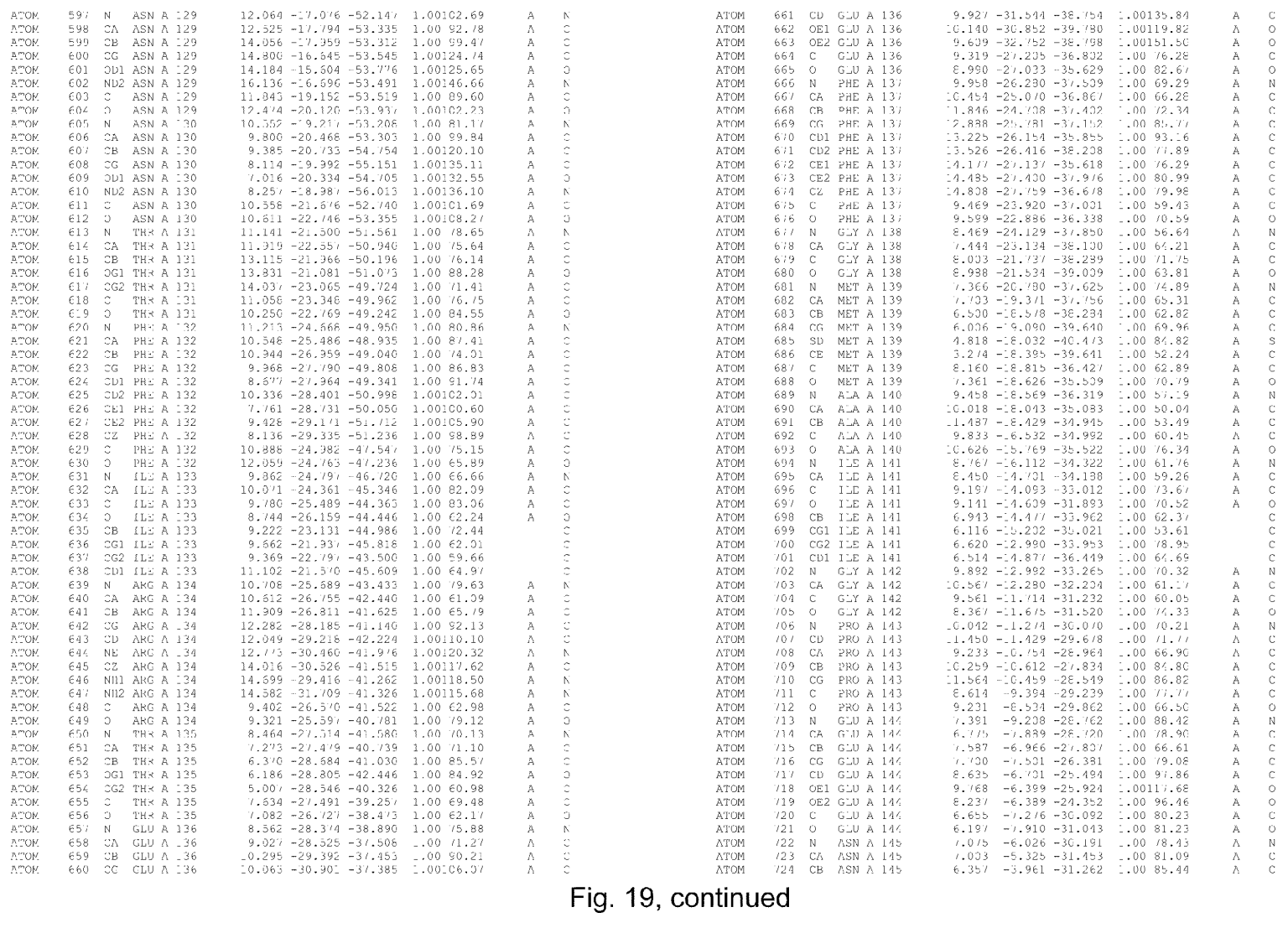
Figure 19:
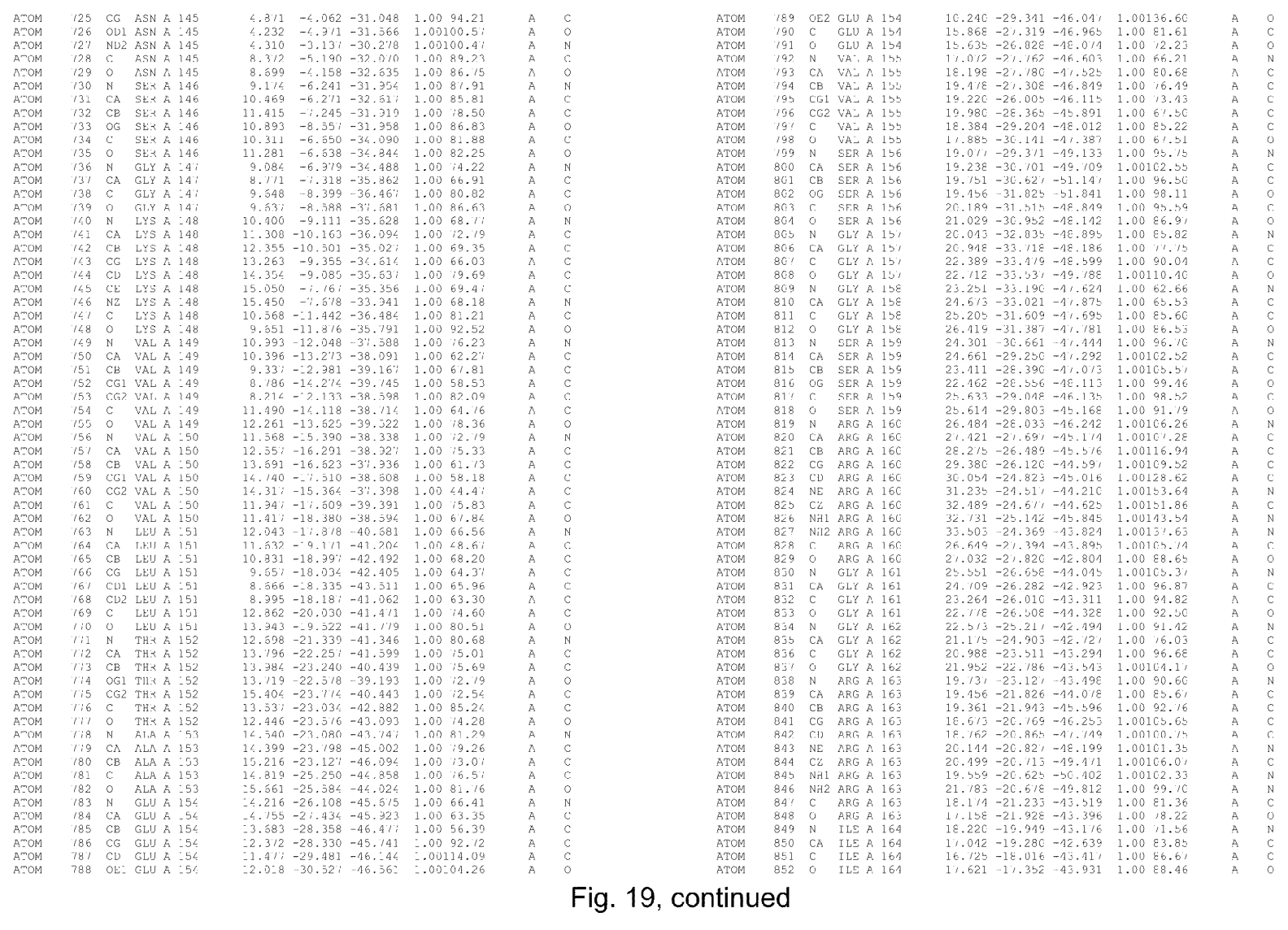
Figure 19:
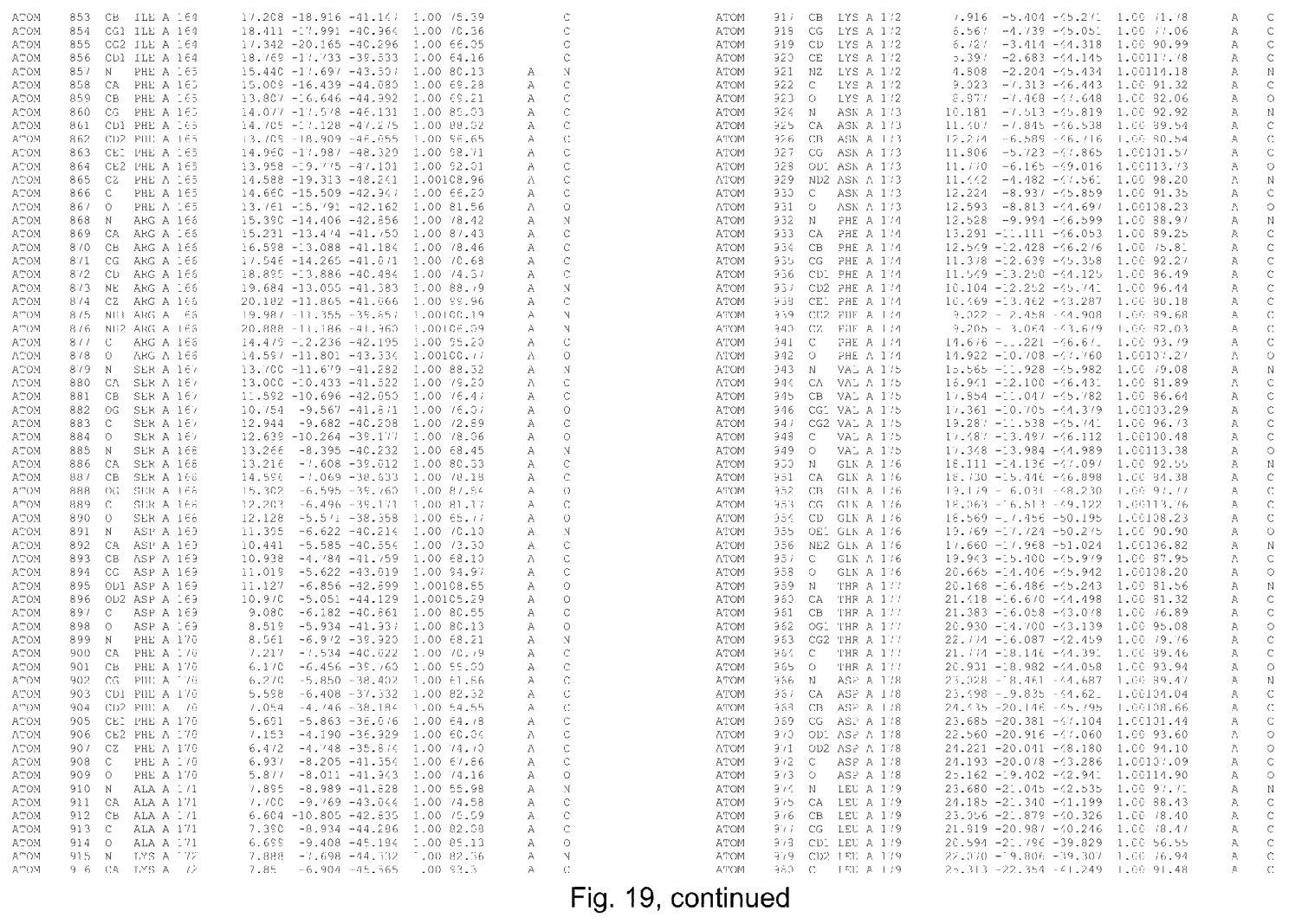
Figure 19:
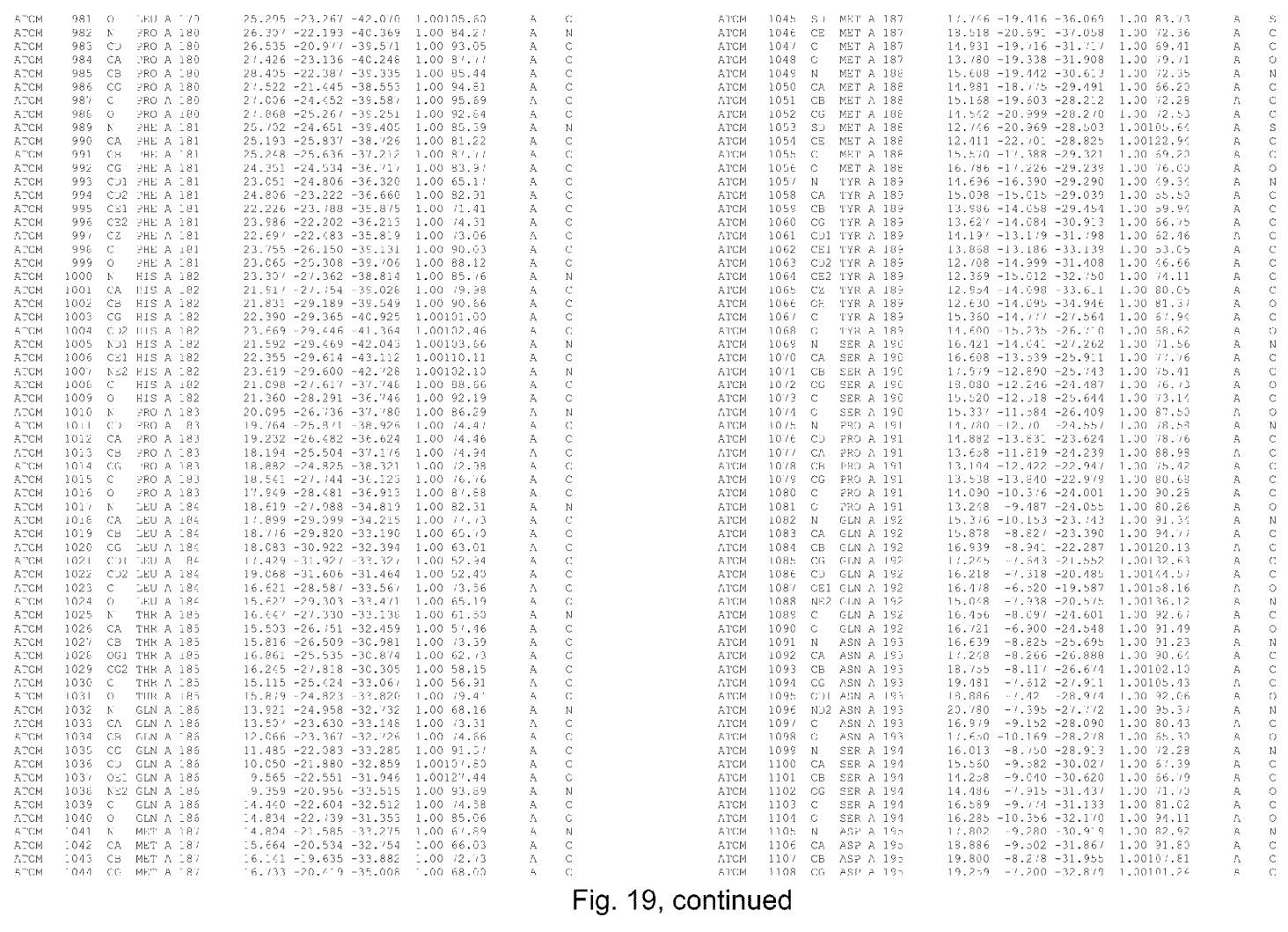
Figure 19:
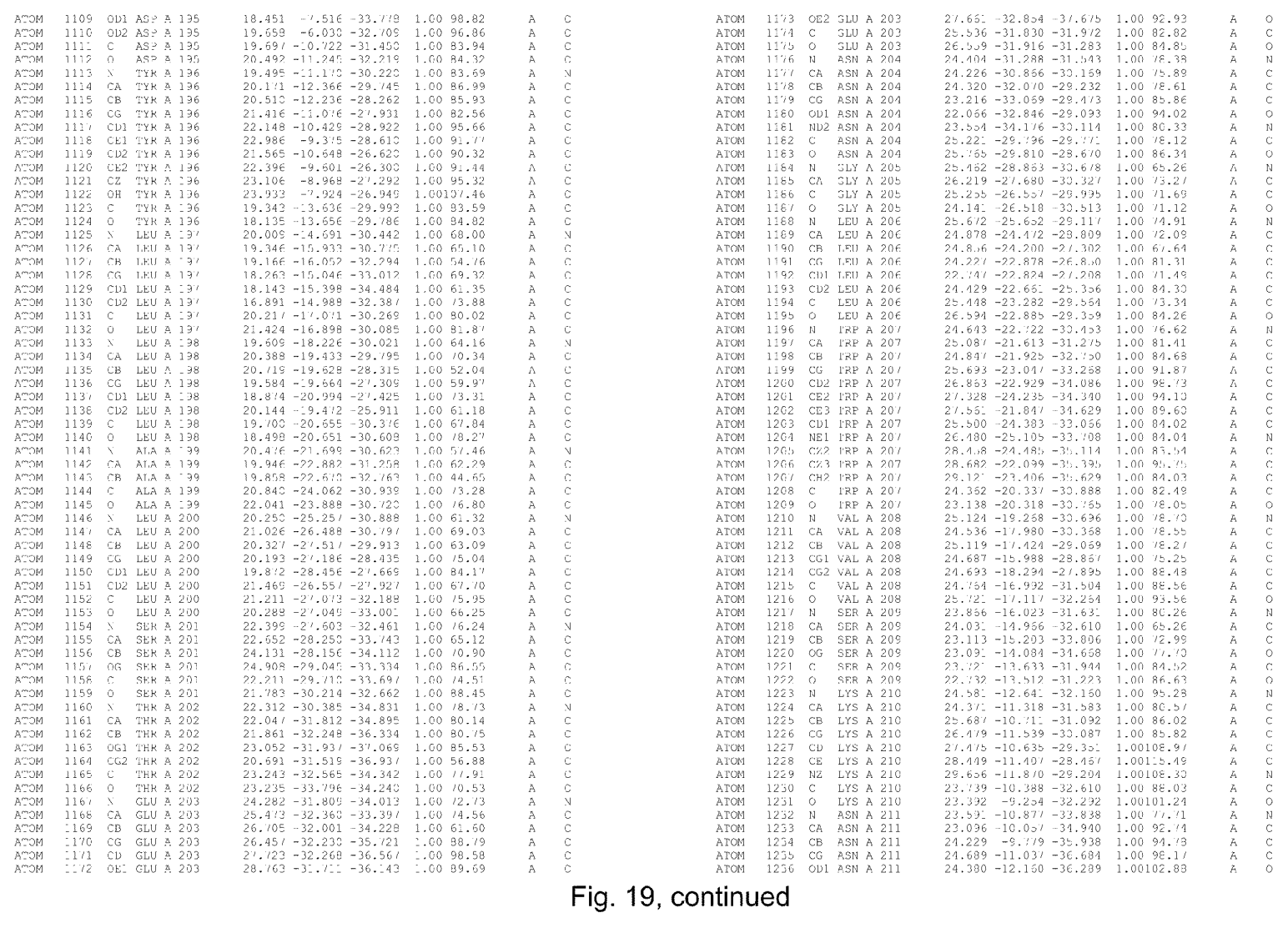
Figure 19:
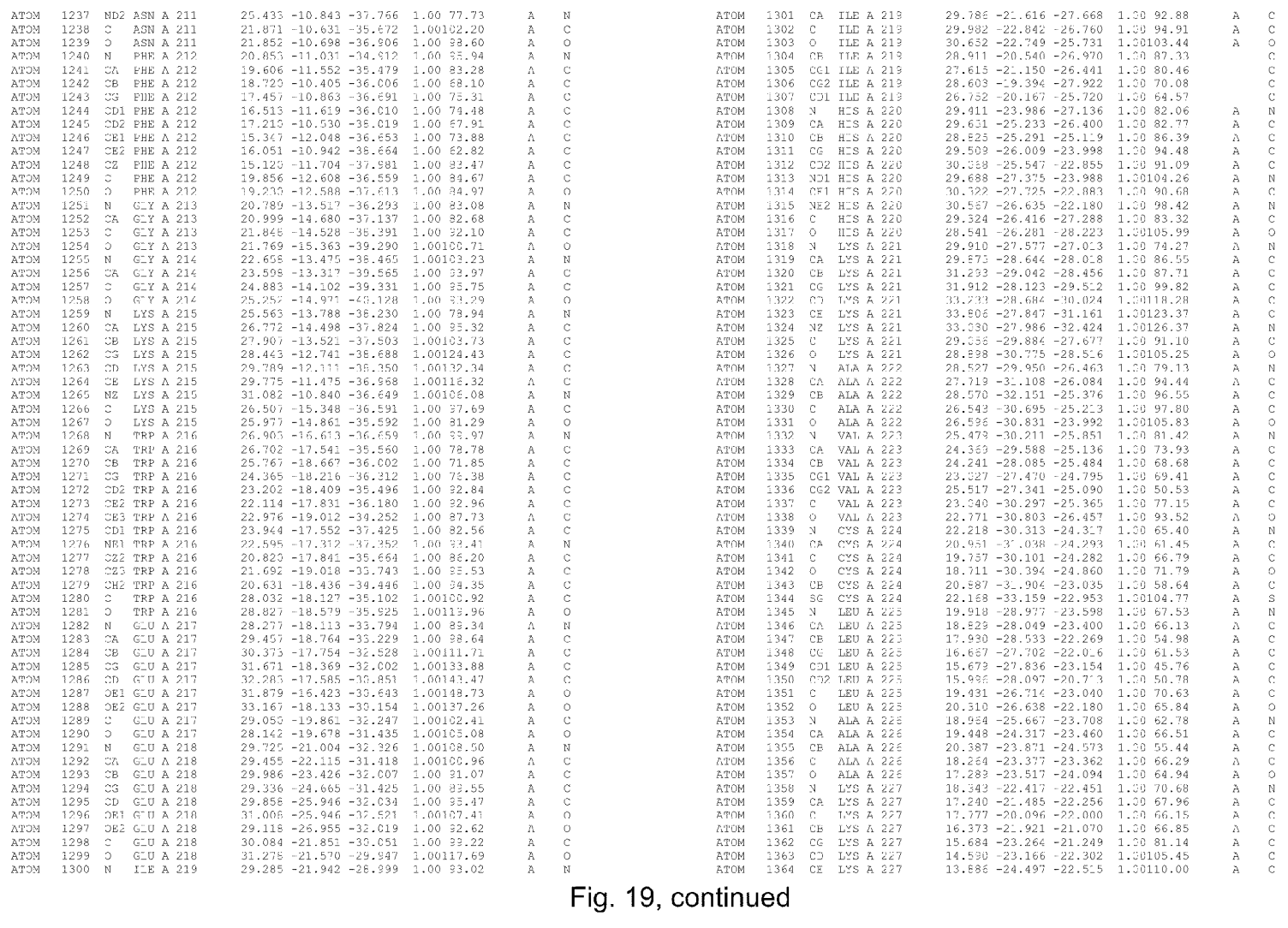
Figure 19:
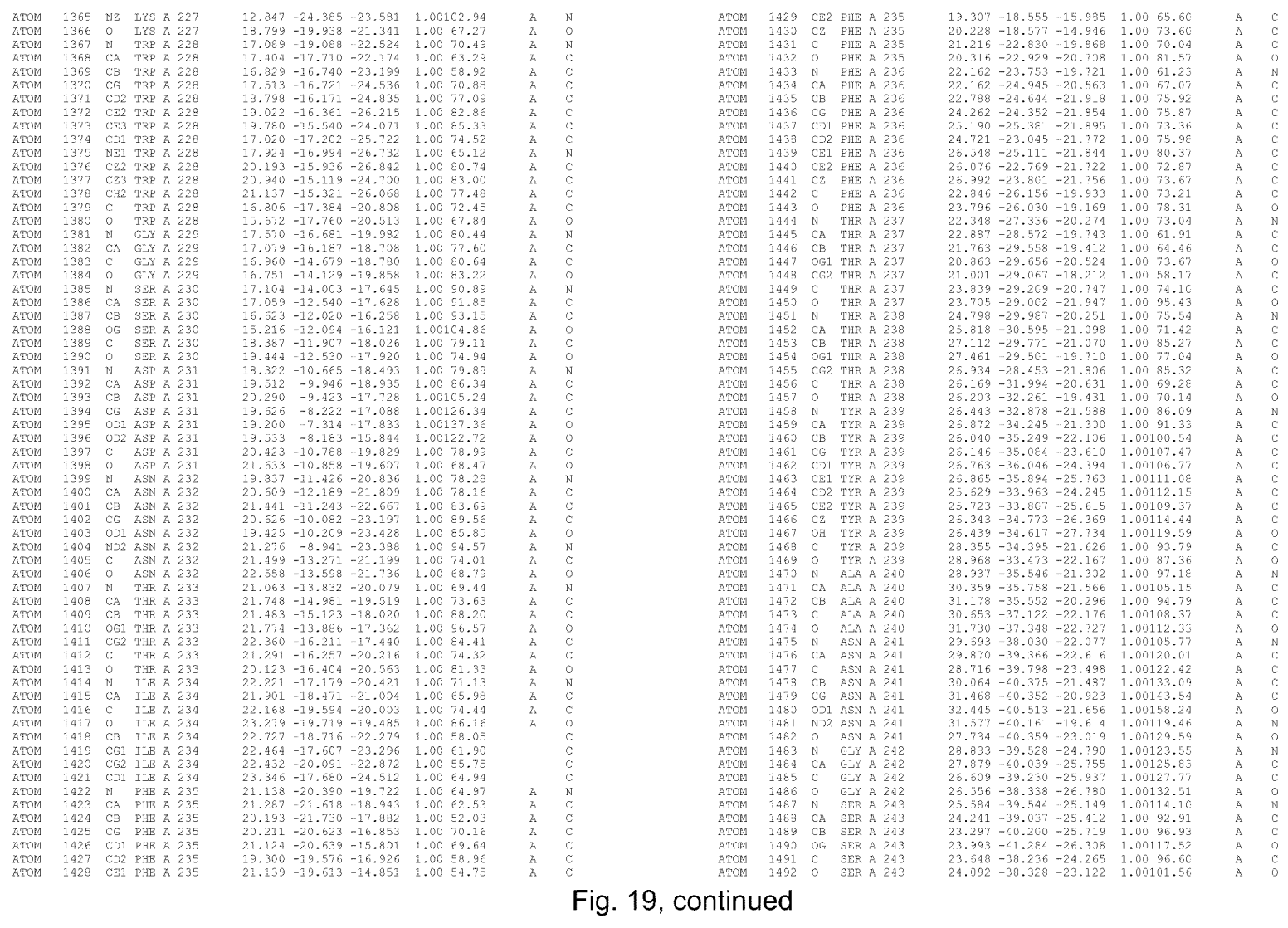
Figure 19:
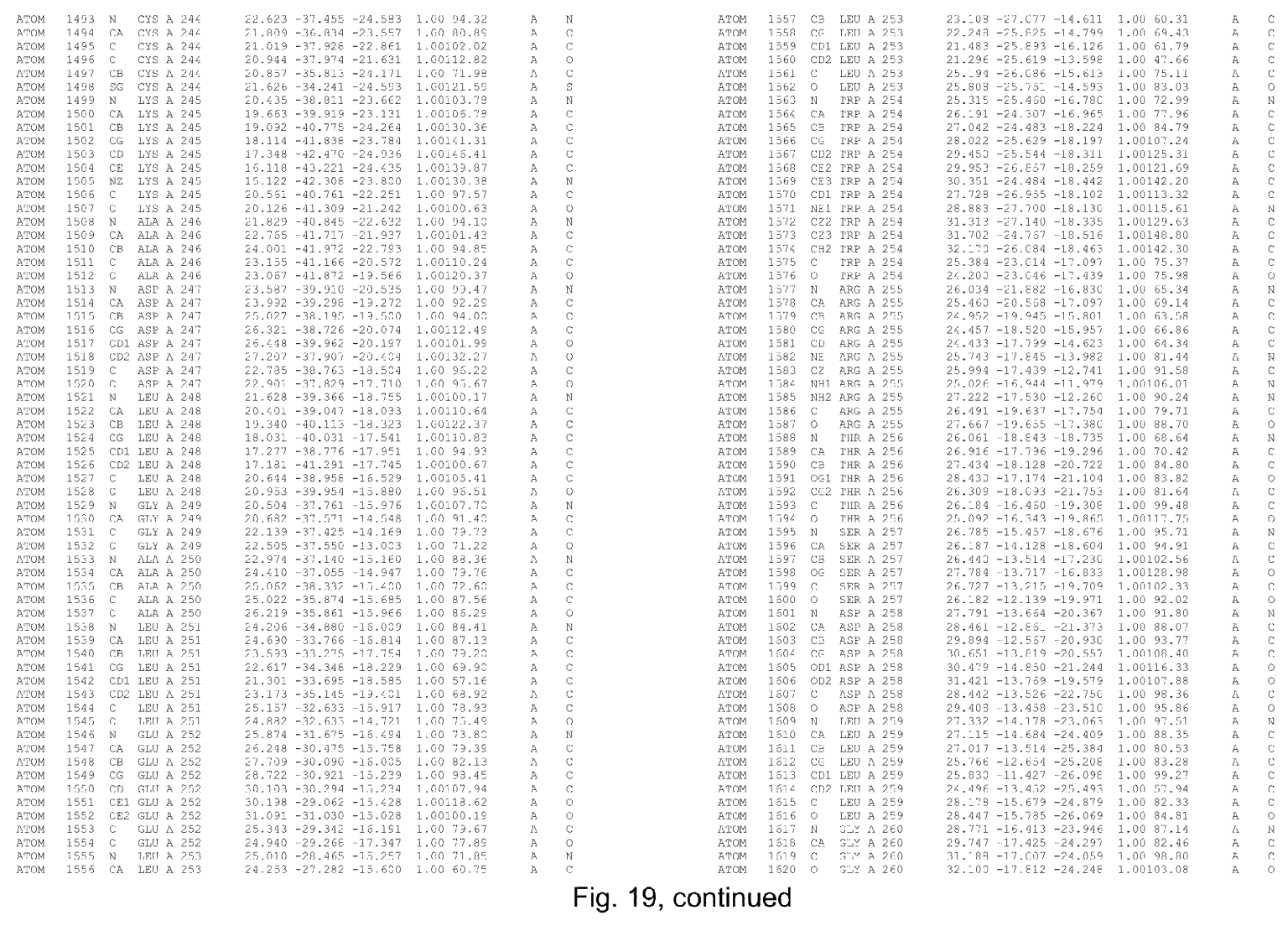
Figure 19:
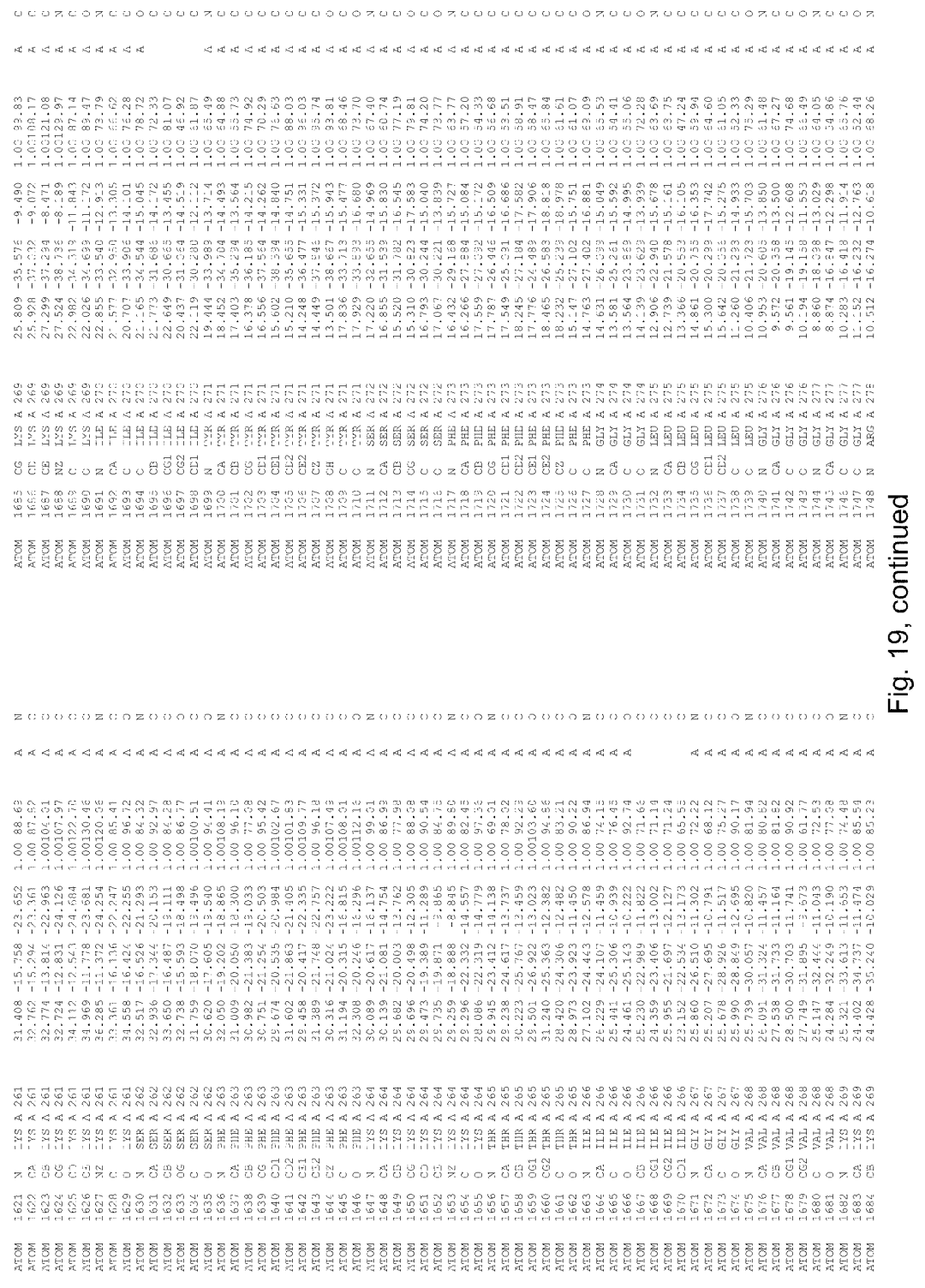
Figure 19:
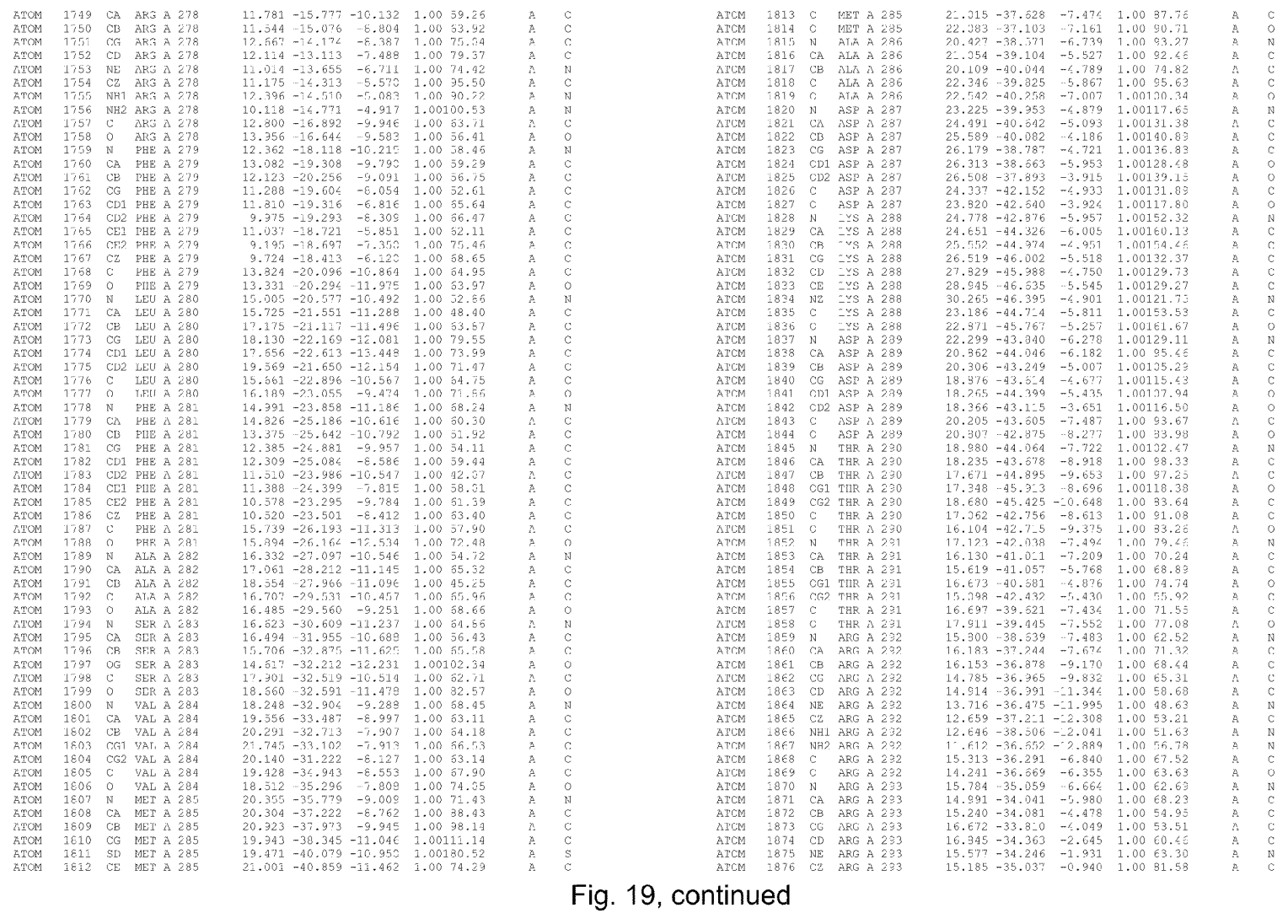
Figure 19:
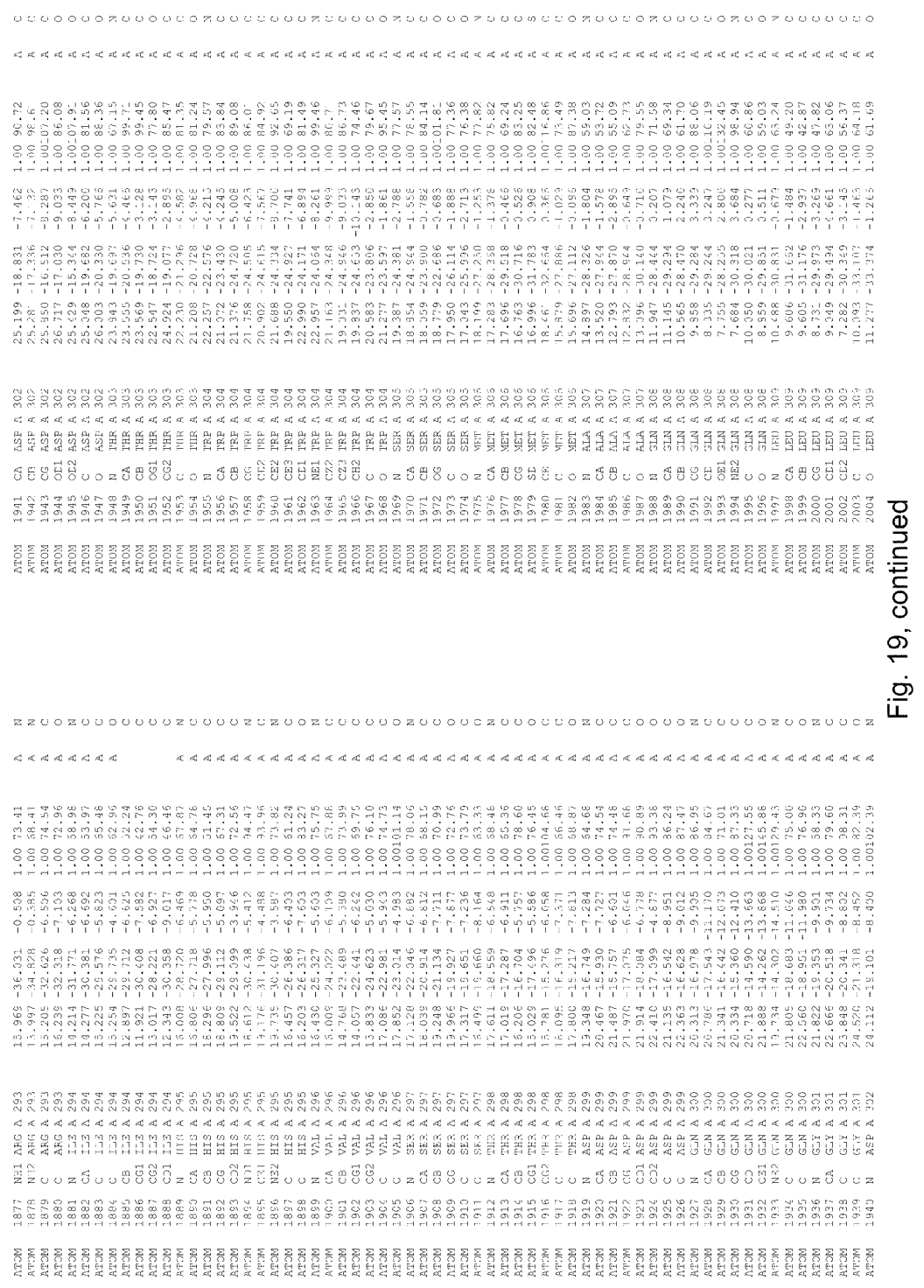
Figure 19:
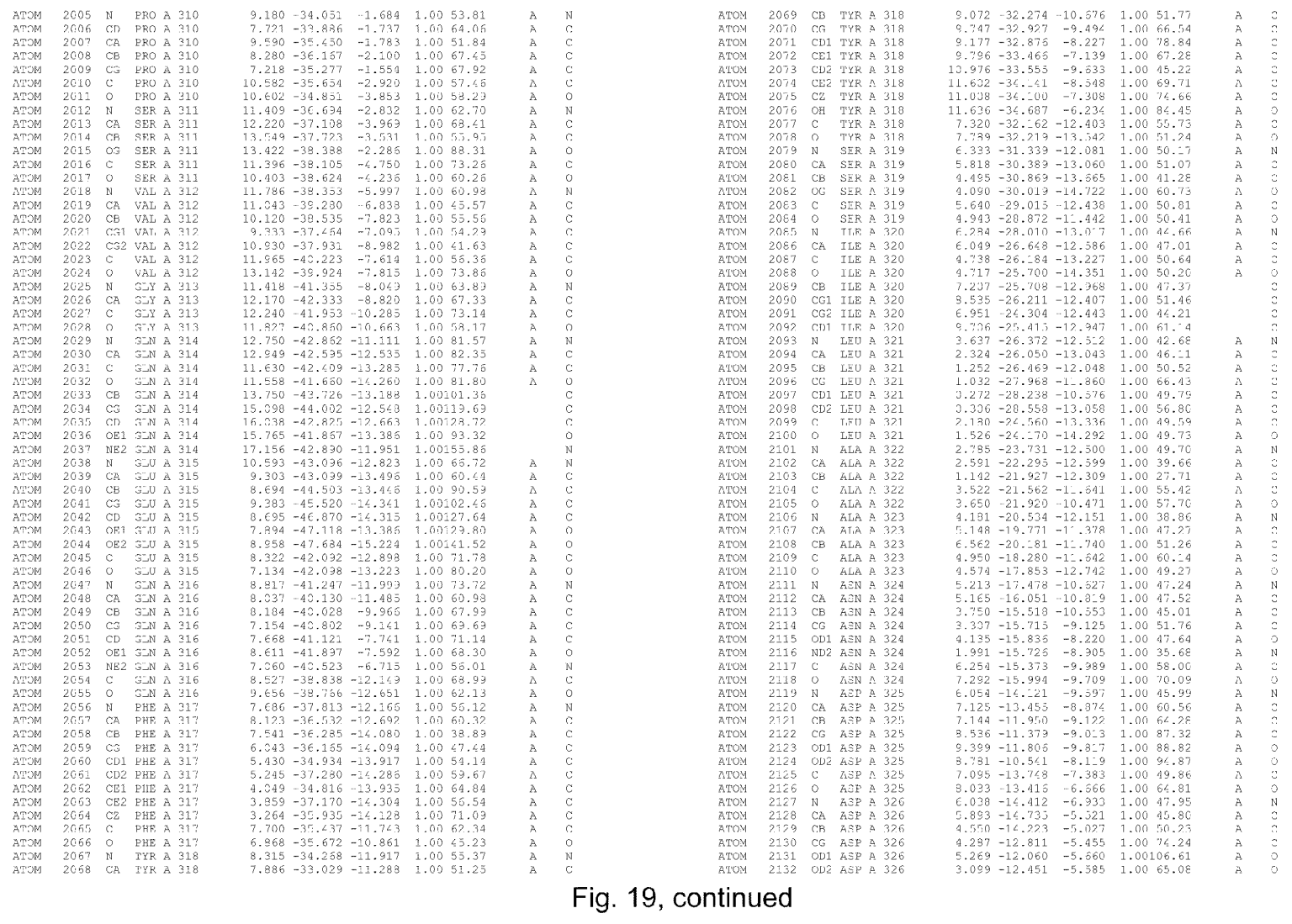
Figure 19:
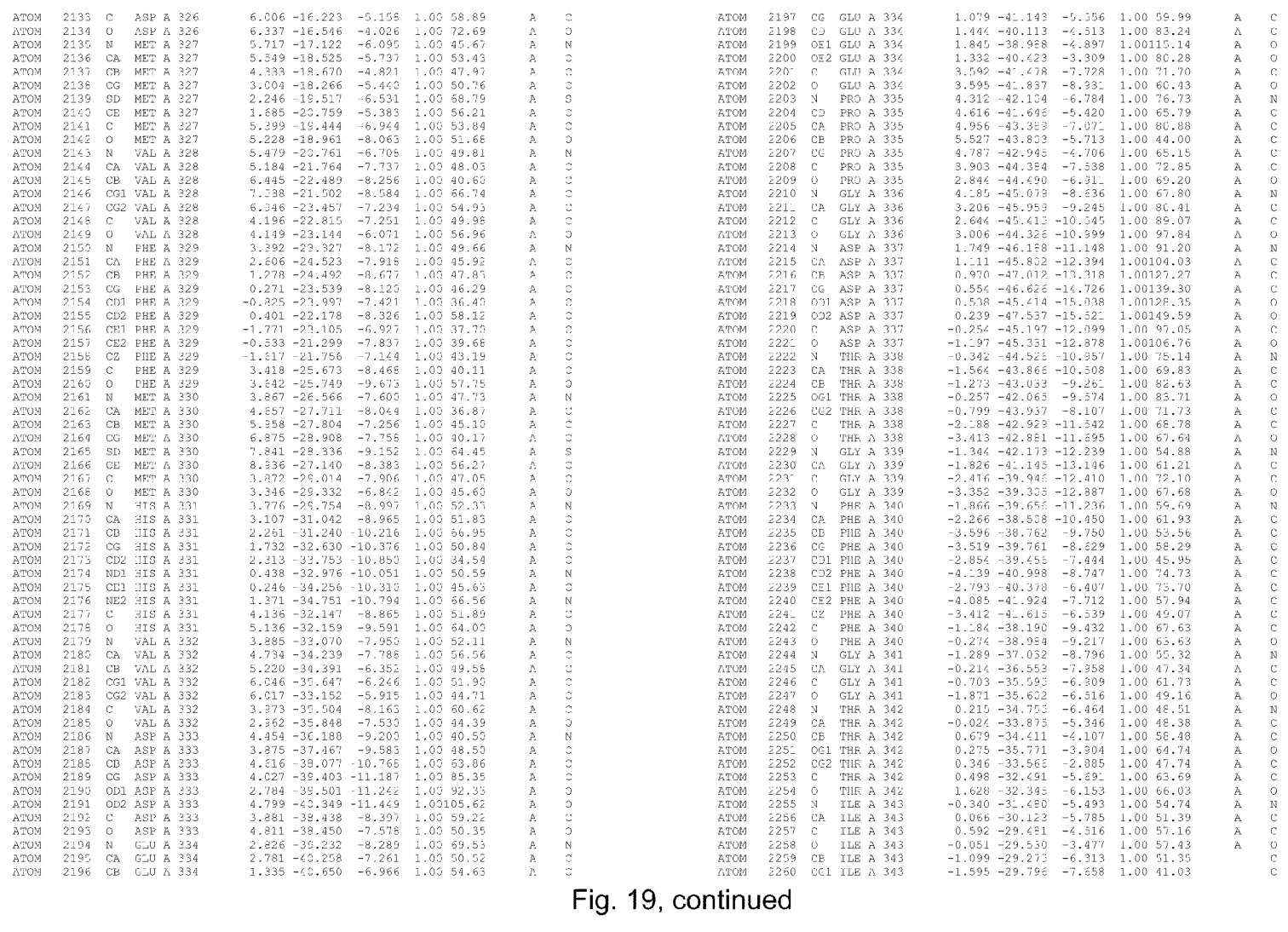
Figure 19:
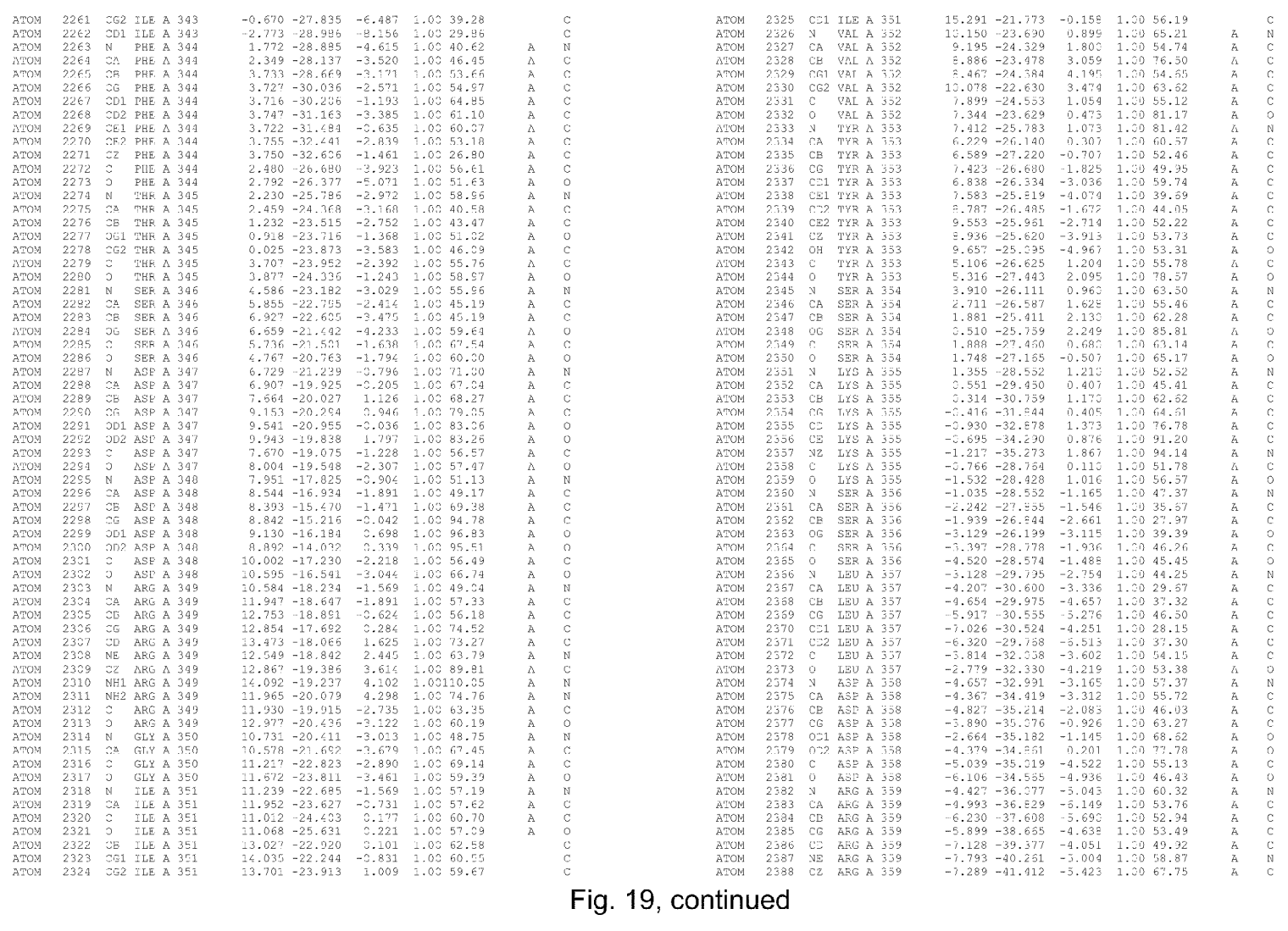
Figure 19:
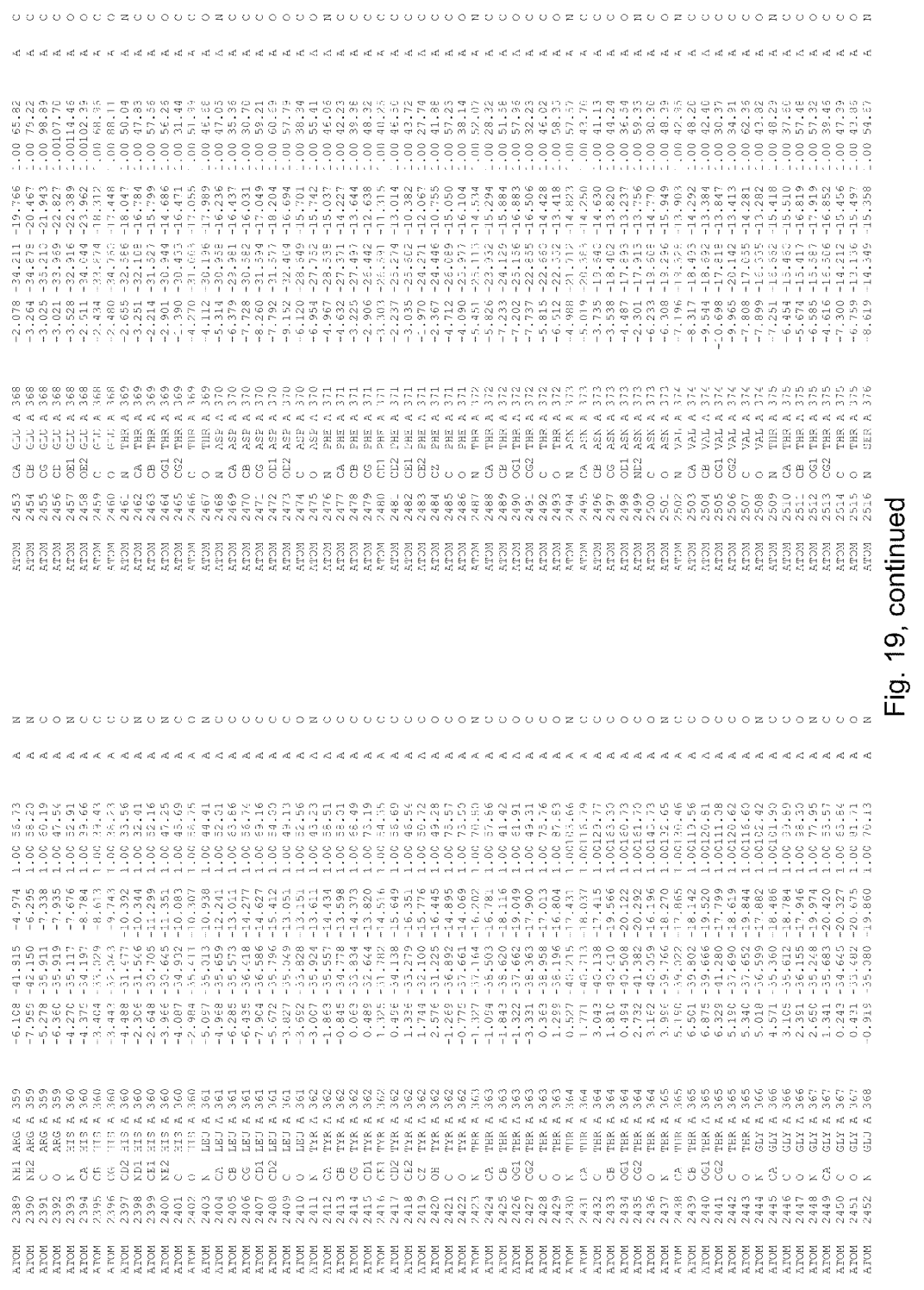
Figure 19:
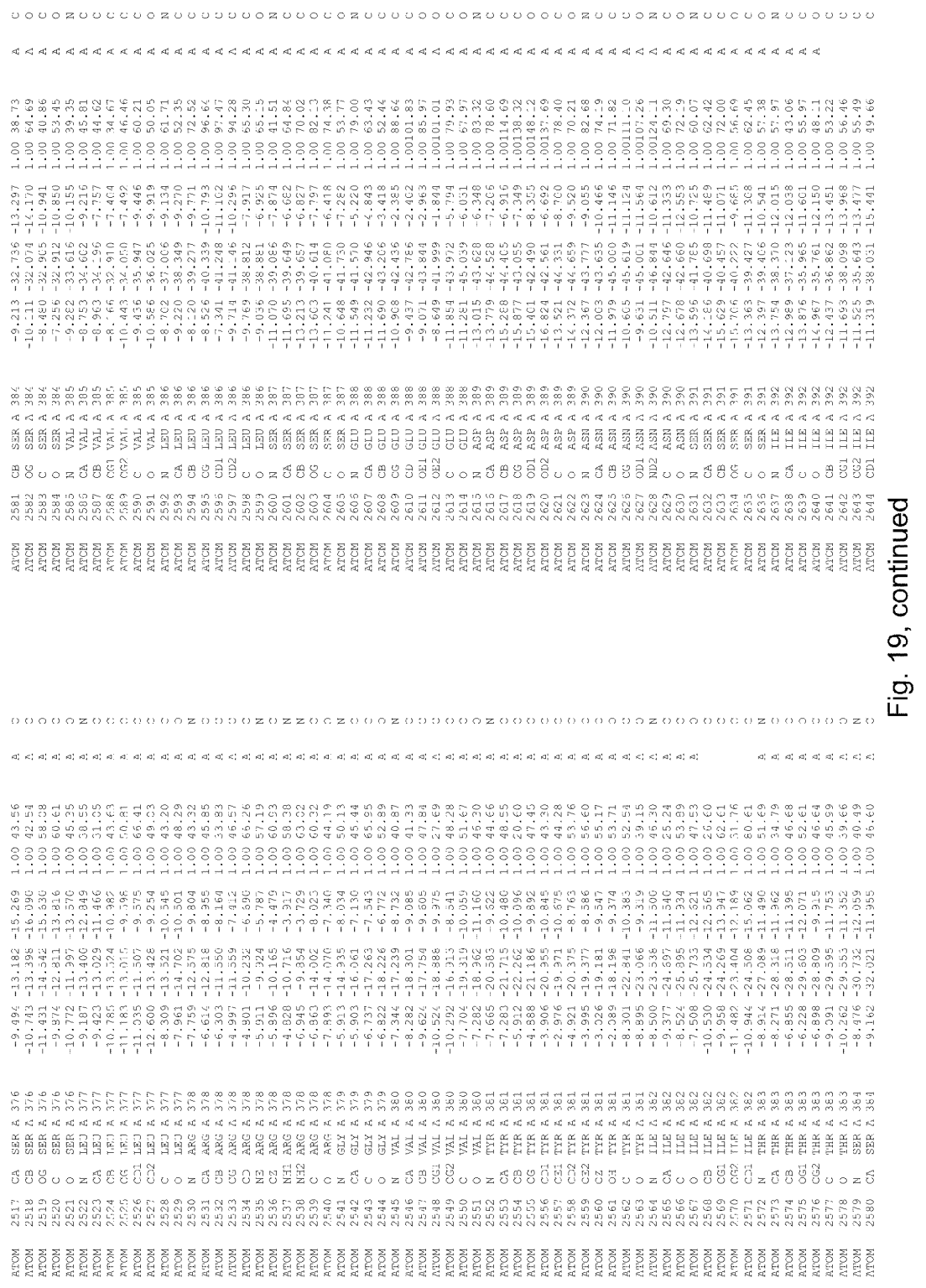
Figure 19:
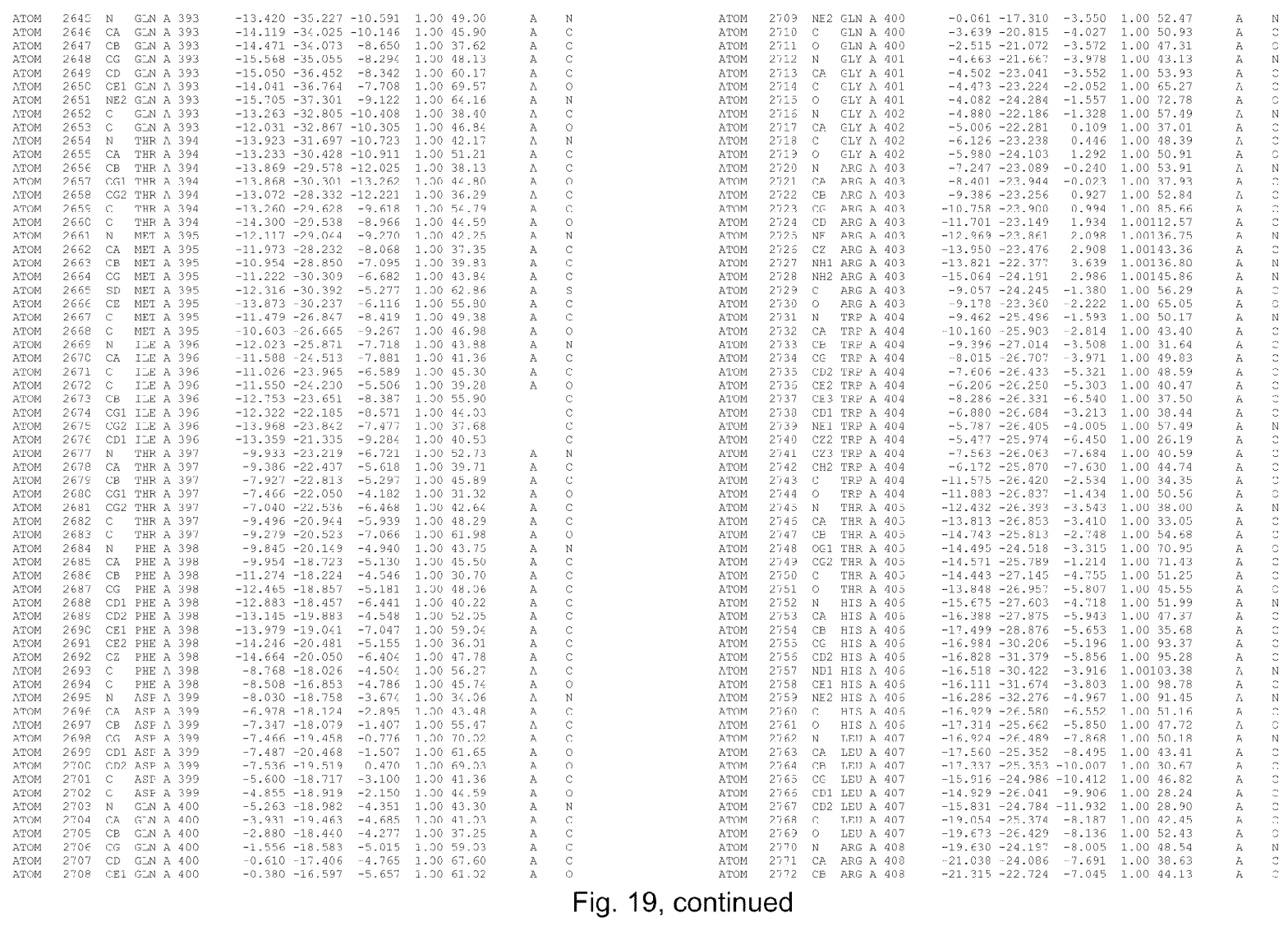
Figure 19:
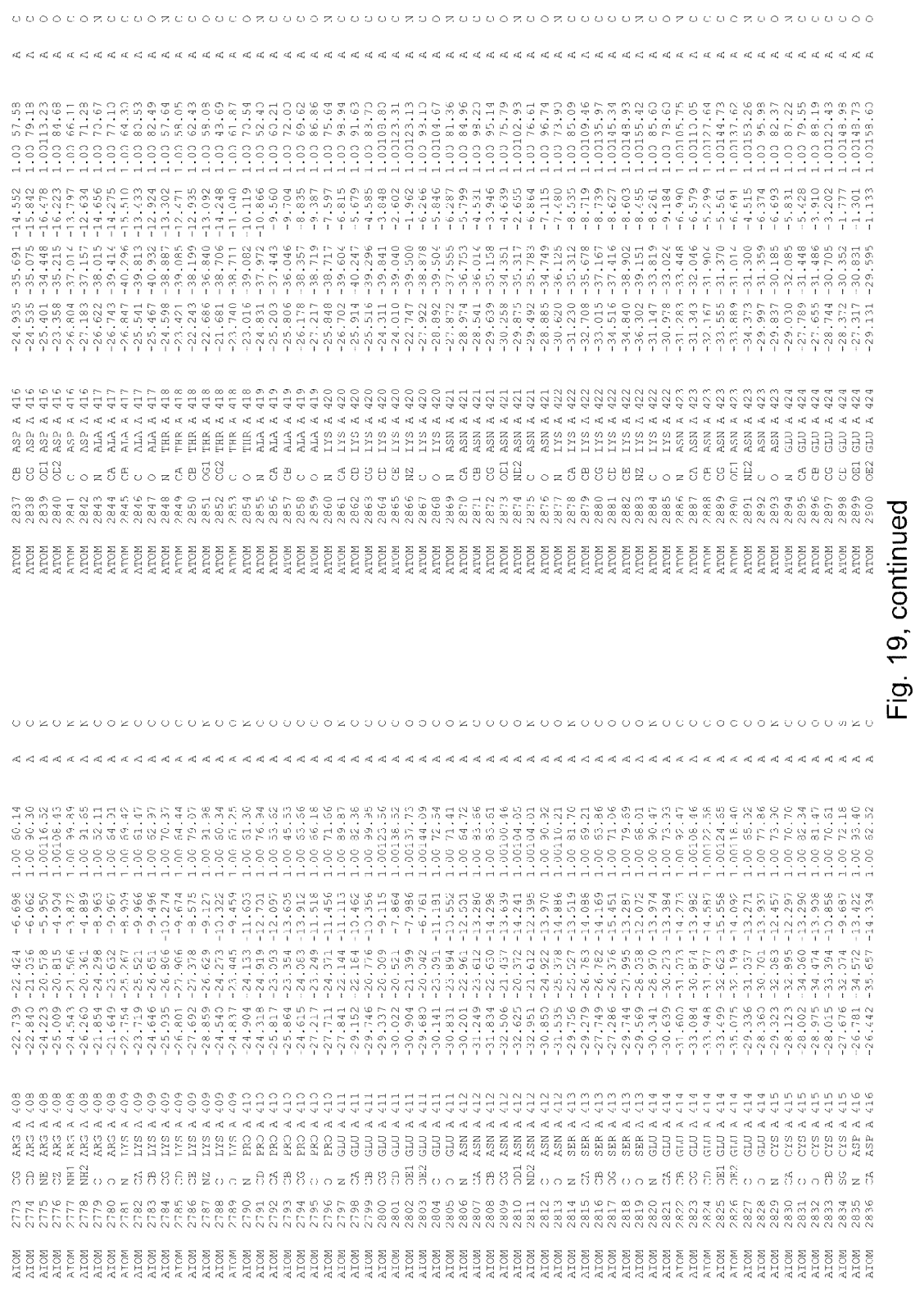
Figure 19:
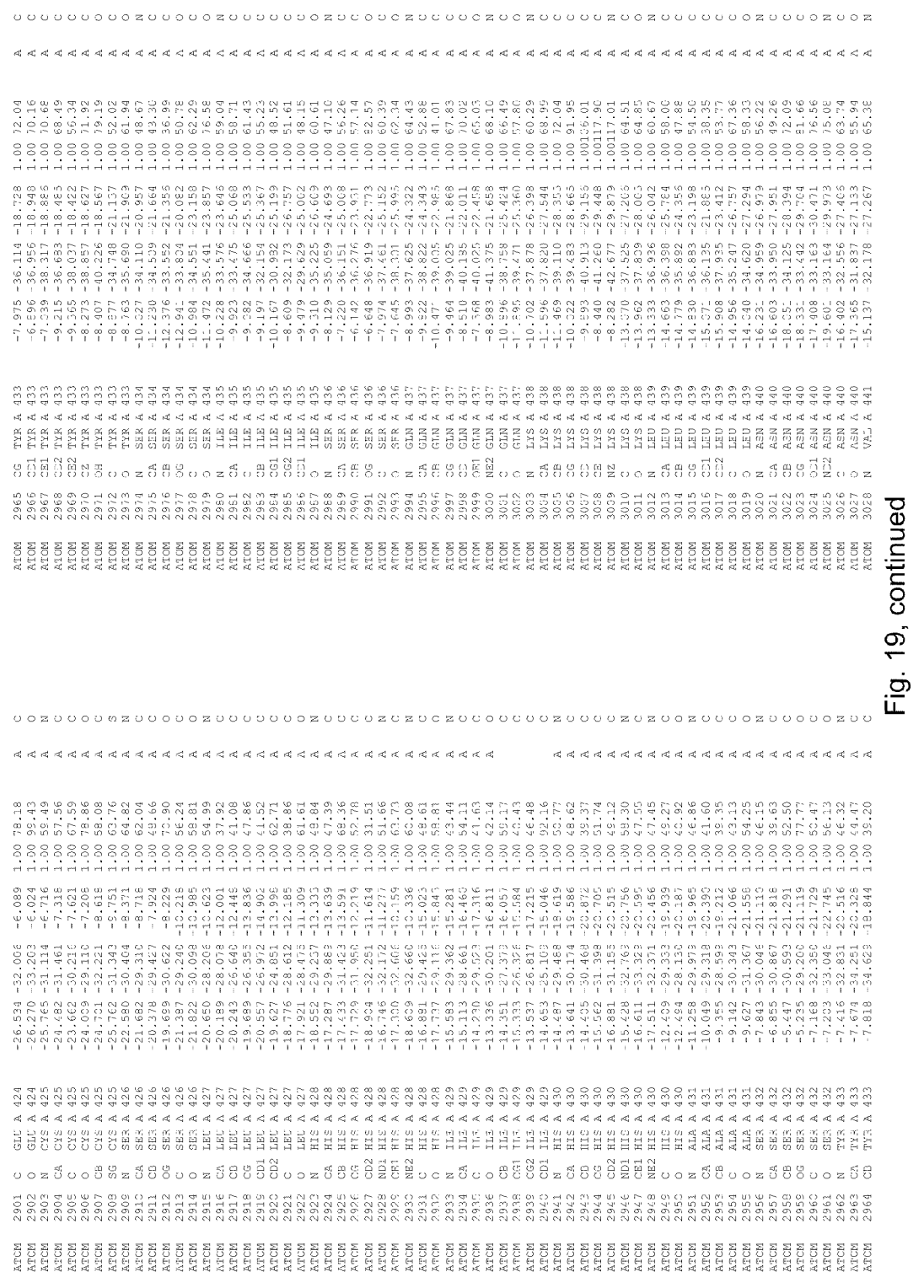
Figure 19:
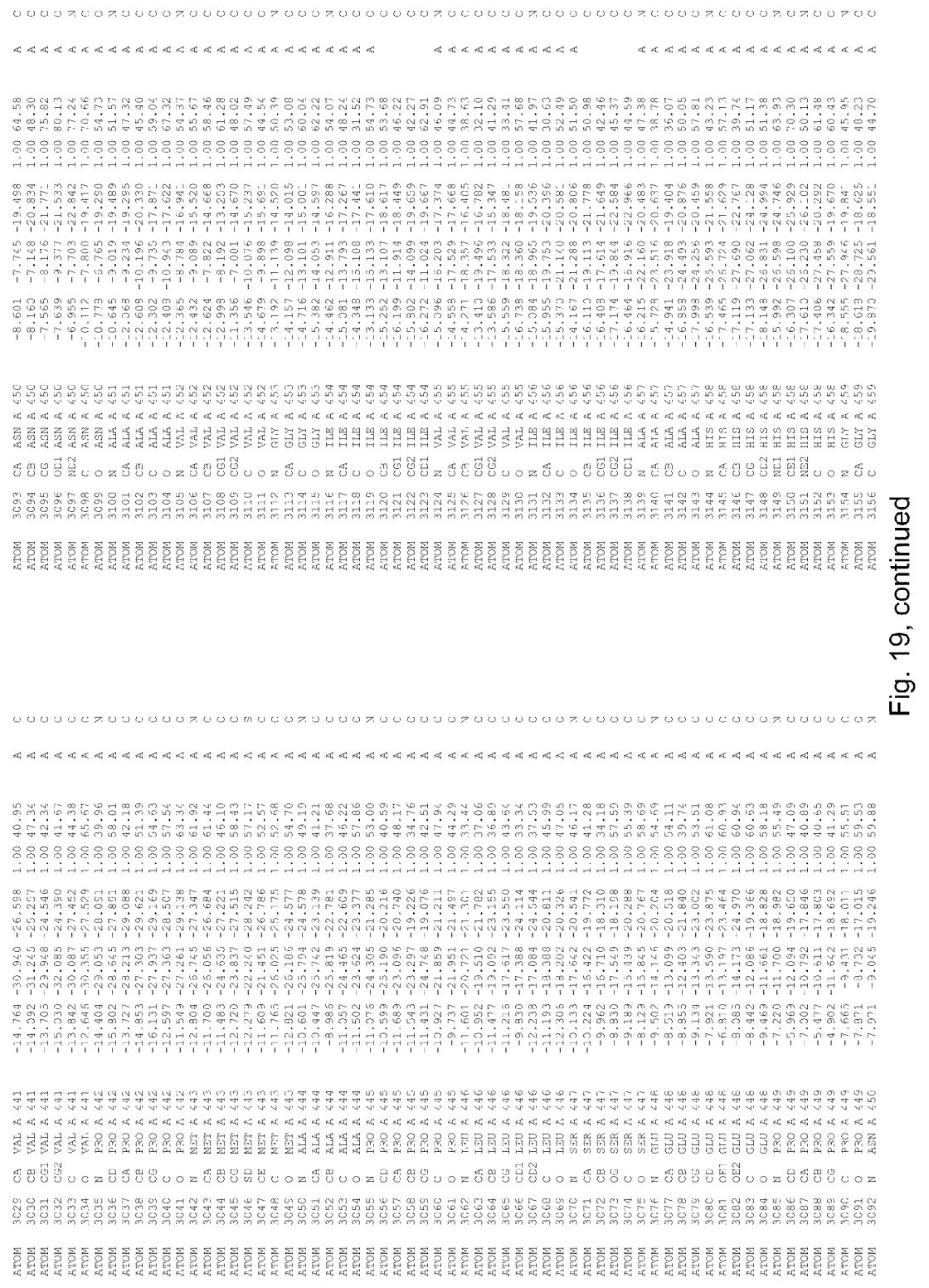
Figure 19:
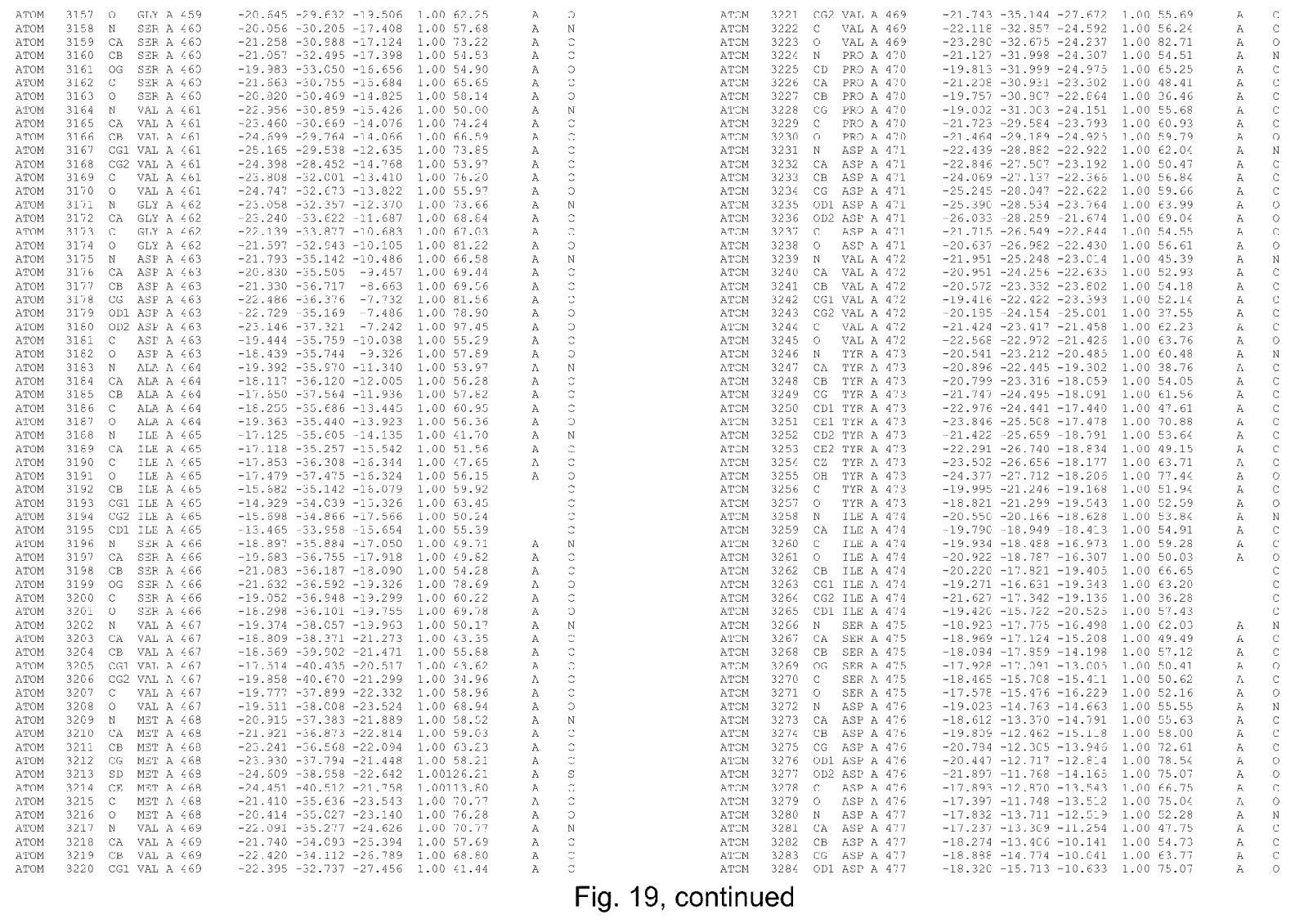
Figure 19:
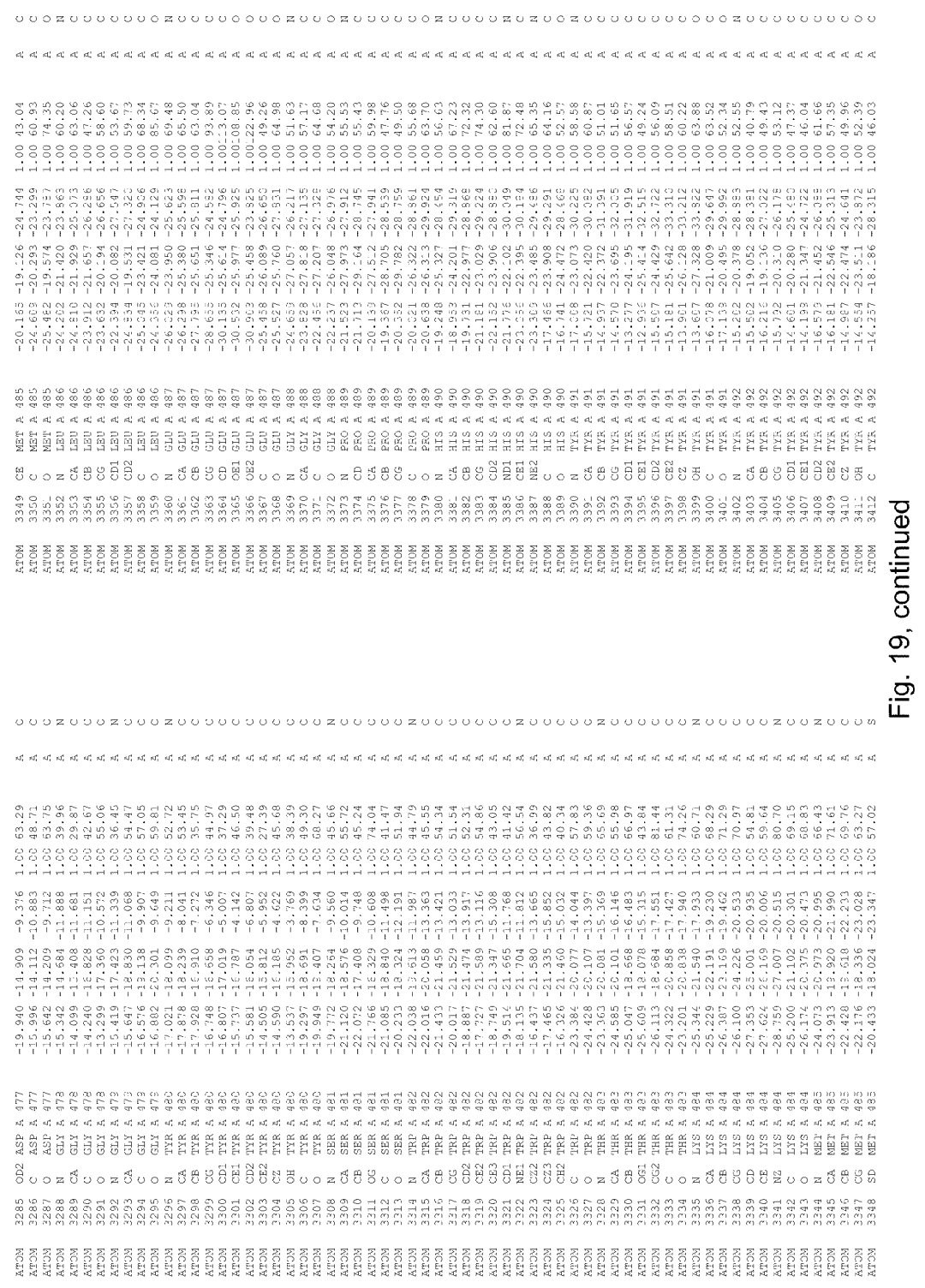
Figure 19:
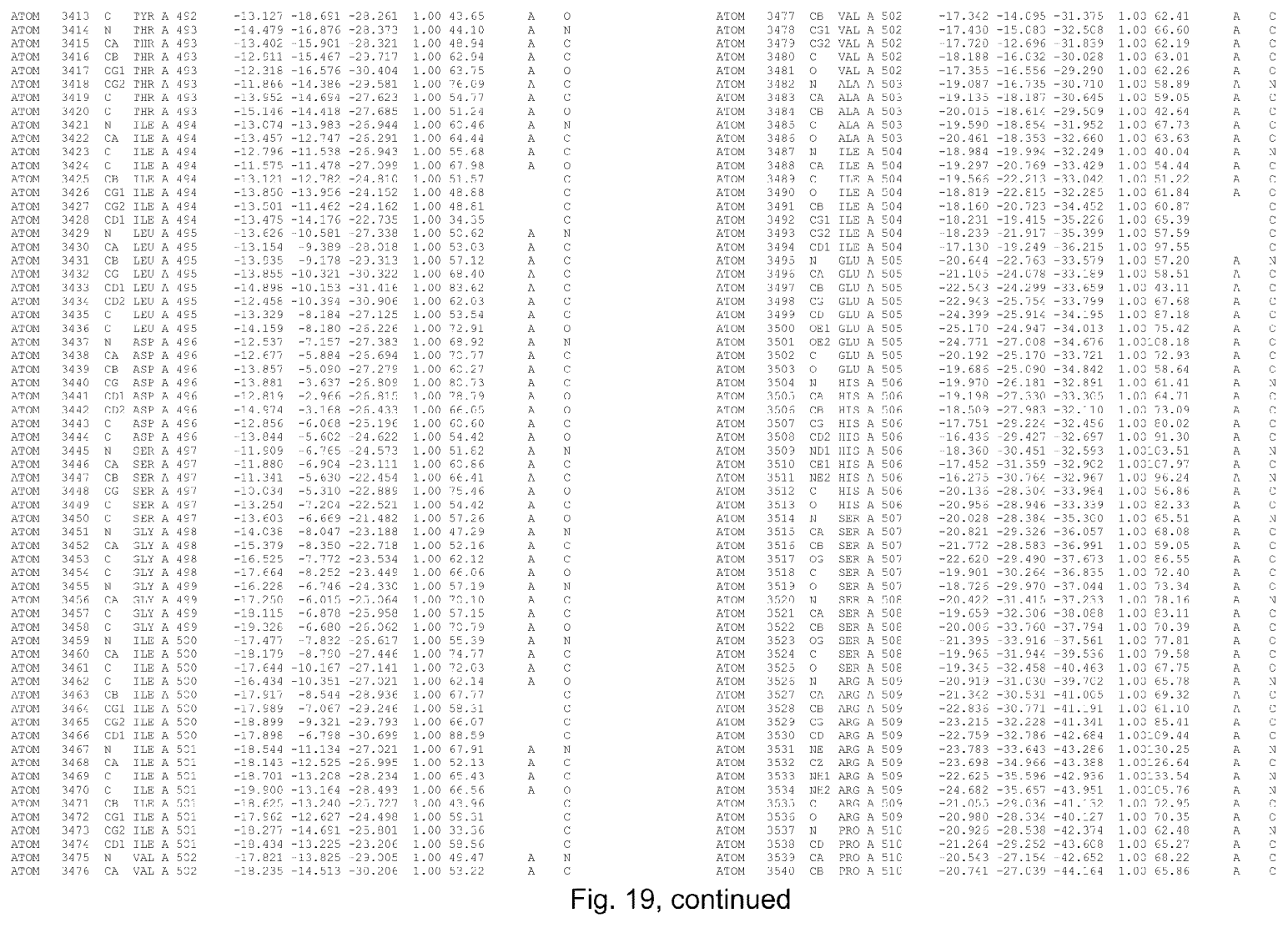
Figure 19:
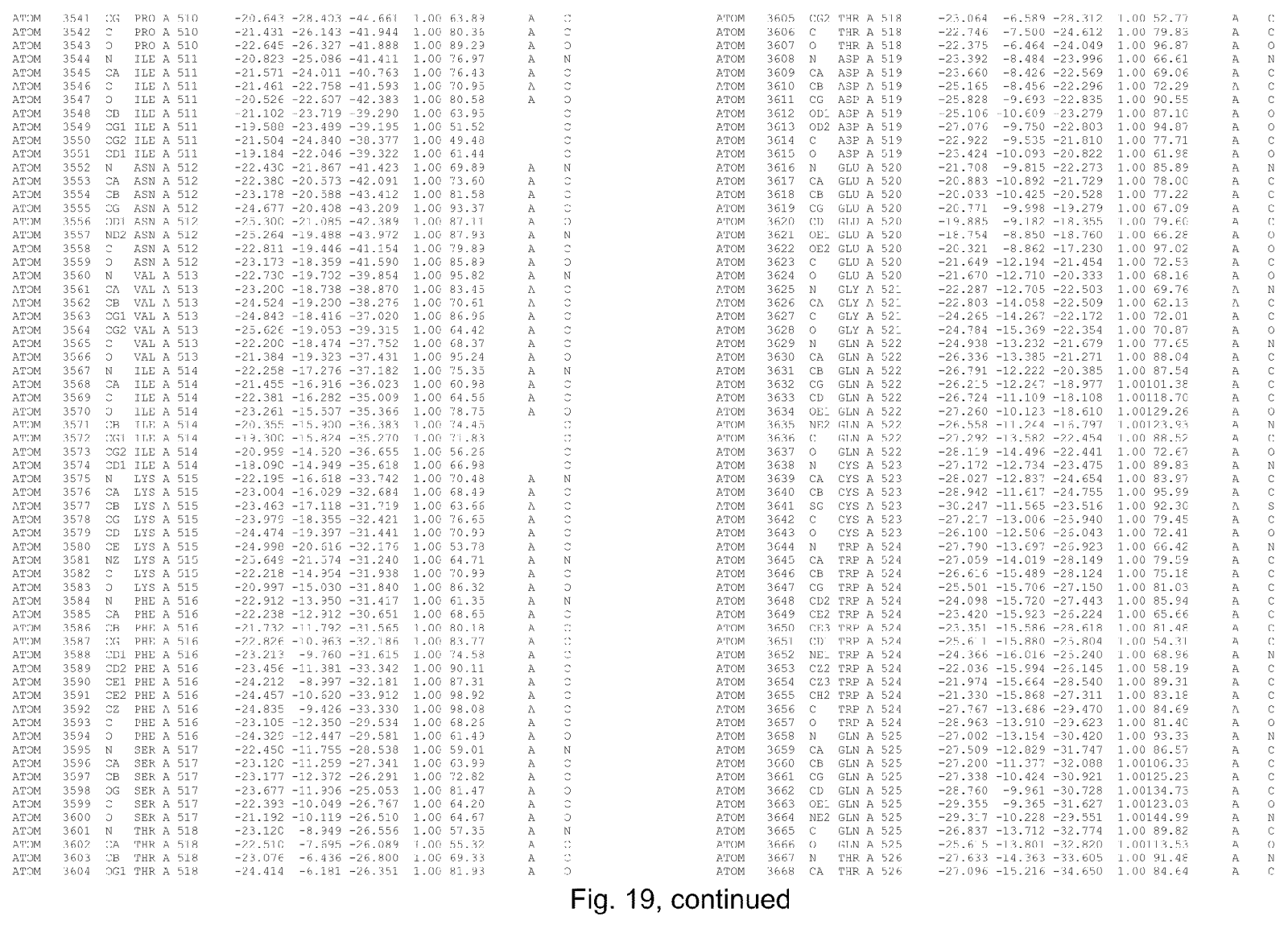
Figure 19:
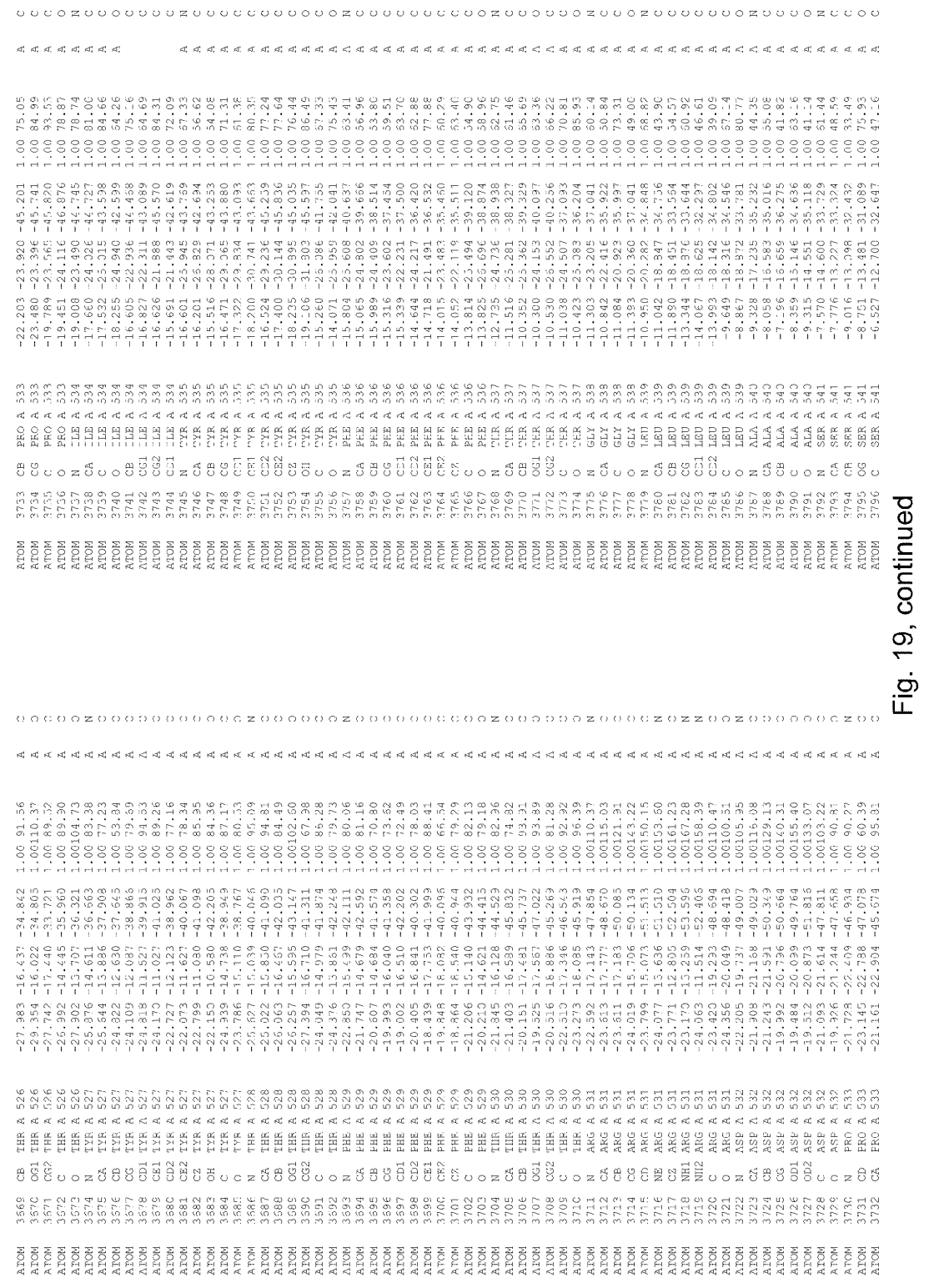
Figure 19:
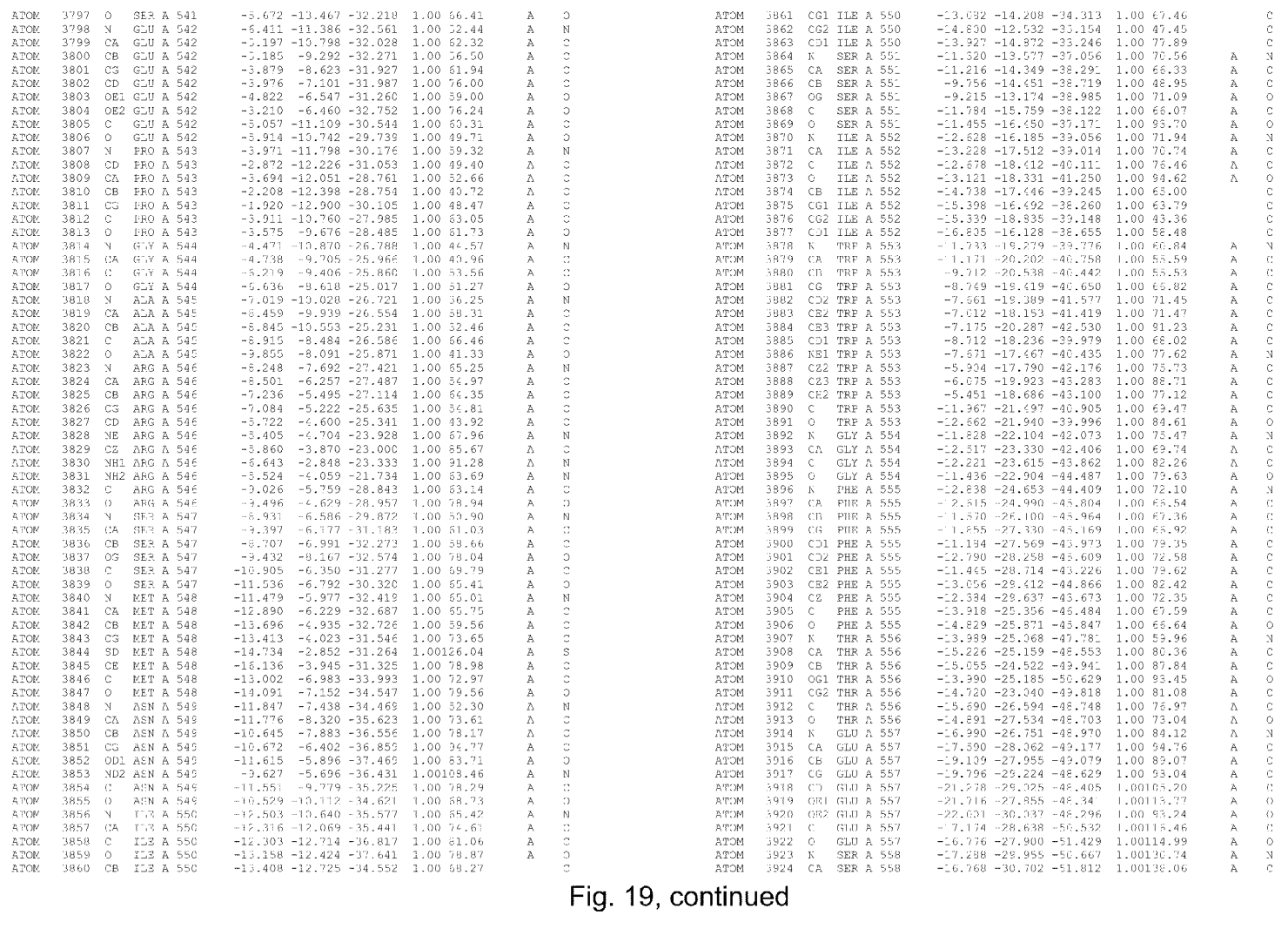
Figure 19:
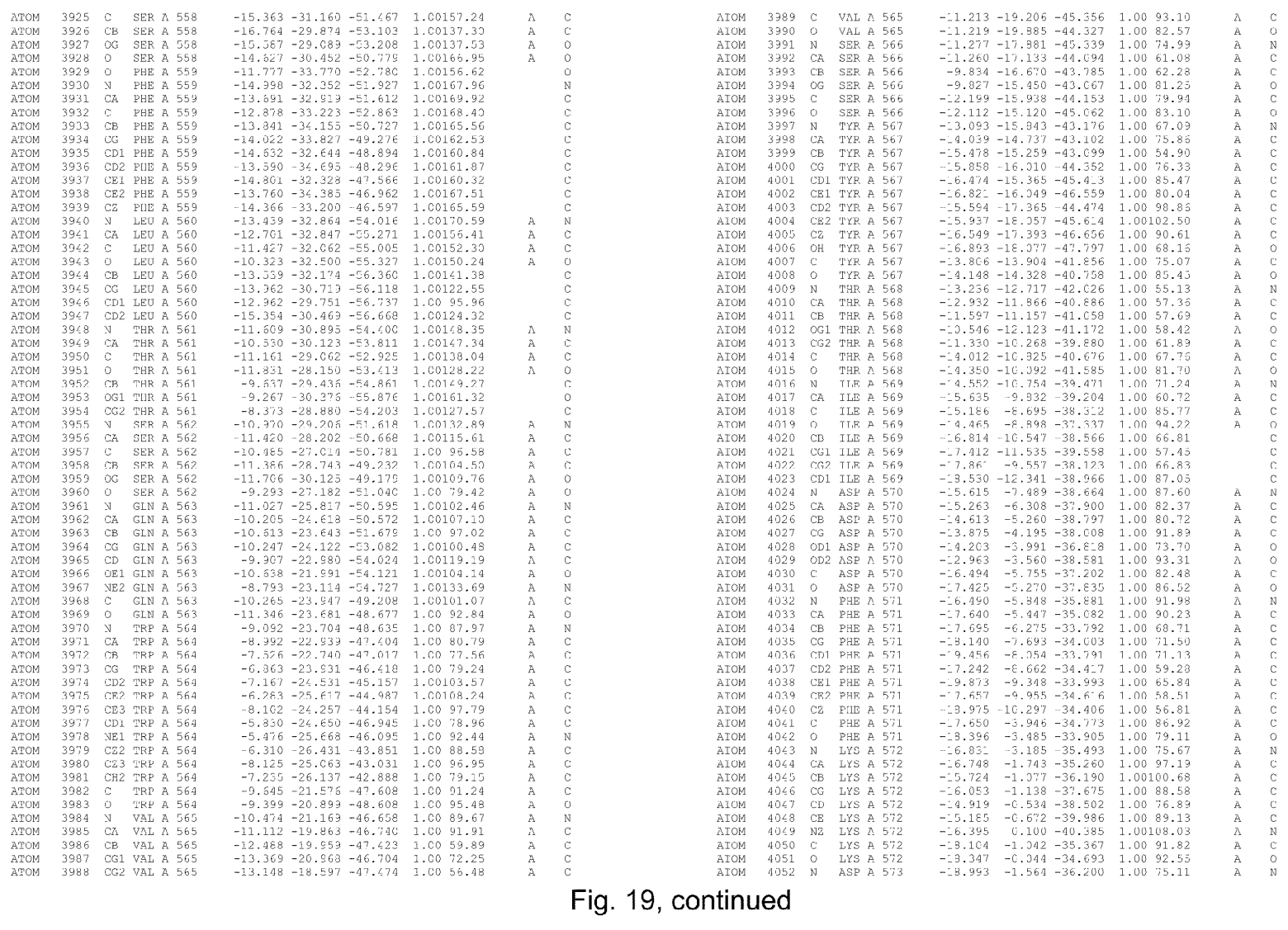
Figure 19:
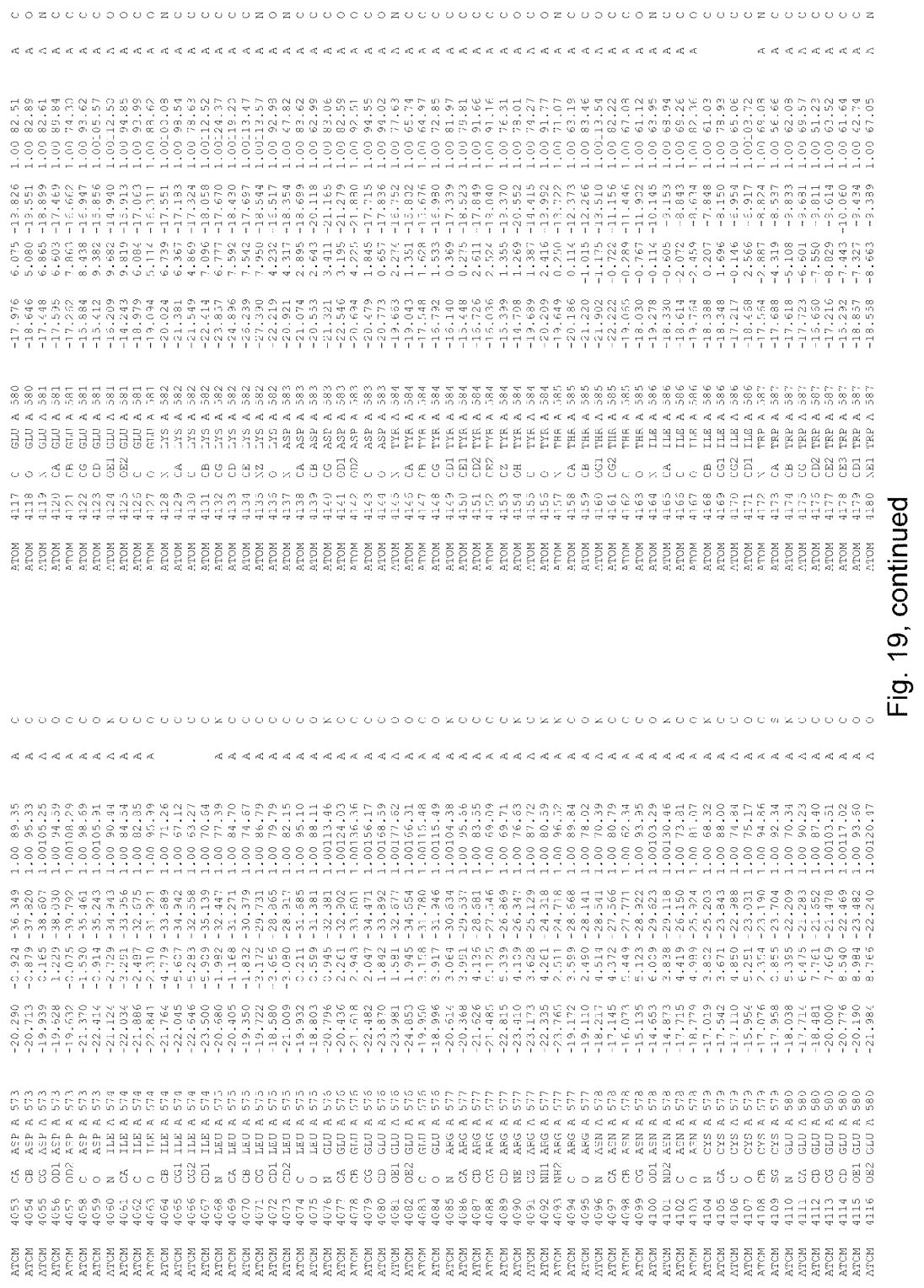
Figure 19:
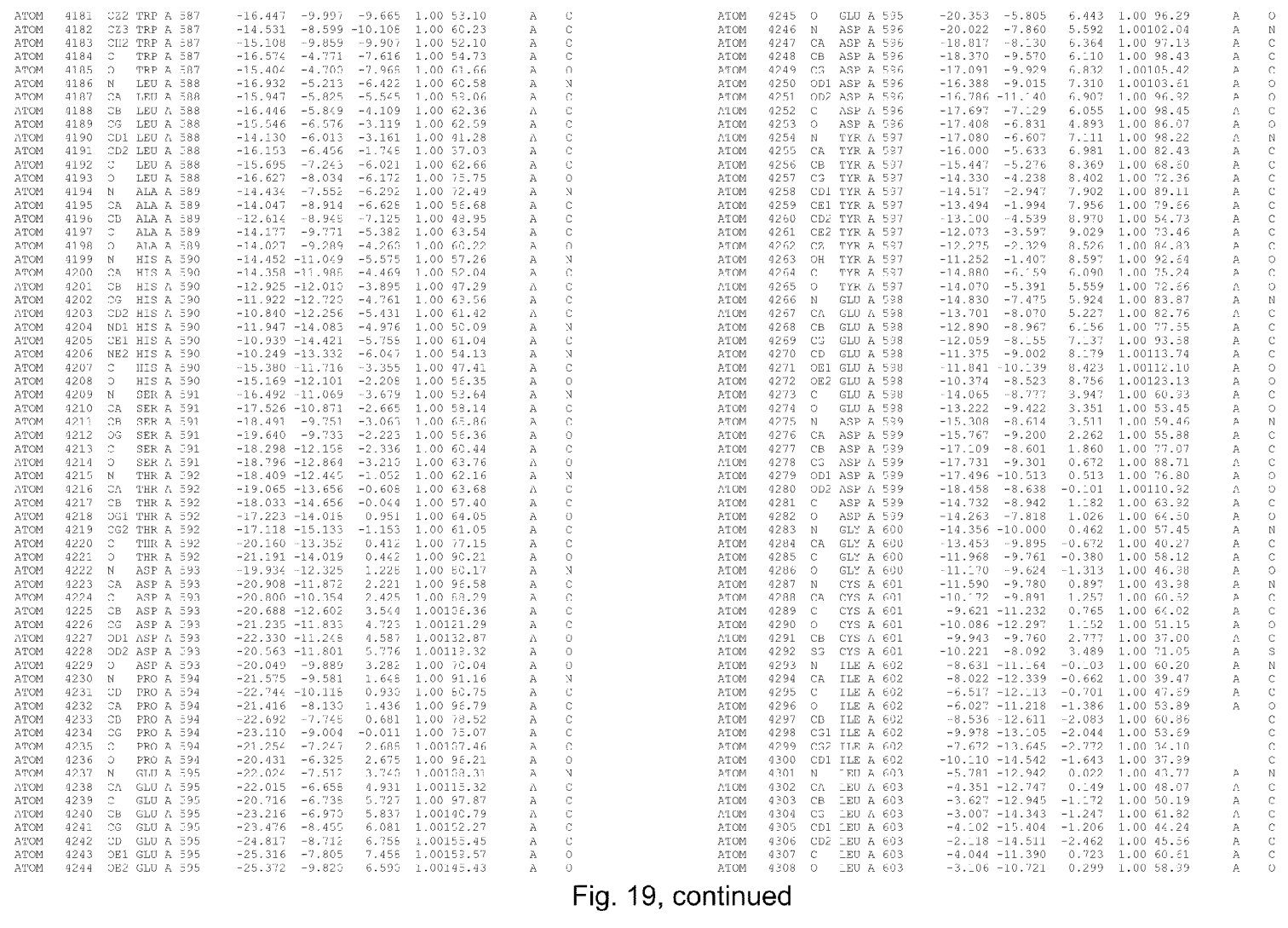
Figure 19:
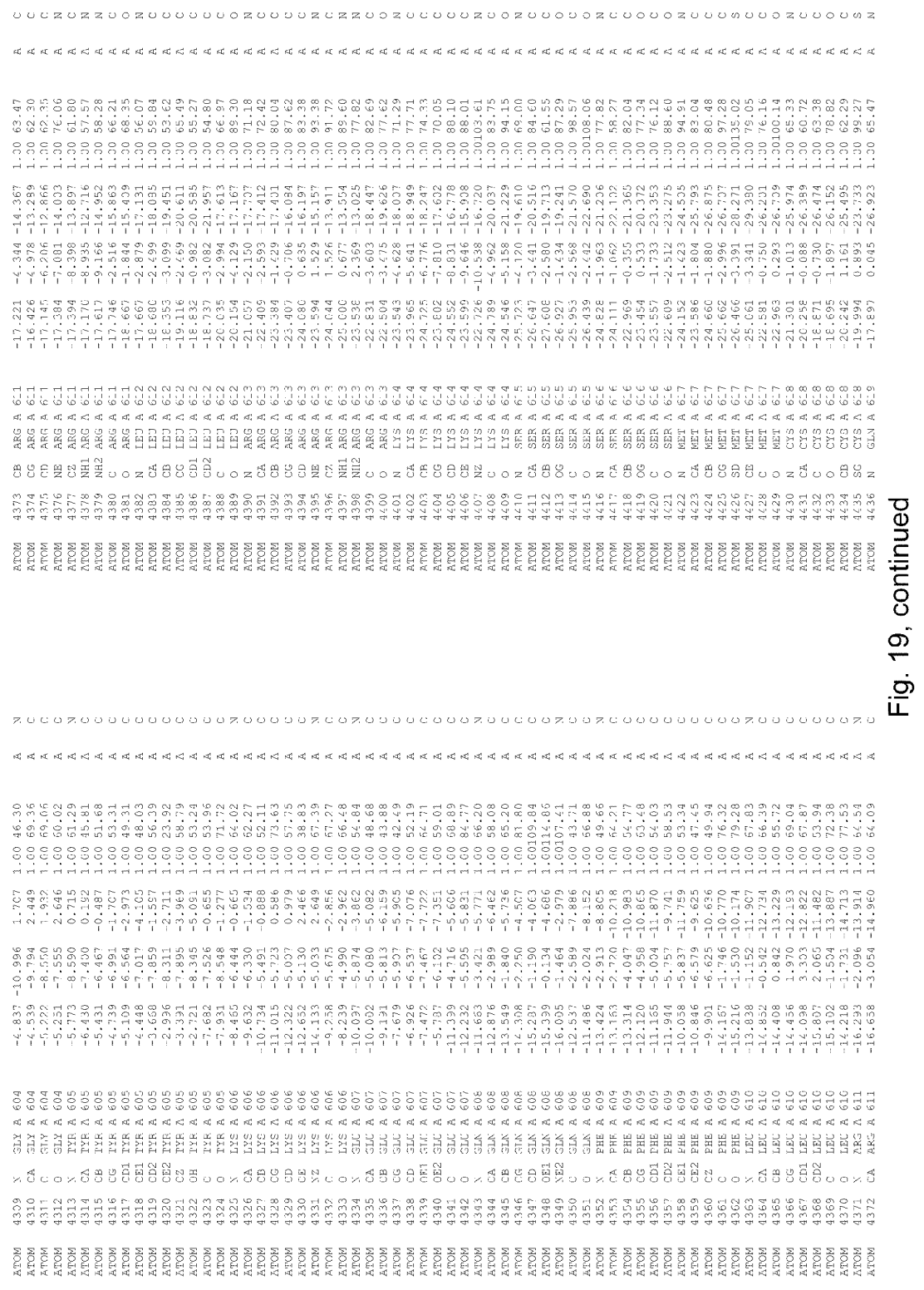
Figure 19:
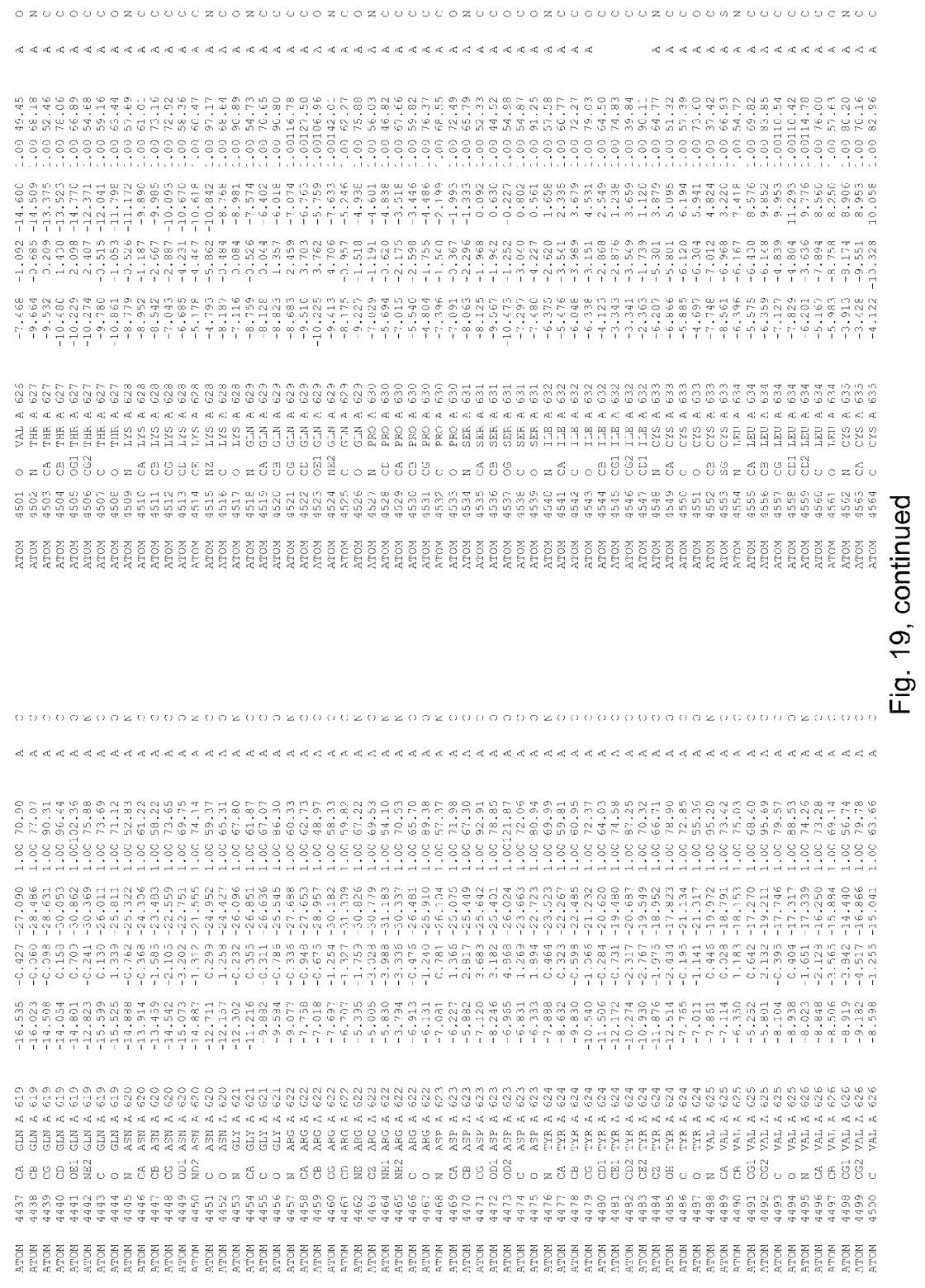
Figure 19:
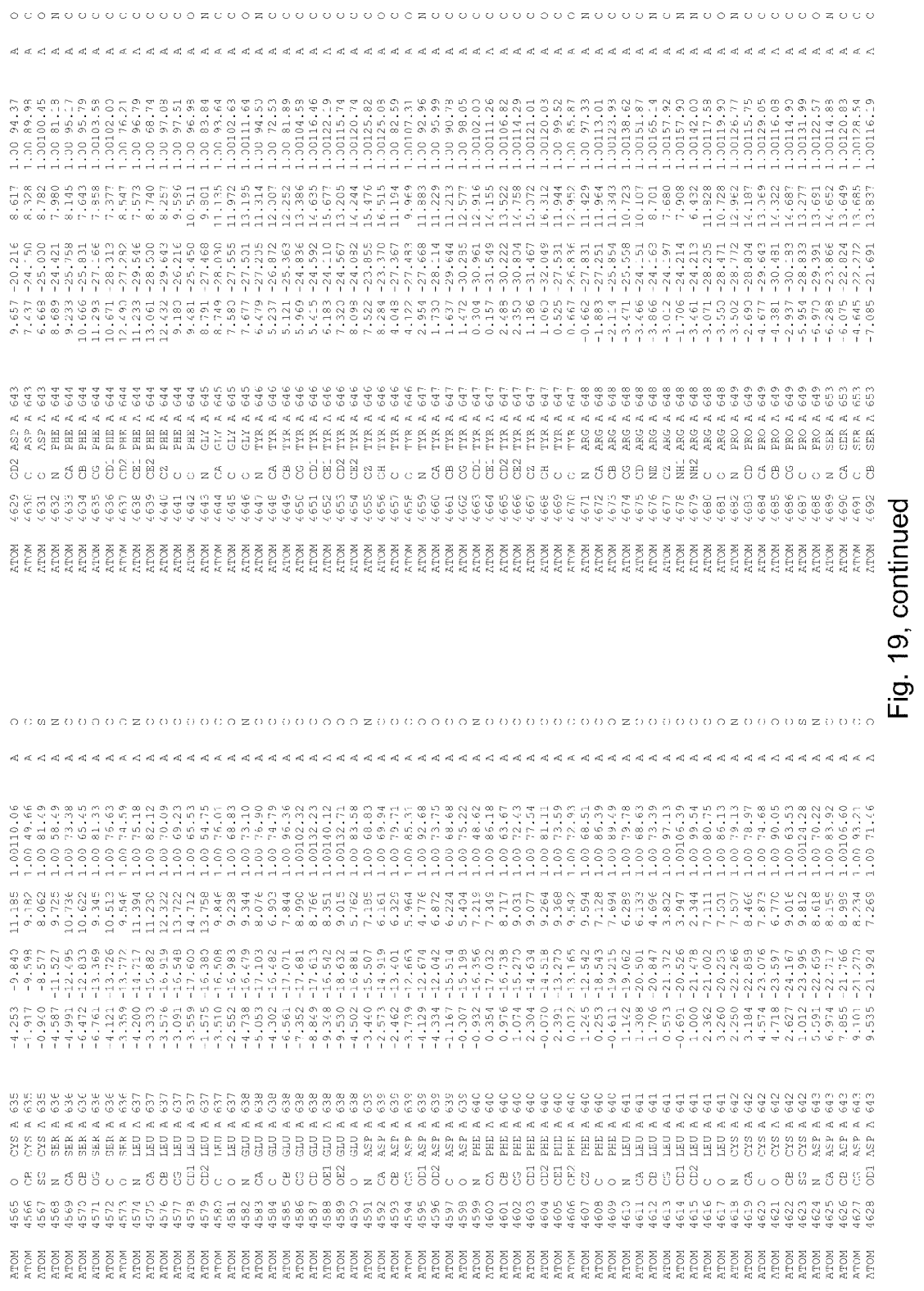
Figure 19:
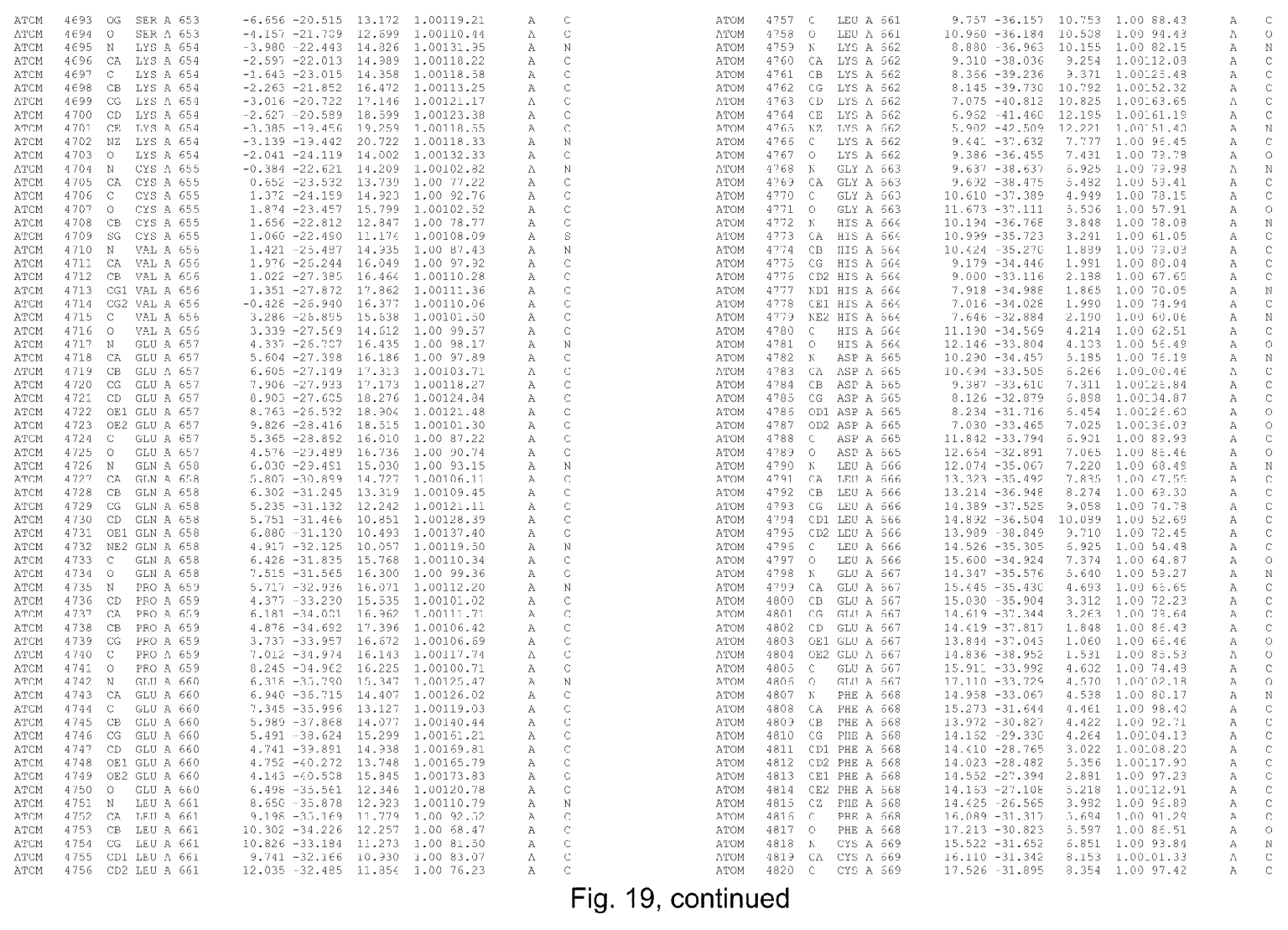
Figure 19:
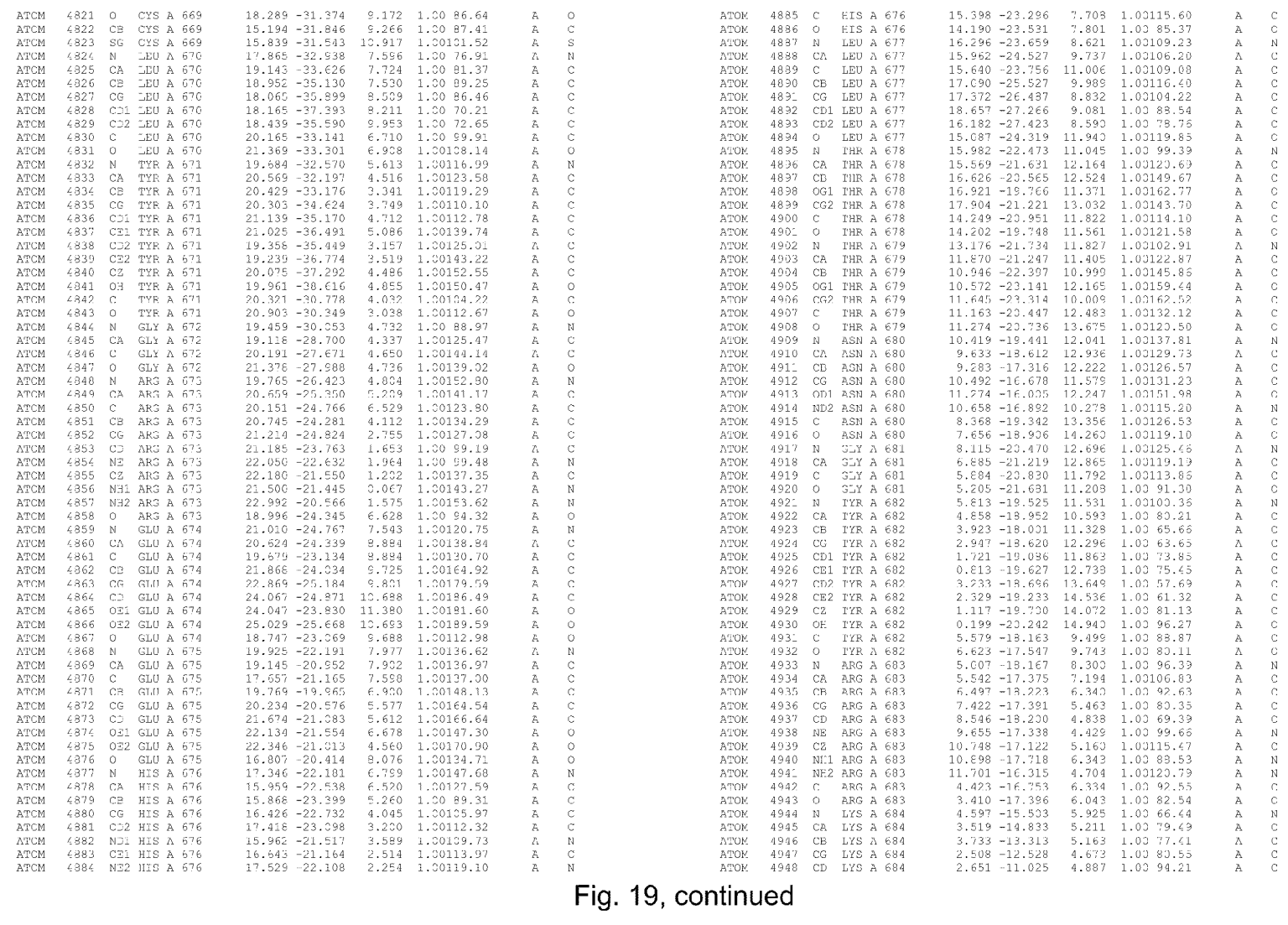
Figure 19:
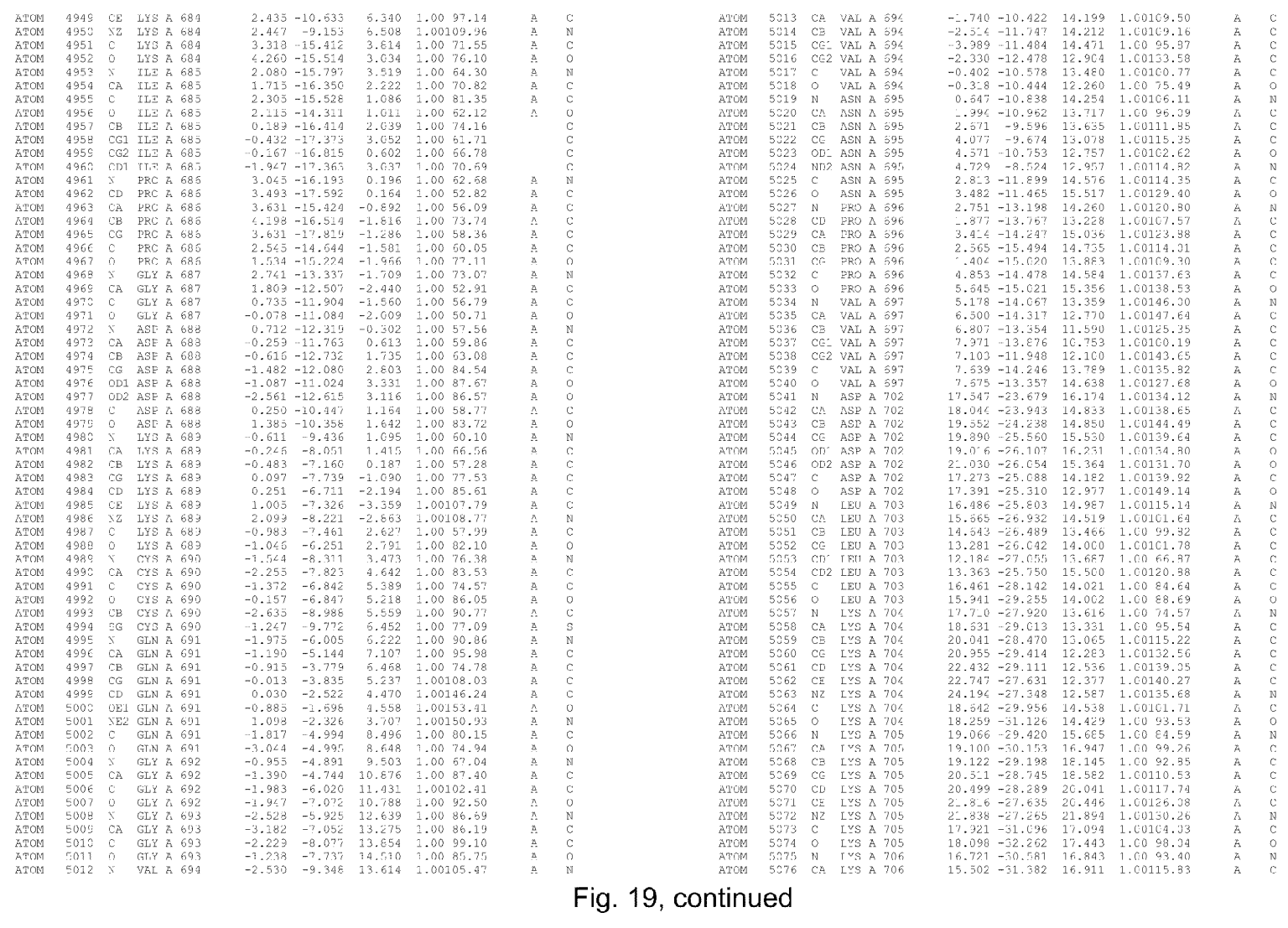
Figure 19:
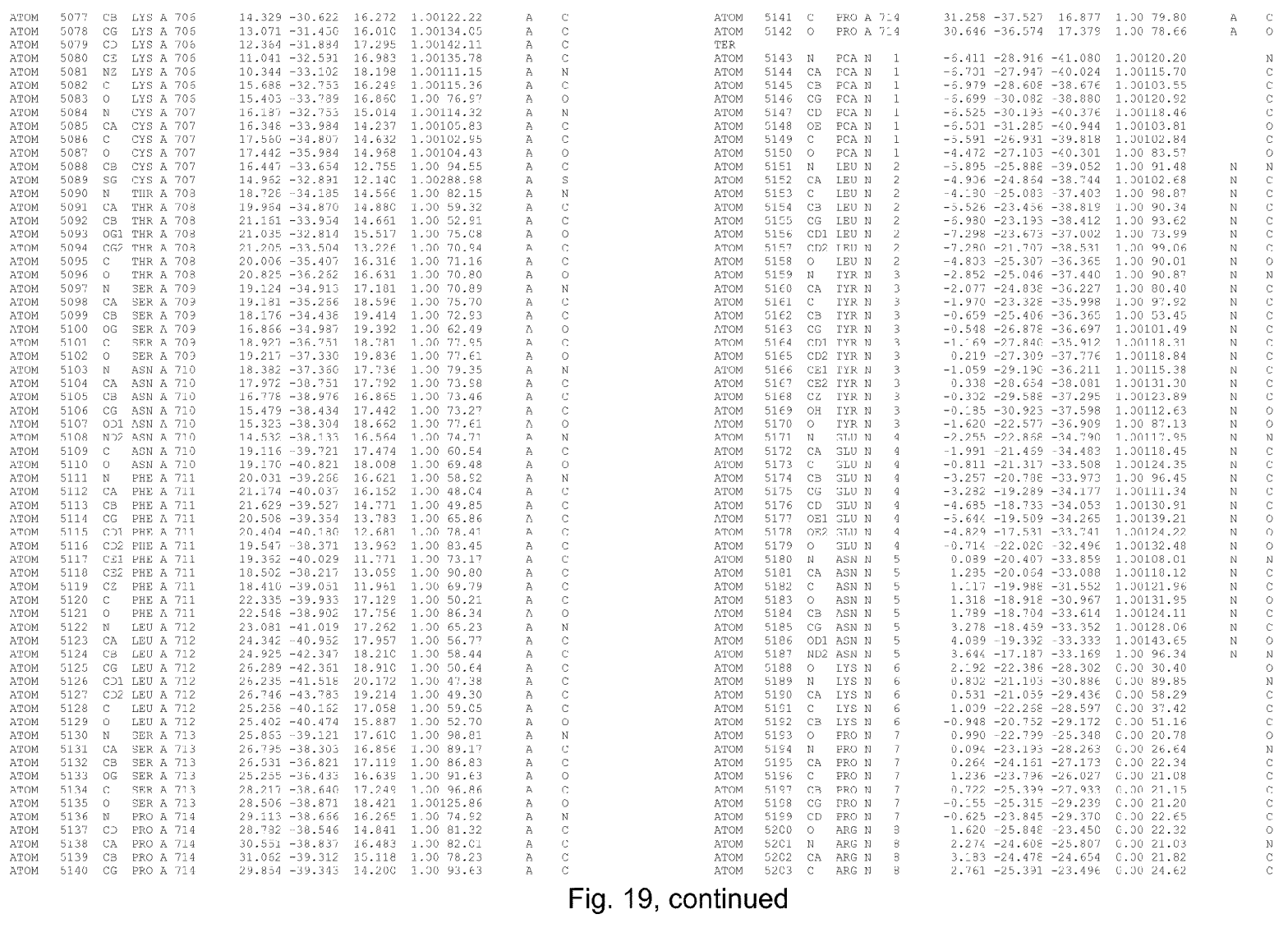
Figure 19:
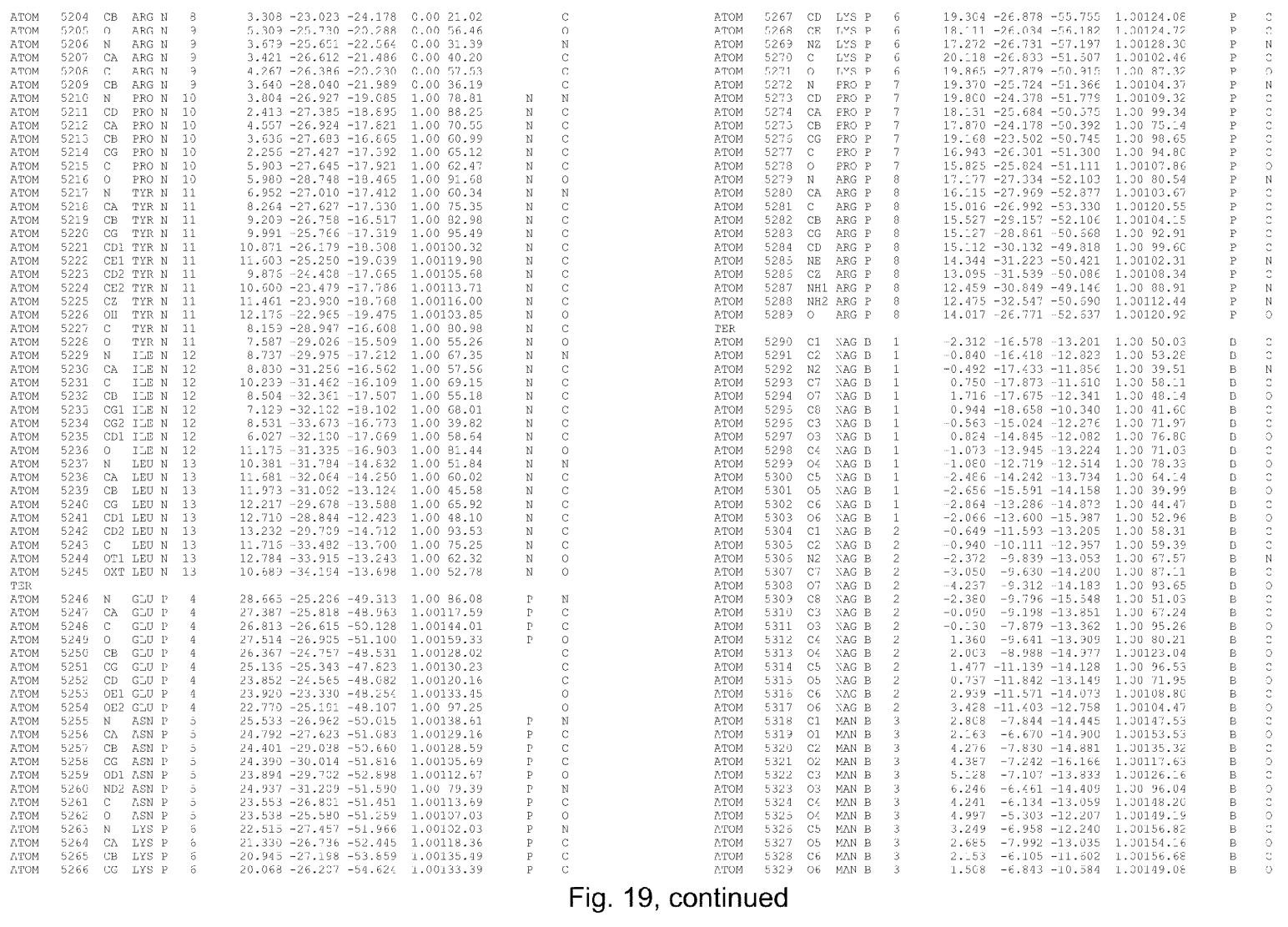
Figure 19:
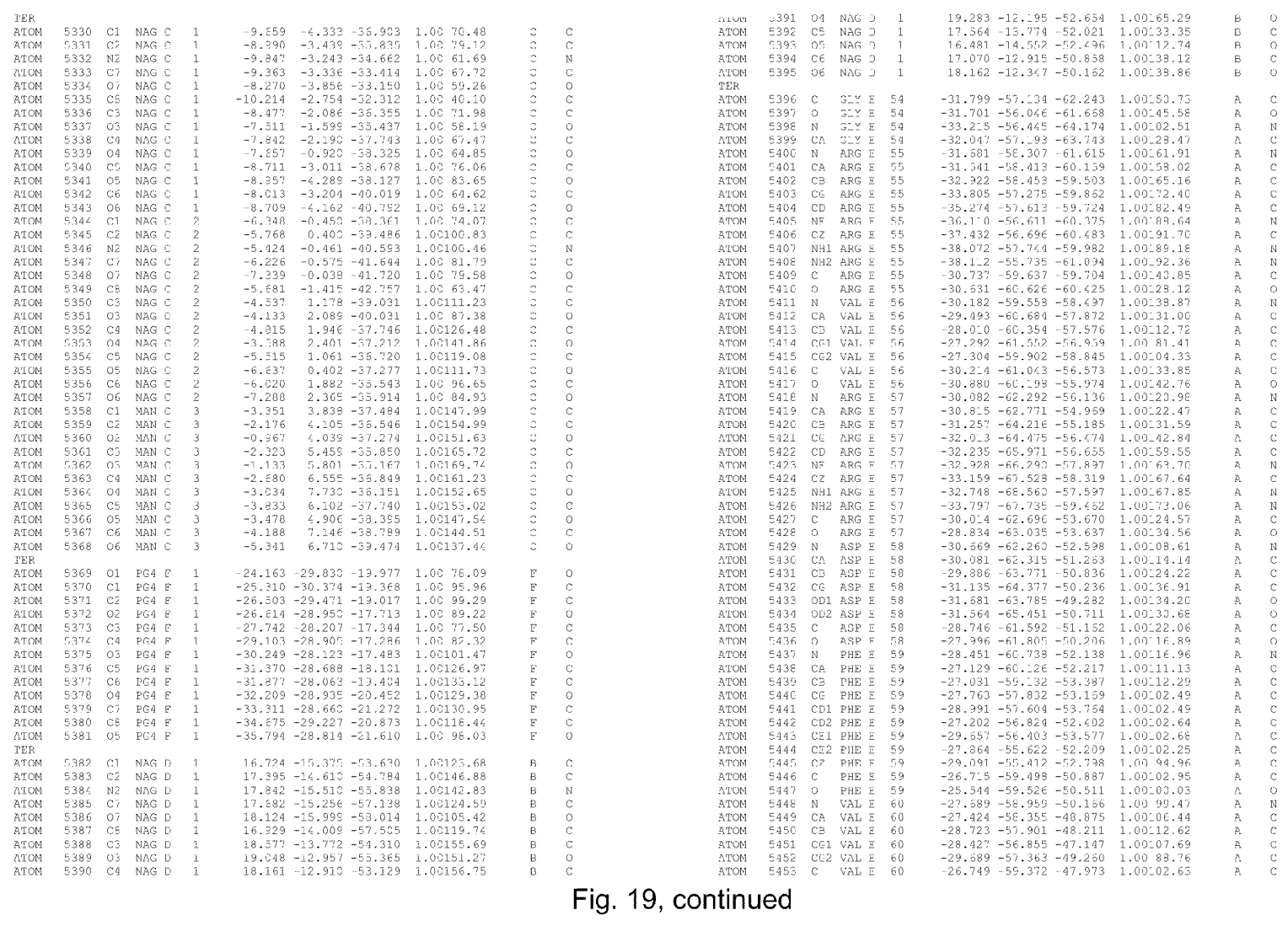
Figure 19:
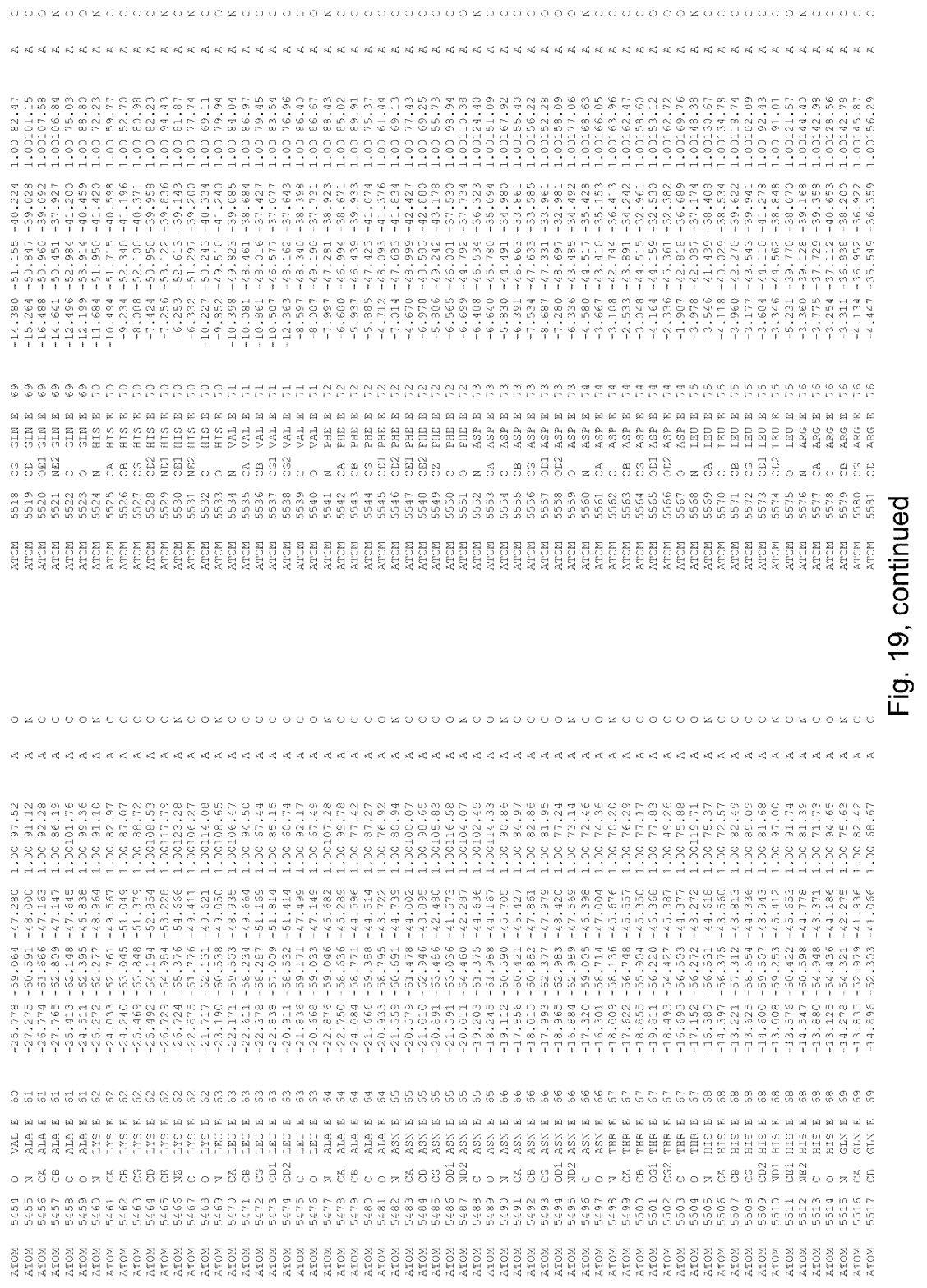
Figure 19:
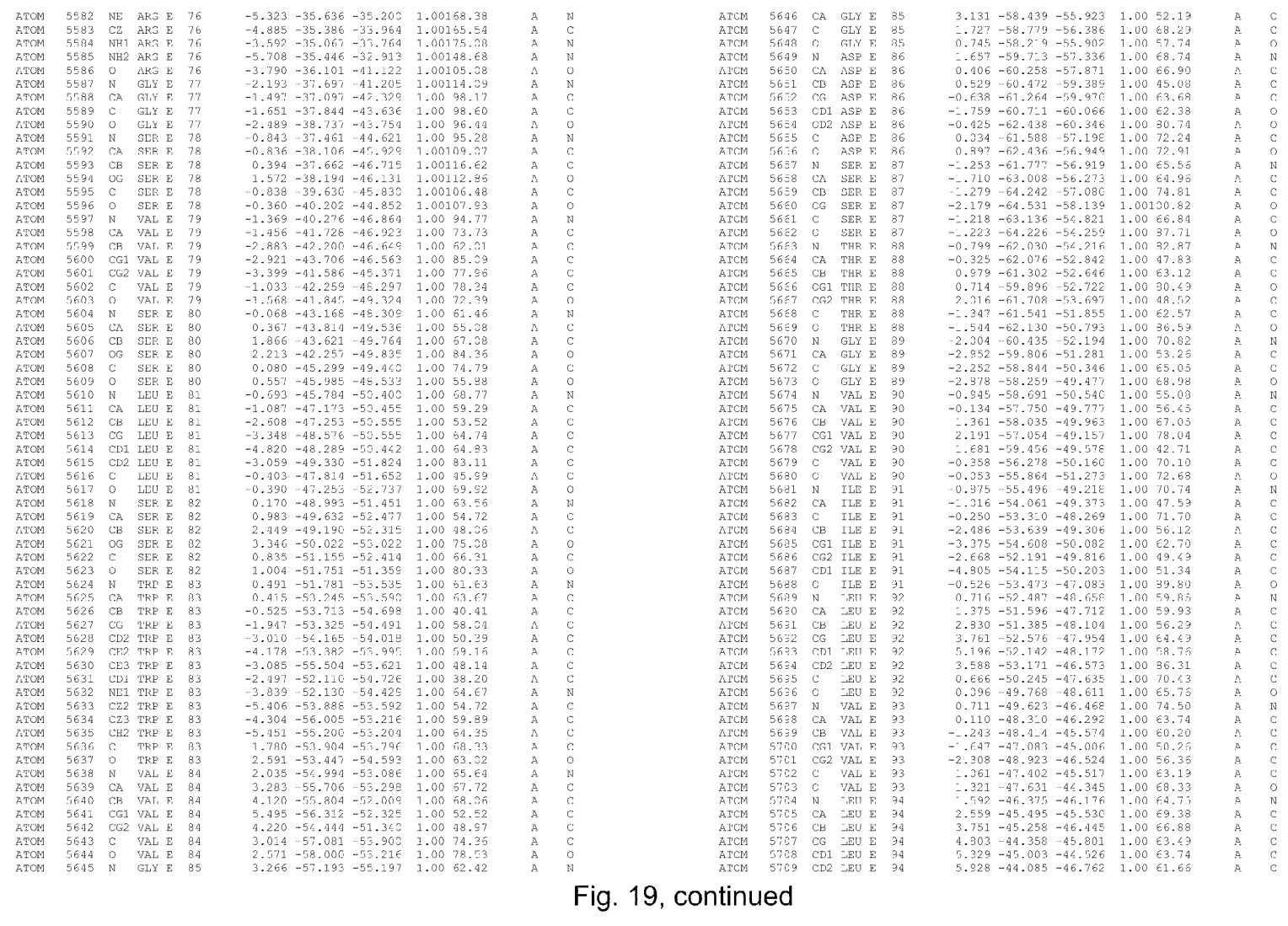
Figure 19:
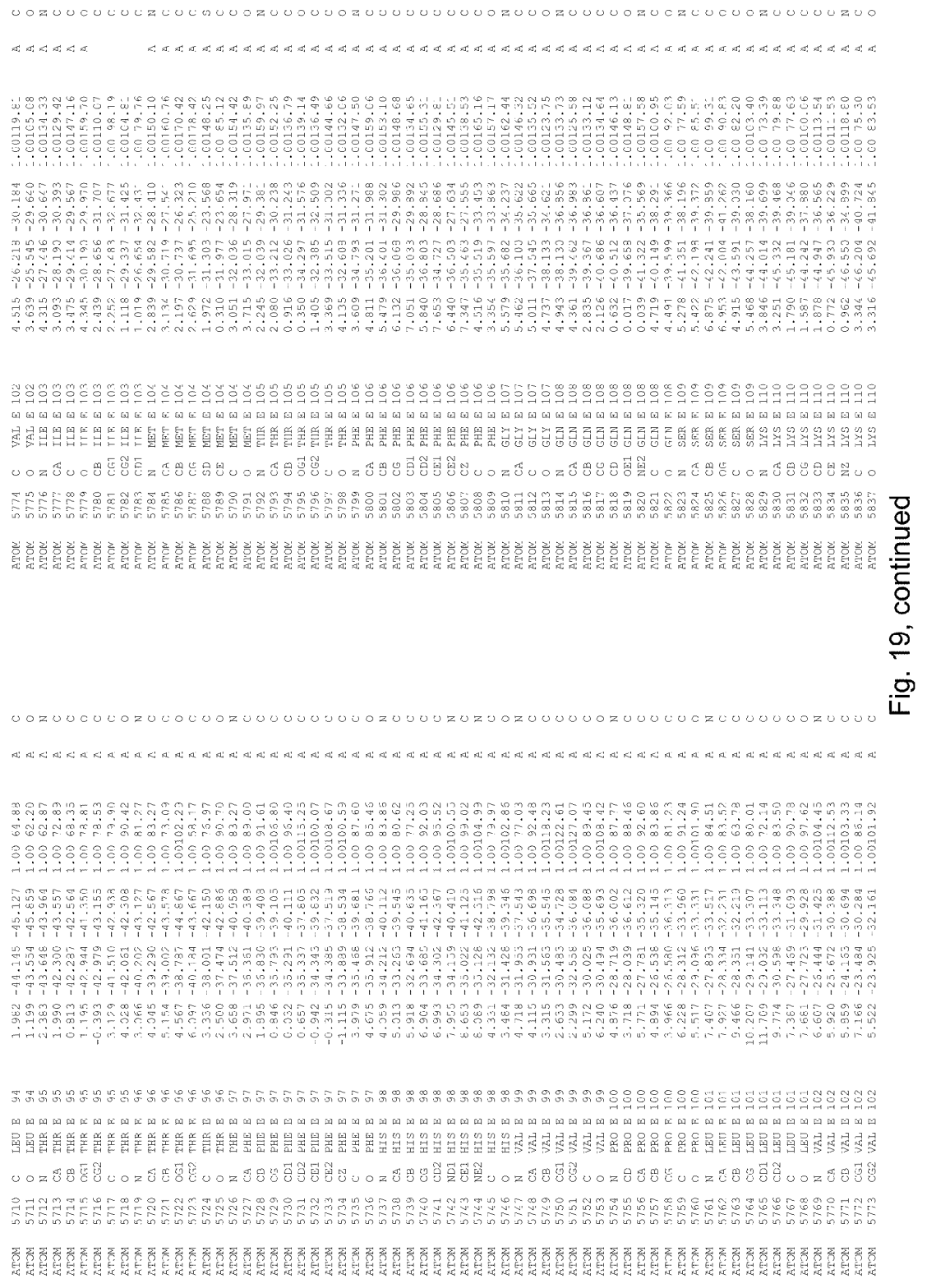
Figure 19:
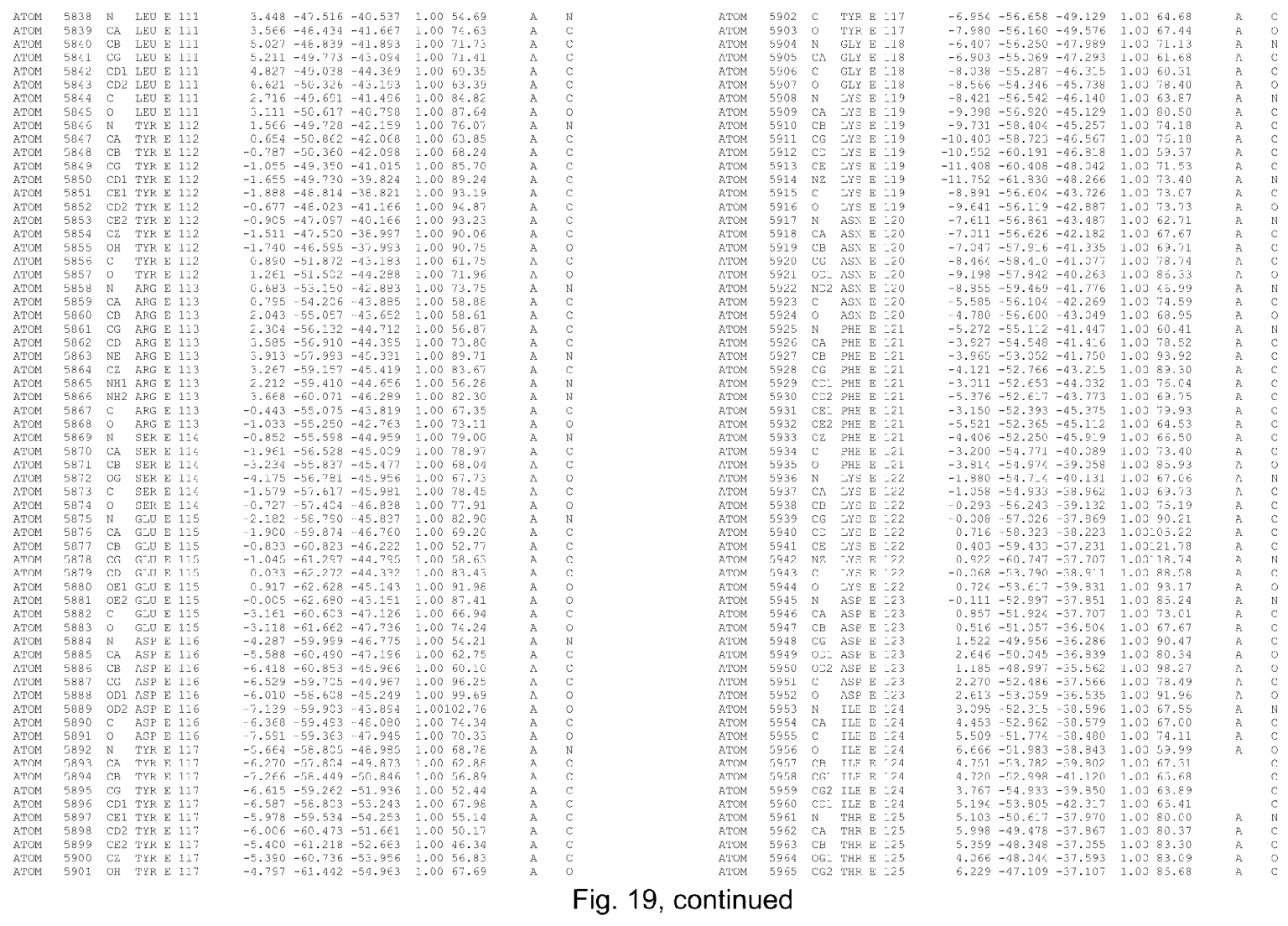
Figure 19:
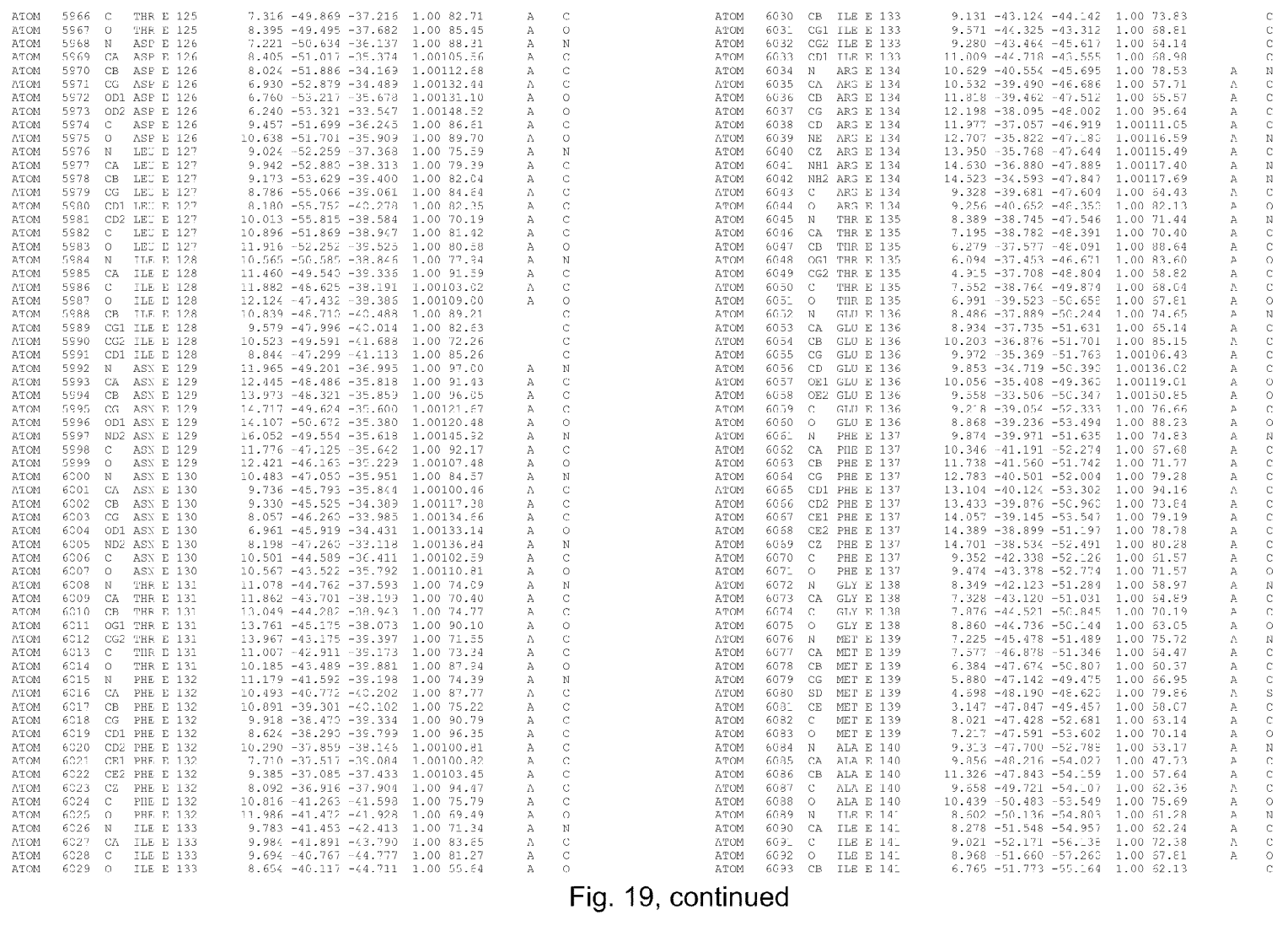
Figure 19:
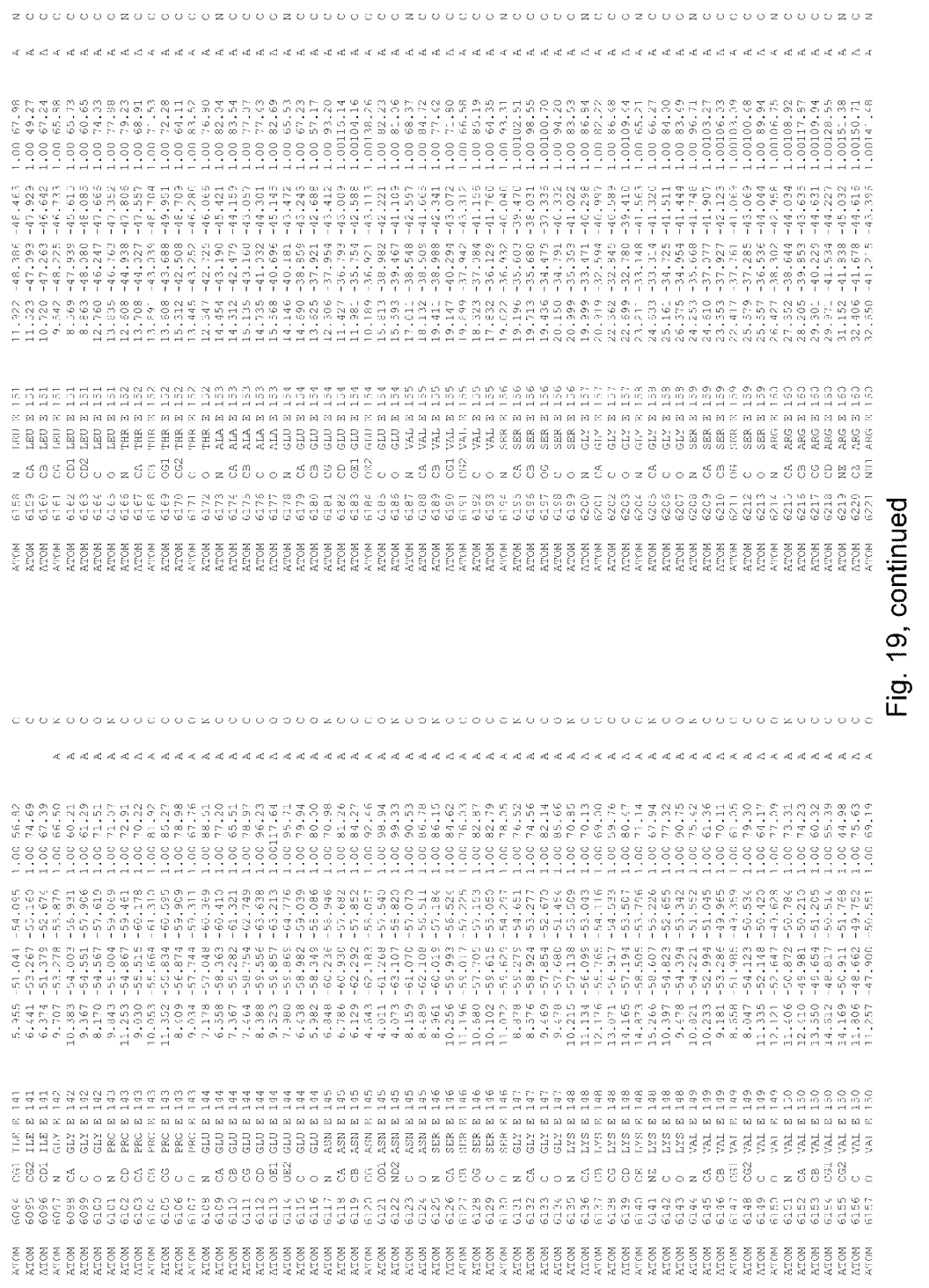
Figure 19:
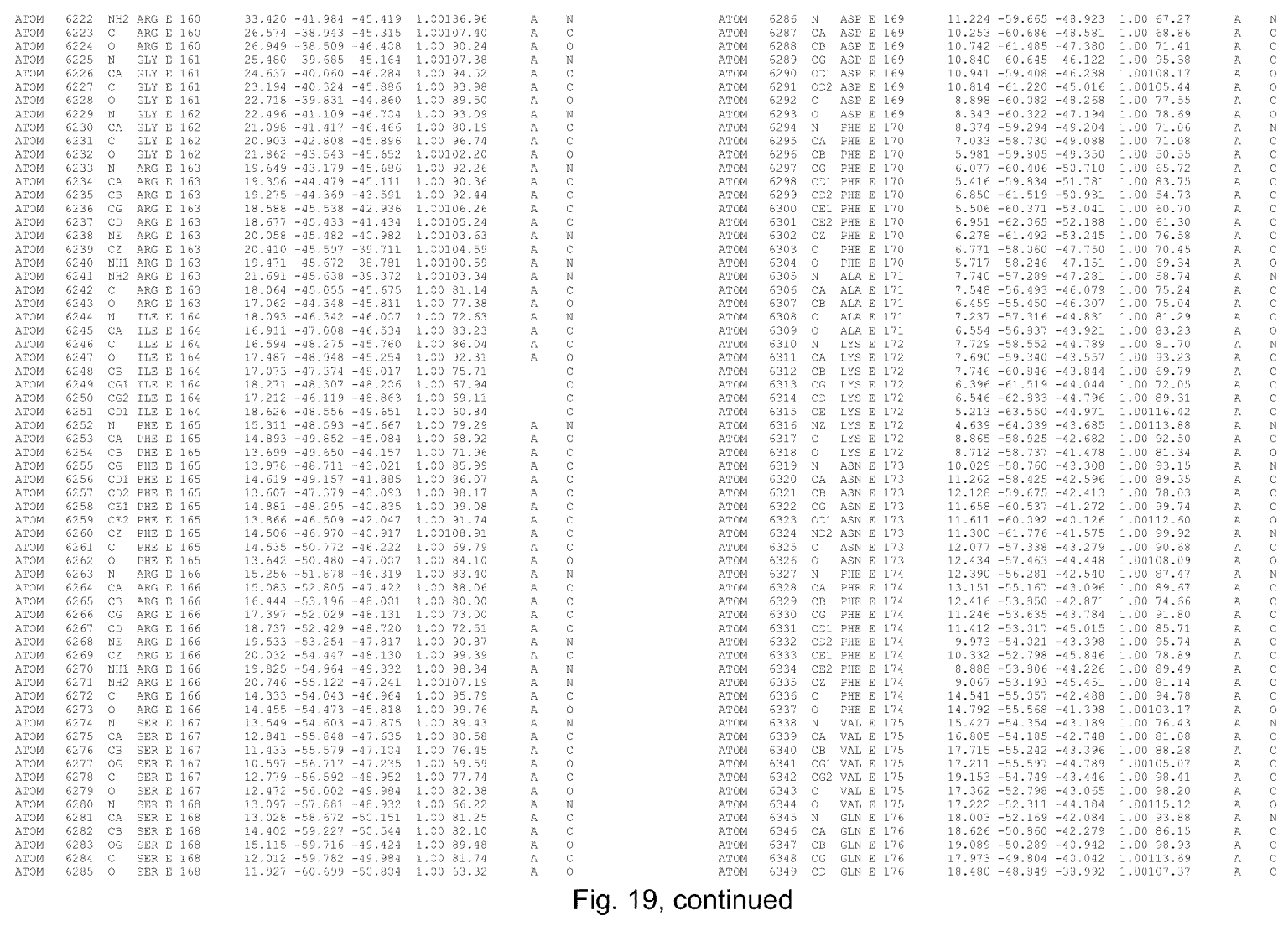
Figure 19:
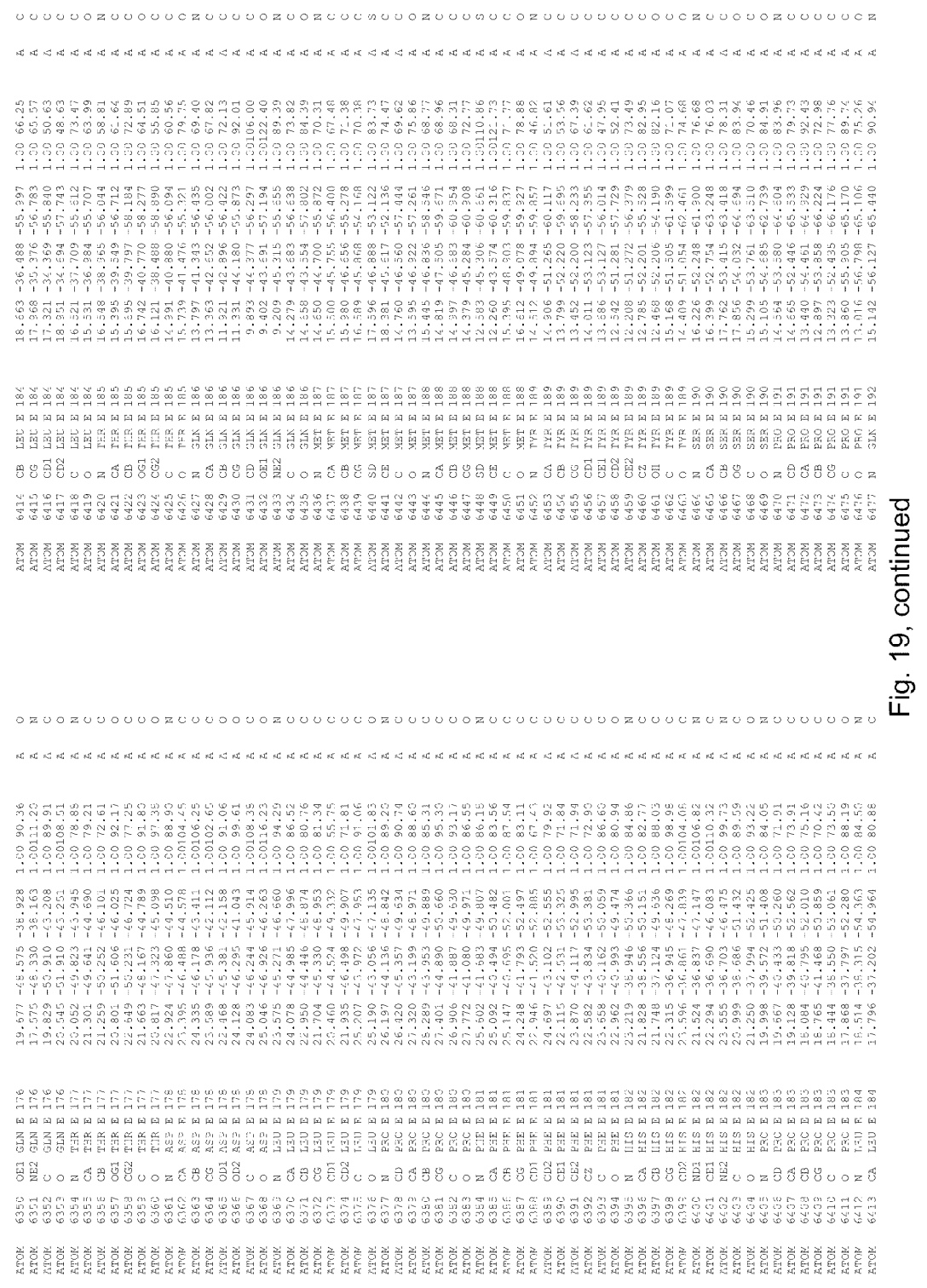
Figure 19:
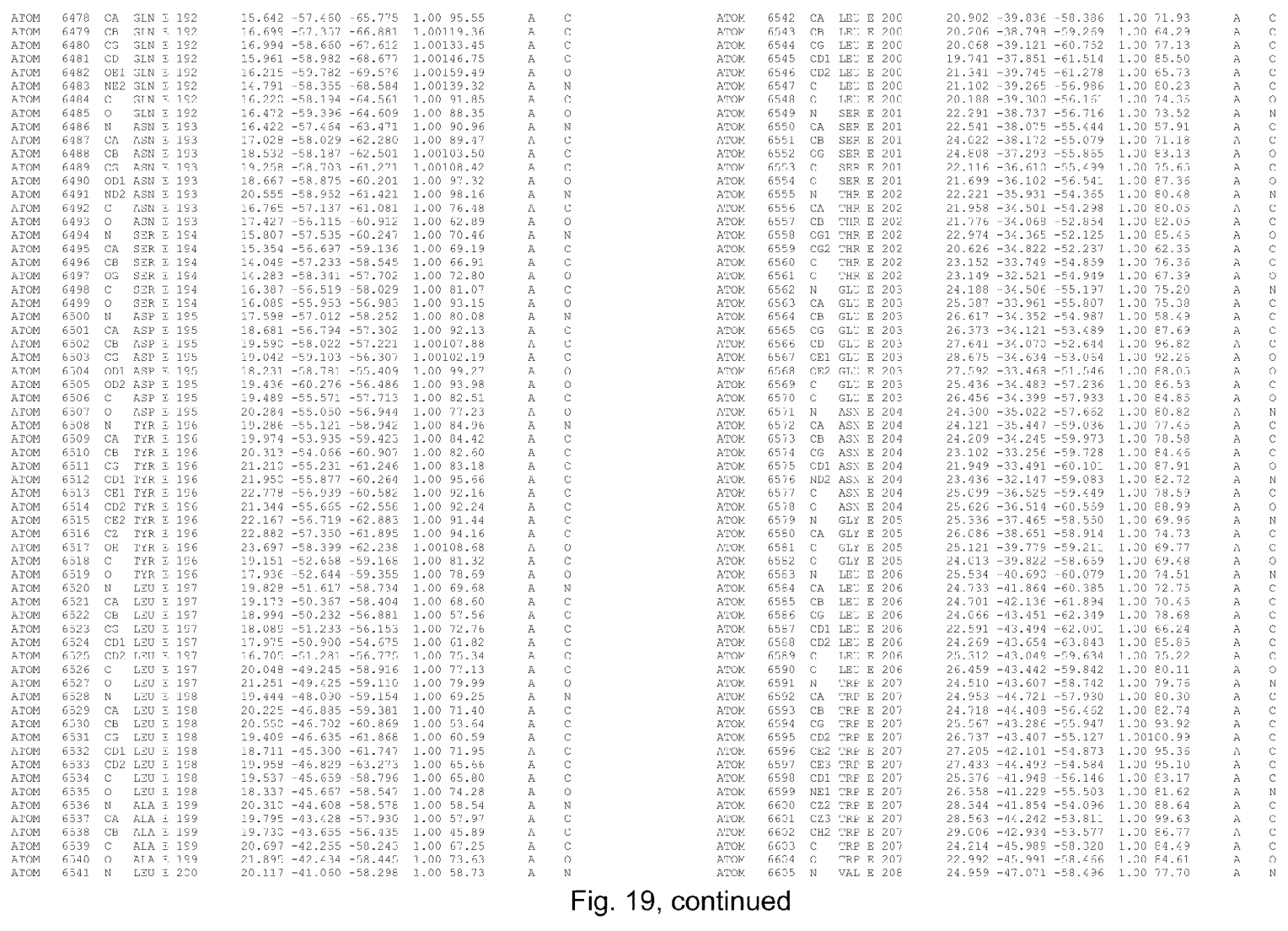
Figure 19:
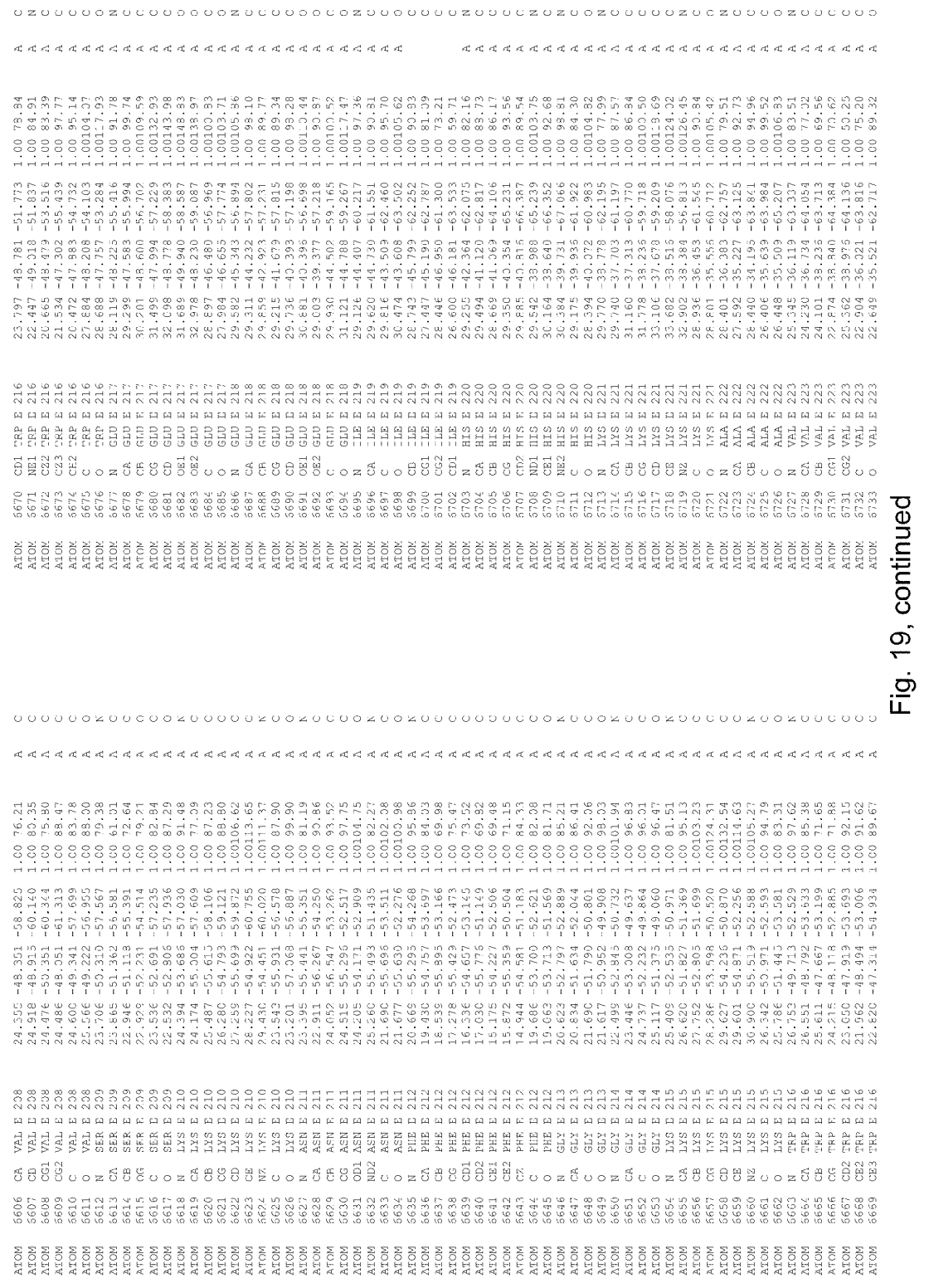
Figure 19:
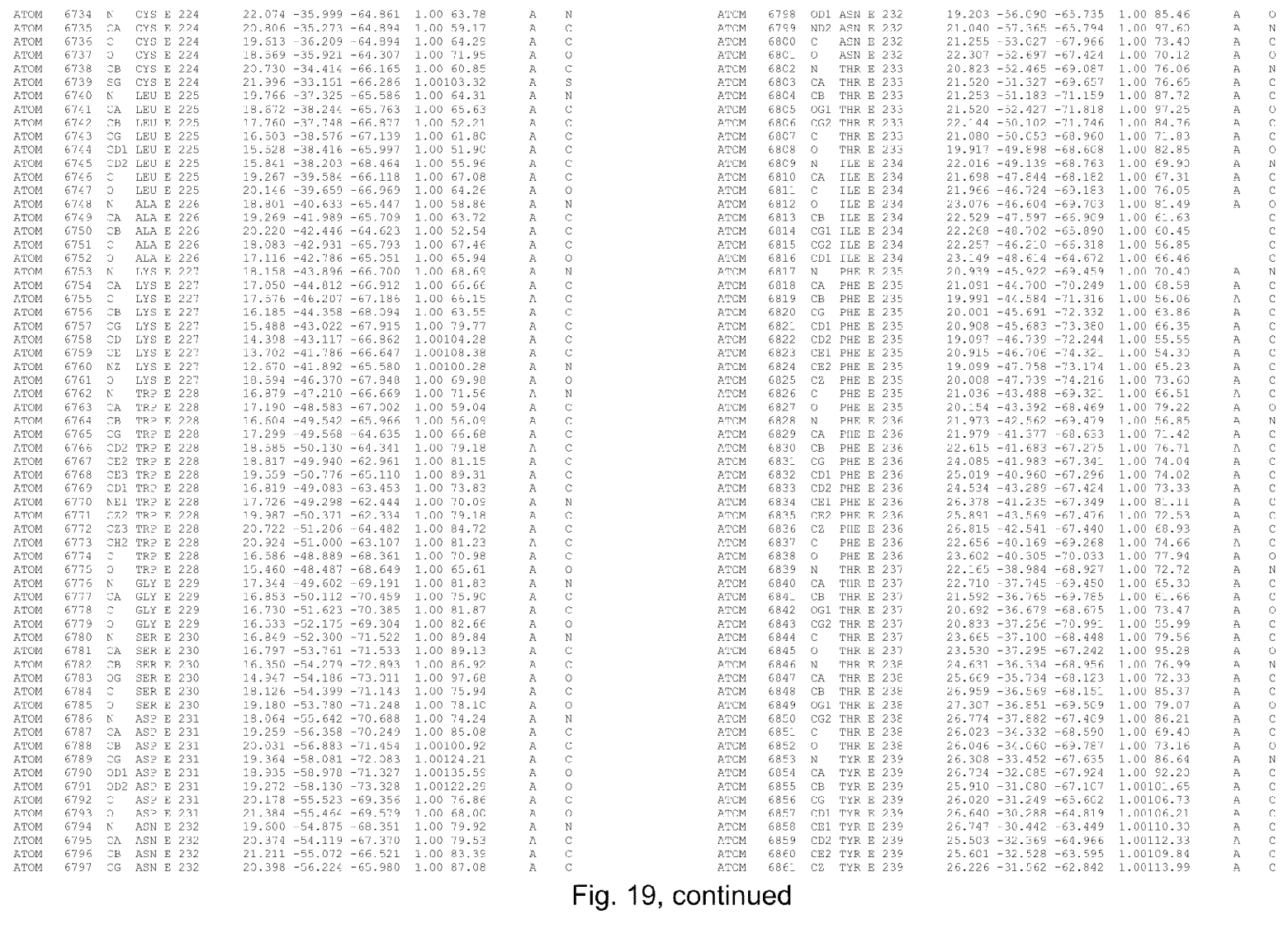
Figure 19:
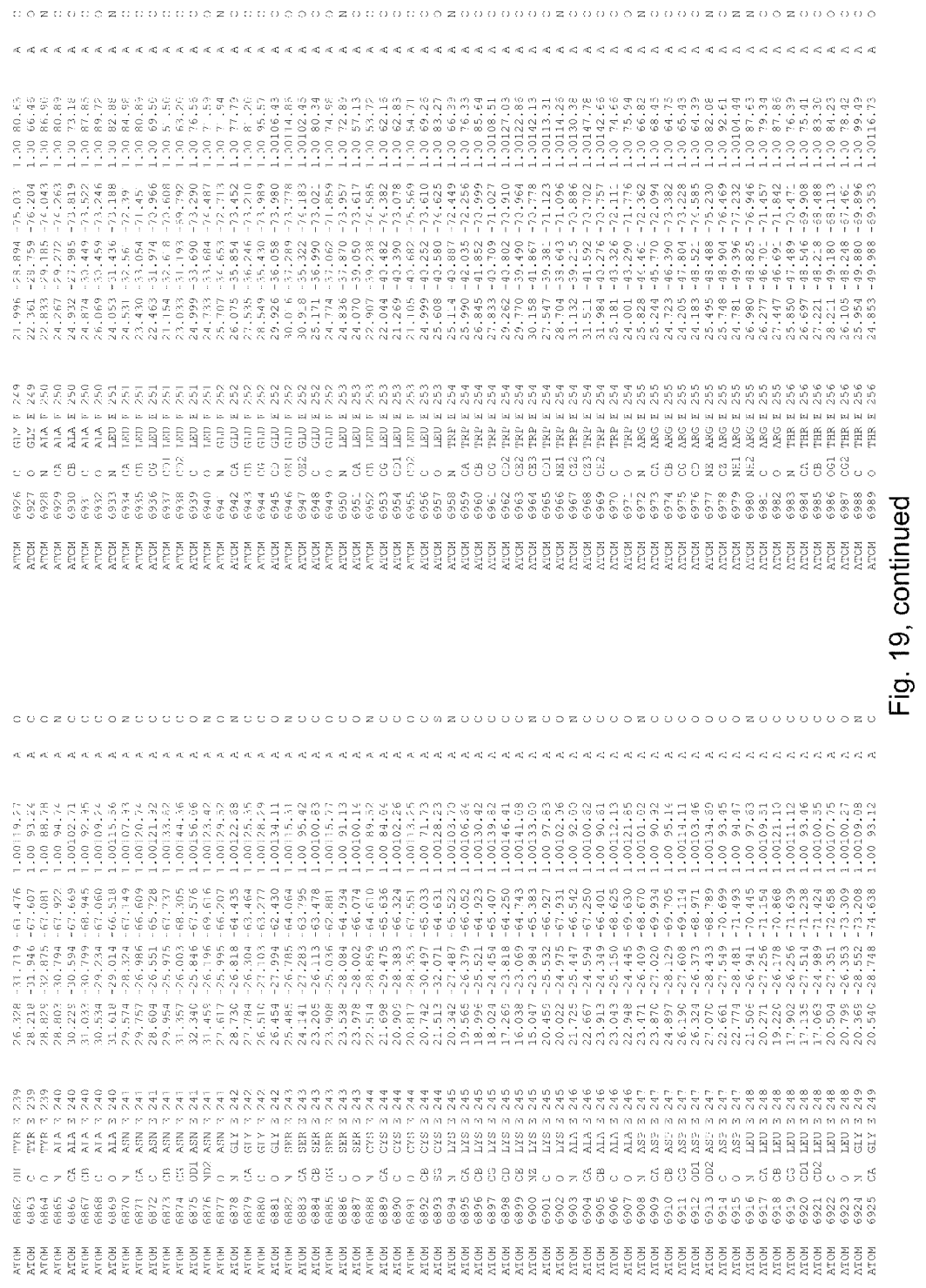
Figure 19:
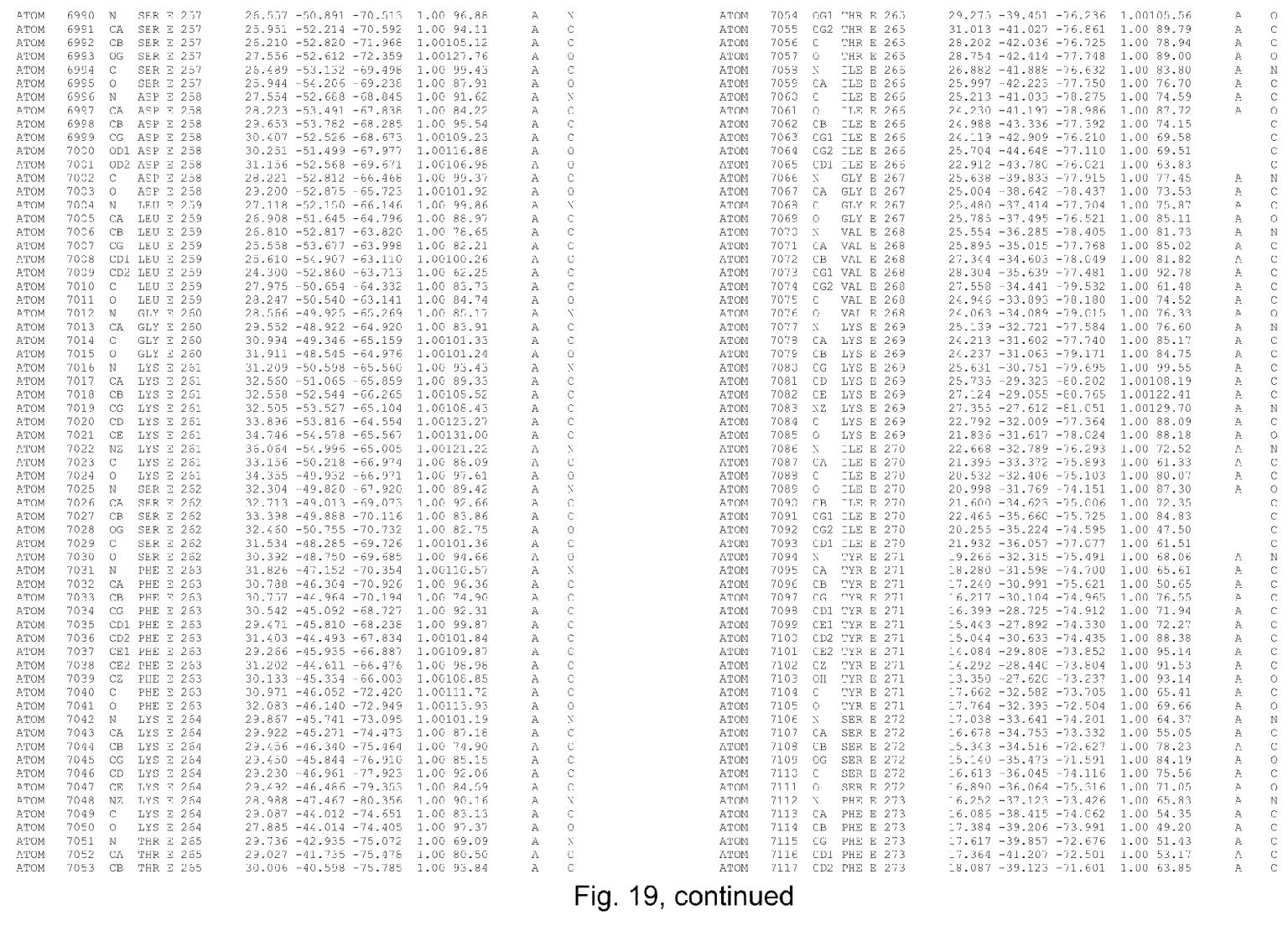
Figure 19:
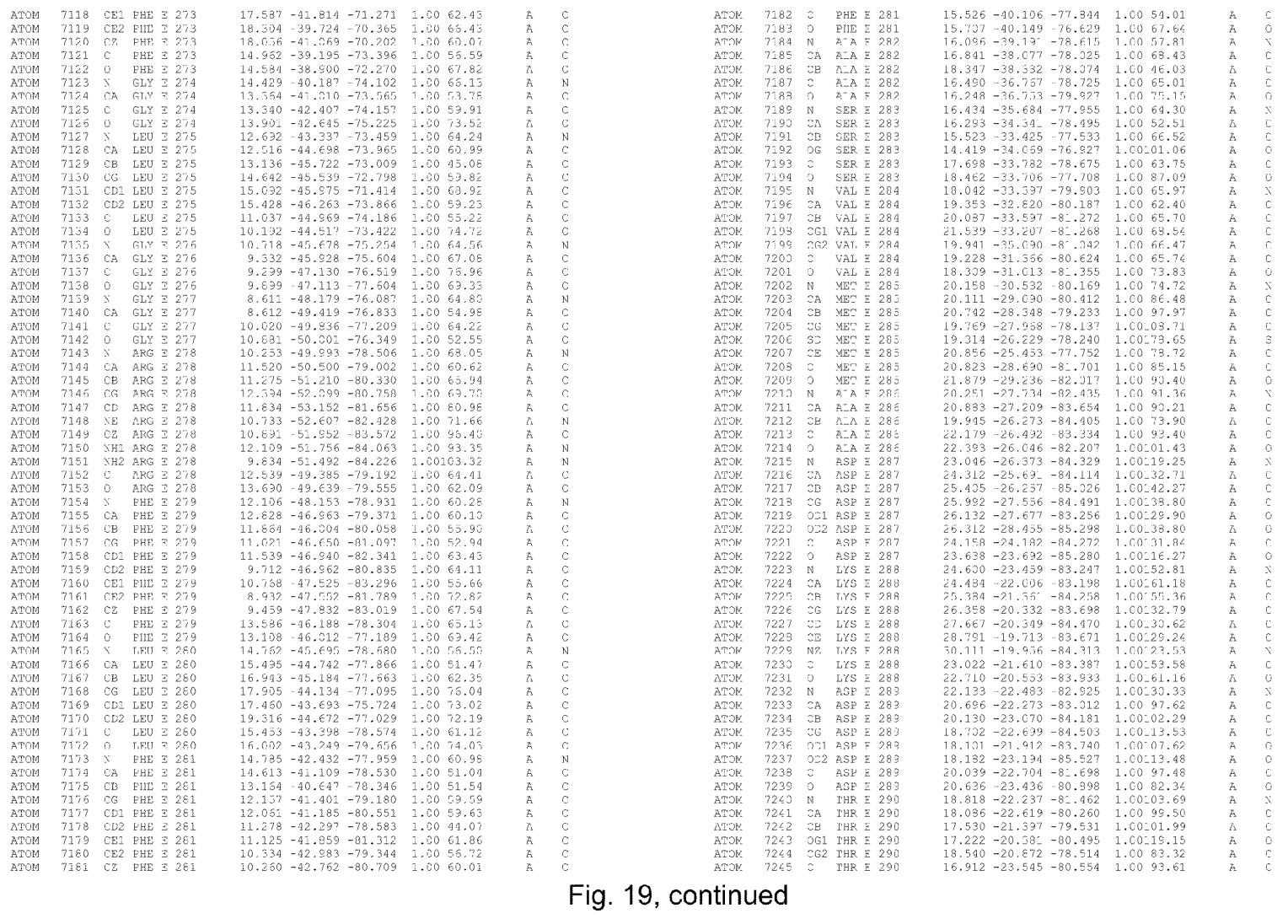
Figure 19:
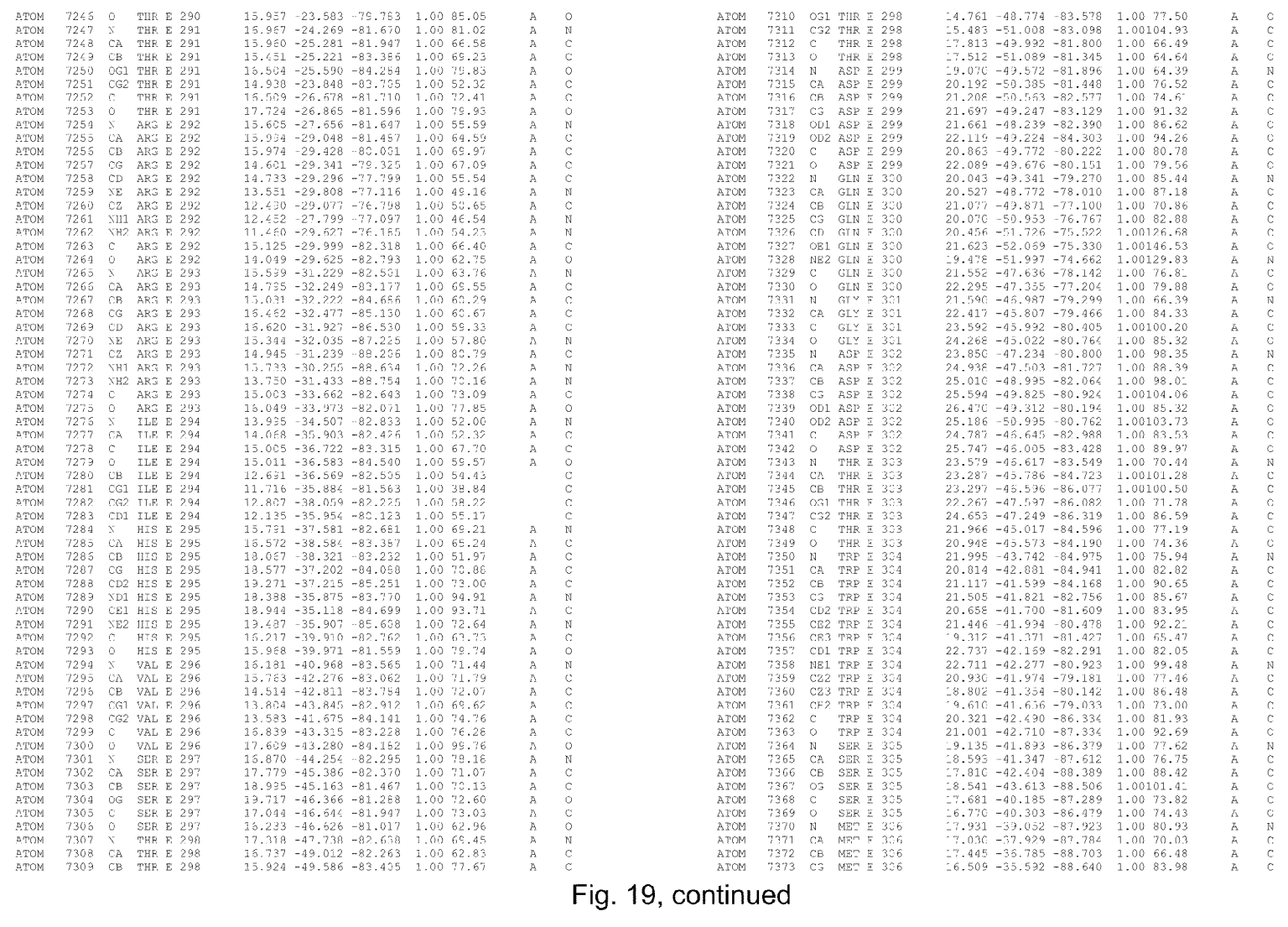
Figure 19:
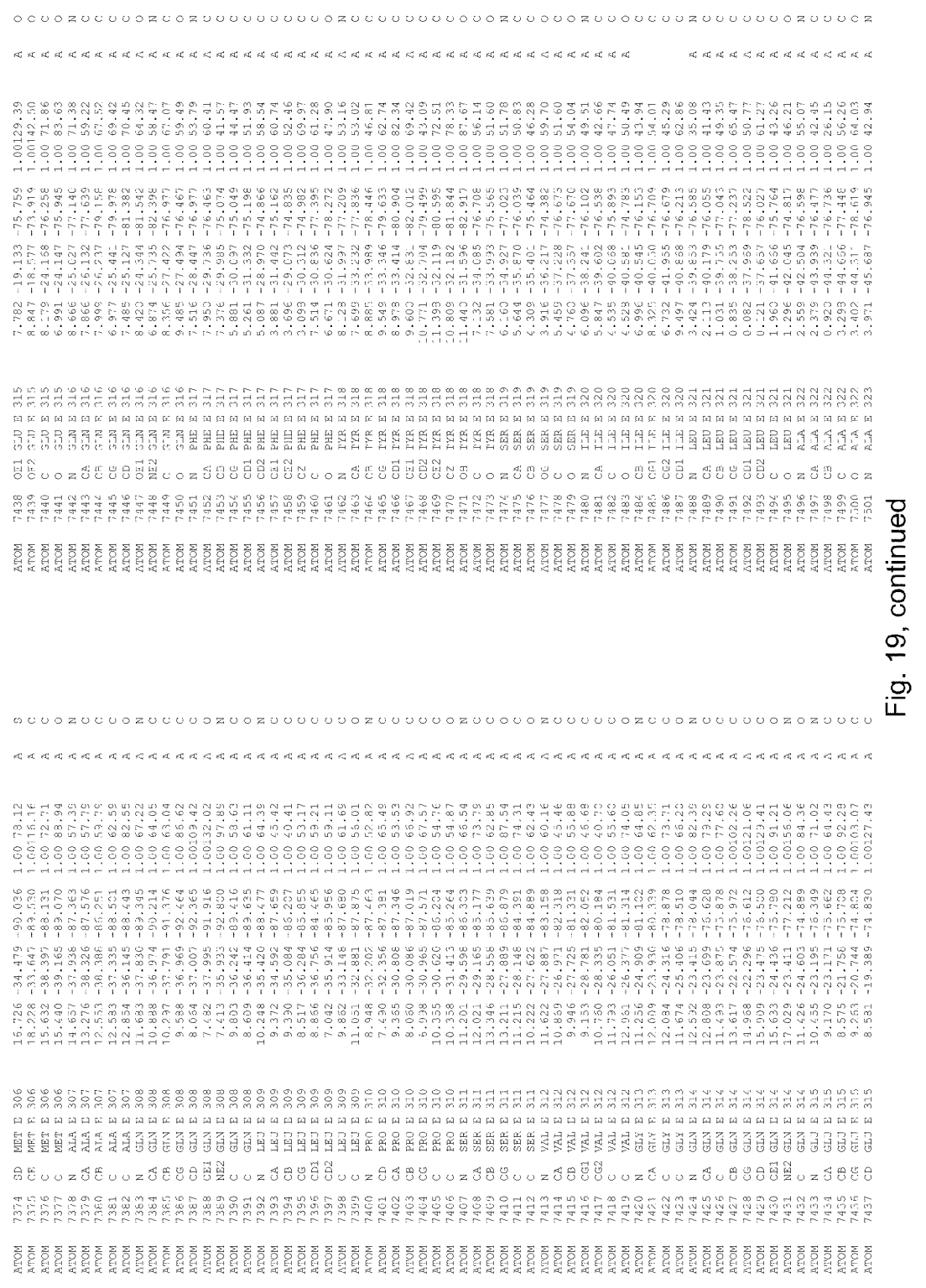
Figure 19:
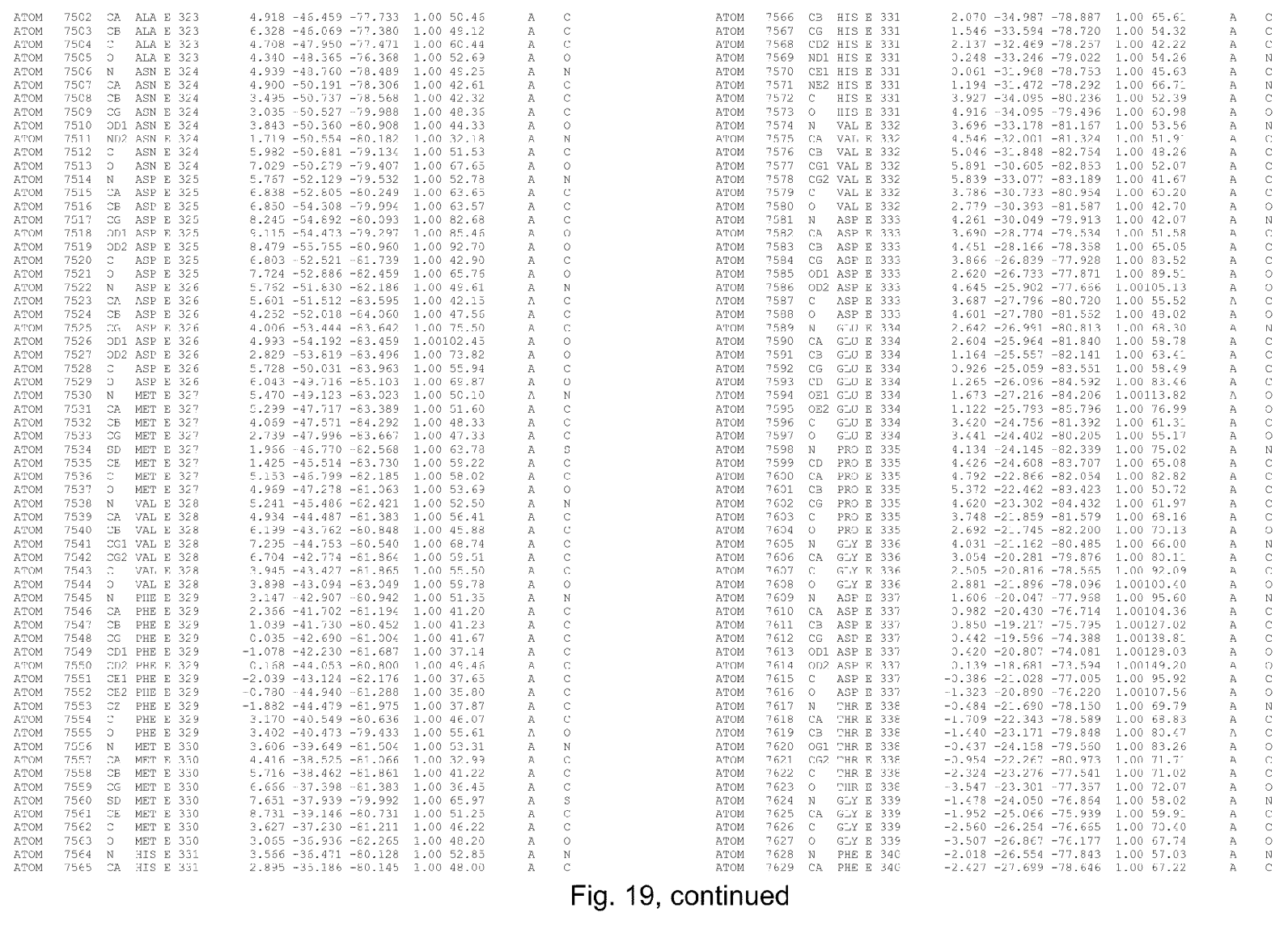
Figure 19:
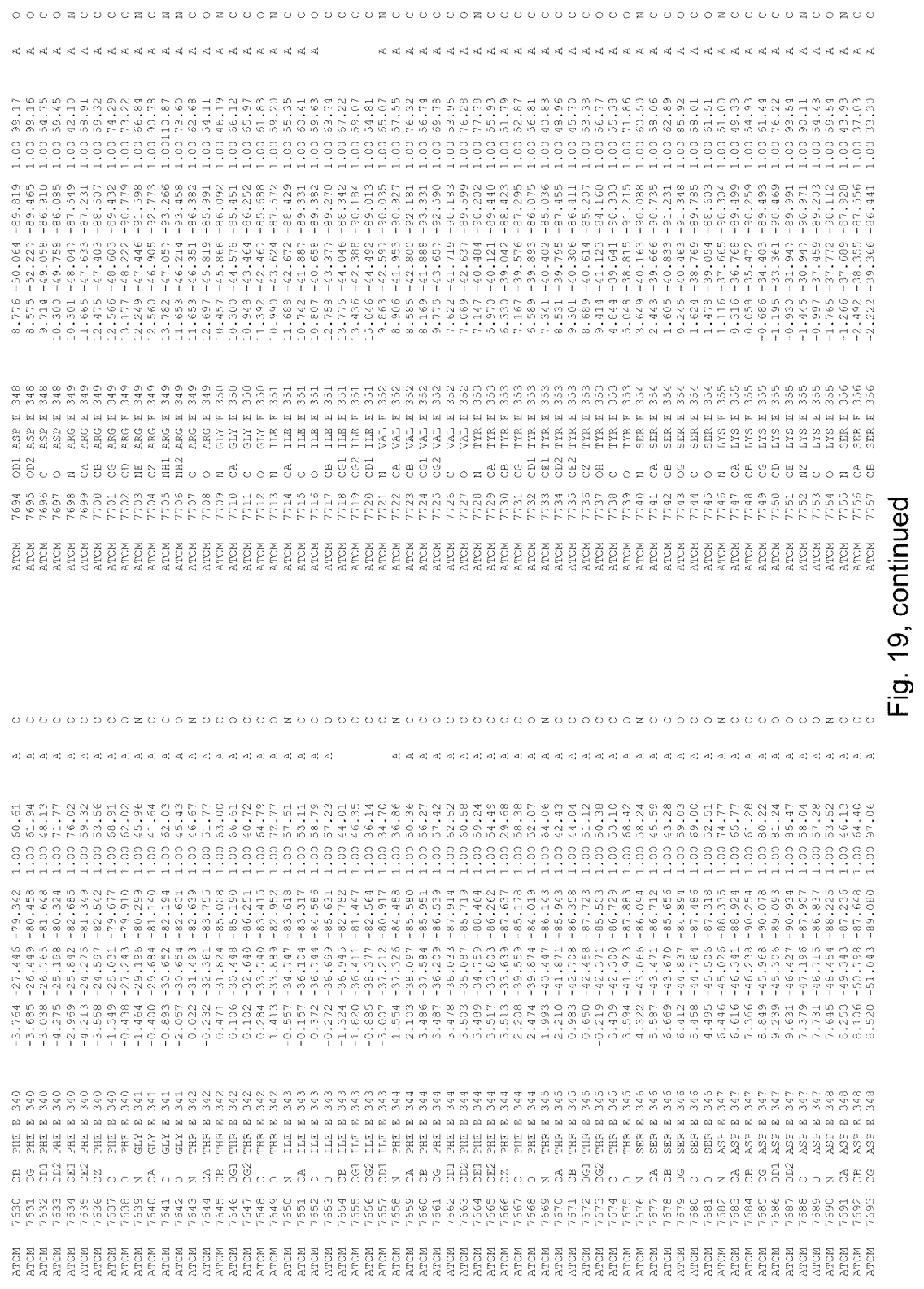
Figure 19:
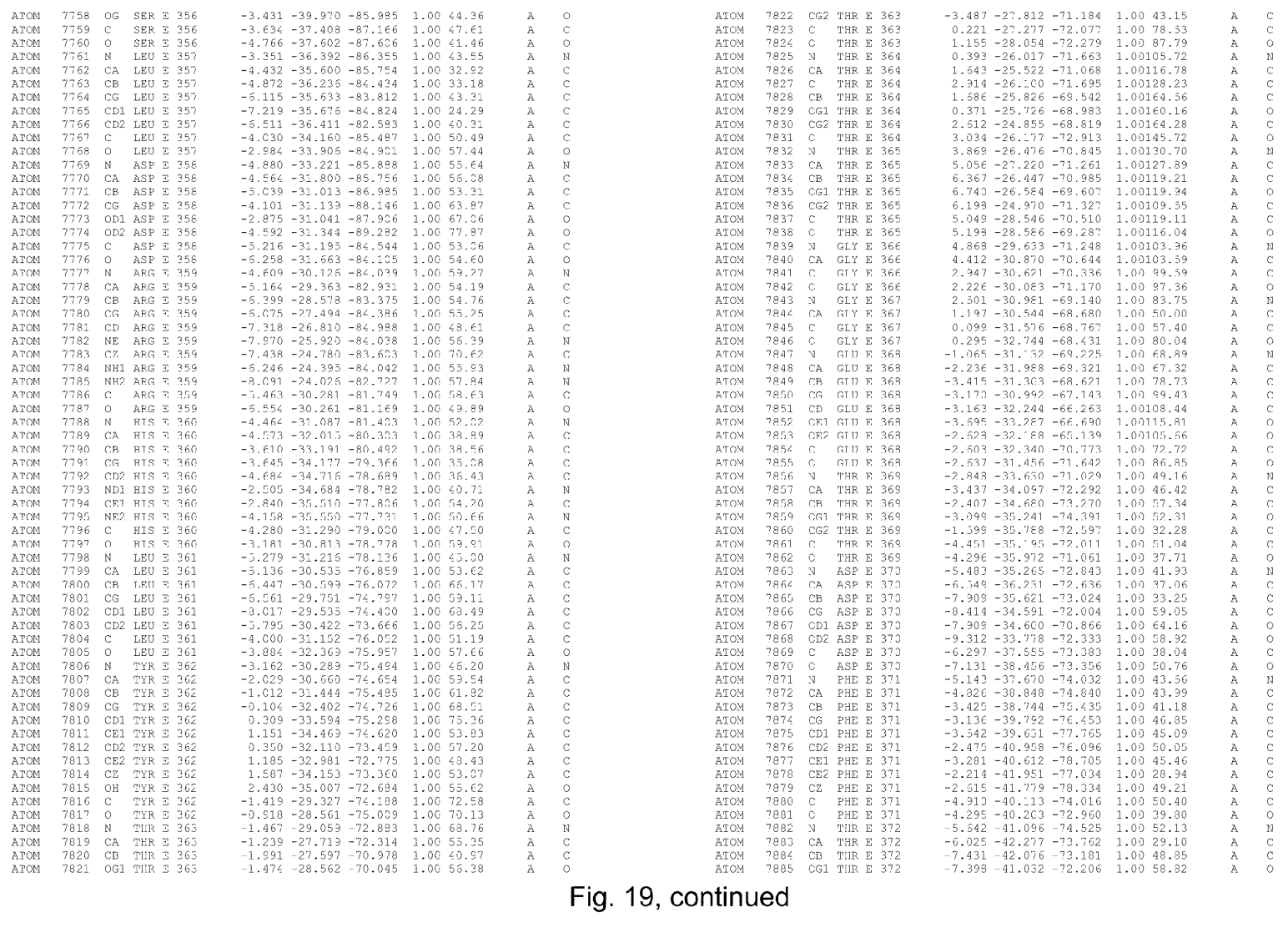
Figure 19:
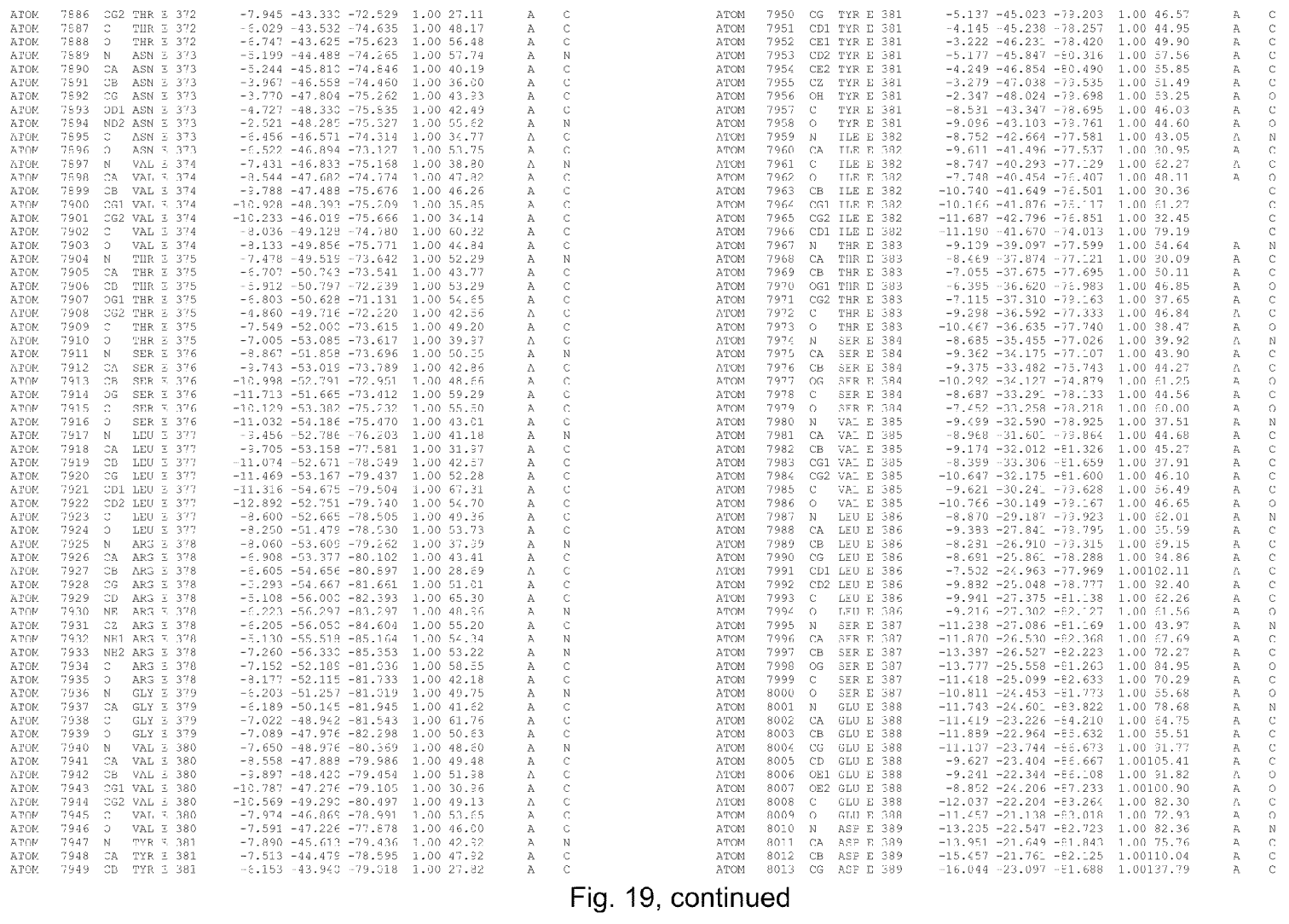
Figure 19:
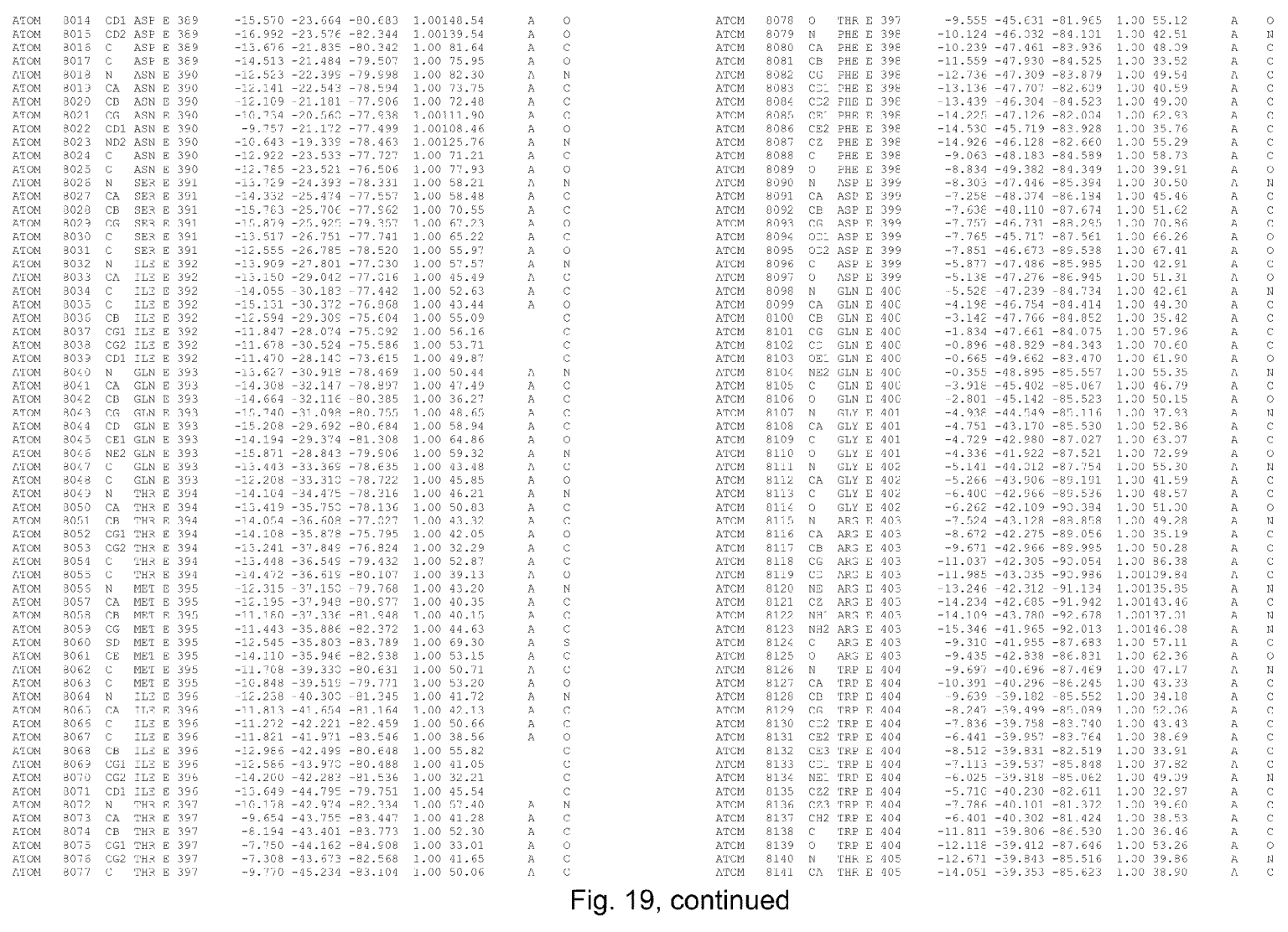
Figure 19:
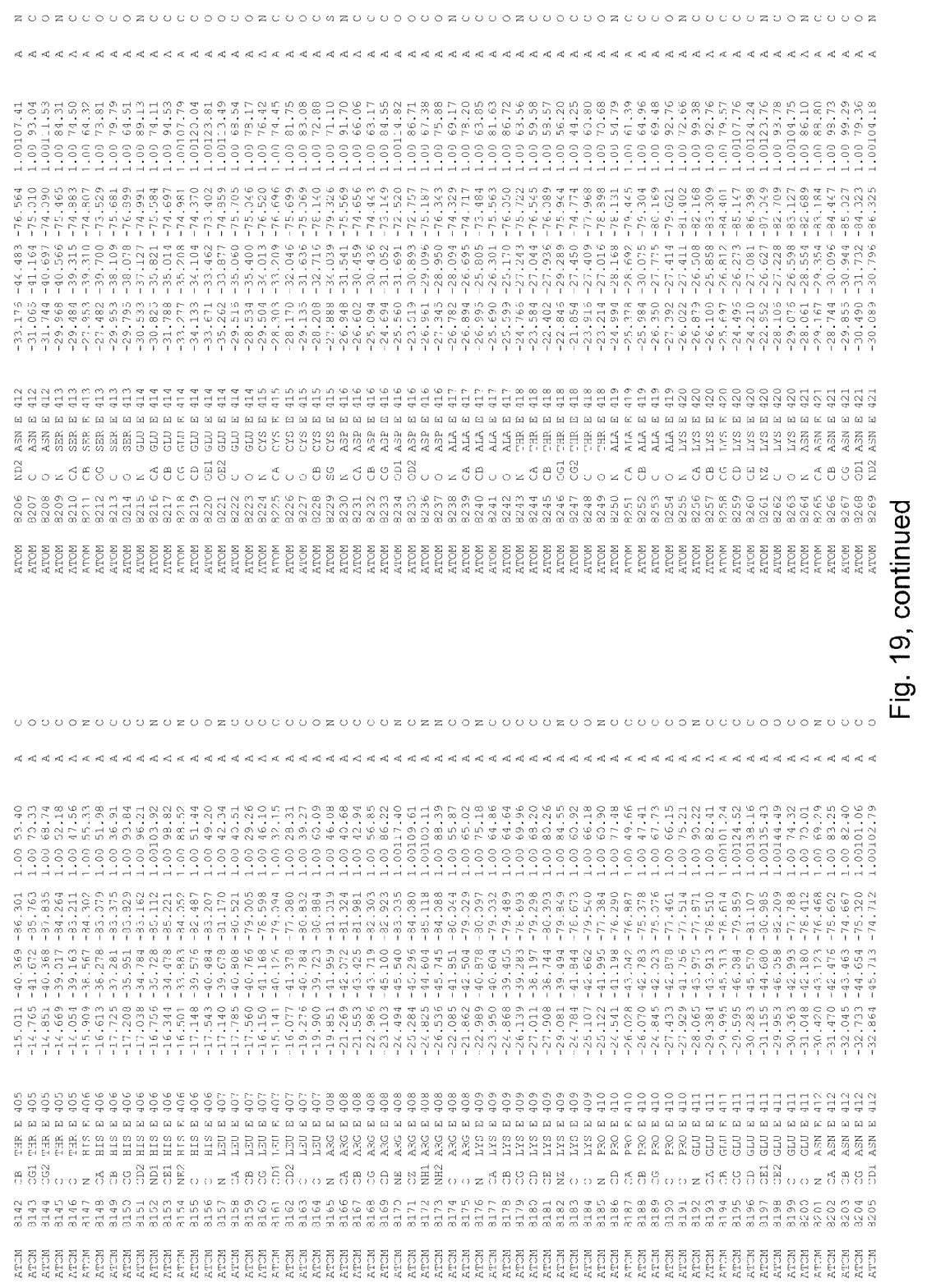
Figure 19:
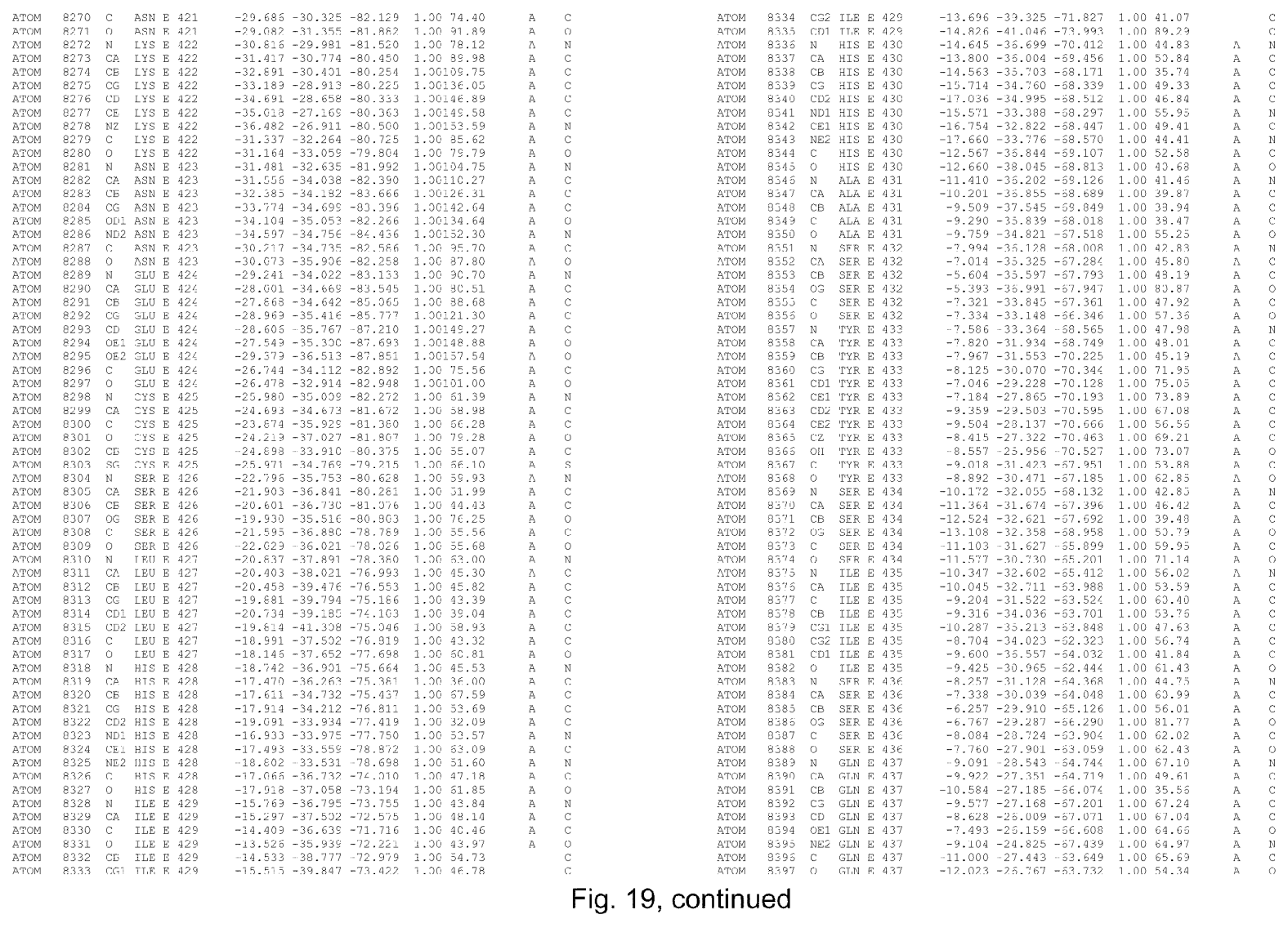
Figure 19:
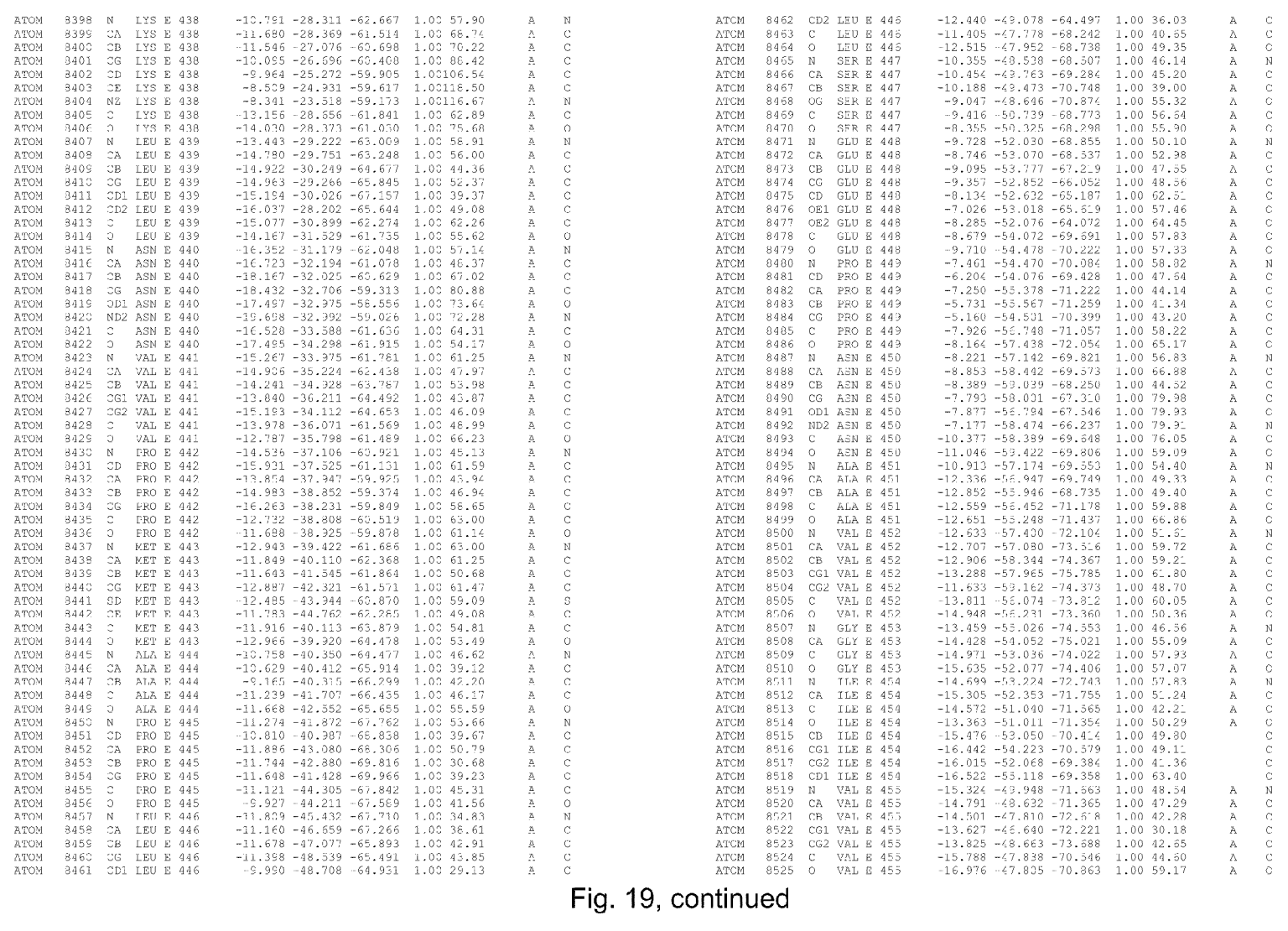
Figure 19:
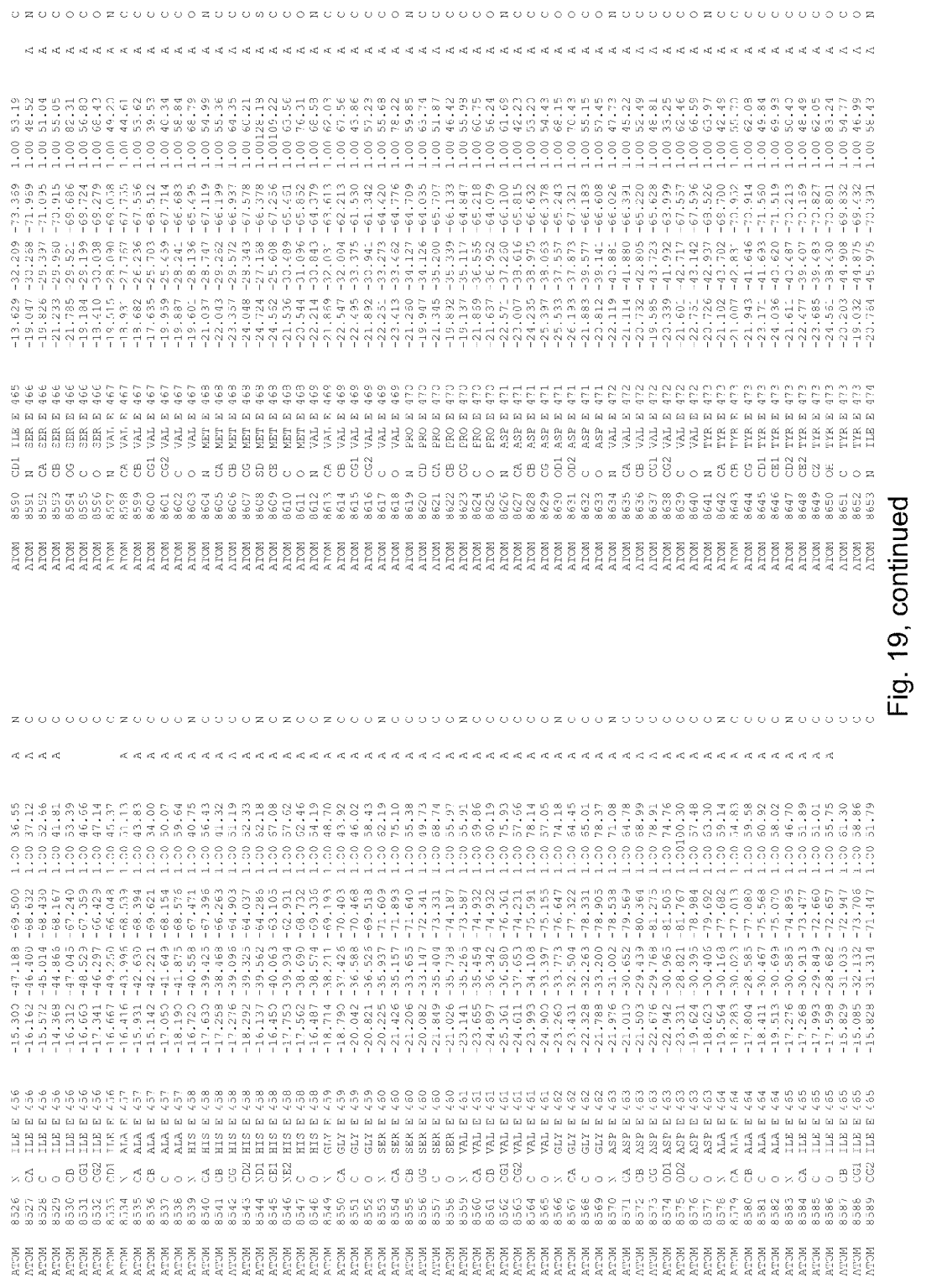
Figure 19:
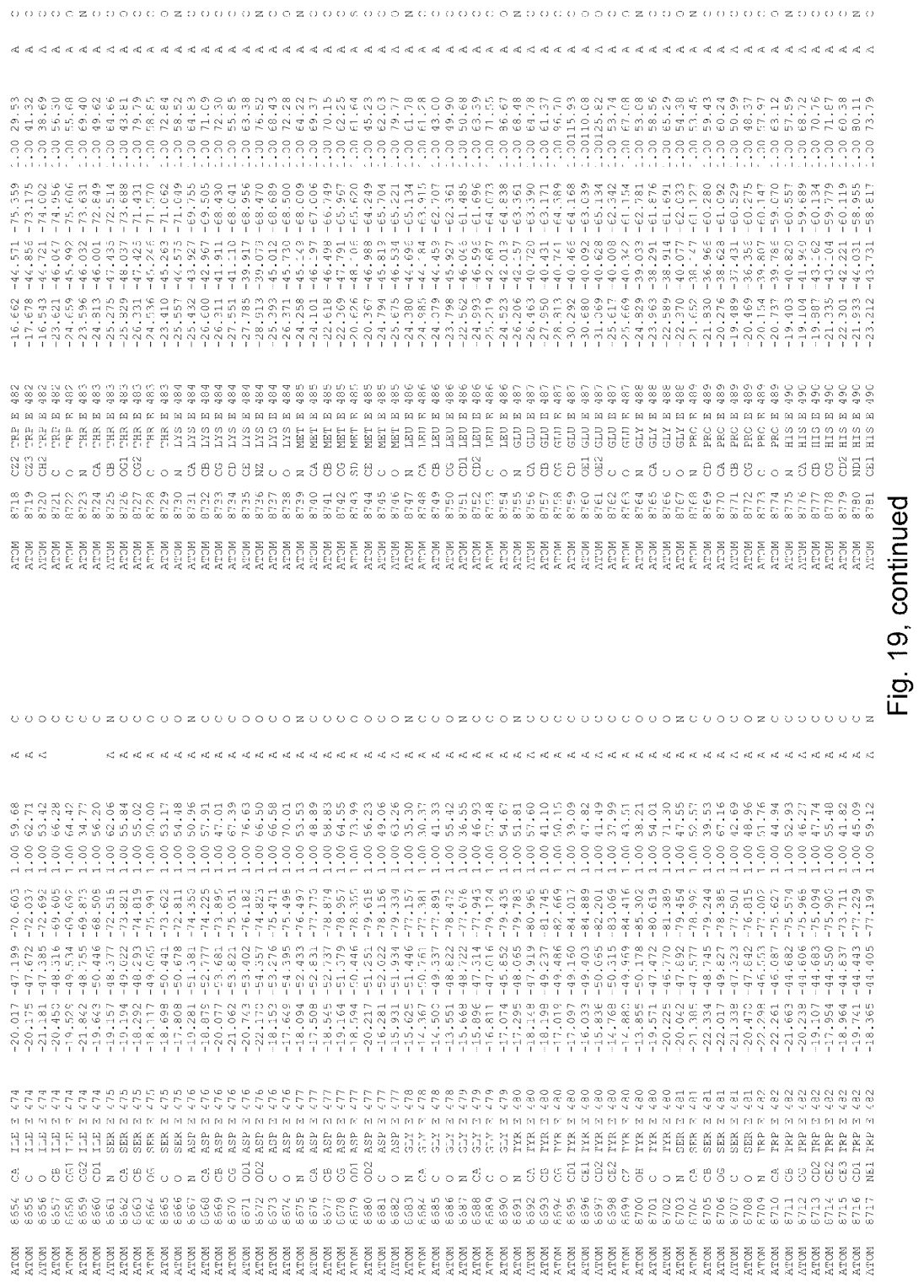
Figure 19:
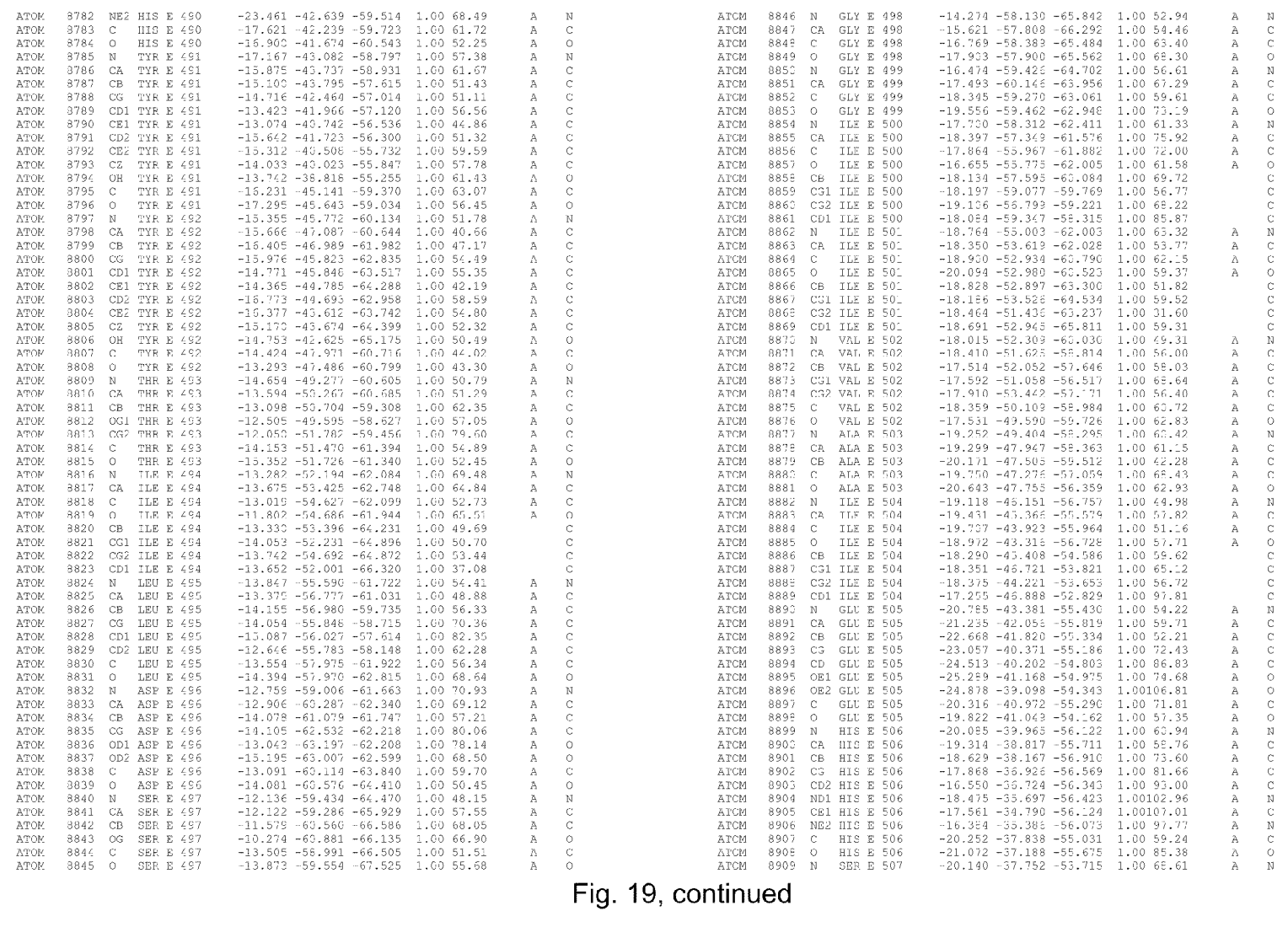
Figure 19:
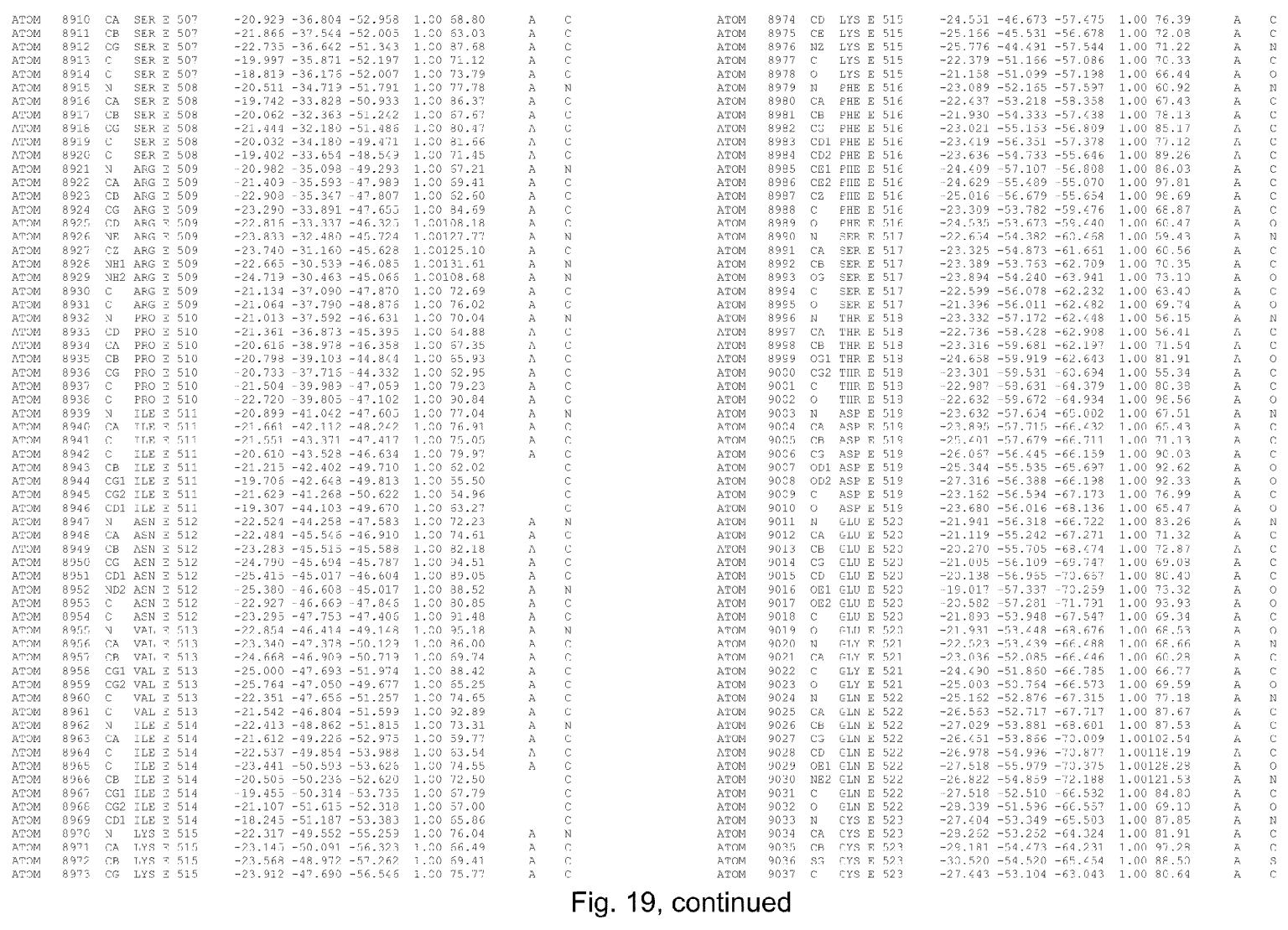
Figure 19:
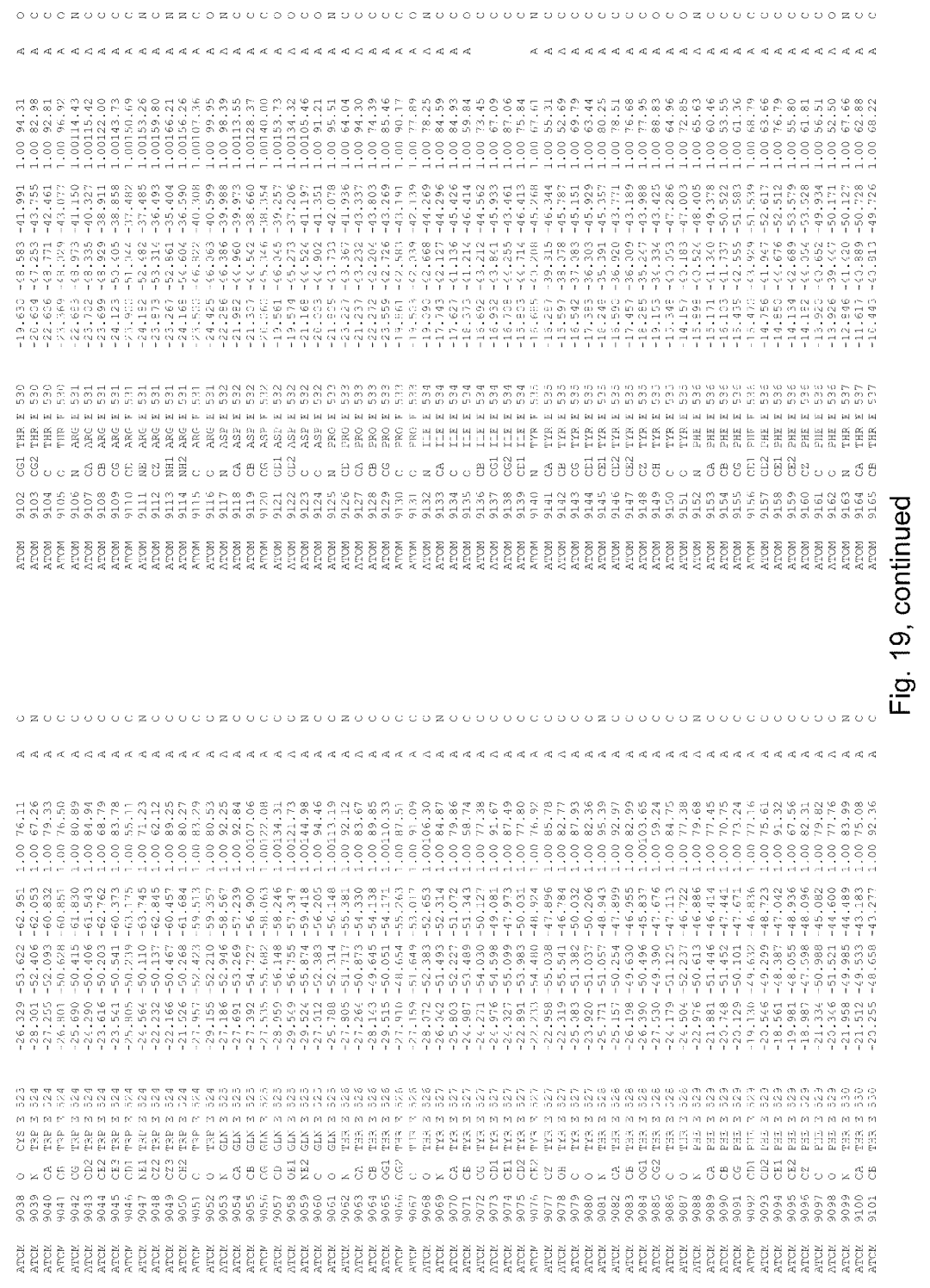
Figure 19:
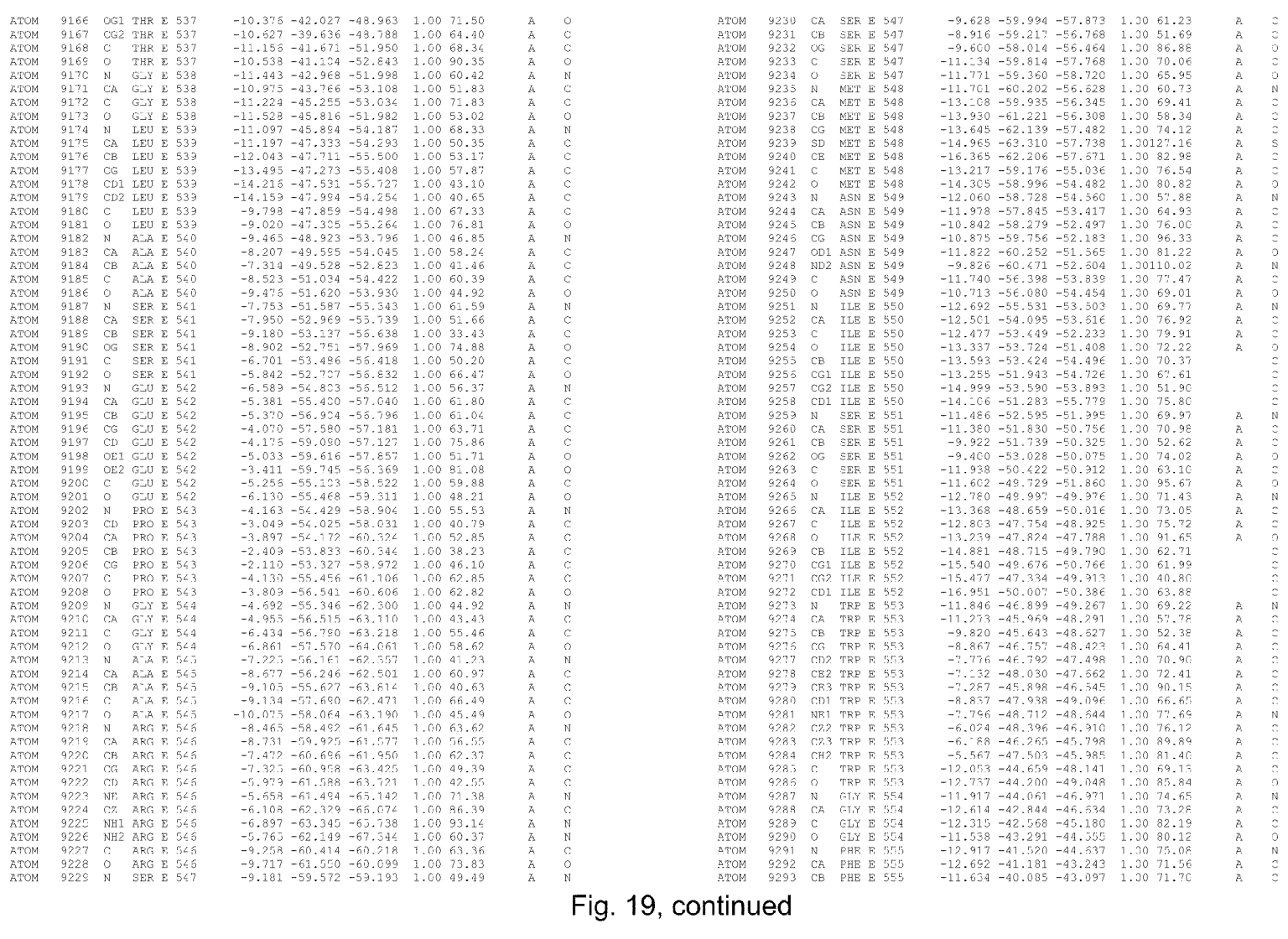
Figure 19:
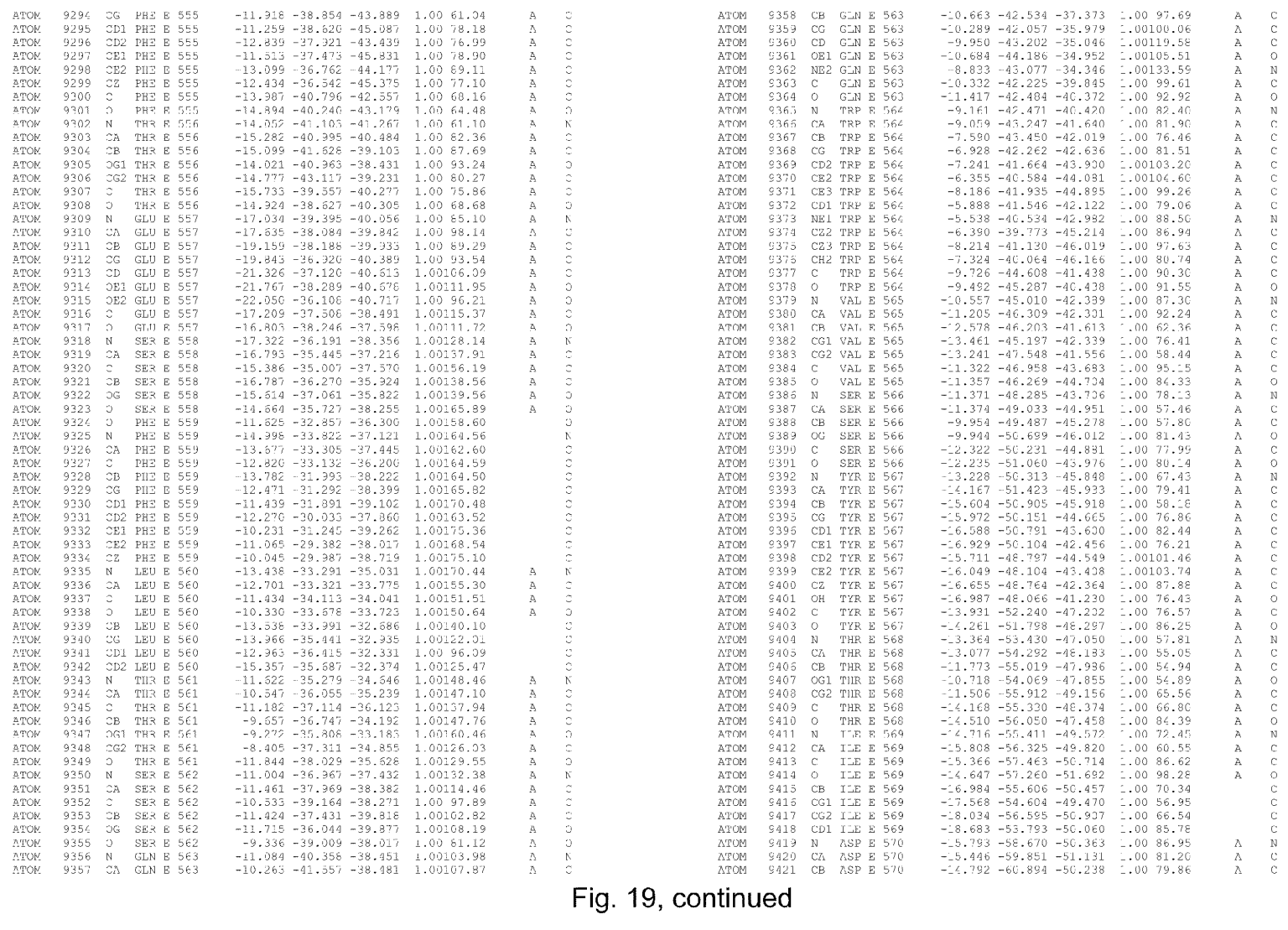
Figure 19:
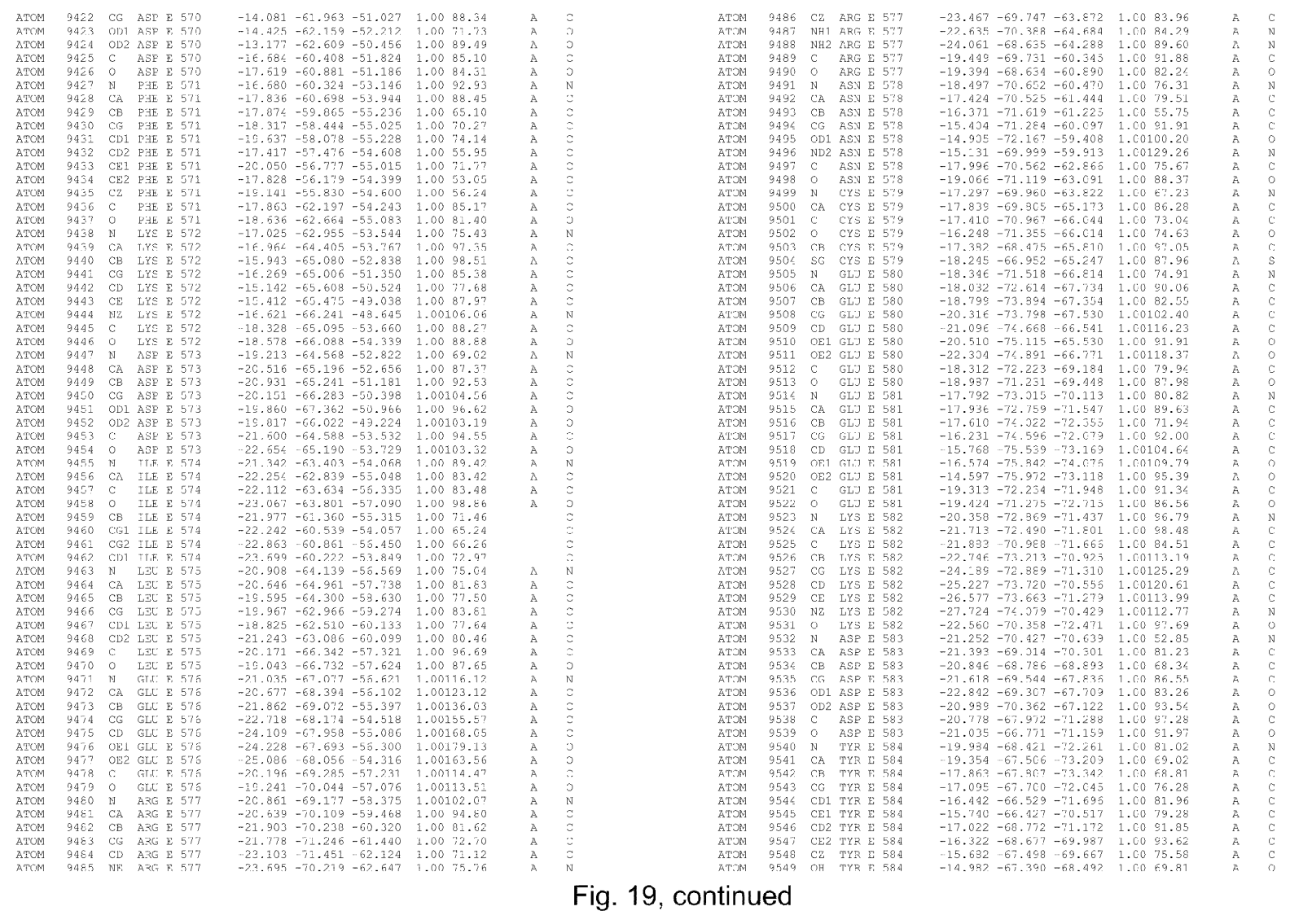
Figure 19:
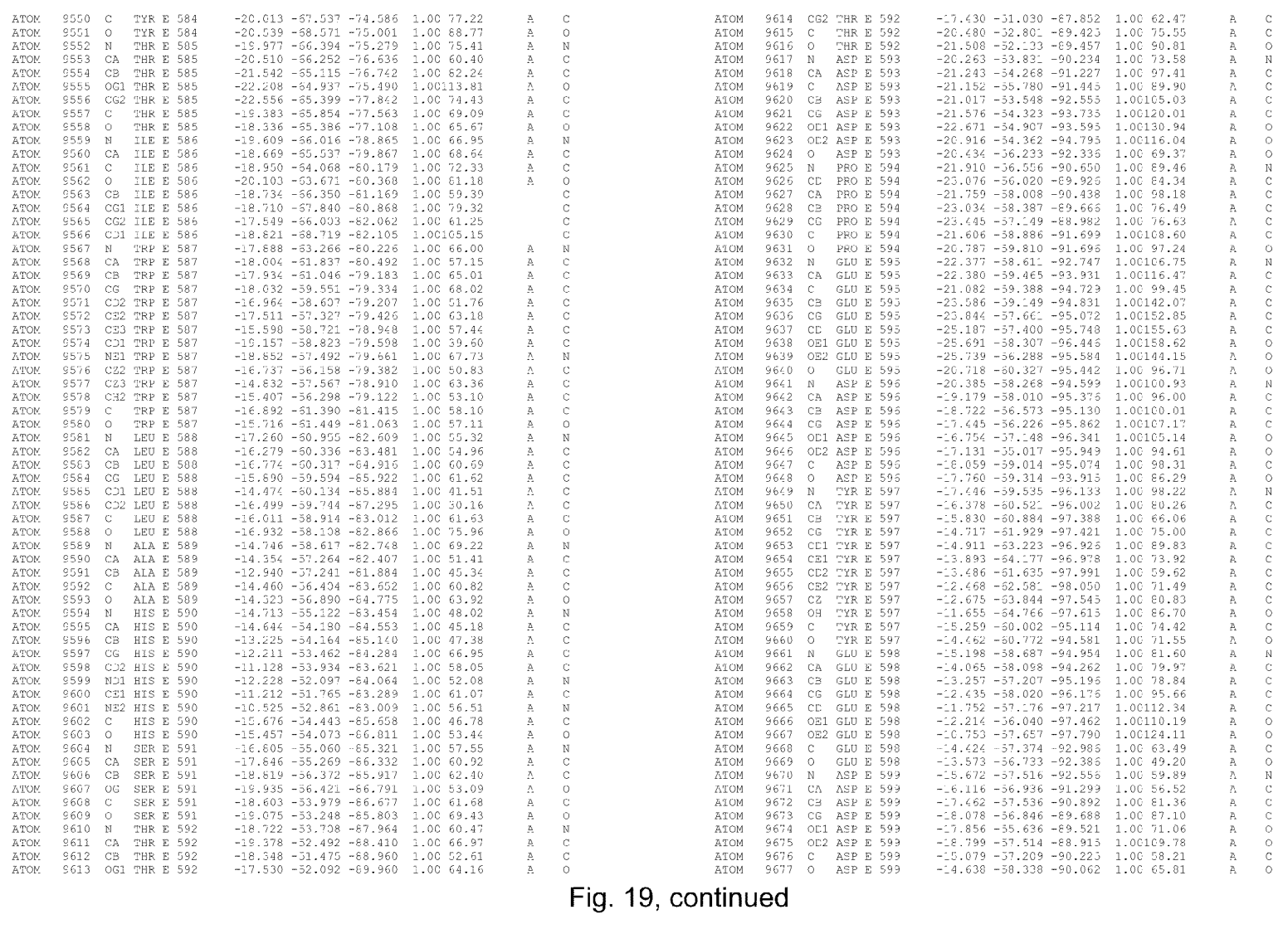
Figure 19:
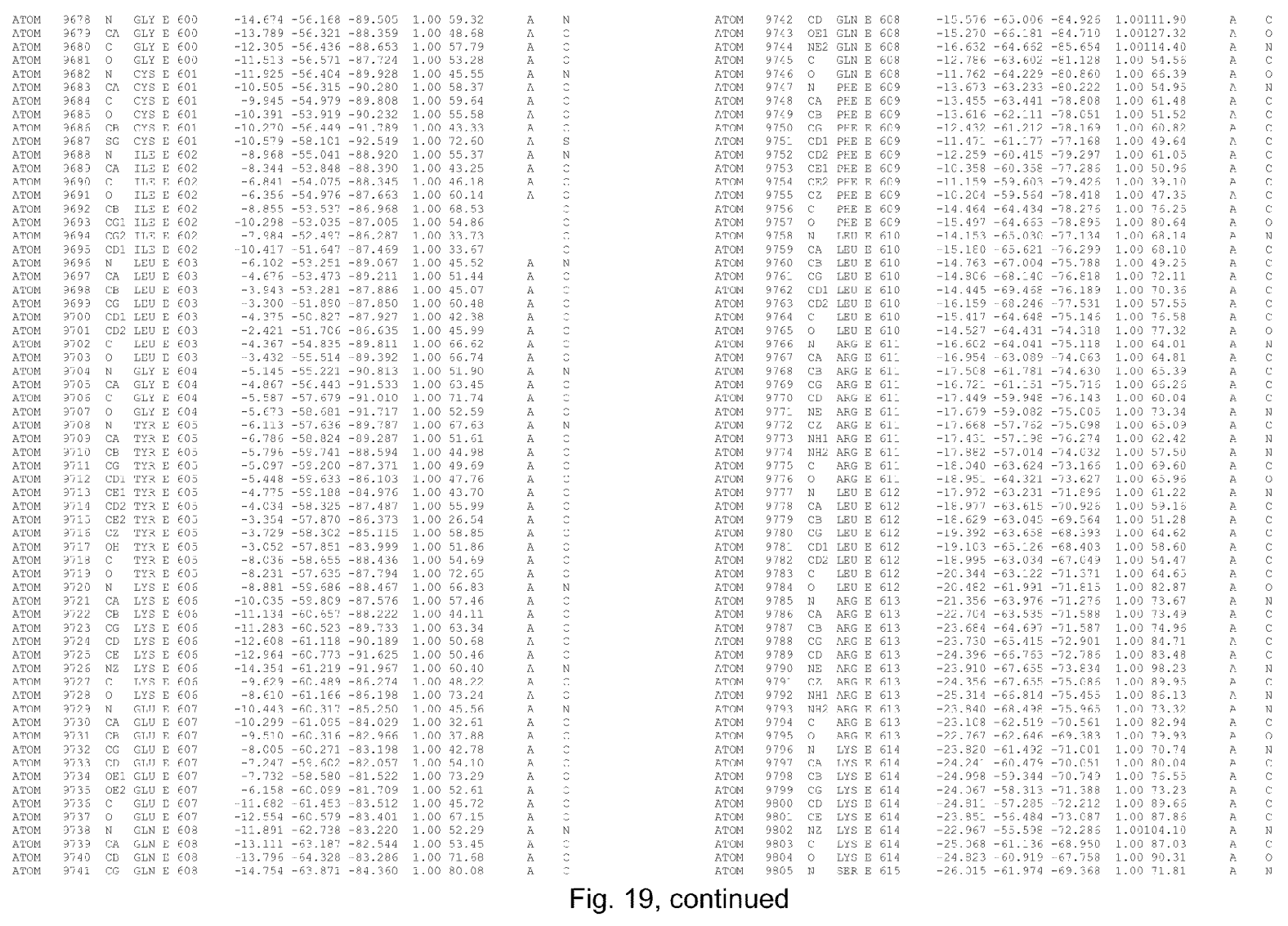
Figure 19:
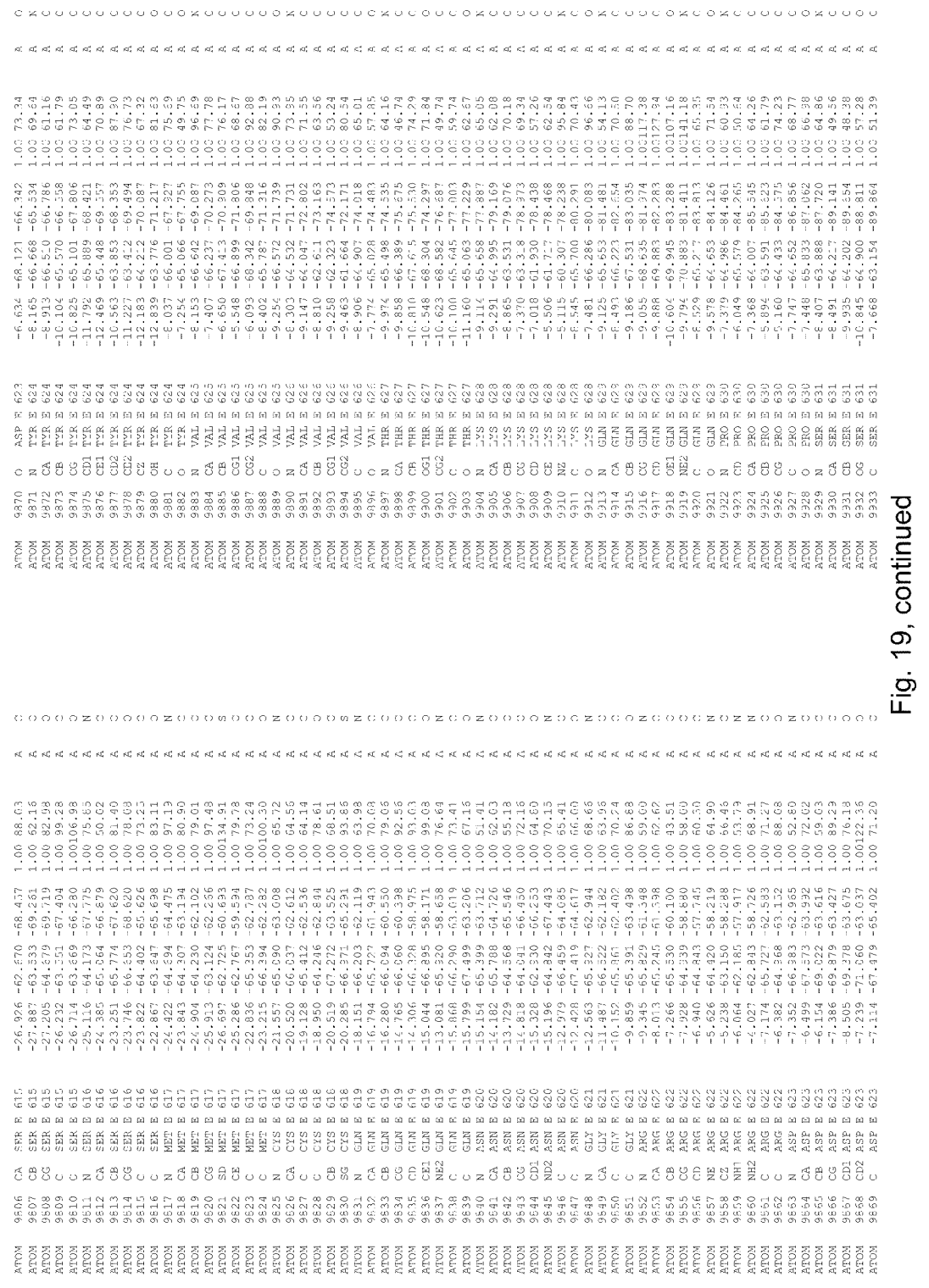
Figure 19:
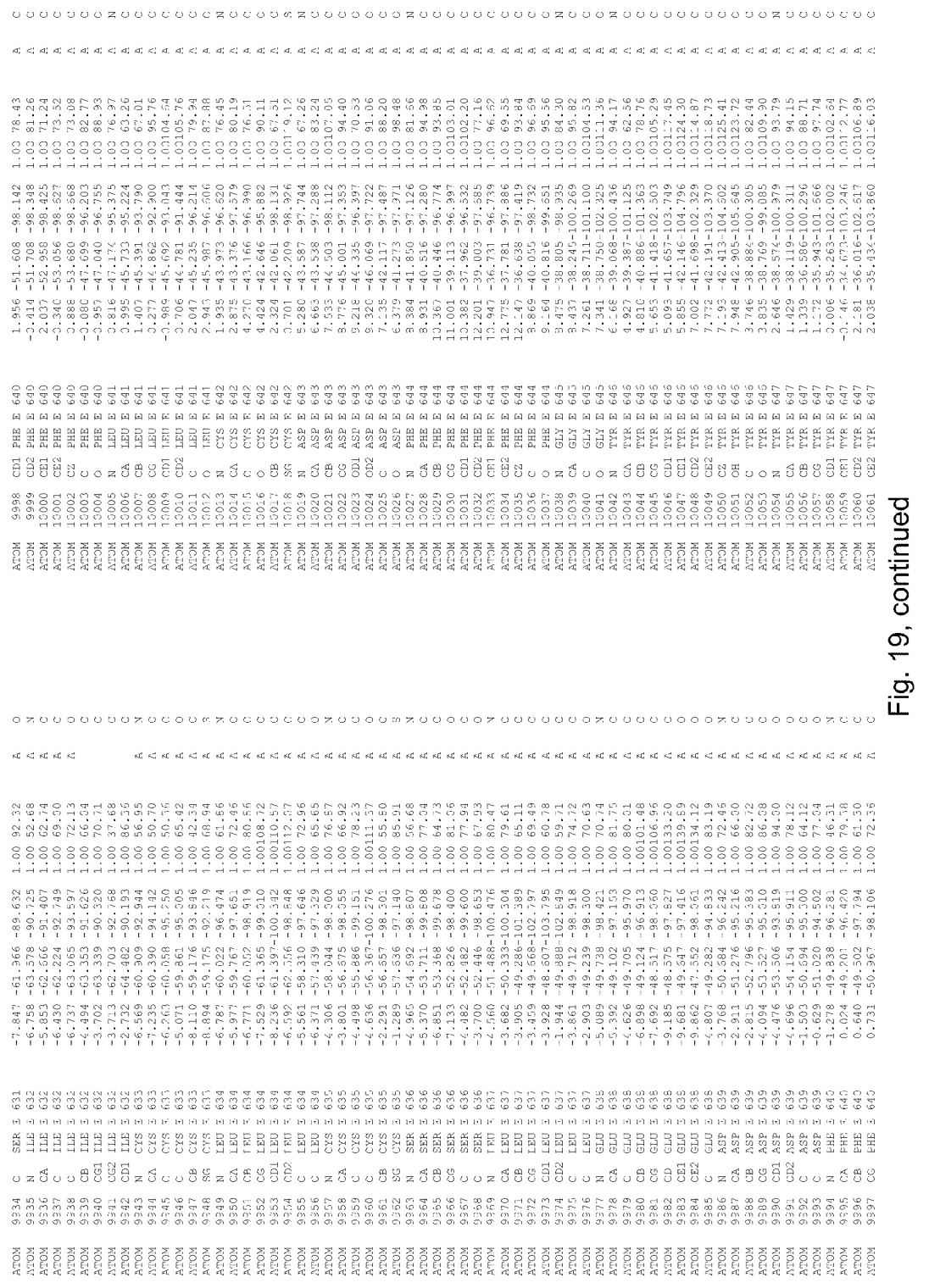
Figure 19:
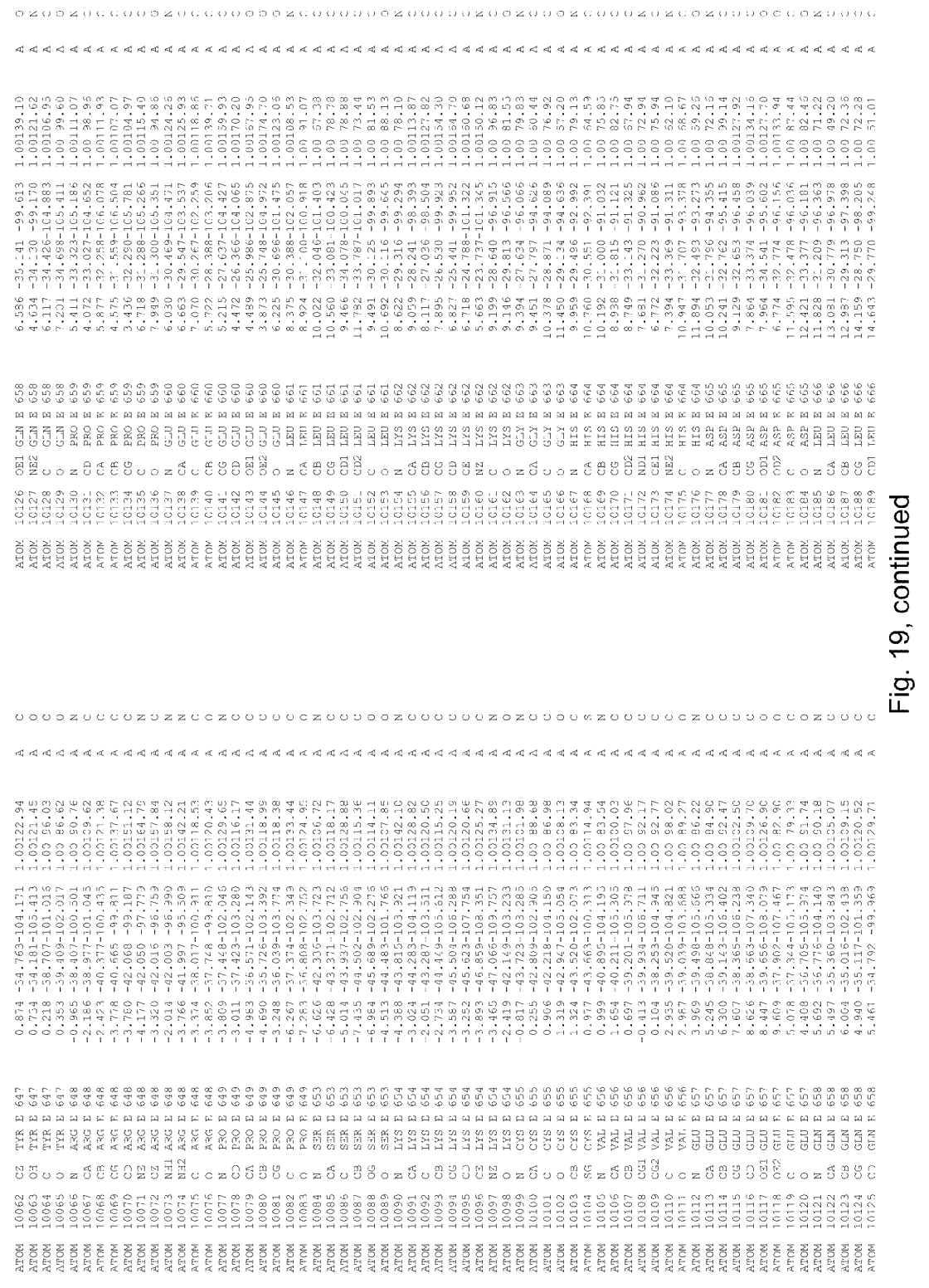
Figure 19:
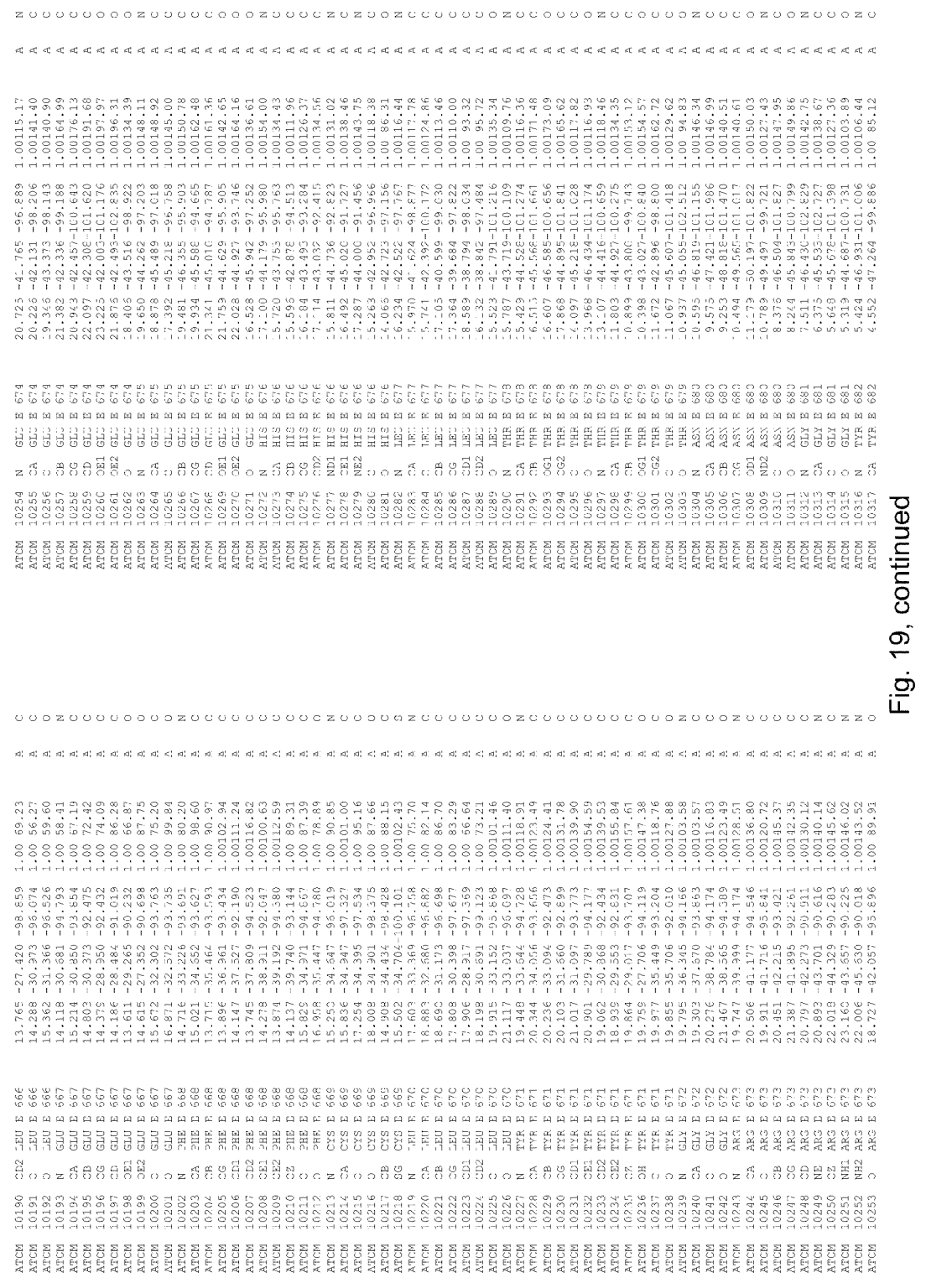
Figure 19:
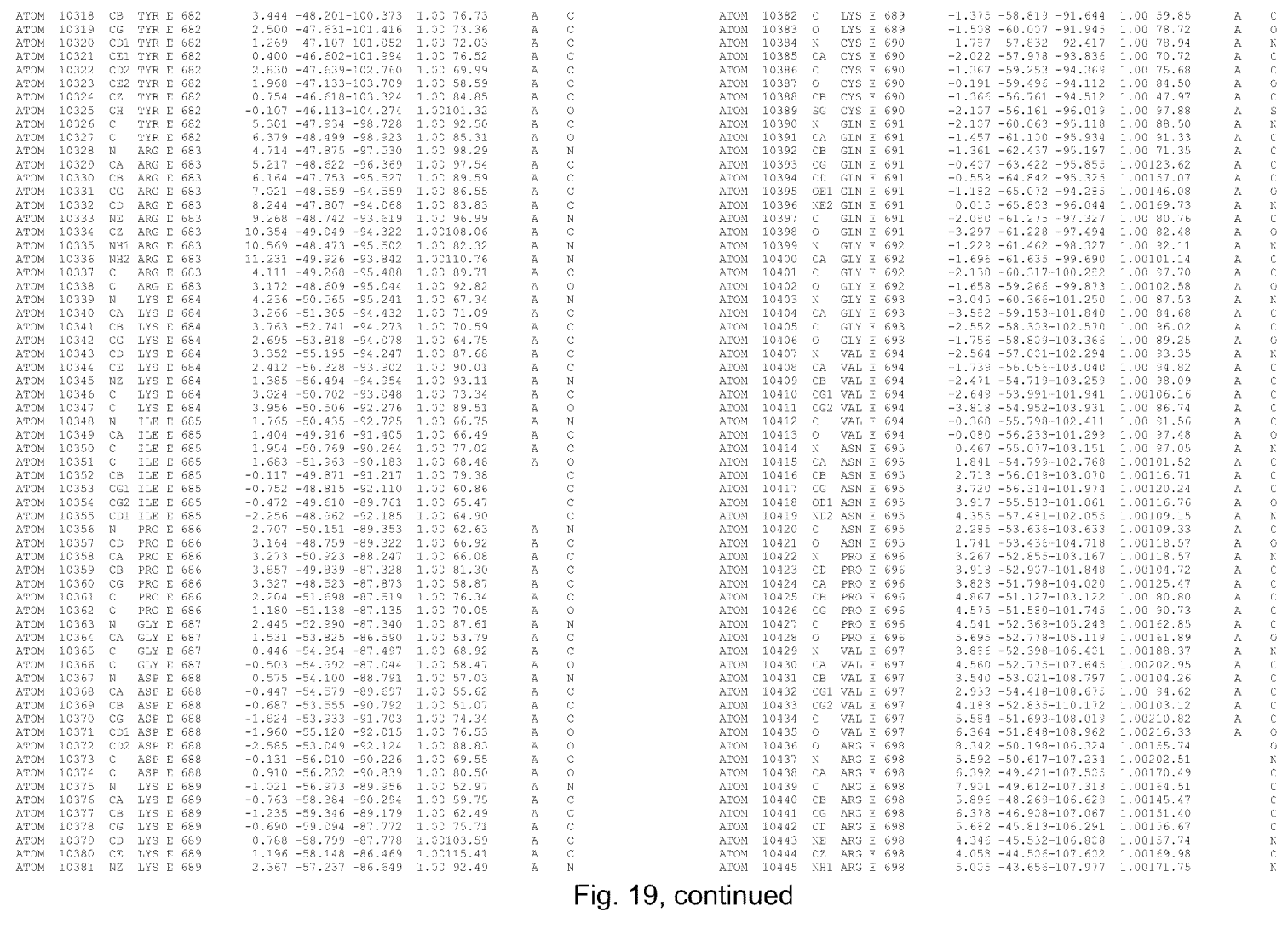
Figure 19:
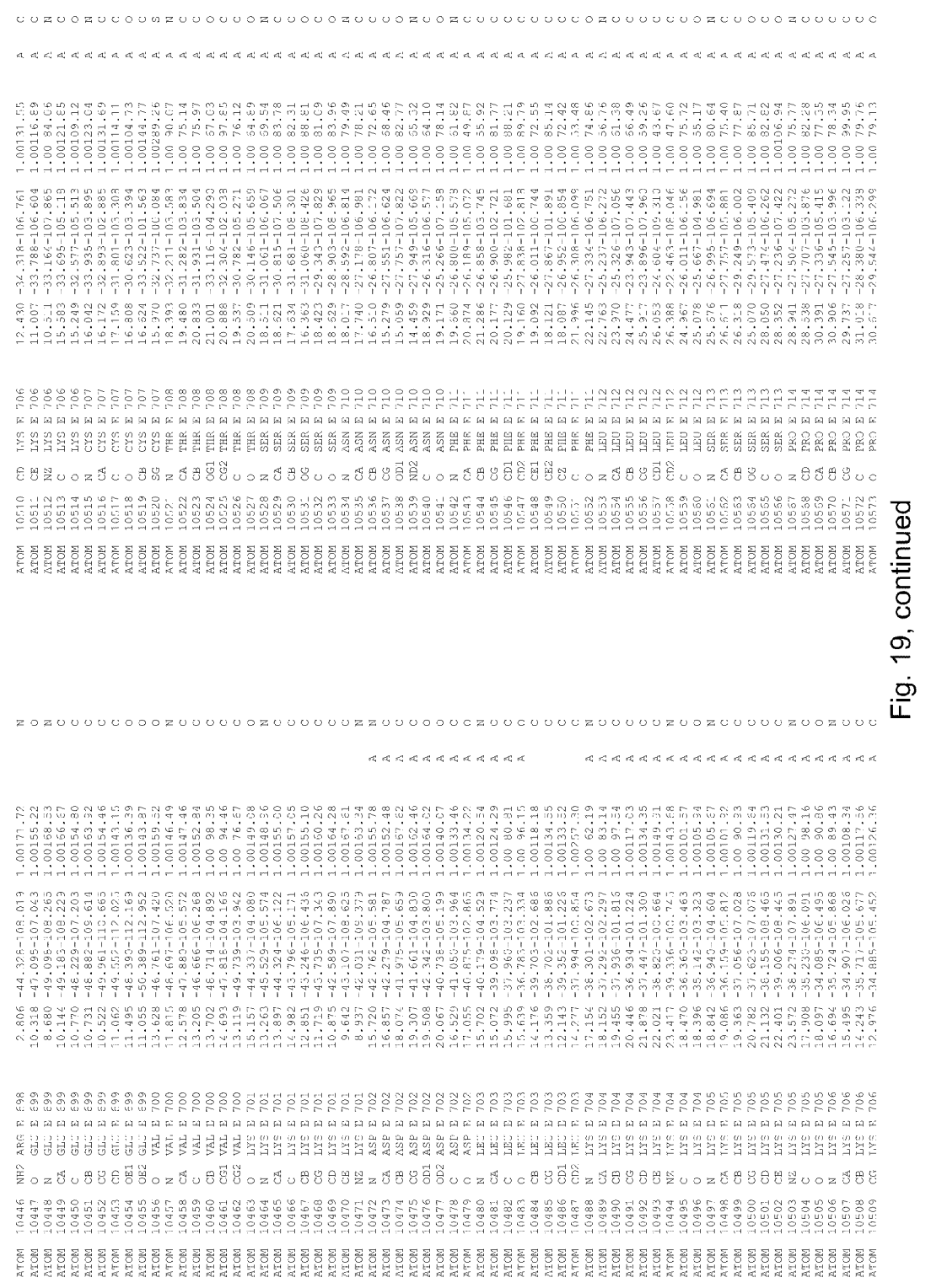
Figure 19:
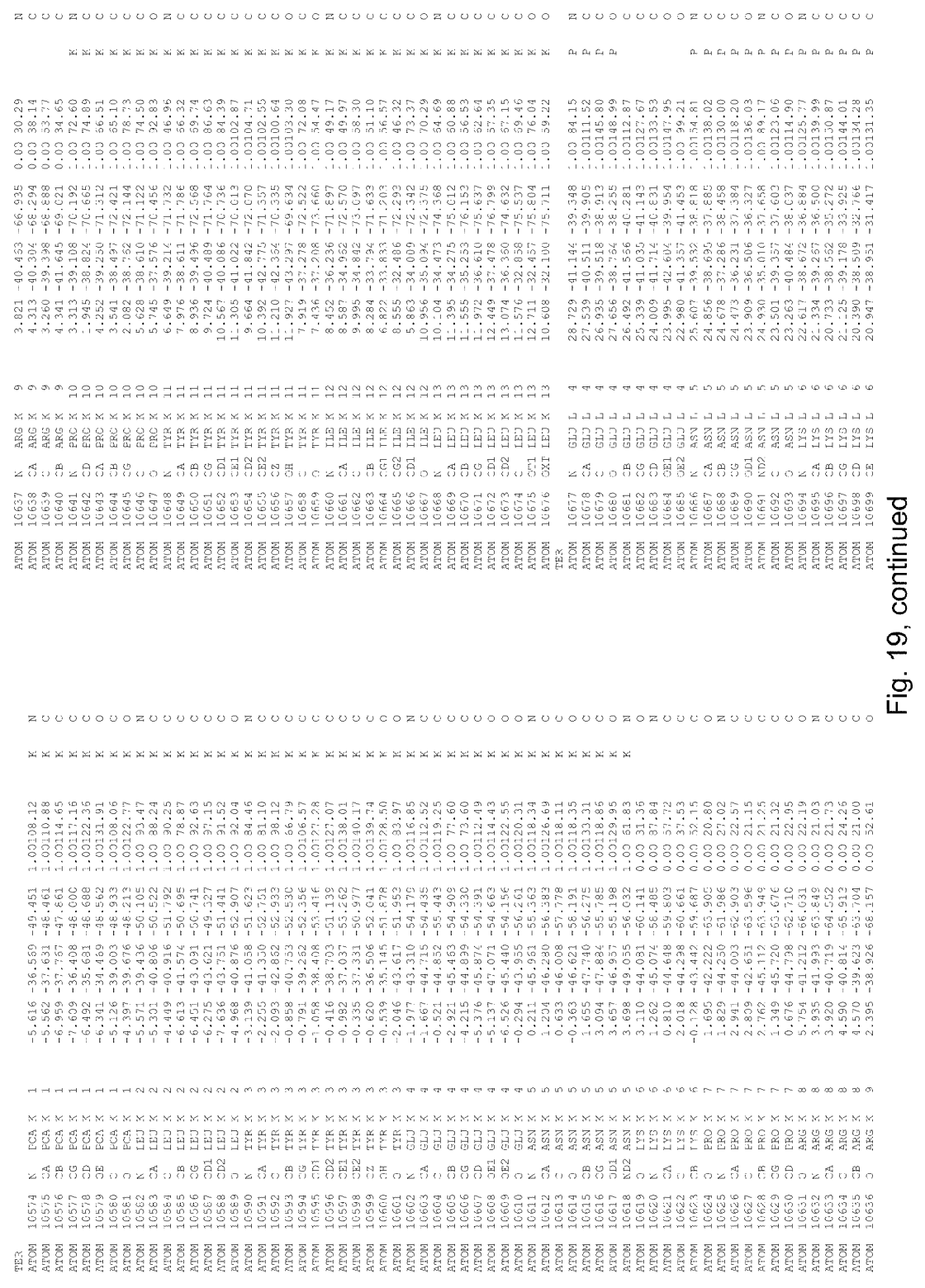
Figure 19:
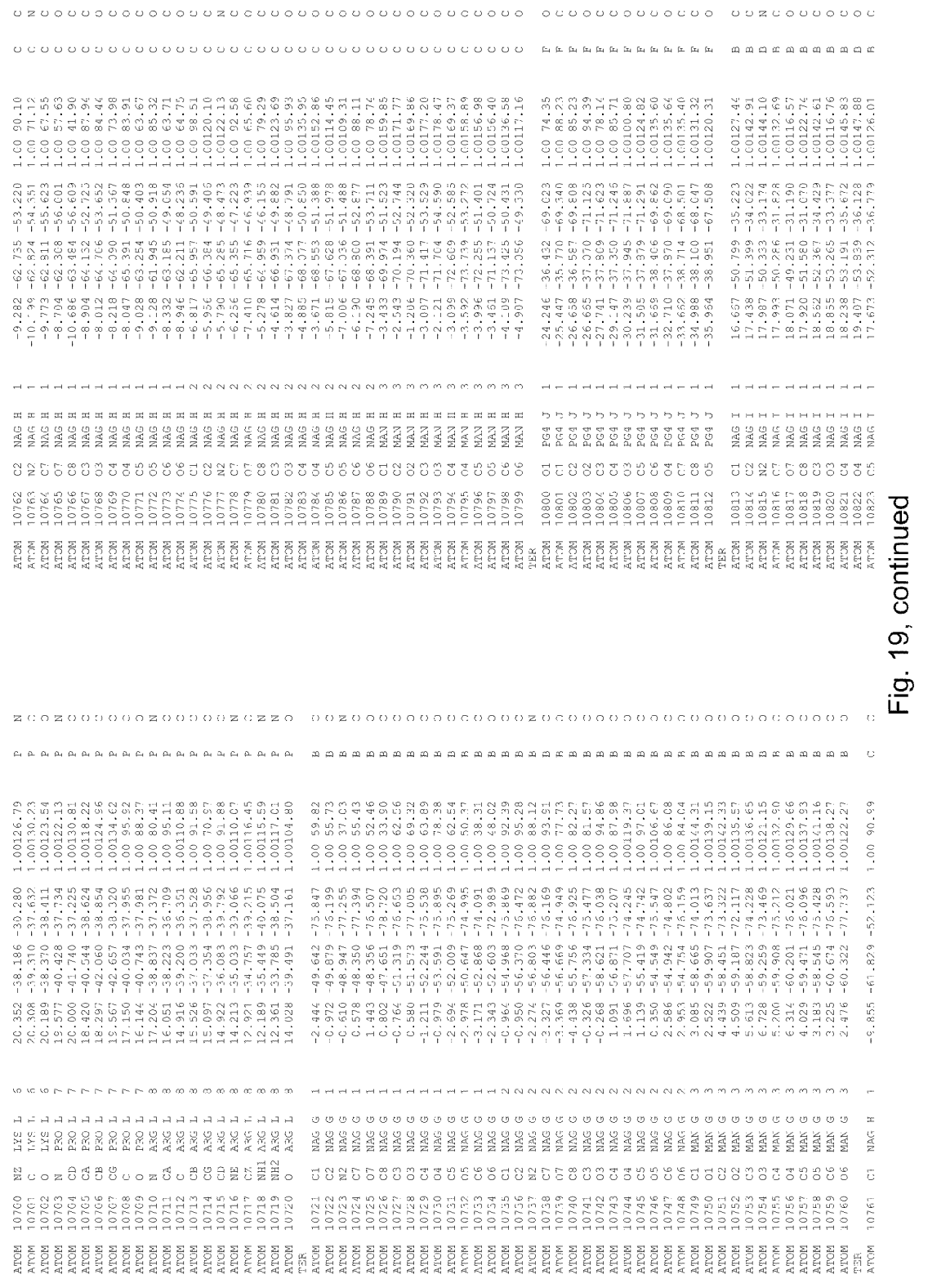
Figure 19:
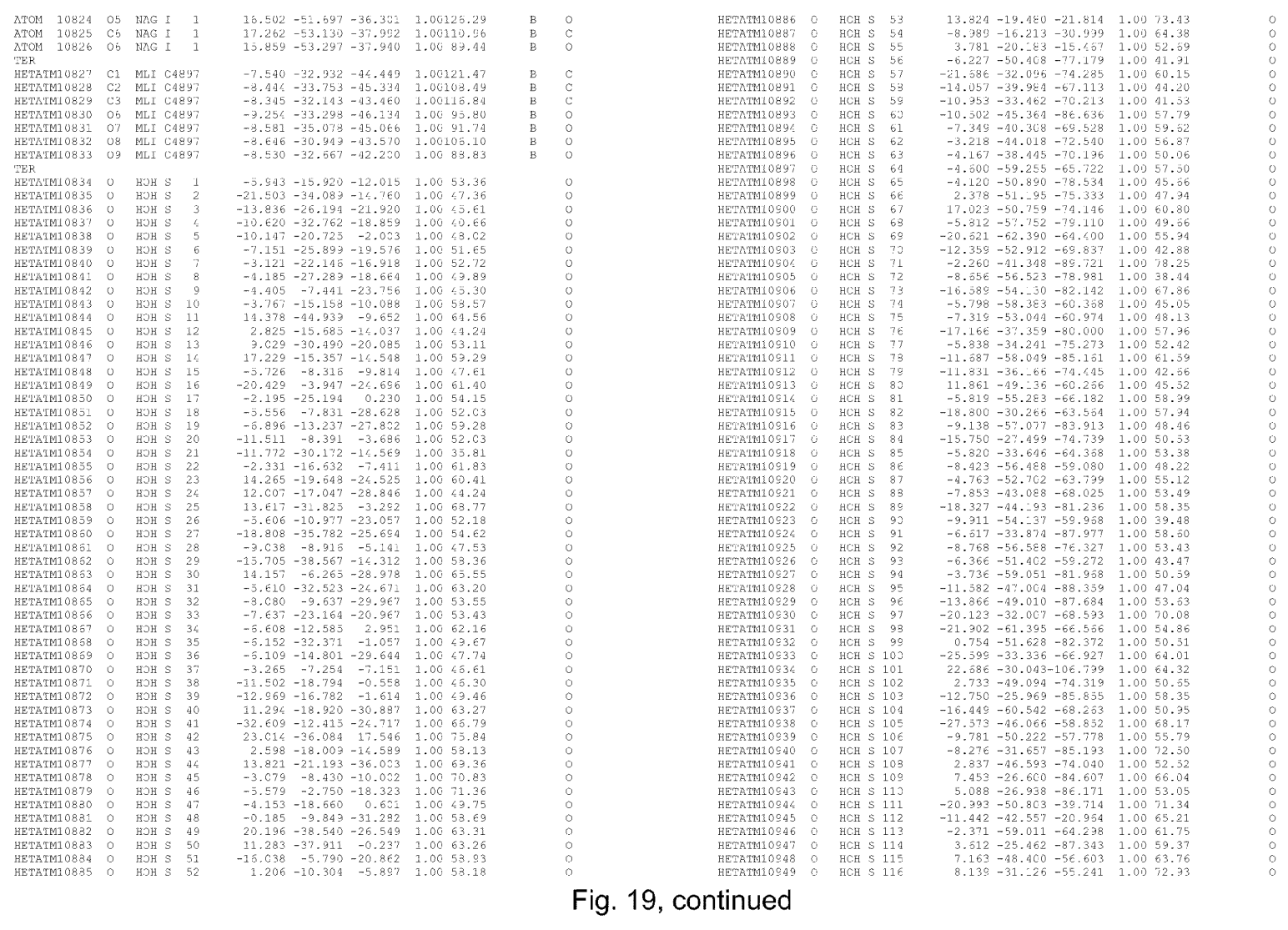
Figure 19:
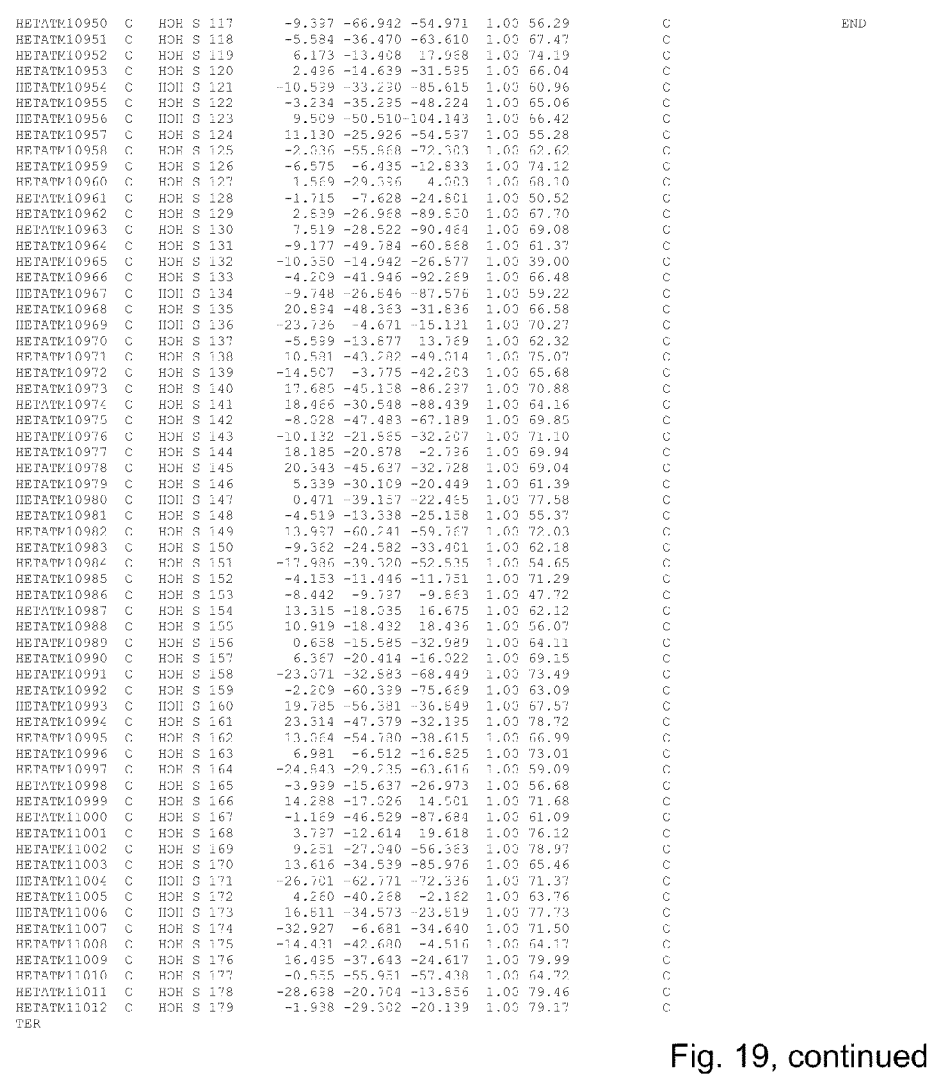

FIG. 19: Atomic coordinates of sSortilin in complex with Neurotensin provided in a molar ration of 1:15 resulting in occupation of both binding site 1 (high affinity site) and binding site 2 (low affinity site). sSortilin (SEQ ID NO:33) has the sequence of amino acid residues 78 to 755 of SEQ ID NO. 1. Neurotensin has the sequence of SEQ ID NO:10. The numbering of the first built Sortilin amino acid residues of this pdb file is G54 which corresponds to G87 of SEQ ID NO:1 which is numbered in accordance with the Expasy database entry Q99523 as of the filing date of the present application. Thus, the sSortilin coordinates provided are those of SEQ ID NO:37 (which corresponds to amino acid residues Gly87 to Pro747 of SEQ ID NO. 1) (atom 1 corresponds to an atom of the first residue (Gly) of SEQ ID NO:37 (Gly87 of SEQ ID NO:1); atom 5142 corresponds to an atom of the last residue (Pro) of SEQ ID NO:37 (Pro747 of SEQ ID NO:1). Atoms 5143-5245 are atoms of Neurotensin (SEQ ID NO:10); atoms 5246-5289 are atoms of an ENKPR (SEQ ID NO:38) peptide fragment of Neurotensin (SEQ ID NO:10); atoms 5396-10573 are atoms of a second molecule of G87-Pro747 sSortilin (SEQ ID NO:37); atoms 10574-10676 are atoms of a second molecule of Neurotensin (SEQ ID NO:10); atoms 10677-10720 are atoms of a second molecule of the ENKPR (SEQ ID NO:38) peptide fragment of Neurotensin (SEQ ID NO:10); NAG (N-acetyl-d-glucosamine); MAN (manose); PE (polyethylene glycol).

Figure 20:
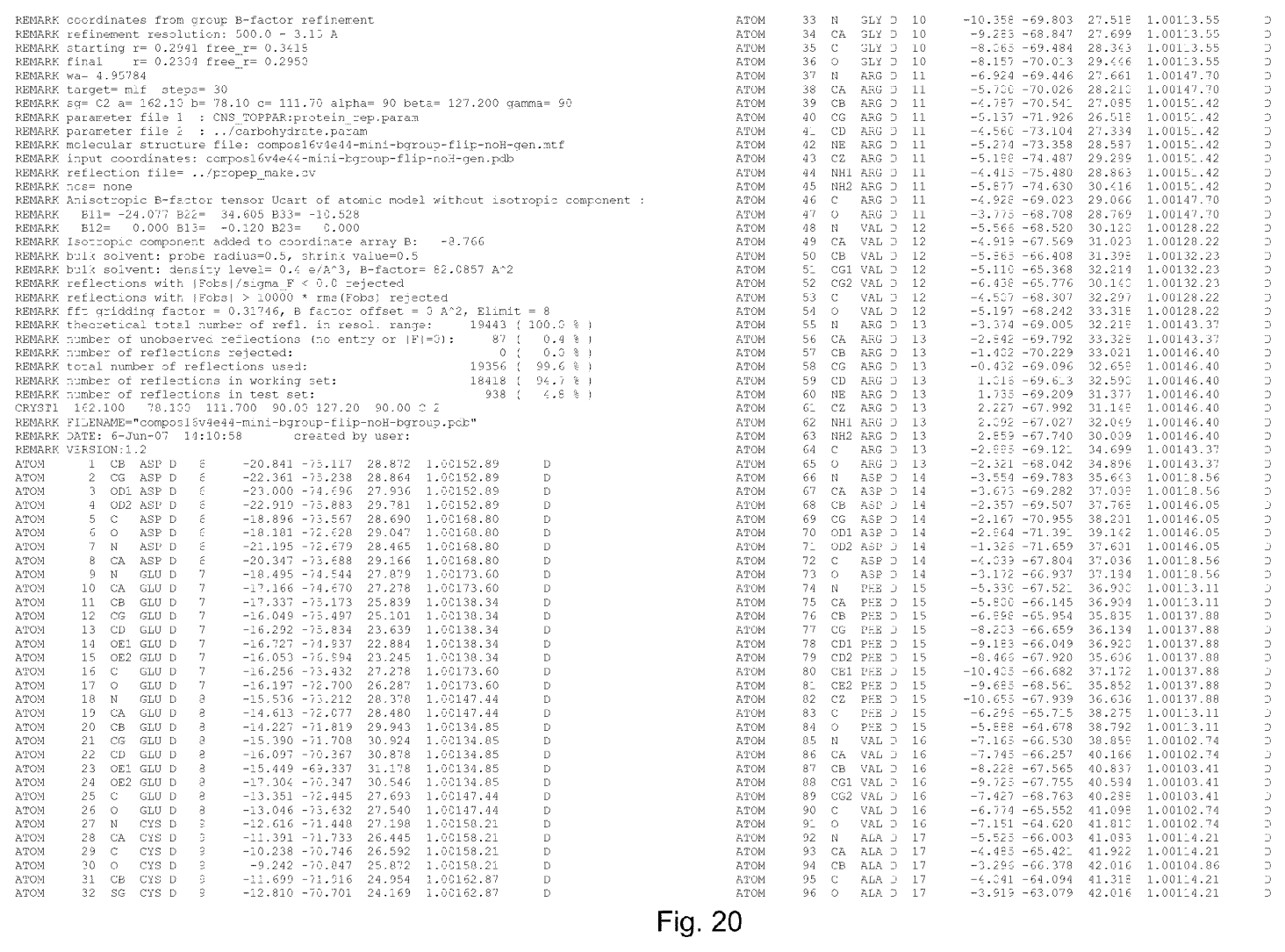
Figure 20:
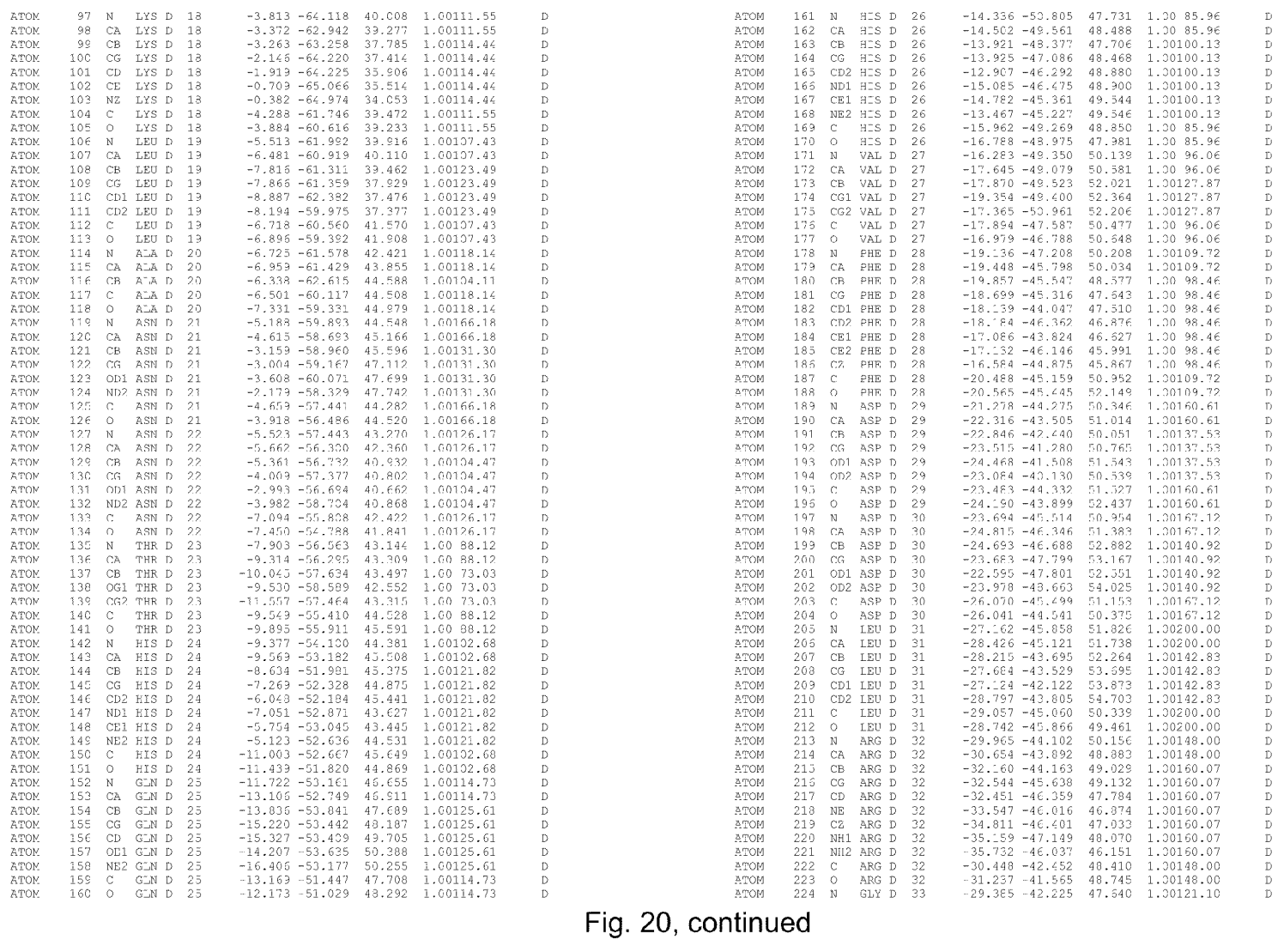
Figure 20:
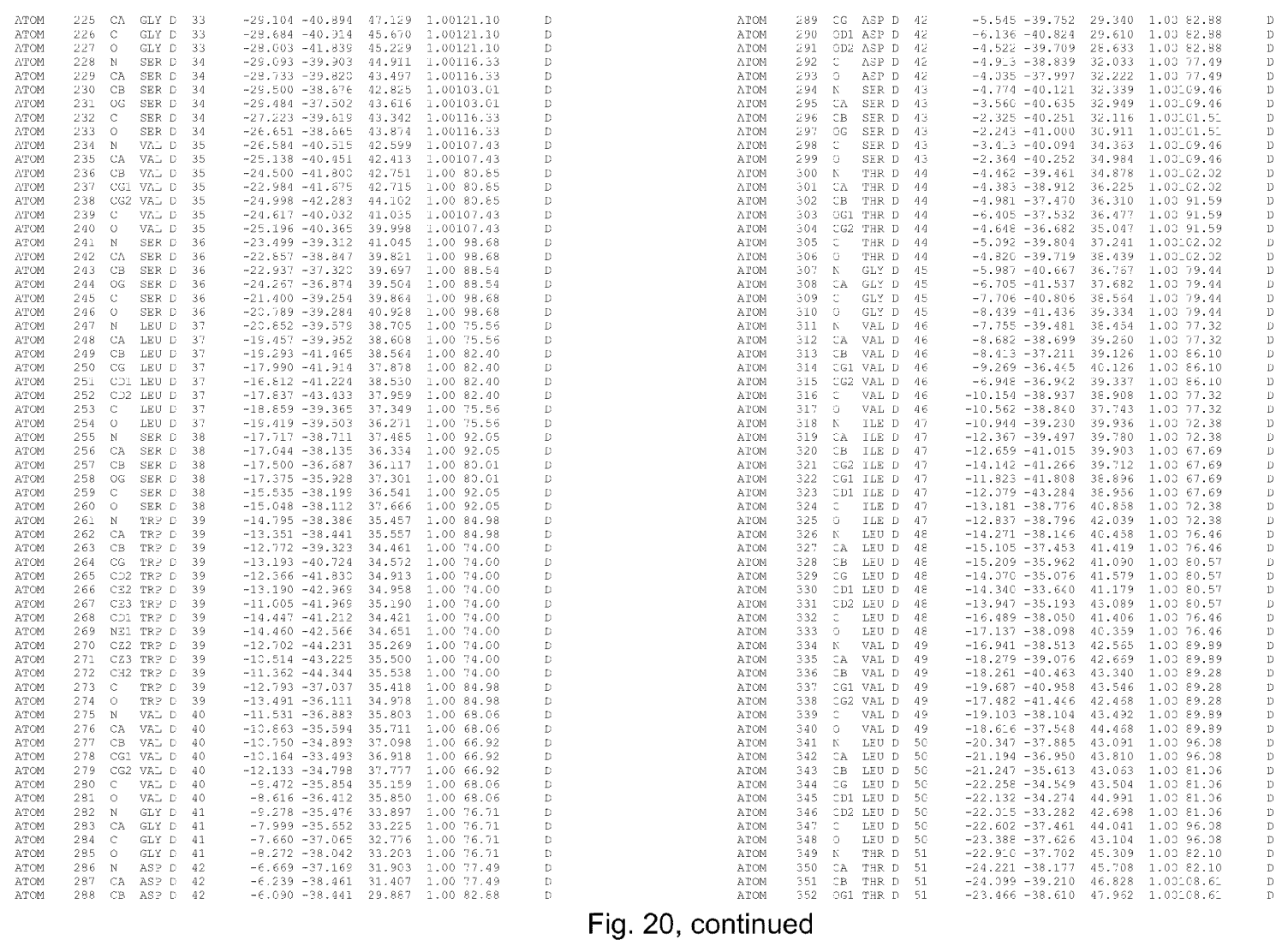
Figure 20:
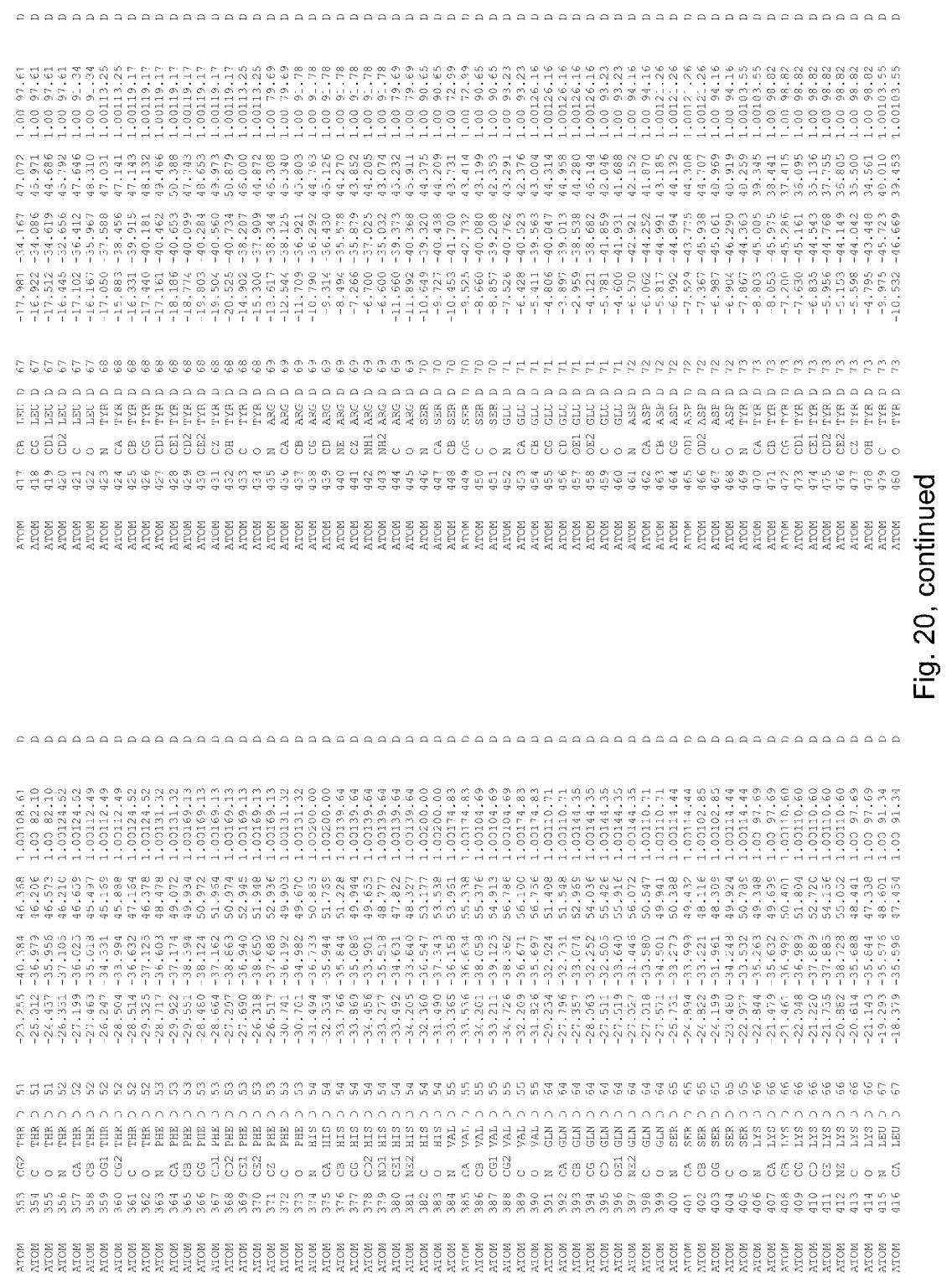
Figure 20:
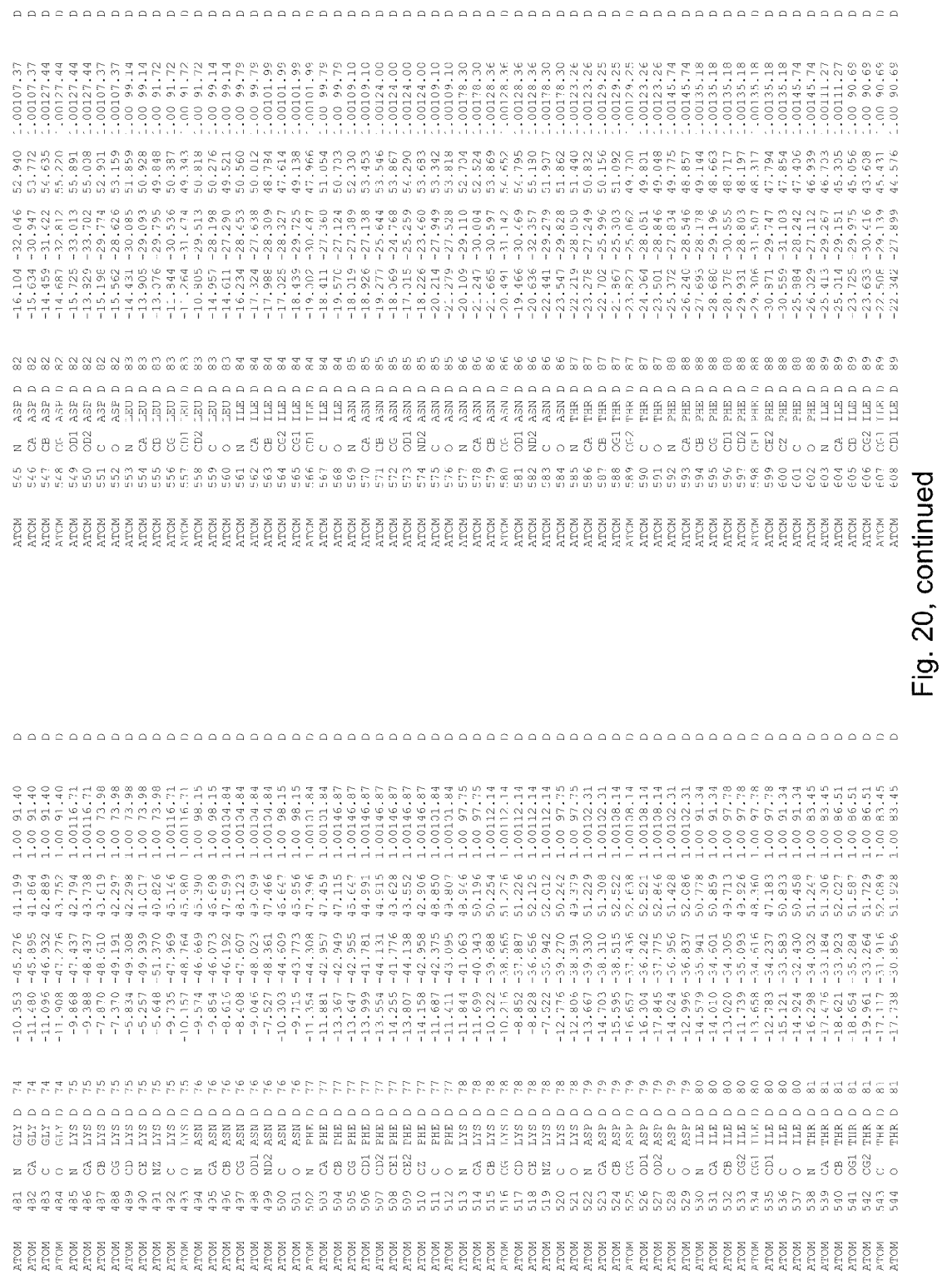
Figure 20:
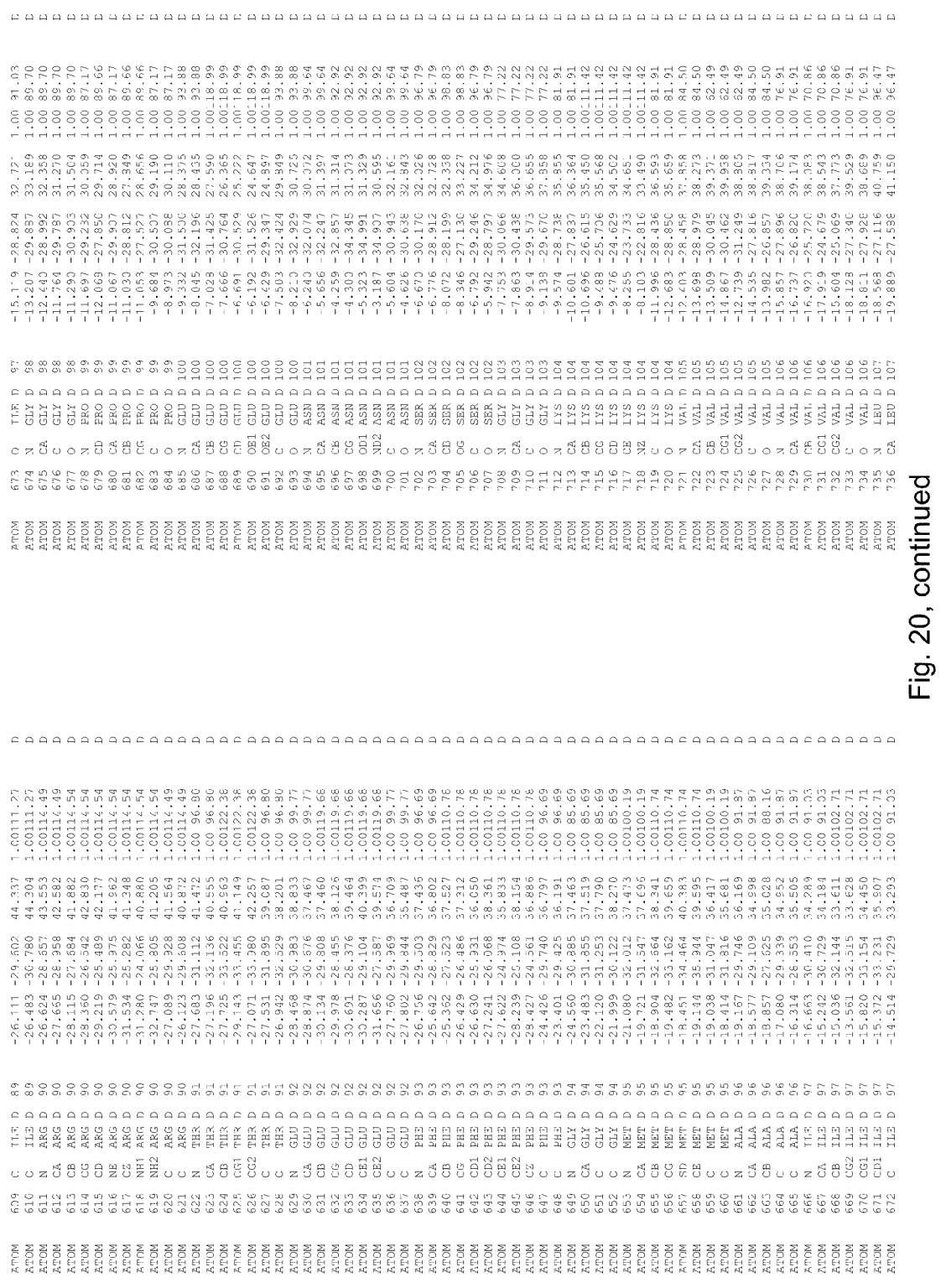
Figure 20:
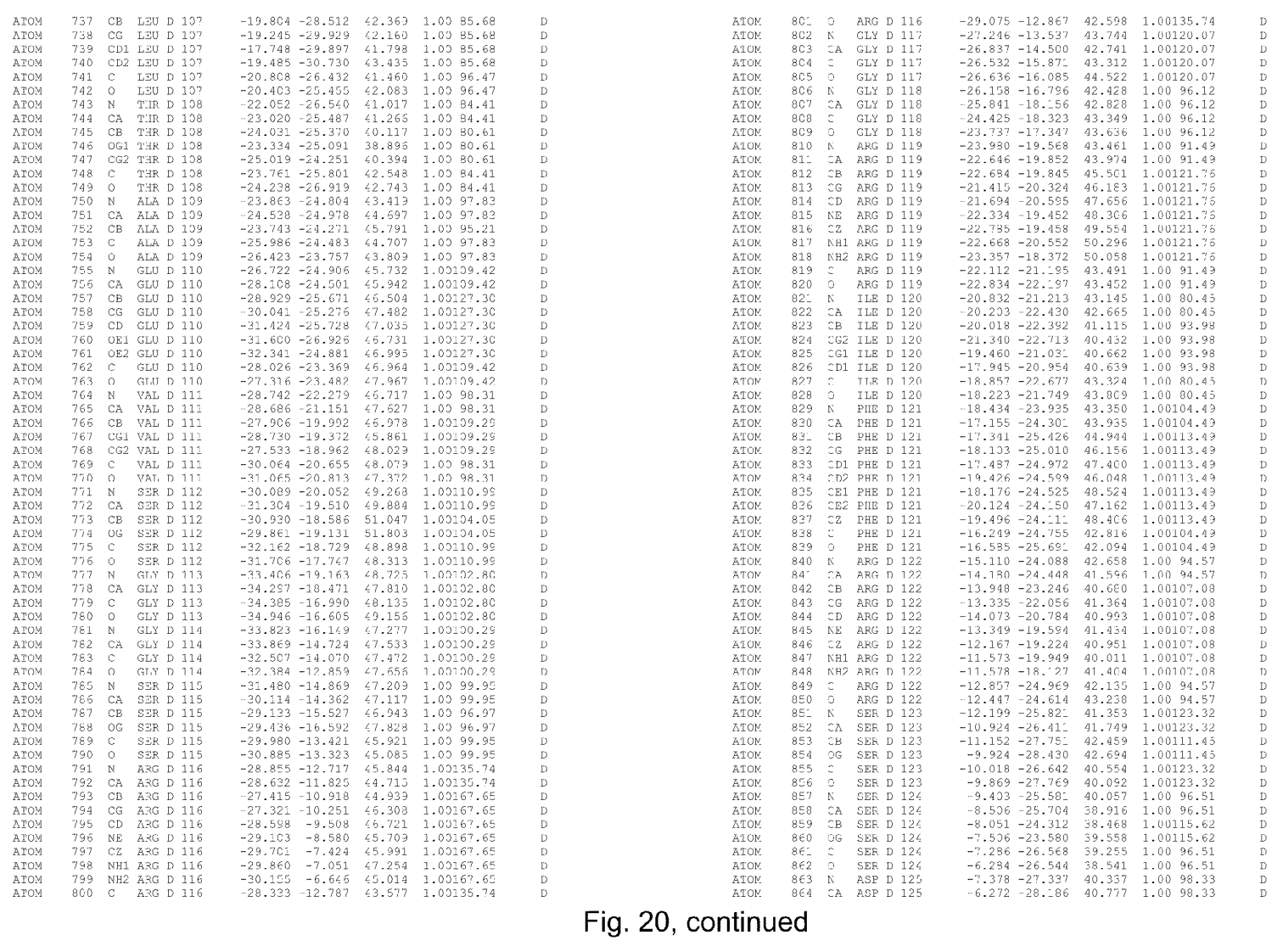
Figure 20:
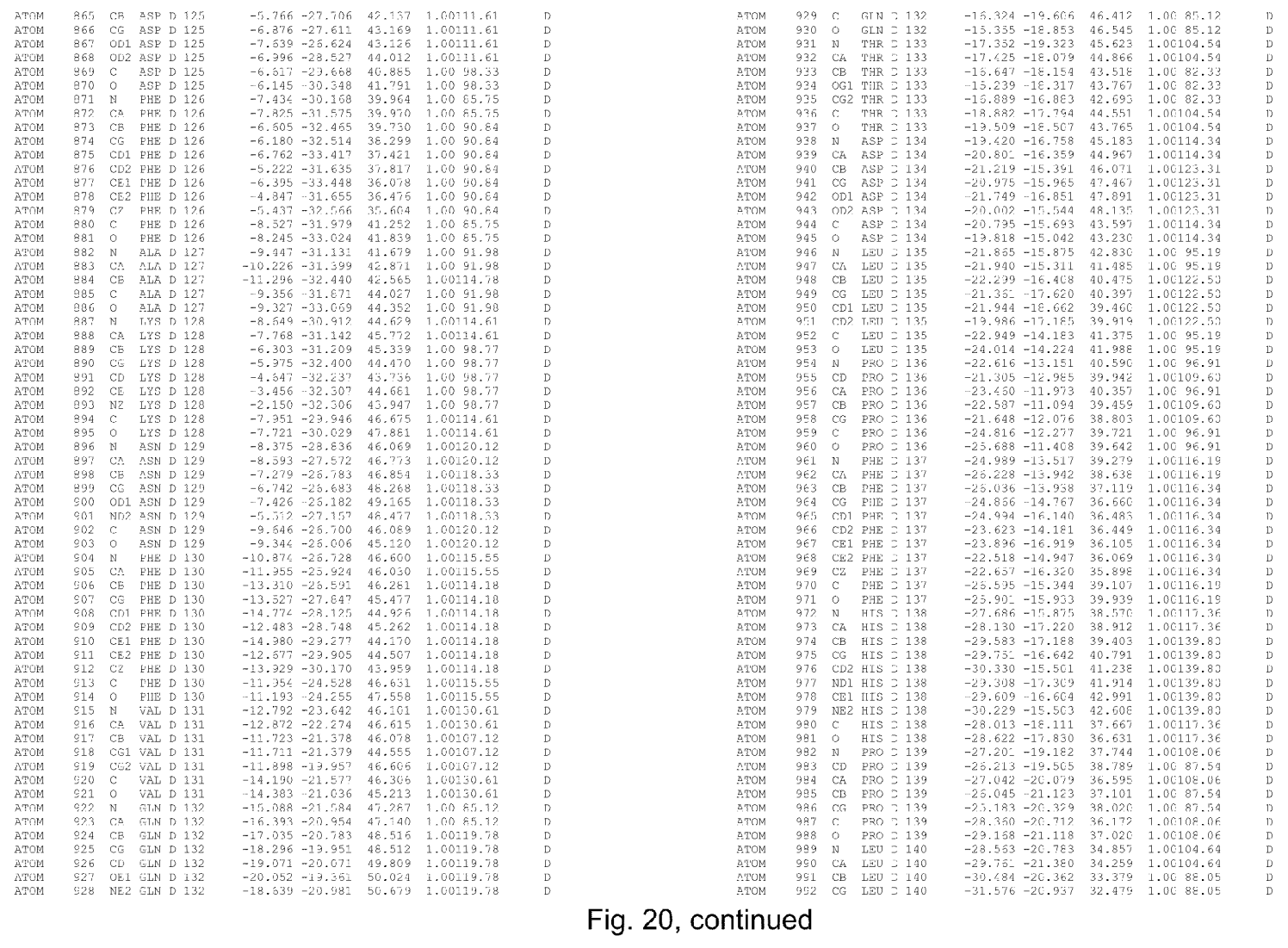
Figure 20:
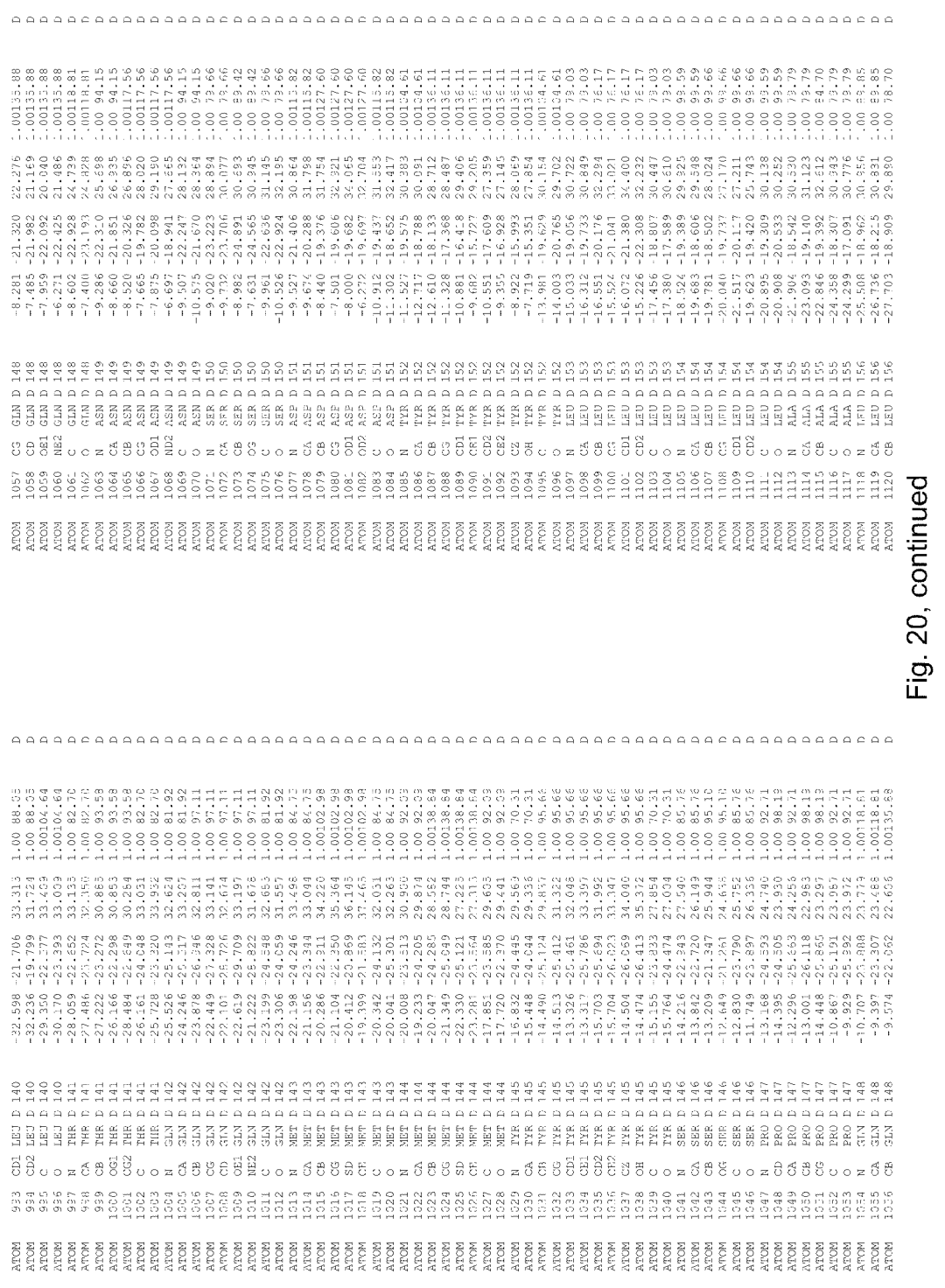
Figure 20:
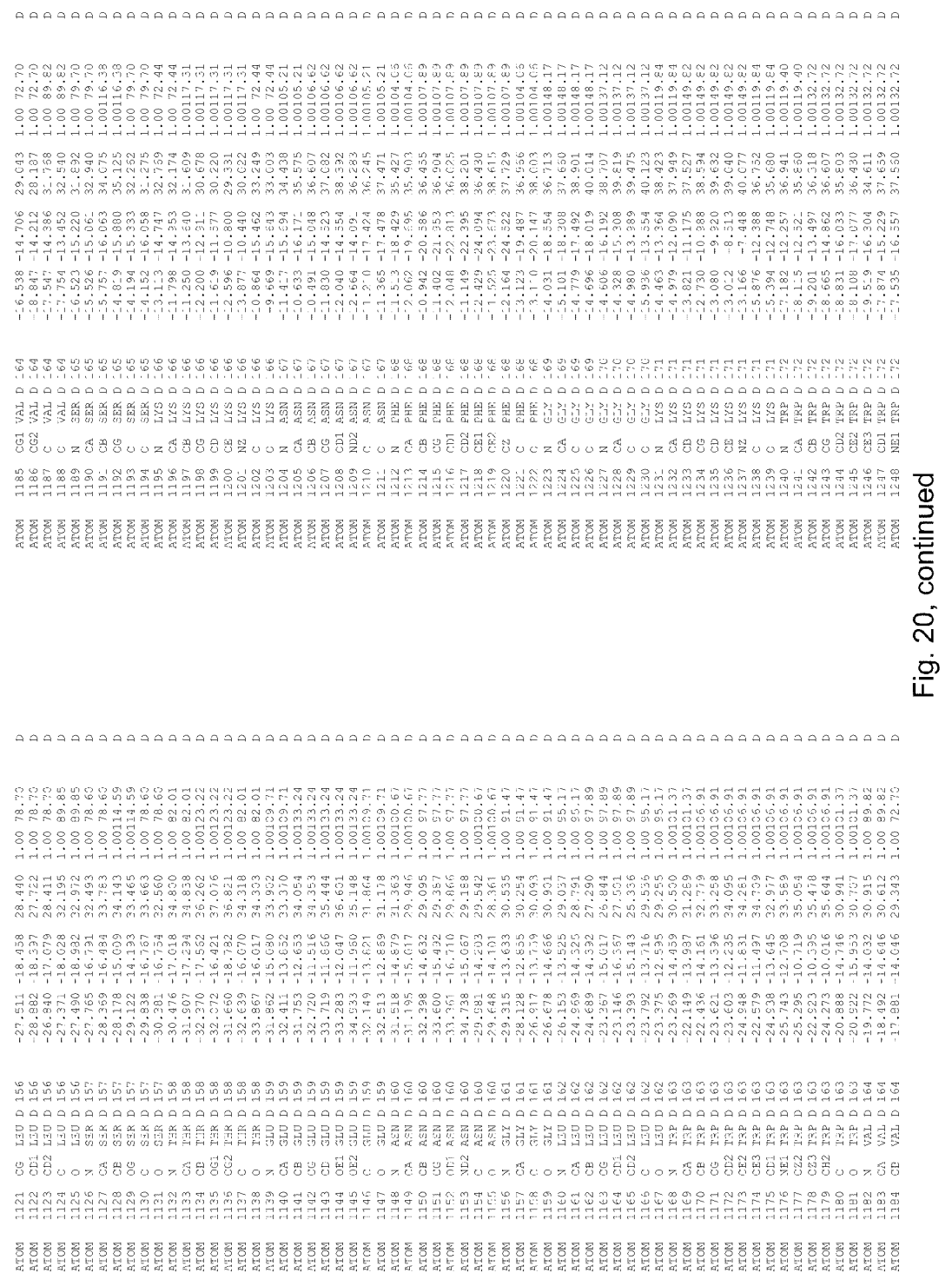
Figure 20:
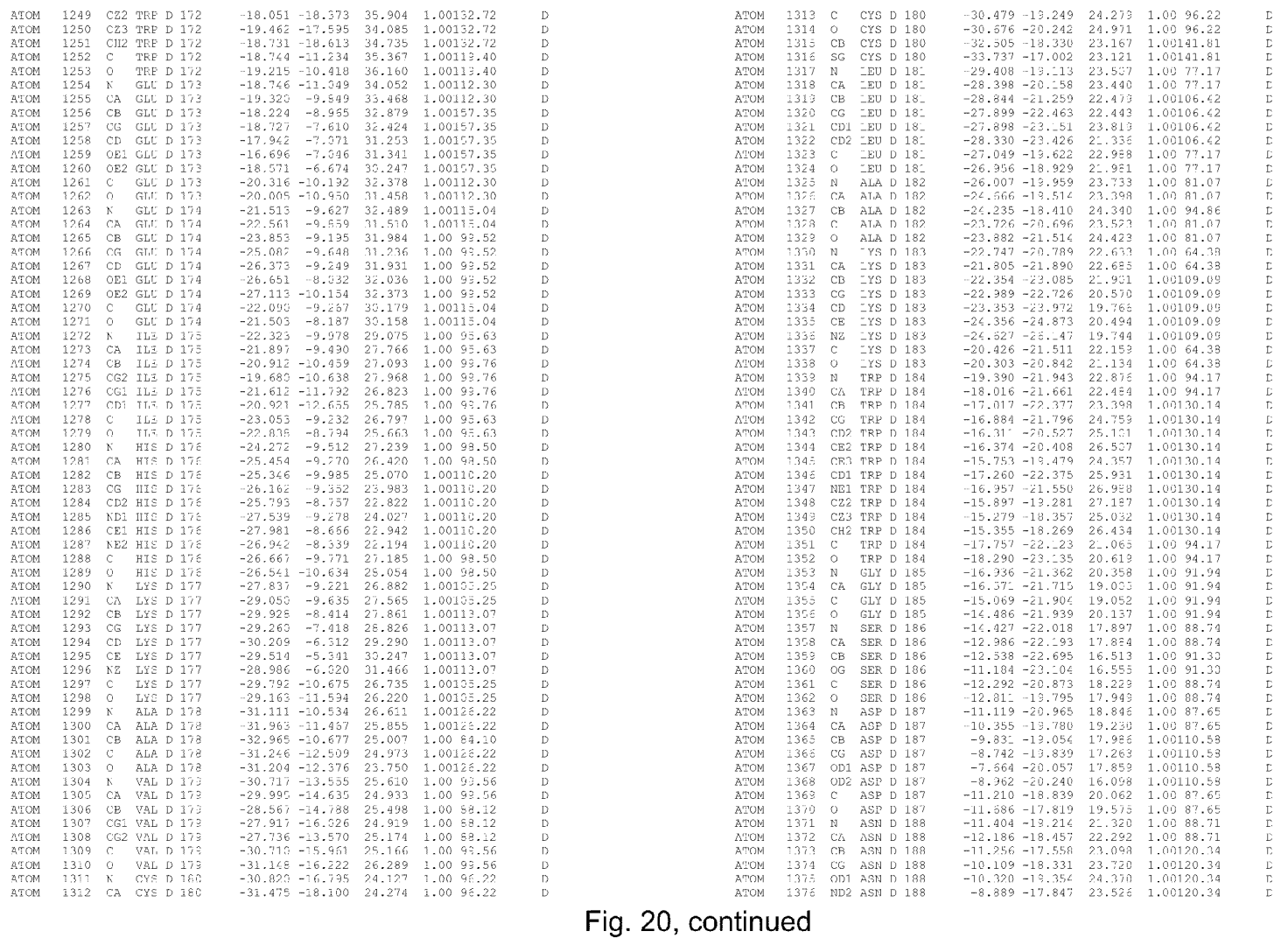
Figure 20:
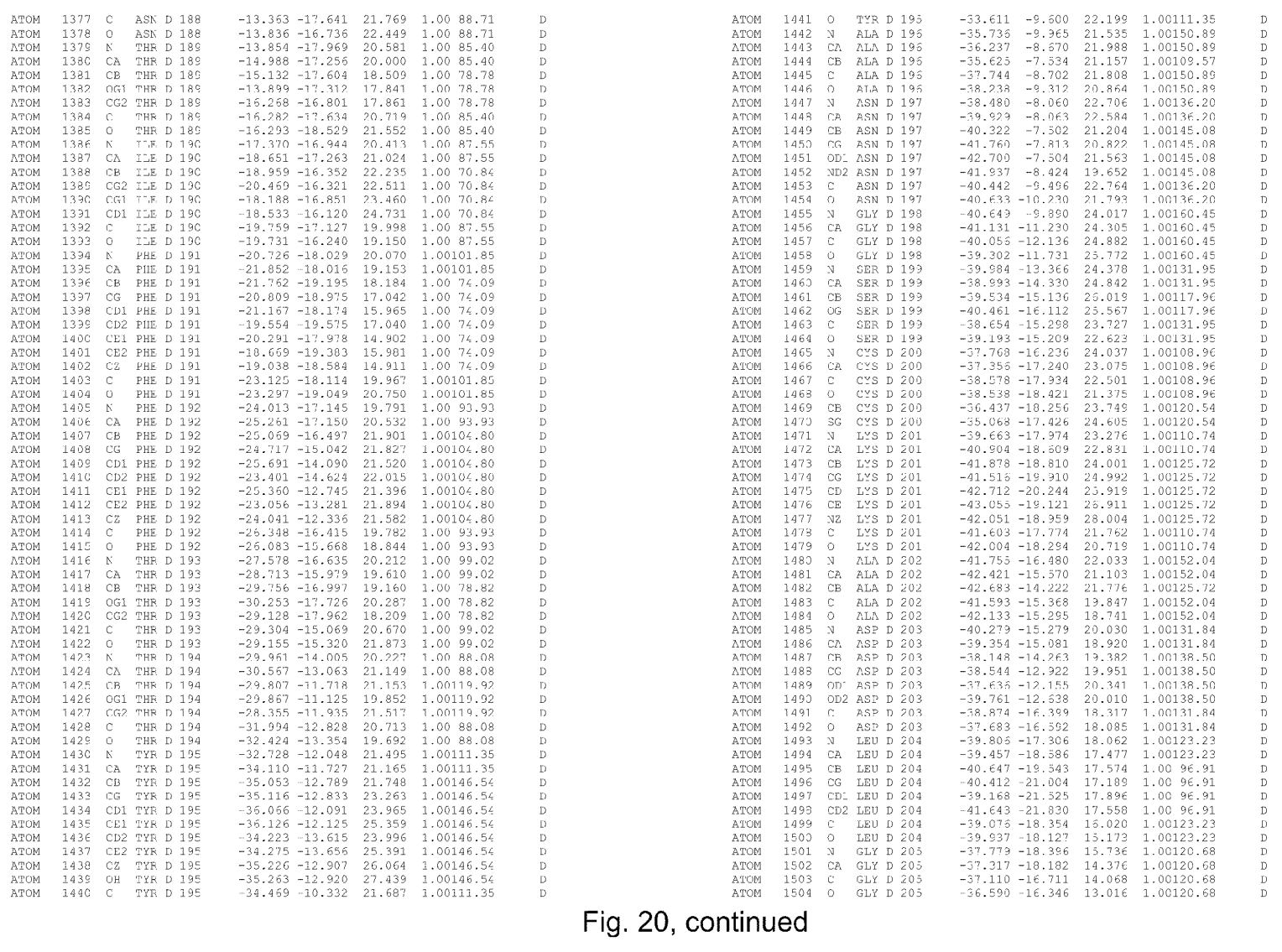
Figure 20:
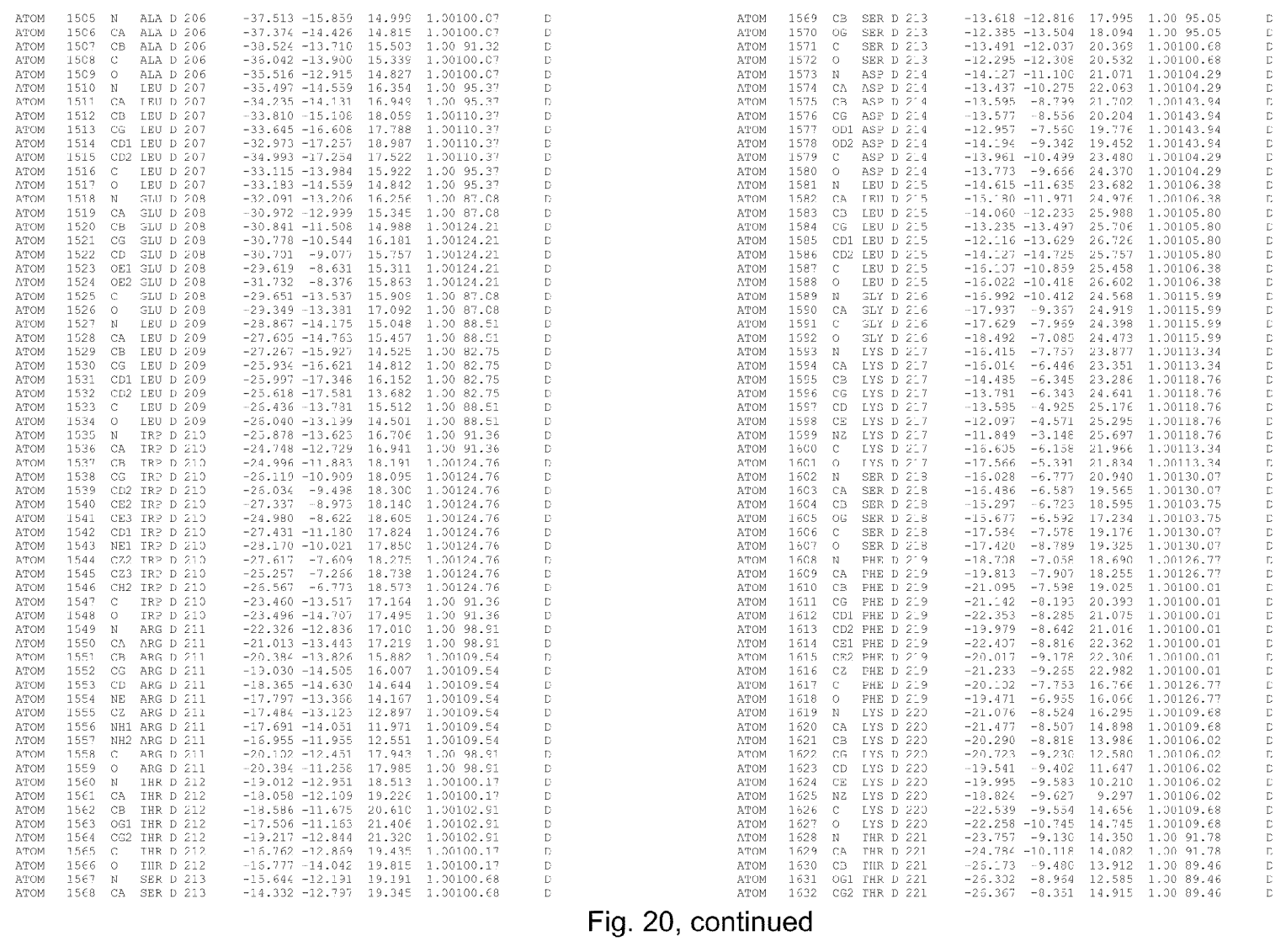
Figure 20:
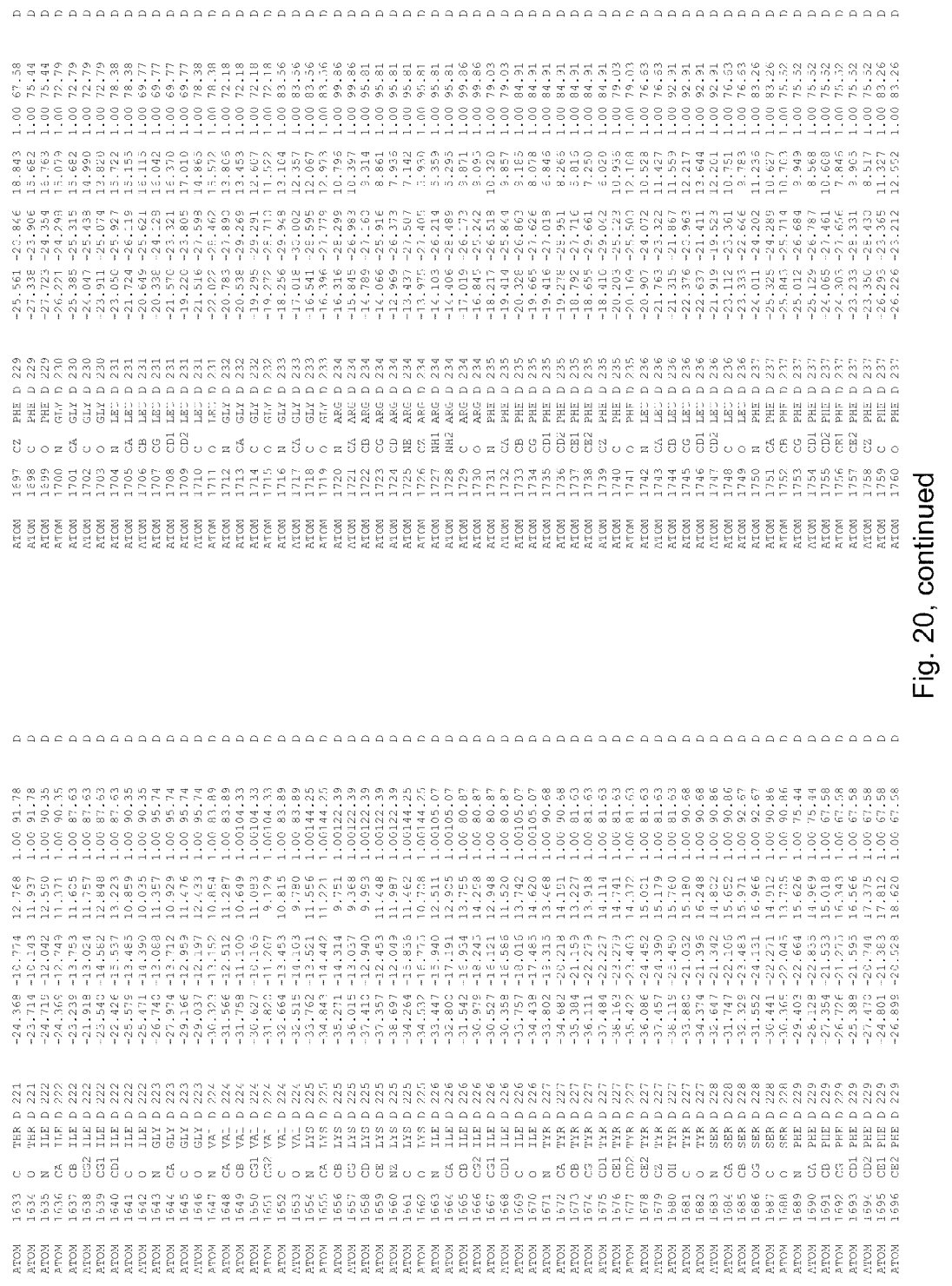
Figure 20:
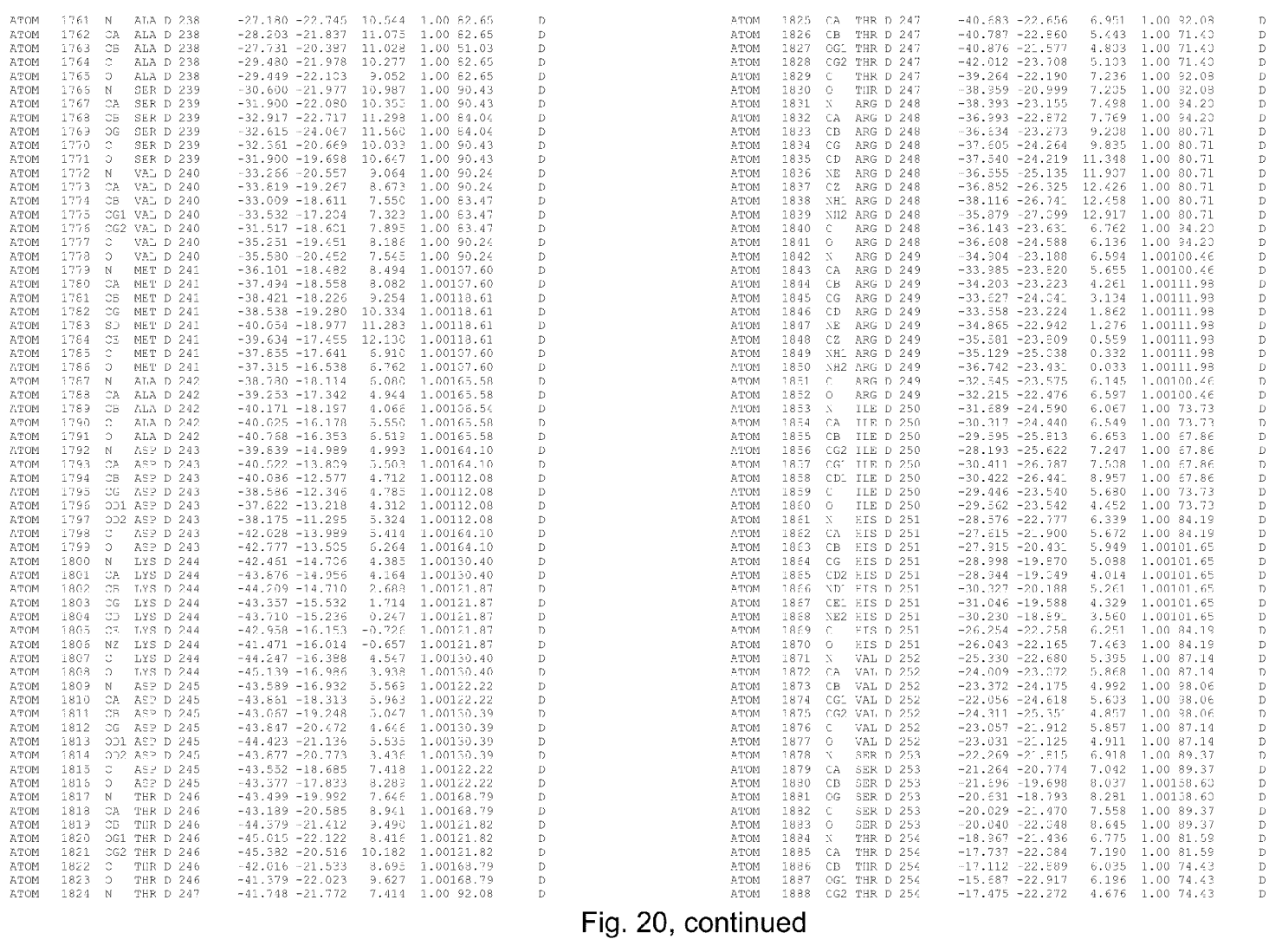
Figure 20:
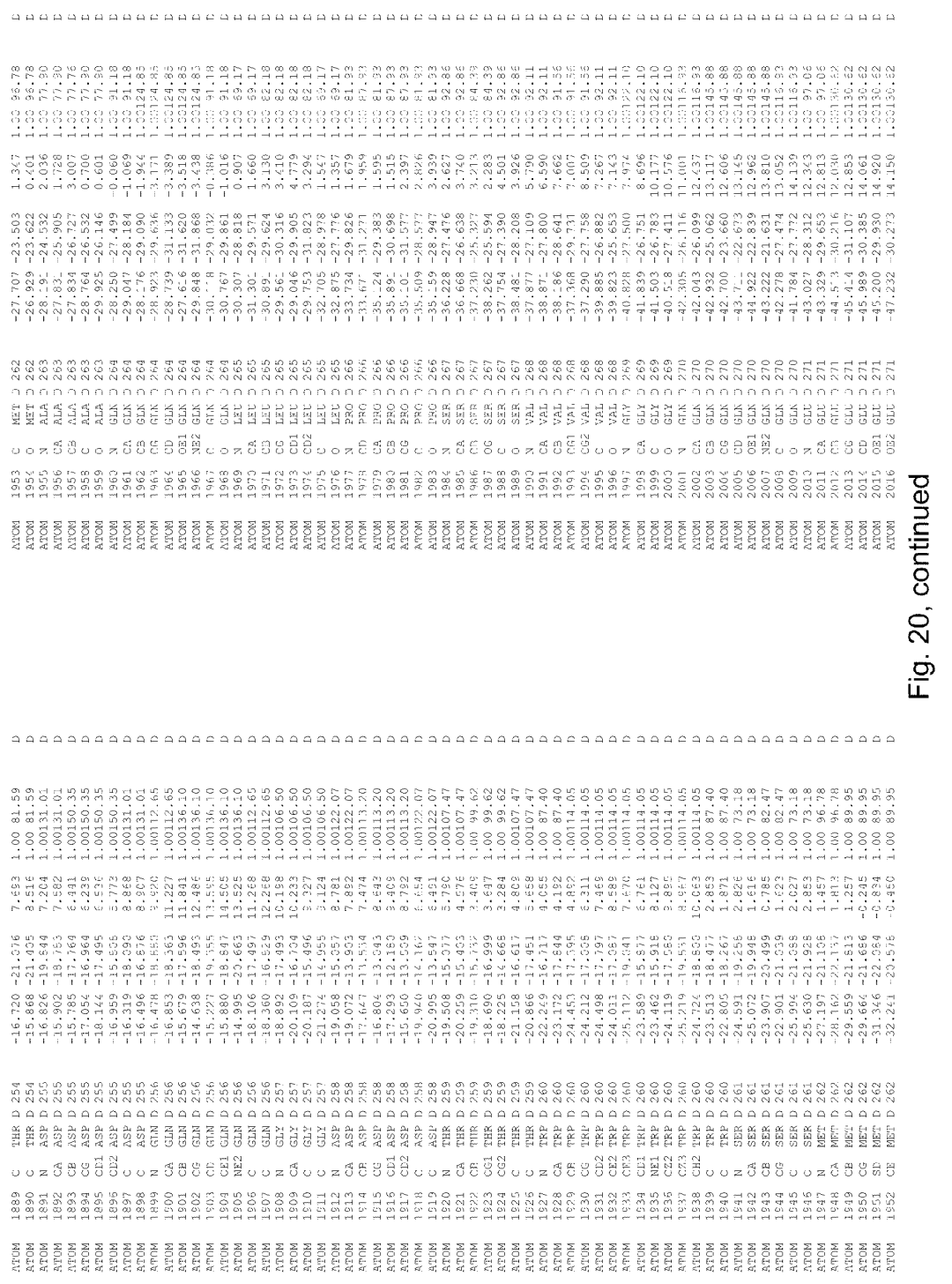
Figure 20:
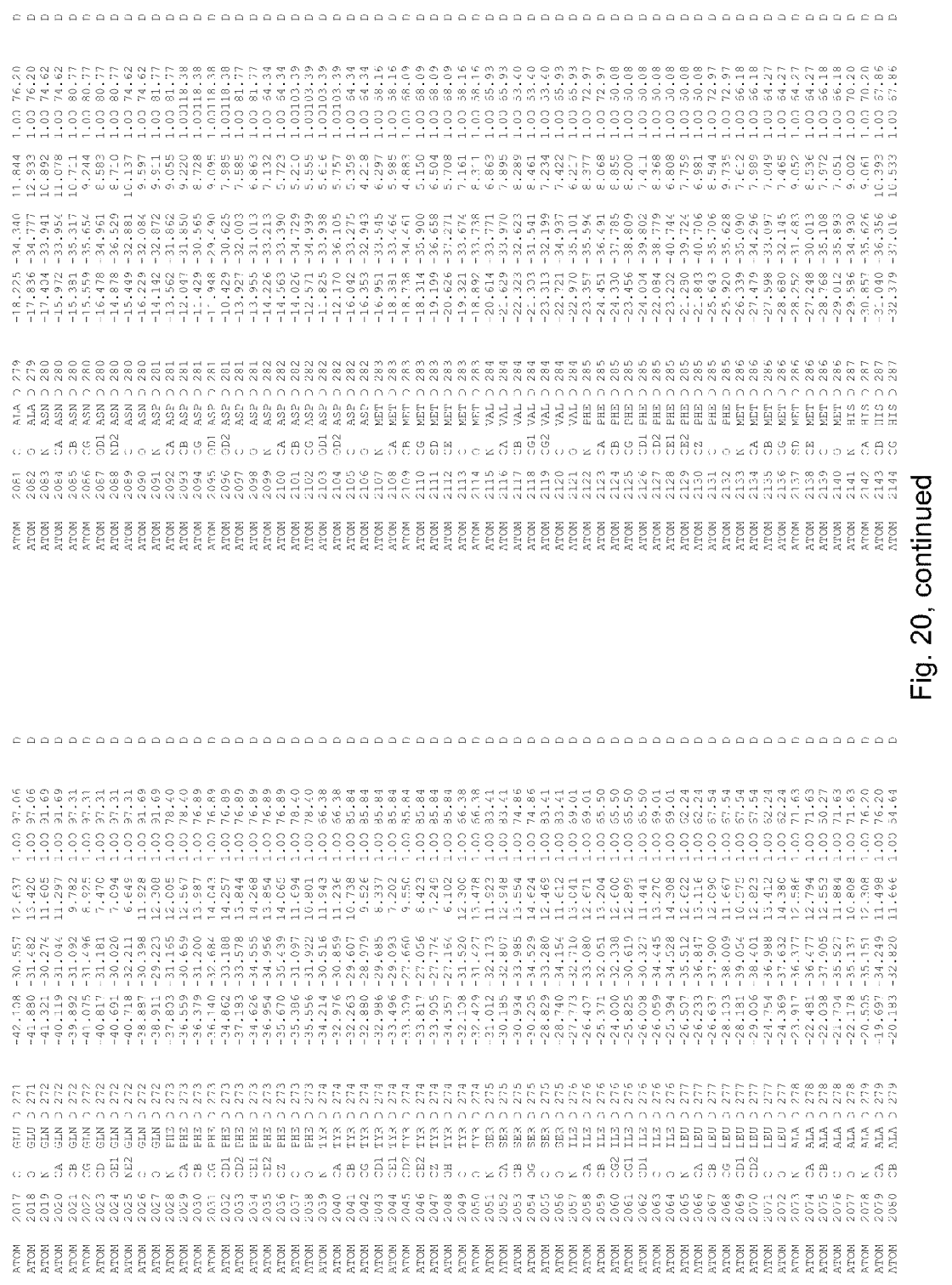
Figure 20:
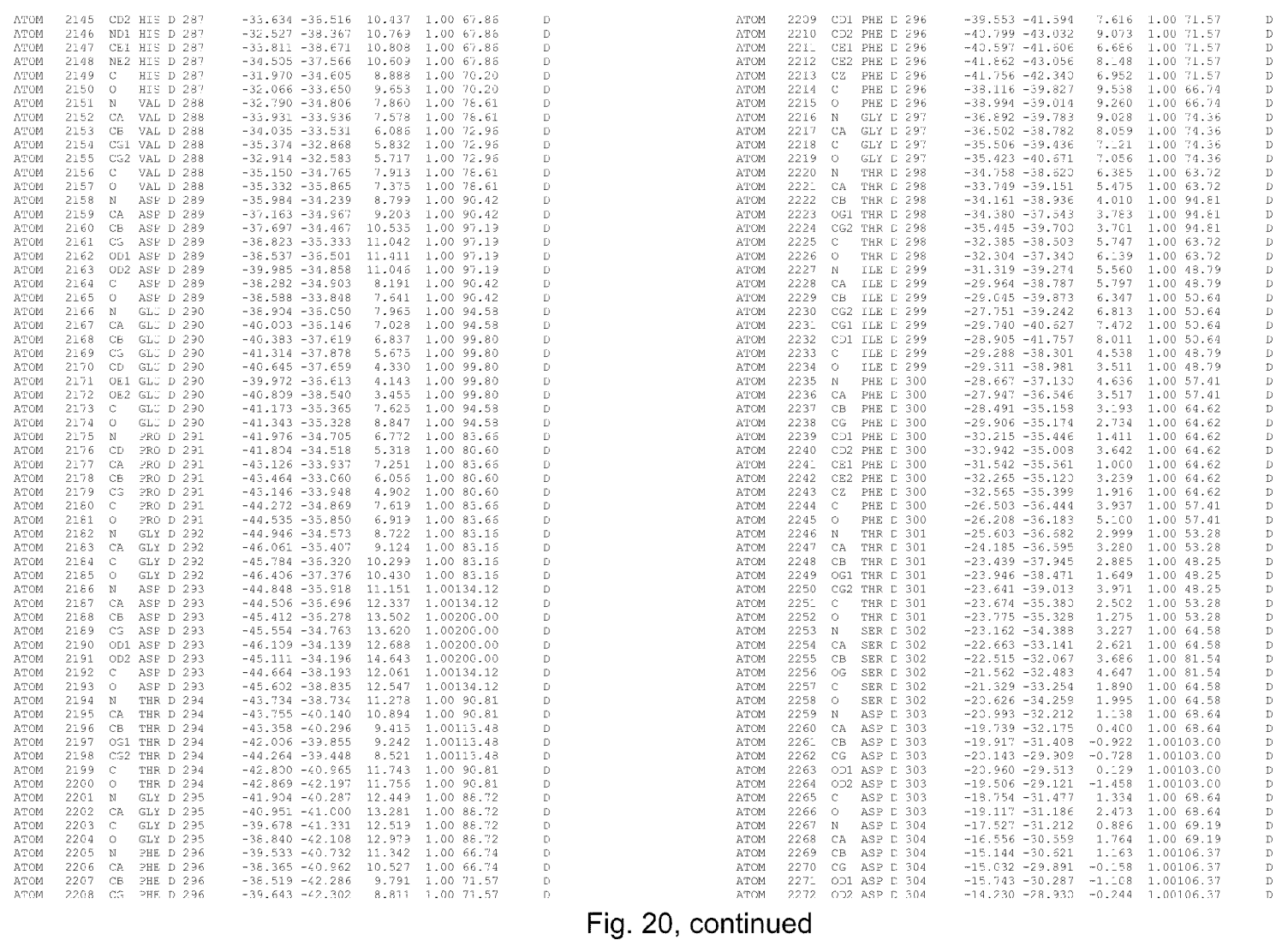
Figure 20:
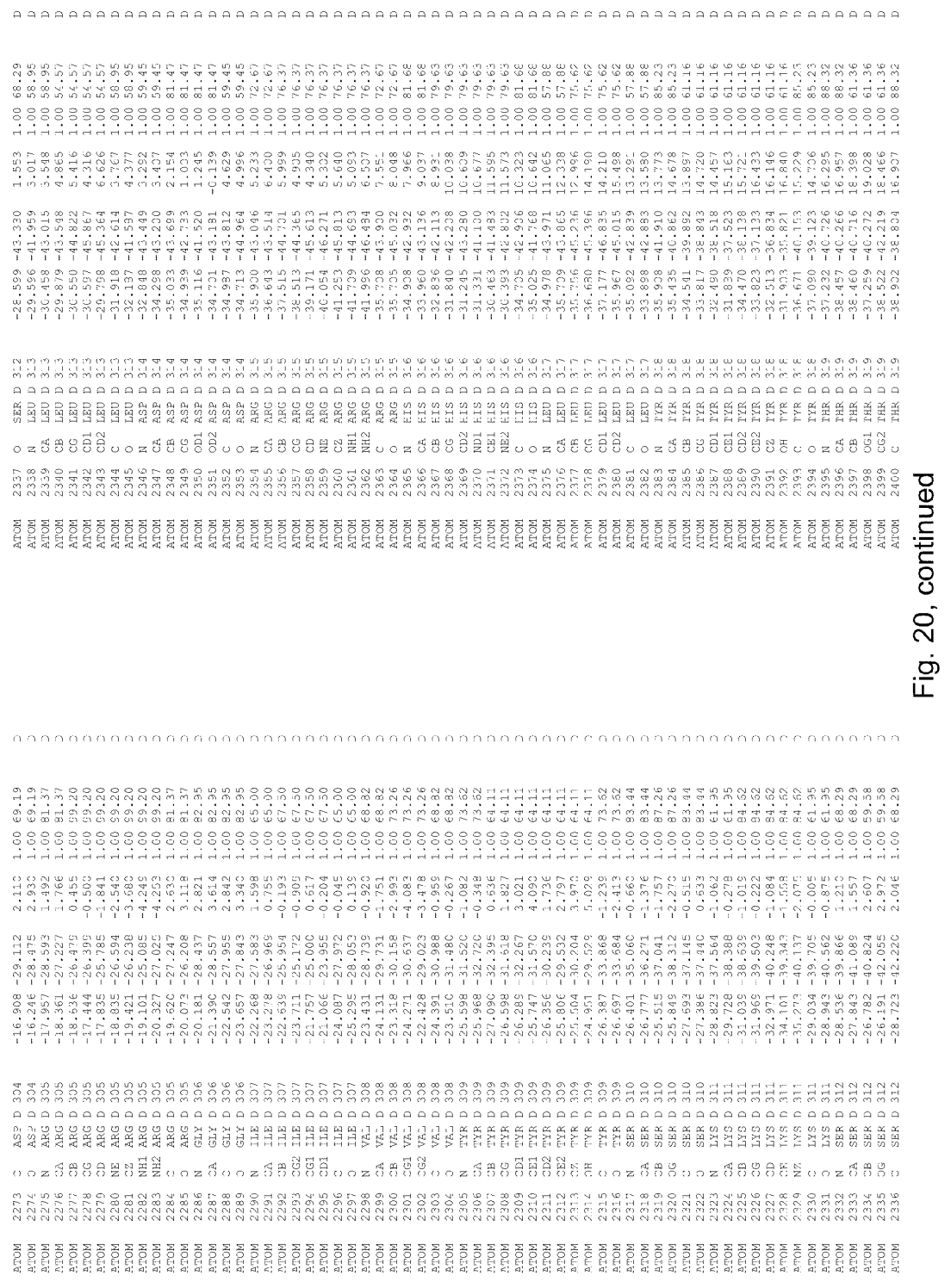
Figure 20:
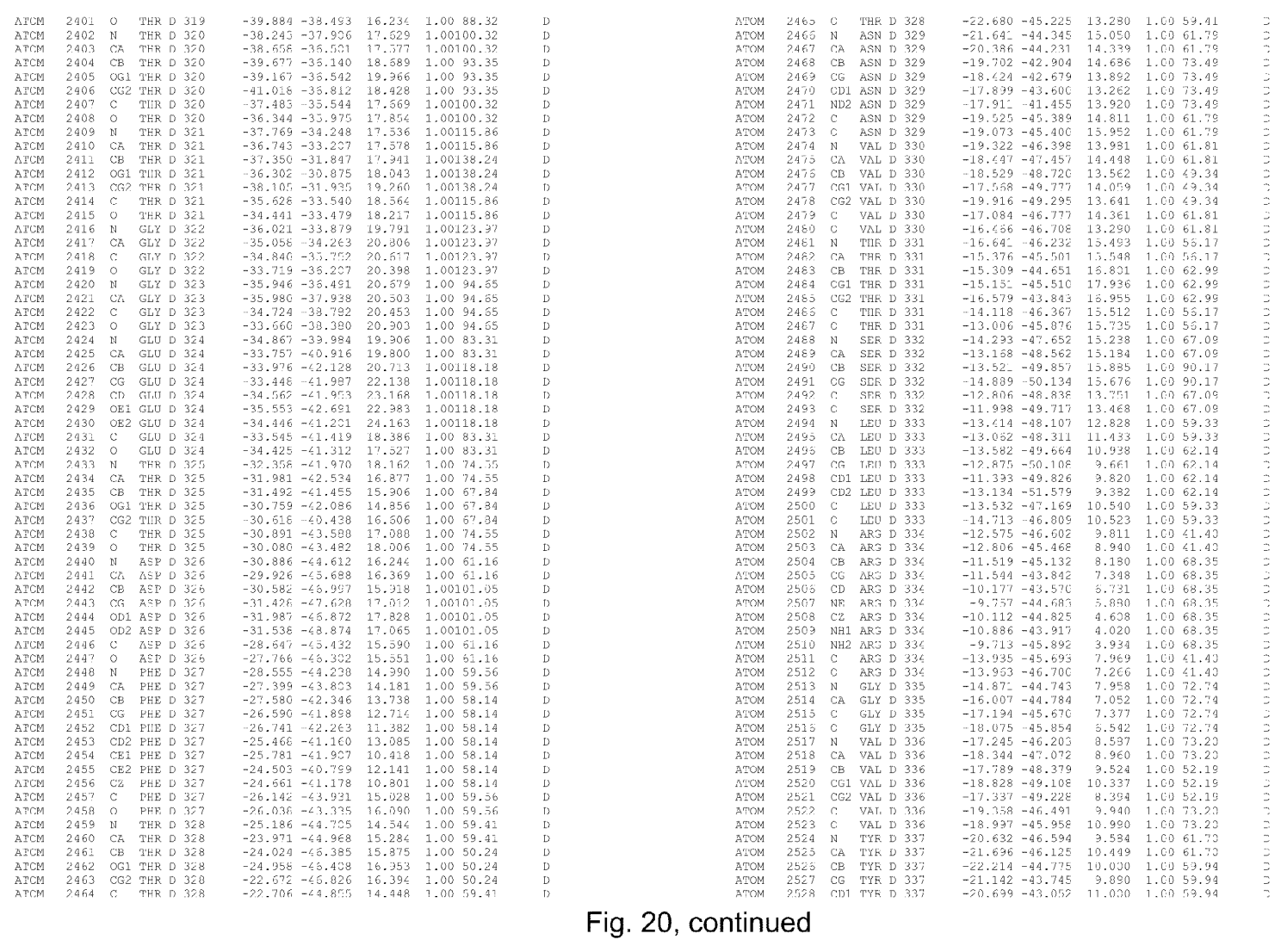
Figure 20:
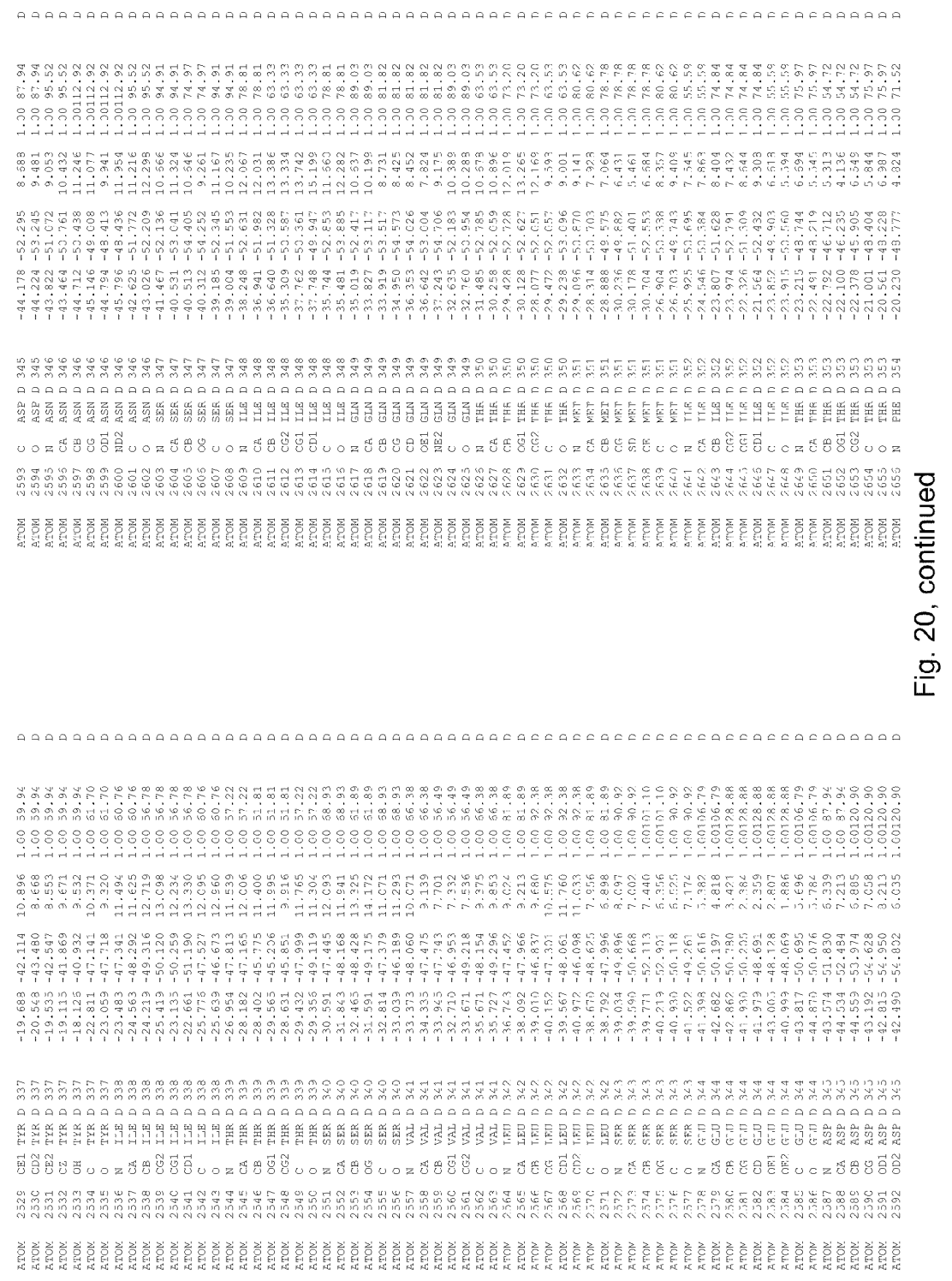
Figure 20:
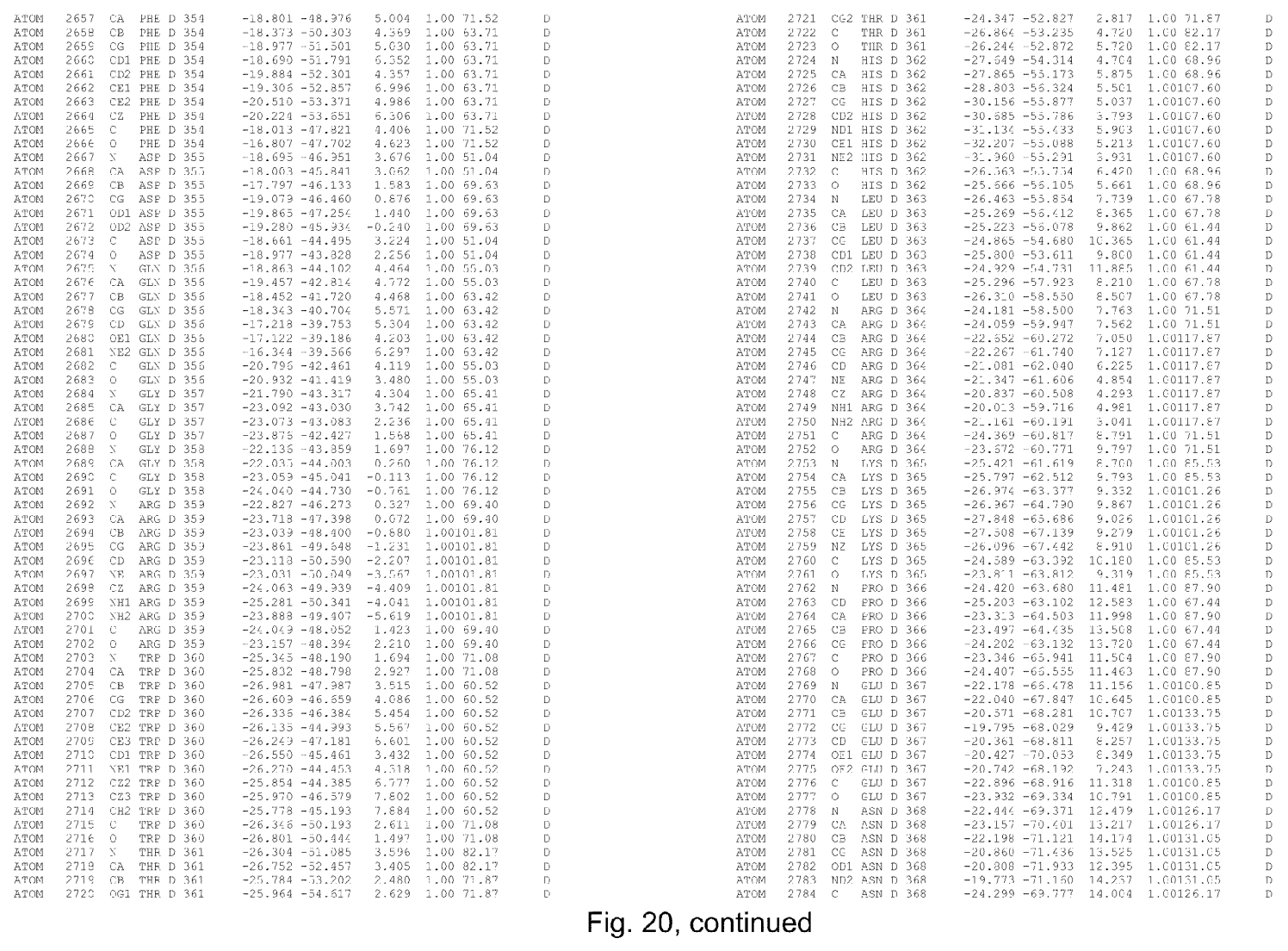
Figure 20:
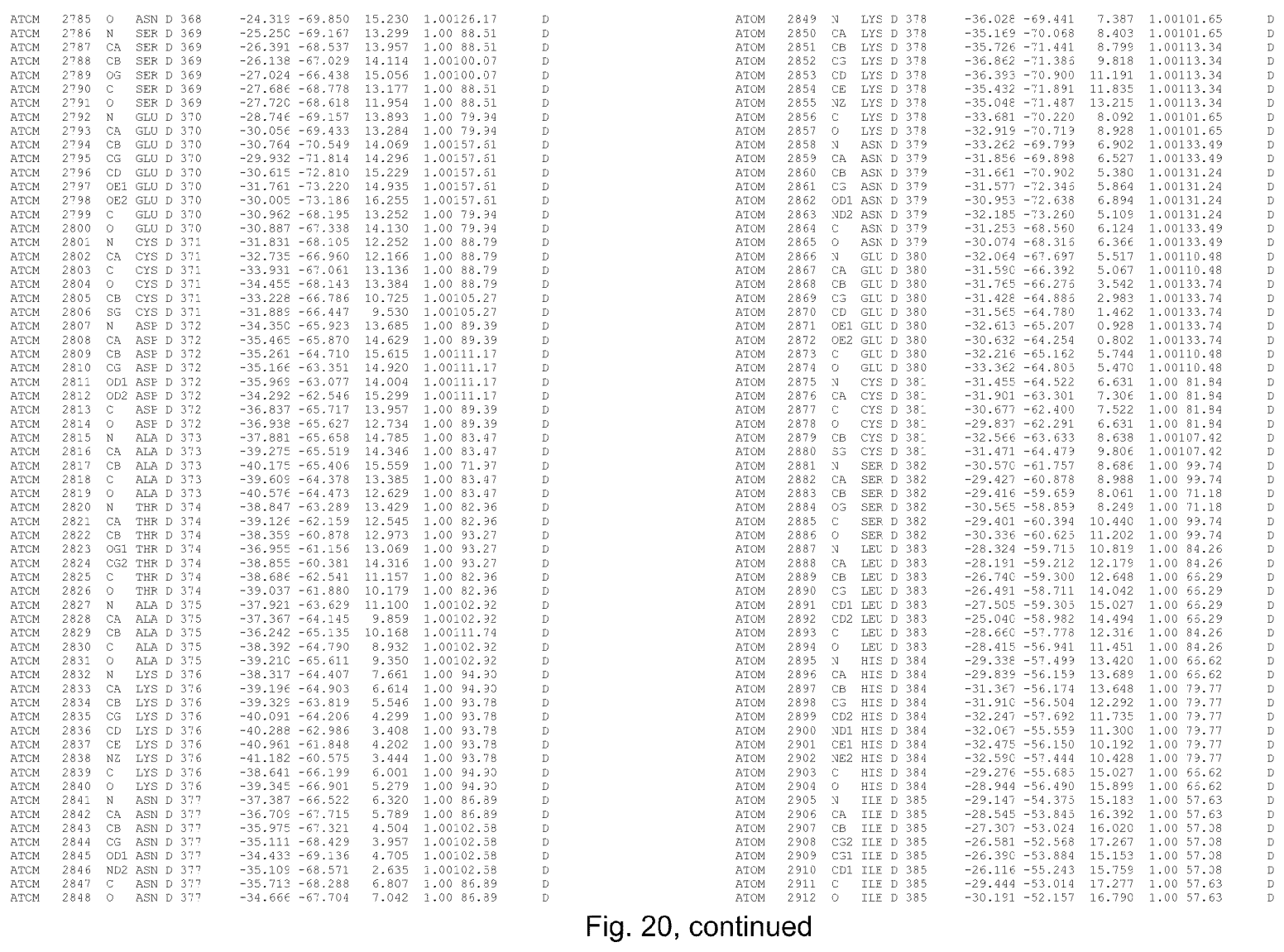
Figure 20:
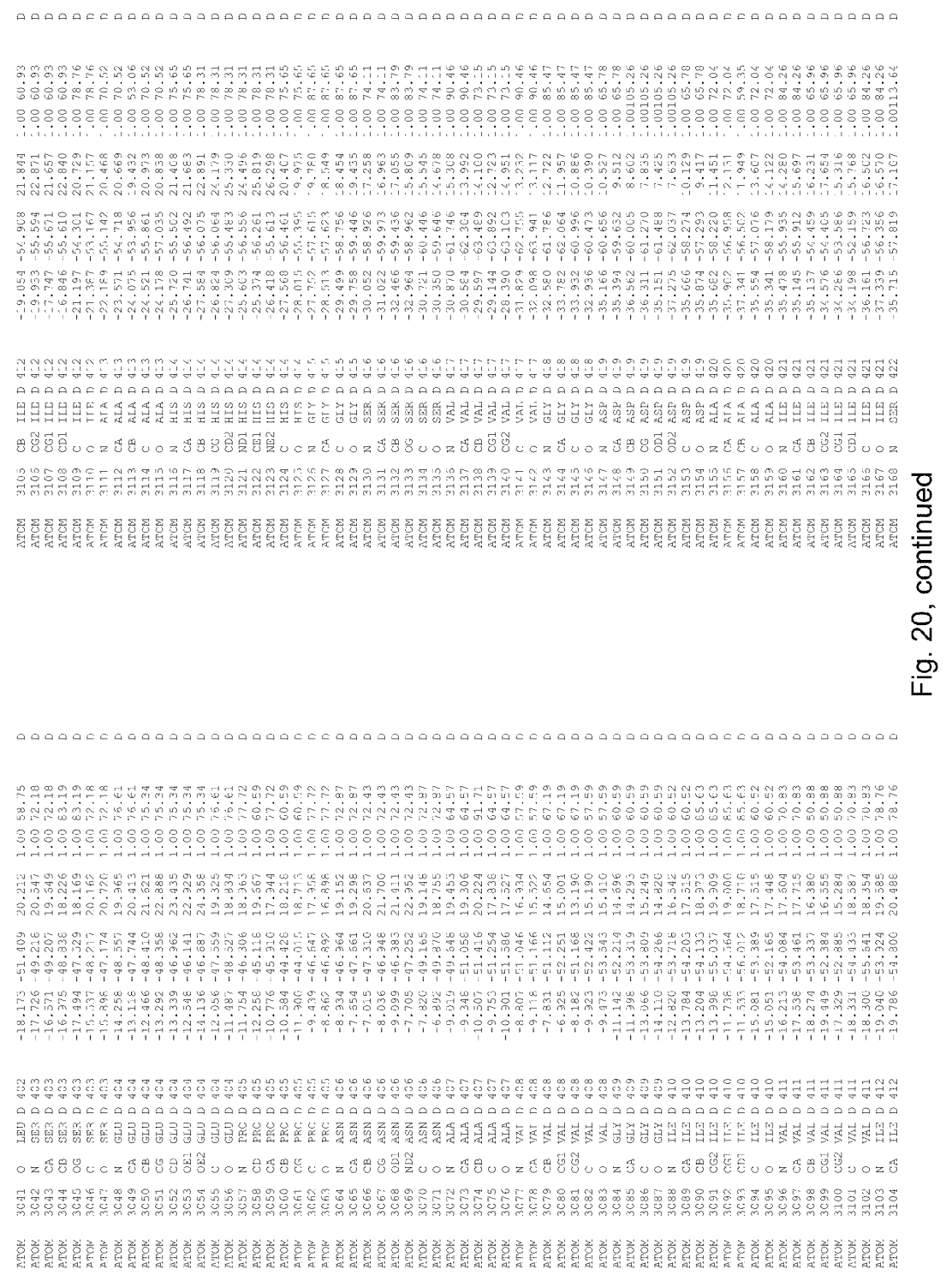
Figure 20:
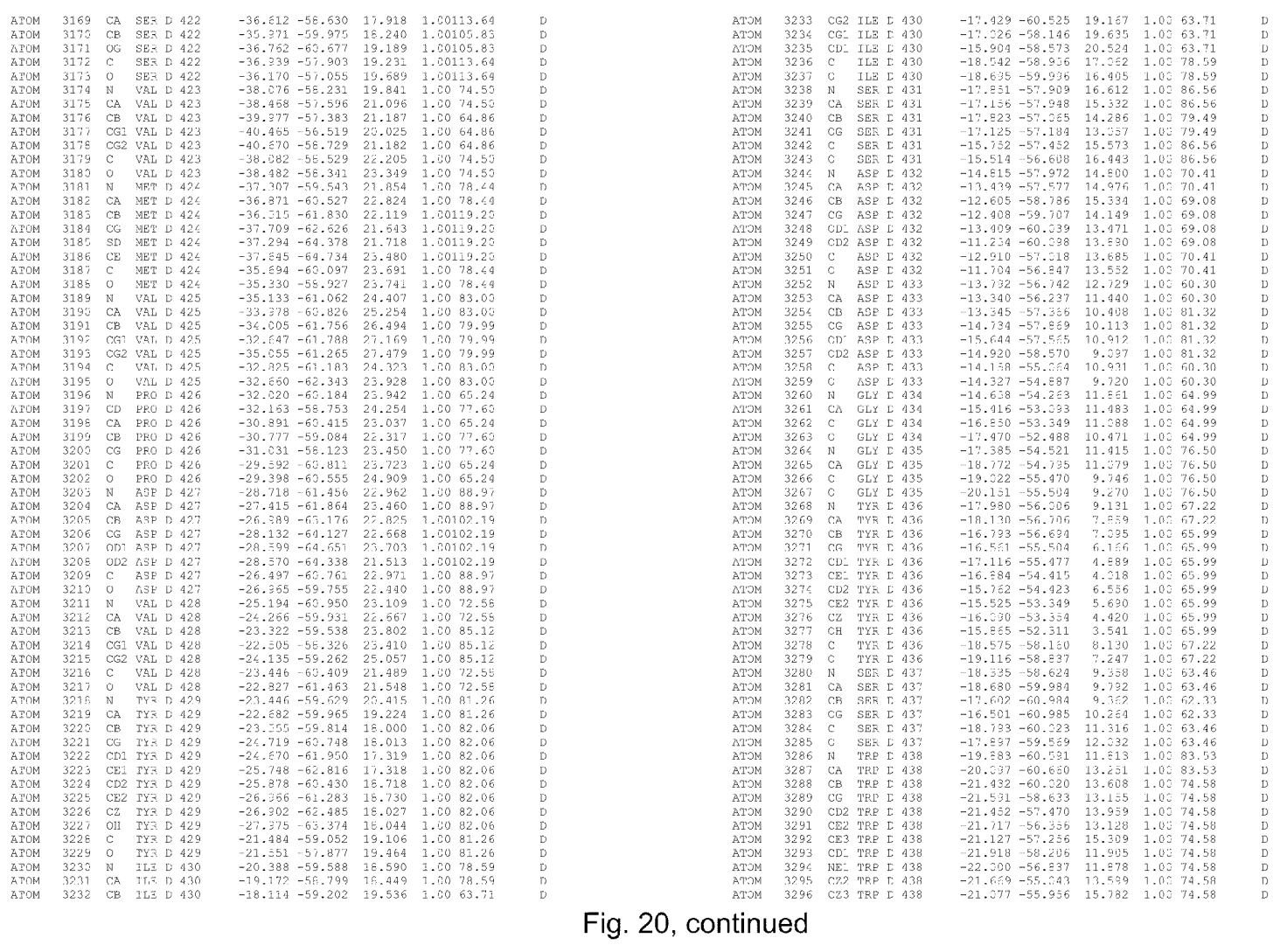
Figure 20:
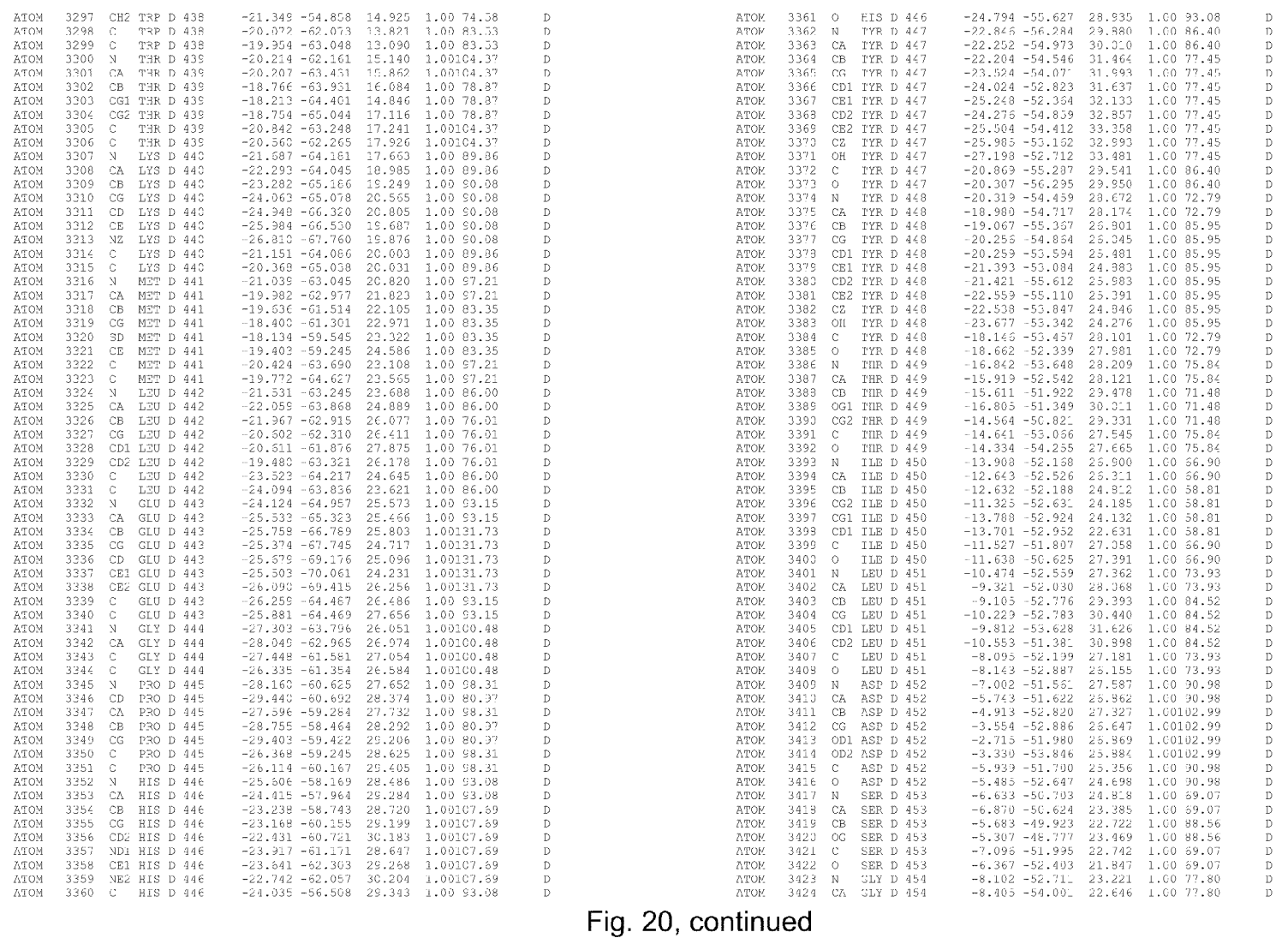
Figure 20:
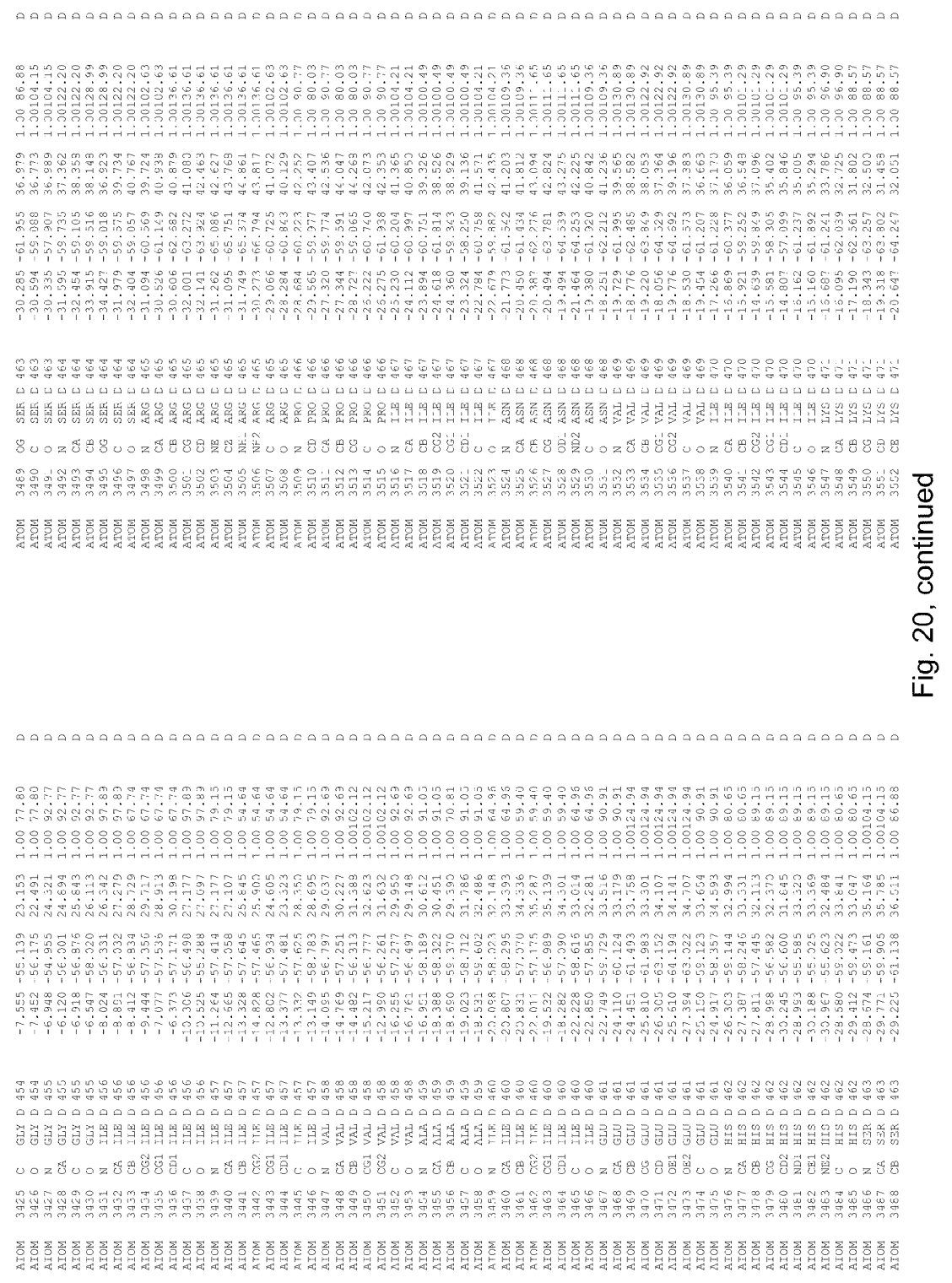
Figure 20:
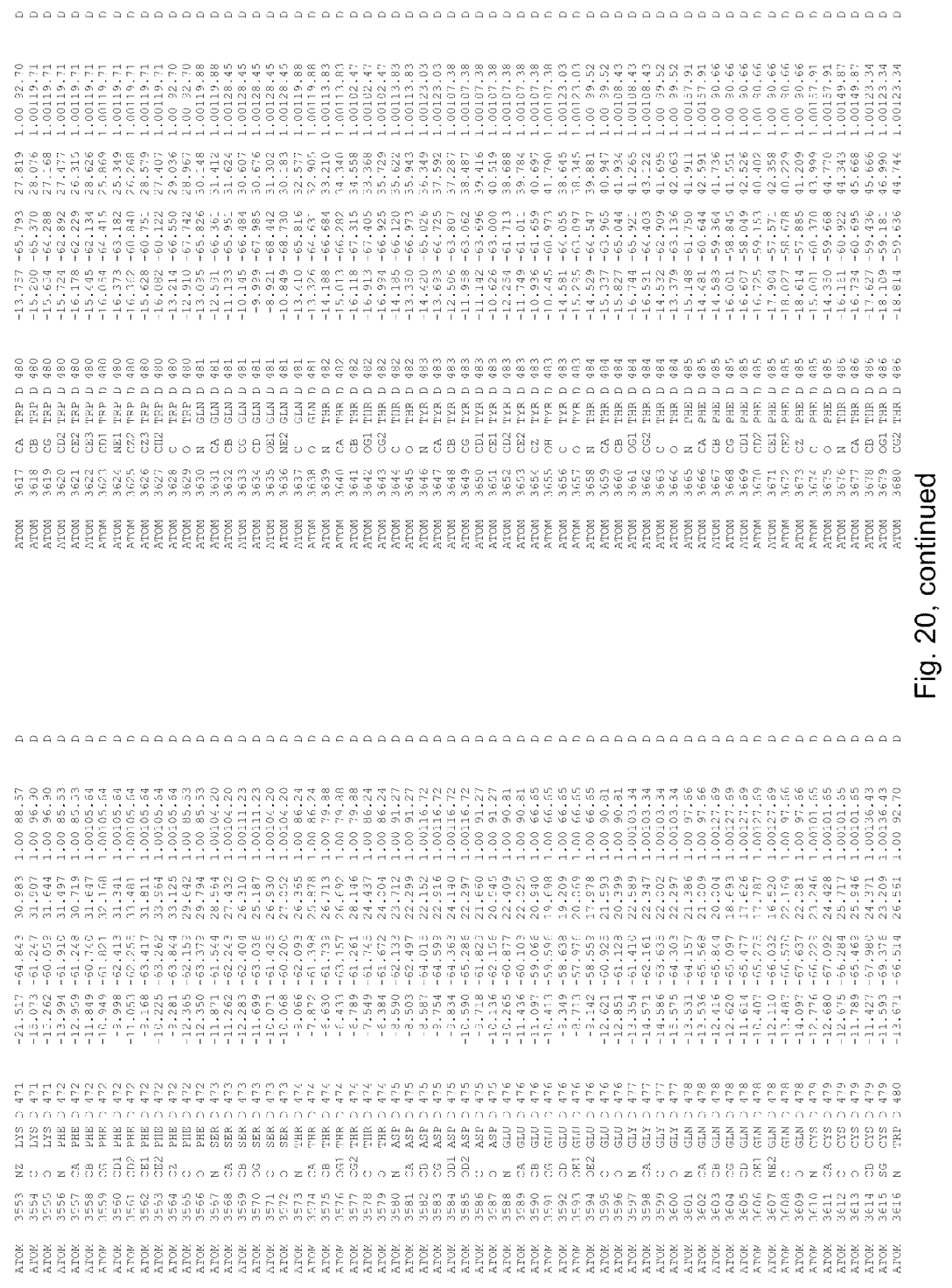
Figure 20:
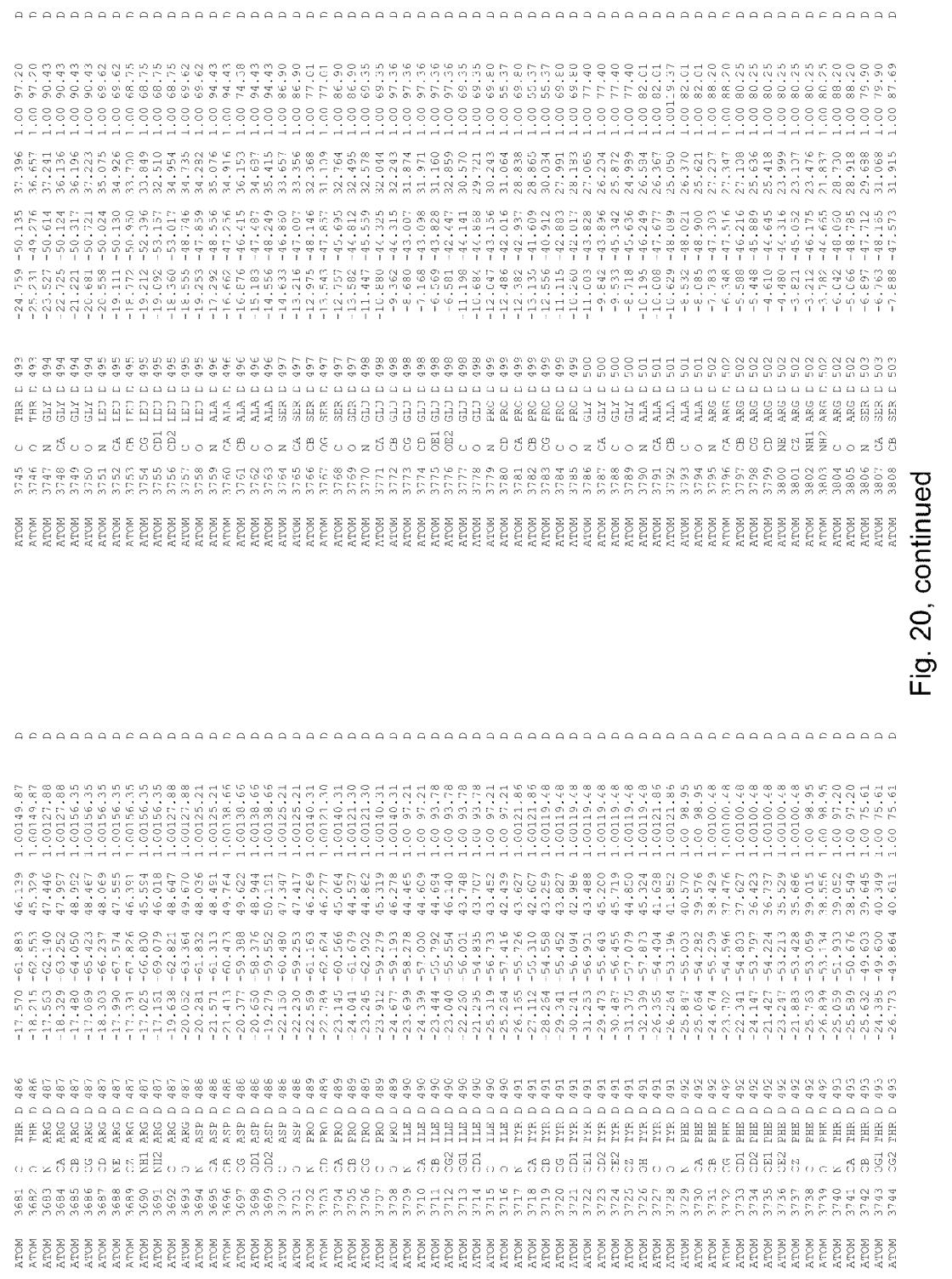
Figure 20:
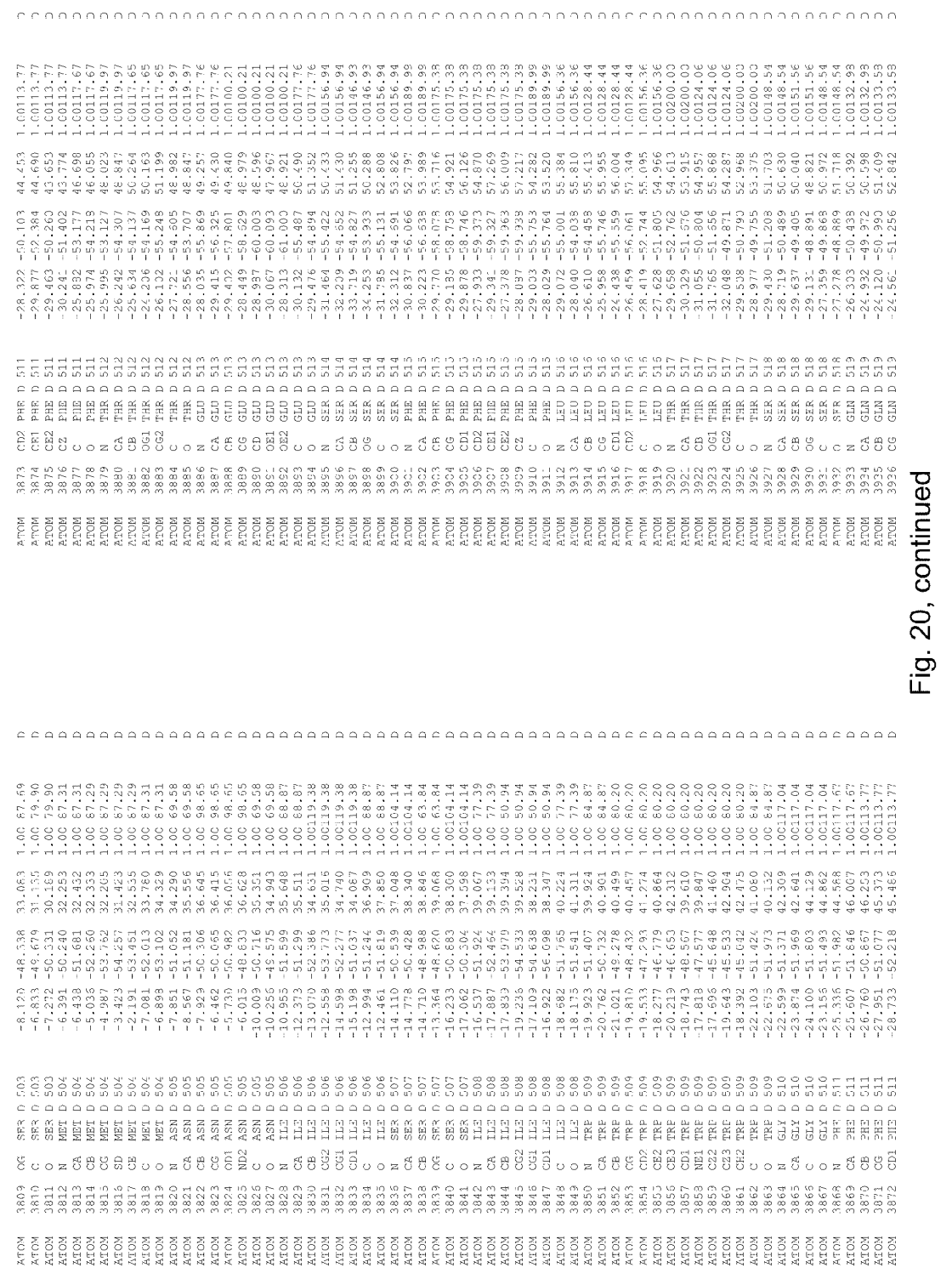
Figure 20:
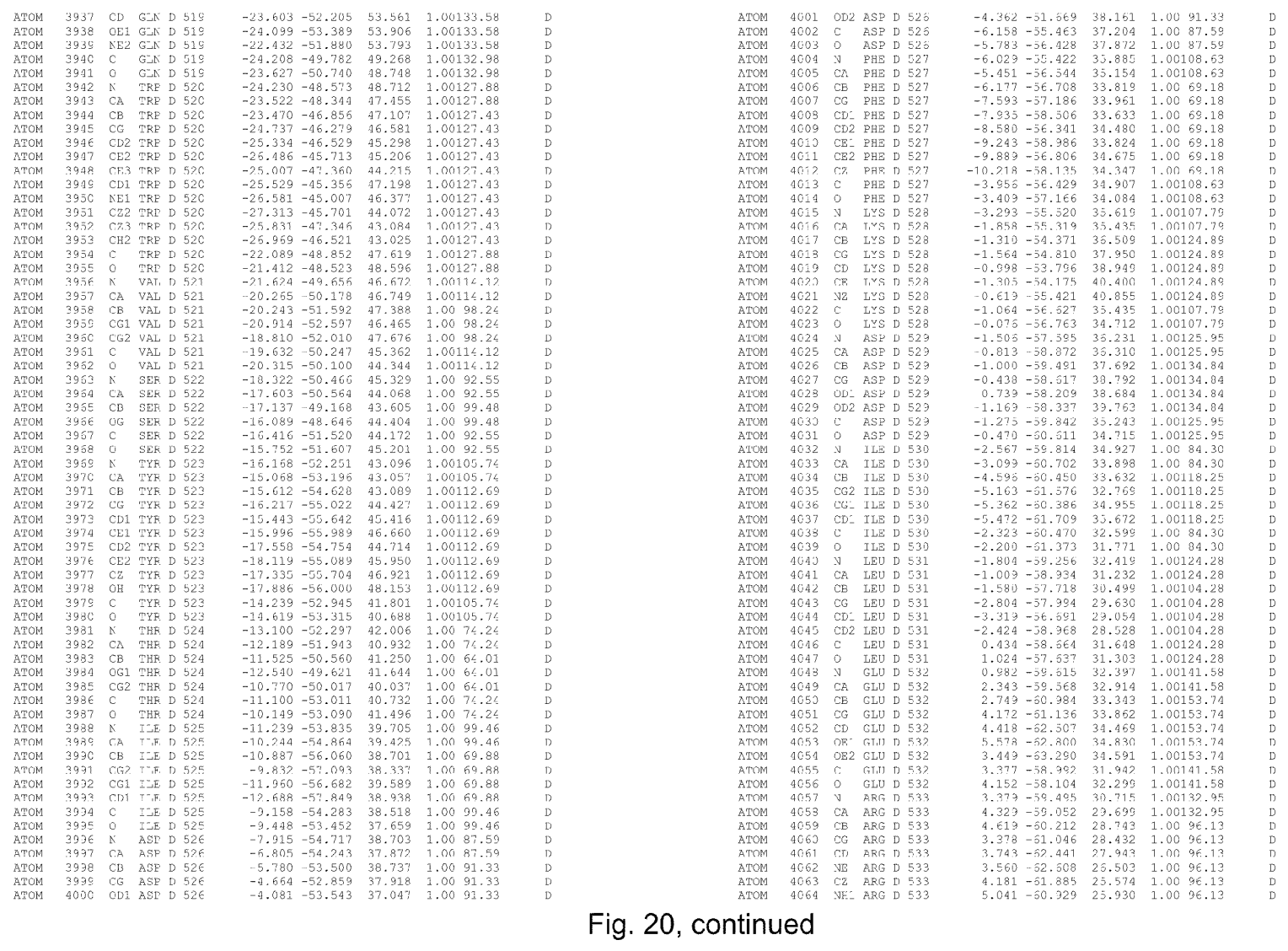
Figure 20:
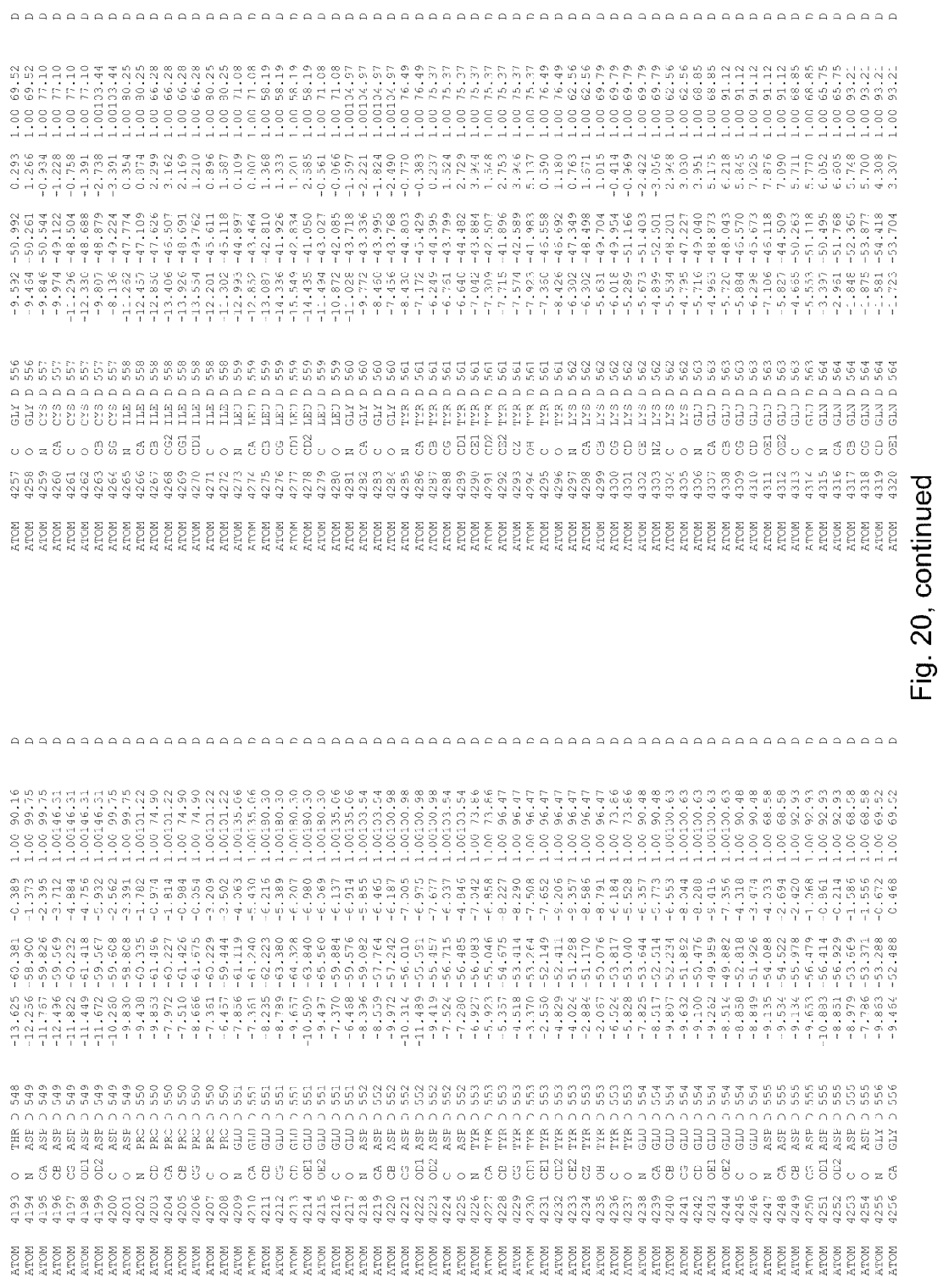
Figure 20:
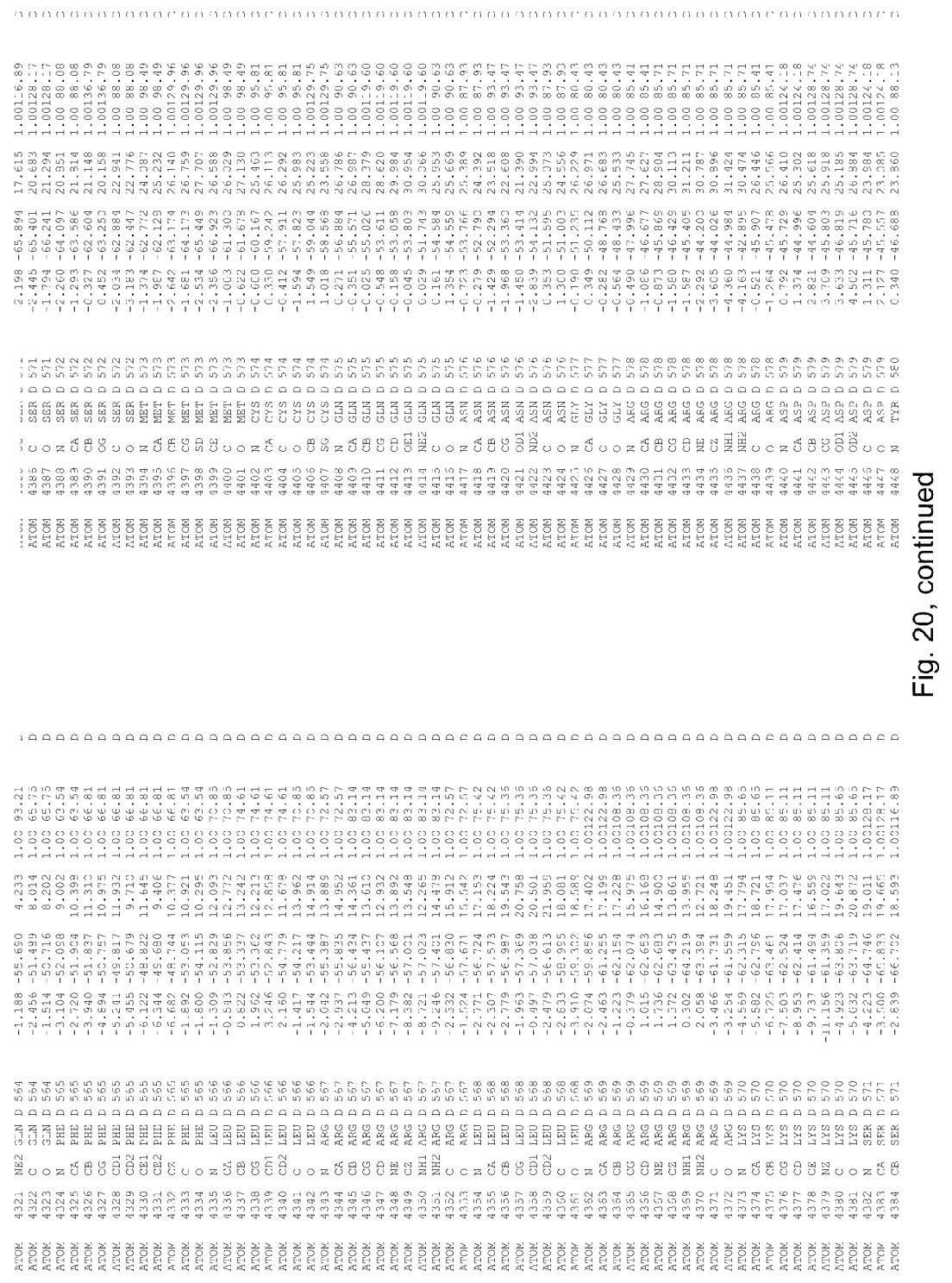
Figure 20:
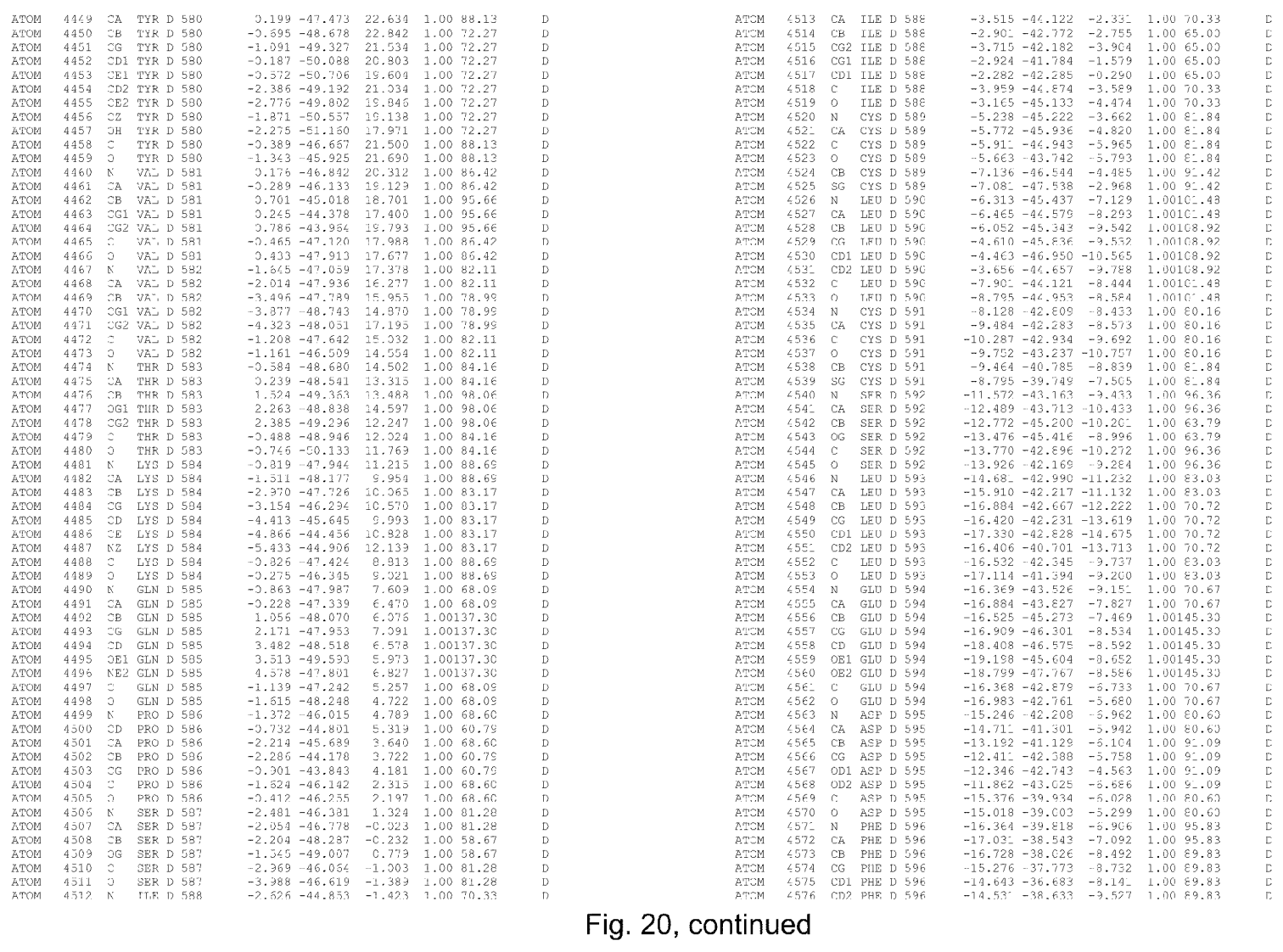
Figure 20:
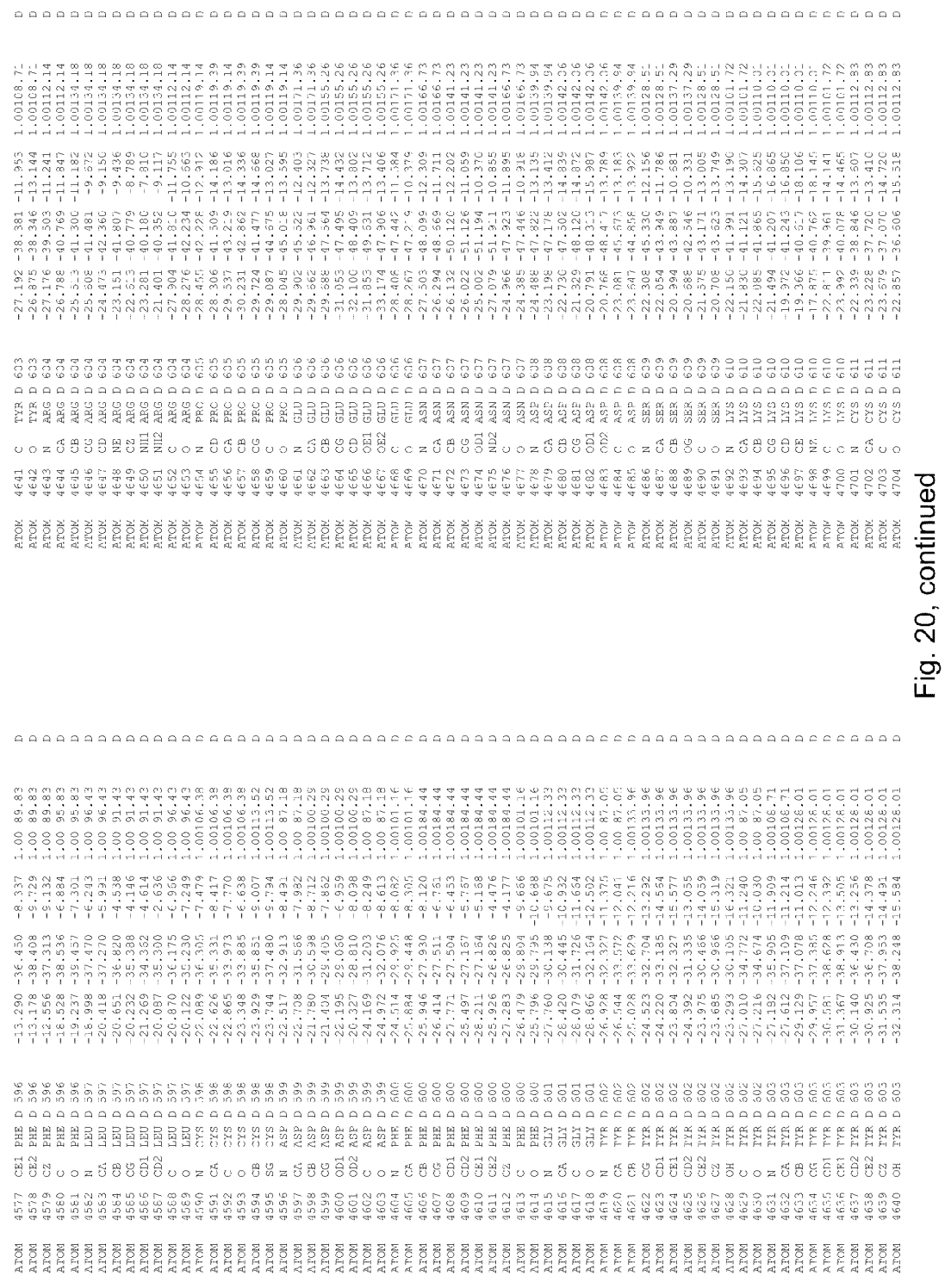
Figure 20:
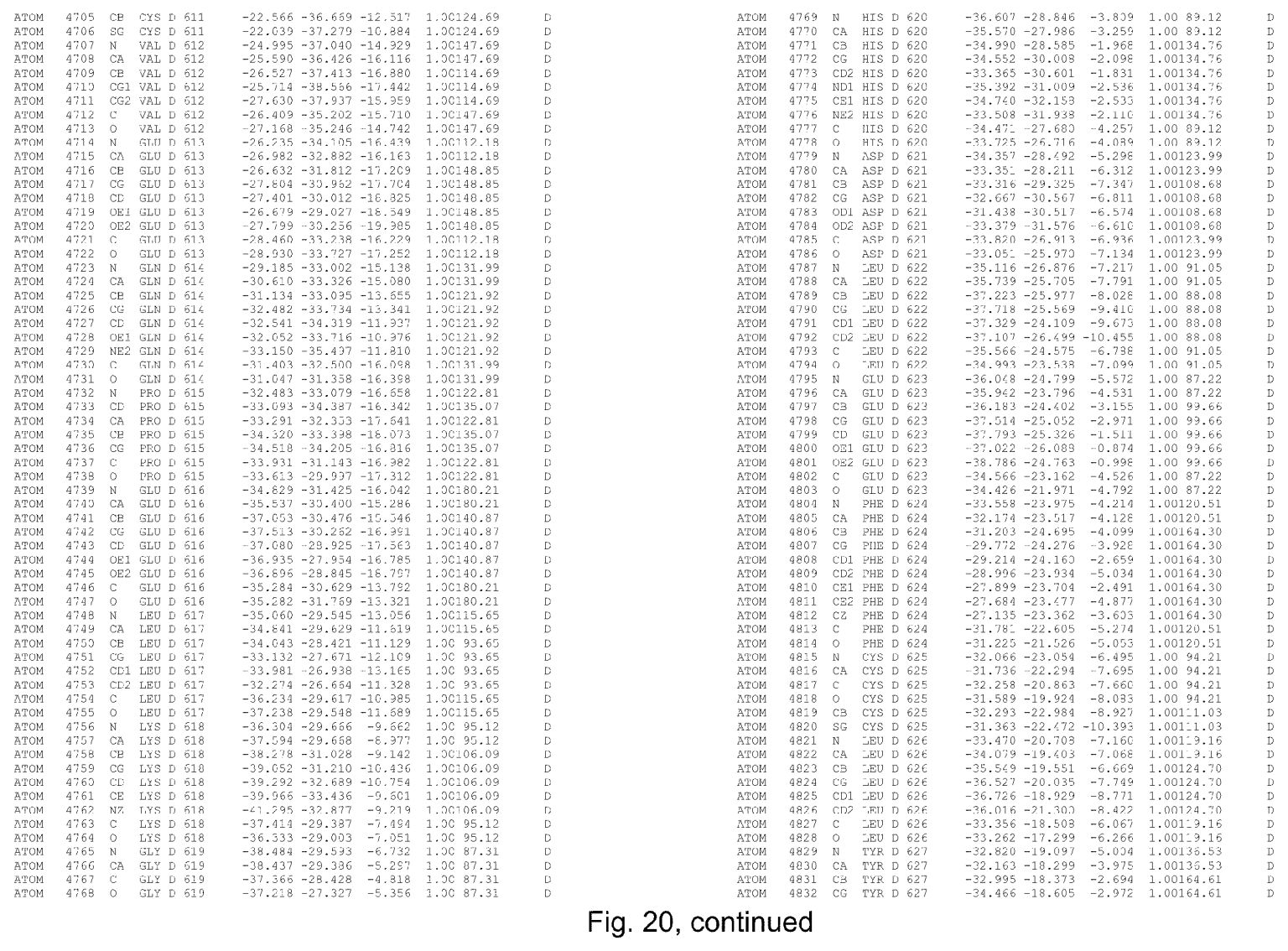
Figure 20:
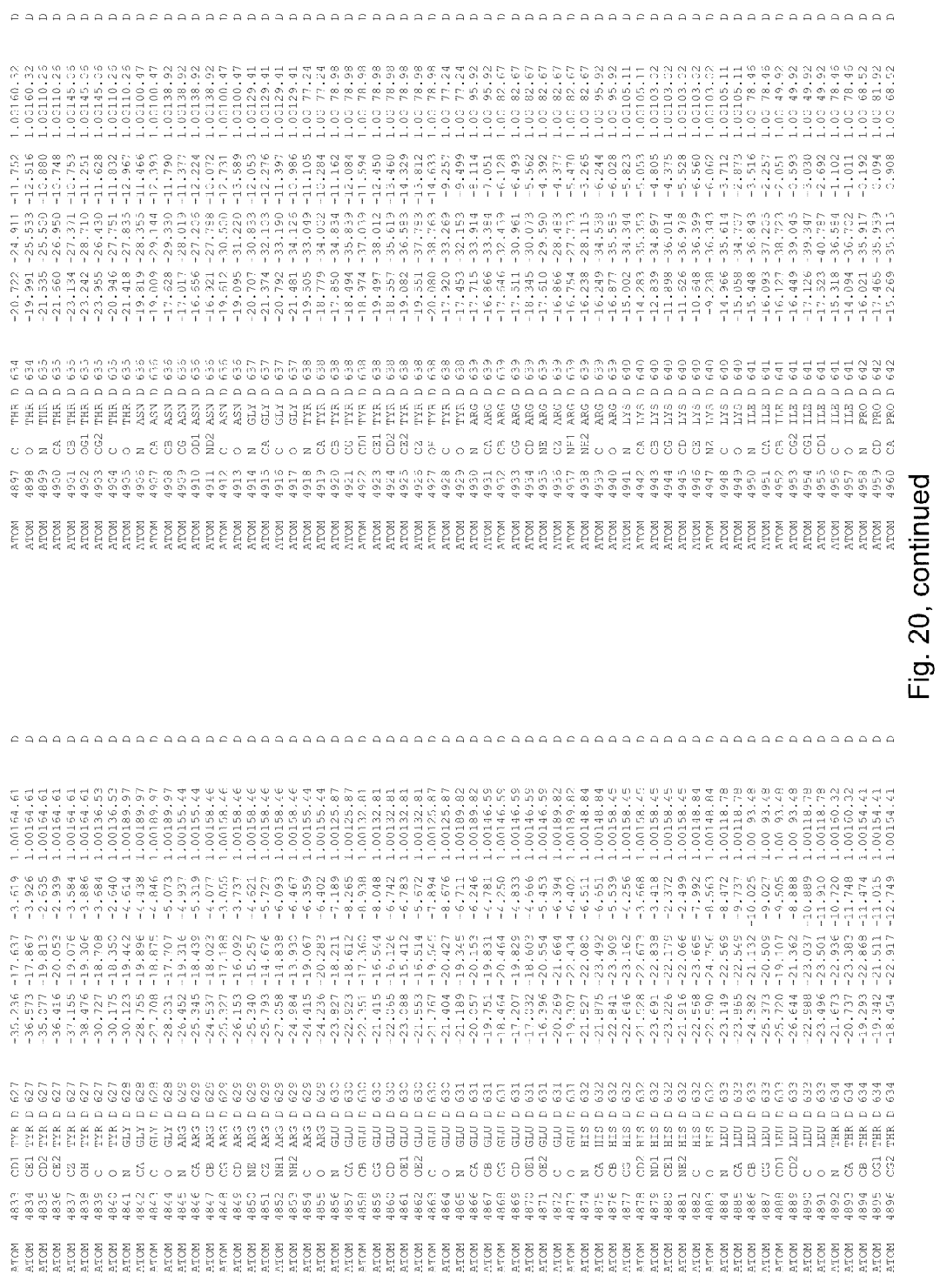
Figure 20:
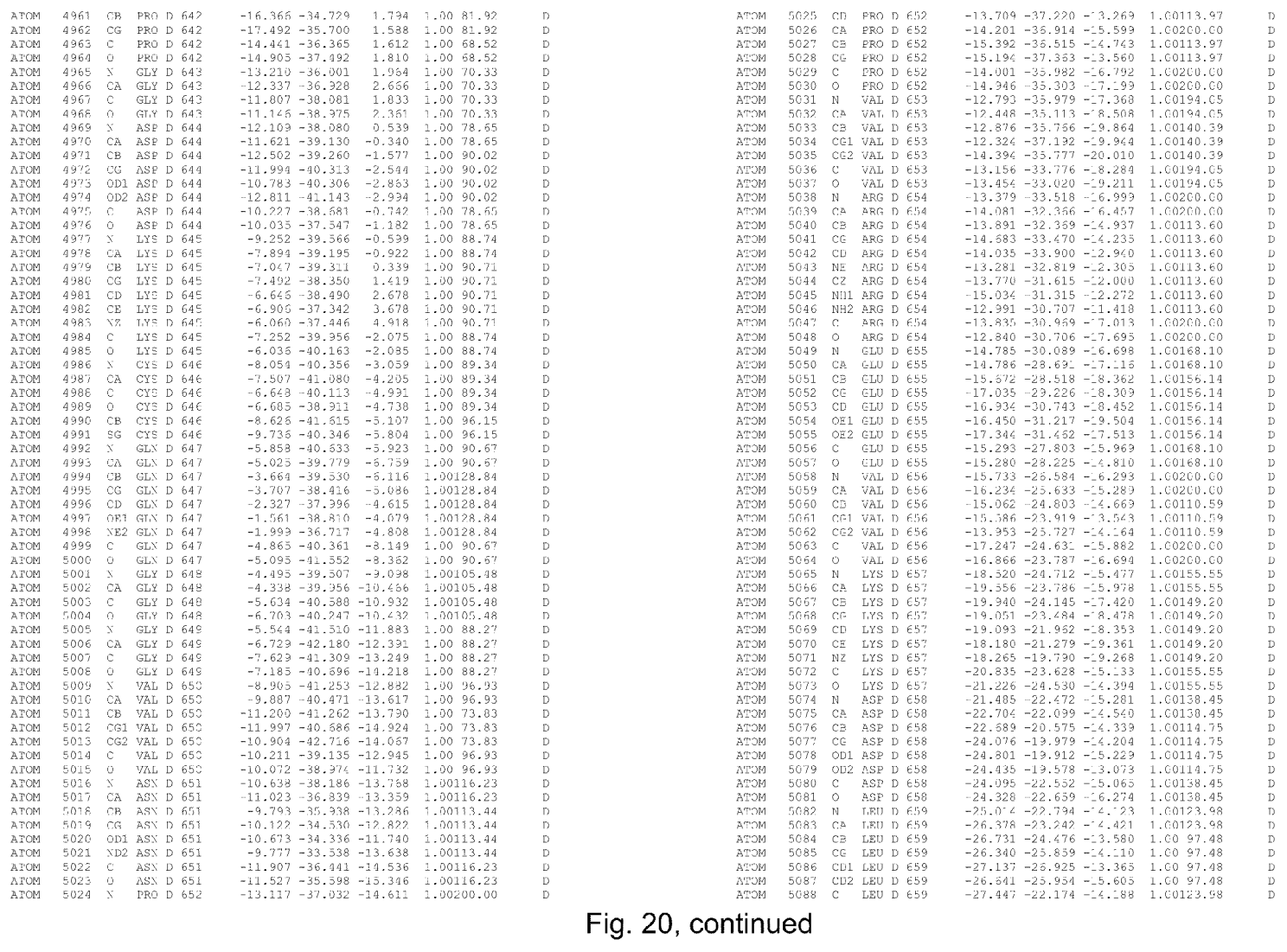
Figure 20:
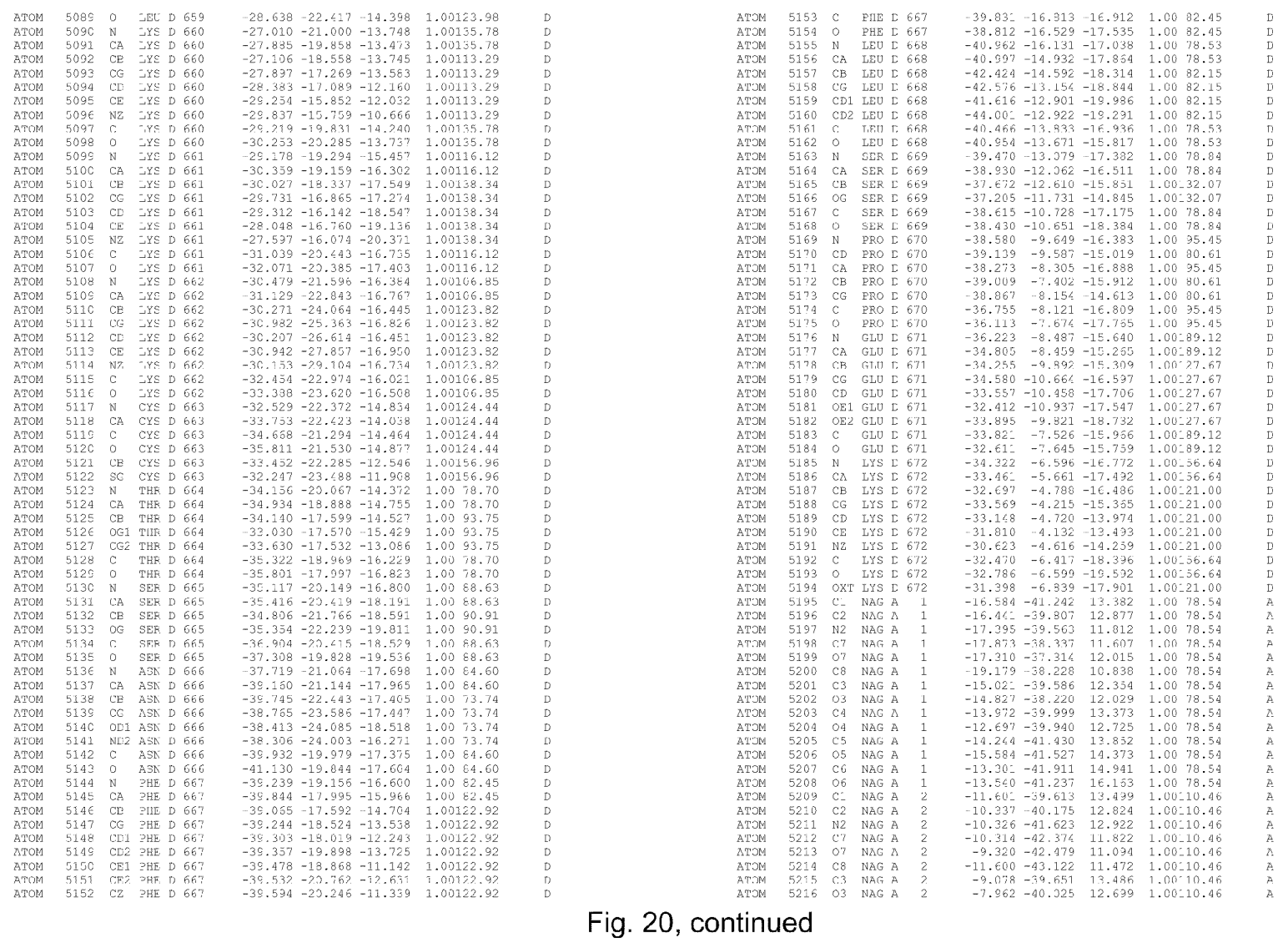
Figure 20:
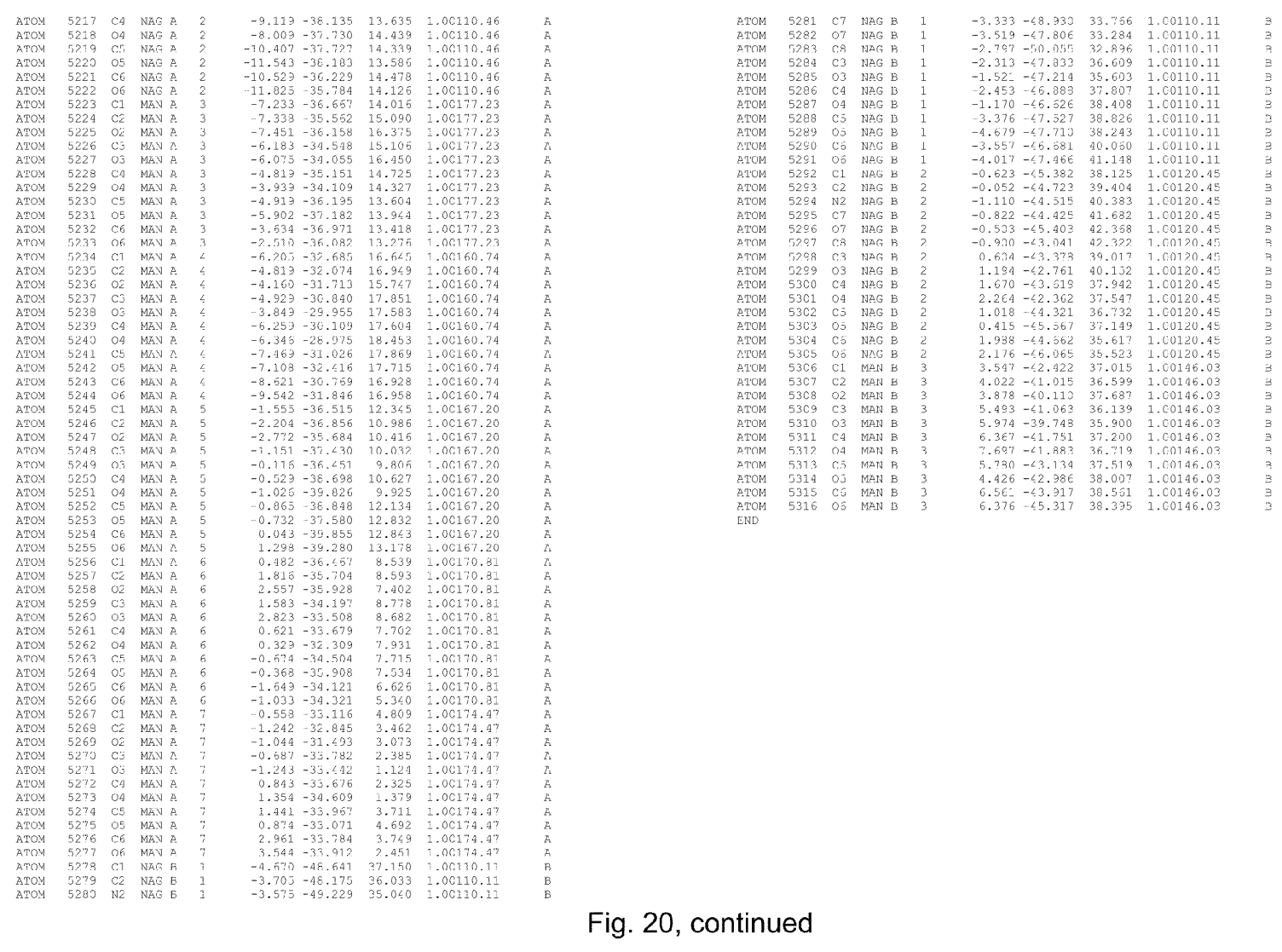

FIG. 20: Atomic coordinates of sSortilin crystallised in complex with Sortilin's own propeptide. sSortilin (SEQ ID NO:33) has the sequence of amino acid residues 78 to 755 of SEQ ID NO. 1. The propeptide is omitted in this model. The numbering of the first built Sortilin amino acid residues of this pdb file is D6 which corresponds to D83 of SEQ ID NO: 1 which is numbered in accordance with the Expasy database entry Q99523 as of the filing date of the present application. Thus, the sSortilin coordinates provided are those of SEQ ID NO:39 (which corresponds to amino acid residues Asp83 to Lys749 of SEQ ID NO. 1). Atom 1 corresponds to an atom of the first residue (Asp) of SEQ ID NO:38 (Asp83 of SEQ ID NO:1); atom 5194 corresponds to an atom of the last residue (Lys) of SEQ ID NO:38 (Lys749 of SEQ ID NO:1). NAG (N-acetyl-d-glucosamine); MAN (manose); PE (polyethylene glycol).

Figure 21:
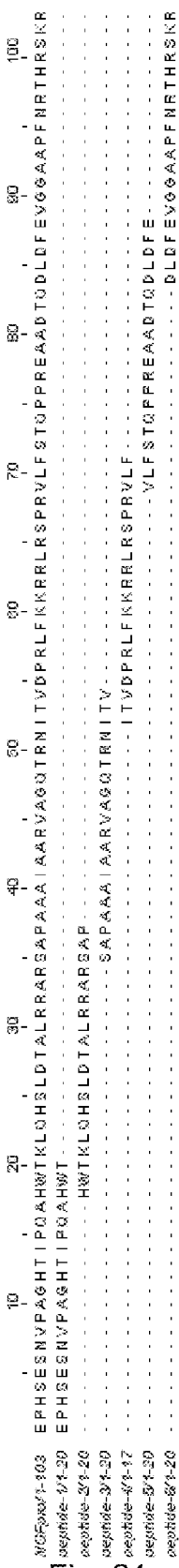

FIG. 21: Overview of the six icosapeptides of the NGF propeptide synthesized to cover the whole propeptide. Shown are the alignments of NGFpro/1-103 (SEQ ID NO:23) and icosapeptide fragments thereof (SEQ ID NOs:24-29).

Figure 22:
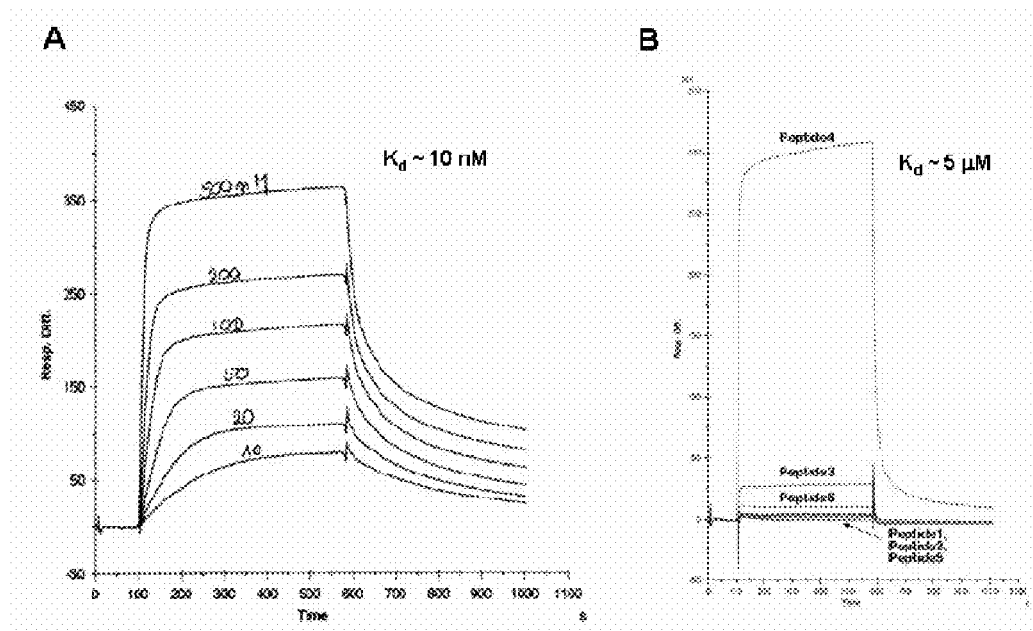

FIG. 22: Surface plasmon resonance analysis of the binding affinity of NGFpro peptide and icosapeptides for immobilized sSortilin.

Figure 23:
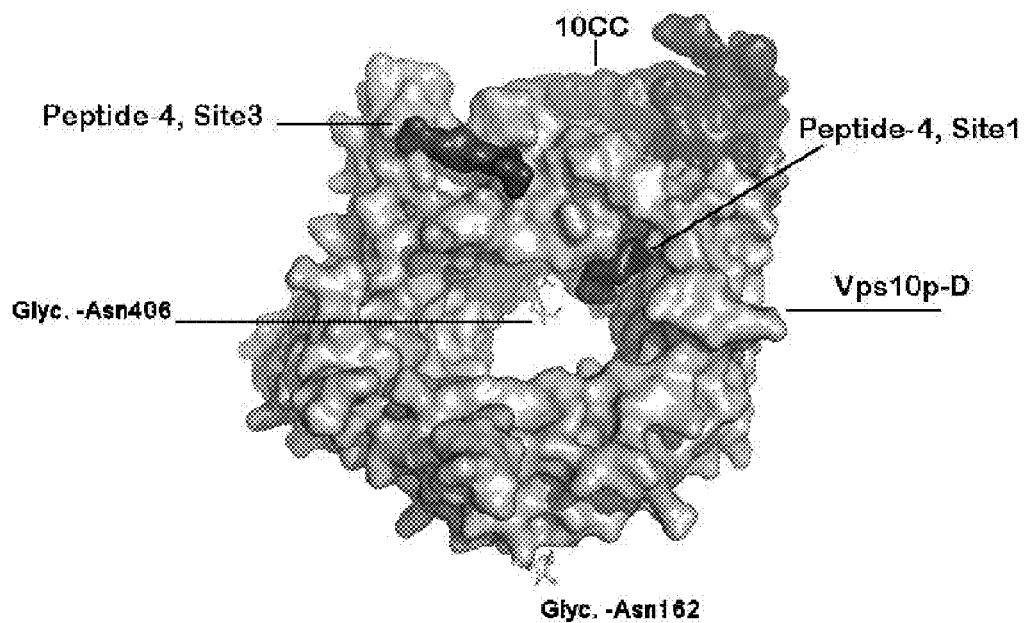

FIG. 23: Overview of the sSortilin-peptide4 complex displayed as surface representation. The surface of Vsp10p-D is light gray, 10 CC domain is gray, peptide4 from NGFpro is black and the glycosylations is displayed using 'ball and stick' representation coloured by atom type.

Figure 24:
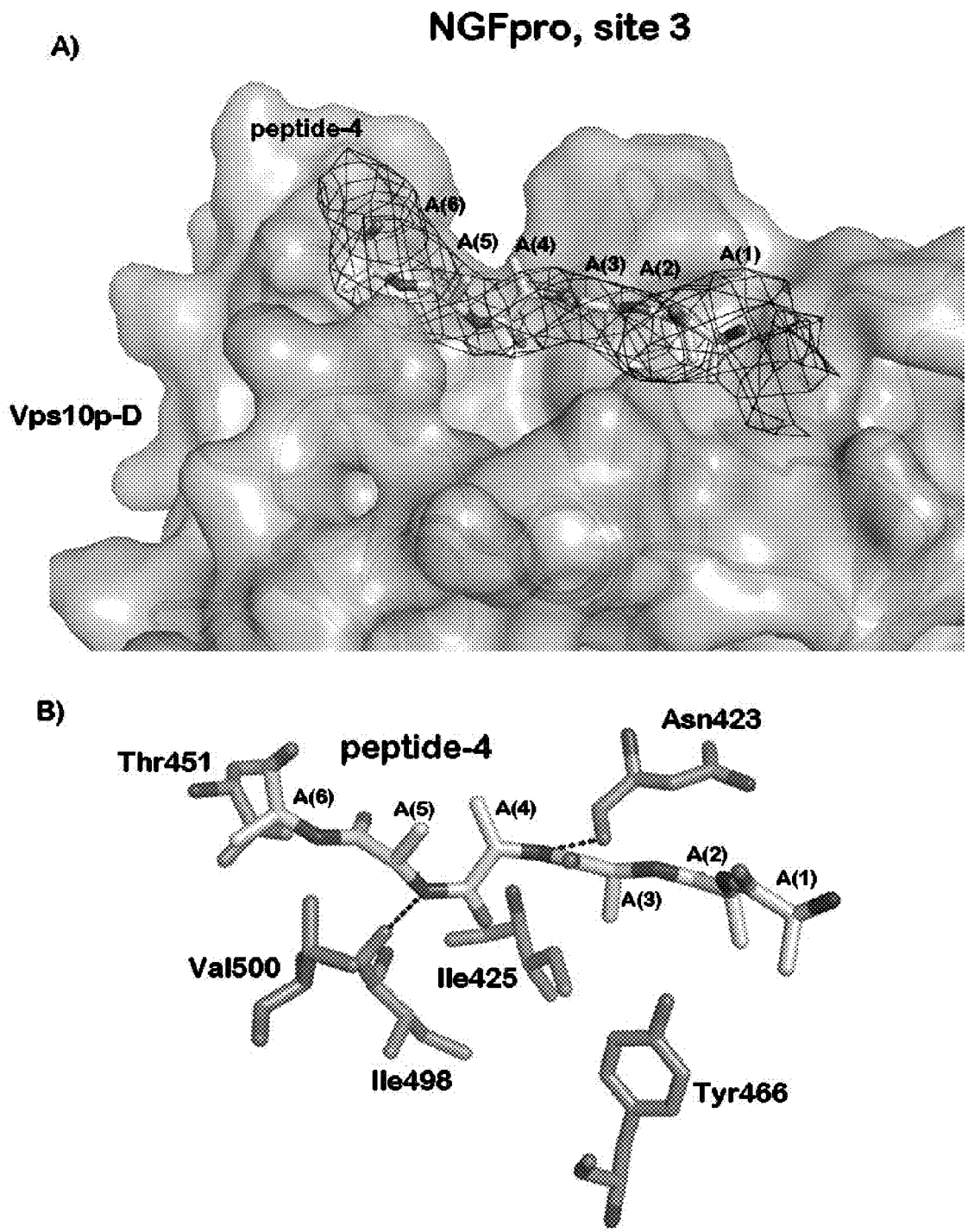

FIG. 24: Binding of the NGF prodomain (Site 3). A) The peptide-4 (SEQ ID NO:51) from NGFpro are shown as 'ball-and-stick' model coloured by atom type. A Fo-Fc electron density map, calculated without the peptides and contoured at 2.66 are superimposed upon the peptide. sSortilin is displayed using surface representation. B) The bound peptide4 is modelled as a hexa-alanine fragment and displayed as a 'ball and stick' model together with interacting residues of sSortilin.

FIG. 25: Binding of the NGF prodomain (Site 1/NTS-site). A) The peptide-4 (SEQ ID NO:51) from NGFpro is displayed as 'ball-and-stick' model coloured by atom type. The electron density map displayed has been calculated as indicated in FIG. 24 and superimposed upon the peptide. sSortilin is displayed using surface representation. B) The bound peptide4 is modelled as tetra-alanine fragment and displayed with interacting residues of sSortilin.

FIG. 26: Competition of peptides ELYENKPRRPYIL (SEQ ID NOs:30), RRPYIL (SEQ ID NO:31) and RRPYI (SEQ ID NO:32) with GST C-terminally tagged with Tyr-Ile-Leu (YIL). Binding to immobilized sSortilin was measured by surface plasmon resonance. 100% corresponds to the measured response units obtained for 100 nM GST-YIL in the absence of competing peptide. The EC50 values is the concentration of peptide at which the GST-YIL binding is reduced to 50%. Sequences are given for the peptides and for peptides that contain non-natural amino acids the structure is also shown.

OVERVIEW OF SEQUENCES

SEQ ID NO:1: Sortilin
SEQ ID NO:2: SorLA
SEQ ID NO:3: SorCS1
SEQ ID NO:4: SorCS2
SEQ ID NO:5: SorCS3
SEQ ID NO:6: pre-pro-NGF
SEQ ID NO:7: pre-pro-BDNF
SEQ ID NO:8: Neurotrophin-3
SEQ ID NO:9: Neurotrophin-4/5
SEQ ID NO:10: Neurotensin (1-13)
SEQ ID NO:11: PYIL (C-term.of Neurotensin)
SEQ ID NO:12 Synthetic peptide
SEQ ID NO:13 RAP
SEQ ID NO:14 *Bos taurus* sortilin
SEQ ID NO:15 *Canis familiaris* sortilin
SEQ ID NO:16 *Rattus norvegicus* sortilin
SEQ ID NO:17 *Mus musculus* sortilin
SEQ ID NO:18 *Ornithorhynchus anatinus* sortilin
SEQ ID NO:19 *Tetraodon nigroviridis* sortilin
SEQ ID NO:20 *Danio rerio* sortilin
SEQ ID NO:21 Residues 34-76 of SEQ ID NO:1 (Sortilin)
SEQ ID NO:22 His6 Tag
SEQ ID NO:23 NGFpro/1-103
SEQ ID NO:24 Synthetic icosapeptide of the NGF propeptide
SEQ ID NO:25 Synthetic icosapeptide of the NGF propeptide
SEQ ID NO:26 Synthetic icosapeptide of the NGF propeptide
SEQ ID NO:27 Synthetic icosapeptide of the NGF propeptide
SEQ ID NO:28 Synthetic icosapeptide of the NGF propeptide
SEQ ID NO:29 Synthetic icosapeptide of the NGF propeptide
SEQ ID NO:30 Synthetic peptide
SEQ ID NO:31 Synthetic peptide
SEQ ID NO:32 Synthetic peptide
SEQ ID NO:33 sSortilin (amino acid residues 78-755 of SEQ ID NO:1)
SEQ ID NO:34 sSortilin fragment (amino acid residues 86-748 of SEQ ID NO:1)
SEQ ID NO:35 Synthetic peptide
SEQ ID NO:36 sSortilin fragment (amino acid residues 87-749 of SEQ ID NO:1)
SEQ ID NO:37 sSortilin fragment (amino acid residues 86-747 of SEQ ID NO:1)
SEQ ID NO:38 peptide fragment of Neurotensin
SEQ ID NO:39 sSortilin fragment (amino acid residues 83-749 of SEQ ID NO:1)
SEQ ID NO:40 NGF pro domain (amino acid residues 19 to 121 of SEQ ID NO 6)
SEQ ID NO:41 NT propeptide (amino acid residues 17-140 of SEQ ID NO:8)
SEQ ID NO:42 NGF pro-domain (amino acid residues 19-121 of SEQ ID NO 6)
SEQ ID NO:43 pro BDNF (amino acid residues 19-246 of SEQ ID NO 7)
SEQ ID NO:44 BDNF pro domain (amino acid residues 19-127 of SEQ ID NO:7)
SEQ ID NO:45 Pro NT3 (amino acid residues 17-257 of SEQ ID NO:8)
SEQ ID NO:46 NT3 pro domain (amino acid residues 17-140 of SEQ ID NO:8)
SEQ ID NO:47 proNT 4/5 (amino acid residues 25-210 of SEQ ID NO 9)
SEQ ID NO:48 NT4/5 pro domain (amino acid residues 25-80 of SEQ ID NO 9)
SEQ ID NO:49 Sortilin propeptide (amino acid residues 34-77 of SEQ ID NO:1)
SEQ ID NO:50 Sortilin propeptide fragment
SEQ ID NO:51 Peptide-4
SEQ ID NO:52 Synthetic peptide

EXAMPLES

Example 1

Expression and Purification of Sortilin

Soluble Sortilin (sSortilin; SEQ ID NO:33), comprising the entire luminal domain (amino acids 1 to 758) but not the transmembrane segment or the cytoplasmic tail of Sortilin, fused C-terminally to His6 (SEQ ID NO:22) was stably expressed in CHO-K1 cells as previously described (5). The CHO-transfectants were cultured in serum-free HyQ-CCM5 CHO medium (HyClone, Logan, Utah) in 500 cm$^3$ Nunclon™ TripleFlasks. Incorporation of seleno-methionine (SeMet) followed a procedure previously described with only minor modifications (22). Both native and SeMet substituted protein were purified by RAP affinity chromatography as previously described (1). The S316E and R325A Sortilin mutants, were stably expressed in CHO-cells and subsequently purified from the medium by His$_6$-tag affinity chromatography in the same way as previously described for Sortilin mutated in the furin propeptide cleavage site (5). Neurotensin was purchased from Sigma and the Sortilin propeptide fragment (SEQ ID NO:50; consisting of residues 37-61 of SEQ ID NO:1) as well as the various Neurotensin fragments were purchased from BIOMOL International L.P. (UK). All peptides were more than 95% pure. Expression and purification has previously been described for the Sortilin propeptide fused to GST (5) and the NGF prodomain (6). Mature BDNF (SEQ ID NO. 7, amino acid residues 128 to 246) was purchased from R&D Systems, Inc. (USA).

Example 2

Surface Plasmon Resonance

Surface plasmon resonance (SPR) measurements were performed on a BIAcore 2000 instrument (Biacore Sweden) equipped with CM5 sensor chips maintained at 20° C. A continuous flow of HBS buffer (10 mM HEPES pH 7.4, 3.4 mM EDTA, 150 mM NaCl, 0.005% surfactant P20) passing over the sensor surface was maintained at 5 µl/min. The carboxylated dextran matrix of the sensor chip flow cells 1-3 was activated by the injection of a solution containing 0.2 M N-ethyl-N-(3 dimethylaminopropyl)carbodiimide and 0.05M N-hydroxysuccimide in water. A sortilin solution (320 µl, 5 µg/ml in 10 mM sodium acetate pH 4.0) was then injected over flow cells 1 and 2 at a flow rate of 15 µl/min. Remaining binding sites in all three flow cells were blocked by injection (5 µl/min) of 70 µl of 1 M ethanolamine pH 8.5. The surface plasmon resonance signal from immobilized sortilin generated 4419 and 6166 BIAcore response units (RU) equivalent to 49 and 69 fmol/mm$^2$. Screening of the samples was performed by injecting aliquots of 50 µl, at concentrations of 0.1-8 µM, through all flow cells with a flow rate of 5 µl/min. Unless otherwise stated, the samples were dissolved in 10 mM HEPES pH 7.4, 150 mM NaCl, 1.5 mM CaCl$_2$, 1 mM EGTA, 0.005% surfactant P20. Sample buffer was also used as running buffer. The BIAcore response is expressed in relative response units (RU), i.e. the difference in response between the immobilized protein flow cell and the corresponding control flow cell (activated and blocked but without protein). Regeneration of the sensor chip after each cycle of analysis was performed by injecting 20 µl of 10 mM glycine/HCl pH 4.0, 500 mM NaCl, 20 mM EDTA and 0.005% surfactant P20. For calciumfree conditions, HBS containing 20 mM EDTA was used as sample as well as running buffer. Kinetic parameters were determined by using the BIAevaluation 3.0 software. For comparison of the response measured for mutant and wt sSortilin they were immobilized in different flow-cells on the same BIAcore chip and subjected to similar concentrations of (GST)Sort-pro, BDNF, NGF-pro and NT.

Determination of Inhibitory Effect

Inhibition of (GST)Sort-pro, BDNF, NGF-pro and NT binding by the tripeptide Tyr-Ile-Leu (YIL) was measured by adding increasing concentrations of YIL to the respective samples. The measure of inhibitory effect is then be given as the concentration of YIL where a 90% decreased binding is observed.

Example 3

Fluorescence Measurements

All intrinsic fluorescence measurements were conducted on a SFM-25, Kontron Instruments, at 20° C. with measurements from 280 nm to 500 nm in 1 nm increments. Data was collected on 0.55 µM sSortilin, 5 µM NT, and 0.55 µM sSortilin with 5 µM NT, all in a 50 mM Tris-HCl pH 7.6, 150 mM NaCl buffer. sSortilin with NT was prepared by addition of NT from a 0.1 M stock solution to a 0.55 µM sSortilin solution, resulting in negligible dilution.

Example 4

Metabolic Labelling

Metabolic labelling was performed using 200 mCi of L-[$^{35}$S]cysteine and L-[$^{35}$S]methionine per ml of medium and in the presence of 10 mg/ml BFA as previously described in detail (5). Chase was performed in the absence of BFA and at given time points receptors were immunoprecipitated from the medium and from corresponding lysed cells. The precipitated proteins were analyzed by reducing PAGE and diphenyloxazole-fluorographed gels were exposed at –70° C.

Example 5

Crystallization, Cryoprotection and Ha Derivatization

The purified protein was dialyzed into a buffer containing 50 mM Tris-HCl pH 7.9 and 150 mM NaCl and concentrated to 4.5-5.5 mg/mL, as determined by a Bradford assay, using Centricon (Millipore Corp.) or Vivaspin (Sartorius Ltd.) concentrators. Mixing with Neurotensin (sSortilin (SEQ ID NO: 33):NT (SEQ ID NO:10) ratio 1:1.5 or 1:15) or NT propeptide residues 17-140 of SEQ ID NO:8; SEQ ID NO:41) (sSortilin:NT propeptide ratio 1:4) was done minutes before the crystallization experiment was set up. Crystallisation drops were set up at 20° C. using 2 µL protein solution and 2 µL of reservoir solution containing: 18-21% w/v PEG 6000, Tris-Hepes pH 7.2-7.8 (40-93 mM Tris and 100 mM Hepes) or 100 mM Tris-HCl pH 7.9, 3-6% glycerol and either 600 mM NaCl or 250-400 mM C$_3$H$_2$Na$_2$O$_4$ (sodium malonate) that was adjusted to pH 6-7.5 by malonic acid. Seleno-methionine (Se-Met) labelled sSortilin:NT crystals diffracting to 3.2 Å were obtained at the same conditions. Crystals for data collection were dehydrated and cryoprotected by increasing the glycerol concentration of the reservoir to 12-15%. After over-night equilibration the crystals were flash frozen in liquid nitrogen. The crystals normally diffracted to about 3.3-3.0 Å, but for the crystals grown with slight excess of NT and with NaCl as the reservoir salt, we rarely obtained crystals, that diffracted considerably better (about 2.5-2.0 Å) and exhibited a change in unit cell parameters (Table 1). For preparation of Hg and Pt derivatives, powder of mercury salicylate and cis-Pt(NH$_3$)$_2$Cl$_2$ was added directly to drops where crystals had formed. Soaking time for the Hg derivative was a month and for the Pt derivative a day. The Ta derivative was prepared by adding 1 µL of 1 mM Ta6Br12 dissolved in water to the drop of a dehydrating crystal for a soak time of 2 days, after which it had turned visibly green. None of the derivatized crystals were backsoaked.

Example 6

Data Collection and Processing

Data collection was performed at the synchrotrons MAX-lab (Lund, Sweden), SLS (Zurich, Switzerland) and DESY/EMBL (Hamburg, Germany), and processed using XDS (23) (see Table 1). Data on the Hg, Pt and Ta derivatives was collected near absorption edges of the respective elements and the dataset for the SeMet labeled crystal was collected directly at the Se peak wavelength (0.97853 Å), as determined by a fluorescence scan. The dataset for the sSortilin in complex with Neurotensin (sSort:NT) crystal was determined with a large excess of NT was corrected for anisotropy effects using the Diffraction Anisotropy Server (24).

TABLE 1

Data collection and processing statistics

| | Se-sSort-NT (slight excess, 1:1.5) | sSort-NT (slight excess, 1:1.5) | sSort-NT (slight excess, 1:1.5) | sSort-NT (slight excess, 1:1.5) | sSort-NT69L |
|---|---|---|---|---|---|
| HA soak | | Cis-Pt(NH$_3$)$_2$Cl$_2$ | Mercury Salicylate | Ta$_6$Br$_{12}$ | Native |
| Beamline | I911-3, MAXlab | I911-5, MAXlab | X12, DESY | PX1, SLS | PX1, SLS |
| Data statistics | | | | | |
| Wavelength (Å) | 0.97853 | 0.90718 | 0.9050 | 1.2548 | 1.2970 |
| Resolution limit (Å) | 3.8 (4.1-3.8) | 4.0 (4.3-4.0) | 6.0 (6.6-6.0) | 5.0 (5.3-5.0) | 2.8 (2.9-2.8) |
| Space group | C2 | C2 | C2 | C2 | C2 |
| Unit-cell a | 162.3 Å | 162.7 Å | 162.6 Å | 162.5 Å | 161.3 Å |
| b | 79.8 Å | 78.5 Å | 75.9 Å | 76.8 Å | 78.4 Å |
| c | 112.1 Å | 111.2 Å | 110.7 Å | 111.1 Å | 112.0 Å |
| β | 126.67° | 126.75° | 127.75° | 127.07° | 126.92° |
| Unique reflections | 21311 | 18332 | 5103 | 9159 | 27362 |
| Rsym(I) | 5.2 (11.7) | 6.8 (15.8) | 2.6 (5.7) | 2.4 (3.1) | 4.5 (31.1) |
| Completeness | 95.2 (96.6) | 97.7 (98.2) | 96.7 (97.3) | 98 (99.2) | 96.3 (93.5) |
| I/sigma | 17.4 (10.5) | 16.5 (8.0) | 40.3 (22.8) | 28.5 (23.7) | 25.5 (6.1) |
| Phasing statistics | | | | | |
| High resolution cutoff for phasing (Å) | 3.8 | 4.0 | 6.0 | 5.0 | 3.8 |
| Sites | 13 Se | 4 Pt | 2 Hg | 1 Ta-cluster | |
| Phasing Power | | | | | |
| Iso_acen | | 0.262 | 0.614 | 0.415 | 0.325 |
| Iso_cen | | 0.276 | 0.674 | 0.390 | 0.315 |
| Ano_acen | | 1.705 | 0.621 | 0.981 | 0.363 |
| Rcullis | | | | | |
| Iso_acen | 0.993 | 0.908 | 0.980 | 0.964 | |
| Iso_cen | 0.946 | 0.825 | 0.873 | 0.898 | |
| Ano_acen | 0.645 | 0.640 | 0.571 | 0.638 | |
| Fom  Acentric | | | | | 0.45 |
|      Centric | | | | | 0.18 |

Example 7

Phasing and Model Building

The inventors found 13 Se sites out of the 14 methionines present in sSortilin using SheIxD (25). SeMet SAD phases calculated using CNS (26) were used for identifying heavy atom sites in Pt, Hg, and Ta derivatives. We used all four derivatives together with an isomorphous 2.8 Å native dataset of sSortilin complexed to a Neurotensin analogue as input for MIRAS phasing in SHARP (27). A partial Cα trace was made with RESOLVE (28), which were extended and corrected by manual rebuilding in O (29). This partial model was then used for molecular replacement by use of MOLREP (30) into the 2.0 Å native dataset collected on sSortilin:NT crystals grown with a slight excess of NT. The complete model was created by cycles of refinement in CNS and manual rebuilding in O. Phasing of data collected on sSort:NT crystals grown with a large excess of NT and on data collected on sSort:propeptide fragment was performed by molecular replacement using an unfinished model for the 2.0 Å structure (NT not included), as input for MOLREP. The models were then completed by subsequent cycles of model building in O and refinement using CNS. For the final refinement, the inventors employed REFMAC (31) using TLS B-factor correction for the 2.0 Å sSort:NT structure, PHENIX(32) refine with TLS B-factor correction for the 2.6 Å sSort:NT structure and CNS for the 3.2 Å sSort:propeptide structure (Table 2).

TABLE 2

Data collection, processing, model building and refinement statistics

| | sSort-NT (slight excess, 1:1.5) | sSort-NT (large excess, 1:15) | sSort-propeptide (fragment 4-28, 1:4) |
|---|---|---|---|
| Beamline | PX1, SLS | I911-5, MAX-lab | I911-5, MAX-lab |
| Data statistics | | | |
| Wavelength (Å) | 0.95008 | 0.90736 | 0.90736 |
| Resolution limit (Å) | 2.0 (2.1-2.0) | 2.64 (2.74-2.64) | 3.15 (3.3-3.15) |
| Space group | C2 | C2 | C2 |

TABLE 2-continued

Data collection, processing, model building and refinement statistics

|  | sSort-NT (slight excess, 1:1.5) | sSort-NT (large excess, 1:15) | sSort-propeptide (fragment 4-28, 1:4) |
|---|---|---|---|
| Unit-cell a | 145.8 Å | 162.1 Å | 162.1 Å |
| b | 74.5 Å | 78.7 Å | 78.1 Å |
| c | 108.3 Å | 111.1 Å | 111.7 Å |
| β | 131.87° | 126.61° | 127.20° |
| Rsym(I) | 7.3 (44.0) | 4.9 (59.9) | 7.4 (50.4) |
| Completeness | 96.9 (98.8) | 98.0 (98.0) | 99.0 (99.5) |
| I/sigma | 11.59 (4.32) | 19.9 (2.9 ) | 14.53 (2.59) |
| Refinement statistics |  |  |  |
| Reflections (work/test) | 53737/2862 | 30813/953 | 18418/938 |
| R-factor | 0.204 | 0.169 | 0.230 |
| Rfree | 0.229 | 0.225 | 0.295 |
| Number of atoms in model |  |  |  |
| sSortilin and NT | 5.213 | 5293 | 5.194 |
| Carbohydrate | 67 | 94 | 122 |
| Water | 307 | 213 | 0 |
| PEG and glycerol | 16 | 13 | 0 |
| Mean B-factor (Å$^2$) |  |  |  |
| sSortilin | 30.4 | 70.5 | 99.7 |
| NT in binding site 1 | 57.1 | 68.3 | — |
| NT in binding site 2 | — | 103.2 | — |
| NT in artefact binding site | — | 126.7 | — |
| Glycosylations | 49.2 | 98.0 | 138.0 |
| Solvent (water, PEG, glycerol) | 46.9 | 60.7 | — |
| Geometry |  |  |  |
| Rmsd Bond-lengths | 0.021 Å | 0.008 Å | 0.0076 Å |
| Rmsd Bond angles | 1.832° | 1.204° | 1.389° |
| Phi-Psi distribution |  |  |  |
| Most favoured | 87.0% | 81.9% | 70.7% |
| Additionally allowed | 12.0% | 16.5% | 27.0% |
| Generously allowed | 0.9% | 1.2% | 2.1% |
| Dissallowed | 0.2% | 0.3% | 0.2% |

Example 8

Identification of the Pro-Neurotrophin Binding Site (Binding Site 3)

sSortilin Purification Soluble Sortilin (sSortilin), comprising SEQ ID NO. 1 (amino acids 78 to 755), fused C-terminally to His$_6$ was stably expressed in CHO-K1 cells as previously described (5). The CHO-transfectants were cultured in serum-free HyQ-CCM5 CHO medium (HyClone, Logan, Utah) in 500 cm$^3$ Nunclon™ TripleFlasks. sSortilin was purified by affinity chromatography with Receptor Associated Protein immobilized on CNBr-activated Sepharose beads (GE health care) as previously described (1).

NGFpro Purification

BL21 (DE3) star RIPL cells were transformed with a pET-30 Ek/LIC vector containing a N-terminal Histidine tag (His$_6$), a tobacco etch virus protease protease (TEV) site and the open reading frame of the propeptide of Nerve Growth Factor (NGFpro). Cells were grown to an OD$_{600nm}$ of 0.8 before induction with 1 mM IPTG over night (O/N) at 20° C. Cells were resuspended in lysis buffer: 50 mM TrisHCl pH=8.0, 1M KCl, 10 mM imidazole, 5 mM BME, 5 mM PMSF, 2 mg/ml DNase 1 and 1 protease inhibitor tablet (Complete, Roche)). Cells were disrupted on a high pressure homogenizer (HPH) and the lysate was clarified by centrifugation at 184.000×g. A Ni$^{2+}$-column (HisTrap 1 ml FF, GE) was equilibrated with buffer A (50 mM TrisHCl pH=8.0, 200 mM KCl and 5 mM BME). The clarified lysate was loaded and NGFpro eluted with a 40 column volume (CV) imidazole (10 mM to 500 mM) gradient with buffer B (50 mM TrisHCl pH=8.0, 200 mM KCl, 500 mM imidazole and 5 mM BME). Fractions containing NGFpro from first Ni$^{2+}$ column was pooled and buffer was exchanged to the TEV compatible buffer C (50 mM TrisHCl pH=8.0, 200 mM KCl, 5 mM BME, 0.5 mM EDTA). TEV digest was conducted at RT O/N. The His$_6$ tag was removed on a Ni$^{2+}$ column (HisTrap 1 ml FF, GE) with a 40 column volume (CV) imidazole (0 mM to 250 mM) gradient. NGFpro from second Ni$^{2+}$ column was concentrated using the Vivaspin 6 column with a 10 kDa cutoff membrane. Preparative gelfiltration was conducted at a Superdex 75 10/300 GL column (GE) with a flow rate of 0.4 ml/min in buffer D (50 mM TrisHCl pH=7.6 and 150 mM NaCl).

Preparation of Peptides of NGF Propeptide

As demonstrated in FIG. 21, icosapeptides (20 aa) of the propeptide of Nerve Growth Factor were synthesized by solid phase chemistry at Caslo Laboratory Aps.

The peptides were amidated at the C-terminal and covered the whole NGFpro with a 3 aa overlap. The peptides (purity >95%) were dissolved in buffer E (10 mM HEPES pH=7.0 and 50 mM NaCl).

Surface Plasmon Resonance Analysis

All measurements were performed on a BIAcore 3000 instrument (Biacore Sweden) maintained at 20° C. A continuous flow of buffer F (10 mM HEPES pH=7.4, 150 mM (NH$_4$)$_2$SO$_4$, 1.5 mM CaCl$_2$, 1.5 mM EGTA and 0.005% Tween-20) was passed over the CM5 chip sensor surface at 5 μl/min. The affinity of NGFpro and the peptides for immobilized sSortilin were determined. The dissociation constant ($K_d$) for NGFpro was ~10 nM and for peptide-4 (SEQ ID NO:51) ~5 μM. The ability of the peptides to compete with NGFpro for binding to sSortilin was tested as well. The results are presented in FIG. 22.

Crystallization of Ssortilin with Ligands

Purified sSortilin (SEQ ID NO: 33) was dialyzed into buffer G (50 mM Tris-HCl pH 8.0 and 150 mM NaCl) and concentrated in Vivaspin (Sartorius Ltd.) concentrators to 4.5-5.5 mg/mL, as determined by a Bradford assay. sSortilin (SEQ ID NO: 33) and NGFpro (residues 19-121 of SEQ ID NO:6) were was mixed in molar ratio of 1:2 and incubated on ice for 1 hour. The complex was crystallized in vapour diffusion experiments using sitting drops. Crystallisation drops were set up at 20° C. using 1 μL complex solution and 1 μL of reservoir solution containing 20-28% Poly Ethylene Glycol (PEG) 5000 monomethyl ether, 100 mM TrisHCl pH=7.5 and 200 mM L12SO4. sSortilin (SEQ ID NO: 33) and peptide-4 (SEQ ID NO:51) was mixed in various molar ratios ranging from 1:5 to 1:28 and incubated on ice for 1 h. The complexes were crystallized in vapour diffusion experiments using sitting drops.

Crystallisation drops were set up at 20° C. using 1 μL complex solution and 1 μL of reservoir solution containing 20-28% PEG 6000, 100 mM TrisHCl pH=7.5 and 200-600 mM $Li_2SO_4$.

Dehydration of the crystals by adding sucrose or glycerol to the reservoir (up to 20% v/v) was carried out before they were flash-frozen in liquid nitrogen.

Data Collection and Processing

X-ray diffraction data of the sSortilin (SEQ ID NO: 33):NGFpro (residues 19-121 of SEQ ID NO:6) complex was collected at station 1D29 at ESRF Grenoble (France) and diffraction data of the sSortilin (SEQ ID NO: 33):Peptide-4 (SEQ ID NO:51) complex crystals were collected at cryo conditions using synchrotron radiation on station I911-3 at Max-lab Lund (Sweden). The data was indexed and processed with XDS (23). Crystals of sSortilin (SEQ ID NO: 33) in complex with NGFpro (residues 19-121 of SEQ ID NO:6) or Peptide-4 (SEQ ID NO:51) were isomorphous belonging to the tetragonal space group P41212 with one sSortilin molecule in the asymmetric unit (Table 3). The structures were determined by molecular replacement using Phaser (36). The structure of sSortilin and neurotensin stripped of all its ligands was used as initial model for phasing. The resulting model was subjected to simulated annealing to reduce model bias and refinement in Phenix (32). Difference fourier maps Fobs-Fcalc were used to locate the bound part of the NGFpro as well as conformational changes of loops and glycosylations of sSortilin.

TABLE 3

| Data collection and processing | | |
|---|---|---|
| Beamline | sSortilin:NGFpro (1:2) ID29, ESRF | sSortilin:peptide-4 (1:17) Max-lab, I911-2 |
| Data statistics | | |
| Wavelength (Å) | 1.07253 | 1.0737 |
| Resolution (Å) | 30.0-4.1 | 25.0-3.2 |
|  | (4.3-4.1) | (3.4-3.2) |
| Space group | $P4_12_12$ | $P4_12_12$ |
| Unit-cell (Å) | | |
| a, b | 159.97 | 159.37 |
| c | 106.55 | 108.72 |
| $R_{merge}$ (I) | 17.9 (73.8) | 9.4 (69.9) |

TABLE 3-continued

| Data collection and processing | | |
|---|---|---|
| Beamline | sSortilin:NGFpro (1:2) ID29, ESRF | sSortilin:peptide-4 (1:17) Max-lab, I911-2 |
| Completeness | 99.5 (99.6) | 99.4 (99.9) |
| I/sigma | 9.4 (2.2) | 17.35 (2.29) |

Example 9

Docking and In Silico Screening

Two grids were calculated using Maestro version 8.0 with Exhaustive Sampling of Optimize H-bonds, one grid with Minimize structure within 0.3 Å and one without Minimize of each available, refined structure of Sortilin-ligand complex. The hydrogen of the —OH of Ser352 of SEQ ID NO:1 and the hydrogen of the NH of Ile353 of SEQ ID NO:1 were specified as possible constraints.

The bounding box was defined as the centroid of residues 325, 260, and 352 of SEQ ID NO:1 with standard value dimensions.

Ligands were built in Maestro as tripeptides with one residue substituted from Tyr-Ile-Leu, resulting in 60 natural peptides. Ligands were energy minimized in MacroModel with the OPLS_2005 force field and maximum iterations set to 10000. Docking was performed into all the grids generated using the XP scoring function. The constraints were applied so that a hydrogen bond from the ligand had to be formed to one of the two hydrogens earlier specified. Peptides were chosen for synthesis and biochemical characterization based on both G-score and manual inspection of the docking pose. Additionally, consistently poorly scoring/docking ligands that were very similar to those chosen for synthesis were also synthesized as negative controls.

Generation of Docking Grid from the Structure Used for Docking

Go to the Workflows menu and choose the Protein Preparation Wizard.

Import your structure, then either leave the default settings in Fix Structure or change Delete Waters to 0.1 A, if you have no structural waters in the binding site, and press Setup. Check in the workspace that any structural waters were not removed. Manually remove any non-structural waters.

Next turn on the radio button for Exhaustive Sampling and click Optimize H-bonds. If you do not have a ligand in your binding pocket, then ignore the Minimize . . . button. If you do have a ligand in the binding pocket you should make two grids, one where you run Minimize . . . with the default settings and one where you either don't minimize or where you minimize Hydrogens only.

Go to Applications menu and choose Glide, then Receptor Grid Generation. If there is a ligand in your binding pocket it must be excluded from the grid generation and this is done by clicking it in the workspace while the Receptor tab is active. Click "Pick to identify ligand" if it isn't already yellow. Selecting the ligand sets a bounding box and you could generate a grid now but if the ligands you wish to dock are much larger than the original one then you should go the tab Site, click "Dock ligands with length <=" and adjust the slider. If there was no ligand in the original structure you should click "Centroid of selected residues" and in the workspace click the residues around the binding site.

If you are running Sortilin with a peptide in the Arg248 (/325/292) site (SEQ ID NO:1), go to Constraints tab and select the hydrogen of the hydroxyl of Ser275 (/352/319) and the polar hydrogen of Ile276 (/353/320). Now click Start.

Generation of Ligands and Energy-Minimization

Click the Build Panel button to open the build panel.

Deselect all entries in the project table. In the blank workspace, use the build panel to build your ligand. Make sure you have the correct charges (LigPrep will assign correct charges though and generate additional ligands for tautomers and multiple charge states as well as minimize the energy) and double click Add Hydrogens. Press the Generate Entry From Workspace button and name your ligand.

If your next ligand is similar to the first, go to the project table and duplicate, then rename, it. Edit the new entry as you built the first ligand. If it is very dissimilar simply deselect everything in the project table and do as you did for the first. If you have SMILES of your ligands, it is faster to convert them to mol2 format with OpenBabel and import them into the project table. .pdbs must have hydrogens specified for Maestro to recognize the bond order and .sdfs do not contain the chirality info.

There are two options for energy minimization: LigPrep or MacroModel.

a) Go to Applications menu and choose MacroModel, then Multiple Minimization.

Select all your ligands from the project table and set the drop-down menu to Project Table (selected entries). In the Potential tab choose Force field: OPLS_2005 (it should be default). Under Mini choose Method: PRCG (default) and Maximum iterations: 10000. If you have saved your ligands to a file and want to use them directly from there, then specify the file under the Mult tab and Start.

b) Go to Applications menu and choose LigPrep.

Select all your ligands from the project table or choose a file with all your ligands and set the drop-down menu accordingly. You might want to set the target pH to 7.4 and +/− lower than 2. Retain chiralities and start. Remember to inspect your ligands after minimization to confirm that they are correct, specifically chiral centers will be present in both enantiomers if they were not unambiguously defined in the original ligand. LigPrep is preferable to MacroModel because it generates all the states of histidine automatically.

Docking

Go to Applications menu and choose Glide, then Ligand Docking.

Select the Receptor grid file. Set Precision to XP. Dock flexibly and allow ring-flips. In the advanced settings set Maximum number of conjugate steps to 5000. Go to the Ligands tab and choose the file generated in the energy minimization step or simply choose them in the project table and set Selected entries on. In the Output tab set Write out at most 5 poses per ligand. Adjust ligands per docking run if you have very many ligands.

If you are running Sortilin with a peptide in the Arg248 (/325/292) site then go to the Constraints tab and in Group 1 add the two h-bond constraints and set Must match: At least: 1. Only poses that include a hydrogen bond to one of the two will be included. This added because Maestro reports many curled up peptides which do not appear natural and have not been observed in the structures—if this had not been observed then the correct approach would have been to dock without constraints.

Steps one and three are repeated for all the available structures. The minimized ligands from step two are re-used.

Evaluation of Results

Go to Applications menu and choose Glide, then Poseviewer.

Manually compare the docking of the highest scoring ligands, compare the same ligands in the other structures, synthesize those that seem reasonable as well as very related compounds that score/dock poorly for negative controls.

Example 10

Methods for Verification of Inhibitors

Subsequent to synthesis of identified ligands performed by methods well known to those skilled in the art of organic chemistry it is important to verify if the ligand candidates possess antagonistic properties, i.e. if said ligands are capable of preventing binding of endogenous ligands to any of binding sites 1, 2 or 3 of Sortilin.

The proposed ligands are tested for inhibitory effect by surface plasmon resonance measurements on immobililzed sSortilin as described in example 2.

The proposed ligands are radiolabeled and used for slice autoradiography. The developed images are compared to slice autoradiography employing radiolabeled monoclonal sortilin antibodies. Those ligands that co-localize with the monoclonal antibodies are tested again in slice autoradiography with slices of sortilin knock-out mice.

Ligands that image sortilin satisfactorily are injected in mice and brain homogenates are tested for radioactivity or the unlabeled ligands are labeled with radioisotopes suitable for either PET or SPECT and injected in mice or swine and their brains are imaged in vivo.

Endogenous stability experiments are performed on brain homogenates. Non-blood-brain barrier permeating compounds are suitable for non-CNS imaging and inhibition of this binding site in sortilin and BBB permeating compounds are suitable for brain scans examining the in vivo levels and distribution of sortilin.

REFERENCES

1. C. M. Petersen et al., J Biol Chem 272, 3599 (1997).
2. L. Jacobsen et al., J Biol Chem 271, 31379 (1996).
3. W. Hampe, M. Rezgaoui, I. Hermans-Borgmeyer, H. C. Schaller, Hum Genet. 108, 529 (2001).
4. J. Mazella et al., J Biol Chem 273, 26273 (1998).
5. C. Munck Petersen et al., Embo J 18, 595 (1999).
6. A. Nykjaer et al., Nature 427, 843 (2004).
7. H. K. Teng et al., J Neurosci 25, 5455 (2005).
8. U. B. Westergaard et al., J Biol Chem 279, 50221 (2004).
9. S. Maeda et al., J Cell Physiol 193, 73 (2002).
10. M. S, Nielsen, C. Jacobsen, G. Olivecrona, J. Gliemann, C. M. Petersen, Biol Chem 274, 8832 (1999).
11. M. S, Nielsen et al., Embo J 20, 2180 (2001).
12. K. Nakamura, K. Namekata, C. Harada, T. Harada, Cell Death Differ 14, 1552 (2007).
13. P. Jansen et al., Nat Neurosci 10, 1449 (2007).
14. P. Chalon et al., FEBS Lett 386, 91 (1996).
15. L. Jacobsen et al., J Biol Chem 276, 22788 (2001).
16. K. Tanaka, M. Masu, S, Nakanishi, Neuron 4, 847 (1990).
17. J. P. Vincent, J. Mazella, P. Kitabgi, Trends Pharmacol Sci 20, 302 (1999).
18. X. L. He, K. C. Garcia, Science 304, 870 (2004).
19. O. M. Andersen et al., Proc Natl Acad Sci USA 102, 13461 (2005).
20. S. M. Clee et al., Nat Genet 38, 688 (2006).
21. E. Rogaeva et al., Nat Genet 39, 168 (2007).

22. J. W. Lustbader et al., *Endocrinology* 136, 640 (February, 1995).
23. W. Kabsch, in *International Tables for Crystallography* E. Arnold, Ed. (Kluwer Academic Publishers, Dordrecht, 2001).
24. M. Strong et al., *Proc Natl Acad Sci USA* 103, 8060 (May 23, 2006).
25. T. R. Schneider, G. M. Sheldrick, *Acta Crystallogr D Biol Crystallogr* 58, 1772 (October, 2002).
26. A. T. Brunger et al., *Acta Crystallogr D Biol Crystallogr* 54, 905 (Sep. 1, 1998).
27. G. Bricogne, C. Vonrhein, C. Flensburg, M. Schiltz, W. Paciorek, *Acta Crystallogr D Biol Crystallogr* 59, 2023 (November, 2003).
28. T. C. Terwilliger, *Acta Crystallogr. D* 59, 38 (2003).
29. T. A. Jones, J. Y. Zou, S. W. Cowan, M. Kjeldgaard, *Acta Crystallogr A* 47 (Pt 2), 110 (Mar. 1, 1991).
30. A. Vagin, A. Teplyakov, *Acta Crystallogr D Biol Crystallogr* 56, 1622 (December, 2000).
31. G. N. Murshudov, A. A. Vagin, E. J. Dodson, *Acta Crystallogr D Biol Crystallogr* 53, 240 (May 1, 1997).
32. P. D. Adams et al., *Acta Crystallogr D Biol Crystallogr* 58, 1948 (November, 2002).
33. W. L. DeLano, *The PyMOL Molecular Graphics System* (DeLano Scientific, Palo Alto, Calif., USA., 2002), pp.
34. M. Clamp, J. Cuff, S. M. Searle, G. J. Barton, *Bioinformatics* 20, 426 (Feb. 12, 2004).
35. W. Kabsch, C. Sander, *Biopolymers* 22, 2577 (December, 1983).
35. A. C. Wallace, R. A. Laskowski, J. M. Thornton, *Protein Eng* 8, 127 (February, 1995).
36. A. J. McCoy, R. W. Grosse-Kunstleve, P. D. Adams, M. D. Winn, L. C. Storoni and
37. R. J. Read J. Appl. Cryst. (2007). 40, 658-674

The invention claimed is:

1. A crystal of a complex of sortilin, consisting of the amino acid sequence of SEQ ID NO:33; with a ligand;
wherein the crystal is selected from the group consisting of:
(a) a tetragonal crystal of said sortilin and the ligand: NGF pro domain (SEQ ID NO:40), wherein said crystal in space group $P4_12_12$ with unit cell dimension of a=b=159.97 Å, c=106.55 Å, α=β=γ=90°,
(b) a tetragonal crystal of said sortilin and the ligand: peptide-4, said peptide-4 (SEQ ID NO:39), wherein and crystal is in space group $P4_12_12$ with unit cell dimensions of a=b=159.37 Å, c=108.72 Å, α=β=γ=90°,
(c) a monoclinic crystal of said sortilin and the ligand: neurotensin (SEQ ID NO:10), wherein and crystal is in space group C2 with unit cell dimensions of a=145.8 Å, b=74.5 Å, c=108.3 Å, α=γ=90°, β=131.87°,
(d) a monoclinic crystal of said sortilin and the ligand: neurotensin (SEQ ID NO:10), wherein and crystal is in space group C2 with unit cell dimensions of a=162.1 Å, b=78.7 Å, c=111.1 Å, α=γ=90°, β=126.61°, and
(e) a monoclinic crystal of said sortilin and the ligand: sSort-propeptide (SEQ ID NO:49), wherein and crystal is in space group C2 with unit cell dimensions of a=162.1 Å, b=78.1 Å, c=111.7 Å, α=γ=90°, β=127.20°.

2. A method of growing the crystal according to claim 1, comprising the steps of:
   a. obtaining a composition comprising 4.5 to 5.5 mg/mL of the polypeptide of SEQ ID NO: 33 in a buffer,
   b. mixing said composition with a ligand, and
   c. subjecting predefined volumes of said composition and a crystallization solution, and
   d. obtaining crystals comprising SEQ ID NO: 33.

3. The method of claim 2, wherein said buffer contains 50 mM Tris-HCl pH 7.9 and 150 mM NaCl.

4. The method of claim 2, wherein said crystallization solution contains 18 to 21% w/v PEG 6000.

5. The method of claim 2, wherein said crystallization solution contains Tris-HEPES pH 7.2-7.8 (40-93 mM Tris and 100 mM HEPES) or 100 mM Tris-HCl pH 7.9.

6. The method of claim 2, wherein said crystallization solution contains 3 to 6% glycerol.

7. The method of claim 2, wherein said crystallization solution contains 300 to 900 mM NaCl or 150 to 400 mM $C_3H_2Na_2O_4$ wherein said $C_3H_2Na_2O_4$ is adjusted to pH 6 to 7.5 by malonic acid, or 300 to 500 mM $LiSO_4$ or 500-700 mM KCl.

8. The method of claim 2, wherein the methionine residues of SEQ ID NO: 33 is replaced by seleno-methionine.

9. The method of claim 2, further comprising the steps of:
   a. isolating an initial precipitate, and
   b. growing these by vapour diffusion from hanging drops.

10. A method for identifying a compound that binds to a sortilin, wherein said method comprises:
   (a) obtaining the crystal of claim 1;
   (b) using the crystal obtained in step (a) to obtain an x-ray diffraction pattern;
   (c) solving the three dimensional structure of the sortilin from the diffraction pattern obtained in step (b), thereby obtaining the three dimensional structure of the sortilin; and
   (d) identifying one or more compounds that binds to sortilin based on the obtained three dimensional structure of the sortilin.

11. The method of claim 10, wherein said compound binds to binding site 1, 2 or 3 of said sortilin, wherein:
   (1) said binding site 1 comprises amino acid residues R325, S316, Y351, I353, K260, I327, F314, F350 to M363, S305, F306, T398 to G400, I303-G309, Q349-A356, Y395 and T402 of SEQ ID NO: 1;
   (2) said binding site 2 comprises amino acid residues L572, L114, V112, R109 to S111, S115 to G118, T570, G571, W586, W597, T168-I174, L572, A573 and S584 to F588 of SEQ ID NO: 1; and
   (3) said binding site 3 comprises amino acid residues D403, S420, D422, N423, S424, I425, E426, T451, Y466, E470, I498, S499 and V500 of SEQ ID NO: 1.

12. The method of claim 11, wherein said compound is selected from the group comprising amino acid residues 19 to 241 of SEQ ID NO: 6 (proNGF), amino acid residues 19 to 121 of SEQ ID NO: 6 (NGF pro domain), amino acid residues 19 to 246 of SEQ ID NO: 7 (proBDNF), amino acid residues 19 to 127 of SEQ ID NO: 7 (BDNF pro domain), amino acid residues 17 to 257 of SEQ ID NO: 8 (proNT3), amino acid residues 17 to 140 of SEQ ID NO: 8 (NT3 pro domain), amino acid residues 25 to 210 of SEQ ID NO: 9 (proNT4/5), amino acid residues 25 to 80 of SEQ ID NO: 9 (NT4/5 pro domain), SEQ ID NO: 10 (Neurotensin), SEQ ID NO: 11 (PYIL), amino acid residues 11 to 13 of SEQ ID NO: 10 (YIL) and SEQ ID NO: 12 (NT69L).

\* \* \* \* \*

UNITED STATES PATENT AND TRADEMARK OFFICE
CERTIFICATE OF CORRECTION

PATENT NO. : 8,377,701 B2
APPLICATION NO. : 12/989895
DATED : February 19, 2013
INVENTOR(S) : Jens Claus Munck Petersen et al.

Page 1 of 1

It is certified that error appears in the above-identified patent and that said Letters Patent is hereby corrected as shown below:

(1) On the title page, item 54 and in the specification, column 1, line 1, Title "SPECIFIC LIGANDS TO SORTILIN" should read:
-- DESIGN OF SPECIFIC LIGANDS TO SORTILIN --.

In the claims (2) Column 165, line 65, "SEQ ID NO:39" should read -- SEQ ID NO:55 --.

Signed and Sealed this
Twenty-ninth Day of December, 2015

Michelle K. Lee
*Director of the United States Patent and Trademark Office*

UNITED STATES PATENT AND TRADEMARK OFFICE
CERTIFICATE OF CORRECTION

PATENT NO. : 8,377,701 B2  Page 1 of 1
APPLICATION NO. : 12/989895
DATED : February 19, 2013
INVENTOR(S) : Jens Claus Munck Petersen et al.

It is certified that error appears in the above-identified patent and that said Letters Patent is hereby corrected as shown below:

(1) On the title page, item 54 and in the specification, column 1, line 1, Title
"SPECIFIC LIGANDS TO SORTILIN" should read:
-- DESIGN OF SPECIFIC LIGANDS TO SORTILIN --.

In the claims (2) Column 165, line 65, "SEQ ID NO:39" should read -- SEQ ID NO:55 --.

This certificate supersedes the Certificate of Correction issued December 29, 2015.

Signed and Sealed this
Fifth Day of April, 2016

Michelle K. Lee
*Director of the United States Patent and Trademark Office*

UNITED STATES PATENT AND TRADEMARK OFFICE
CERTIFICATE OF CORRECTION

PATENT NO. : 8,377,701 B2  
APPLICATION NO. : 12/989895  
DATED : February 19, 2013  
INVENTOR(S) : Jens Claus Munck Petersen et al.

Page 1 of 1

It is certified that error appears in the above-identified patent and that said Letters Patent is hereby corrected as shown below:

In the claims

Column 165, line 65, which originally read as "SEQ ID NO:39" and which was previously corrected to read as "SEQ ID NO:55", should read -- SEQ ID NO:51 --.

This certificate supersedes the Certificate of Correction issued December 29, 2015.

Signed and Sealed this  
Third Day of May, 2016

Michelle K. Lee  
*Director of the United States Patent and Trademark Office*